United States Patent
Ahmad et al.

(10) Patent No.: US 11,117,900 B2
(45) Date of Patent: *Sep. 14, 2021

(54) COMPOUNDS USEFUL AS INHIBITORS OF ATR KINASE

(71) Applicant: Vertex Pharmaceuticals Incorporated, Boston, MA (US)

(72) Inventors: Nadia Ahmad, Didcot (GB); Dean Boyall, Faringdon (GB); Jean-Damien Charrier, Wantage (GB); Chris Davis, Salisbury (GB); Rebecca Davis, Witney (GB); Steven Durrant, Abingdon (GB); Gorka Etxebarria I Jardi, Abingdon (GB); Damien Fraysse, Abingdon (GB); Juan-Miguel Jimenez, Abingdon (GB); David Kay, Purton (GB); Ronald Knegtel, Abingdon (GB); Donald Middleton, Sandwich (GB); Michael O'Donnell, Abingdon (GB); Maninder Panesar, Didcot (GB); Francoise Pierard, Abingdon (GB); Joanne Pinder, Didcot (GB); David Shaw, Oxford (GB); Pierre-Henri Storck, Abingdon (GB); John Studley, Witney (GB); Heather Twin, Wantage (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/532,596

(22) Filed: Aug. 6, 2019

(65) Prior Publication Data
US 2020/0140441 A1  May 7, 2020

Related U.S. Application Data

(60) Continuation of application No. 15/633,477, filed on Jun. 26, 2017, now Pat. No. 10,392,391, which is a
(Continued)

(51) Int. Cl.
*C07D 487/04* (2006.01)
*C07D 453/02* (2006.01)
(Continued)

(52) U.S. Cl.
CPC ......... *C07D 487/04* (2013.01); *C07D 453/02* (2013.01); *C07D 471/08* (2013.01);
(Continued)

(58) Field of Classification Search
CPC .. C07D 487/04; C07D 453/02; C07D 471/08; C07D 487/08; C07D 491/107; C07D 498/04; C07D 498/10
See application file for complete search history.

(56) References Cited

U.S. PATENT DOCUMENTS

| 4,309,430 A | 1/1982 | Bock et al. |
| 5,143,824 A | 9/1992 | Yamakawa et al. |

(Continued)

FOREIGN PATENT DOCUMENTS

| CN | 101537007 | 9/2009 |
| CN | 103373996 | 10/2013 |

(Continued)

OTHER PUBLICATIONS

Abdel-Magid, "Inhibitors of ATR Kinase for Treatment of Cancer," ACS Med Chem Left. Jun. 13, 2013;4(8):688-9. doi: 10.1021/ml4002198. eCollection 2013.

(Continued)

*Primary Examiner* — Jared Barsky
(74) *Attorney, Agent, or Firm* — Andrea L. C. Reid; Danielle M. Nihan; Dechert LLP

(57) ABSTRACT

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I:

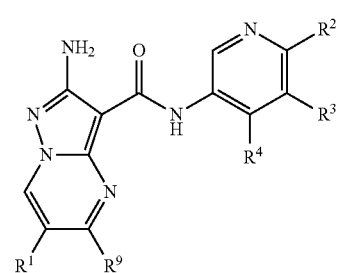

or a pharmaceutically acceptable salt, wherein the variables are as devined herein.

Moreover, The compounds of this invention have formula I-A:

(Continued)

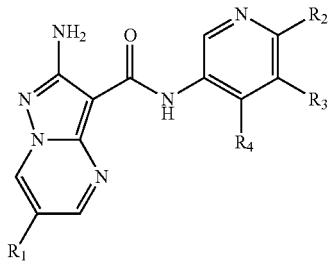

or a pharmaceutically acceptable salt, wherein the variables are as defined herein.

17 Claims, No Drawings

Specification includes a Sequence Listing.

Related U.S. Application Data continuation of application No. 15/142,338, filed on Apr. 29, 2016, now Pat. No. 9,718,827, which is a division of application No. 14/098,606, filed on Dec. 6, 2013, now Pat. No. 9,340,546.

(60) Provisional application No. 61/868,132, filed on Aug. 21, 2013, provisional application No. 61/734,726, filed on Dec. 7, 2012, provisional application No. 61/787,568, filed on Mar. 15, 2013.

(51) Int. Cl.
  C07D 471/08 (2006.01)
  C07D 487/08 (2006.01)
  C07D 491/107 (2006.01)
  C07D 498/04 (2006.01)
  C07D 498/10 (2006.01)

(52) U.S. Cl.
  CPC ....... C07D 487/08 (2013.01); C07D 491/107 (2013.01); C07D 498/04 (2013.01); C07D 498/10 (2013.01)

(56) References Cited

U.S. PATENT DOCUMENTS

| | | |
|---|---|---|
| 5,902,773 A | 5/1999 | Benoit et al. |
| 6,060,478 A | 5/2000 | Ford et al. |
| 6,191,131 B1 | 2/2001 | He et al. |
| 6,235,741 B1 | 5/2001 | Bilodeau et al. |
| 6,420,637 B1 | 7/2002 | Ueda et al. |
| 6,660,753 B2 | 12/2003 | Van Wagenen et al. |
| 6,858,600 B2 | 2/2005 | Hamilton et al. |
| 6,992,087 B2 | 1/2006 | Verhoest et al. |
| 7,041,672 B2 | 5/2006 | Verhoest et al. |
| 7,199,123 B2 | 4/2007 | Munchhof |
| 7,452,993 B2 | 11/2008 | Arnold et al. |
| 7,528,138 B2 | 5/2009 | Knegtel et al. |
| 7,550,470 B2 | 6/2009 | Fraley et al. |
| 7,622,583 B2 | 11/2009 | Ungashe et al. |
| 7,626,021 B2 | 12/2009 | Arnold et al. |
| 7,700,601 B2 | 4/2010 | Chan et al. |
| 7,704,995 B2 | 4/2010 | Buhr et al. |
| 7,829,558 B2 | 11/2010 | Arnold et al. |
| 7,872,031 B2 | 1/2011 | Lauffer et al. |
| 7,902,197 B2 | 3/2011 | Elworthy et al. |
| 7,932,254 B2 | 4/2011 | DuBois et al. |
| 7,939,531 B2 | 5/2011 | Bamberg et al. |
| 7,981,893 B2 | 7/2011 | Mortensen et al. |
| 8,063,032 B2 | 11/2011 | Chytil et al. |
| 8,106,197 B2 | 1/2012 | Cui et al. |
| 8,410,112 B2 | 4/2013 | Charrier et al. |
| 8,492,582 B2 | 7/2013 | Yokotani et al. |
| 8,623,869 B2 | 1/2014 | Charrier et al. |
| 8,822,469 B2 | 9/2014 | MacCormick et al. |
| 8,957,078 B2 | 2/2015 | Brenchley et al. |
| 8,962,631 B2 | 2/2015 | Charrier et al. |
| 8,969,360 B2 | 3/2015 | Charrier et al. |
| 8,999,632 B2 | 4/2015 | Falcon et al. |
| 9,096,602 B2 | 8/2015 | Everitt et al. |
| 9,309,250 B2 | 3/2016 | Storck et al. |
| 9,340,546 B2 | 5/2016 | Ahmad et al. |
| 9,365,557 B2 | 6/2016 | Charrier et al. |
| 9,650,381 B2 | 5/2017 | Ahmad et al. |
| 9,701,674 B2 | 7/2017 | Charrier et al. |
| 9,718,827 B2 | 8/2017 | Ahmad et al. |
| 9,791,456 B2 | 10/2017 | Falcon et al. |
| 9,862,709 B2 | 1/2018 | Charrier et al. |
| 10,392,391 B2 | 8/2019 | Ahmad et al. |
| 10,787,452 B2 | 9/2020 | Ahmad et al. |
| 2002/0041880 A1 | 4/2002 | Canella et al. |
| 2003/0008882 A1 | 1/2003 | Hamilton et al. |
| 2003/0055085 A1 | 3/2003 | Wagenen et al. |
| 2004/0034037 A1 | 2/2004 | Harbeson et al. |
| 2004/0043998 A1 | 3/2004 | Kato et al. |
| 2004/0180905 A1 | 9/2004 | Munchhof |
| 2005/0261339 A1 | 11/2005 | Ohi et al. |
| 2006/0156482 A1 | 7/2006 | Lim |
| 2006/0211709 A1 | 9/2006 | Buhr et al. |
| 2007/0037794 A1 | 2/2007 | Ungashe et al. |
| 2007/0112006 A1 | 5/2007 | Schiemann et al. |
| 2007/0197389 A1 | 8/2007 | Schwogler et al. |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2008/0176892 A1 | 7/2008 | Heinrich et al. |
| 2008/0287463 A1 | 11/2008 | Herrmann et al. |
| 2009/0005381 A1 | 1/2009 | Brown et al. |
| 2009/0156512 A1 | 6/2009 | Umemura et al. |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |
| 2009/0318436 A1 | 12/2009 | Albrecht et al. |
| 2010/0036118 A1 | 2/2010 | Arnold et al. |
| 2010/0167931 A1 | 7/2010 | Mueller et al. |
| 2010/0168138 A1 | 7/2010 | DeGoey et al. |
| 2010/0204214 A1 | 8/2010 | Chytil et al. |
| 2010/0222318 A1 | 9/2010 | Charrier et al. |
| 2010/0233091 A1 | 9/2010 | Neumann et al. |
| 2011/0015231 A1 | 1/2011 | Al-Abed et al. |
| 2011/0275797 A1 | 11/2011 | Yokotani et al. |
| 2011/0288067 A1 | 11/2011 | Hendricks et al. |
| 2011/0288097 A1 | 11/2011 | Hendricks et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0040020 A1 | 2/2012 | Charrier et al. |
| 2012/0046295 A1 | 2/2012 | Charrier et al. |
| 2012/0065247 A1 | 3/2012 | Thompson et al. |
| 2012/0115874 A1 | 5/2012 | Wang et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |
| 2012/0178915 A1 | 7/2012 | Xu |
| 2013/0017273 A1 | 1/2013 | Everitt et al. |
| 2013/0018035 A1 | 1/2013 | MacCormick et al. |
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |

(56) References Cited

U.S. PATENT DOCUMENTS

| | | |
|---|---|---|
| 2013/0115313 A1 | 5/2013 | Charrier et al. |
| 2013/0115314 A1 | 5/2013 | Charrier et al. |
| 2013/0172273 A1 | 7/2013 | Aizpurua Iparraguirre et al. |
| 2013/0184292 A1 | 7/2013 | Charrier et al. |
| 2014/0044802 A1 | 2/2014 | Pollard et al. |
| 2014/0100229 A1 | 4/2014 | Follmann et al. |
| 2014/0113005 A1 | 4/2014 | Charrier et al. |
| 2014/0163000 A1 | 6/2014 | Ahmad et al. |
| 2014/0249157 A1 | 9/2014 | Ahmad et al. |
| 2014/0275009 A1 | 9/2014 | Brenchley et al. |
| 2014/0275021 A1 | 9/2014 | Charrier et al. |
| 2014/0275130 A1 | 9/2014 | Charrier et al. |
| 2014/0288347 A1 | 9/2014 | Charrier et al. |
| 2014/0356456 A1 | 12/2014 | Pollard et al. |
| 2015/0158868 A1 | 6/2015 | Boyall et al. |
| 2015/0158872 A1 | 6/2015 | Charrier et al. |
| 2015/0216175 A1 | 8/2015 | Heil et al. |
| 2015/0291601 A1 | 10/2015 | Brenchley et al. |
| 2015/0299205 A1 | 10/2015 | Charrier et al. |
| 2015/0353560 A1 | 12/2015 | Ahmad et al. |
| 2015/0359797 A1 | 12/2015 | Helleday et al. |
| 2015/0376187 A1 | 12/2015 | Everitt et al. |
| 2016/0009723 A1 | 1/2016 | Charrier et al. |
| 2016/0030424 A1 | 2/2016 | Pollard et al. |
| 2016/0311809 A1 | 10/2016 | Charrier et al. |
| 2016/0326180 A1 | 11/2016 | Boyall et al. |
| 2017/0349596 A1 | 12/2017 | Ahmad et al. |
| 2018/0072735 A1 | 3/2018 | Ahmad et al. |
| 2018/0155346 A1 | 6/2018 | Ahmad et al. |
| 2018/0170922 A1 | 6/2018 | Charrier et al. |
| 2020/0140441 A1 | 5/2020 | Ahmad et al. |

FOREIGN PATENT DOCUMENTS

| | | |
|---|---|---|
| CN | 101671336 | 11/2013 |
| EP | 313724 | 5/1989 |
| EP | 1217000 | 6/2002 |
| EP | 2157090 | 2/2010 |
| JP | 2001302666 | 10/2001 |
| RU | 2010129928 | 1/2012 |
| WO | WO1996035690 | 11/1996 |
| WO | WO1997043267 | 11/1997 |
| WO | WO1998003510 | 1/1998 |
| WO | WO1998033799 | 8/1998 |
| WO | WO1998042701 | 10/1998 |
| WO | WO1998054093 | 12/1998 |
| WO | WO2000004014 | 1/2000 |
| WO | WO2000053605 | 9/2000 |
| WO | WO2001040231 | 6/2001 |
| WO | WO2001044206 | 6/2001 |
| WO | WO2000192257 | 12/2001 |
| WO | WO2000209648 | 2/2002 |
| WO | WO2002040485 | 5/2002 |
| WO | WO2002066481 | 8/2002 |
| WO | WO2003000187 | 1/2003 |
| WO | WO2003004472 | 1/2003 |
| WO | WO2003004475 | 1/2003 |
| WO | WO2003037900 | 5/2003 |
| WO | WO2003045924 | 6/2003 |
| WO | WO2003076422 | 9/2003 |
| WO | WO2003080610 | 10/2003 |
| WO | WO2003087057 | 10/2003 |
| WO | WO2003091256 | 11/2003 |
| WO | WO2003092686 | 11/2003 |
| WO | WO2003093297 | 11/2003 |
| WO | WO2003101968 | 12/2003 |
| WO | WO2003101993 | 12/2003 |
| WO | WO2004000318 | 12/2003 |
| WO | WO2004022559 | 3/2004 |
| WO | WO2004022560 | 3/2004 |
| WO | WO2004022561 | 3/2004 |
| WO | WO2004026229 | 4/2004 |
| WO | WO2004033431 | 4/2004 |
| WO | WO2004052315 | 6/2004 |
| WO | WO2004055005 | 7/2004 |
| WO | WO2004055006 | 7/2004 |
| WO | WO2004076458 | 9/2004 |
| WO | WO2004080982 | 9/2004 |
| WO | WO2004084813 | 10/2004 |
| WO | WO2004084824 | 10/2004 |
| WO | WO2004085409 | 10/2004 |
| WO | WO2004103279 | 12/2004 |
| WO | WO2005028434 | 3/2005 |
| WO | WO2005028475 | 3/2005 |
| WO | WO2005051906 | 6/2005 |
| WO | WO2005054246 | 6/2005 |
| WO | WO2005077954 | 8/2005 |
| WO | WO2005079802 | 9/2005 |
| WO | WO2005080396 | 9/2005 |
| WO | WO2005117909 | 12/2005 |
| WO | WO2005123672 | 12/2005 |
| WO | WO2006015124 | 2/2006 |
| WO | WO2006052913 | 5/2006 |
| WO | WO2006053342 | 5/2006 |
| WO | WO2006058074 | 6/2006 |
| WO | WO2006067462 | 6/2006 |
| WO | WO2006071548 | 7/2006 |
| WO | WO2006071752 | 7/2006 |
| WO | WO2006075152 | 7/2006 |
| WO | WO2006087120 | 8/2006 |
| WO | WO2006088837 | 8/2006 |
| WO | WO2006114180 | 11/2006 |
| WO | WO2006120573 | 11/2006 |
| WO | WO2006128184 | 11/2006 |
| WO | WO2007015632 | 2/2007 |
| WO | WO2007041712 | 4/2007 |
| WO | WO2007044401 | 4/2007 |
| WO | WO2007044407 | 4/2007 |
| WO | WO2007044410 | 4/2007 |
| WO | WO2007044420 | 4/2007 |
| WO | WO2007044426 | 4/2007 |
| WO | WO2007044441 | 4/2007 |
| WO | WO2007044449 | 4/2007 |
| WO | WO2007046548 | 4/2007 |
| WO | WO2007048066 | 4/2007 |
| WO | WO2007058850 | 5/2007 |
| WO | WO2007063012 | 6/2007 |
| WO | WO2007066805 | 6/2007 |
| WO | WO2007076360 | 7/2007 |
| WO | WO2007096151 | 8/2007 |
| WO | WO2007096764 | 8/2007 |
| WO | WO2007096765 | 8/2007 |
| WO | WO2007102770 | 9/2007 |
| WO | WO2007111904 | 10/2007 |
| WO | WO2007126841 | 11/2007 |
| WO | WO2007126964 | 11/2007 |
| WO | WO2007139732 | 12/2007 |
| WO | WO2007139856 | 12/2007 |
| WO | WO2007139860 | 12/2007 |
| WO | WO2007147874 | 12/2007 |
| WO | WO2008004698 | 1/2008 |
| WO | WO2008008539 | 1/2008 |
| WO | WO2008037477 | 4/2008 |
| WO | WO2008038010 | 4/2008 |
| WO | WO2008040651 | 4/2008 |
| WO | WO2008045266 | 4/2008 |
| WO | WO2008045268 | 4/2008 |
| WO | WO2008060907 | 5/2008 |
| WO | WO2008063671 | 5/2008 |
| WO | WO2008071456 | 6/2008 |
| WO | WO2008074997 | 6/2008 |
| WO | WO2008079291 | 7/2008 |
| WO | WO2008079903 | 7/2008 |
| WO | WO2008079906 | 7/2008 |
| WO | WO2008103277 | 8/2008 |
| WO | WO2008106692 | 9/2008 |
| WO | WO2008122375 | 10/2008 |
| WO | WO2008124850 | 10/2008 |
| WO | WO2008130569 | 10/2008 |
| WO | WO2008130570 | 10/2008 |
| WO | WO2008141065 | 11/2008 |
| WO | WO2008144463 | 11/2008 |
| WO | WO2008144464 | 11/2008 |
| WO | WO2008151735 | 12/2008 |

(56) References Cited

FOREIGN PATENT DOCUMENTS

| WO | WO2008157191 | 12/2008 |
|---|---|---|
| WO | WO2009006580 | 1/2009 |
| WO | WO2009007390 | 1/2009 |
| WO | WO2009012482 | 1/2009 |
| WO | WO2009014637 | 1/2009 |
| WO | WO2010002483 | 1/2009 |
| WO | WO2010006086 | 1/2009 |
| WO | WO2009016460 | 2/2009 |
| WO | WO2009017954 | 2/2009 |
| WO | WO2009024825 | 2/2009 |
| WO | WO2009037247 | 3/2009 |
| WO | WO2009053737 | 4/2009 |
| WO | WO2009070567 | 6/2009 |
| WO | WO2009075790 | 6/2009 |
| WO | WO2009088986 | 7/2009 |
| WO | WO2009091374 | 7/2009 |
| WO | WO2009095254 | 8/2009 |
| WO | WO2009106885 | 9/2009 |
| WO | WO2009117157 | 9/2009 |
| WO | WO2010015803 | 2/2010 |
| WO | WO2010017047 | 2/2010 |
| WO | WO2010034738 | 4/2010 |
| WO | WO2010048131 | 4/2010 |
| WO | WO2010051549 | 5/2010 |
| WO | WO2010054398 | 5/2010 |
| WO | WO2010059836 | 5/2010 |
| WO | WO2010063634 | 6/2010 |
| WO | WO2010068483 | 6/2010 |
| WO | WO2010071837 | 6/2010 |
| WO | WO2010086040 | 8/2010 |
| WO | WO2010091409 | 8/2010 |
| WO | WO2011003065 | 1/2011 |
| WO | WO2011006074 | 1/2011 |
| WO | WO2011008830 | 1/2011 |
| WO | WO2011022439 | 2/2011 |
| WO | WO2011025706 | 3/2011 |
| WO | WO2011068667 | 6/2011 |
| WO | WO2011121096 | 6/2011 |
| WO | WO2011113606 | 9/2011 |
| WO | WO2011117145 | 9/2011 |
| WO | WO2011124998 | 10/2011 |
| WO | WO2011130689 | 10/2011 |
| WO | WO2011143399 | 11/2011 |
| WO | WO2011143419 | 11/2011 |
| WO | WO2011143422 | 11/2011 |
| WO | WO2011143423 | 11/2011 |
| WO | WO2011143425 | 11/2011 |
| WO | WO2011143426 | 11/2011 |
| WO | WO2011144584 | 11/2011 |
| WO | WO2011144585 | 11/2011 |
| WO | WO2011163518 | 12/2011 |
| WO | WO2012007375 | 1/2012 |
| WO | WO2012022045 | 2/2012 |
| WO | WO2012027236 | 3/2012 |
| WO | WO2012067822 | 5/2012 |
| WO | WO2012074754 | 6/2012 |
| WO | WO2012078855 | 6/2012 |
| WO | WO2012100342 | 8/2012 |
| WO | WO2012138938 | 10/2012 |
| WO | WO2012143510 | 10/2012 |
| WO | WO2012143796 | 10/2012 |
| WO | WO2012158785 | 11/2012 |
| WO | WO2012177997 | 12/2012 |
| WO | WO2012178124 | 12/2012 |
| WO | WO2013010136 | 1/2013 |
| WO | WO2013049720 | 4/2013 |
| WO | WO2013049726 | 4/2013 |
| WO | WO2013052263 | 4/2013 |
| WO | WO2013059587 | 4/2013 |
| WO | WO2013138436 | 10/2013 |
| WO | WO2013151930 | 10/2013 |
| WO | WO2013151938 | 10/2013 |
| WO | WO2013154878 | 10/2013 |
| WO | WO2013171470 | 11/2013 |
| WO | WO2013174930 | 11/2013 |
| WO | WO2013174931 | 11/2013 |
| WO | WO2014011911 | 1/2014 |
| WO | WO2014015523 | 1/2014 |
| WO | WO2014023691 | 2/2014 |
| WO | WO2014025850 | 2/2014 |
| WO | WO2014025852 | 2/2014 |
| WO | WO2014025854 | 2/2014 |
| WO | WO2014026984 | 2/2014 |
| WO | WO2014029723 | 2/2014 |
| WO | WO2014035140 | 3/2014 |
| WO | WO2014039831 | 3/2014 |
| WO | WO2014042433 | 3/2014 |
| WO | WO2014044691 | 3/2014 |
| WO | WO2014047648 | 3/2014 |
| WO | WO2014066435 | 5/2014 |
| WO | WO2014066552 | 5/2014 |
| WO | WO2014089379 | 6/2014 |

OTHER PUBLICATIONS

Ahmed et al., "Synthesis and anti-tumor activities of some new pyridines and pyrazolo[1,5-a]pyrimidines", European Journal of Medicinal Chemistry, vol. 44, No. 9, May 2009 (pp. 3519-3523).

Ahmed et al., "Synthesis of some Pyrazolopyrimidines as Purine Analogues", Journal of Heterocyclic Chemistry, vol. 44, No. 4, Jul.-Aug. 2007 (pp. 803-810).

Ammar et al., "3-Ethoxycarbonylmethylenequinoxalin-2-one in heterocyclic synthesis. Part 1: Synthesis of new substituted and condensed quinoxalines," Afinidad. 2005;62(516):151-60.

Banker et al., Modern Pharmaceuticals. 1996;596, 451.

Boylan et al., "Parenteral Products," Chapter 12, Modern Pharmaceuticals, Fourth Edition (1997) 34 pages.

Charrier et al., "Discovery of potent and selective inhibitors of ataxia telangiectasia mutated and Rad3 related (ATR) protein kinase as potential anticancer agents," J Med Chem. Apr. 14, 2011;54(7):2320-30. doi: 10.1021/jm101488z. Epub Mar. 17, 2011. E-pub version.

Charrier et al., "Discovery of Potent and Selective Inhibitors of ATR (Ataxia Telangiectasia Mutated and Rad3 Related) as Potential AntiCancer Agents," Supplementary Information, Apr. 14, 2011: 47 pages.

Charrier, "Discovery of potent and selective inhibitors of Ataxia Telangiectasia mutated and Rad3 related (ATR) protein kinase as potential anticancer agents," Presentation, ACS Denver 2011. Aug. 28, 2011.21 pages.

Chawla et al., "Challenges in Polymorphism of Pharmaceuticals," CRIPS. 2004;5(1):9-12.

Clark et al., "Mass spectrometry of pyrrolo [2, 3-b] pyrazines and pyrazino [2, 3-b]indole," Organic Mass Spectrometry. 1977;12(7):421-3.

Curtin, "Inhibiting the DNA damage response as a therapeutic manoeuvre in cancer," Br J Pharmacol. Aug. 2013;169(8):1745-65. doi: 10.1111/bph.12244.

El-Emary, "Synthesis and Biological Activity of Some New Pyrazolo [3,4-b]pyrazines," J Chinese Chem Soc (Taipei, Taiwan). 2006;53(2): 391-401.

Elnagdi et al., "Synthesis of Substituted Azaindenes: Synthesis of New Pyrazolo[1,5-a]pyrimidine Derivatives," Bull. Chem. Soc. Jpn., 63, 1854-1856 (1990).

Fernandes et al., "Synthesis and Biological Activity of Heterocyclic Derivatives derived from Ethyl-2-hydroxy-quinoxaline-3-carboxylate," J Indian Chem Soc. 1986;63(4):427-9.

Finlay et al., "Modulation of DNA repair by pharmacological inhibitors of the PIKK protein kinase family," Bioorg Med Chem Lett. Sep. 1, 2012;22(17):5352-9. doi: 10.1016/j.bmcl.2012.06.053. Epub Jul. 1, 2012.

Fokas et al., "Targeting ATR in DNA damage response and cancer therapeutics," Cancer Treat Rev (2013), http://dx.doi.org/10.1016/j.ctrv.2013.03.002.

Fokas et al., "Targeting ATR in vivo using the novel inhibitor VE-822 results in selective sensitization of pancreatic tumors to radiation," Cell Death Dis. Dec. 6, 2012;3:e441. doi: 10.1038/cddis. 2012.181.

(56) References Cited

OTHER PUBLICATIONS

Gentili et al., "Alpha2-adrenoreceptors profile modulation. 4. From antagonist to agonist behavior," J Med Chem. Jul. 24, 2008;51(14):4289-99. doi: 10.1021/jm800250z. Epub Jun. 25, 2008.
Hackam et al., "Translation of research evidence from animals to humans," JAMA, Oct. 11, 2006, 296(14), pp. 1731-1732.
Hall-Jackson et al., "ATR is a caffeine-sensitive, DNA-activated protein kinase with a substrate specificity distinct from DNA-PK," Oncogene. Nov. 18, 1999;18(48):6707-13.
Hickson et al., "Identification and characterization of a novel and specific inhibitor of the ataxia-telangiectasia mutated kinase ATM," Cancer Res. Dec. 15, 2004;64(24):9152-9.
Hilton et al., "Identification and characterisation of 2-aminopyridine inhibitors of checkpoint kinase 2," Bioorg Med Chem. Jan. 15, 2010;18(2):707-18. doi: 10.1016/j.bmc.2009.11.058. Epub Dec. 6, 2009.
Ho, "Studies on the Synthesis of New 3-(3,5-Diamino-1-substituted-pyrazol-4-yl)azo-thieno[2,3-b]pyridines and 3-(2Amino-5,7-disubstituted-pyrazolo[1,5-a]pyrimidine-3-yl)azo-thieno[2,3-b]pyridines," Journal of the Chinese Chemical Society, vol. 46, n. 6, Dec. 1999 (pp. 955-967).
Hubackova et al., "Regulation of the PML tumor suppressor in drug-induced senescence of human normal and cancer cells by JAK/STAT-mediated signaling," Cell Cycle. Aug. 1, 2010;9(15):3085-99. doi: 10.4161/cc.9.15.12521. Epub Aug. 26, 2010.
Huntoon et al., "ATR inhibition broadly sensitizes ovarian cancer cells to chemotherapy independent of BRCA status," Cancer Res. Jun. 15, 2013;73(12):3683-91. doi: 10.1158/0008-5472.CAN-13-0110. Epub Apr. 2, 2013.
Hussein, "Novel Synthesis of Some New Pyrinnido[1,6-a]pyrimidine and Pyrazolo[1,5-a]pyrirnidine Derivatives," J. Heterocyclic Chem., 49, 446, (2012).
International Search Report and Written Opinion dated Apr. 1, 2014 in connection with Application No. PCT/US2013/073468 (V0138.70036W000).
International Search Report and Written Opinion dated Feb. 6, 2014 in connection with Application No. PCT/US2013/073482 (V0138.70002W000).
International Search Report and Written Opinion dated Jan. 29, 2014 in connection with Application No. PCT/US2013/073457 (V0138.70013W000).
International Search Report and Written Opinion dated Jan. 29, 2015 in connection with Application No. PCT/US2014/068713 (V0138.70035W000).
International Search Report and Written Opinion dated Oct. 1, 2015 in connection with Application No. PCT/US2015/032879 (V0138.70011W000).
International Search Report and Written Opinion in connection with Application No. PCT/US2011/041705 dated Aug. 23, 2011 (V0138.70055W000).
International Search Report and Written Opinion in connection with Application No. PCT/US2012/043895 dated Aug. 28, 2012. (V0138.70007W000).
International Search Report and Written Opinion in connection with Application No. PCT/US2012/043896 dated Oct. 9, 2012. (V0138.70006W000).
International Search Report and Written Opinion in connection with Application No. PCT/US2012/043897 dated Jul. 20, 2012. (V0138.70005W000).
International Search Report and Written Opinion dated Feb. 17, 2014 in connection with Application No. PCT/US2013/073471 (V0138.70015W000).
International Search Report and Written Opinion dated Jan. 30, 2014 in connection with Application No. PCT/US2013/073477 (V0138.70014W000).
International Search Report and Written Opinion dated Sep. 24, 2015 in connection with Application No. PCT/US2015/036137 (V0138.70000W000).
International Search Report for PCT/US2005/040344 dated Mar. 20, 2006.
Jiang et al., "Synthesis and cytotoxicity evaluation of novel indolylpyrimidines and indolylpyrazines as potential antitumor agents," Bioorg Med Chem. May 2001;9(5):1149-54.
Jordan et al., "Tamoxifen: a most unlikely pioneering medicine," Nat Rev Drug Discov., Mar. 2003, 2(3), pp. 205-213.
Katritzky et al., "Efficient synthesis of 3,5-functionalized isoxazoles and isoxazolines via 1,3-dipolar cycloaddition reactions of 1-propargyl- and 1-allylbenzotriazoles," J Heterocyclic Chem. 2000;37(6):1505-10.
Kim et al., "Substrate specificities and identification of putative substrates of ATM kinase family members," J Biol Chem. Dec. 31, 1999;274(53):37538-43.
Klicnar et al., "Studien in der chinoxalinreihe III. Synthese, reaktionen and ir-spektren einiger 3-hydroxy-2-carboxymethylchinoxalin-derivate," Collection of Czechoslovak Chemical Communications. 1965;30(9):3092-101.
Kumpathy et al., "Synthesis of N-methyl secondary amines," Synth Commun. 2003;33(8):1411-6.
Kurasawa et al., "Revised Structure for the Product from the Reaction of 3-Hydrazinocarbonylmethylene-2-oxo-1,2,3,4-tetrahydroquinoxaline with Nitrous Acid," Chem. Pharm. Bull. 1984;32(10):4140-3.
Luo et al., "Molecular dynamics-based self-organizing molecular field analysis on 3-amino-6-arylpyrazines as the ataxia telangiectasia mutated and Rad3 related (ATR) protein kinase inhibitors," Med Chem Res. Published online: Jun. 19, 2013. 12 pages.
McKenna et al., "Evaluation of a potent and highly selective inhibitor of ATR kinase: an approach to selectively sensitize cancer cells to genotoxic drugs," Abstract. Mar. 31, 2012. 1page.
McKenna et al., "Evaluation of the first potent and highly selective inhibitor of ATR inhibitor, VE-821: an approach to selectively sensitize cancer cells to ionizing radiation and hypoxia," Poster. Mar. 31, 2012. 1 page.
Middleton et al., "ATR as a Therapeutic Target. In: Advances in DNA Repair in Cancer Therapy," Cancer Drug Discovery and Development. 2013;72:211-28.
Nakamura et al., "Bimodal Chemiluminescence of 8-Chlorostyryl-6-phenylethynylimidazopyrazinone: Large Bathochromic Shift Caused by a Styryl Group at 8-Position," Tetrahedron Letters, vol. 39, No. 3-4, Jan. 1998 (pp. 301-304).
Non-Final Office Action dated Jun. 27, 2014 in U.S. Appl. No. 14/098,640.
Non-Final Office Action dated Jun. 27, 2014 in U.S. Appl. No. 14/098,655.
Otero et al., "Syntheses of Acyclo-C-nucleoside Analogs from 2,3:4,5-Di-Oisopropylidene-Di-O-isopropylidene-D-xylose," Journal of Carbohydrate Chemistry, 24:809-829, 2005.
Otero et al., "Synthesis of Iso-C-nucleoside Analogues from 1-(Methyl 2-0-benzyl]-4,6-0-benzylidene-3-deoxy-a-D-altropyranosid-3-yl)but-3-yn-2-ones," Z. Naturforsch. 60b, 1175-1185 (2005).
Pires et al., "Targeting radiation-resistant hypoxic tumour cells through ATR inhibition," British Journal of Cancer, vol. 107, No. 2, Jul. 2012 (pp. 291-299)
Pollard, "Inhibition of the DNA Damage Response Kinase, ATR, as a Promising Anti-Cancer Approach," Presentation, Mar. 8, 2012 (28 pages).
Qi et al., "Chemi- and Bio-Iuminescence of Coelenterazine Analogues with Phenyl Homologues at the C-2 Position," Journal of the Chemical Society, Perkins Transactions 1, vol. 13, No Month Listed 1992 (pp. 1601-1611).
Ram et al., "Synthesis of bioisosteric pyrazolo[1,5-a]pyrimidines as leishmanicides," Indian Journal of Chemistry, vol. 34B, Jun. 1995 (pp. 514-520).
Reaper et al., "Evaluation of a potent and highly selective inhibitor of ATR kinase: an approach to selectively sensitize cancer cells to genotoxic drugs," 102nd AACR Annual Meeting. Orlando, 2011. Abstract.
Reaper et al., "Evaluation of a Potent and Highly Selective Inhibitor of ATR Kinase: An Approach to Selectively Sensitize Cancer Cells to Genotoxic Drugs," 102nd AACR Annual Meeting. Orlando, 2011. Poster.

(56) References Cited

OTHER PUBLICATIONS

Reaper et al., "Selective killing of ATM- or p53-deficient cancer cells through inhibition of ATR," Nat Chem Biol. Apr. 13, 2011;7(7):428-30. doi: 10.1038/nchembio.573. Advance online publication.
Reaper et al., "Selective Killing of ATM- or p53-deficient cancer cells through inhibition of ATR," Presentation, Nov. 21, 2011.
Reaper et al., "Selective Killing of ATM- or p53-deficient cancer cells through inhibition of ATR," Presentation, Nov. 29, 2011.
Reaper et al., "Selective killing of ATM- or p53-deficient cancer cells through inhibition of ATR," Supplementary Information, Nature Chemical Biology, Apr. 13, 2011. doi:10.1038/nchembio.573. (26 pages).
Ried "Synthese neuer Heterocyclen ausgehend von Aminopyrazolen", Chemiker-Zeitung, 113. Jahrgang (1989) Nr. 5.
Saito et al., "Synthesis and in vitro evaluation of botryllazine B analogues as a new class of inhibitor against human aldose reductase," Tetrahedron, vol. 65, No. 15, Apr. 2009 (pp. 3019-3026).
Sarkaria et al., "Inhibition of ATM and ATR kinase activities by the radiosensitizing agent, caffeine," Cancer Research, vol. 59, No. 17, Sep. 1999 (pp. 4375-4382).
Sevilla et al., "Microwave-assisted synthesis of 1,3-dihydro-[1,2,5]thiadiazolo[3,4-b]pyrazine-2,2-dioxides," Tetrahedron Letters, vol. 47, No. 48, Nov. 2006 (pp. 8603-8606).
Smith et al., "Addition to Carbon—Hetero Multiple Bonds," Chapter 16. In: March's Advanced Organic Chemistry: Reactions, Mechanisms, and Structure, Sixth Edition. John Wiley & Sons, Inc. 2007 (26 pages).
Sugimoto et al., "Imidazopteridines. I. Synthesis of Imidazo[1,2-c]pteridine and Its Alkyl Derivatives," Bulletin of the Chemical Society of Japan, vol. 50, No. 10, No Month Listed 1977 (pp. 2744-2747).
U.S. Appl. No. 15/693,521 of Falcon et al., filed Sep. 1, 2017.
U.S. Appl. No. 15/763,366 of Pollard et al., filed Mar. 26, 2018.
U.S. Appl. No. 15/849,241 of Charrier et al., filed Dec. 20, 2017.
U.S. Appl. No. 15/967,110 of Charrier et al., filed Apr. 30, 2018.
Vippagunta et al., "Crystalline solids," Advanced Drug Delivery Reviews, vol. 48, No. 1, May 2001 (pp. 3-26).
Ward et al., "Histone H2AX is phosphorylated in an ATR-dependent manner in response to replicational stress," Journal of Biological Chemistry, vol. 276, No. 51, Dec. 2001 (pp. 47759-47762).
Wolff, Burger's Medicinal Chemistry and Drug Discovery. Fifth Edition. Volume I: Principles and Practice. 1995 (pp. 975-977).
Wuts et al., "Protection for the Amino Group," Chapter 7. In: Greene's Protective Groups in Organic Synthesis, 4th Edition. John Wiley & Sons, Inc. No Month Listed 2007 (235 pages).
Wuts et al., "Protection for the Carbonyl Group," Chapter 4. In: Greene's Protective Groups in Organic Synthesis, 4th Edition. John Wiley & Sons, Inc. No Month Listed 2007 (106 pages).

COMPOUNDS USEFUL AS INHIBITORS OF ATR KINASE

CROSS-REFERENCE TO RELATED APPLICATIONS

This application is a continuation of U.S. application Ser. No. 15/633,477, filed Jun. 26, 2017, which is a continuation of U.S. application Ser. No. 15/142,338, filed Apr. 29, 2016, issued as U.S. Pat. No. 9,718,827, which is a divisional of U.S. application Ser. No. 14/098,606, filed Dec. 6, 2013, and issued as U.S. Pat. No. 9,340,546, which claims the benefit under 35 U.S.C. § 119(e) of U.S. Provisional Application No. 61/734,726, filed Dec. 7, 2012; U.S. Provisional Application No. 61/787,568, filed Mar. 15, 2013; and U.S. Provisional Application No. 61/868,132, filed Aug. 21, 2013, each of which is incorporated herein by reference in its entirety.

SEQUENCE LISTING

The instant application contains a Sequence Listing in .txt format which has been submitted via EFS-Web and is hereby incorporated by reference in its entirety. The Sequence Listing, created on Jun. 2, 2014 is named VPI121142US.txt and is 1148 bytes in size.

BACKGROUND OF THE INVENTION

ATR ("ATM and Rad3 related") kinase is a protein kinase involved in cellular responses to certain forms of DNA damage (e.g., double strand breaks and replication stress). ATR kinase acts with ATM ("ataxia telangiectasia mutated") kinase and many other proteins to regulate a cell's response to double strand DNA breaks and replication stress, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinases ATR and ATM. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

ATR peptide can be expressed and isolated using a variety of methods known in the literature (see e.g., Ünsal-Kaçaz et al, PNAS 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

For all of these reasons, there is a need for the development of potent and selective ATR inhibitors for the treatment of cancer, either as single agents or as combination therapies with radiotherapy or genotoxic chemotherapy.

SUMMARY OF THE INVENTION

The present invention relates to compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of the invention are very potent ATR inhibitors. These compounds also show surprising synergy with other cancer agents, such as cisplatin and gemcitabine, in combination therapies.

DETAILED DESCRIPTION OF THE INVENTION

One aspect of the invention provides a compound of Formula I:

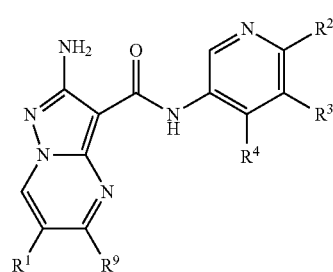

or a pharmaceutically acceptable salt or prodrug thereof, wherein:

$R^1$ is independently selected from —C(J$^1$)$_2$CN, halo, -(L)$_k$-W, or M;

$R^9$ is independently selected from H, —C(J$^1$)$_2$CN, halo, -(L)$_k$-W, or M;

$J^1$ is independently selected from H or $C_{1-2}$alkyl; or two occurrences of $J^1$, together with the carbon atom to which they are attached, form a 3-4 membered optionally substituted carbocyclic ring;

k is 0 or 1;

M and L are a $C_{1-8}$aliphatic wherein up to three methylene units are optionally replaced with —O—, —NR—, —C(O)—, or —S(O)$_n$—, each M and L$^1$ is optionally substituted with 0-3 occurrences of J$^{LM}$;

J$^{LM}$ is independently selected from halo, —CN, or a C$_{1-4}$aliphatic chain wherein up to two methylene units of the aliphatic chain are optionally replaced with —O—, —NR—, —C(O)—, or —S(O)$_n$—;

W is independently selected from a 3-7 membered fully saturated, partially unsaturated, or aromatic monocyclic ring having 0-3 heteroatoms selected from oxygen, nitrogen or sulfur; or a 7-12 membered fully saturated, partially unsaturated, or aromatic bicyclic ring having 0-5 heteroatoms selected from oxygen, nitrogen, or sulfur; wherein W is optionally substituted with 0-5 occurrences of J$^W$;

J$^W$ is independently selected from —CN, halo, —CF$_3$; a C$_{1-4}$aliphatic wherein up to two methylene units are optionally replaced with —O—, —NR—, —C(O)—, or —S(O)$_n$—; or a 3-6 membered non-aromatic ring having 0-2 heteroatoms selected from oxygen, nitrogen, or sulfur; two occurrences of J$^W$ on the same atom, together with atom to which they are joined, form a 3-6 membered ring having 0-2 heteroatoms selected from oxygen, nitrogen, or sulfur; or two occurrences of J$^W$, together with W, form a 6-10 membered saturated or partially unsaturated bridged ring system;

R$^2$ is independently selected from H; halo; —CN; NH$_2$; a C$_{1-2}$alkyl optionally substituted with 0-3 occurrences of fluoro; or a C$_{1-3}$ aliphatic chain wherein up to two methylene units of the aliphatic chain are optionally replaced with —O—, —NR—, —C(O)—, or —S(O)$_n$;

R$^3$ is independently selected from H; halo; C$_{1-4}$alkyl optionally substituted with 1-3 occurrences of halo; C$_{3-4}$cycloalkyl; 3-4 membered heterocyclyl; —CN; or a C$_{1-3}$ aliphatic chain wherein up to two methylene units of the aliphatic chain are optionally replaced with —O—, —NR—, —C(O)—, or —S(O)$_n$;

R$^4$ is independently selected from Q$^1$ or a C$_{1-10}$aliphatic chain wherein up to four methylene units of the aliphatic chain are optionally replaced with —O—, —NR—, —C(O)—, or —S(O)$_n$—; each R$^4$ is optionally substituted with 0-5 occurrences of J$^Q$; or R$^3$ and R$^4$, taken together with the atoms to which they are bound, form a 5-6 membered aromatic or non-aromatic ring having 0-2 heteroatoms selected from oxygen, nitrogen or sulfur; the ring formed by R$^3$ and R$^4$ is optionally substituted with 0-3 occurrences of J$^Z$;

Q$^1$ is independently selected from a 3-7 membered fully saturated, partially unsaturated, or aromatic monocyclic ring, the 3-7 membered ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;

J$^Z$ is independently selected from C$_{1-6}$aliphatic, =O, halo, or →O;

J$^Q$ is independently selected from —CN; halo; =O; Q$^2$; or a C$_{1-8}$aliphatic chain wherein up to three methylene units of the aliphatic chain are optionally replaced with —O—, —NR—, —C(O)—, or —S(O)$_n$—; each occurrence of J$^Q$ is optionally substituted by 0-3 occurrences of J$^R$; or two occurrences of J$^Q$ on the same atom, taken together with the atom to which they are joined, form a 3-6 membered ring having 0-2 heteroatoms selected from oxygen, nitrogen, or sulfur; wherein the ring formed by two occurrences of J$^Q$ is optionally substituted with 0-3 occurrences of J$^X$; or two occurrences of J$^Q$, together with Q$^1$, form a 6-10 membered saturated or partially unsaturated bridged ring system;

Q$^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

J$^R$ is independently selected from —CN; halo; =O; →O; Q$^3$; or a C$_{1-6}$ aliphatic chain wherein up to three methylene units of the aliphatic chain are optionally replaced with —O—, —NR—, —C(O)—, or —S(O)$_n$—; each J$^R$ is optionally substituted with 0-3 occurrences of J$^T$; or two occurrences of J$^R$ on the same atom, together with the atom to which they are joined, form a 3-6 membered ring having 0-2 heteroatoms selected from oxygen, nitrogen, or sulfur; wherein the ring formed by two occurrences of J$^R$ is optionally substituted with 0-3 occurrences of J$^X$; or two occurrences of J$^R$, together with Q$^2$, form a 6-10 membered saturated or partially unsaturated bridged ring system;

Q$^3$ is a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

J$^X$ is independently selected from —CN; =O; halo; or a C$_{1-4}$aliphatic chain wherein up to two methylene units of the aliphatic chain are optionally replaced with —O—, —NR—, —C(O)—, or —S(O)$_n$—;

J$^T$ is independently selected from halo, —CN; →O; =O; —OH; a C$_{1-6}$ aliphatic chain wherein up to two methylene units of the aliphatic chain are optionally replaced with —O—, —NR—, —C(O)—, or —S(O)$_n$—; or a 3-6 membered non-aromatic ring having 0-2 heteroatoms selected from oxygen, nitrogen, or sulfur; each occurrence of J$^T$ is optionally substituted with 0-3 occurrences of J$^M$; or two occurrences of J$^T$ on the same atom, together with the atom to which they are joined, form a 3-6 membered ring having 0-2 heteroatoms selected from oxygen, nitrogen, or sulfur; or two occurrences of J$^T$, together with Q$^3$, form a 6-10 membered saturated or partially unsaturated bridged ring system;

J$^M$ is independently selected from halo or C$_{1-6}$aliphatic;

n is 0, 1 or 2; and

R is independently selected from H or C$_{1-4}$aliphatic.

In another embodiment, the present invention is a compound of formula I, wherein R$^9$ is H.

In one or more aspects, the present invention is a compound of formula I, wherein R$^9$ is M. In another aspect, the present invention is a compound of formula I, wherein M is a C$_{1-8}$aliphatic wherein up to three methylene units are optionally replaced with —O— or —NR—. In some aspects, the present invention is a compound of formula I, wherein M is C$_{1-4}$alkyl, —(C$_{1-4}$alkyl)O(C$_{1-3}$aliphatic), —(C$_{1-3}$alkyl)OH, —O(C$_{1-4}$alkyl)N(C$_{1-2}$alkyl)$_2$, —NH(C$_{1-4}$alkyl), or —(C$_{1-4}$alkyl)NH(C$_{1-4}$alkyl). In yet another aspect, the present invention is a compound of formula I, wherein M is C$_{1-4}$alkyl.

In one or more embodiments, the present invention is a compound of formula I, wherein J$^{LM}$ is halo.

In some embodiments, the present invention is a compound of formula I, wherein R$^9$ is -(L)$_k$-W.

In another example, the present invention is a compound of formula I, wherein k is 1. In other examples, the present invention is a compound of formula I, wherein k is 0.

In one or more aspects, the present invention is a compound of formula I, wherein L is a $C_{1-8}$aliphatic wherein up to three methylene units are optionally replaced with —O— or —NR—. In other aspects of the invention, the present invention is a compound of formula I, wherein L is —O—, —O(C1-4aliphatic)-, or —NR($C_{1-3}$ alkyl)-.

In one or more embodiments, the present invention is a compound of formula I, wherein W is a 3-7 membered fully saturated, partially unsaturated, or aromatic monocyclic ring having 0-3 heteroatoms selected from oxygen, nitrogen or sulfur. In some embodiments, the present invention is a compound of formula I, wherein W is a 3-7 membered heterocyclyl. In another embodiment, the present invention is a compound of formula I, wherein W is independently selected from pyrrolidinyl, piperidinyl, piperazinyl, oxetanyl, or azetidinyl.

In other embodiments, the present invention is a compound of formula I, wherein W is a 7-12 membered fully saturated, partially unsaturated, or aromatic bicyclic ring having 0-5 heteroatoms selected from oxygen, nitrogen, or sulfur. In yet another embodiment, the present invention is a compound of formula I, wherein W is octahydropyrrolo[1,2-a]pyrazine.

In some aspects, the present invention is a compound of formula I, wherein $J^W$ is selected form $C_{1-3}$ alkyl or $CF_3$. In other aspects, the present invention is a compound of formula I, wherein two occurrences of $J^W$ on the same atom, together with atom to which they are joined, form a 3-6 membered ring having 0-2 heteroatoms selected from oxygen, nitrogen, or sulfur. In yet another aspect, the present invention is a compound of formula I, wherein the ring formed by the two occurrences of $J^W$ on the same atom is oxetanyl.

Another aspect of the invention provides a compound of Formula I-A:

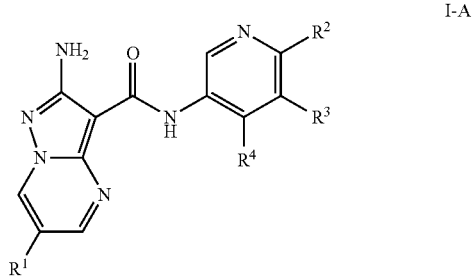

I-A or a pharmaceutically acceptable salt or prodrug thereof, wherein:
$R^1$ is independently selected from fluoro, chloro, or —C($J^1$)$_2$CN;
$J^1$ is independently selected from H or $C_{1-2}$alkyl; or
two occurrences of $J^1$, together with the carbon atom to which they are attached, form a 3-4 membered optionally substituted carbocyclic ring;
$R^2$ is independently selected from H; halo; —CN; $NH_2$; a $C_{1-2}$alkyl optionally substituted with 0-3 occurrences of fluoro; or a $C_{1-3}$ aliphatic chain wherein up to two methylene units of the aliphatic chain are optionally replaced with —O—, —NR—, —C(O)—, or —S(O)$_n$;
$R^3$ is independently selected from H; halo; $C_{1-4}$alkyl optionally substituted with 1-3 occurrences of halo; $C_{3-4}$cycloalkyl; —CN; or a $C_{1-3}$ aliphatic chain wherein up to two methylene units of the aliphatic chain are optionally replaced with —O—, —NR—, —C(O)—, or —S(O)$_n$;

$R^4$ is independently selected from $Q^1$ or a $C_{1-10}$aliphatic chain wherein up to four methylene units of the aliphatic chain are optionally replaced with —O—, —NR—, —C(O)—, or —S(O)$_n$—; each $R^4$ is optionally substituted with 0-5 occurrences of $J^Q$; or $R^3$ and $R^4$, taken together with the atoms to which they are bound, form a 5-6 membered aromatic or non-aromatic ring having 0-2 heteroatoms selected from oxygen, nitrogen or sulfur; the ring formed by $R^3$ and $R^4$ is optionally substituted with 0-3 occurrences of $J^Z$;

$Q^1$ is independently selected from a 3-7 membered fully saturated, partially unsaturated, or aromatic monocyclic ring, the 3-7 membered ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;

$J^Z$ is independently selected from $C_{1-6}$aliphatic, =O, halo, or →O;

$J^Q$ is independently selected from —CN; halo; =O; $Q^2$; or a $C_{1-8}$aliphatic chain wherein up to three methylene units of the aliphatic chain are optionally replaced with —O—, —NR—, —C(O)—, or —S(O)$_n$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^R$ is independently selected from —CN; halo; =O; →O; $Q^3$; or a $C_{1-6}$aliphatic chain wherein up to three methylene units of the aliphatic chain are optionally replaced with —O—, —NR—, —C(O)—, or —S(O)$_n$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^X$ is independently selected from —CN; =O; halo; or a $C_{1-4}$aliphatic chain wherein up to two methylene units of the aliphatic chain are optionally replaced with —O—, —NR—, —C(O)—, or —S(O)$_n$—;

$J^T$ is independently selected from halo, —CN; →O; =O; —OH; a $C_{1-6}$ aliphatic chain wherein up to two methylene units of the aliphatic chain are optionally replaced with —O—, —NR—, —C(O)—, or —S(O)$_n$—; or a 3-6 membered non-aromatic ring having 0-2 heteroatoms selected from oxygen, nitrogen, or sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from oxygen, nitrogen, or sulfur; or two occurrences of $J^T$, together with $Q^3$, form a 6-10 membered saturated or partially unsaturated bridged ring system;

$J^M$ is independently selected from halo or $C_{1-6}$ aliphatic;

n is 0, 1 or 2; and

R is independently selected from H or $C_{1-4}$ aliphatic.

Another aspect of the invention provides a compound of Formula I-A:

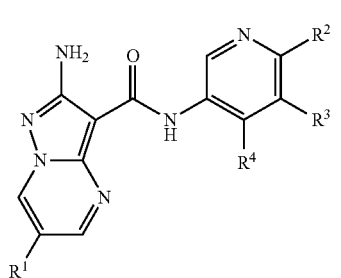

I-A or a pharmaceutically acceptable salt or prodrug thereof, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form a 3-4 membered optionally substituted carbocyclic ring;

$R^2$ is independently selected from H; halo; —CN; NH$_2$; a $C_{1-2}$alkyl optionally substituted with 0-3 occurrences of fluoro; or a $C_{1-3}$ aliphatic chain wherein up to two methylene units of the aliphatic chain are optionally replaced with —O—, —NR—, —C(O)—, or —S(O)$_n$;

$R^3$ is independently selected from H; halo; $C_{1-4}$ alkyl optionally substituted with 1-3 occurrences of halo; $C_{3-4}$ cycloalkyl; —CN; or a $C_{1-3}$ aliphatic chain wherein up to two methylene units of the aliphatic chain are optionally replaced with —O—, —NR—, —C(O)—, or —S(O)$_n$;

$R^4$ is independently selected from $Q^1$ or a $C_{1-10}$aliphatic chain wherein up to four methylene units of the aliphatic chain are optionally replaced with —O—, —NR—, —C(O)—, or —S(O)$_n$—; each $R^4$ is optionally substituted with 0-5 occurrences of $J^Q$; or $R^3$ and $R^4$, taken together with the atoms to which they are bound, form a 5-6 membered non-aromatic ring having 0-2 heteroatoms selected from oxygen, nitrogen or sulfur; the ring formed by $R^3$ and $R^4$ is optionally substituted with 0-3 occurrences of $J^Z$;

$Q^1$ is independently selected from a 3-7 membered fully saturated, partially unsaturated, or aromatic monocyclic ring, the 3-7 membered ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;

$J^Z$ is independently selected from $C_{1-6}$aliphatic, =O, halo, or →O;

$J^Q$ is independently selected from —CN; halo; =O; $Q^2$; or a $C_{1-8}$aliphatic chain wherein up to three methylene units of the aliphatic chain are optionally replaced with —O—, —NR—, —C(O)—, or —S(O)$_n$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^R$ is independently selected from —CN; halo; =O; →O; $Q^3$; or a $C_{1-6}$ aliphatic chain wherein up to three methylene units of the aliphatic chain are optionally replaced with —O—, —NR—, —C(O)—, or —S(O)$_n$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of 0.0; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^X$ is independently selected from —CN; halo; or a $C_{1-4}$ aliphatic chain wherein up to two methylene units of the aliphatic chain are optionally replaced with —O—, —NR—, —C(O)—, or —S(O)$_n$—;

$J^T$ is independently selected from —CN; =O; —OH; a $C_{1-6}$aliphatic chain wherein up to two methylene units of the aliphatic chain are optionally replaced with —O—, —NR—, —C(O)—, or —S(O)$_n$—; or a 3-6 membered non-aromatic ring having 0-2 heteroatoms selected from oxygen, nitrogen, or sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from oxygen, nitrogen, or sulfur; or two occurrences of $J^T$, together with $Q^3$, form a 6-10 membered saturated or partially unsaturated bridged ring system;

$J^M$ is independently selected from halo or $C_{1-6}$ aliphatic;

n is 0, 1 or 2; and

R is independently selected from H or $C_{1-4}$ aliphatic.

Another aspect of the invention provides a compound of formula I-A:

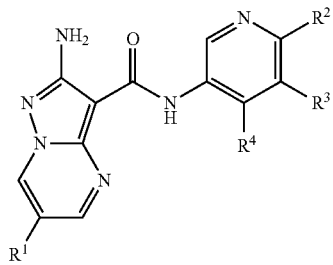

I-A or a pharmaceutically acceptable salt or prodrug thereof, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form an optionally substituted 3-4 membered carbocyclic ring;

$R^2$ is independently selected from H; chloro; NH$_2$; or a $C_{1-2}$alkyl optionally substituted with fluoro;

$R^3$ is independently selected from H; chloro; fluoro; $C_{1-4}$alkyl optionally substituted with 1-3 occurrences of halo; $C_{3-4}$cycloalkyl; or —CN;

$R^4$ is independently selected from $Q^1$ or a $C_{1-10}$aliphatic chain wherein up to three methylene units of the aliphatic chain are optionally replaced with —O—, —NR—, or —S—; each $R^4$ is optionally substituted with 0-5 occurrences of $J^Q$; or $R^3$ and $R^4$, taken together with the atoms to which they are bound, form a 5-6 membered non-aromatic ring having 0-2 heteroatoms selected from oxygen, nitrogen or sulfur; the ring formed by $R^3$ and $R^4$ is optionally substituted with 0-3 occurrences of $J^Z$;

$Q^1$ is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring; having 0-5 heteroatoms selected from oxygen, nitrogen, or sulfur;

$J^Z$ is independently selected from $C_{1-6}$ aliphatic, =O, halo, or →O;

$J^Q$ is independently selected from halo; =O; $Q^2$; or a $C_{1-8}$aliphatic chain wherein up to two methylene units of the aliphatic chain are optionally replaced with —O—, —NR—, —S—, —C(O)—, or —S(O)$_n$—; each occurrence of $J^Q$ is optionally substituted by 0-3 occurrences of $J^R$; or two occurrences of $J^Q$ on the same atom, taken together with the atom to which they are joined, form a 3-6 membered ring having 0-2 heteroatoms selected from oxygen, nitrogen, or sulfur; wherein the ring formed by two occurrences of $J^Q$ is optionally substituted with 0-3 occurrences of $J^X$; or two occurrences of $J^Q$, together with $Q^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 8-12 membered fully saturated, partially unsaturated, or aromatic bicyclic ring having 0-5 heteroatoms selected from oxygen, nitrogen, or sulfur;

$J^R$ is independently selected from halo; =O; →O; a 3-7 membered fully saturated, partially unsaturated, or aromatic monocyclic ring having 0-3 heteroatoms selected from oxygen, nitrogen, or sulfur; or a $C_{1-4}$ aliphatic chain wherein up to two methylene units of the aliphatic chain are optionally replaced with —O—, —NR—, —S—, —C(O)—, or —S(O)$_n$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$J^X$ is independently selected from halo or a $C_{1-4}$aliphatic chain wherein up to two methylene units of the aliphatic chain are optionally replaced with —O—, —NR—, —S—, —C(O)—, or —S(O)$_n$—; or $J^T$ is independently selected from a $C_{1-6}$aliphatic or a 3-6 membered non-aromatic ring having 0-2 heteroatoms selected from oxygen, nitrogen, or sulfur; each occurrence of $J^T$ is optionally substituted with 0-3 occurrences of $J^M$;

$J^M$ is independently selected from halo or $C_{1-6}$aliphatic;

n is 1 or 2; and

R is independently selected from H or $C_{1-4}$aliphatic.

In some embodiments, the present invention is a compound represented by structural formula I or I-A, wherein $R^1$ is fluoro. In another embodiment, the present invention is a compound represented by structural formula I or I-A, wherein $R^1$ is —CH$_2$CN. In another embodiment $R^1$ is —CH(C$_{1-2}$alkyl)CN. In another embodiment, the present invention is a compound represented by structural formula I or I-A, wherein $R^1$ is C(CH$_3$)$_2$CN. In yet another embodiment, the present invention is a compound represented by structural formula I or I-A, wherein $R^1$ is chloro.

In one example, the present invention is a compound represented by structural formula I or I-A, wherein $R^2$ is independently selected from —CF$_3$, —NH(C$_{1-2}$alkyl), chloro, or H. In another example, the present invention is a compound represented by structural formula I or I-A, wherein $R^2$ is H. In other examples, the present invention is a compound represented by structural formula I or I-A, wherein $R^2$ is -chloro.

In yet another embodiment, the present invention is a compound represented by structural formula I or I-A, wherein $R^3$ is independently selected from H, chloro, fluoro, CHF$_2$, —CN, cyclopropyl, or $C_{1-4}$alkyl. In some embodiments, the present invention is a compound represented by structural formula I or I-A, wherein $R^3$ is independently selected from H, chloro, or fluoro. In another embodiment, the present invention is a compound represented by structural formula I or I-A, wherein $R^3$ is H. In another embodiment, the present invention is a compound represented by structural formula I or I-A, wherein $R^3$ is —O(C$_{1-2}$alkyl). In other embodiments, the present invention is a compound represented by structural formula I or I-A, wherein $R^3$ is chloro. In yet another embodiment, the present invention is a compound represented by structural formula I or I-A, wherein $R^3$ is fluoro.

In some embodiments, the present invention is a compound represented by structural formula I or I-A, wherein $R^4$ is independently selected from:

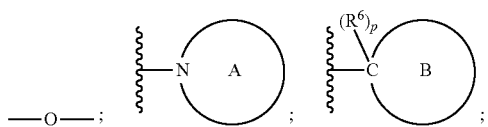

or —CH$_2$—R$^7$, wherein:
—O— is substituted with one J$^Q$;
Ring A is independently selected from a 3-7 membered fully saturated, partially unsaturated, or aromatic monocyclic ring having 1-3 heteroatoms selected from oxygen, nitrogen or sulfur; or an 7-12 membered fully saturated, partially unsaturated, or aromatic bicyclic ring having 1-5 heteroatoms selected from oxygen, nitrogen, or sulfur;
Ring B is independently selected from a 3-7 membered fully saturated, partially unsaturated, or aromatic monocyclic ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;
R$^6$ is H;
R$^7$ is independently selected from H or a C$_{1-8}$aliphatic chain wherein up to three methylene units of the aliphatic chain are optionally replaced with —O—, —NR—, —S—, —C(O)—, or —S(O)$_n$—; and
p is 0 or 1.

In one example, the present invention is a compound represented by structural formula I or I-A, wherein R$^4$ is —O—. In some examples, the present invention is a compound represented by structural formula I or I-A, wherein when R$^4$ is —O—, J$^Q$ is independently selected from —(C$_{1-4}$alkyl), —(C$_{1-4}$alkyl)N(C$_{1-4}$alkyl)$_2$, —(C$_{1-3}$ alkyl)O (C$_{1-2}$ alkyl)N(C$_{1-3}$alkyl)$_2$, (C$_{1-4}$ alkyl)OH, —(C$_{1-4}$ alkyl)NH$_2$, or —(C$_{1-4}$alkyl)O(C$_{1-4}$ alkyl).

In another example, the present invention is a compound represented by structural formula I or I-A, wherein when R$^4$ is —O—, J$^Q$ is Q$^2$. In yet another example, the present invention is a compound represented by structural formula I or I-A, wherein when R$^4$ is —O—, Q$^2$ is a 3-7 membered fully saturated, partially unsaturated, or aromatic monocyclic ring having 0-3 heteroatoms selected from oxygen, sulfur, or nitrogen.

In other embodiments, the present invention is a compound represented by structural formula I or I-A, wherein when R$^4$ is —O—, Q$^2$ is independently selected from a 5-6 membered aryl, a 5-6 membered heteroaryl, a 4-6 membered cycloaliphatic, or a 4-7 membered heterocyclyl. In yet another embodiment, the present invention is a compound represented by structural formula I or I-A, wherein when R$^4$ is —O—, Q$^2$ is a 4-7 membered heterocyclyl. In yet another embodiment, the present invention is a compound represented by structural formula I or I-A, wherein when R$^4$ is —O—, Q$^2$ is independently selected from pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, tetrahydrothiopyranyl, tetrahydrofuranyl, tetrahydropyranyl, azetidinyl, and oxetanyl. In some embodiments, the present invention is a compound represented by structural formula I or I-A, wherein when R$^4$ is —O—, Q$^2$ is independently selected from tetrahydrothiopyranyl, pyrrolidinyl, piperidinyl, piperazinyl, tetrahydrofuranyl, tetrahydropyranyl, or azetidinyl. In other embodiments, the present invention is a compound represented by structural formula I or I-A, wherein when R$^4$ is —O—, Q$^2$ is piperidinyl.

In another embodiment, the present invention is a compound represented by structural formula I or I-A, wherein when R$^4$ is —O—, Q$^2$ is a 5-6 membered heteroaryl. In some embodiments, the present invention is a compound represented by structural formula I or I-A, wherein when R$^4$ is —O—, Q$^2$ is independently selected from imidazolyl, pyrrolyl, pyridinyl, pyrazinyl, pyrimidinyl, pyrazolyl, 1,2,3-triazolyl, or 1,2,4-triazolyl. In yet another embodiment, the present invention is a compound represented by structural formula I or I-A, wherein when R$^4$ is —O—, Q$^2$ is pyridinyl.

In another example, the present invention is a compound represented by structural formula I or I-A, wherein when R$^4$ is —O—, Q$^2$ is a 4-6 membered cycloaliphatic. In yet another example, the present invention is a compound represented by structural formula I or I-A, wherein when R$^4$ is —O—, Q$^2$ is independently selected from cyclobutyl or cyclohexyl. In other examples, the present invention is a compound represented by structural formula I or I-A, wherein when R$^4$ is —O—, Q$^2$ is phenyl.

In some embodiments, the present invention is a compound represented by structural formula I or I-A, wherein when R$^4$ is —O—, Q$^2$ is an 8-12 membered fully saturated, partially unsaturated, or aromatic bicyclic ring having 0-5 heteroatoms selected from oxygen, nitrogen, or sulfur. In some embodiments, the present invention is a compound represented by structural formula I or I-A, wherein when R$^4$ is —O—, Q$^2$ is a 7-12 membered fully saturated, partially unsaturated, or aromatic bicyclic ring having 0-5 heteroatoms selected from oxygen, nitrogen, or sulfur. In another embodiment, the present invention is a compound represented by structural formula I or I-A, wherein when R$^4$ is —O—, Q$^2$ is 6,7-dihydro-5H-pyrrolo[1,2-a]imidazole.

In another embodiment, the present invention is a compound represented by structural formula I or I-A, wherein when R$^4$ is —O—, J$^R$ is a C$_{1-6}$ aliphatic chain wherein up to two methylene units of the aliphatic chain are optionally replaced with —O—, —NR—, —S—, —C(O)—, or —S(O)$_n$—. In other embodiments, the present invention is a compound represented by structural formula I or I-A, wherein when R$^4$ is —O—, J$^R$ is independently selected from C$_{1-4}$alkyl, —N(C$_{1-4}$alkyl)$_2$, —C(O)OH, —C(O)O(C$_{1-4}$alkyl), —C(O)N(C$_{1-4}$alkyl)$_2$, —(C$_{1-4}$alkyl)O(C$_{1-4}$alkyl), or —C(O)—. In still other embodiments, the present invention is a compound represented by structural formula I or I-A, wherein when R$^4$ is —O—, J$^R$ is C$_{1-4}$alkyl.

In some embodiments, the present invention is a compound represented by structural formula I or I-A, wherein when R$^4$ is —O—, J$^R$ is a 3-6 membered fully saturated, partially unsaturated, or aromatic monocyclic ring having 0-3 heteroatoms selected from oxygen, sulfur, or nitrogen. In yet another embodiment, the present invention is a compound represented by structural formula I or I-A, wherein when R$^4$ is —O—, J$^R$ is a 3-6 membered heterocyclyl having 1-3 heteroatoms selected from oxygen, nitrogen, or sulfur. In another embodiment, the present invention is a compound represented by structural formula I or I-A, wherein when R$^4$ is —O—, J$^R$ is independently selected from oxetanyl, piperidinyl, azetidinyl, piperazinyl, pyrrolidinyl, morpholinyl. In other embodiments, the present invention is a compound represented by structural formula I or I-A, wherein when R$^4$ is —O—, J$^R$ is oxetanyl. In still other embodiments, the present invention is a compound represented by structural formula I or I-A, wherein when R$^4$ is —O—, J$^R$ is cyclopropyl.

In some embodiments, the present invention is a compound represented by structural formula I or I-A, wherein when $R^4$ is —O—, $J^R$ is $Q^3$. In another embodiment, the present invention is a compound represented by structural formula I or I-A, wherein $Q^3$ is a 3-6 membered fully saturated, partially unsaturated, or aromatic monocyclic ring having 0-3 heteroatoms selected from oxygen, sulfur, or nitrogen. In yet another embodiment, the present invention is a compound represented by structural formula I or I-A, wherein when $R^4$ is —O—, $Q^3$ is a 3-6 membered heterocyclyl having 1-3 heteroatoms selected from oxygen, nitrogen, or sulfur. In another embodiment, the present invention is a compound represented by structural formula I or I-A, wherein when $R^4$ is —O—, $Q^3$ is independently selected from oxetanyl, piperidinyl, azetidinyl, piperazinyl, pyrrolidinyl, morpholinyl. In other embodiments, when $R^4$ is —O—, $Q^3$ is oxetanyl. In still other embodiments, the present invention is a compound represented by structural formula I or I-A, wherein when $R^4$ is —O—, $Q^3$ is cyclopropyl.

In another embodiment, the present invention is a compound represented by structural formula I or I-A, wherein when $R^4$ is —O—, $J^R$ is =O or halo.

In other embodiments, the present invention is a compound represented by structural formula I or I-A, wherein when $R^4$ is —O—, two occurrences of $J^R$ on the same atom, taken together with the atom to which they are joined, form a 3-6 membered non-aromatic ring having 0-2 heteroatoms selected from oxygen, nitrogen, or sulfur. In yet another embodiment, the present invention is a compound represented by structural formula I or I-A, wherein when $R^4$ is —O—, the ring formed by the two occurrences of $J^R$ on the same atom, taken together with the atom to which they are joined, is selected from oxetanyl, cyclobutyl, or azetidinyl.

In other examples, the present invention is a compound represented by structural formula I or I-A, wherein when $R^4$ is —O—, $J^T$ is a 4-6 membered heterocyclyl ring having 1-2 heteroatoms selected from oxygen, nitrogen, or sulfur. In some examples, the present invention is a compound represented by structural formula I or I-A, wherein when $R^4$ is —O—, $J^T$ is piperazinyl.

In another example, the compounds of formula I and I-A of this invention are represented in Table 1. It will be appreciated by those skilled in the art that the compounds of the present invention may be represented in varying tautomeric forms.

TABLE 1

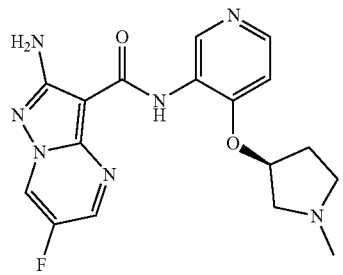 [SMILES: CN1CC[C@H](Oc2ccncc2NC(=O)c2c(N)nn3cc(F)cnc23)C1]

I-O-1

TABLE 1-continued

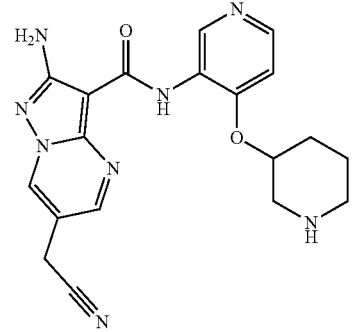 [SMILES: N#CCc1cnc2c(C(=O)Nc3cnccc3OC3CCCNC3)c(N)nn2c1]

I-O-2

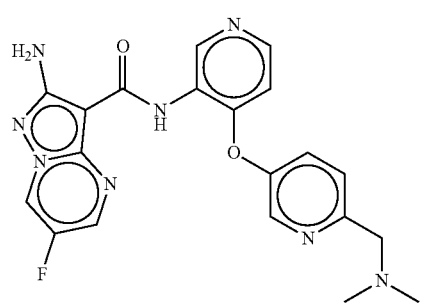

I-O-3

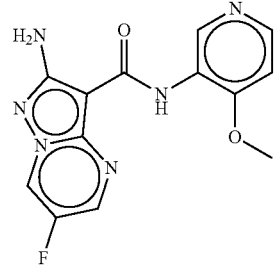

I-O-4

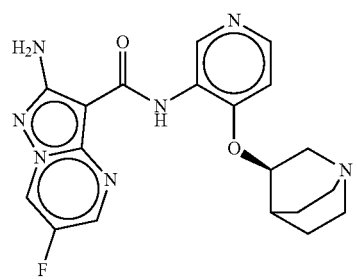

I-O-5

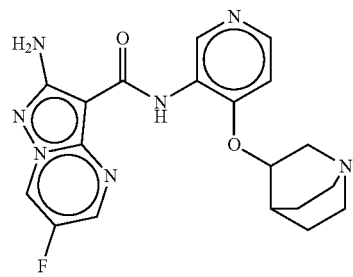

I-O-6

TABLE 1-continued
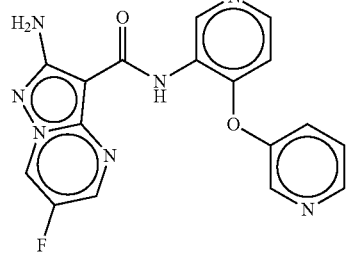
I-O-7
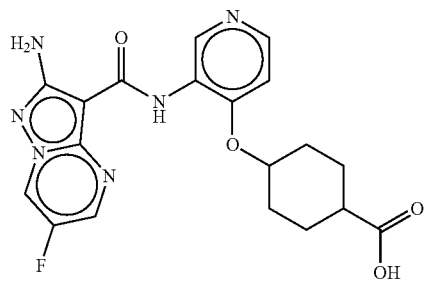
I-O-8
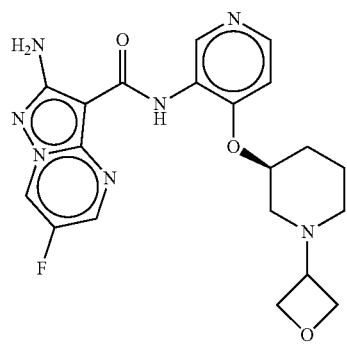
I-O-9
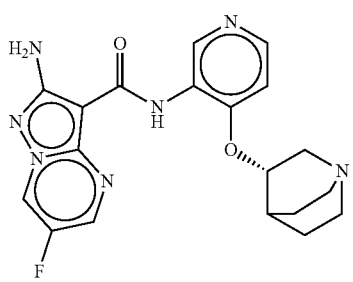
I-O-10
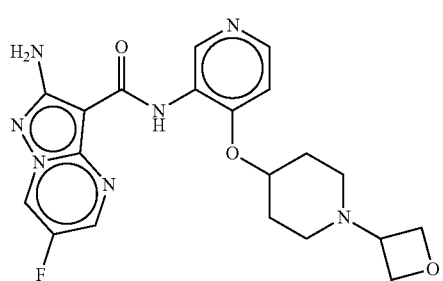
I-O-11
TABLE 1-continued
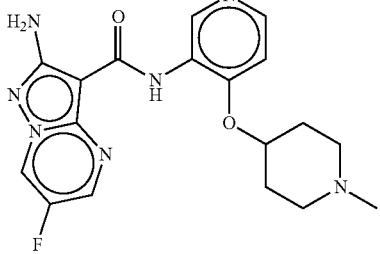
I-O-12
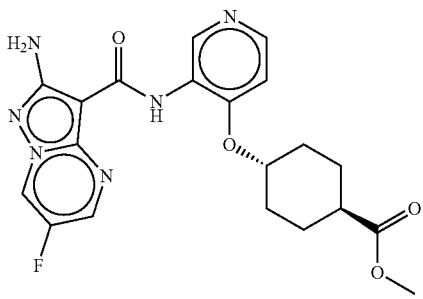
I-O-13
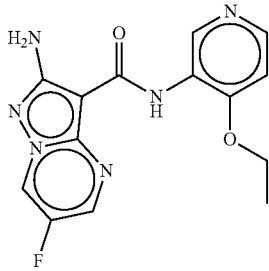
I-O-14
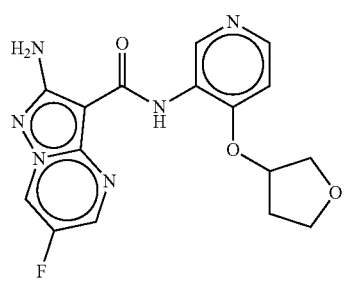
I-O-15
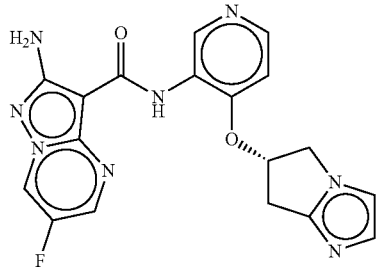
I-O-16

TABLE 1-continued

| Compound | Structure |
|---|---|
| I-O-17 | 3-amino-6-fluoro-pyrazolo[1,5-a]pyrimidine-2-carboxylic acid [4-(4-dimethylcarbamoyl-cyclohexyloxy)-pyridin-3-yl]-amide |
| I-O-18 | 3-amino-6-fluoro-pyrazolo[1,5-a]pyrimidine-2-carboxylic acid [4-(4-methoxycarbonyl-cyclohexyloxy)-pyridin-3-yl]-amide |
| I-O-19 | 3-amino-6-fluoro-pyrazolo[1,5-a]pyrimidine-2-carboxylic acid {4-[4-(4-methyl-piperazine-1-carbonyl)-cyclohexyloxy]-pyridin-3-yl}-amide |
| I-O-20 | 3-amino-6-(1-cyano-propyl)-pyrazolo[1,5-a]pyrimidine-2-carboxylic acid (4-methoxy-pyridin-3-yl)-amide |
| I-O-21 | 3-amino-6-(1-cyano-ethyl)-pyrazolo[1,5-a]pyrimidine-2-carboxylic acid (4-methoxy-pyridin-3-yl)-amide |
| I-O-22 | 3-amino-6-cyanomethyl-pyrazolo[1,5-a]pyrimidine-2-carboxylic acid [4-(quinuclidin-3-yloxy)-pyridin-3-yl]-amide |
| I-O-23 | 3-amino-6-cyanomethyl-pyrazolo[1,5-a]pyrimidine-2-carboxylic acid [4-(1-methyl-piperidin-4-yloxy)-pyridin-3-yl]-amide |
| I-O-24 | 3-amino-6-cyanomethyl-pyrazolo[1,5-a]pyrimidine-2-carboxylic acid [4-(2-dimethylamino-ethoxy)-pyridin-3-yl]-amide |
| I-O-25 | 3-amino-6-cyanomethyl-pyrazolo[1,5-a]pyrimidine-2-carboxylic acid (4-phenoxy-pyridin-3-yl)-amide |

TABLE 1-continued
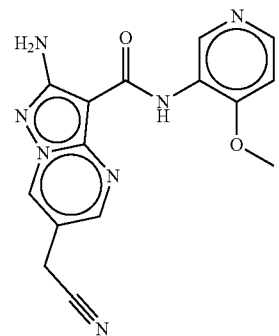 I-O-26
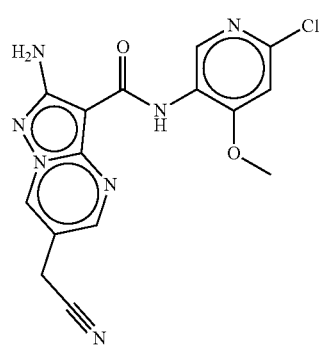 I-O-27
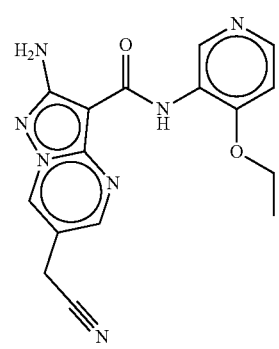 I-O-28
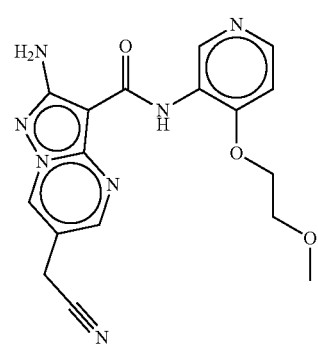 I-O-29
TABLE 1-continued
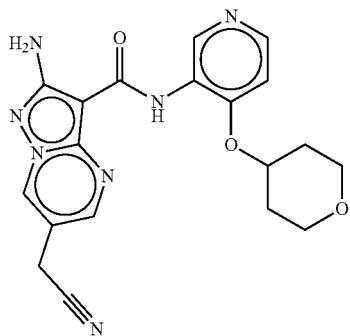 I-O-30
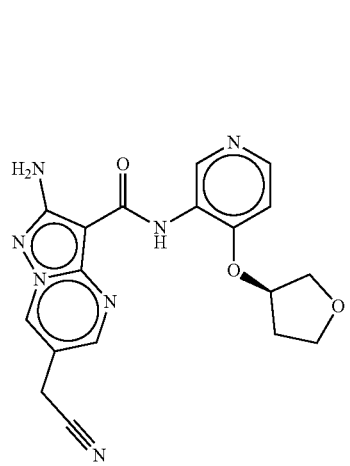 I-O-31
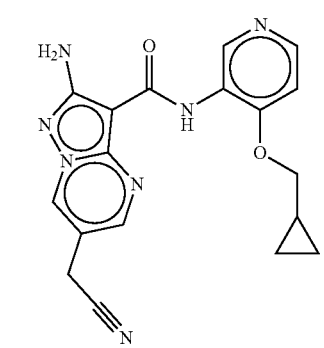 I-O-32
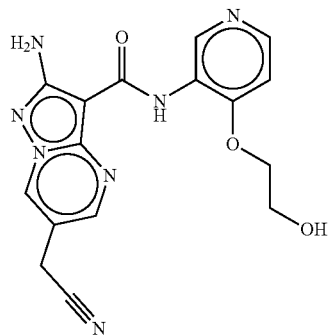 I-O-33

TABLE 1-continued
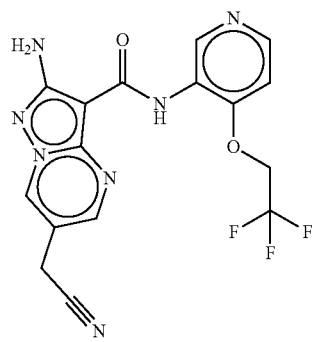
I-O-34
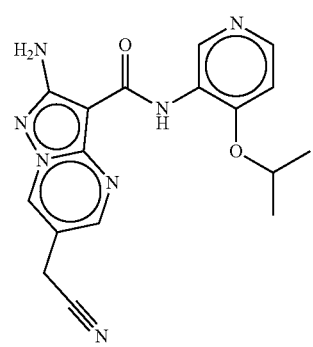
I-O-35
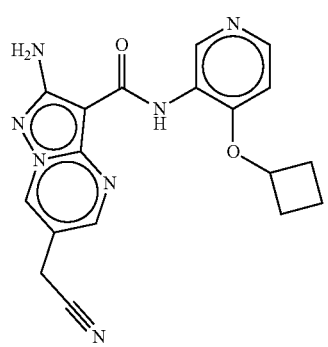
I-O-36
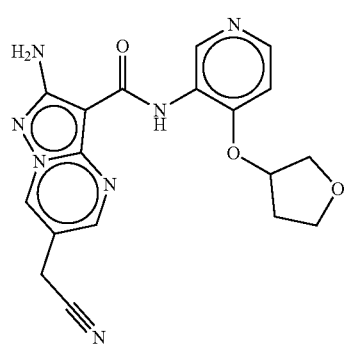
I-O-37
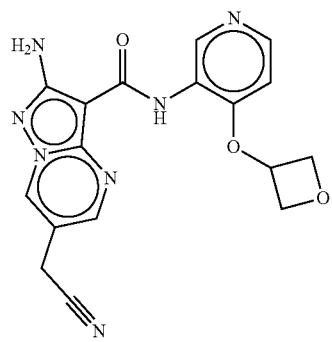
I-O-38
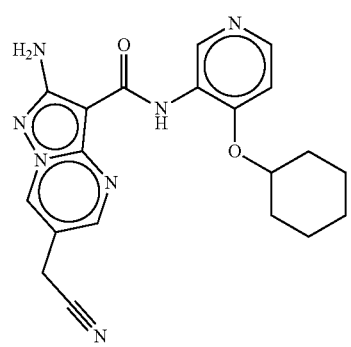
I-O-39
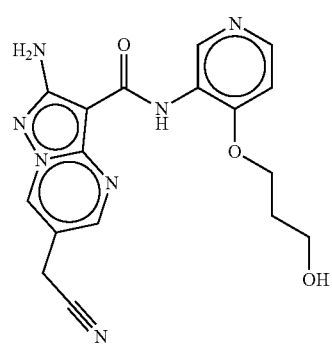
I-O-40
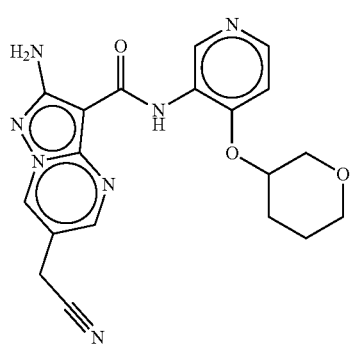
I-O-41

TABLE 1-continued
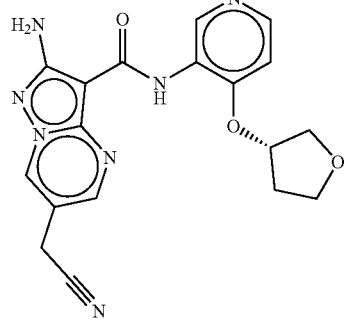 I-O-42
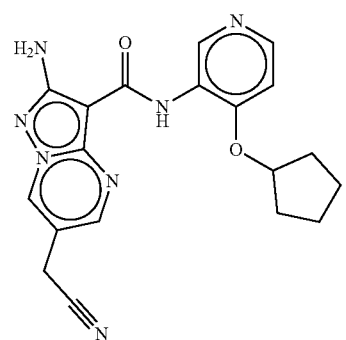 I-O-43
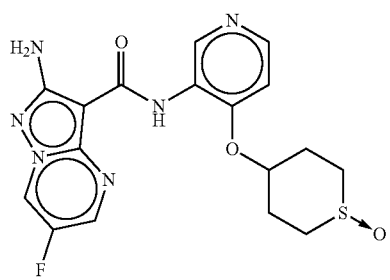 I-O-44
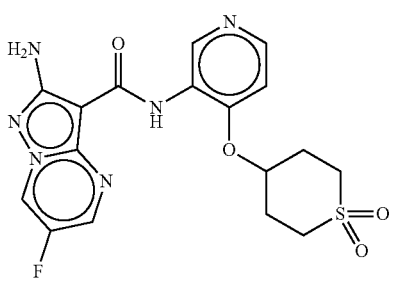 I-O-45
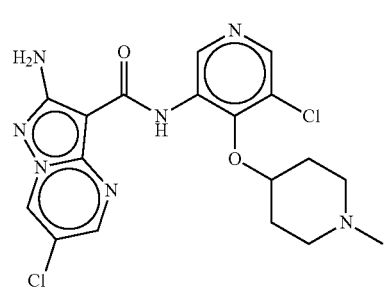 I-O-46
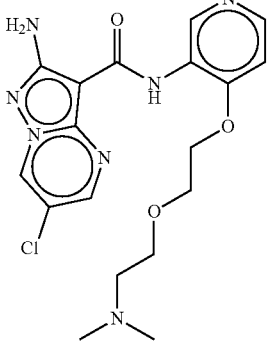 I-O-47
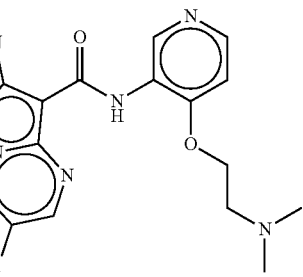 I-O-48
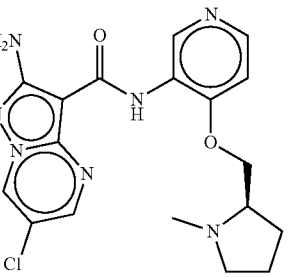 I-O-49
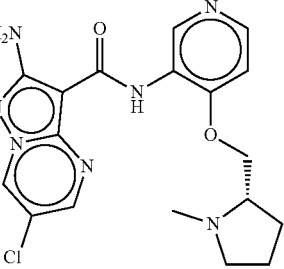 I-O-50
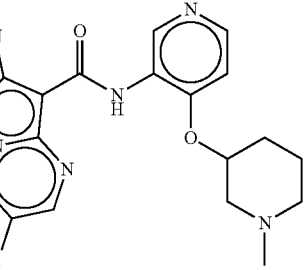 I-O-51

TABLE 1-continued
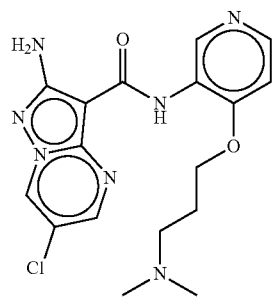 I-O-52
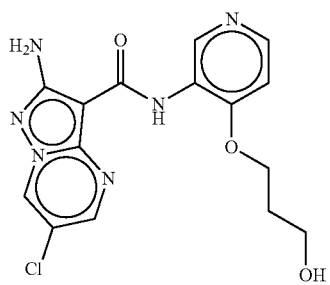 I-O-53
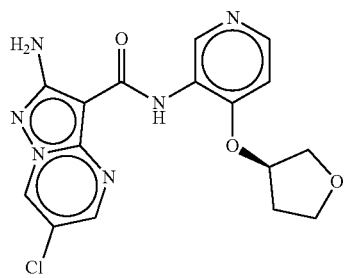 I-O-54
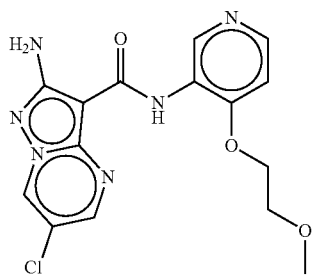 I-O-55
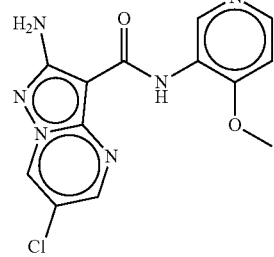 I-O-56
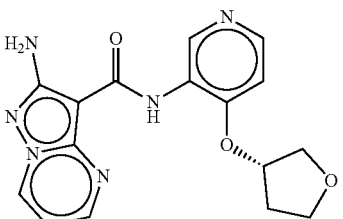 I-O-57
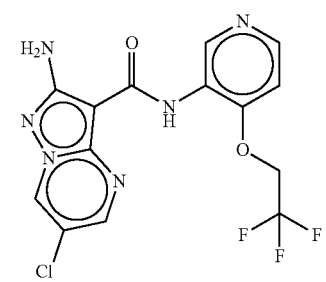 I-O-58
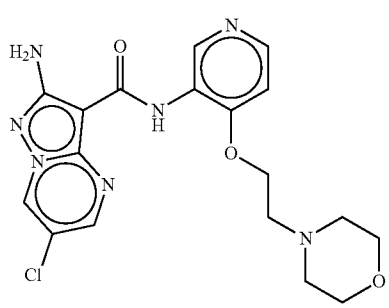 I-O-59
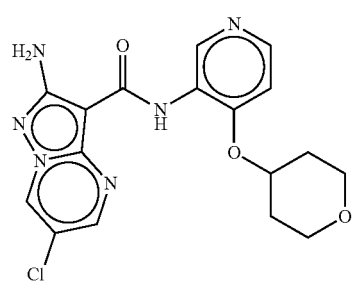 I-O-60
 I-O-61

TABLE 1-continued
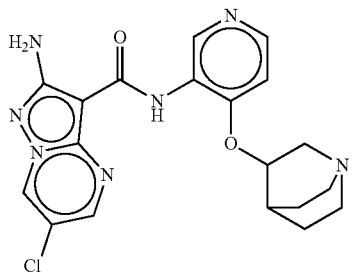 I-O-62
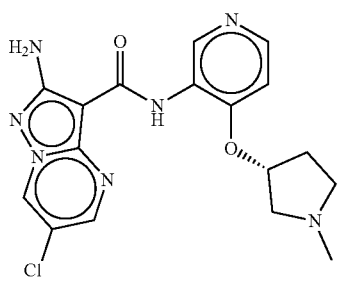 I-O-63
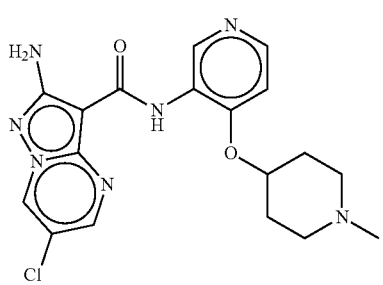 I-O-64
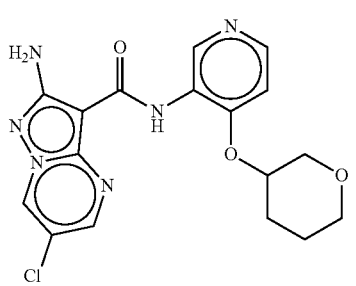 I-O-65
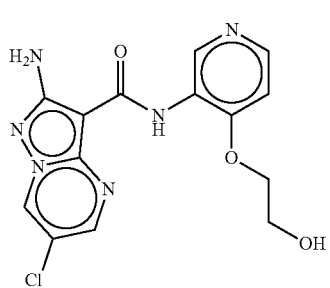 I-O-66
TABLE 1-continued
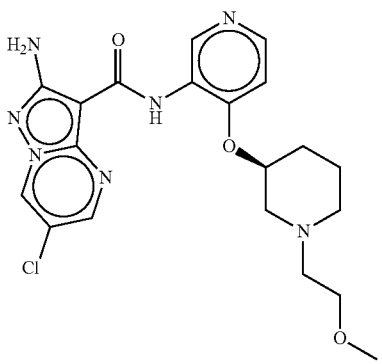 I-O-67
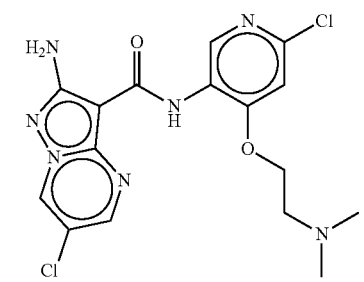 I-O-68
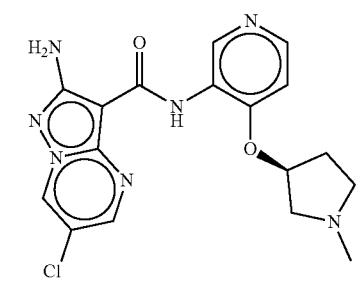 I-O-69
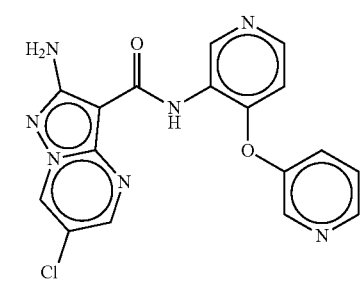 I-O-70
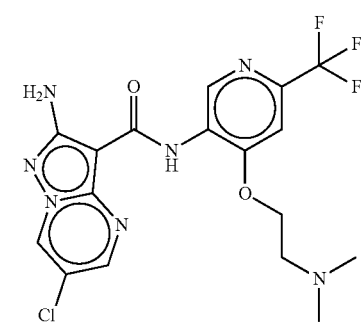 I-O-71

TABLE 1-continued
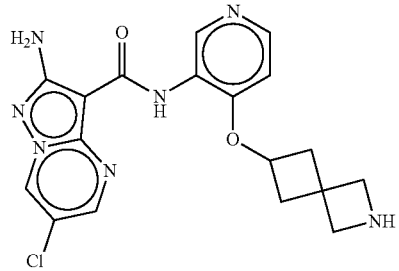 I-O-72
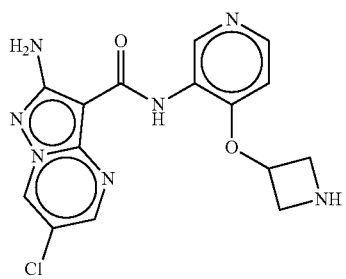 I-O-73
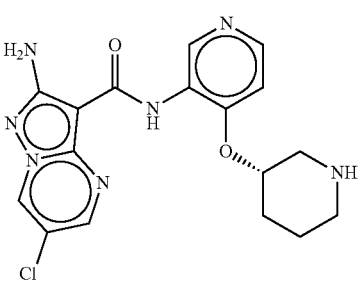 I-O-74
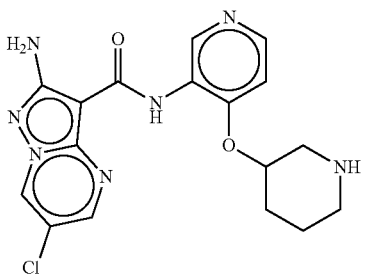 I-O-75
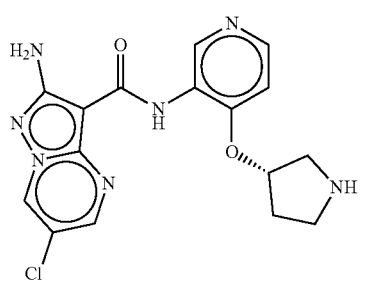 I-O-76
TABLE 1-continued
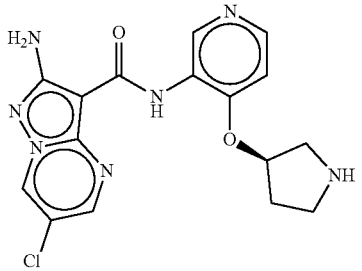 I-O-77
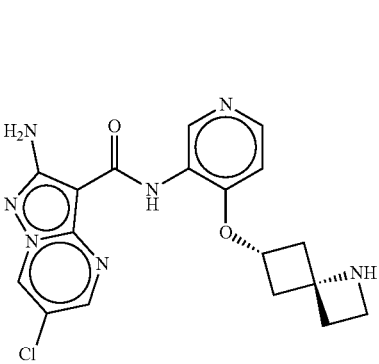 I-O-78
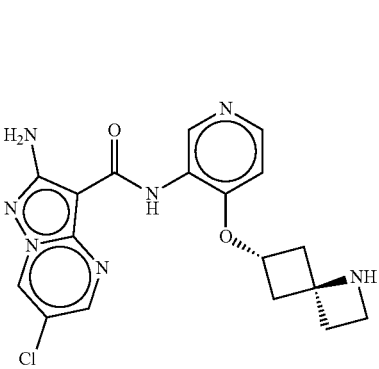 I-O-79
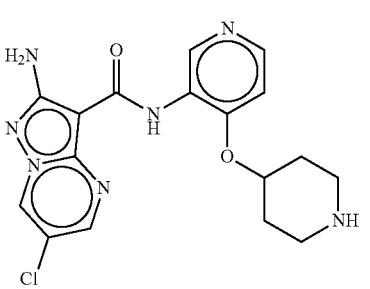 I-O-80
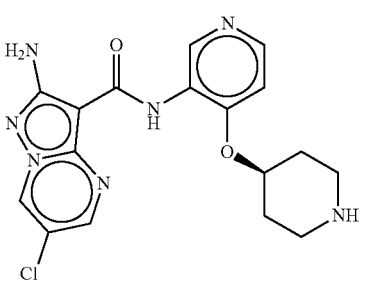 I-O-81

TABLE 1-continued
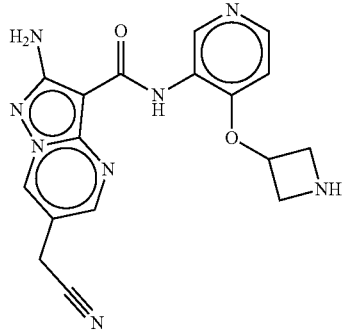
I-O-82
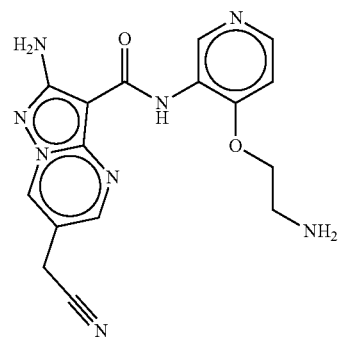
I-O-83
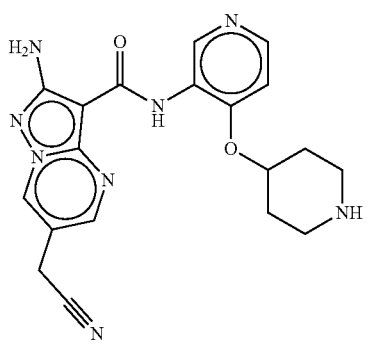
I-O-84
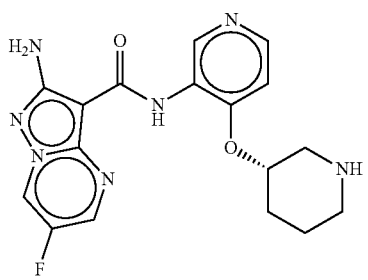
I-O-85
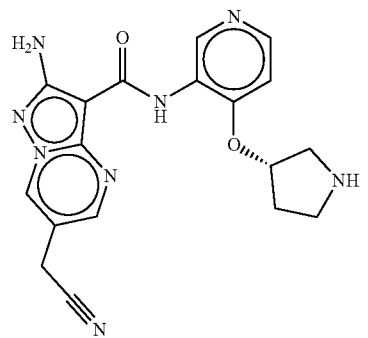
I-O-86
TABLE 1-continued
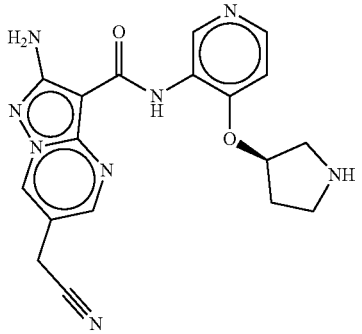
I-O-87
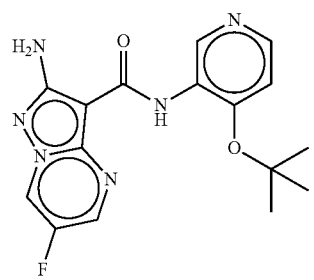
I-O-88
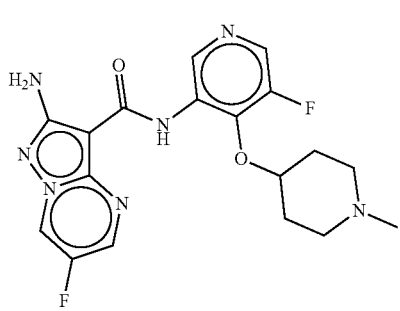
I-O-89
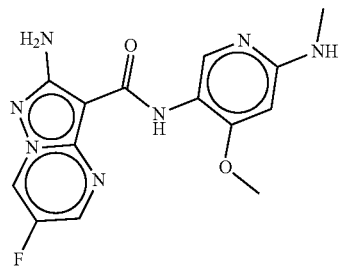
I-O-90
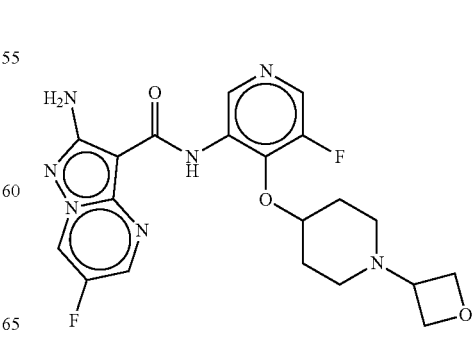
I-O-91

TABLE 1-continued

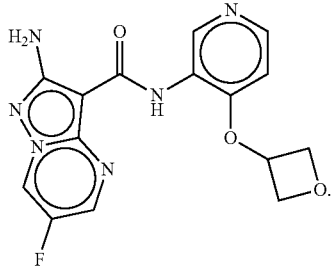

I-O-92

In another example, the present invention is a compound represented by structural formula I or I-A, wherein $R^4$ is Ring A, which is represented by the structure:

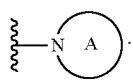

In some embodiments, the present invention is a compound represented by structural formula I or I-A, wherein Ring A is a is a 3-7 membered fully saturated, partially unsaturated, or aromatic monocyclic ring having 1-3 heteroatoms selected from oxygen, nitrogen or sulfur. In other embodiments, the present invention is a compound represented by structural formula I or I-A, wherein Ring A is a 4-6 membered heterocyclyl. In other embodiments, the present invention is a compound represented by structural formula I or I-A, wherein Ring A is a 3-7 membered heterocyclyl. In still other embodiments, the present invention is a compound represented by structural formula I or I-A, wherein Ring A is independently selected from pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, and azetidinyl. In yet another embodiment, the present invention is a compound represented by structural formula I or I-A, wherein Ring A is independently selected from piperidinyl, piperazinyl, 1,4-diazepanyl, thiomorpholinyl, pyrrolidinyl, azepanyl, and morpholinyl. In some embodiments, the present invention is a compound represented by structural formula I or I-A, wherein Ring A is independently selected from piperazinyl or piperidinyl.

In another embodiment, the present invention is a compound represented by structural formula I or I-A, wherein Ring A is a 5 membered heteroaryl. In other embodiments, the present invention is a compound represented by structural formula I or I-A, wherein Ring A is independently selected from pyrrolyl, imidazolyl, pyrazolyl, 1,2,3-triazolyl, or 1,2,4-triazolyl. In still other embodiments, the present invention is a compound represented by structural formula I or I-A, wherein Ring A is independently selected from pyrazolyl or imidazolyl.

In some embodiments, the present invention is a compound represented by structural formula I or I-A, wherein Ring A is a 7-12 membered fully saturated, partially unsaturated, or aromatic bicyclic ring having 1-5 heteroatoms selected from oxygen, nitrogen, or sulfur. In another example, the present invention is a compound represented by structural formula I or I-A, wherein Ring A is independently selected from octahydropyrrolo[1,2-a]pyrazinyl, 5,6,7,8-tetrahydroimidazo[1,2-a]pyridinyl, octahydro-1H-pyrazino[1,2-a]pyrazinyl, 5,6,7,8-tetrahydroimidazo[1,5-a]pyrazinyl, 2,5-diazabicyclo[4.1.0], or octahydropyrazino[2,1-c][1,4]oxazinyl.

In yet another embodiment, the present invention is a compound represented by structural formula I or I-A, wherein when $R^4$ is Ring A, $J^Q$ is $C_{1-8}$ aliphatic chain wherein up to two methylene units of the aliphatic chain are optionally replaced with —O—, —NR—, or —C(O)—. In yet another embodiment, the present invention is a compound represented by structural formula I or I-A, wherein when $R^4$ is Ring A, $J^Q$ is a $C_{1-6}$ aliphatic chain wherein up to two methylene units of the aliphatic chain are optionally replaced with —O—, —NR—, or —C(O)—. In some embodiments, the present invention is a compound represented by structural formula I or I-A, wherein when $R^4$ is Ring A, $J^Q$ is independently selected from —O—, —C(O)—, —S(O)$_2$—, $C_{1-4}$ alkyl, —(C$_{0-4}$ alkyl)NH$_2$, —(C$_{0-4}$ alkyl)NH(C$_{1-4}$ alkyl), —(C$_{0-4}$alkyl)N(C$_{1-4}$ alkyl)$_2$, —(C$_{0-4}$alkyl)OH, —(C$_{0-4}$ alkyl)O(C$_{1-4}$ alkyl), —C(O)OH, —S(O)$_2$N(C$_{1-3}$ alkyl)-, —C(O)(C$_{1-4}$alkyl)-, —(O)C(C$_{1-4}$ alkyl)N(C$_{1-2}$alkyl)$_2$ or —C(O)O(C$_{1-4}$ alkyl). In some embodiments, the present invention is a compound represented by structural formula I or I-A, wherein when $R^4$ is Ring A, $J^Q$ is independently selected from —C(O)—, $C_{1-4}$alkyl, —(C$_{0-4}$alkyl)NH$_2$, —(C$_{0-4}$alkyl)NH(C$_{1-4}$alkyl), —(C$_{0-4}$alkyl)N(C$_{1-4}$ alkyl)$_2$, —(C$_{0-4}$ alkyl)OH, —(C$_{0-4}$ alkyl)O(C$_{1-4}$ alkyl), —C(O)OH, —C(O)O(C$_{1-4}$alkyl). In still other embodiments, the present invention is a compound represented by structural formula I or I-A, wherein when $R^4$ is Ring A, $J^Q$ is $C_{1-4}$alkyl. In still other embodiments, the present invention is a compound represented by structural formula I or I-A, wherein when $R^4$ is Ring A, $J^Q$ is $C_{1-4}$alkyl, —O—, or —C(O)—.

In one or more examples, when $R^4$ is Ring A, $J^Q$ is $Q^2$.

In another example, the present invention is a compound represented by structural formula I or I-A, wherein when $R^4$ is Ring A, $Q^2$ is a 3-7 membered heterocyclyl or carbocyclyl; the heterocyclyl having 1-3 heteroatoms selected from oxygen, nitrogen, or sulfur. In other examples, the present invention is a compound represented by structural formula I or I-A, wherein when $R^4$ is Ring A, $Q^2$ is independently selected from oxetanyl, tetrahydropyranyl, tetrahydrofuranyl, cyclopropyl, azetidinyl, pyrrolidinyl, piperazinyl, cyclobutyl, thiomorpholinyl, or morpholinyl. In yet other examples, the present invention is a compound represented by structural formula I or I-A, wherein when $R^4$ is Ring A, $Q^2$ is independently selected from oxetanyl, tetrahydropyranyl, or tetrahydrofuranyl. In some examples, the present invention is a compound represented by structural formula I or I-A, wherein when $R^4$ is Ring A, $Q^2$ is oxetanyl.

In some embodiments, the present invention is a compound represented by structural formula I or I-A, wherein when $R^4$ is Ring A, $Q^2$ is a 7-12 membered fully saturated, partially unsaturated, or aromatic bicyclic ring having 0-5 heteroatoms selected from oxygen, nitrogen, or sulfur. In some embodiments, the present invention is a compound represented by structural formula I or I-A, wherein when $R^4$ is Ring A, $Q^2$ is an 8-12 membered fully saturated, partially unsaturated, or aromatic bicyclic ring having 0-5 heteroatoms selected from oxygen, nitrogen, or sulfur. In another example, the present invention is a compound represented by structural formula I or I-A, wherein when $R^4$ is Ring A, $Q^2$ is independently selected from 5,6,7,8-tetrahydroimidazo[1,5-a]pyrazinyl or 5,6,7,8-tetrahydroimidazo[1,2-a]pyrazinyl.

In yet another embodiment, the present invention is a compound represented by structural formula I or I-A, wherein two occurrences of $J^Q$, together with Ring A, form a bridged ring system.

In other embodiments, the present invention is a compound represented by structural formula I or I-A, wherein when $R^4$ is Ring A, $J^Q$ is =O.

In another embodiment, the present invention is a compound represented by structural formula I or I-A, wherein when $R^4$ is Ring A, $J^R$ is a 3-6 membered heterocyclyl having 1-3 heteroatoms selected from oxygen, nitrogen, or sulfur. In still other embodiments, the present invention is a compound represented by structural formula I or I-A, wherein when $R^4$ is Ring A, $J^R$ is independently selected from oxetanyl, piperadinyl, azetidinyl, piperazinyl, pyrrolidinyl, or morpholinyl. In yet another embodiment, the present invention is a compound represented by structural formula I or I-A, wherein when $R^4$ is Ring A, $J^R$ is a piperazinyl.

In some embodiments, the present invention is a compound represented by structural formula I or I-A, wherein when $R^4$ is Ring A, $J^R$ is independently selected from halo, =O, —OH, $C_{1-4}$ alkyl, —($C_{0-4}$ alkyl)N($C_{1-4}$alkyl)$_2$, or —($C_{0-4}$alkyl)O($C_{1-4}$ alkyl).

In another embodiment, the present invention is a compound represented by structural formula I or I-A, wherein when $R^4$ is Ring A, two occurrences of $J^R$ on the same atom, together with the atom to which they are joined, form a 3-6 membered aromatic or non-aromatic ring having 0-2 heteroatoms selected from oxygen, nitrogen, or sulfur. In other embodiments, the present invention is a compound represented by structural formula I or I-A, wherein when $R^4$ is Ring A, $J^R$ is independently selected from oxetanyl or azetidinyl.

In yet another embodiment, the present invention is a compound represented by structural formula I or I-A, wherein two occurrences of $J^R$, together with Ring A, form a bridged ring system.

In some embodiments, the present invention is a compound represented by structural formula I or I-A, wherein $J^T$ is a 3-6 membered non-aromatic ring having 0-2 heteroatoms selected from oxygen, nitrogen, or sulfur. In other embodiments, the present invention is a compound represented by structural formula I or I-A, wherein $J^T$ is oxytanyl. In another embodiment, $J^T$ is a $C_{1-6}$aliphatic. In another embodiment, $J^T$ is methyl.

Another aspect of the present invention provides a compound of formula I-A-1:

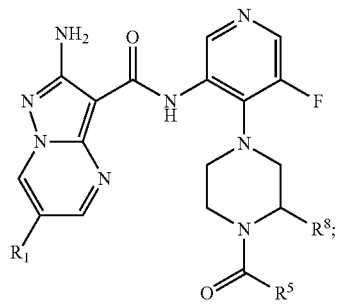

I-A-1 wherein:
$R^5$ is selected from $C_{1-4}$ aliphatic, a 3-6 membered cycloalkyl, or a 3-6 membered heterocyclyl having 1-2 heteroatoms selected from oxygen or sulfur;

$R^8$ is selected from H or $C_{1-3}$ alkyl; or
$R^5$ and $R^8$, taken together with the atoms to which they are bound, form a 5-6 membered non-aromatic ring having 1-2 heteroatoms selected from oxygen, nitrogen or sulfur.

In another embodiment, the present invention is a compound represented by structural formula I-A-1, wherein $R^1$ in formula I-A-1 is fluoro.

In another example, the present invention is a compound represented by structural formula I-A-1, wherein $R^5$ is $C_{1-4}$ aliphatic. In yet other embodiments, the present invention is a compound represented by structural formula I-A-1, wherein $R^5$ is independently selected from methyl or ethyl.

In some embodiments, the present invention is a compound represented by structural formula I-A-1, wherein $R^5$ is a 3-6 membered cycloalkyl. In other embodiments, the present invention is a compound represented by structural formula I-A-1, wherein $R^5$ is cyclopropyl.

In yet another embodiment, the present invention is a compound represented by structural formula I-A-1, wherein $R^5$ is a 3-6 membered heterocyclyl having 1-2 heteroatoms selected from oxygen or sulfur. In some embodiments, the present invention is a compound represented by structural formula I-A-1, wherein $R^5$ is tetrahydrofuranyl or oxetanyl.

In other embodiments, the present invention is a compound represented by structural formula I-A-1, wherein $R^5$ and $R^8$, taken together with the atoms to which they are bound, form a 5-6 membered non-aromatic ring having 1-2 heteroatoms selected form oxygen, nitrogen or sulfur. In another embodiment, the present invention is a compound represented by structural formula I-A-1, wherein the ring formed by $R^5$ and $R^8$ is a five-membered ring. In yet another embodiment, the present invention is a compound represented by structural formula I-A-1, wherein the ring formed by $R^5$ and $R^8$ is a six-membered ring.

In another example, the compounds of formula I, I-A, and I-A-1 of this invention are represented in Table 2.

TABLE 2

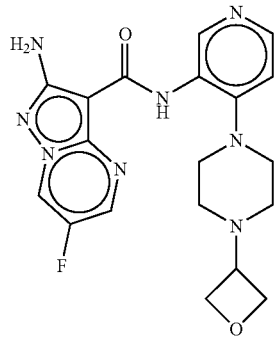

I-N-1

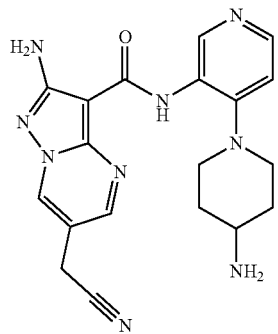 [SMILES: N#CCc1cnc2c(C(=O)Nc3cnccc3N3CCC(N)CC3)c(N)nn2c1]

I-N-2

TABLE 2-continued
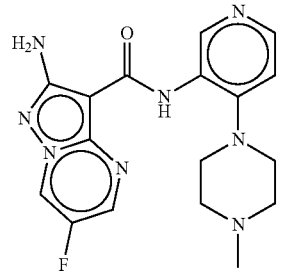
I-N-3
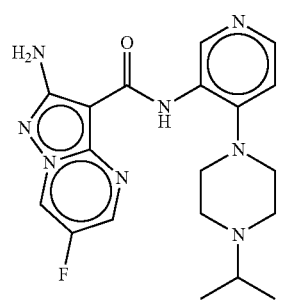
I-N-4
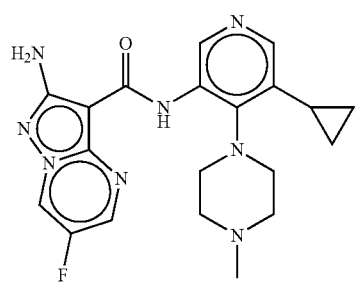
I-N-5
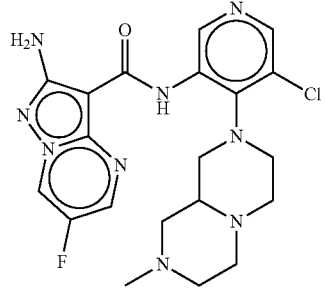
I-N-6
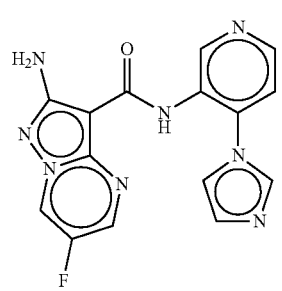
I-N-7
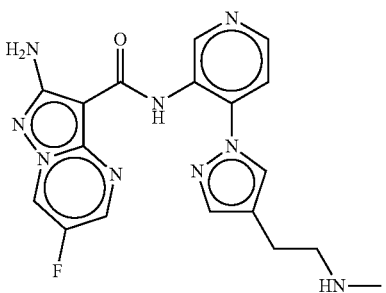
I-N-8
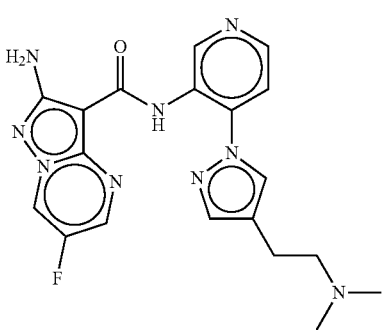
I-N-9
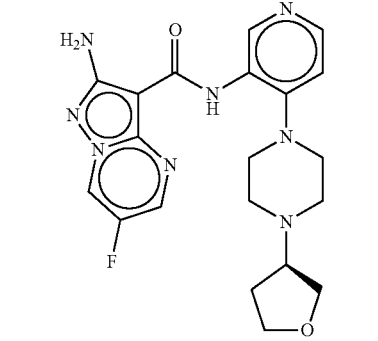
I-N-10
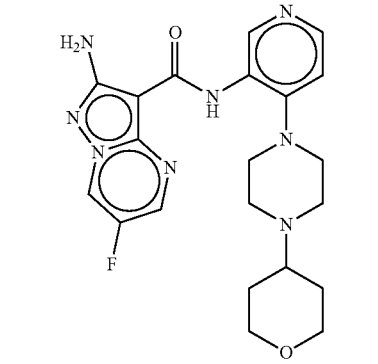
I-N-11

TABLE 2-continued
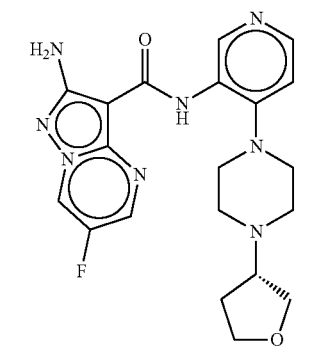 I-N-12
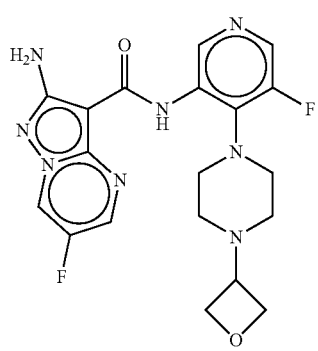 I-N-13
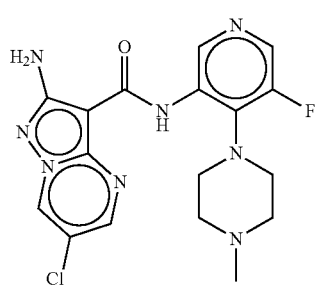 I-N-14
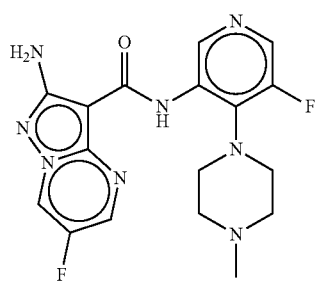 I-N-15
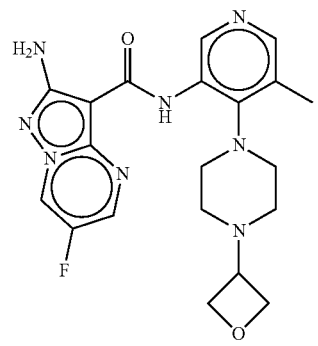 I-N-16
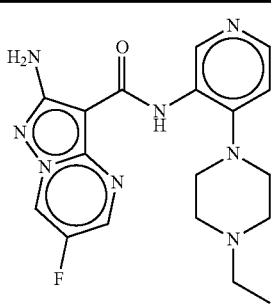 I-N-17
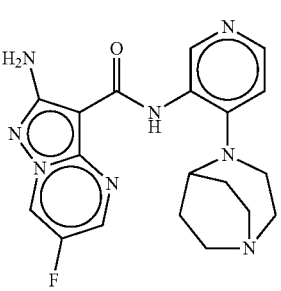 I-N-18
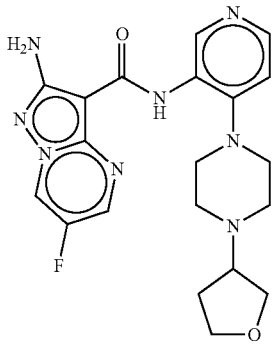 I-N-19
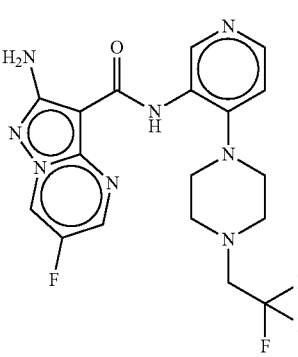 I-N-20
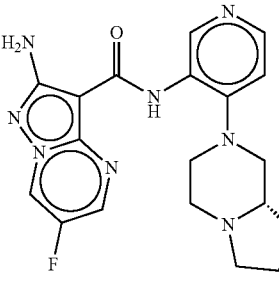 I-N-21

TABLE 2-continued
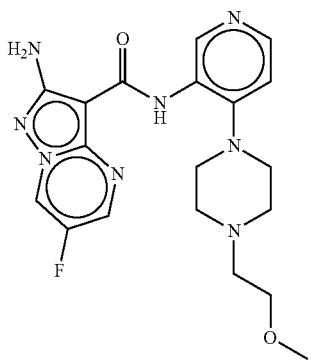 I-N-22
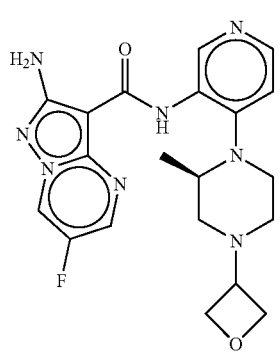 I-N-23
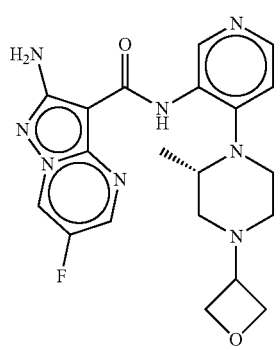 I-N-24
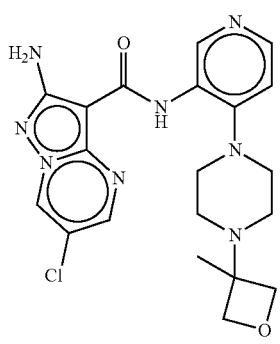 I-N-25
TABLE 2-continued
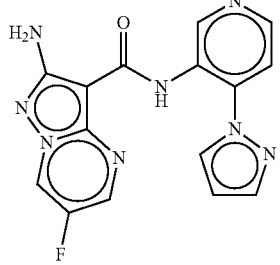 I-N-26
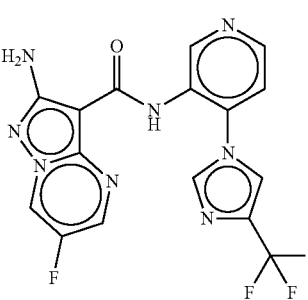 I-N-27
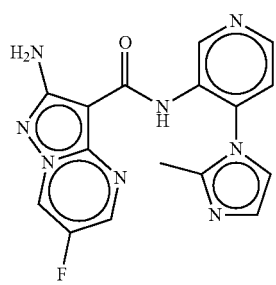 I-N-28
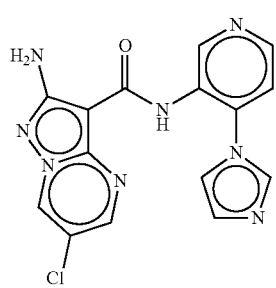 I-N-29
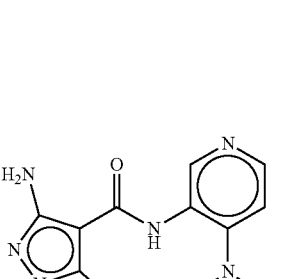 I-N-30

TABLE 2-continued
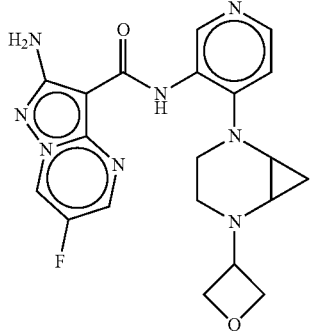
I-N-31
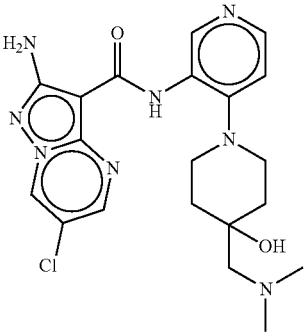
I-N-36
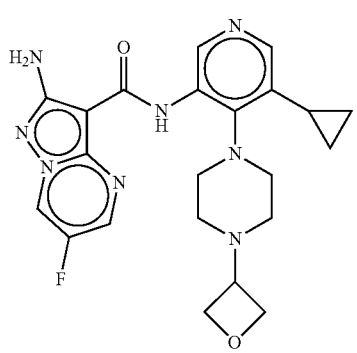
I-N-32
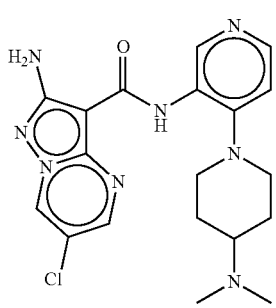
I-N-37
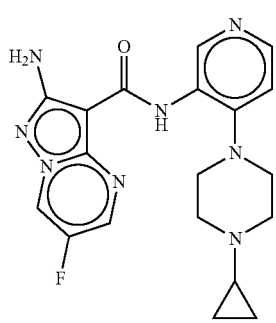
I-N-33
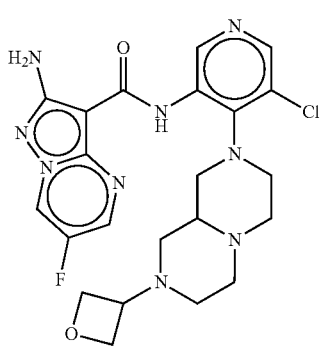
I-N-38
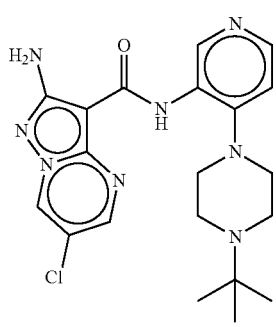
I-N-34
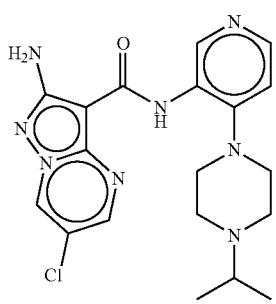
I-N-39
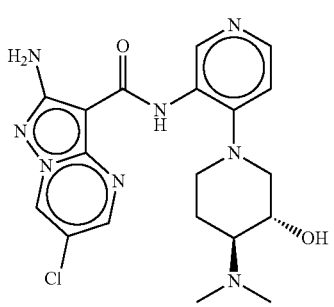
I-N-35
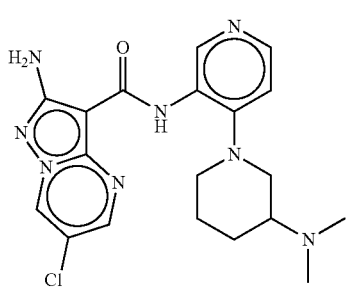
I-N-40

TABLE 2-continued
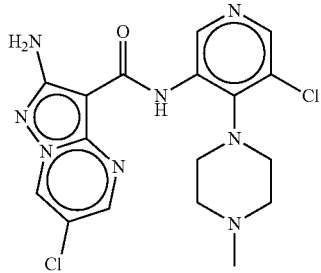 I-N-41
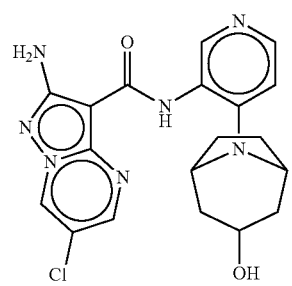 I-N-42
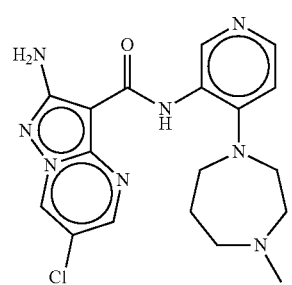 I-N-43
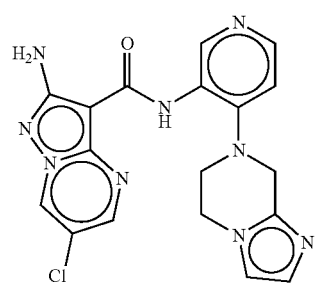 I-N-44
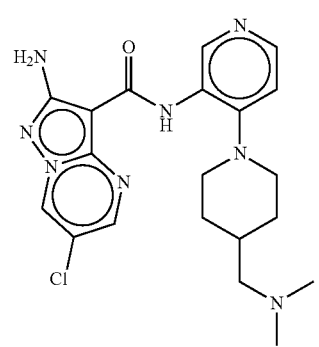 I-N-45
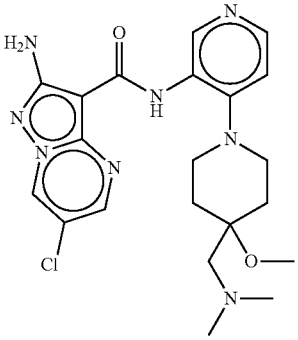 I-N-46
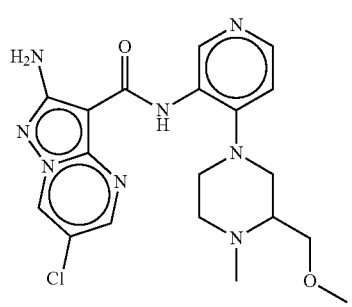 I-N-47
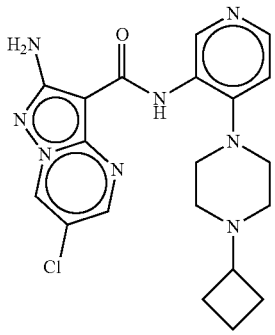 I-N-48
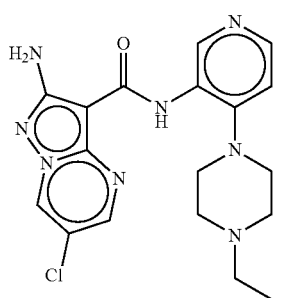 I-N-49
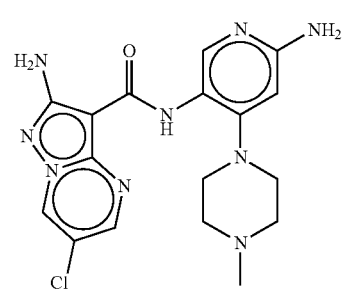 I-N-50

TABLE 2-continued
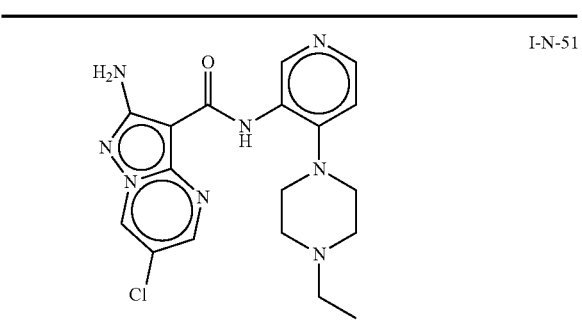 I-N-51
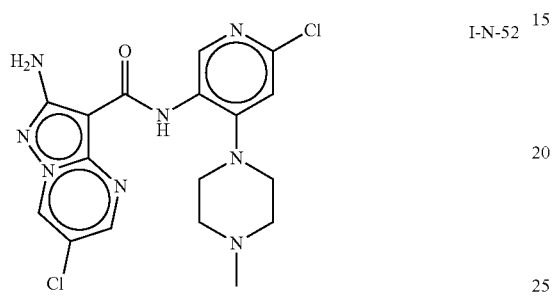 I-N-52
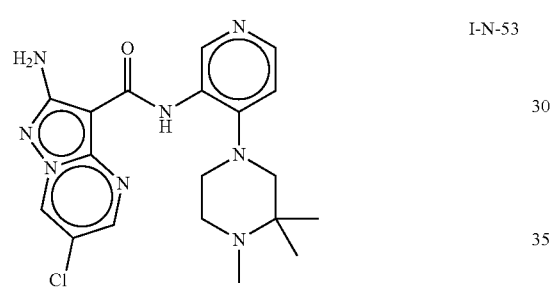 I-N-53
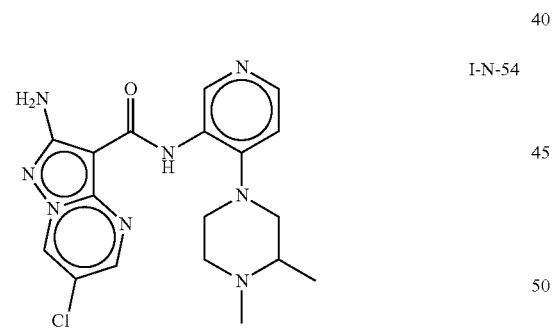 I-N-54
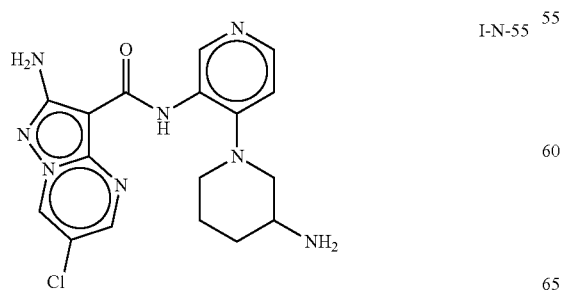 I-N-55
TABLE 2-continued
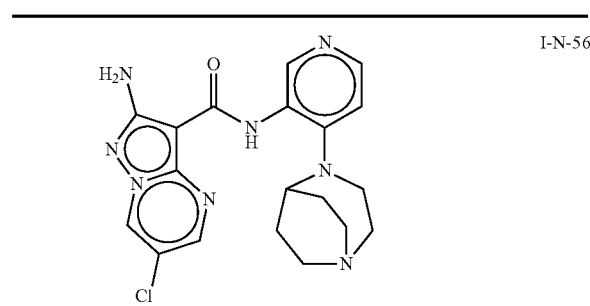 I-N-56
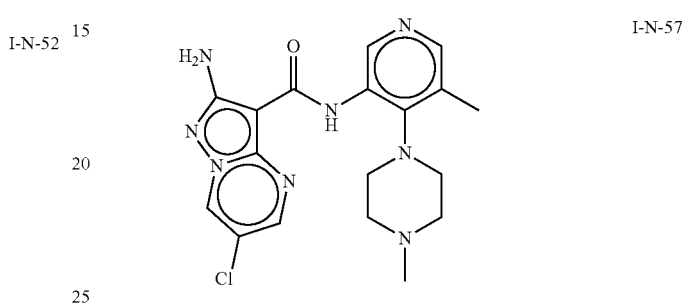 I-N-57
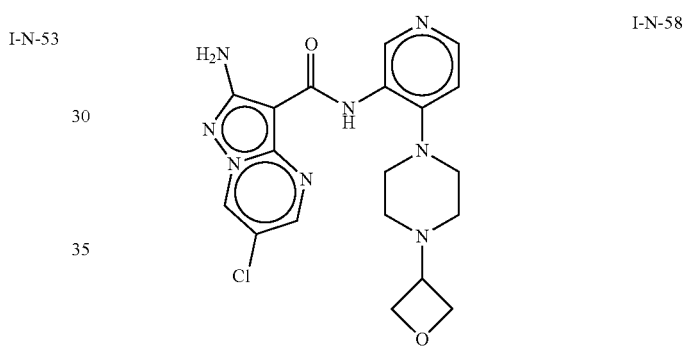 I-N-58
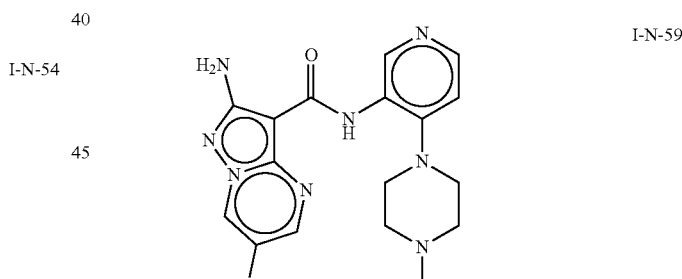 I-N-59
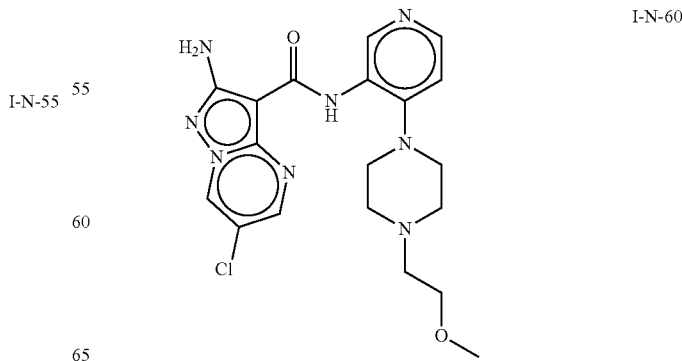 I-N-60

TABLE 2-continued
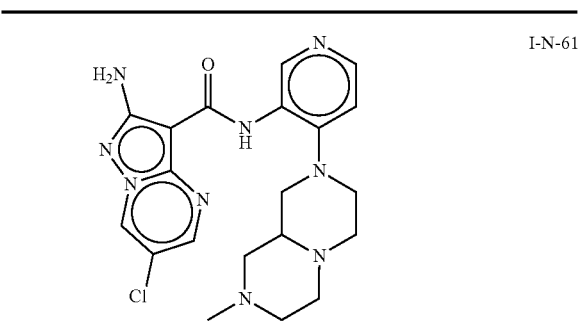
I-N-61
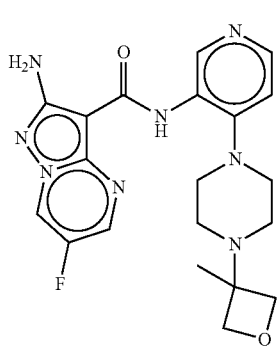
I-N-62
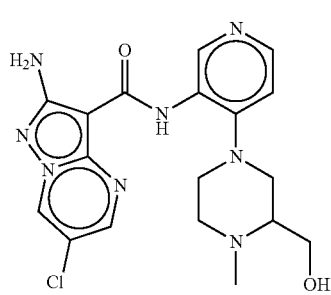
I-N-63
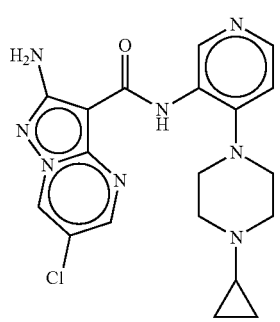
I-N-64
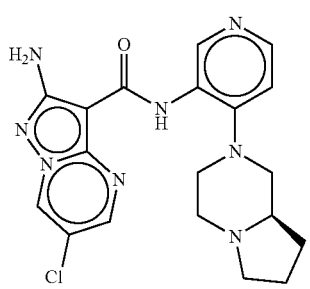
I-N-65
TABLE 2-continued
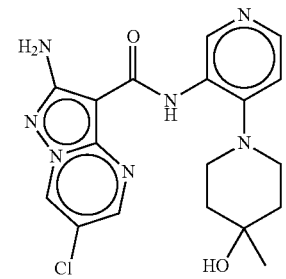
I-N-66

I-N-67
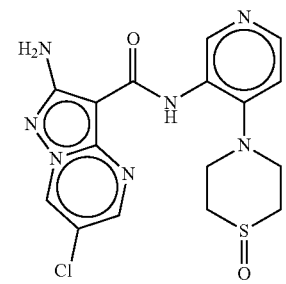
I-N-68
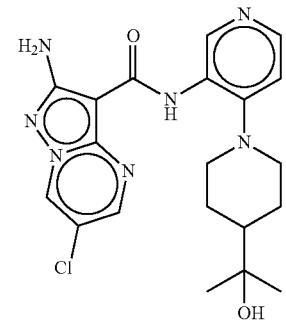
I-N-69
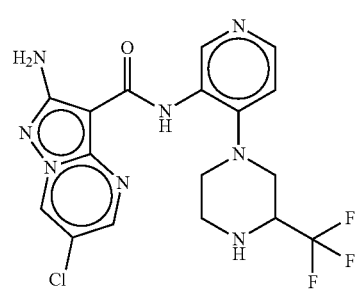
I-N-70

TABLE 2-continued
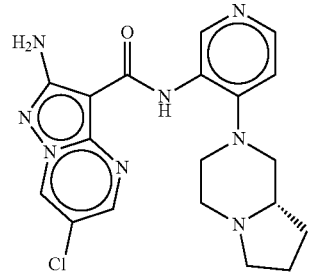 I-N-71
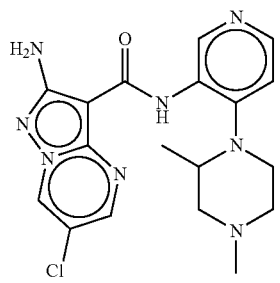 I-N-72
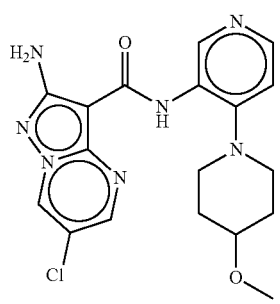 I-N-73
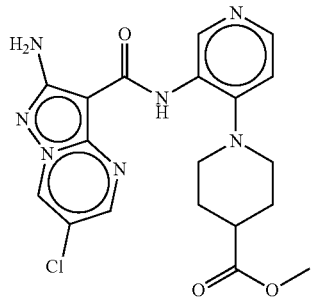 I-N-74
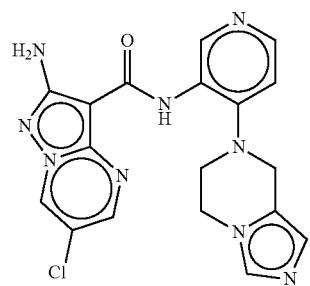 I-N-75
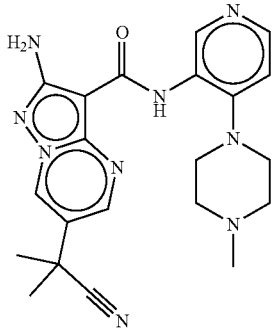 I-N-76
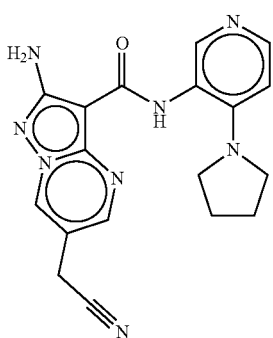 I-N-77
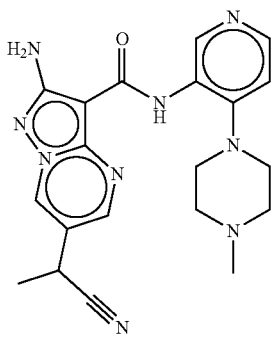 I-N-78
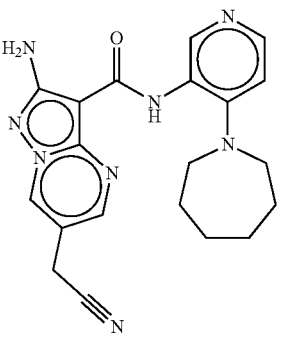 I-N-79

TABLE 2-continued
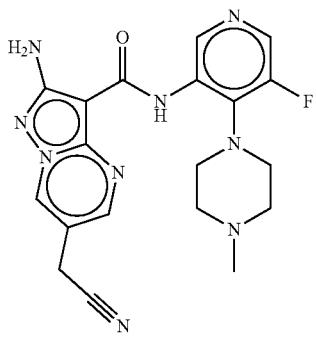 I-N-80
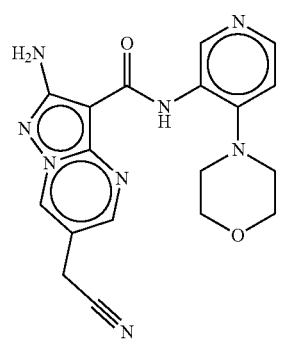 I-N-81
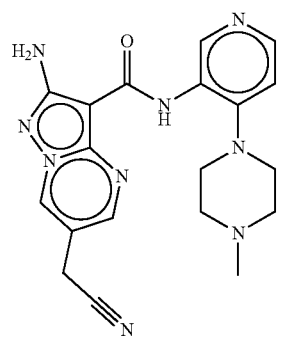 I-N-82
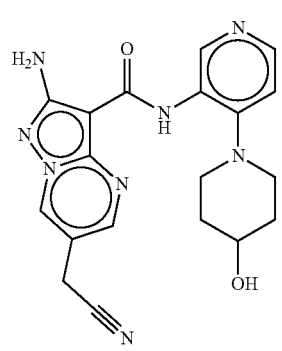 I-N-83
TABLE 2-continued
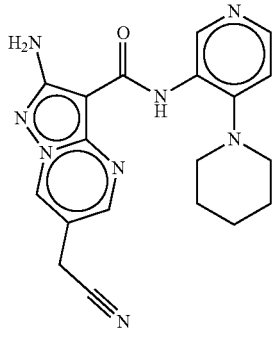 I-N-84
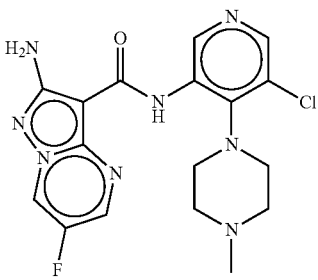 I-N-85
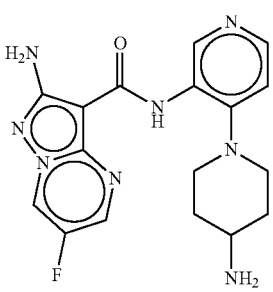 I-N-86
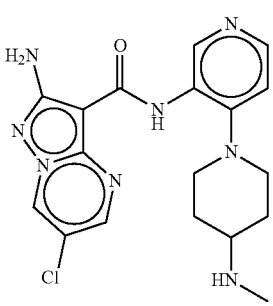 I-N-87
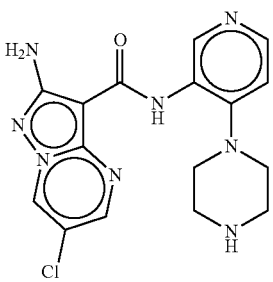 I-N-88

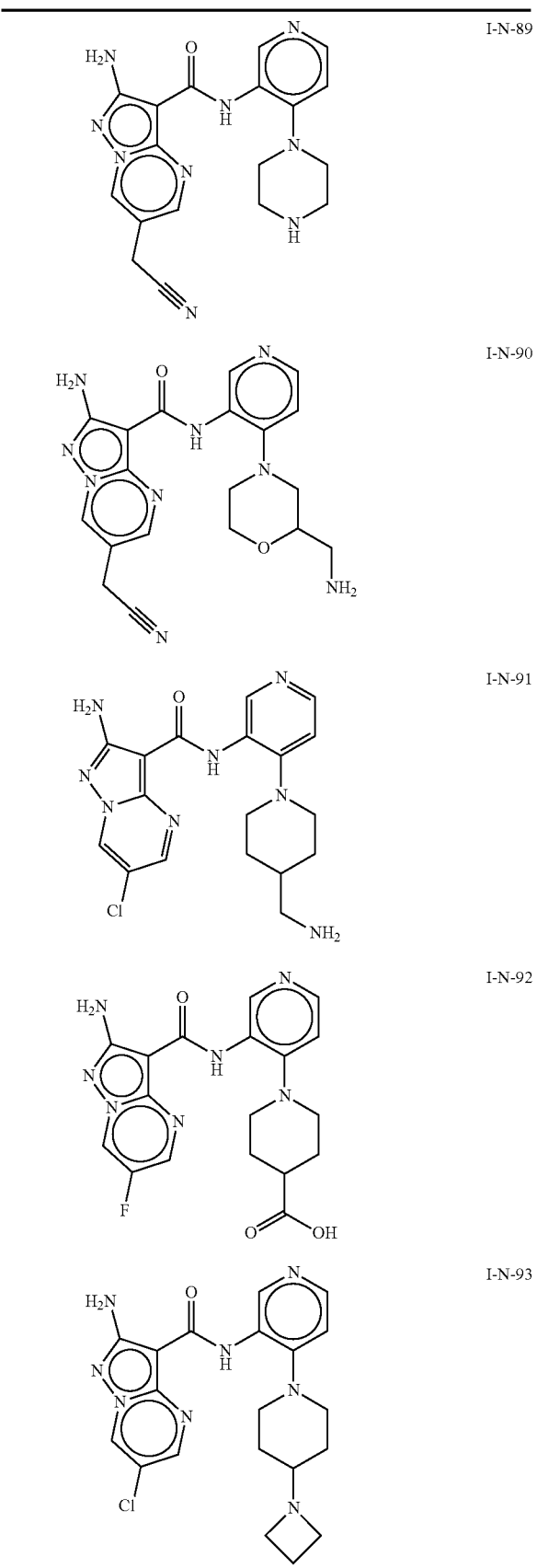

TABLE 2-continued
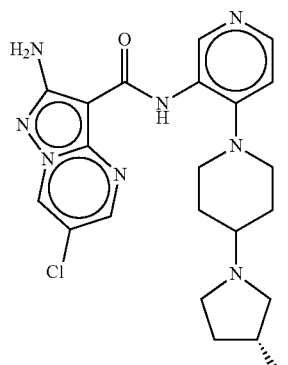 I-N-98
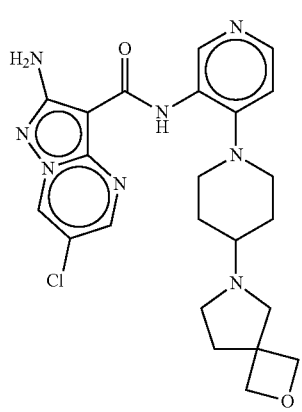 I-N-99
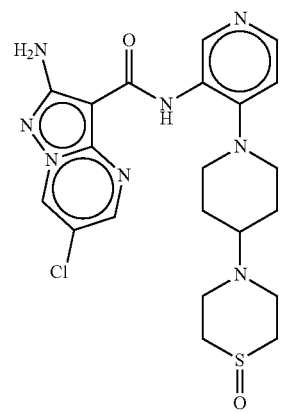 I-N-100
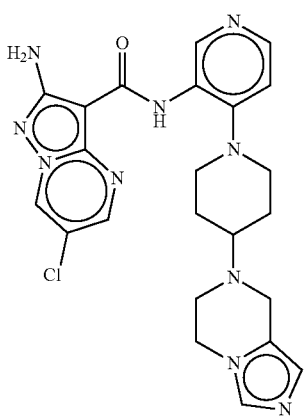 I-N-101
TABLE 2-continued
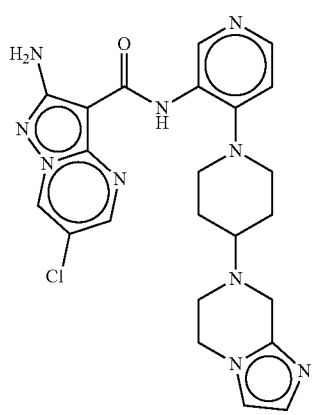 I-N-102
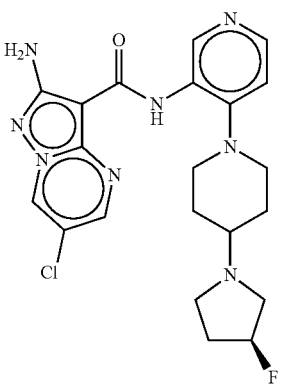 I-N-103
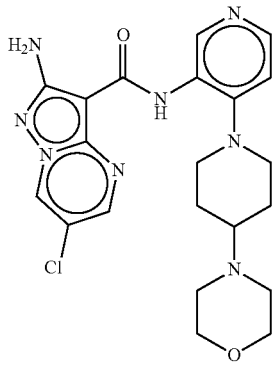 I-N-104
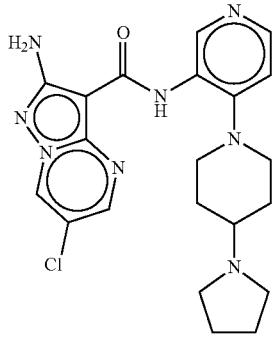 I-N-105

TABLE 2-continued
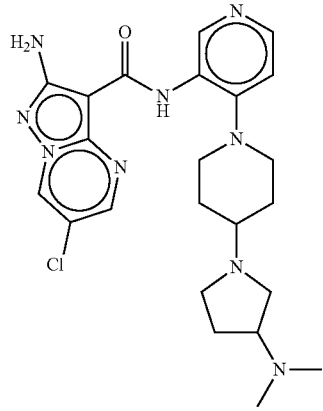 I-N-106
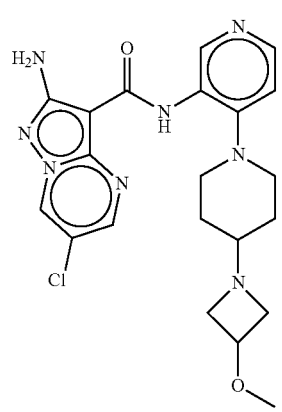 I-N-107
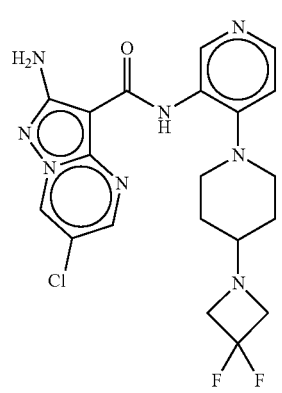 I-N-108
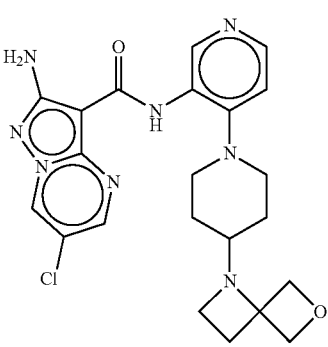 I-N-109
TABLE 2-continued
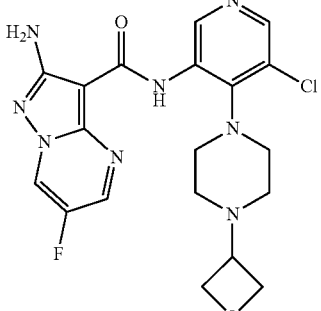 I-N-110
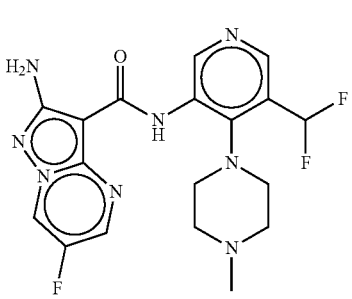 I-N-111
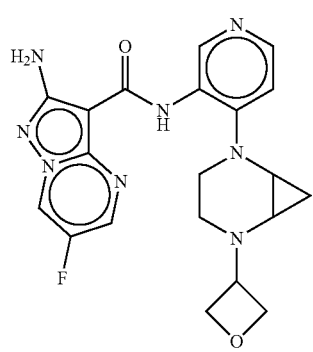 I-N-112
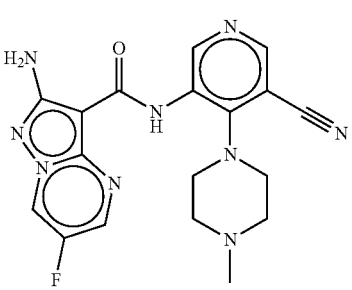 I-N-113
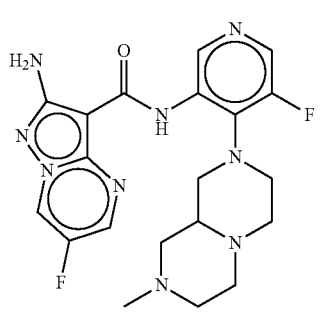 I-N-114

TABLE 2-continued
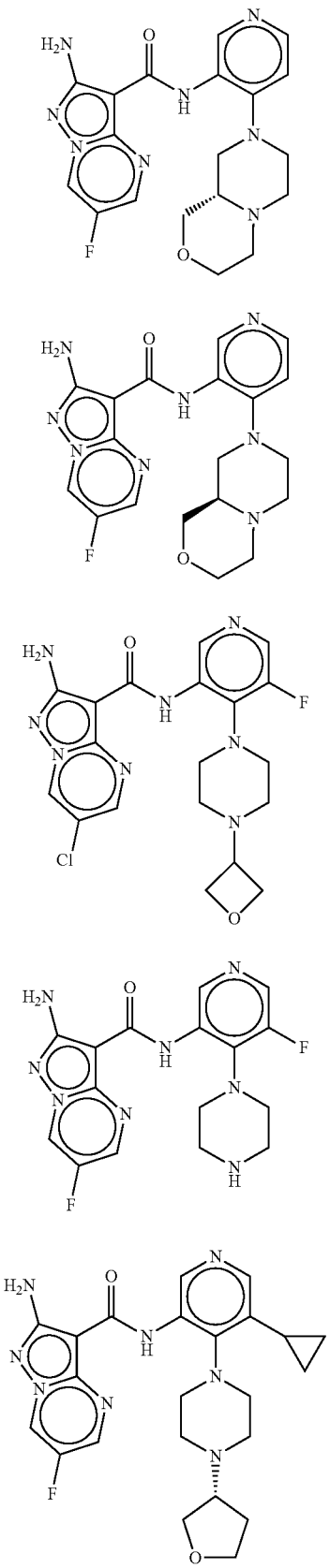
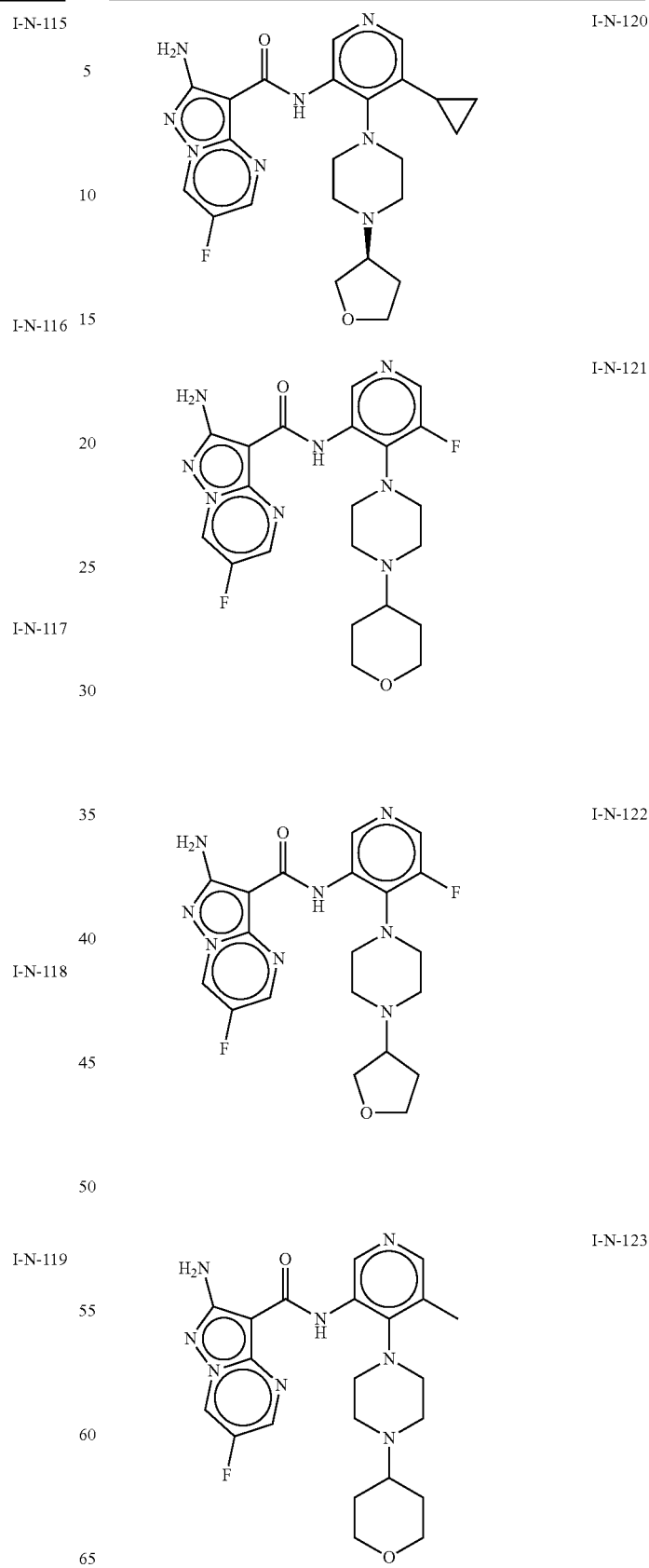

TABLE 2-continued
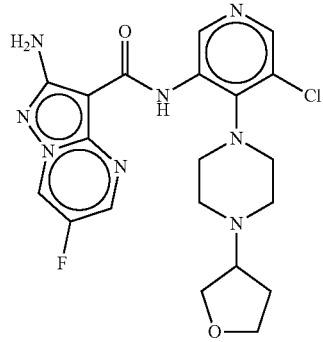
I-N-124
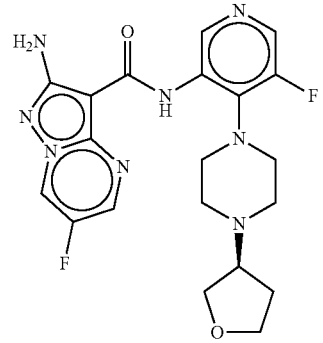
I-N-125
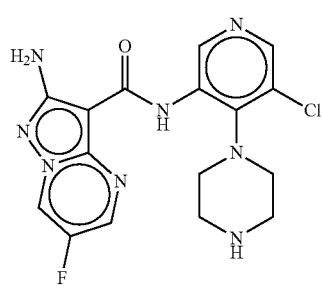
I-N-126
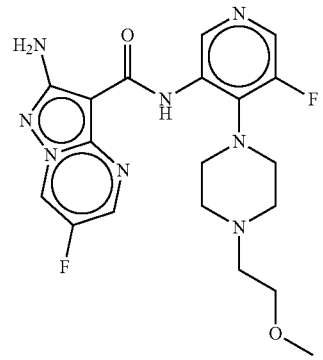
I-N-127
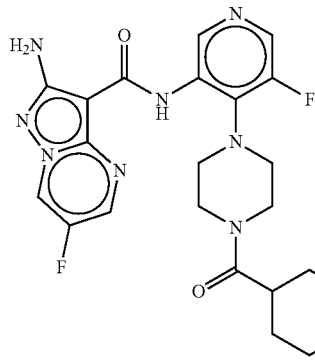
I-N-128
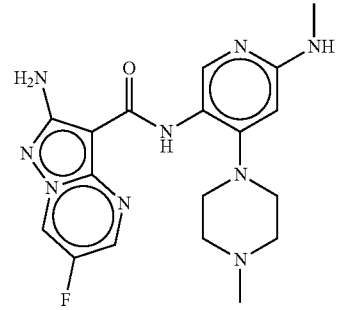
I-N-129
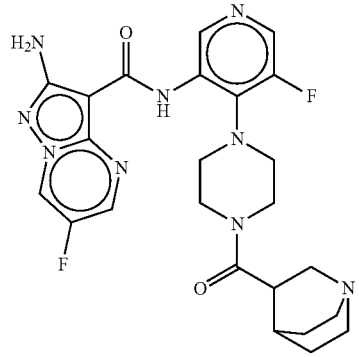
I-N-130
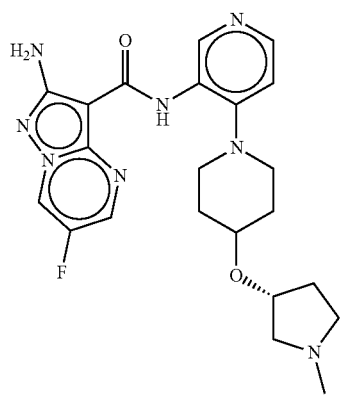
I-N-131

TABLE 2-continued
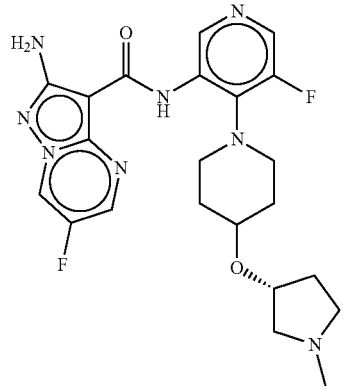 I-N-132
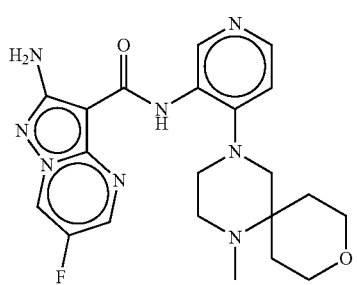 I-N-133
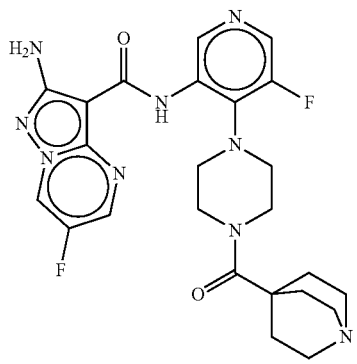 I-N-134
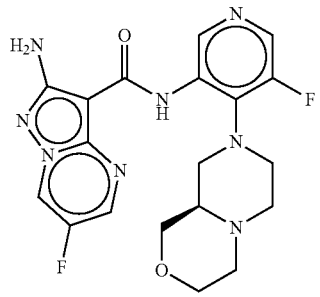 I-N-135
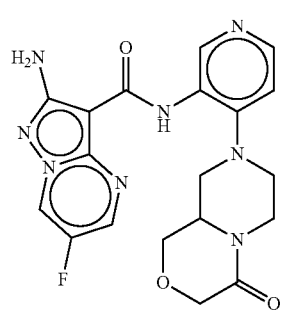 I-N-136
TABLE 2-continued
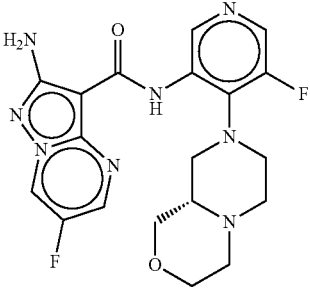 I-N-137
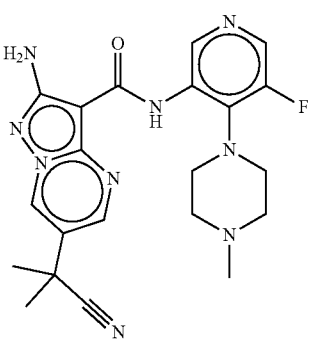 I-N-138
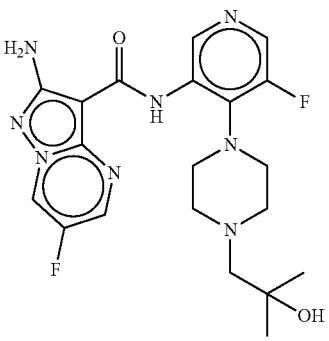 I-N-139
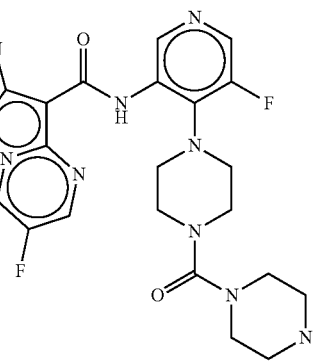 I-N-140
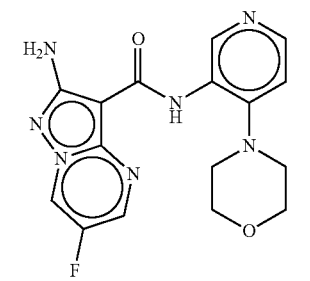 I-N-141

TABLE 2-continued
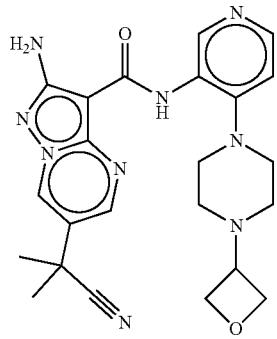 I-N-142
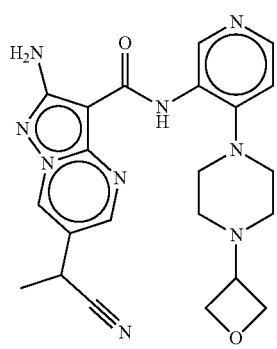 I-N-143
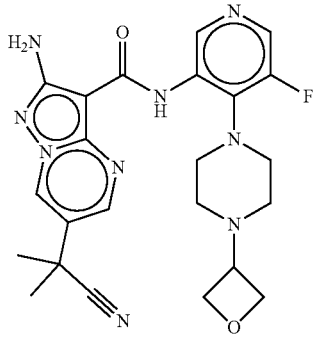 I-N-144
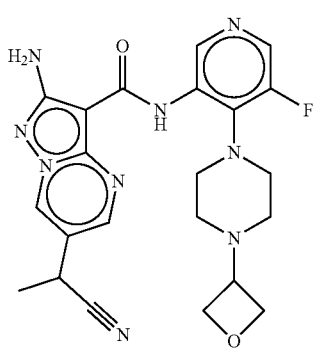 I-N-145
TABLE 2-continued
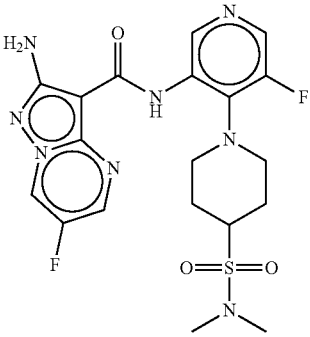 I-N-146
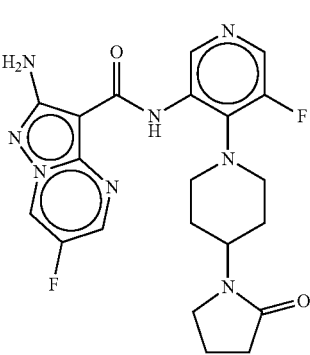 I-N-147
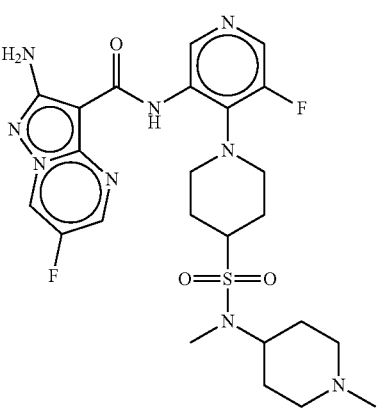 I-N-148
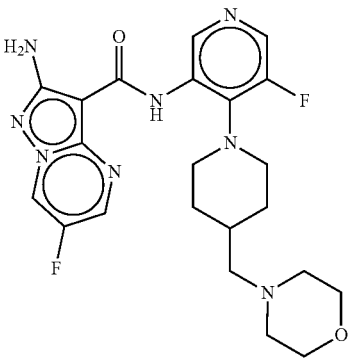 I-N-149

TABLE 2-continued
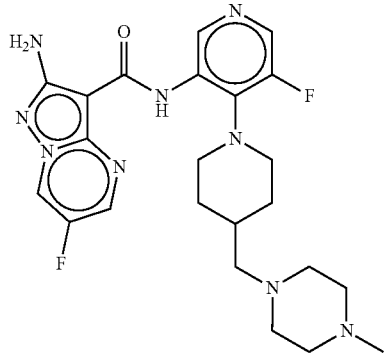
I-N-150
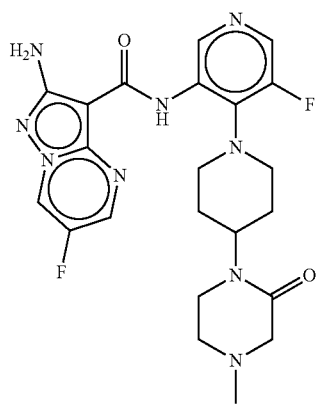
I-N-151
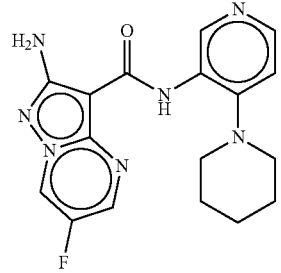
I-N-152
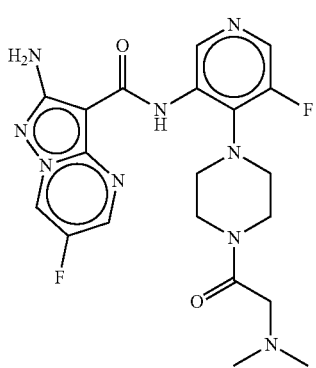
I-N-153
TABLE 2-continued
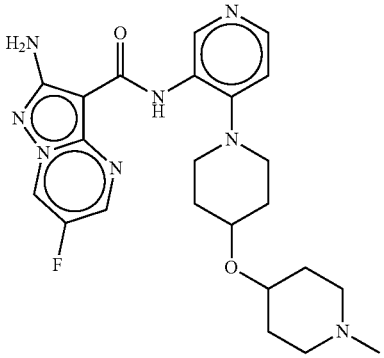
I-N-154
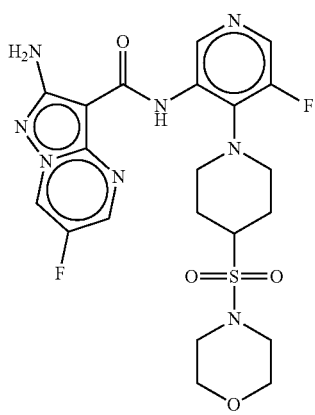
I-N-155
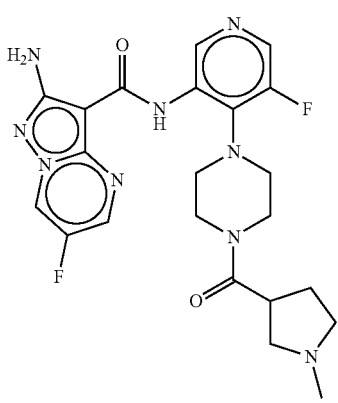
I-N-156
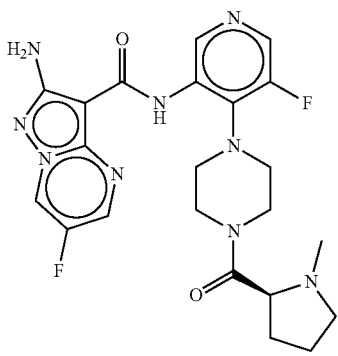
I-N-157

TABLE 2-continued
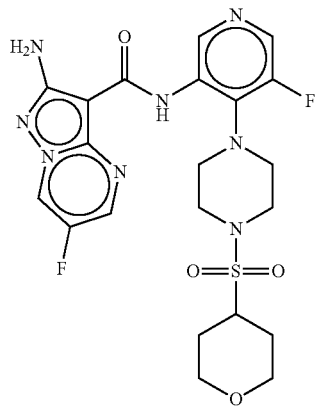 I-N-158
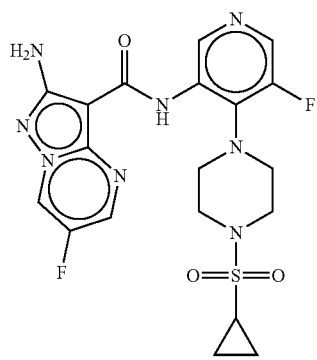 I-N-159
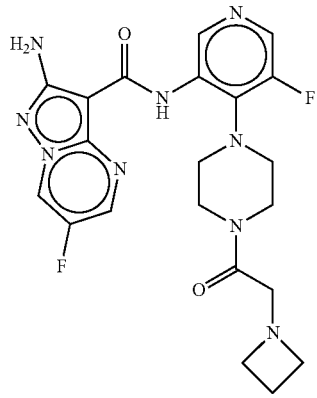 I-N-160
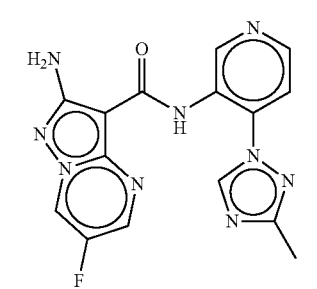 I-N-161
TABLE 2-continued
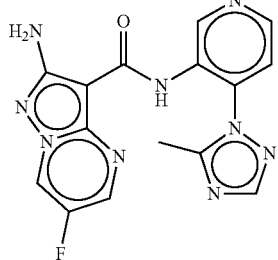 I-N-162
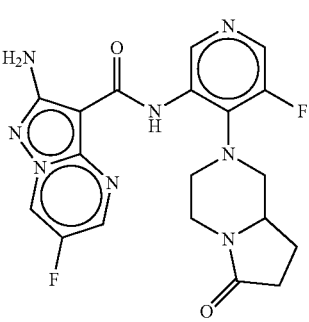 I-N-163
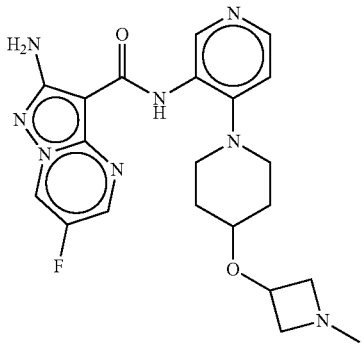 I-N-164
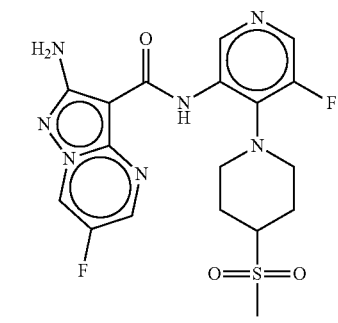 I-N-165

TABLE 2-continued
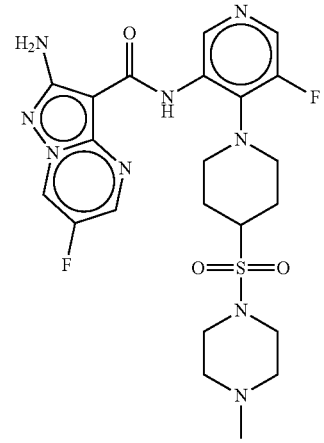
I-N-166
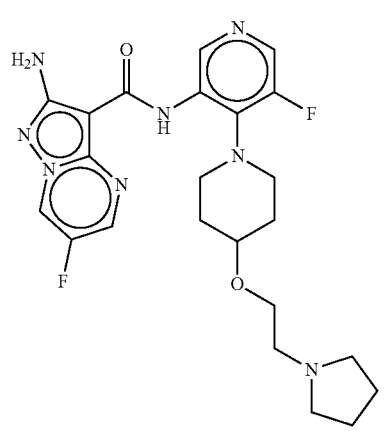
I-N-167
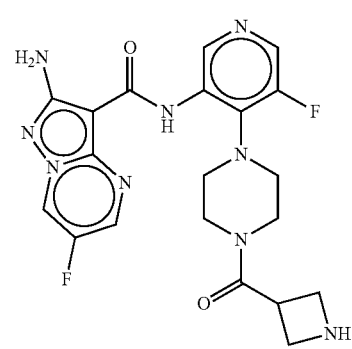
I-N-168
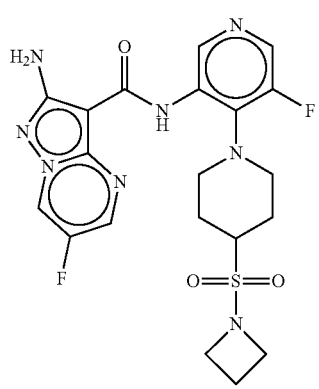
I-N-169
TABLE 2-continued
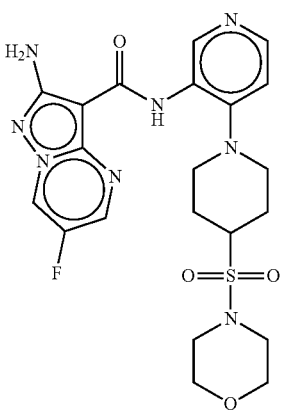
I-N-170
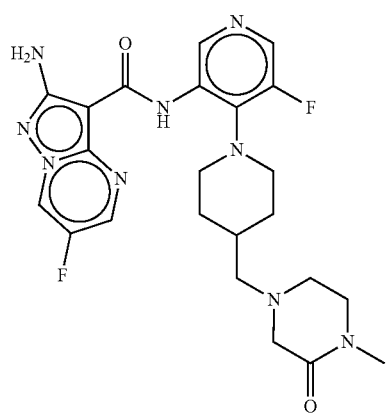
I-N-171
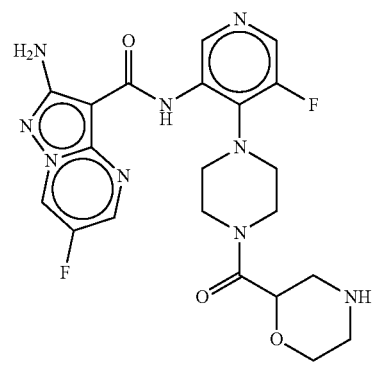
I-N-172
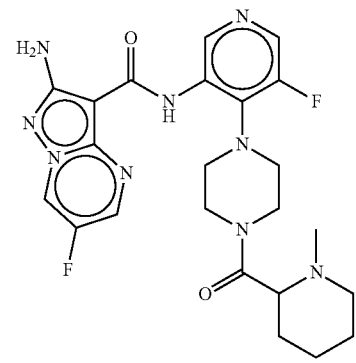
I-N-173

TABLE 2-continued
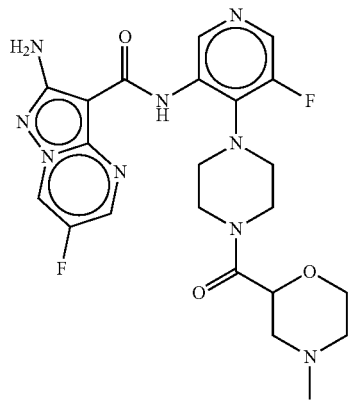 I-N-174
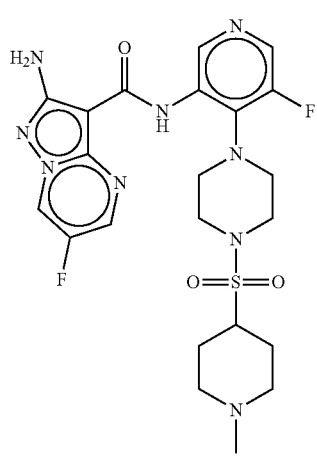 I-N-175
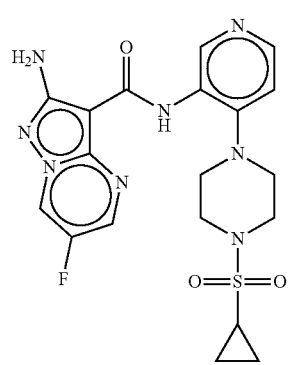 I-N-176
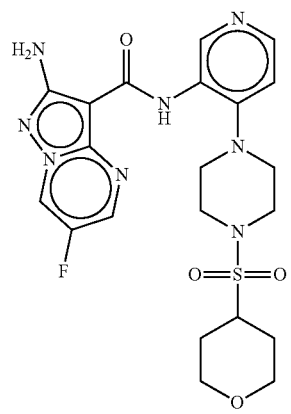 I-N-177
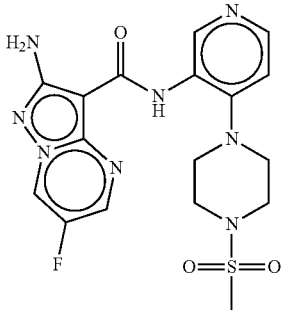 I-N-178
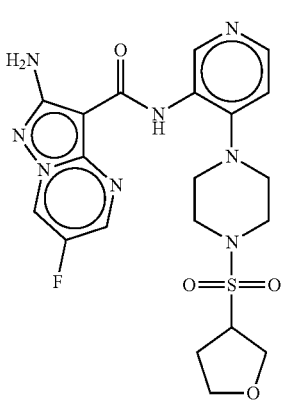 I-N-179
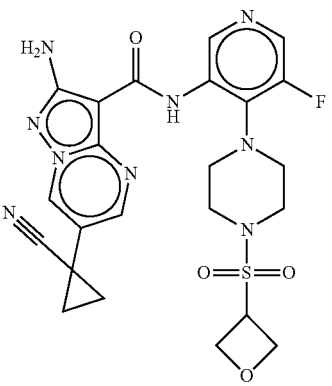 I-N-180
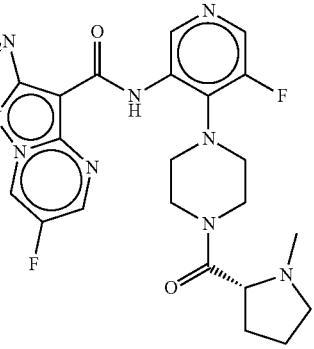 I-N-181

TABLE 2-continued
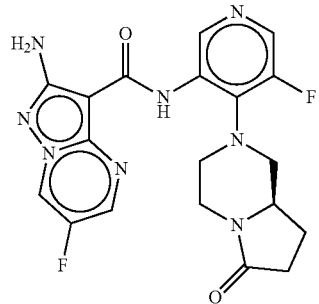
I-N-182
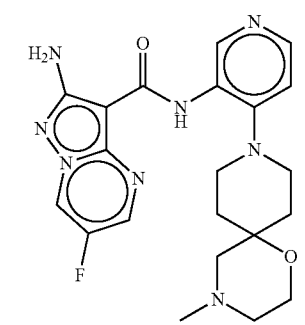
I-N-183
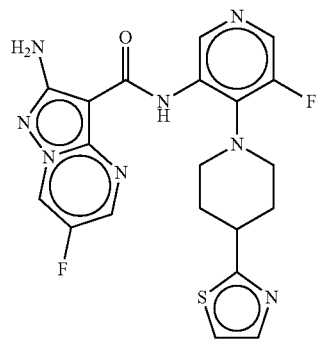
I-N-184
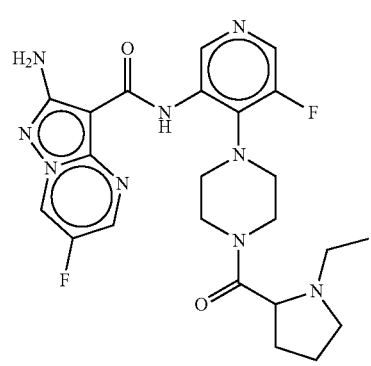
I-N-185
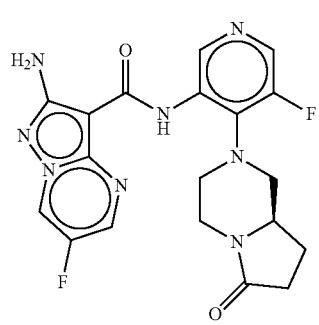
I-N-186
TABLE 2-continued
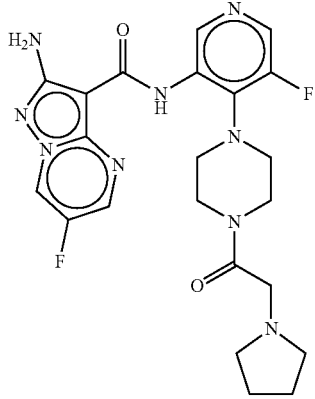
I-N-187
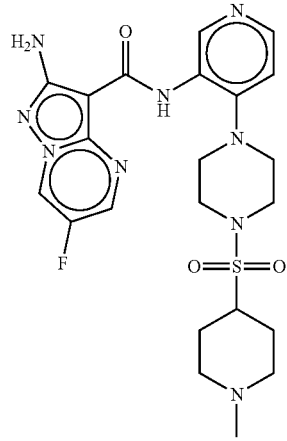
I-N-188
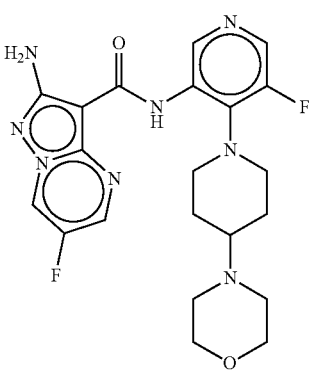
I-N-189
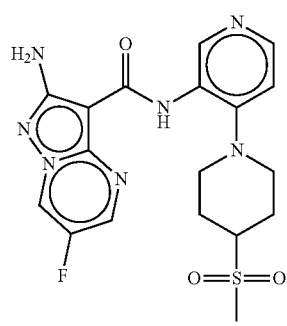
I-N-190

TABLE 2-continued
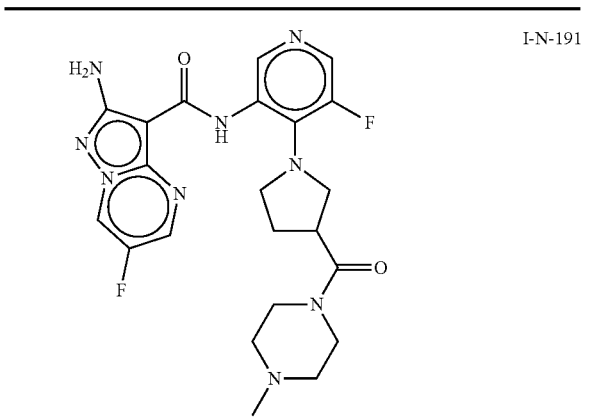 I-N-191
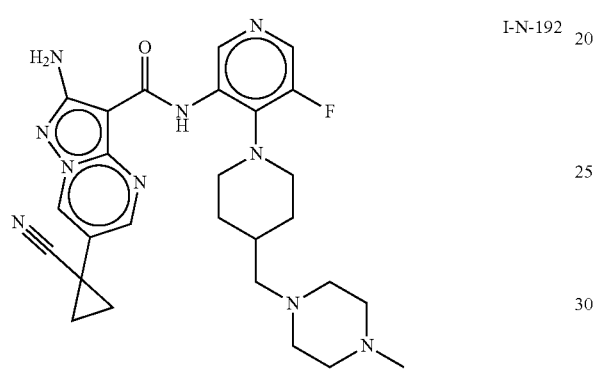 I-N-192
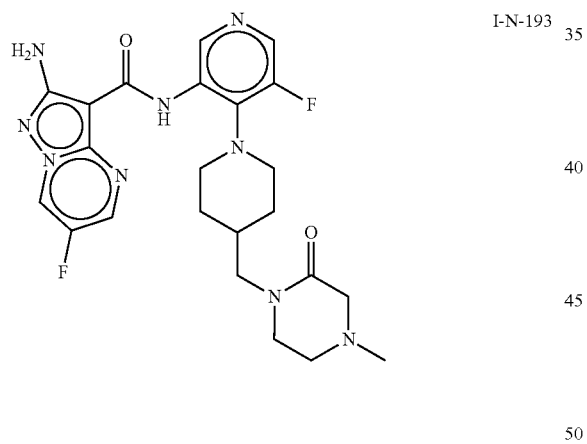 I-N-193
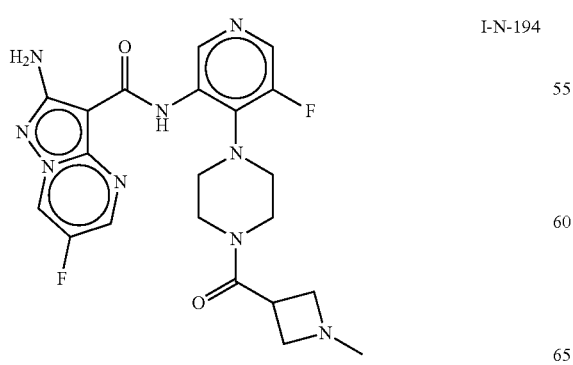 I-N-194
TABLE 2-continued
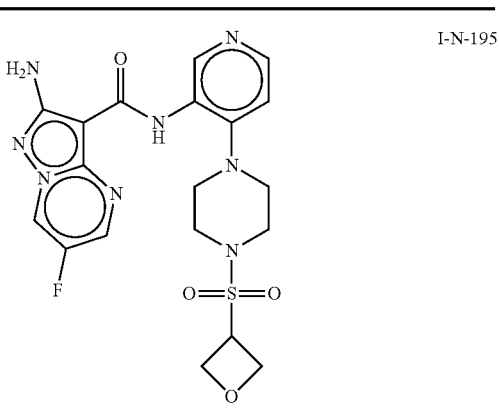 I-N-195
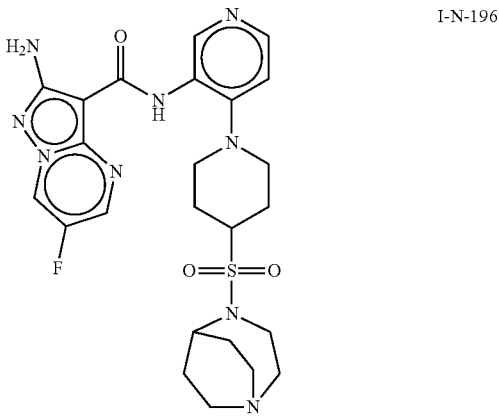 I-N-196
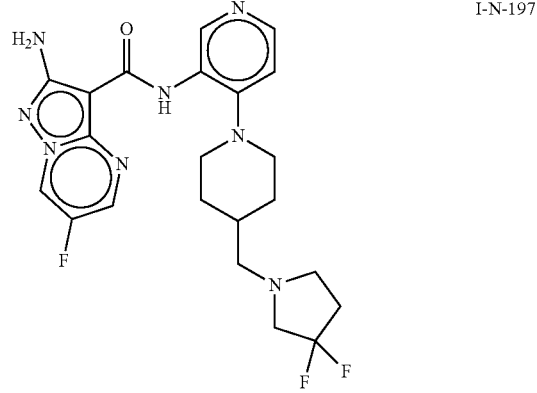 I-N-197
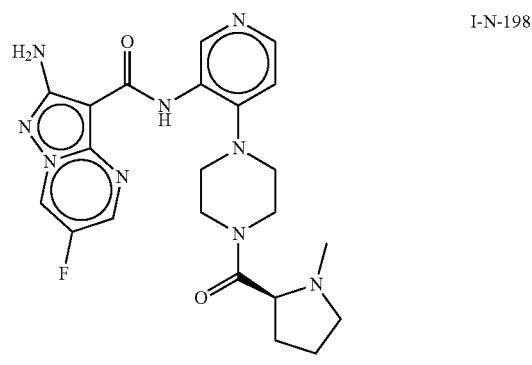 I-N-198

TABLE 2-continued
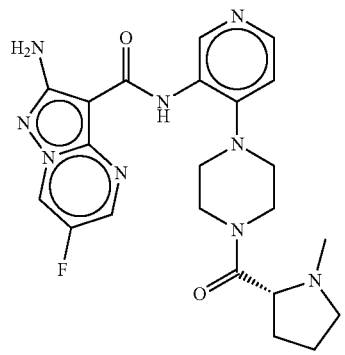
I-N-199
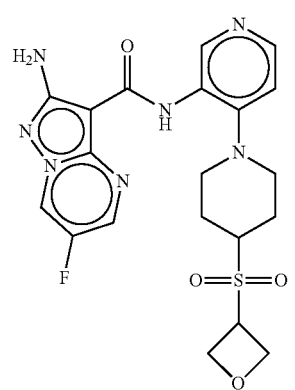
I-N-200
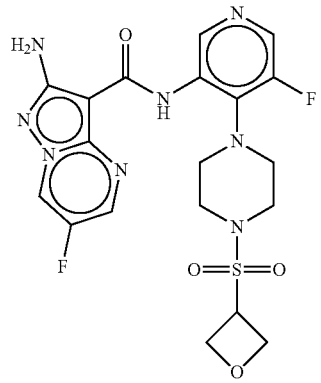
I-N-201
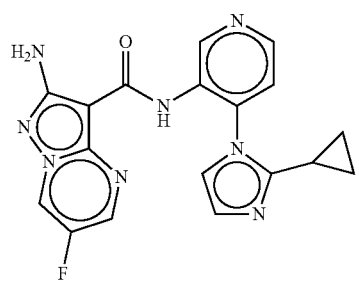
I-N-202
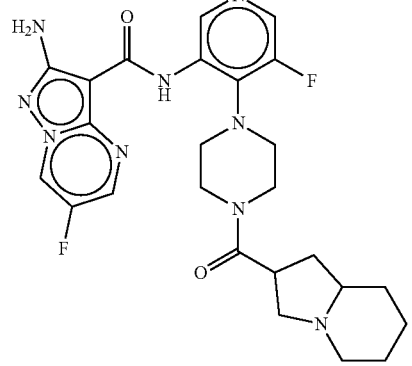
I-N-203
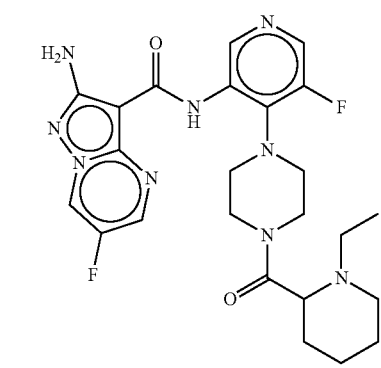
I-N-204
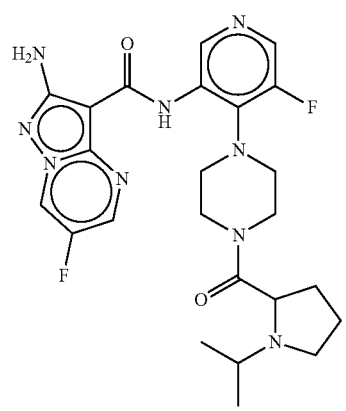
I-N-205
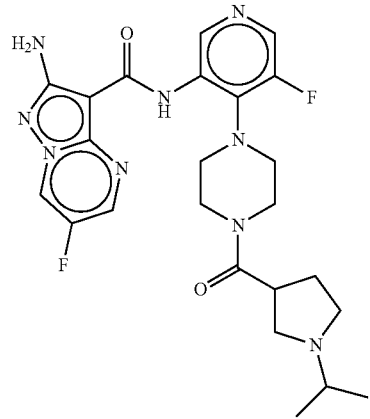
I-N-206

TABLE 2-continued
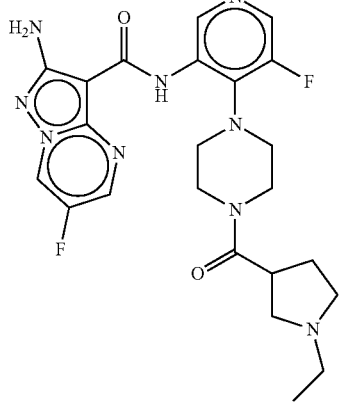
I-N-207
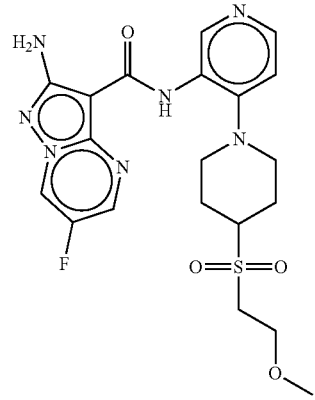
I-N-208
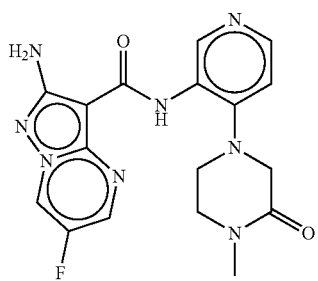
I-N-209
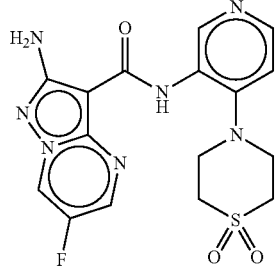
I-N-210
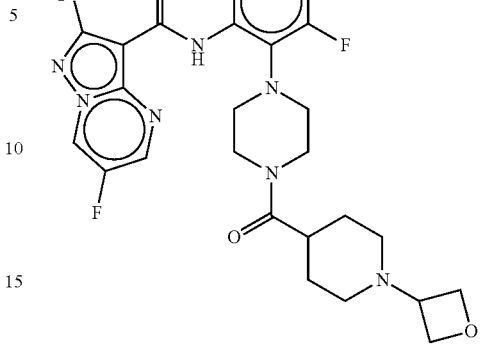
I-N-211
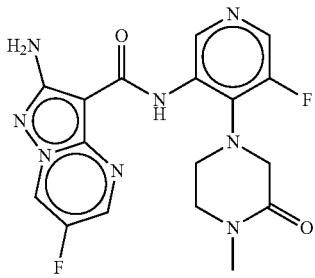
I-N-212
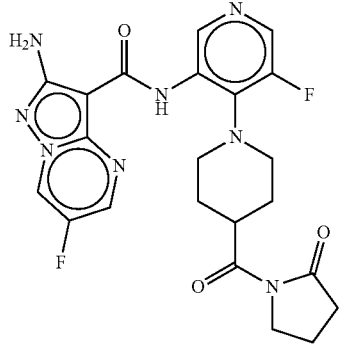
I-N-213
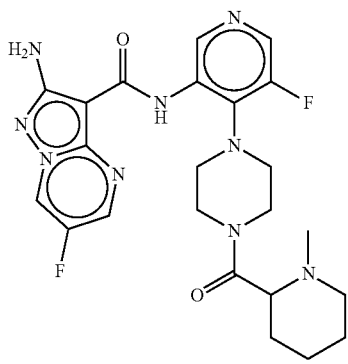
I-N-214

TABLE 2-continued
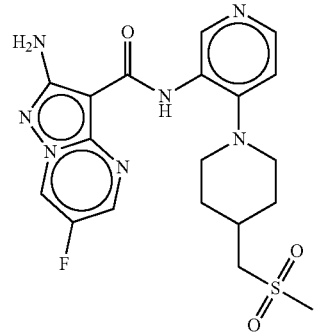 I-N-215
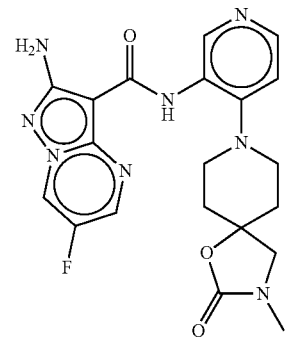 I-N-216
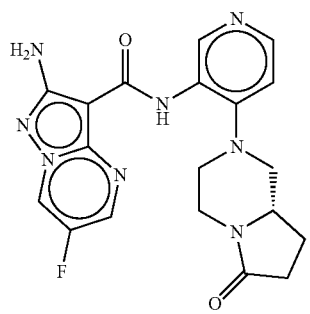 I-N-217
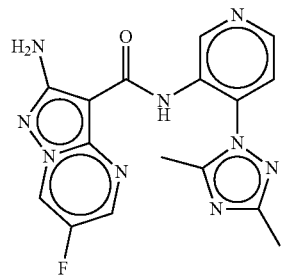 I-N-218
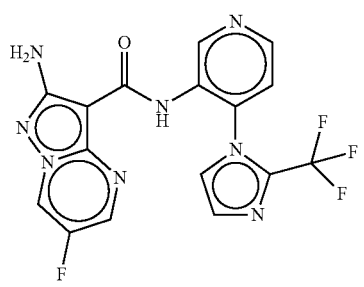 I-N-219
TABLE 2-continued
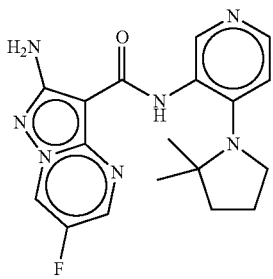 I-N-220
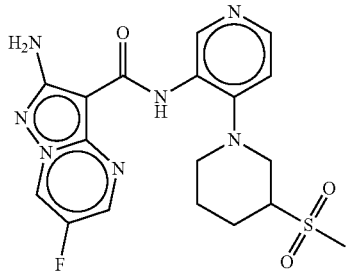 I-N-221
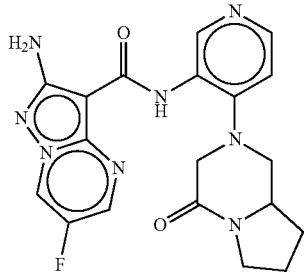 I-N-222
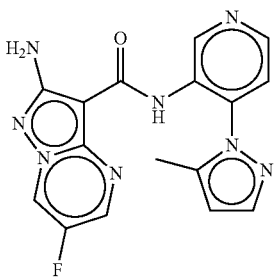 I-N-223
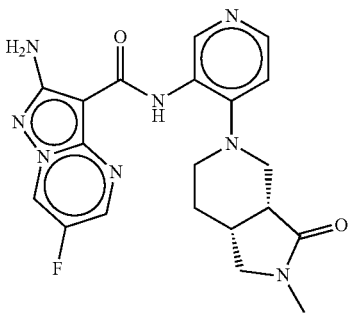 I-N-224

TABLE 2-continued
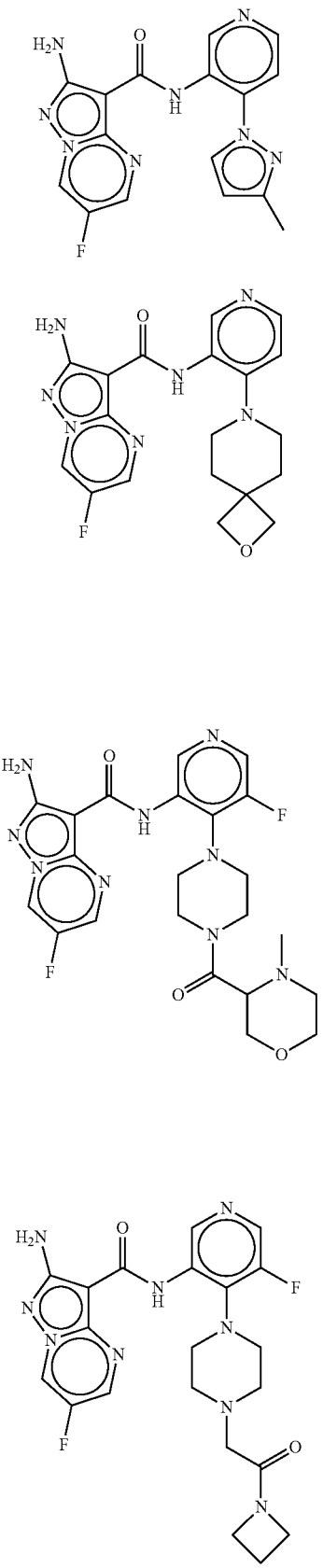
I-N-225
I-N-226
I-N-227
I-N-228
TABLE 2-continued
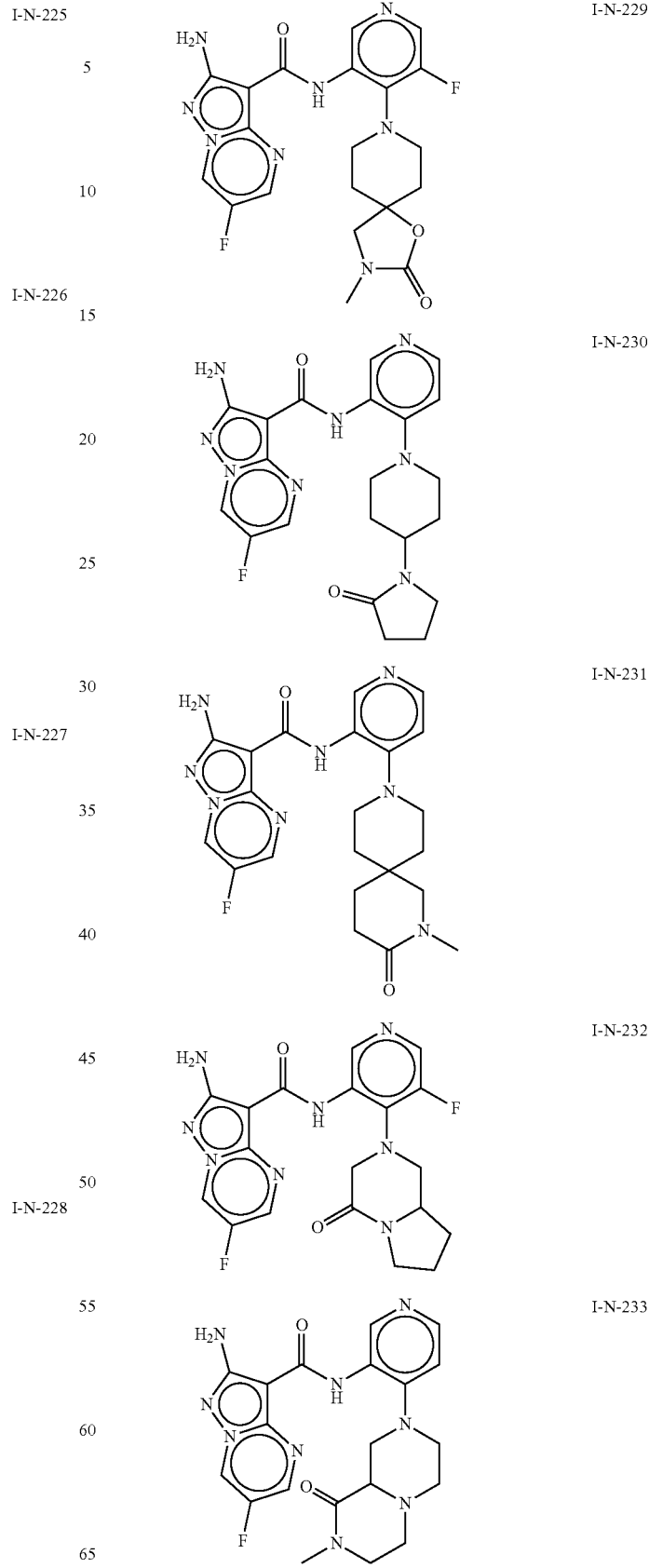
I-N-229
I-N-230
I-N-231
I-N-232
I-N-233

TABLE 2-continued
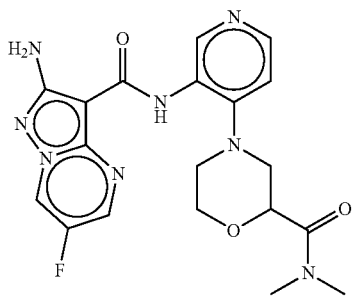 I-N-234
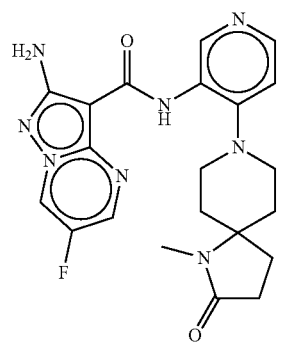 I-N-235
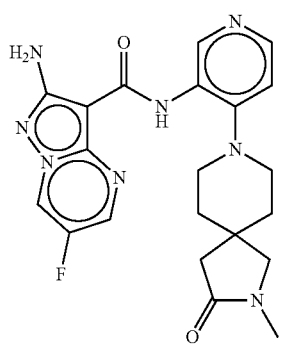 I-N-236
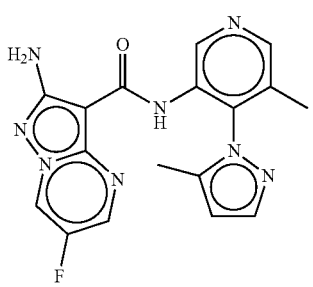 I-N-237
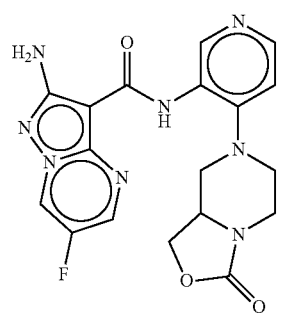 I-N-238
TABLE 2-continued
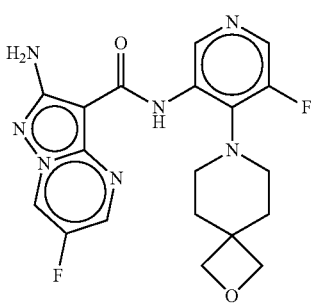 I-N-239
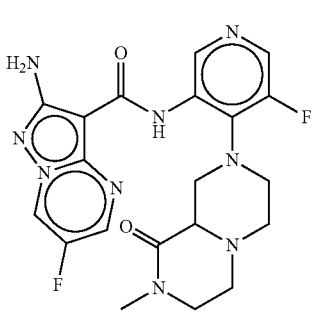 I-N-240
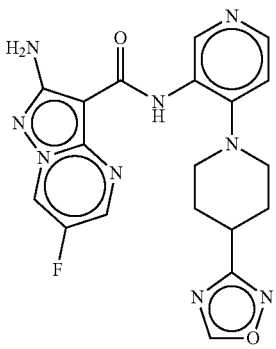 I-N-241
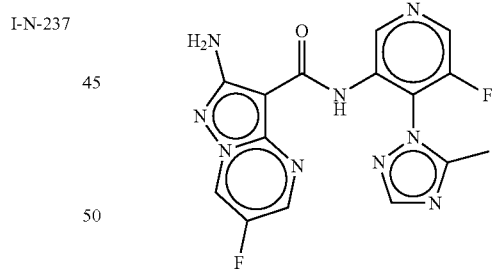 I-N-242
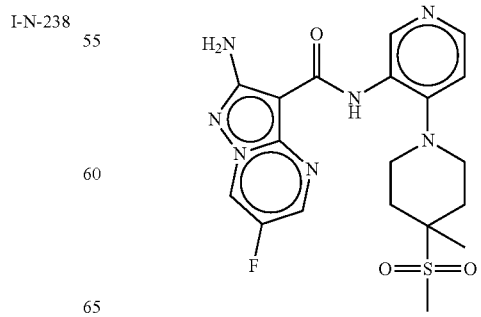 I-N-243

TABLE 2-continued
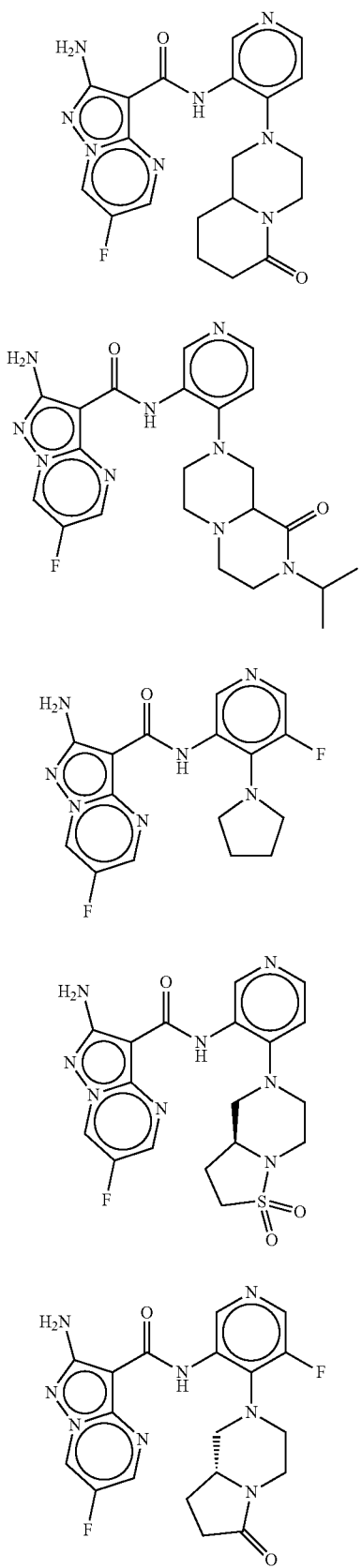
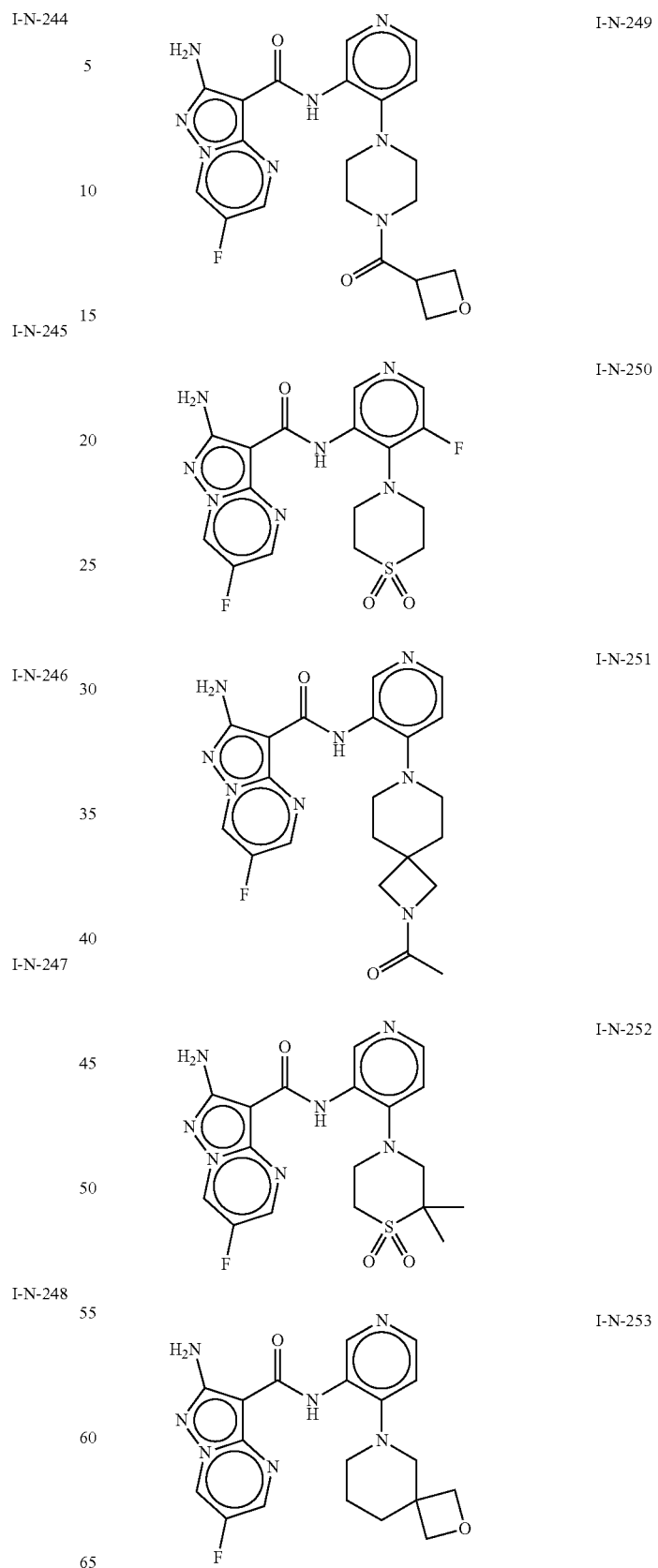

TABLE 2-continued
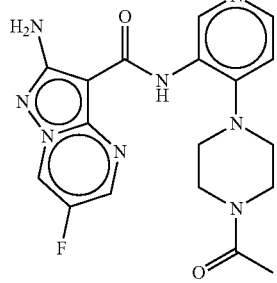 I-N-254
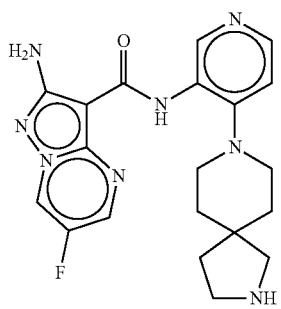 I-N-255
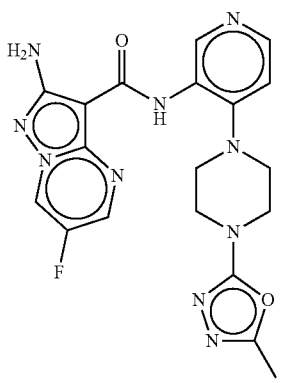 I-N-256
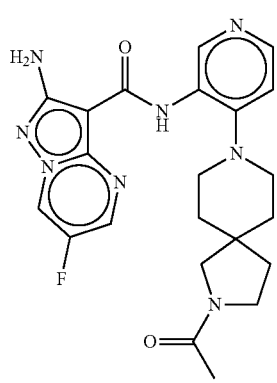 I-N-257
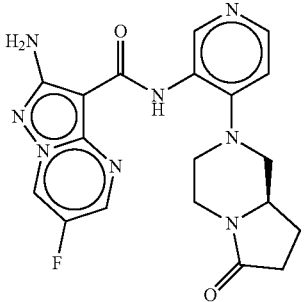 I-N-258
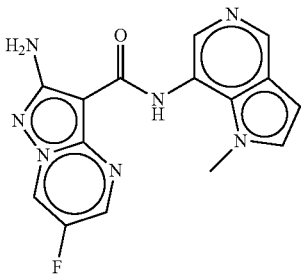 I-N-259
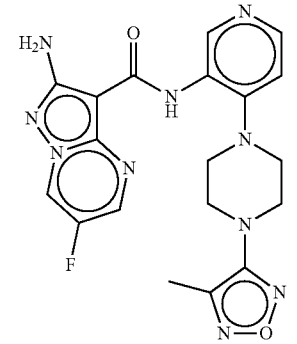 I-N-260
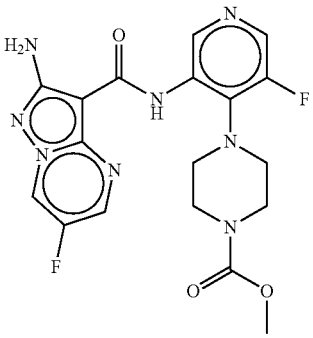 I-N-261
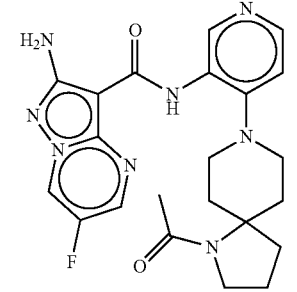 I-N-262

TABLE 2-continued
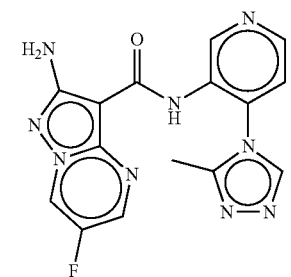
I-N-263
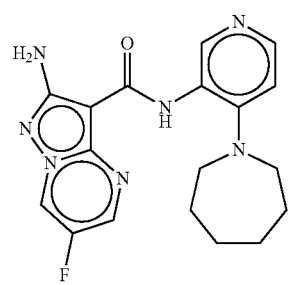
I-N-264
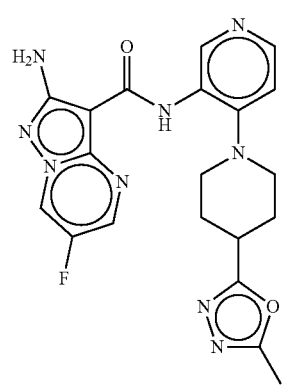
I-N-265
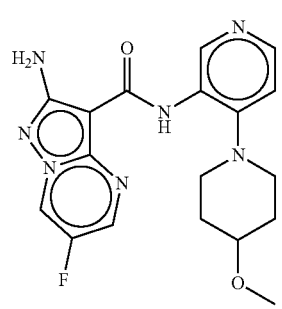
I-N-266
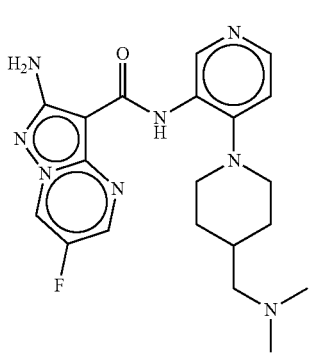
I-N-267
TABLE 2-continued
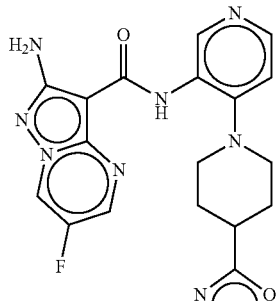
I-N-268
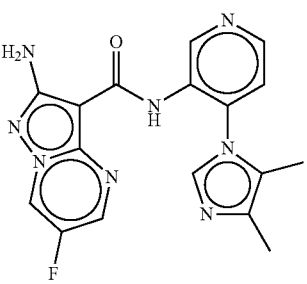
I-N-269
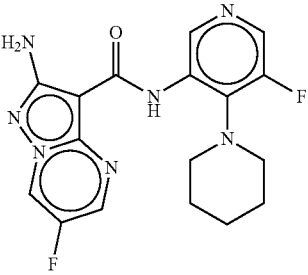
I-N-270
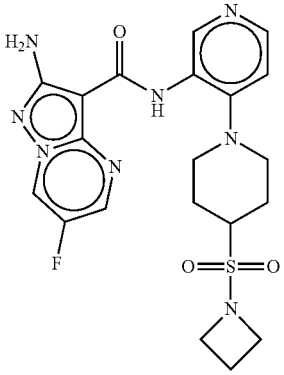
I-N-271
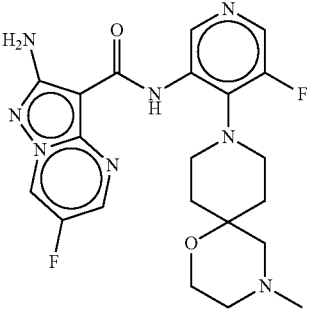
I-N-272

TABLE 2-continued
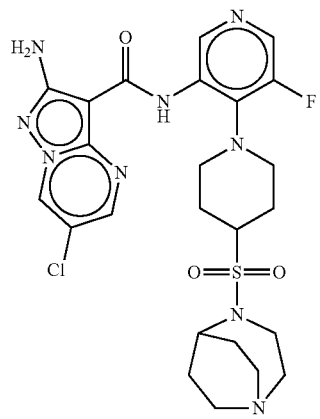
I-N-273
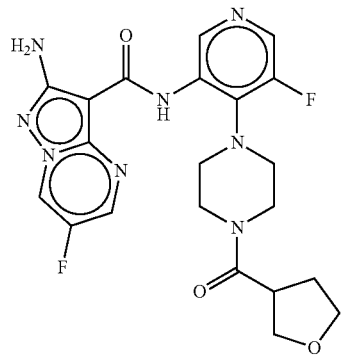
I-N-274
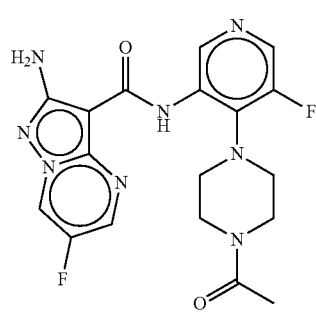
I-N-275
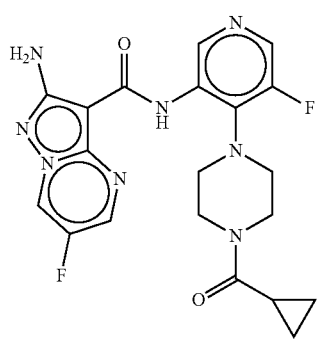
I-N-276
TABLE 2-continued
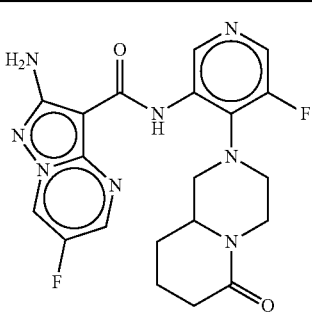
I-N-277
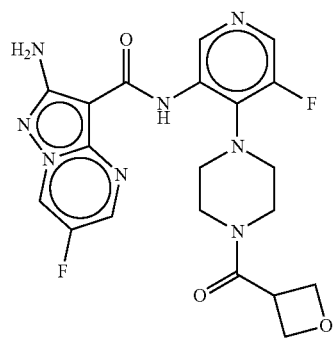
I-N-278
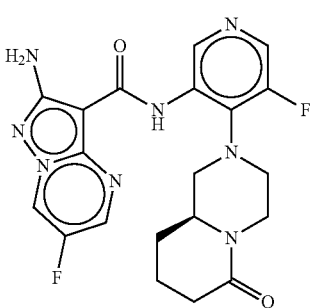
I-N-279
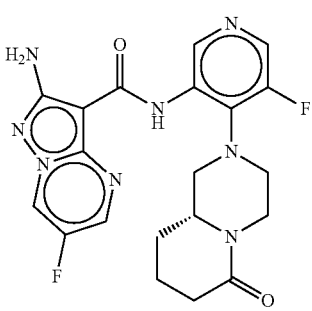
I-N-280
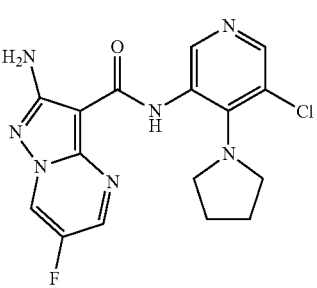 [SMILES: Nc1nn2cc(F)cnc2c1C(=O)Nc1cncc(Cl)c1N1CCCC1]
I-N-281

TABLE 2-continued
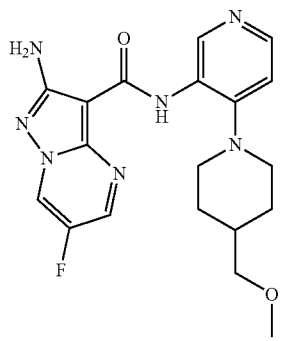 [SMILES: COCC1CCN(c2ccncc2NC(=O)c2c(N)nn3cc(F)cnc23)CC1]
I-N-282
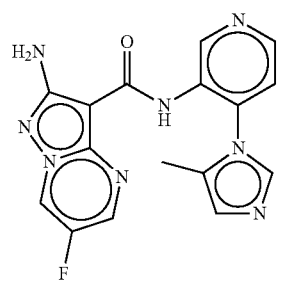
I-N-283
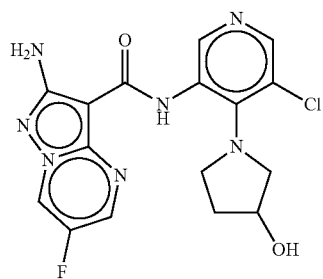
I-N-284
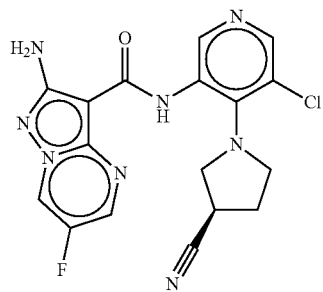
I-N-285
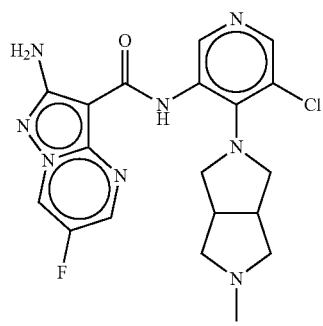
I-N-286
TABLE 2-continued
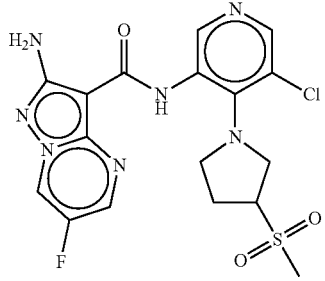
I-N-287
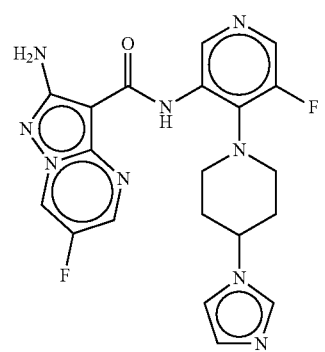
I-N-288
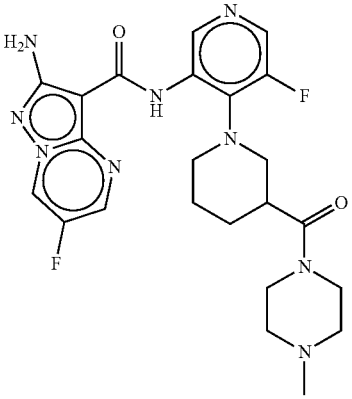
I-N-289
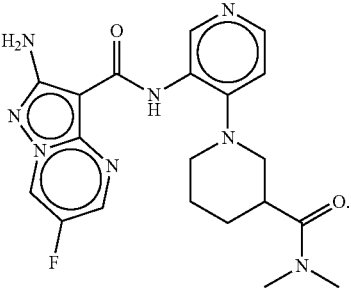
I-N-290

In other embodiments, the compounds of the present invention are selected from one of the following:

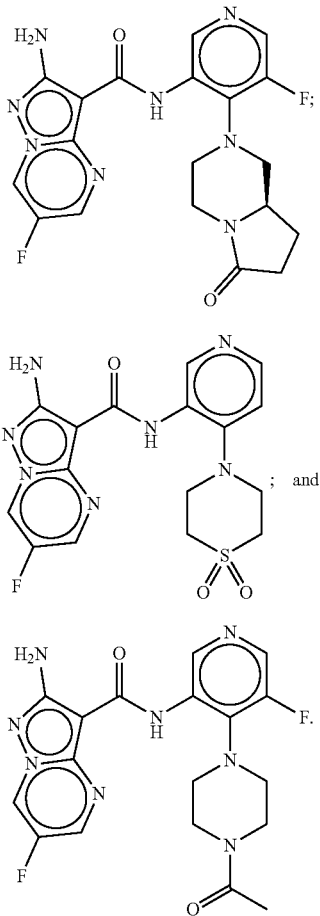

I-N-182

I-N-210

I-N-275

In another example, the present invention is a compound represented by structural formula I or I-A, wherein R⁴ is Ring B, which is represented by the structure:

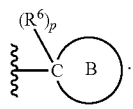

In some embodiments, the present invention is a compound represented by structural formula I or I-A, wherein p is 1.

In another embodiment, the present invention is a compound represented by structural formula I or I-A, wherein when p is 1, Ring B is a 3-7 membered cycloaliphatic or heterocyclyl ring having 1-2 heteroatoms selected from oxygen, nitrogen or sulfur. In other embodiments, the present invention is a compound represented by structural formula I or I-A, wherein when p is 1, Ring B is independently selected from selected from cyclopropyl, cyclobutyl, cyclopentyl, cyclohexyl, cycloheptyl, pyrrolidinyl, piperidinyl, azepanyl, pyrazolidinyl, isoxazolidinyl, oxazolidinyl, thiazolidinyl, imidazolidinyl, piperazinyl, morpholinyl, thiomorpholinyl, 1,3-oxazinanyl, 1,3-thiazinanyl, dihydropyridinyl, dihydroimidazolyl, 1,3-tetrahydropyrimidinyl, dihydropyrimidinyl, 1,4-diazepanyl, 1,4-oxazepanyl, 1,4-thiazepanyl, 1,2,3,6-tetrahydropyridine, and azetidinyl. In still other embodiments, the present invention is a compound represented by structural formula I or I-A, wherein Ring B is piperidinyl.

In some embodiments, the present invention is a compound represented by structural formula I or I-A, wherein when R⁴ is Ring B, $J^Q$ is —C(O)— or $C_{1-4}$alkyl. In some embodiments, the present invention is a compound represented by structural formula I or I-A, wherein when R⁴ is Ring B, $J^Q$ is $C_{1-4}$alkyl.

In yet another embodiment, the present invention is a compound represented by structural formula I or I-A, wherein when R⁴ is Ring B, $J^Q$ is $Q^2$. In some embodiments, when R⁴ is Ring B, the present invention is a compound represented by structural formula I or I-A, wherein $Q^2$ is independently selected from $Q^2$ is independently selected from oxetanyl, tetrahydropyranyl, tetrahydrofuranyl, cyclopropyl, azetidinyl, pyrrolidinyl, piperazinyl, piperidinyl, cyclobutyl, thiomorpholinyl, or morpholinyl. In other embodiments, the present invention is a compound represented by structural formula I or I-A, wherein when R⁴ is Ring B, $Q^2$ is oxetanyl.

In one embodiment, the present invention is a compound represented by structural formula I or I-A, wherein p is 0.

In some embodiments, the present invention is a compound represented by structural formula I or I-A, wherein when p is 0, Ring B is independently selected from phenyl, pyridinyl, pyrazinyl, pyrimidinyl, tetrahydropyridinyl, pyridizinyl, or pyrazolyl. In yet another embodiment, the present invention is a compound represented by structural formula I or I-A, wherein when p is 0, Ring B is imidazolyl. In other embodiments, the present invention is a compound represented by structural formula I or I-A, wherein when p is 0, Ring B is independently selected from phenyl or pyridinyl.

In another embodiment, the present invention is a compound represented by structural formula I or I-A, wherein R⁴ is —CH₂—(R⁷). In yet another embodiment, the present invention is a compound represented by structural formula I or I-A, wherein R⁷ is H.

In still other embodiments, the present invention is a compound represented by structural formula I or I-A, wherein R³ and R⁴, taken together with the atoms to which they are bound, form a 5-6 membered non-aromatic ring having 0-2 heteroatoms selected from oxygen.

In some embodiments, the present invention is a compound represented by structural formula I or I-A, wherein $J^Z$ is independently selected from →O or $C_{1-4}$alkyl.

In another example, the present invention is a compound represented by structural formula I or I-A, wherein the compounds of this invention are represented in Table 3.

TABLE 3

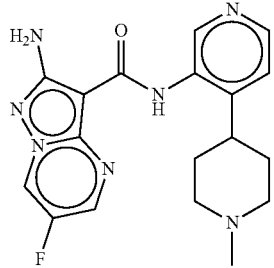

I-C-1

TABLE 3-continued
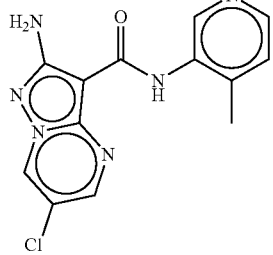 I-C-2
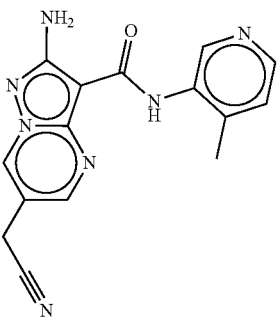 I-C-3
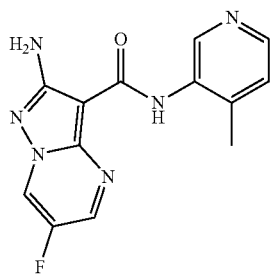 [SMILES: Cc1ccncc1NC(=O)c1c(N)nn2cc(F)cnc12] I-C-4
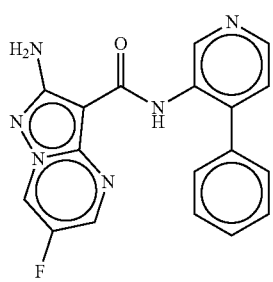 I-C-5
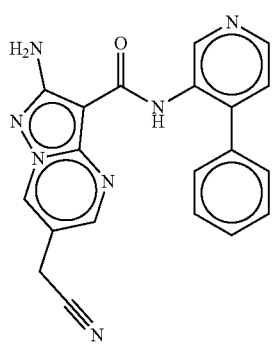 I-C-6
TABLE 3-continued
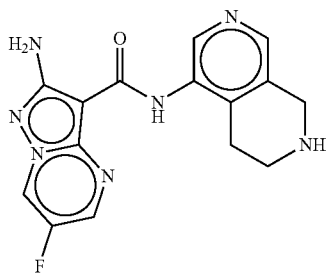 I-C-7
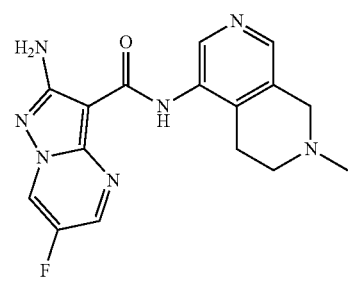 [SMILES: CN1CCc2c(cncc2NC(=O)c2c(N)nn3cc(F)cnc23)C1] I-C-8
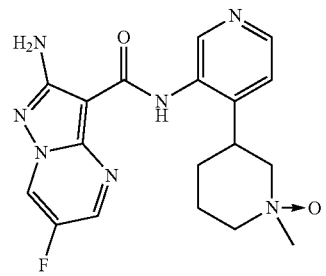 [SMILES: C[N+]1([O-])CCCC(c2ccncc2NC(=O)c2c(N)nn3cc(F)cnc23)C1] I-C-9
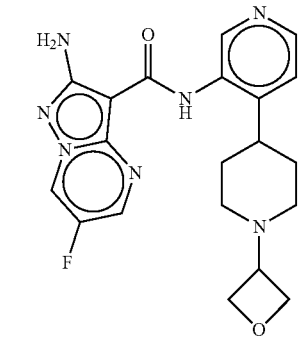 I-C-10
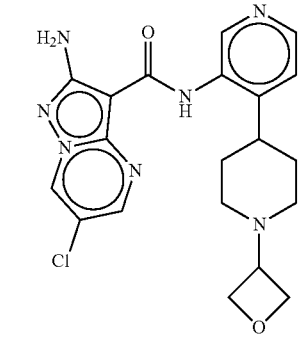 I-C-11

TABLE 3-continued
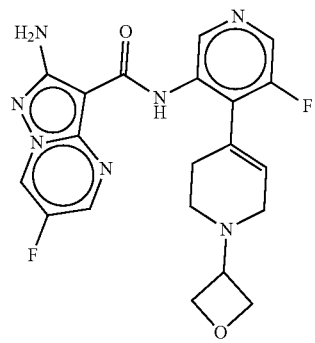
I-C-12
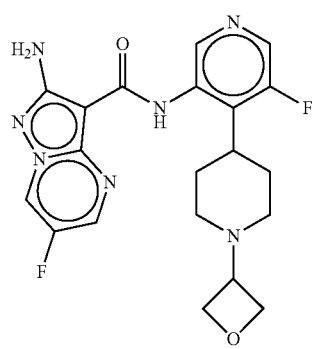
I-C-13
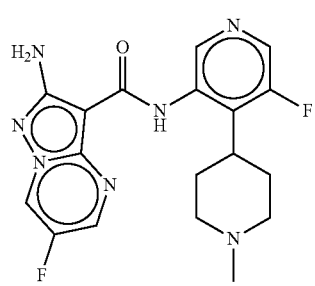
I-C-14
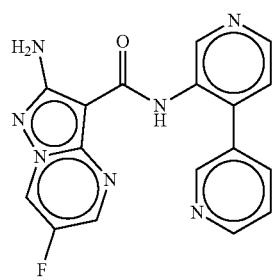
I-C-15
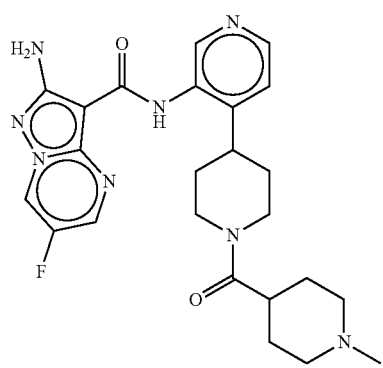
I-C-16
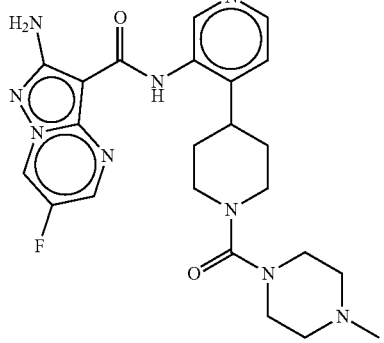
I-C-17
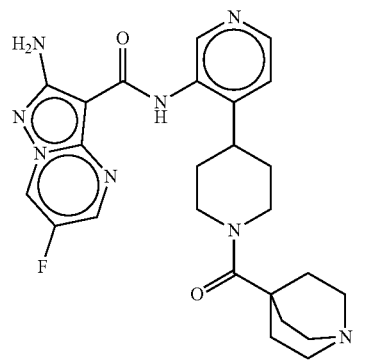
I-C-18
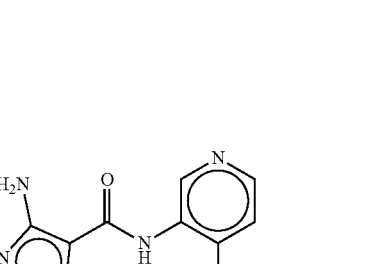
I-C-19
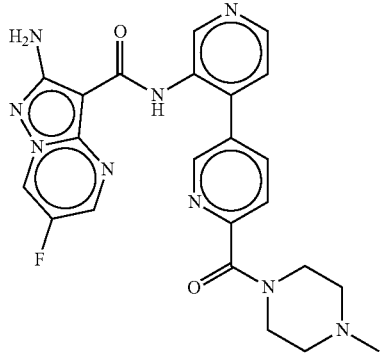
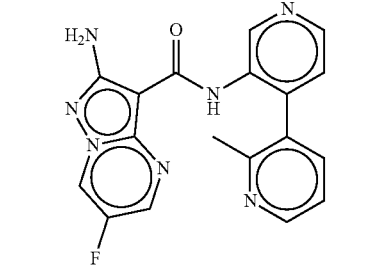
I-C-20

TABLE 3-continued
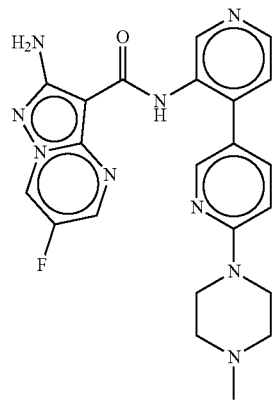
I-C-21
I-C-22
I-C-23
I-C-24
I-C-25
TABLE 3-continued
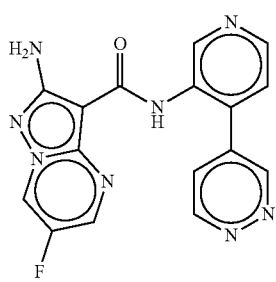
I-C-26
I-C-27
I-C-28
I-C-29
I-C-30

TABLE 3-continued
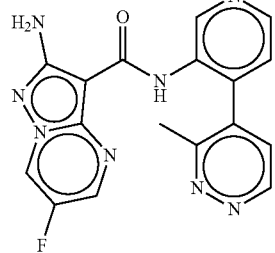
I-C-31
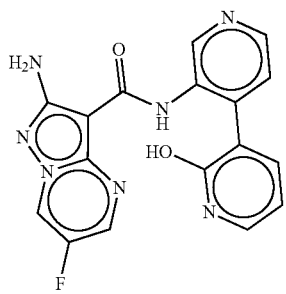
I-C-32
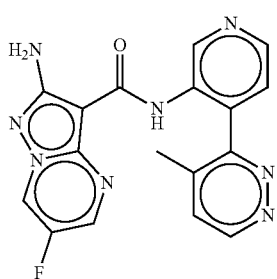
I-C-33
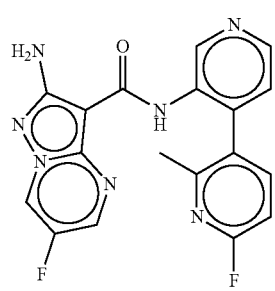
I-C-34
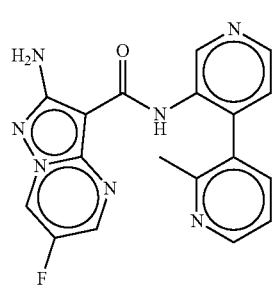
I-C-35
TABLE 3-continued
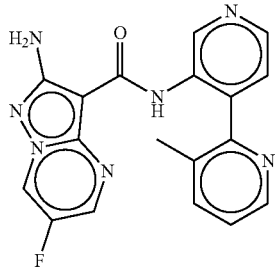
I-C-36
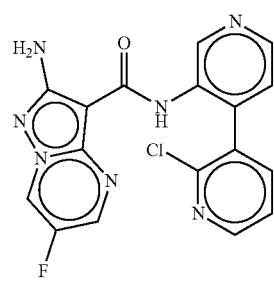
I-C-37
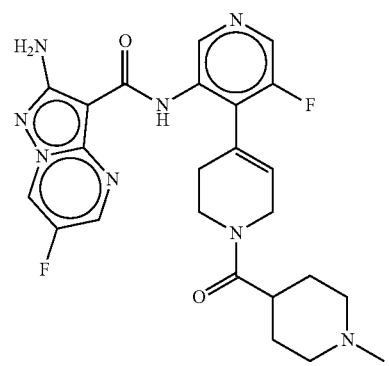
I-C-38
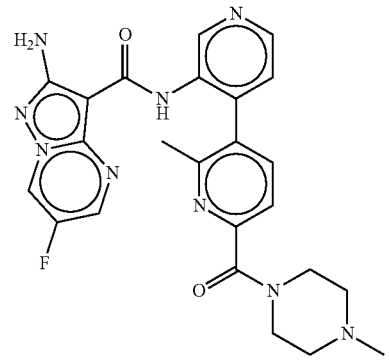
I-C-39

TABLE 3-continued
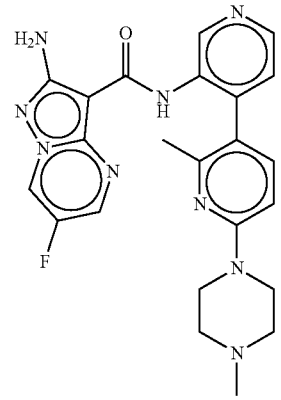 I-C-40
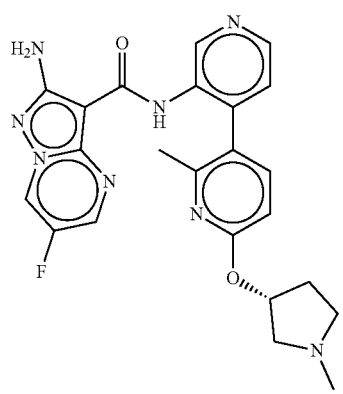 I-C-41
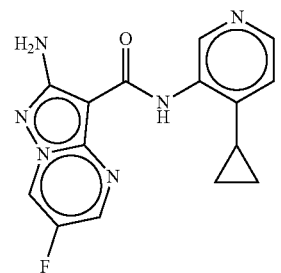 I-C-42
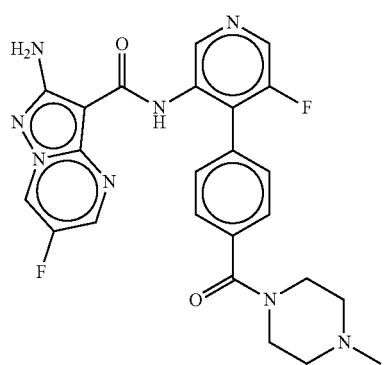 I-C-43
TABLE 3-continued
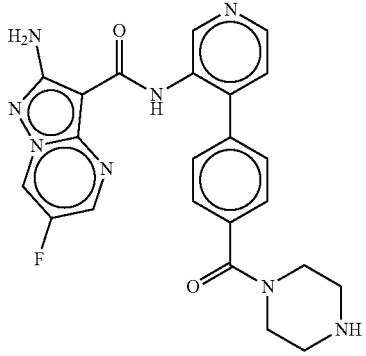 I-C-44
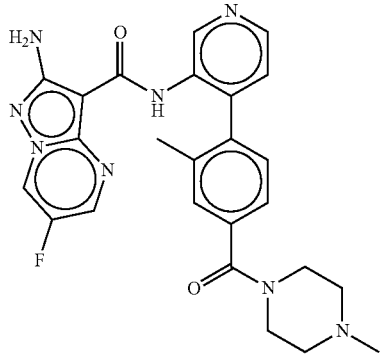 I-C-45
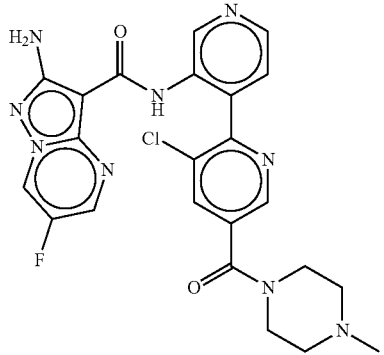 I-C-46
I-C-47

TABLE 3-continued
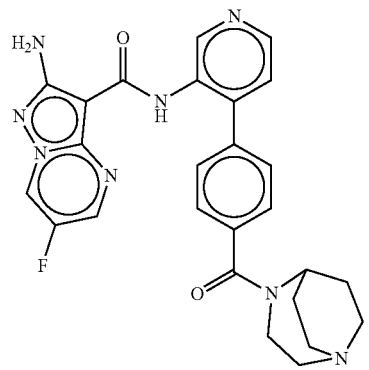
I-C-48
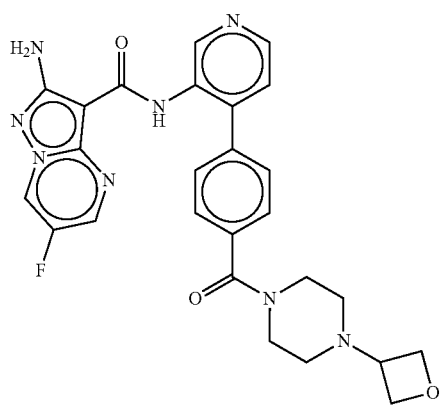
I-C-49
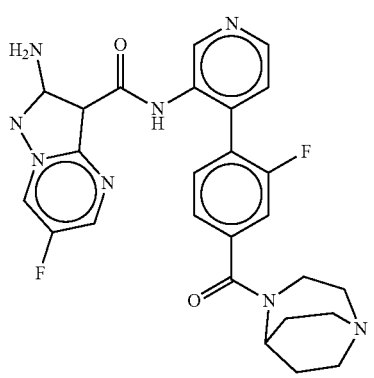
I-C-50
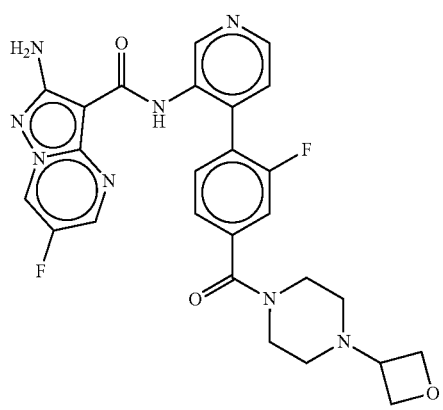
I-C-51
TABLE 3-continued
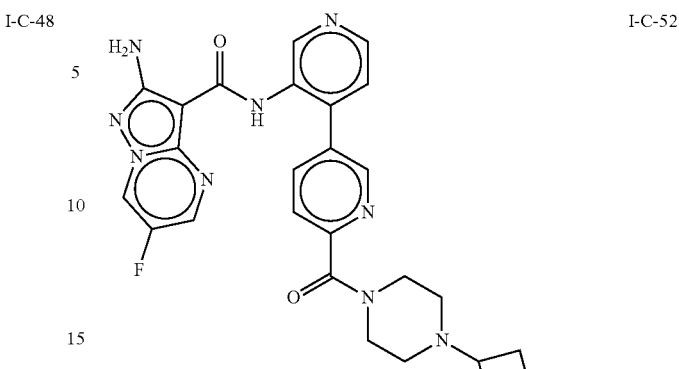
I-C-52
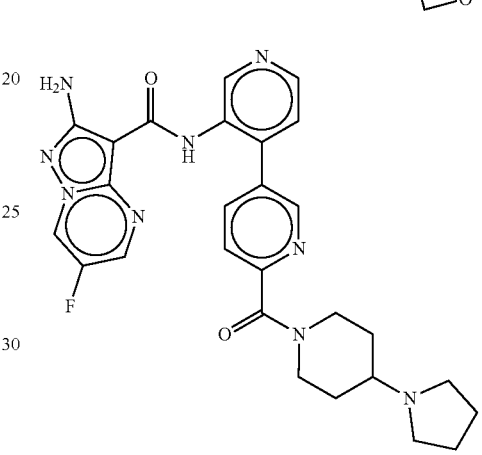
I-C-53
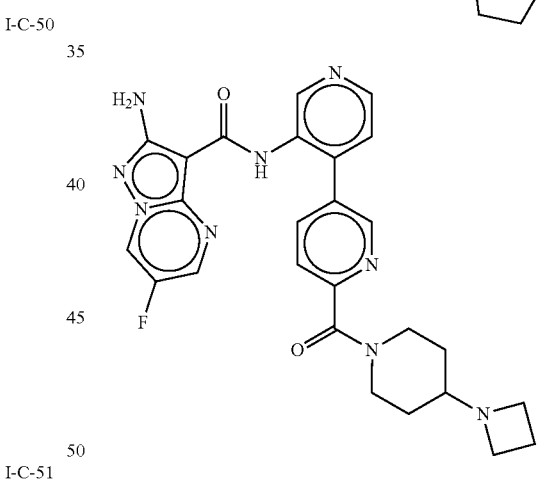
I-C-54
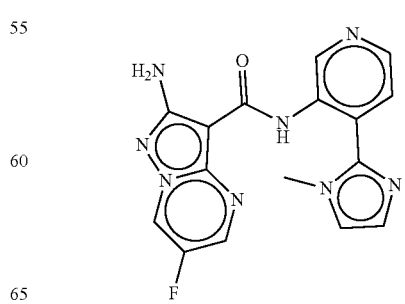
I-C-55

TABLE 3-continued
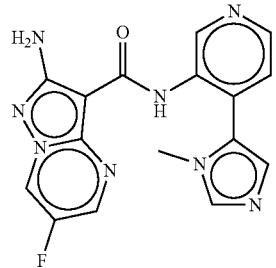 I-C-56
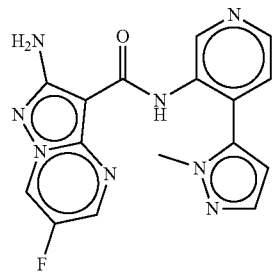 I-C-57
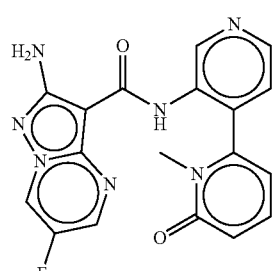 I-C-58
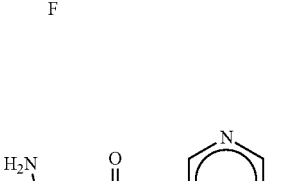 I-C-59
 I-C-60
TABLE 3-continued
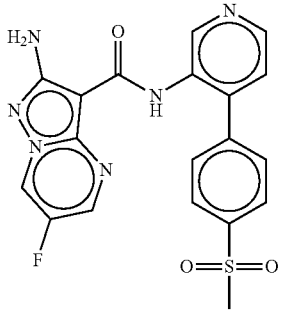 I-C-61
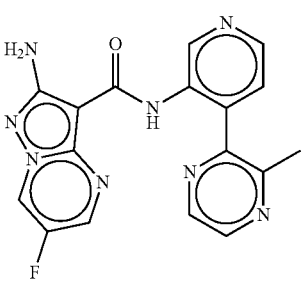 I-C-62
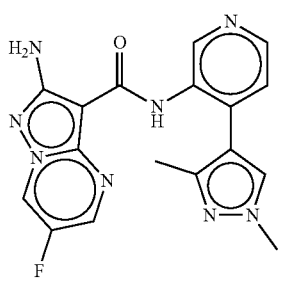 I-C-63
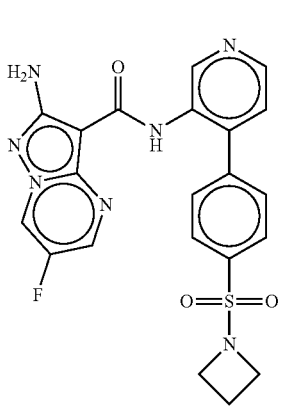 I-C-64
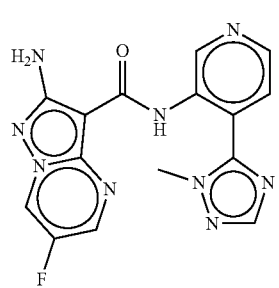 I-C-65

TABLE 3-continued
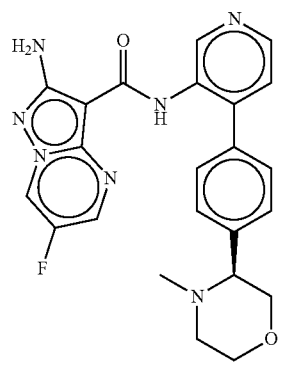
I-C-66
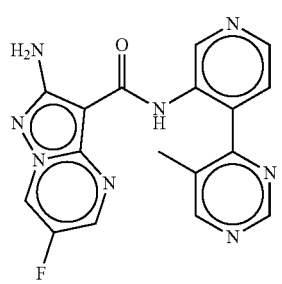
I-C-67
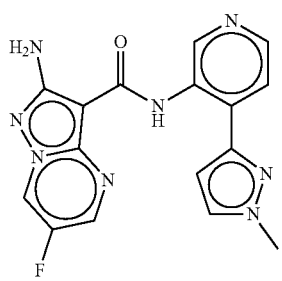
I-C-68
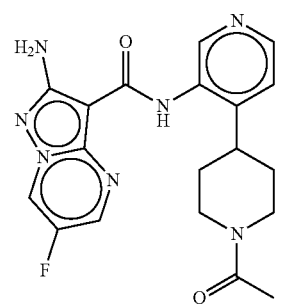
I-C-69
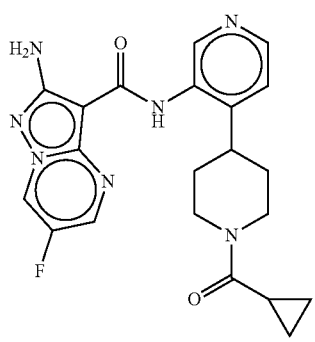
I-C-70
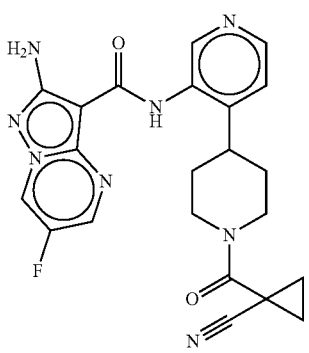
I-C-71
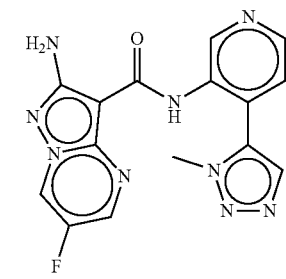
I-C-72
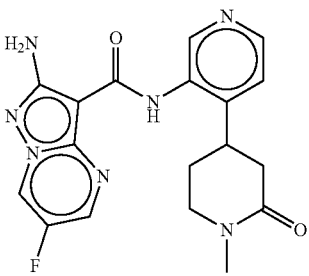
I-C-73
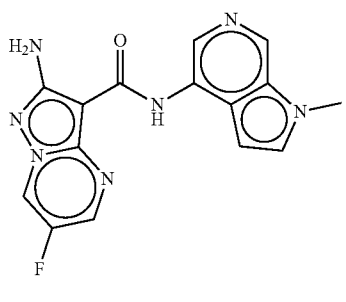
I-C-74
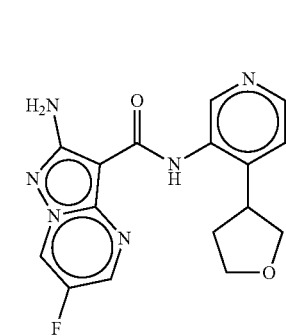
I-C-75

TABLE 3-continued
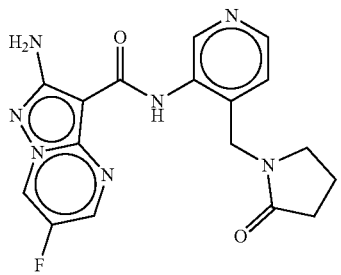  I-C-76
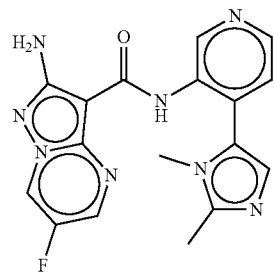  I-C-77
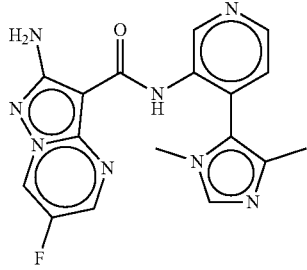  I-C-78
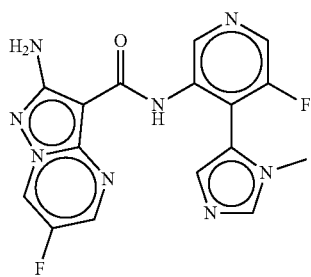  I-C-79
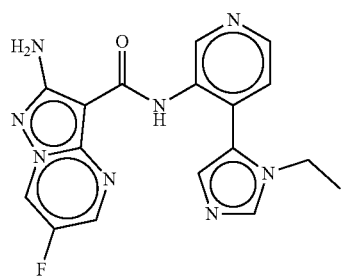  I-C-80
TABLE 3-continued
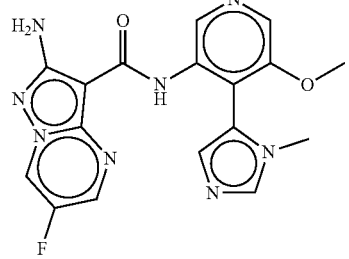  I-C-81
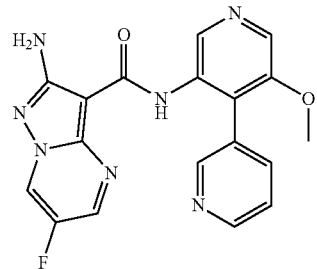  I-C-82
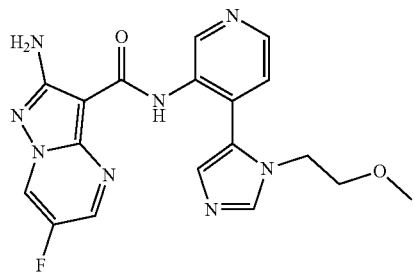 [SMILES: COCCn1cncc1-c1ccncc1NC(=O)c1c(N)nn2cc(F)cnc12]  I-C-83
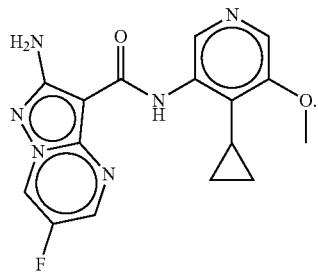  I-C-84
In another embodiment, the compounds of the present invention are selected from one of the following:
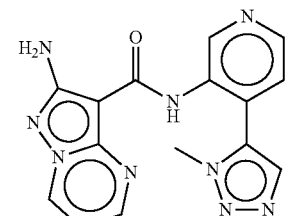  I-C-72
and -continued

I-C-79

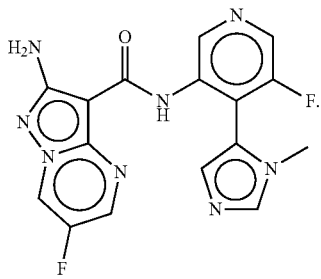

A compound having the formula I-B:

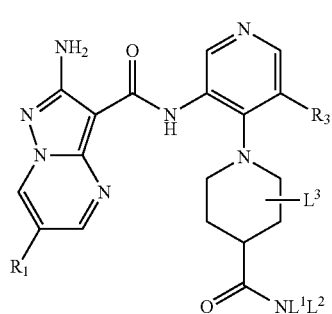

or a pharmaceutically acceptable salt or prodrug thereof, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form an optionally substituted 3-4 membered carbocyclic ring;

$R^3$ is independently selected from H; chloro; fluoro; $C_{1-4}$alkyl optionally substituted with 1-3 occurrences of halo; $C_{3-4}$ cycloalkyl; —CN; or a $C_{1-3}$ aliphatic chain wherein up to two methylene units of the aliphatic chain are optionally replaced with —O—, —NR—, —C(O)—, or —S(O)$_n$;

$L^1$ is H; a 3-7 membered aromatic or non-aromatic ring having 0-2 heteroatoms selected from oxygen nitrogen or sulfur; or a $C_{1-6}$ aliphatic chain wherein up to two methylene units of the aliphatic chain are optionally replaced with —O—, —NR—, —C(O)—, or —S(O)$_n$; each $L^1$ is optionally substituted with $C_{1-4}$ aliphatic; —CN; halo; —OH; or a 3-6 membered non-aromatic ring having 0-2 heteroatoms selected from oxygen, nitrogen, or sulfur;

$L^2$ is H; a 3-7 membered aromatic or non-aromatic ring having 0-2 heteroatoms selected from oxygen nitrogen or sulfur; or a $C_{1-6}$ aliphatic chain wherein up to two methylene units of the aliphatic chain are optionally replaced with —O—, —NR—, —C(O)—, or —S(O)$_n$; each $L^2$ is optionally substituted with $C_{1-4}$ aliphatic; —CN; halo; —OH; or a 3-6 membered non-aromatic ring having 0-2 heteroatoms selected from oxygen, nitrogen, or sulfur; or $L^1$ and $L^2$, together with the nitrogen to which they are attached, form a Ring D; Ring D is optionally substituted with 0-5 occurrences of $J^G$;

Ring D is independently selected from a 3-7 membered heterocyclyl ring having 1-2 heteroatoms selected from oxygen, nitrogen or sulfur; or an 7-12 membered fully saturated or partially unsaturated bicyclic ring having 1-5 heteroatoms selected from oxygen, nitrogen, or sulfur;

$J^G$ is independently selected from halo; —N(R$^o$)$_2$; a 3-6 membered carbocyclyl; a 3-6 membered heterocyclyl having 1-2 heteroatoms selected from oxygen nitrogen, or sulfur; or a $C_{1-4}$ alkyl chain wherein up to two methylene units of the alkyl chain are optionally replaced with —O—, —NR—, —C(O)—, or —S(O)$_n$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from oxygen, nitrogen, or sulfur;

two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from oxygen, nitrogen, or sulfur;

$L^3$ is independently selected from H; chloro; fluoro; $C_{1-4}$ alkyl optionally substituted with 1-3 occurrences of halo; —CN; or a $C_{1-3}$ aliphatic chain wherein up to two methylene units of the aliphatic chain are optionally replaced with —O—, —NR—, —C(O)—, or —S(O)$_n$;

n is 0, 1, or 2; and

R and R$^o$ are H or $C_{1-4}$ alkyl.

Another aspect of the present invention provides a compound of Formula I-B:

I-B

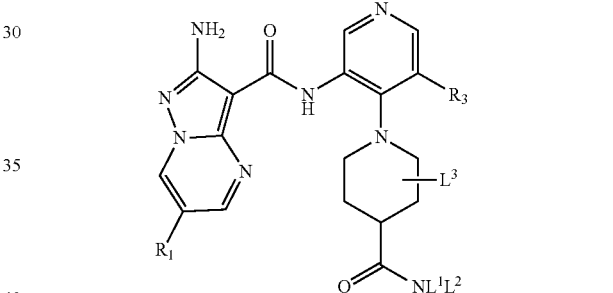

or a pharmaceutically acceptable salt or prodrug thereof, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form an optionally substituted 3-4 membered carbocyclic ring;

$R^3$ is independently selected from H; chloro; fluoro; $C_{1-4}$alkyl optionally substituted with 1-3 occurrences of halo; $C_{3-4}$ cycloalkyl; —CN; or a $C_{1-3}$ aliphatic chain wherein up to two methylene units of the aliphatic chain are optionally replaced with —O—, —NR—, —C(O)—, or —S(O)$_n$;

$L^1$ is H; a 3-7 membered aromatic or non-aromatic ring having 0-2 heteroatoms selected from oxygen nitrogen or sulfur; or a $C_{1-6}$ aliphatic chain wherein up to two methylene units of the aliphatic chain are optionally replaced with —O—, —NR—, —C(O)—, or —S(O)$_n$; each $L^1$ is optionally substituted with $C_{1-4}$ aliphatic; —CN; halo; —OH; or a 3-6 membered non-aromatic ring having 0-2 heteroatoms selected from oxygen, nitrogen, or sulfur;

$L^2$ is H; a 3-7 membered aromatic or non-aromatic ring having 0-2 heteroatoms selected from oxygen nitrogen or sulfur; or a $C_{1-6}$ aliphatic chain wherein up to two methylene units of the aliphatic chain are optionally replaced with —O—, —NR—, —C(O)—, or —S(O)$_n$; each $L^2$ is optionally substituted with $C_{1-4}$ aliphatic; —CN; halo; —OH; or a 3-6 membered non-aromatic ring having 0-2 heteroatoms selected from oxygen, nitrogen, or sulfur; or $L^1$ and $L^2$, together with the nitrogen to which they are attached, form a Ring D; Ring D is optionally substituted with 0-5 occurrences of $J^G$;

Ring D is independently selected from a 3-7 membered heterocyclyl ring having 1-2 heteroatoms selected from oxygen, nitrogen or sulfur; or an 7-12 membered fully saturated or partially unsaturated bicyclic ring having 1-5 heteroatoms selected from oxygen, nitrogen, or sulfur;

$J^G$ is independently selected from halo; —CN; —N$(R^o)_2$; a 3-6 membered carbocyclyl; a 3-6 membered heterocyclyl having 1-2 heteroatoms selected from oxygen nitrogen, or sulfur; or a $C_{1-4}$ alkyl chain wherein up to two methylene units of the alkyl chain are optionally replaced with —O—, —NR—, —C(O)—, or —S(O)$_n$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from oxygen, nitrogen, or sulfur;

two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from oxygen, nitrogen, or sulfur; n is 0, 1, or 2; and R and $R^o$ are H or $C_{1-4}$ alkyl.

Another aspect of the present invention provides a compound of Formula I-B:

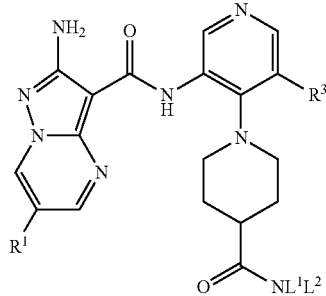

I-B or a pharmaceutically acceptable salt or prodrug thereof, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form an optionally substituted 3-4 membered carbocyclic ring;

$R^3$ is independently selected from H; chloro; fluoro; $C_{1-4}$alkyl optionally substituted with 1-3 occurrences of halo; $C_{3-4}$ cycloalkyl; —CN; or a $C_{1-3}$ aliphatic chain wherein up to two methylene units of the aliphatic chain are optionally replaced with —O—, —NR—, —C(O)—, or —S(O)$_n$;

$L^1$ is H; a 3-7 membered aromatic or non-aromatic ring having 0-2 heteroatoms selected from oxygen nitrogen or sulfur; or a $C_{1-6}$ aliphatic chain wherein up to two methylene units of the aliphatic chain are optionally replaced with —O—, —NR—, —C(O)—, or —S(O)$_n$; each $L^1$ is optionally substituted with $C_{1-4}$ aliphatic; —CN; halo; —OH; or a 3-6 membered non-aromatic ring having 0-2 heteroatoms selected from oxygen, nitrogen, or sulfur;

$L^2$ is H; a 3-7 membered aromatic or non-aromatic ring having 0-2 heteroatoms selected from oxygen nitrogen or sulfur; or a $C_{1-6}$ aliphatic chain wherein up to two methylene units of the aliphatic chain are optionally replaced with —O—, —NR—, —C(O)—, or —S(O)$_n$; each $L^2$ is optionally substituted with $C_{1-4}$ aliphatic; —CN; halo; —OH; or a 3-6 membered non-aromatic ring having 0-2 heteroatoms selected from oxygen, nitrogen, or sulfur; or $L^1$ and $L^2$, together with the nitrogen to which they are attached, form a Ring D; Ring D is optionally substituted with 0-5 occurrences of $J^G$;

Ring D is independently selected from a 3-7 membered heterocyclyl ring having 1-2 heteroatoms selected from oxygen, nitrogen or sulfur; or an 7-12 membered fully saturated or partially unsaturated bicyclic ring having 1-5 heteroatoms selected from oxygen, nitrogen, or sulfur;

$J^G$ is independently selected from halo; →O; —CN; —$(R^o)_2$; a 3-6 membered carbocyclyl; a 3-6 membered heterocyclyl having 1-2 heteroatoms selected from oxygen nitrogen, or sulfur; or a $C_{1-4}$ alkyl chain wherein up to two methylene units of the alkyl chain are optionally replaced with —O—, —NR—, —C(O)—, or —S(O)$_n$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from oxygen, nitrogen, or sulfur;

two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from oxygen, nitrogen, or sulfur; n is 0, 1, or 2; and R and $R^o$ are H or $C_{1-4}$ alkyl.

Another aspect of the present invention provides a compound of Formula I-B:

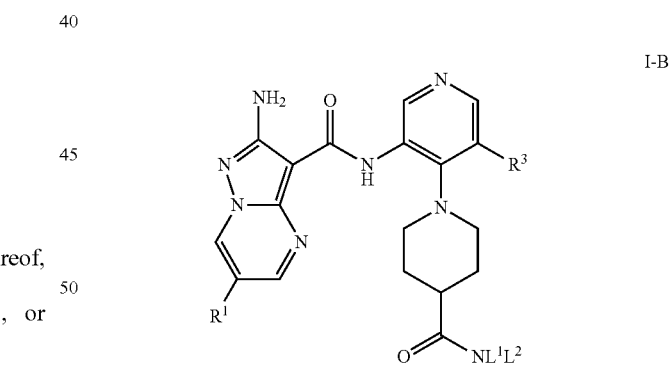

I-B or a pharmaceutically acceptable salt or prodrug thereof, wherein:

$R^1$ is independently selected from fluoro, chloro, or —C($J^1$)$_2$CN;

$J^1$ is independently selected from H or $C_{1-2}$alkyl; or two occurrences of $J^1$, together with the carbon atom to which they are attached, form an optionally substituted 3-4 membered carbocyclic ring;

$R^3$ is independently selected from H; chloro; fluoro; $C_{1-4}$alkyl optionally substituted with 1-3 occurrences of halo; $C_{3-4}$ cycloalkyl; or —CN;

$L^1$ is an optionally substituted $C_{1-6}$ aliphatic;

$L^2$ is an optionally substituted $C_{1-6}$ aliphatic; or

L¹ and L², together with the nitrogen to which they are attached, form a Ring D; Ring D is optionally substituted with 0-5 occurrences of J$^G$;

Ring D is independently selected from a 3-7 membered heterocyclyl ring having 1-2 heteroatoms selected from oxygen, nitrogen or sulfur; or an 8-12 membered fully saturated or partially unsaturated bicyclic ring having 0-5 heteroatoms selected from oxygen, nitrogen, or sulfur;

J$^G$ is independently selected from C$_{1-4}$alkyl, —N(R°)$_2$, or a 3-5 membered carbocycyl; or two occurrences of J$^G$, together with Ring D, form a 6-10 membered saturated or partially unsaturated bridged ring system; and R° is H or C$_{1-4}$alkyl.

In another example, R¹ of formula I-B is fluoro. In yet another example, R¹ of formula I-B is —CH$_2$CN. In still other examples, R¹ of formula I-B is chloro.

In some embodiments, R³ of formula I-B is independently selected from H, chloro, fluoro, cyclopropyl, or C$_{1-4}$alkyl. In one or more embodiments, R³ of formula I-B is independently selected from H, chloro, or fluoro. In yet another embodiment, R³ of formula I-B is H. In other embodiments, R³ of formula I-B is chloro. In still other embodiments, R³ of formula I-B is fluoro.

In another embodiment, the present invention is a compound represented by structural formula I-B, wherein L¹ and L² are independently selected from H; —(C$_{1-3}$alkyl)O(C$_{1-2}$alkyl); —(C$_{1-3}$ alkyl)N(C$_{1-2}$alkyl)$_2$; C$_{1-4}$alkyl; azetidinyl; piperidinyl; oxytanyl; or pyrrolidinyl. In another embodiment, the present invention is a compound represented by structural formula I-B, wherein L¹ and L² are C$_{1-3}$alkyl.

In other embodiments, the present invention is a compound represented by structural formula I-B, wherein L¹ and L², together with the nitrogen to which they are attached, form Ring D. In yet another embodiment, the present invention is a compound represented by structural formula I-B, wherein Ring D is a 3-7 membered heterocyclyl ring having 1-2 heteroatoms selected from oxygen, nitrogen, or sulfur. In some embodiments, the present invention is a compound represented by structural formula I-B, wherein Ring D is independently selected from piperazinyl, piperidinyl, morpholinyl, tetrahydropyranyl, azetidinyl, pyrrolidinyl, or 1,4-diazepanyl. In another embodiment, the present invention is a compound represented by structural formula I-B, wherein Ring D is piperazinyl, piperidinyl, 1,4-diazepanyl, pyrrolidinyl or azetidinyl. In still other embodiments, the present invention is a compound represented by structural formula I-B, wherein Ring D is piperidinyl or piperazinyl. In still other embodiments, Ring D is piperazinyl.

In one or more aspects, the present invention is a compound represented by structural formula I-B, wherein Ring D is an 8-12 membered fully saturated or partially unsaturated bicyclic ring having 0-5 heteroatoms selected from oxygen, nitrogen, or sulfur. In other examples, the present invention is a compound represented by structural formula I-B, wherein Ring D is octahydropyrrolo[1,2-a]pyrazine or octahydropyrrolo[3,4-c]pyrrole. In another example, Ring D is octahydropyrrolo[1,2-a]pyrazine.

In yet another example, the present invention is a compound represented by structural formula I-B, wherein J$^G$ is halo, C$_{1-4}$alkyl, —O(C$_{1-3}$alkyl), C$_{3-6}$cycloalkyl, a 3-6 membered heterocyclyl, —NH(C$_{1-3}$ alkyl), —OH, or —N(C$_{1-4}$ alkyl)$_2$. In other embodiments, the present invention is a compound represented by structural formula I-B, wherein J$^G$ is methyl, —N(C$_{1-4}$ alkyl)$_2$, ethyl, —O(C$_{1-3}$ alkyl), cyclopropyl, oxetanyl, cyclobutyl, pyrrolidinyl, piperidinyl, or azetidinyl. In still other embodiments, the present invention is a compound represented by structural formula I-B, wherein J$^G$ is methyl, —O(C$_{1-3}$alkyl), oxetanyl, pyrrolidinyl, piperidinyl, or azetidinyl. In yet another example, the present invention is a compound represented by structural formula I-B, wherein J$^G$ is C$_{1-4}$alkyl, C$_{3-5}$cycloalkyl, or —N(C$_{1-4}$alkyl)$_2$. In other embodiments, the present invention is a compound represented by structural formula I-B, wherein J$^G$ is methyl, ethyl, or cyclopropyl. In some embodiments, the present invention is a compound represented by structural formula I-B, wherein J$^G$ is methyl. In still other embodiments, the present invention is a compound represented by structural formula I-B, wherein J$^G$ is oxetanyl.

In another example, the present invention is represented by structural formula I-B, wherein two occurrences of J$^G$, together with Ring D, form a 6-10 membered saturated or partially unsaturated bridged ring system. In some examples, the present invention is a compound represented by structural formula I-B, wherein the bridged ring system is 1,4-diazabicyclo[3.2.2]nonane, 1,4-diazabicyclo[3.2.1]octane, or 2,5-diazabicyclo[2.2.1]heptane. In some examples, the present invention is a compound represented by structural formula I-B, wherein the bridged ring system is 1,4-diazabicyclo[3.2.2]nonane.

In some embodiments, the present invention is a compound represented by structural formula I-B, wherein two occurrences of J$^G$ on the same atom, together with the atom to which they are joined, form a 3-6 membered ring having 0-2 heteroatoms selected from oxygen, nitrogen, or sulfur. the present invention is a compound represented by structural formula I-B, wherein In other embodiments, the ring formed by the two occurrences of J$^G$ on the same atom is selected from oxetanyl or cyclopropyl In another example, the present invention is a compound represented by structural formula I, I-A, and I-B, wherein the compounds of this invention are represented in Table 4.

TABLE 4

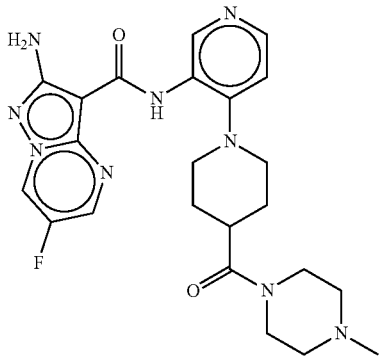

I-G-1

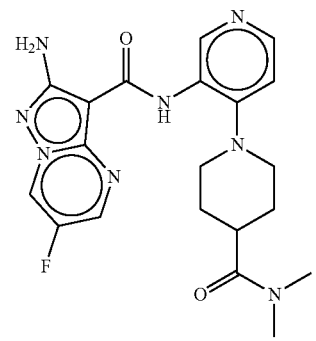

I-G-2

TABLE 4-continued
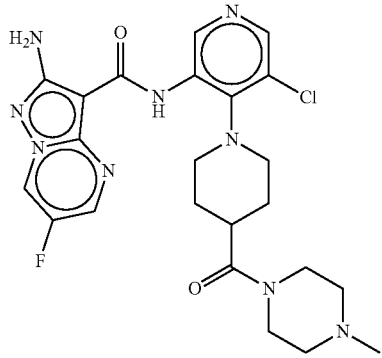 I-G-3
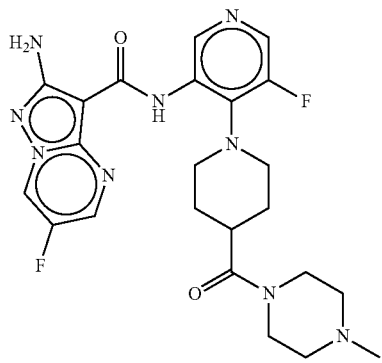 I-G-4
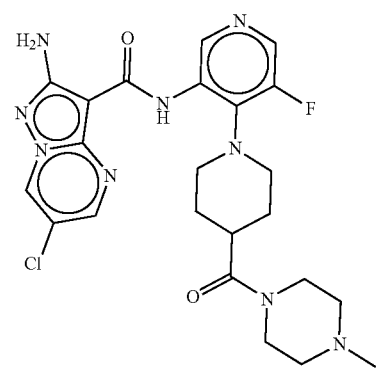 I-G-5
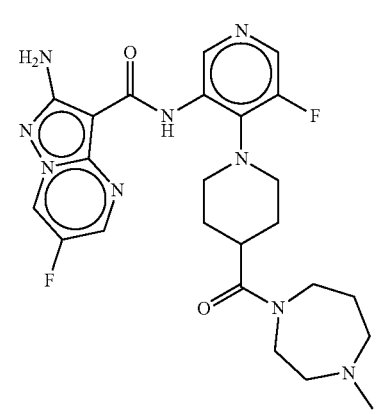 I-G-6
TABLE 4-continued
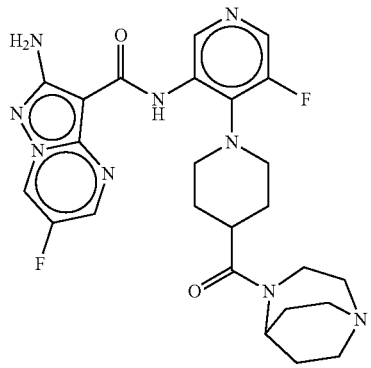 I-G-7
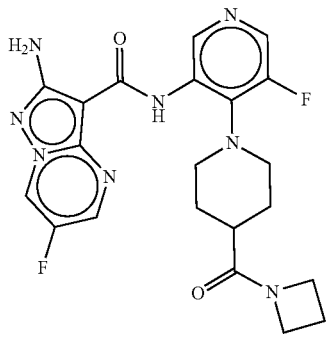 I-G-8
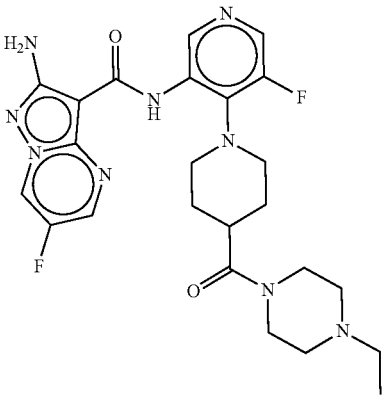 I-G-9
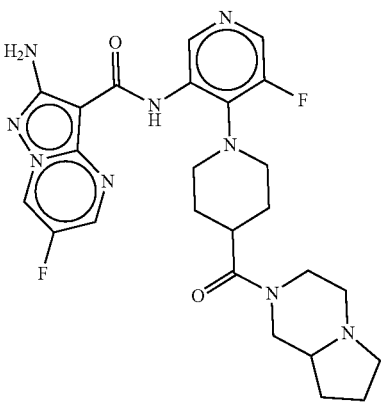 I-G-10

TABLE 4-continued
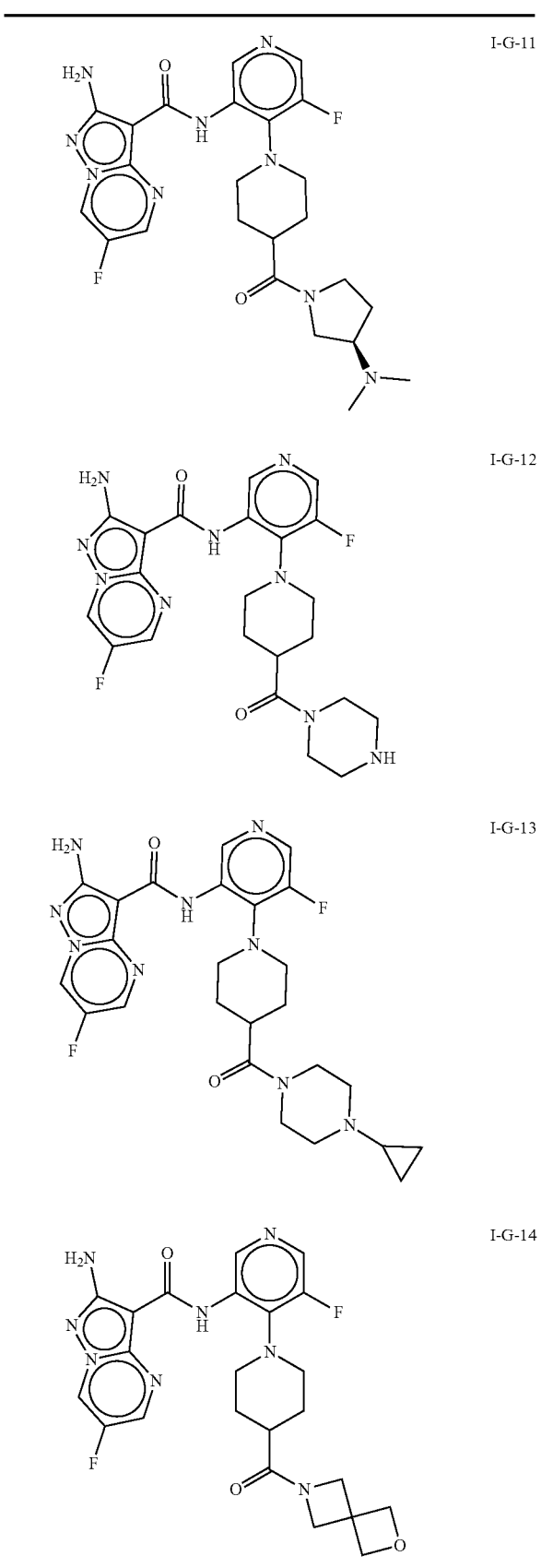
I-G-11
I-G-12
I-G-13
I-G-14
TABLE 4-continued
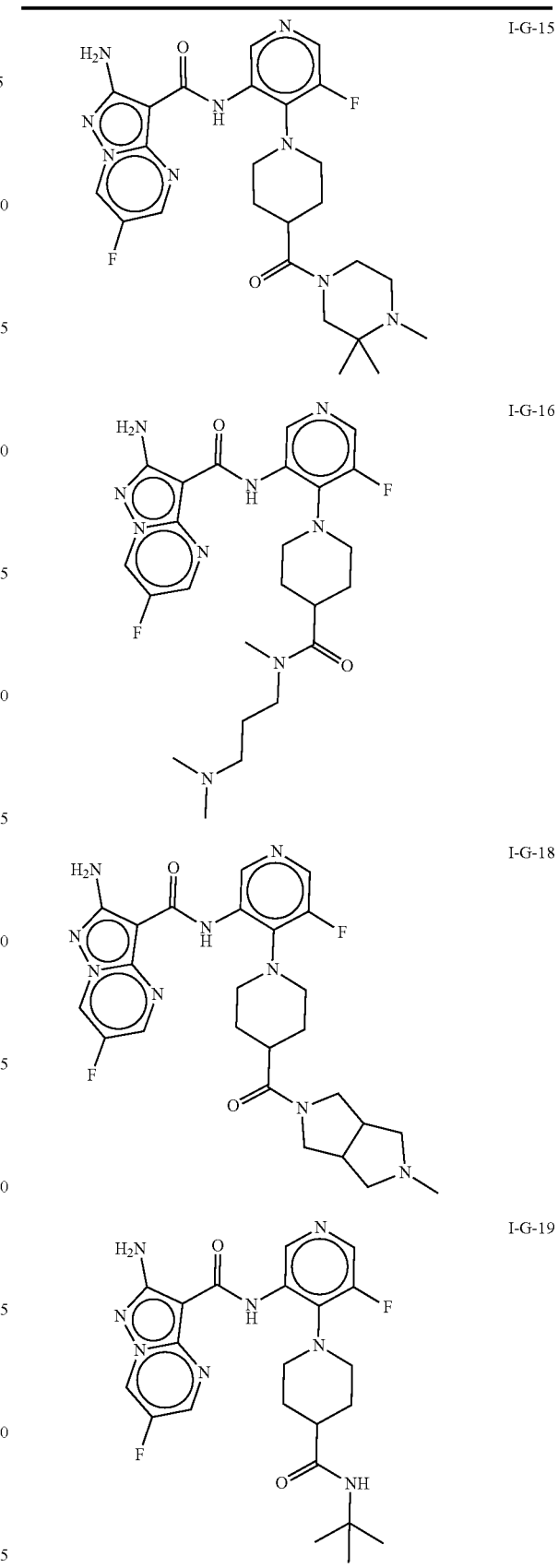
I-G-15
I-G-16
I-G-18
I-G-19

TABLE 4-continued
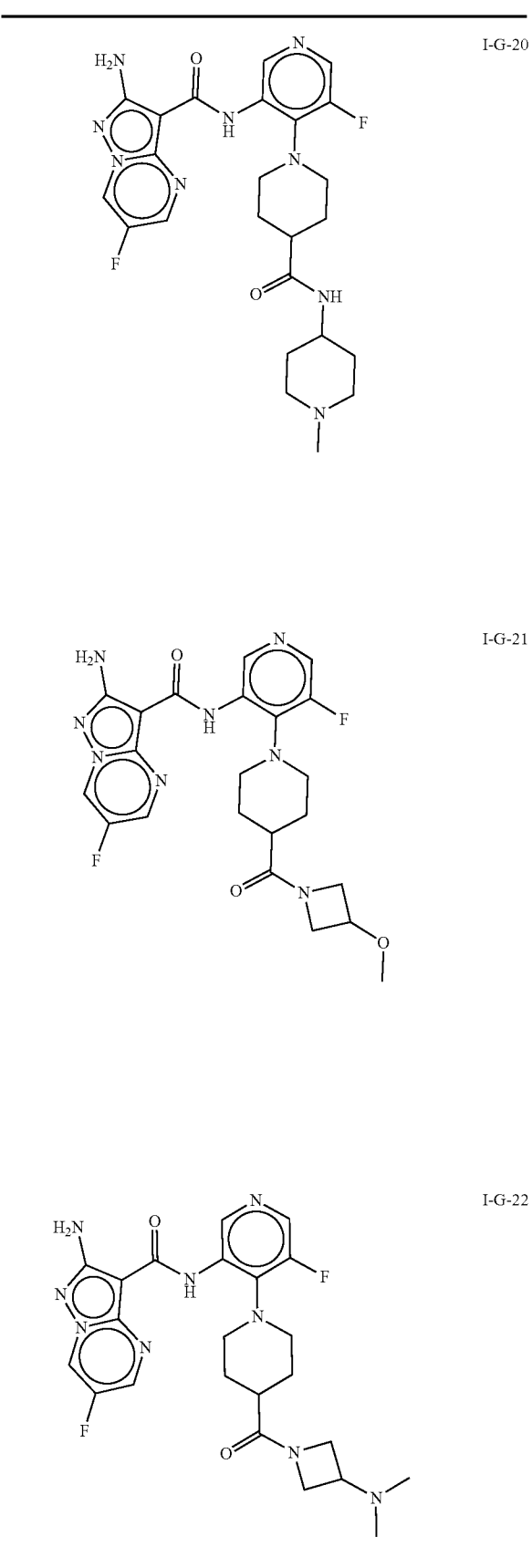
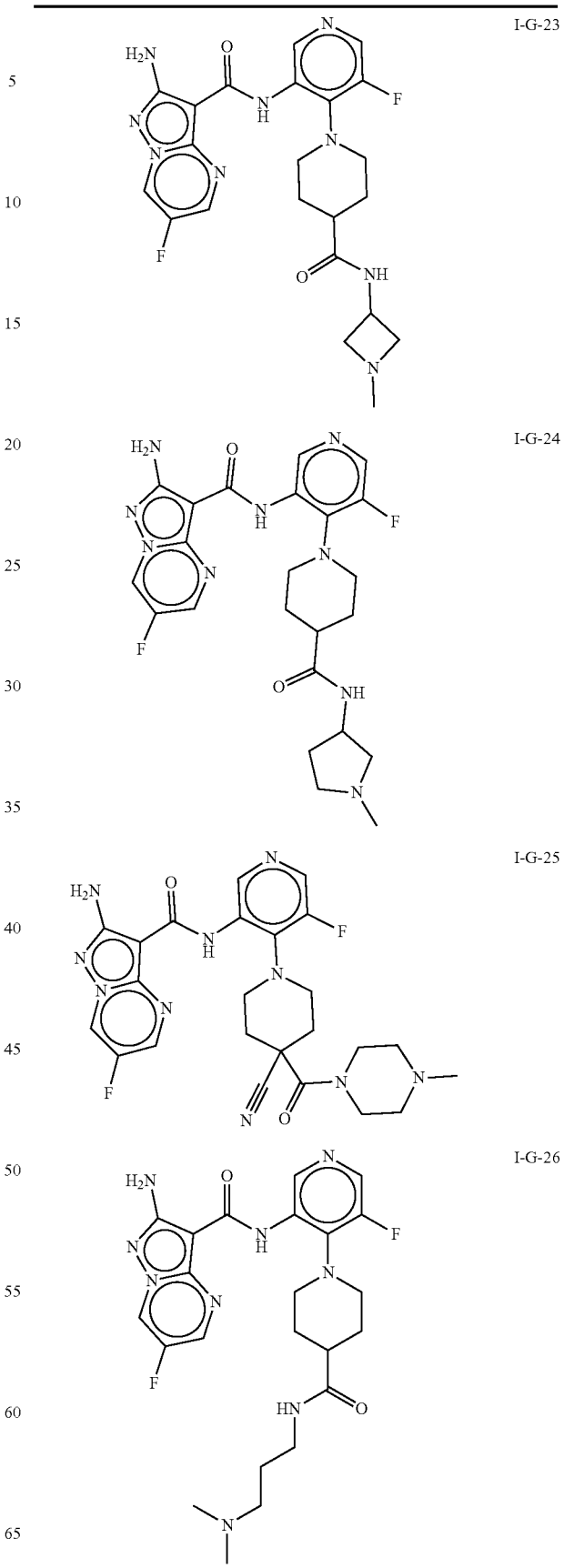

TABLE 4-continued
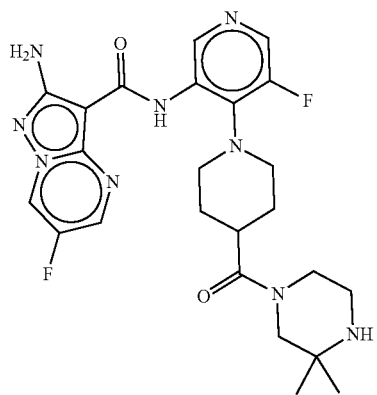
I-G-27
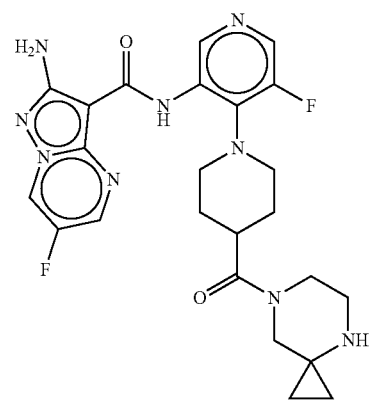
I-G-28
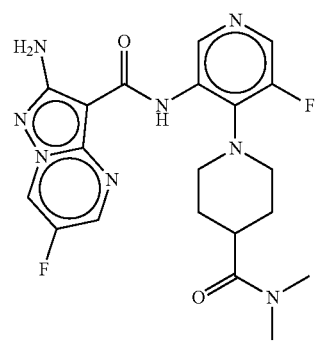
I-G-29
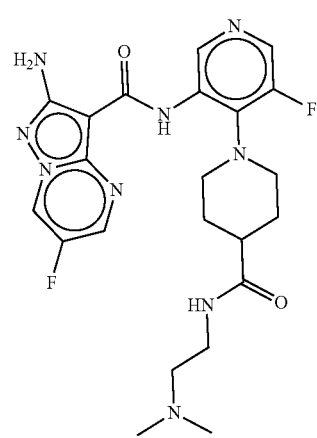
I-G-30
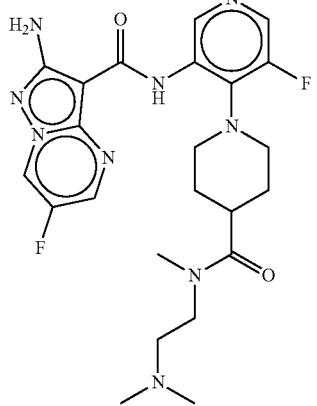
I-G-31
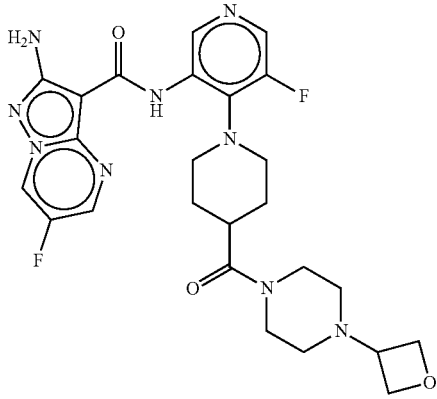
I-G-32
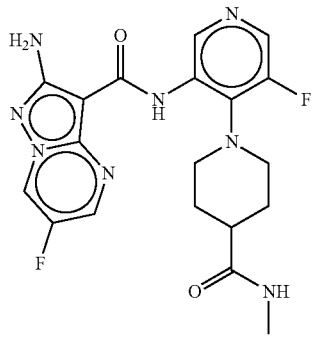
I-G-33
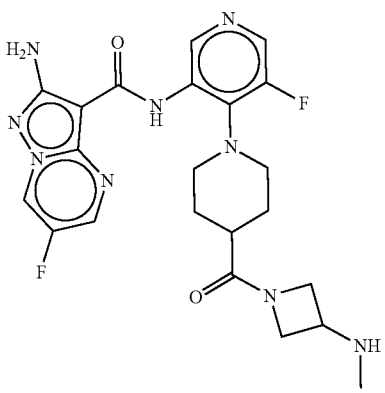
I-G-34

TABLE 4-continued
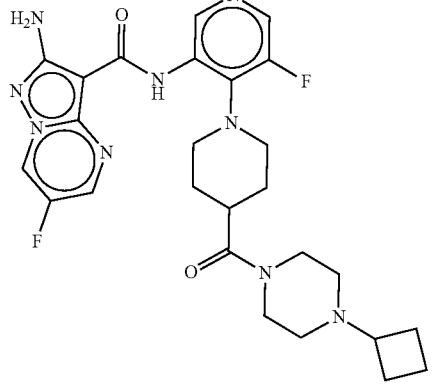 I-G-35
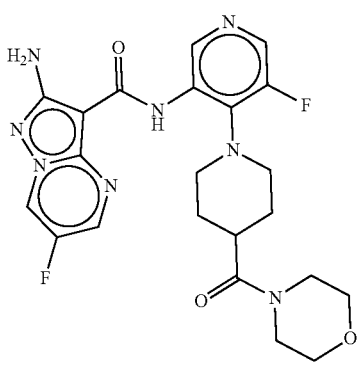 I-G-36
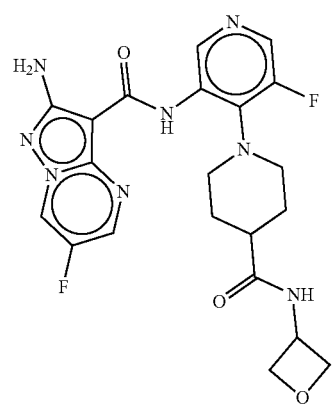 I-G-37
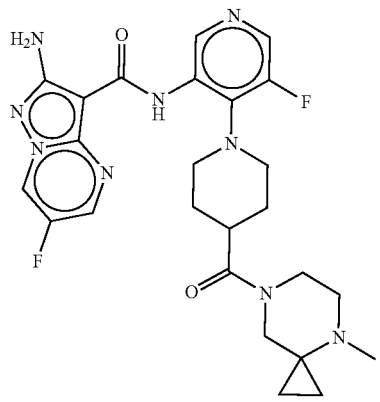 I-G-38
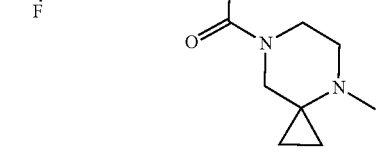
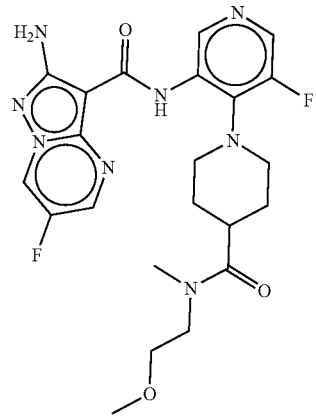 I-G-40
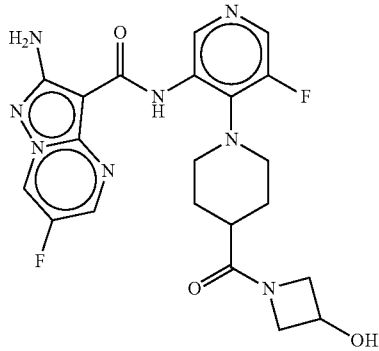 I-G-41
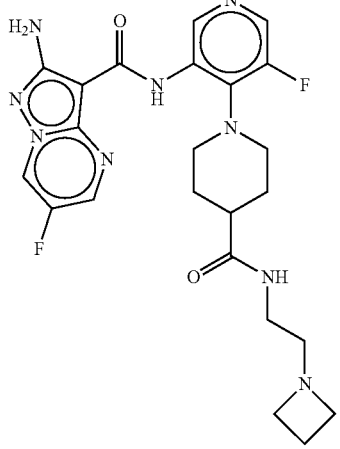 I-G-42
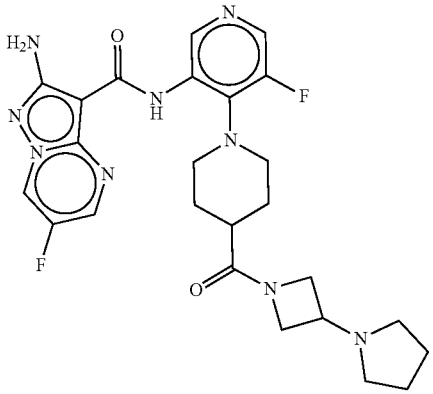 I-G-43

TABLE 4-continued
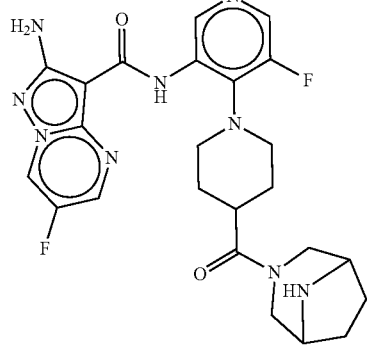
I-G-44
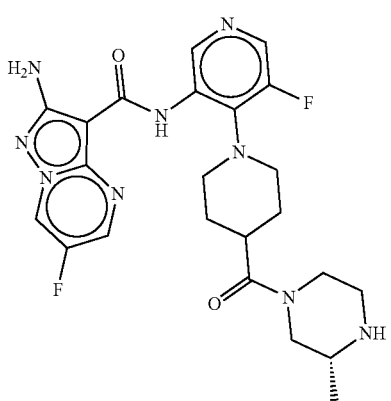
I-G-46
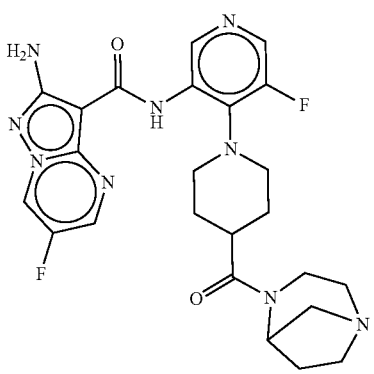
I-G-46
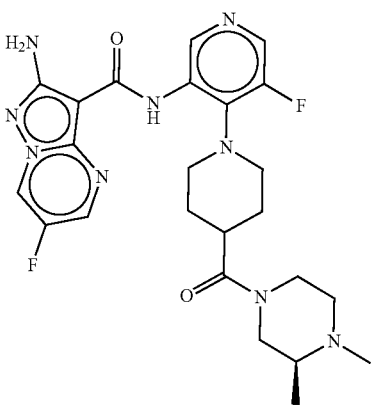
I-G-47
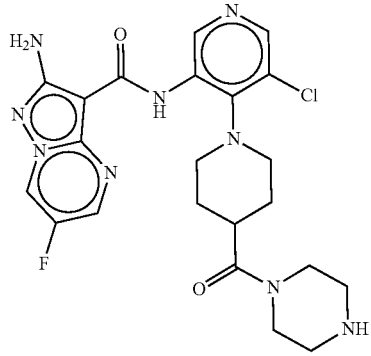
I-G-48
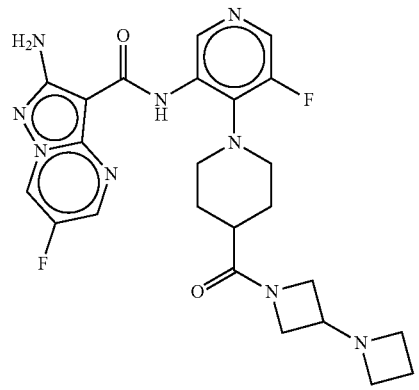
I-G-49
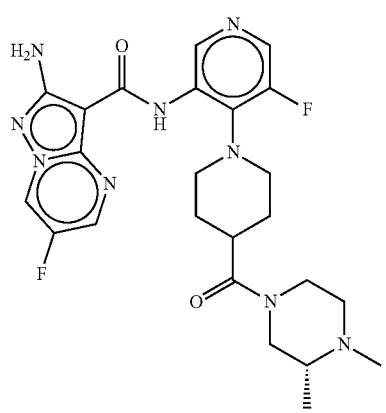
I-G-50
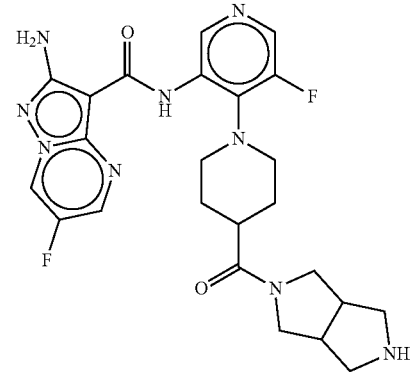
I-G-51

TABLE 4-continued
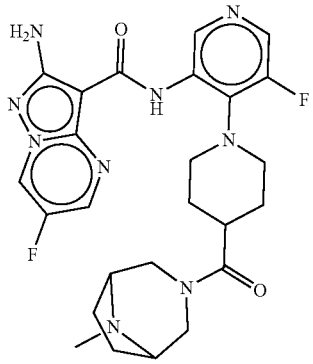 I-G-52
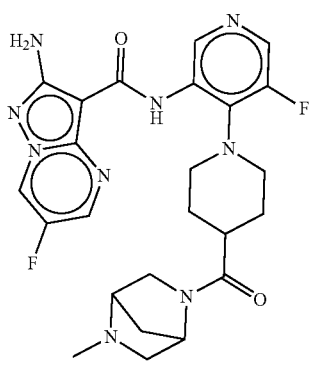 I-G-53
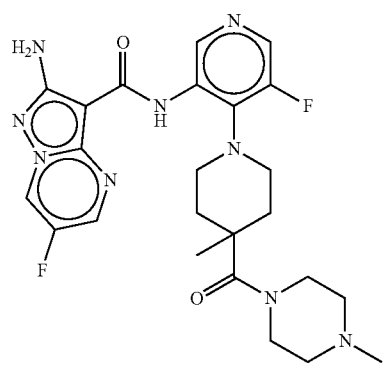 I-G-54
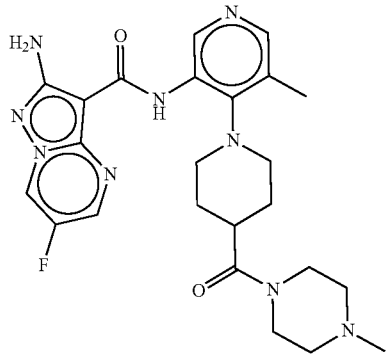 I-G-55
TABLE 4-continued
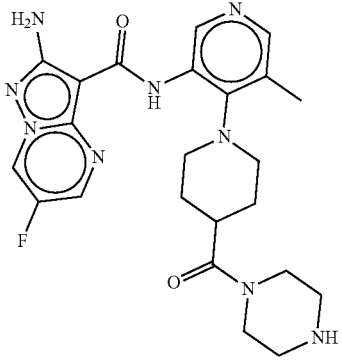 I-G-56
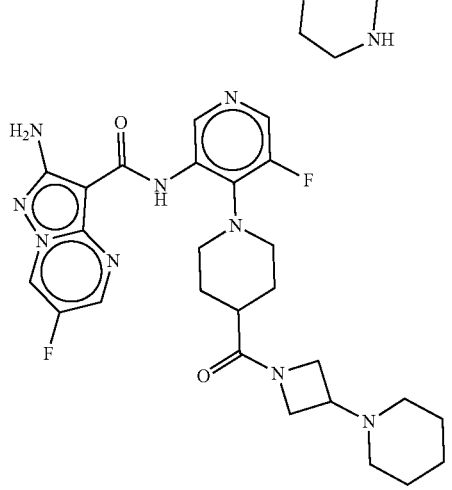 I-G-57
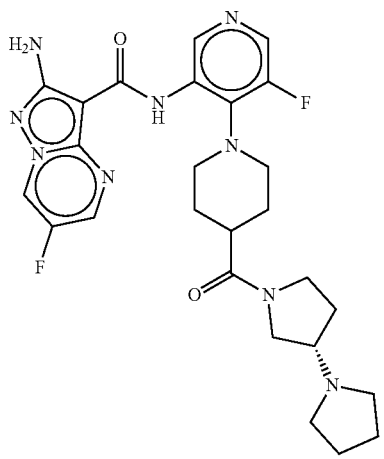 I-G-58
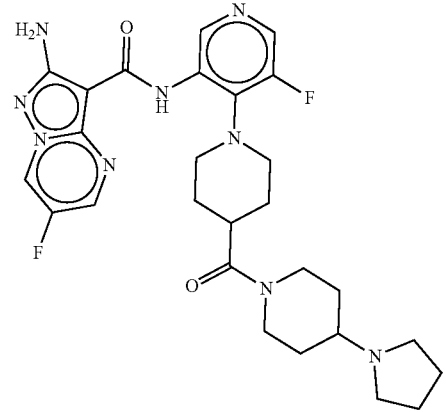 I-G-59

TABLE 4-continued
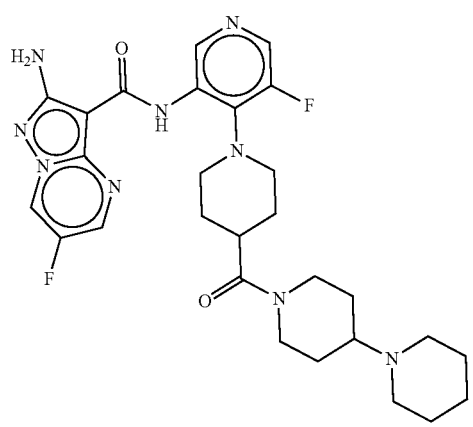
I-G-60
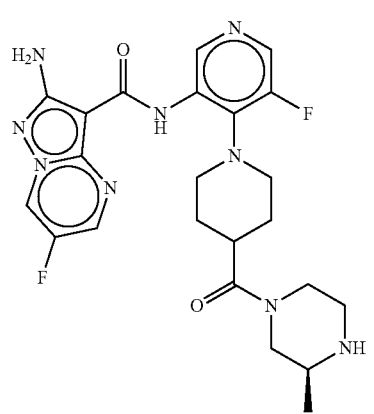
I-G-61
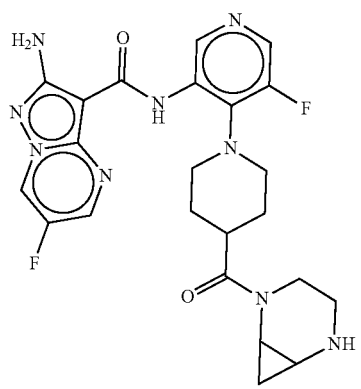
I-G-62
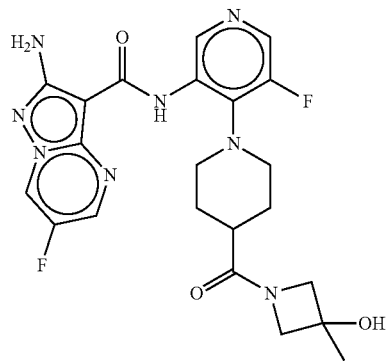
I-G-63
TABLE 4-continued
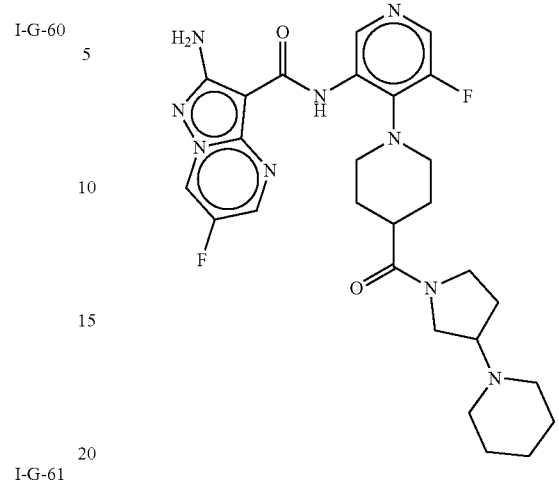
I-G-64
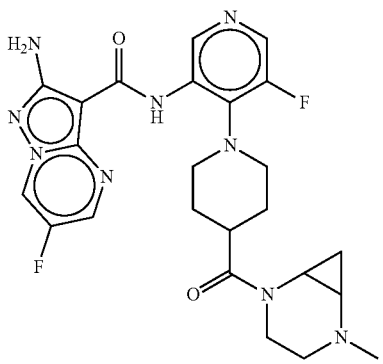
I-G-65
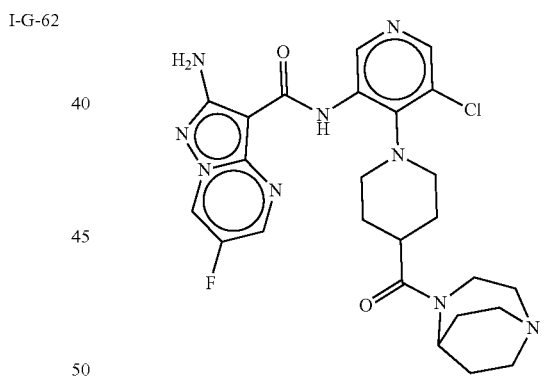
I-G-66
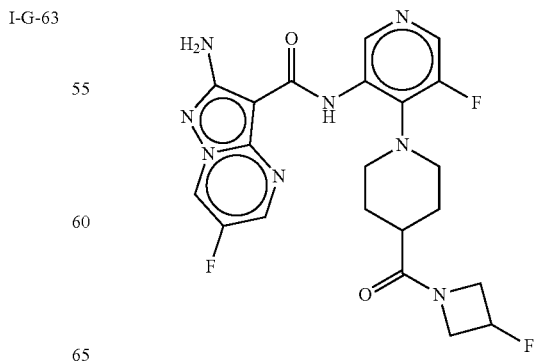
I-G-67

TABLE 4-continued
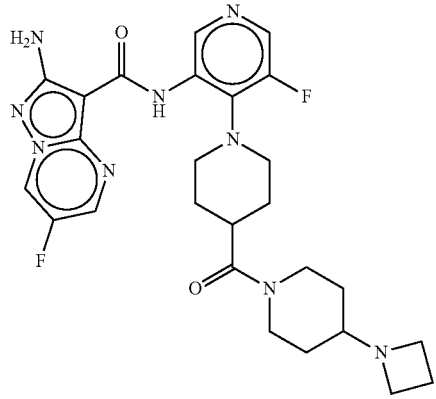 I-G-68
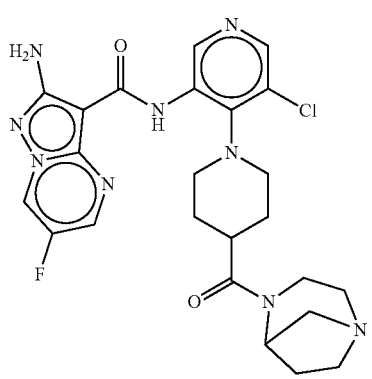 I-G-69
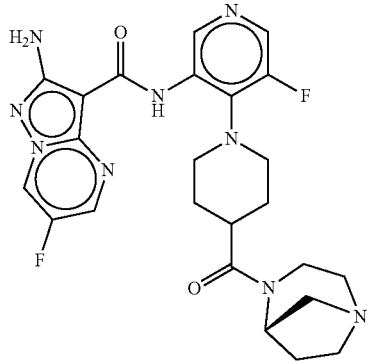 I-G-70
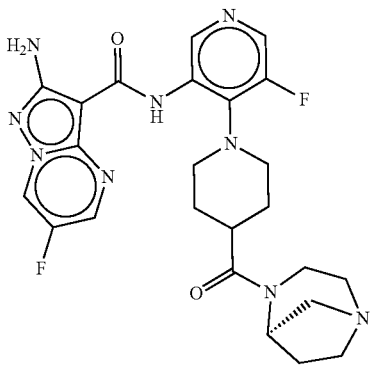 I-G-71
TABLE 4-continued
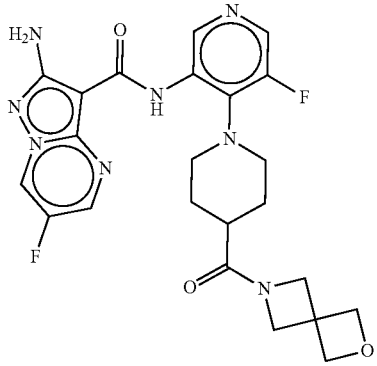 I-G-72
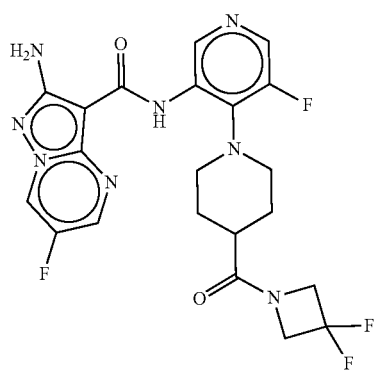 I-G-73
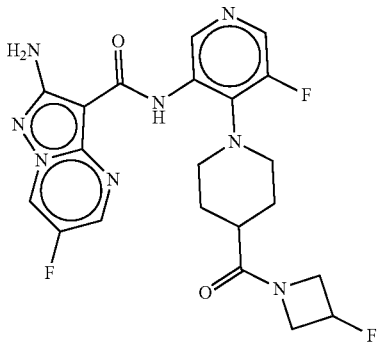 I-G-74
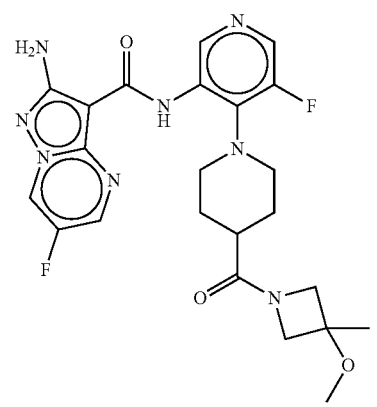 I-G-75

TABLE 4-continued
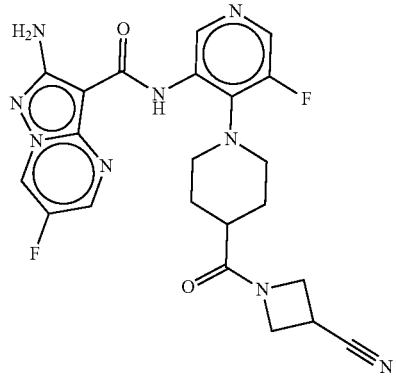
I-G-76
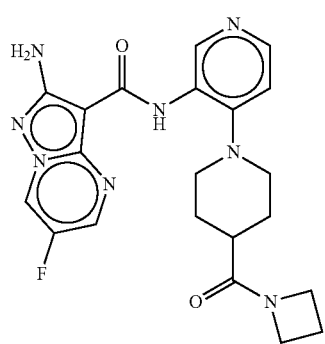
I-G-77
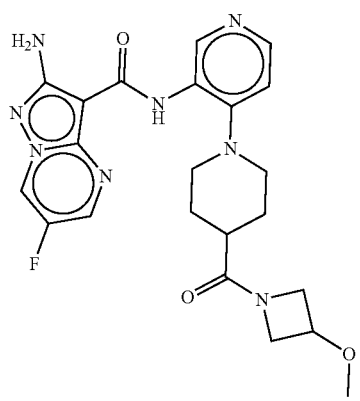
I-G-78
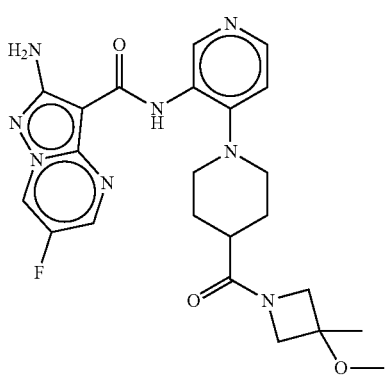
I-G-79
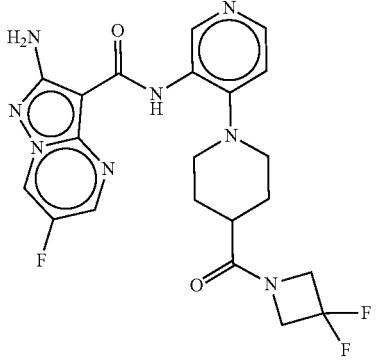
I-G-80
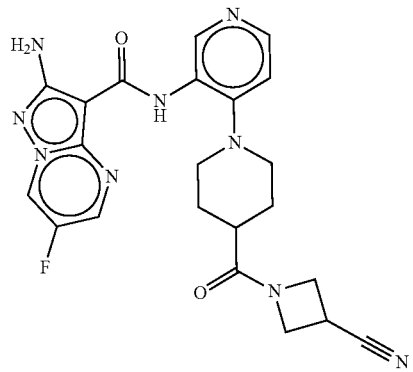
I-G-81
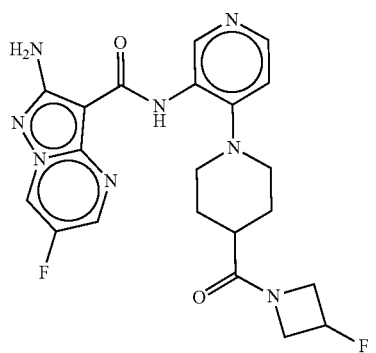
I-G-82
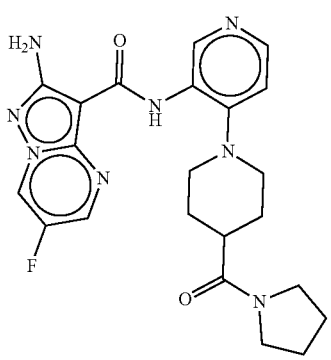
I-G-83

TABLE 4-continued
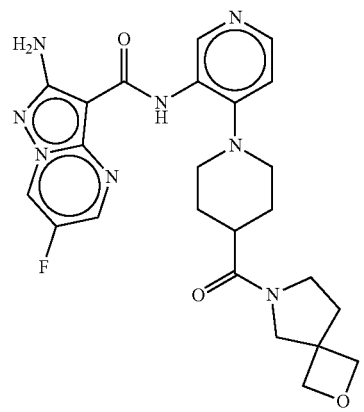
I-G-84
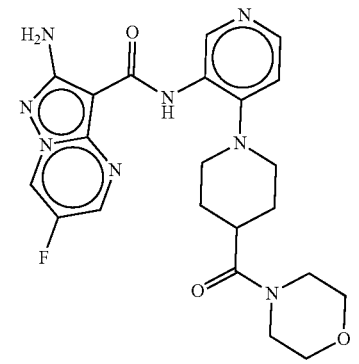
I-G-85
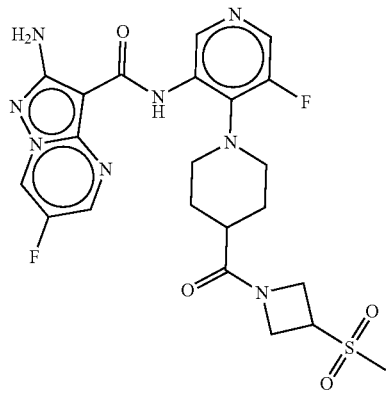
I-G-86
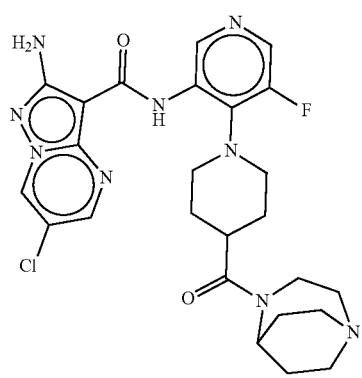
I-G-87
TABLE 4-continued
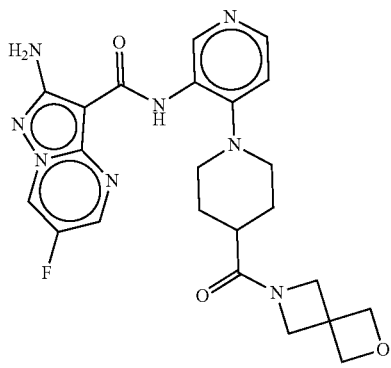
I-G-88
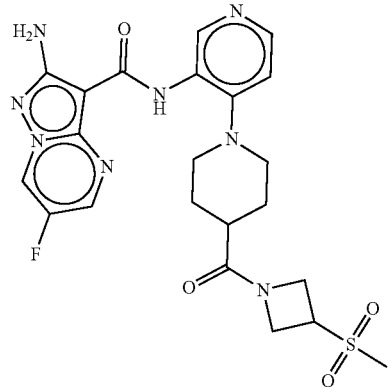
I-G-89
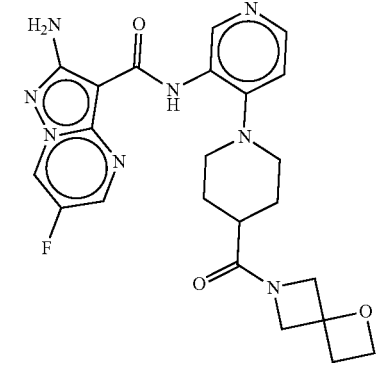
I-G-90
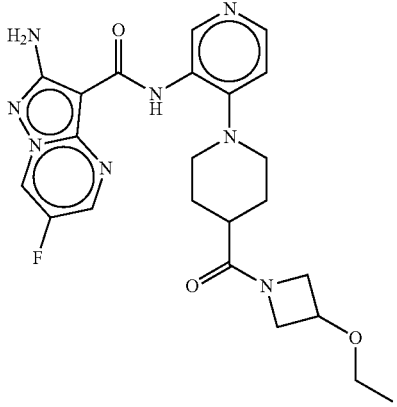
I-G-91

TABLE 4-continued
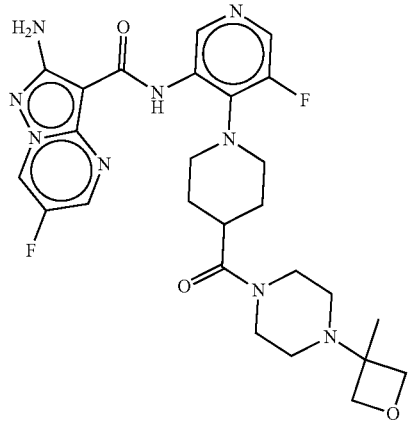
I-G-92
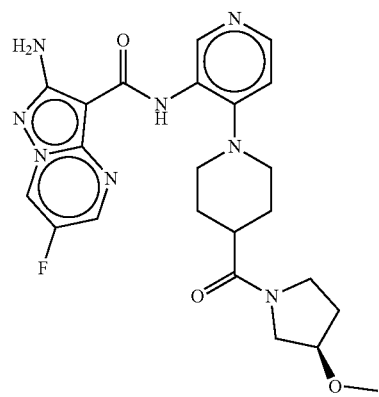
I-G-93
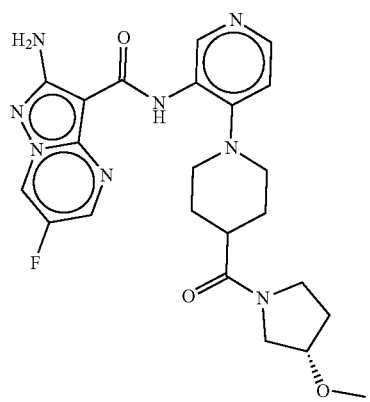
I-G-94
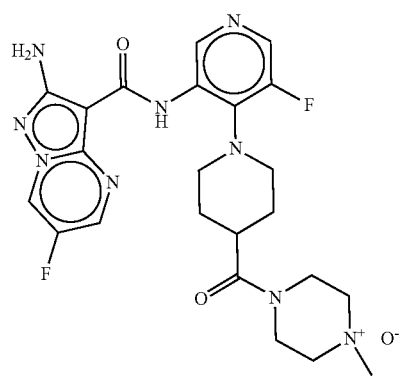
I-G-95
TABLE 4-continued
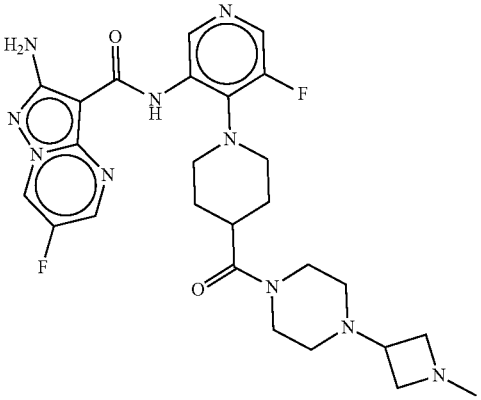
I-G-96
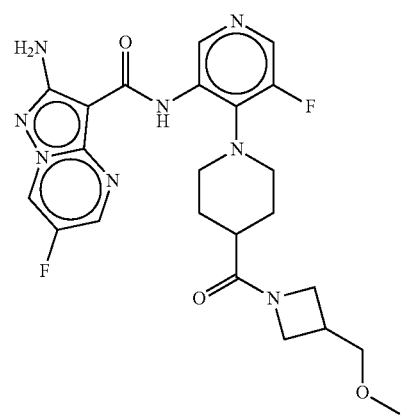
I-G-98
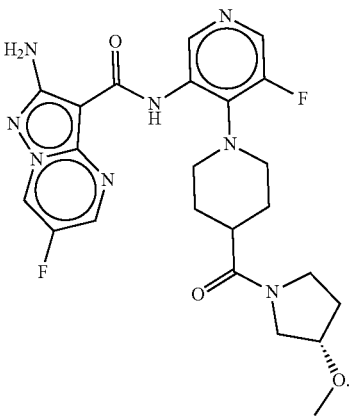
I-G-99

In another embodiment, the compound of the present invention is selected from one of the following:

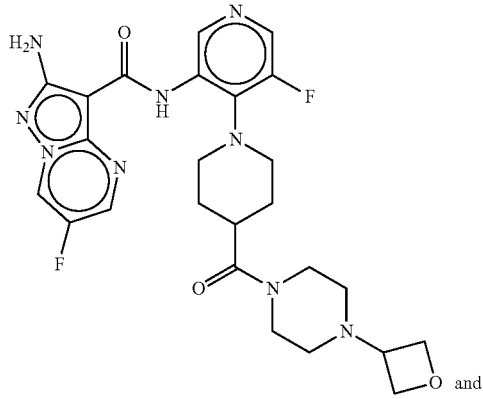

I-G-32 and

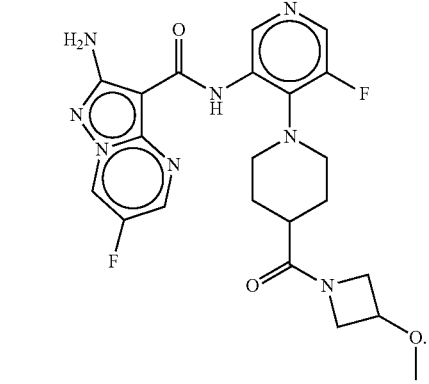

I-G-21

Preferably, the compound has the structure I-G-32:

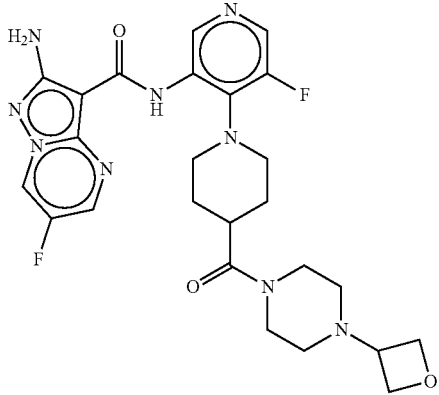

I-G-32 or a pharmaceutically acceptable salt.

Another aspect of the present invention comprises a process for preparing a compound of formula I-A:

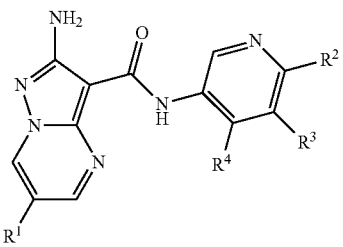

I-A comprising reacting a compound of formula 6:

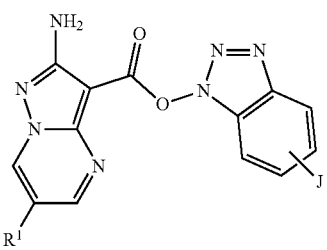

6 under suitable conditions to form an amide bond, wherein J, $R^1$, $R^2$, $R^3$, and $R^4$ are as defined herein.

In some examples, the suitable conditions for forming the amide bond comprises reacting the compound of formula 6 with a substituted 3-amino pyridine in an aprotic solvent under heat. In other examples, the aprotic solvent is selected from NMP, optionally substituted pyridine, or DMF. In another embodiment, the aprotic solvent is optionally substituted pyridine. In still other embodiments, the reaction temperature is at least 80° C. In another embodiment, the reaction temperature is at least 100° C.

In another embodiment, the process, described above, further comprises preparing a compound of formula 6:

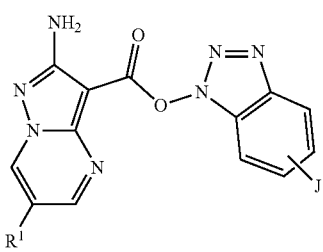

6 by reacting a compound of formula 5:

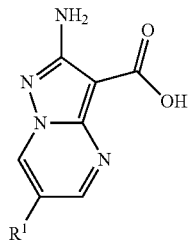

under suitable conditions to form an activated ester, wherein J and $R^1$ is as defined herein.

In some embodiments, suitable conditions for forming the activated ester comprises reacting the compound of formula 5 with an amide coupling agent in the presence of an organic base. In other embodiments, the organic base is an aliphatic amine. In still other embodiments, the organic base is independently selected from triethylamine or DIPEA. In one or more embodiments, the amide coupling agent is independently selected from EDCI, TBTU, TCTU, HATU, T3P, or COMU. In yet another embodiment, the amide coupling agent is independently selected from TBTU or TCTU. In another embodiment, the amide coupling agent is TCTU.

Another aspect of the invention comprises a process for preparing a compound of formula I-A:

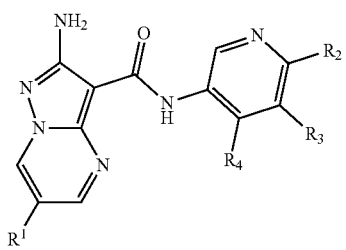

comprising reacting a compound of formula 5:

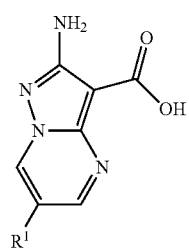

under suitable conditions to form an amide bond, wherein $R^1$, $R^2$, $R^3$, and $R^4$ are as defined herein.

Yet another aspect of the present invention comprises a process for preparing a compound of formula 5:

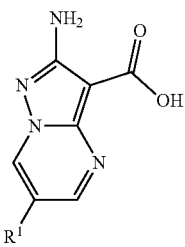

by reacting a compound of formula 4:

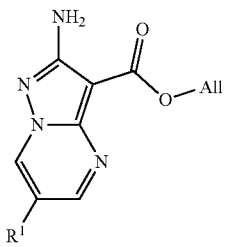

under suitable hydrolytic conditions, wherein $R^1$ is as defined herein.

In some embodiments, suitable hydrolytic conditions comprise reacting the compound of formula 4 with a silane in the presence of a metal catalyst. In other embodiments, the silane is a phenylsilane. In another embodiment, the metal catalyst is a palladium catalyst. In yet another embodiment, the palladium catalyst is $Pd(PPh_3)_4$. In another embodiment suitable hydrolytic conditions comprise reacting the compound of formula 4 with 4-methylbenzenesulfinate in the presence of a metal catalyst.

In still other embodiments, suitable hydrolytic conditions comprise reacting the compound of formula 4 with an aqueous alkali. In some embodiments, the aqueous alkali is selected from LiOH, NaOH or KOH.

Another aspect of the present invention comprises a process for preparing a compound of formula 4:

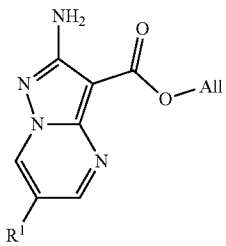

by reacting a compound of formula 3:

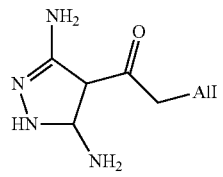

3 under suitable condensation conditions to form a pyrimidine ring.

In some embodiments, suitable condensation conditions to form a pyrimidine ring comprise reacting the compound of formula 3 with a 1,3-dielectrophilic species in the presence of a solvent. In another embodiment, the 1,3-dielectrophilic species is selected from 1,3-dialdehyde or 3-(dialkylamino)-prop-2-enal. In still other embodiments, the solvent is selected from DMF or DMSO in water. In other embodiments, the 1,3-dielectrophilic species is generated in situ from a protected 1,3-dielectrophilic species. In another embodiment the 1,3-dielectrophilic species is generated from a ketal in the presence of a sulfonic acid. In yet another embodiment, the sulfonic acid is PTSA.

Another aspect of the present invention comprises a process for preparing the compound of formula 3:

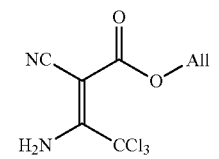

3 by reacting a compound of formula 2:

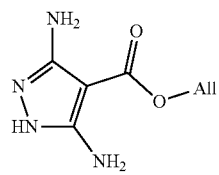

2 under suitable condensation conditions to form a pyrazole ring.

In some embodiments, suitable condensation conditions to form a pyrazole ring comprise reacting the compound of formula 2 with a hydrazine or hydrazine hydrate in the presence of an aprotic solvent under basic conditions. In another embodiment, the aprotic solvent is DMF. In yet another embodiment, the basic conditions comprise reacting the compound of formula 2 in the presence of potassium acetate or sodium acetate.

Yet another aspect of the present invention comprises a process for preparing a compound of formula 2:

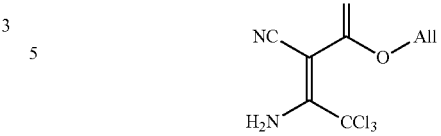

2 by reacting a compound of formula 1:

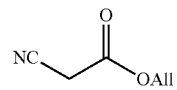

1 under suitable anion condensation conditions.

In some embodiments, suitable anion condensation conditions comprise 1) reacting the compound of formula 1 with a base, in the presence of a solvent, to generate the anion of the compound of formula 1; and 2) reacting the anion of the compound of formula 1 with trichloroacetonitrile. In still other embodiments, the base is potassium acetate. In yet another embodiment, the solvent is an alcohol. In other embodiments, the solvent is isopropylalcohol.

One embodiment of the present invention comprises a process for preparing a compound of formula I-A:

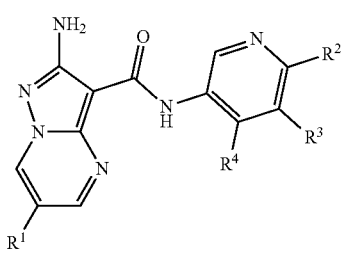

I-A comprising reacting a compound of formula 9:

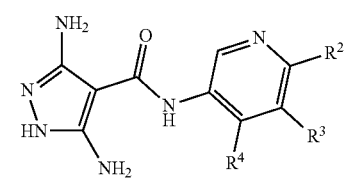

9 under suitable condensation conditions to form a pyrimidine ring, wherein $R^1$, $R^2$, $R^3$ and $R^4$ are as defined herein.

In some embodiments, suitable condensation conditions to form a pyrimidine ring comprise reacting the compound of formula 9 with a 1,3-dielectrophilic species in the presence of a solvent. In another embodiment, the 1,3-dielectrophilic species is selected from 1,3-dialdehyde or 3-(dialkylamino)-prop-2-enal. In still other embodiments, the solvent is selected from DMF or DMSO in water. In other embodiments, the 1,3-dielectrophilic species is generated in situ from a protected 1,3-dielectrophlic species. In another embodiment the 1,3-dielectrophilic species is generated from a ketal in the presence of a sulfonic acid. In yet another embodiment, the sulfonic acid is PTSA.

Another embodiment of the present invention comprises a process for preparing a compound of formula 9:

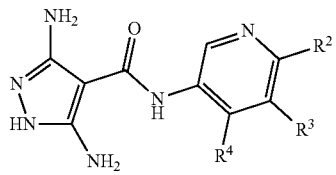

9 by reacting a compound of formula 8:

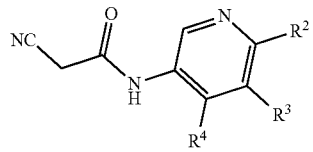

8 under suitable condensation conditions to form a pyrazole ring.

In some embodiments, suitable condensation conditions to form a pyrazole ring comprise 1) reacting the compound of formula 8 with a base, in the presence of a solvent, to generate the anion of the compound of formula I; 2) reacting the anion with trichloroacetonitrile; and 3) reacting the product from 2) with a hydrazine or hydrazine hydrate in the presence of an aprotic solvent. In another embodiment, the aprotic solvent is NMP or DMF. In some embodiments, the base is selected from sodium acetate or potassium acetate.

Yet another embodiment comprises a process for preparing a compound of formula 8:

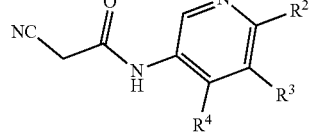

8 by reacting a compound of formula 7:

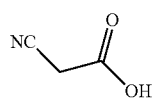

7 under suitable conditions to form an amide bond.

In some examples, the suitable conditions for forming the amide bond comprises reacting the compound of formula 7 with a substituted 3-amino pyridine with an amide coupling agent in the presence of an aprotic solvent and an organic base. In other examples, the aprotic solvent is selected from NMP or DMF. In another embodiment, the organic base is an aliphatic amine. In still other embodiments, the organic base is independently selected from triethylamine or DIPEA. In yet another embodiment, the amide coupling agent is independently selected from TBTU or TCTU.

Another aspect of the present invention provides a process of preparing a compound of formula I-G-32:

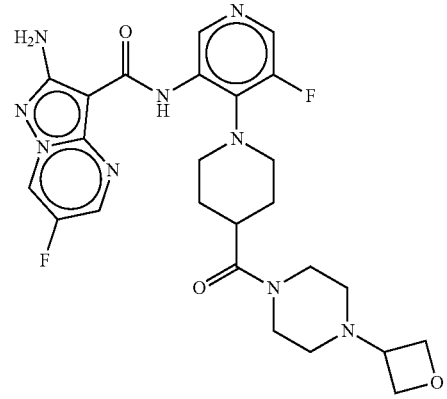

I-G-32 comprising the step of reacting the compound of formula 29:

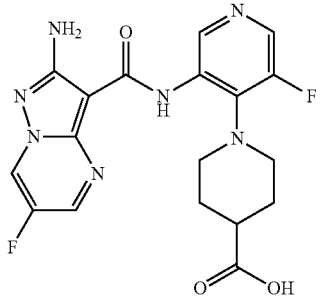

29 with a compound of formula 25:

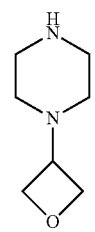

25 under suitable conditions to form an amide bond.

Still other embodiments of the present invention comprise provides a process for preparing the compound of formula 29:

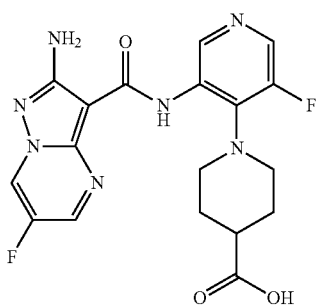

29

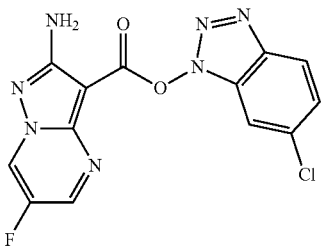

6a* by reacting the compound of formula 28:

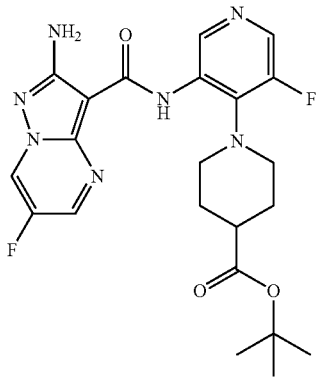

28 with a compound of formula 27:

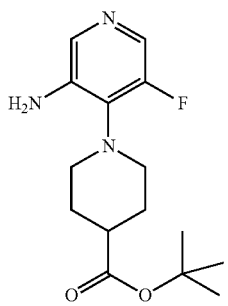

27 under suitable deprotection conditions to form the carboxylic acid.

Another embodiment provides a process for preparing a compound of formula 28:

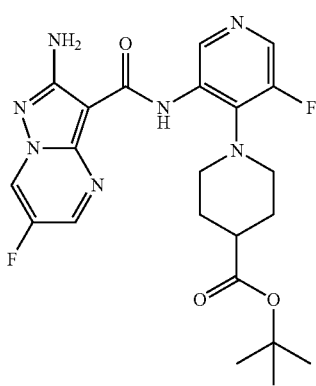

28 under suitable conditions to form an amide bond.

In some embodiments, suitable conditions for forming the amide bond comprise reacting the compound of formula 29 with the compound of formula 25 in the presence of an amide coupling partner, an aprotic solvent, and a base. In other embodiments, the aprotic solvent is independently selected from NMP, DMF, or tetrahydrofuran. In still other embodiments, the aprotic solvent is tetrahydrofuran. In another embodiment, the base is an aliphatic amine. In yet another embodiment, the base is DIPEA. In some embodiments, the amide coupling partner is independently selected from TBTU or TCTU. In one or more embodiments, the amide coupling partner is TCTU.

In other embodiments, suitable deprotection conditions comprise reacting the compound of formula 28 with an acid in the presence of a solvent. In some embodiments, the acid is HCl. In another embodiment, the solvent is 1,4-dioxane.

In yet another embodiment, suitable conditions for forming the amide bond comprise reacting the compound of formula 6a* with the compound of formula 27 in an aprotic solvent under heat. In still other embodiments, the aprotic solvent is independently selected from NMP, pyridine, or DMF. In another embodiment, the aprotic solvent is pyridine. In some embodiments, the reaction is carried out at a temperature of at least 80° C.

by reacting the compound of formula 6a*:

Another aspect of the present invention provides a process of preparing a compound of formula 27:

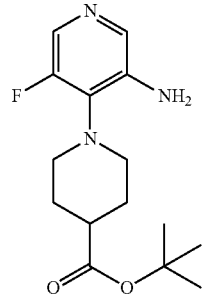

27 comprising the step of reacting a compound of formula 26:

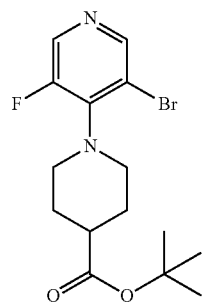

26 under suitable conditions to form an amine.

In some embodiments, suitable conditions to form an amine comprise reacting the compound of formula 27 under Buchwald-Hartwig amination conditions, known to those skilled in the art.

Yet another embodiment provides a process for preparing a compound of formula 26:

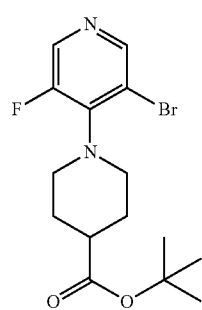

26 by 1) reacting a compound of formula 18:

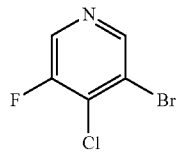

18 under suitable halogen exchange conditions to generate the compound of formula 32

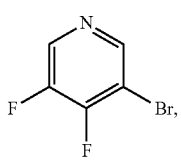

32 and
2) reacting the compound of formula 32:

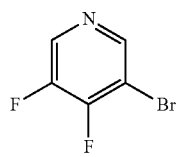

32 with a compound of formula 22:

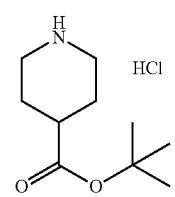

22 under suitable displacement conditions.

In some embodiments, suitable halogen exchange conditions comprise reacting the compound of formula 18 with potassium fluoride in the presence of an aprotic solvent and a phase transfer catalyst. In other embodiments, the aprotic solvent is independently selected from DMSO, DMF, or sulfolane. In still other embodiments, the phase transfer catalyst is Me$_4$NCl. In still other embodiments, suitable displacement conditions comprise reacting the compound of formula 32 with a compound of formula 22 in the presence of a base. In another embodiment, the base is an aliphatic amine. In some embodiments, the aliphatic amine is DIPEA.

Other embodiments of the present invention provides a process for preparing a compound of formula 18:

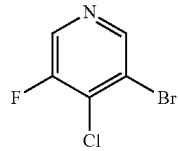

by reacting the compound of formula 31:

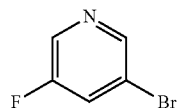

under suitable halogenation conditions.

In some embodiments, suitable halogenation conditions comprise 1) reacting the compound of formula 31 with a base to generate an anion; and 2) reacting the anion with a chlorinating agent. In yet another embodiment, the base is LDA. In another embodiment, the chlorinating agent is 1,1,1,2,2,2-hexachloroethane.

For purposes of this application, it will be understood that the terms embodiment, example, and aspect are used interchangeably.

For purposes of this application, it will be understood that when two occurrences of $J^Q$, together with $Q^1$, form a bridged ring system, the two occurrences of $J^Q$ are attached to separate atoms of $Q^1$. Additionally, when two occurrences of $J^R$, together with $Q^2$, form a bridged ring system, the two occurrences of $J^R$ are attached to separate atoms of $Q^2$. Moreover, when two occurrences of $J^T$, together with $Q^3$, form a bridged ring system, the two occurrence of $J^T$ are attached to separate atoms of $Q^3$. Further, when two occurrences of $J^W$, together with W, form a bridged ring system, the two occurrences of $J^W$ are attached to separate atoms of W. Finally, when two occurrences of $J^G$, together with Ring D, form a bridged ring system, the two occurrences of $J^G$ are attached to separate atoms of Ring D.

It will be understood by those skilled in the art that the arrow in →O represents a dative bond.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^W$ can be bonded to any position on the pyridyl ring. For bicyclic rings, a bond drawn through both rings indicates that the substituent can be bonded from any position of the bicyclic ring. In example ii below, for instance, $J^W$ can be bonded to the 5-membered ring (on the nitrogen atom, for instance), and to the 6-membered ring.

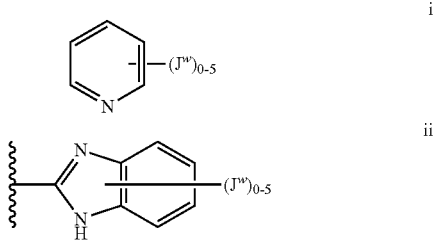

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$-cyclopropyl, CH$_2$CH$_2$CH (CH$_3$)-cyclohexyl.

The term "cycloaliphatic" (or "carbocycle" or "carbocyclyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

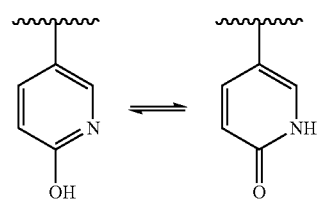 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$ aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N≡N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. In another example, if a methylene unit of —CH$_2$CH$_2$CH$_3$ was optionally replaced with —NH—, the resulting compound could be —NHCH$_2$CH$_3$, —CH$_2$NHCH$_3$, or —CH$_2$CH$_2$NH$_2$. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

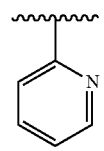

also represents

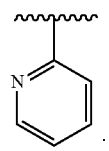

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N, N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

Abbreviations

The following abbreviations are used:
DMSO dimethyl sulfoxide
DCM dichloromethane
ATP adenosine triphosphate
$^1$HNMR proton nuclear magnetic resonance
HPLC high performance liquid chromatography
LCMS liquid chromatography-mass spectrometry
Rt retention time
RT room temperature
TEA triethylamine
NMP N-methyl-2-pyrrolidone
TFA trifluoroacetic acid
Bp boiling point
DMF dimethylformamide
PTSA p-Toluenesulfonic acid
DIPEA N,N-diisopropylethylamine
mCPBA meta-chloroperoxybenzoic acid
HOBt hydroxybenzotriazole
HATU 1-[Bis(dimethylamino)methylene]-1H-1,2,3-triazolo [4,5-b]pyridinium 3-oxid hexafluorophosphate
TBTU 2-(1H-benzotriazole-1-yl)-1,1,3,3-tetramethyluronium tetrafluoroborate
T3P Propylphosphonic anhydride
COMU 1-[(1-(Cyano-2-ethoxy-2-oxoethylideneaminooxy)-dimethylamino-morpholino)]uroniumhexafluorophosphate
TCTU [(6-chlorobenzotriazol-1-yl)oxy-(dimethylamino) methylene]-dimethyl-ammonium tetrafluoroborate
HBTU O-Benzotriazole-N,N,N',N'-tetramethyl-uronium-hexafluoro-phosphate
LDA Lithium diisopropylamide
EDCI 1-Ethyl-3-(3-dimethylaminopropyl)carbodiimide Compound Uses One aspect of this invention provides compounds that are inhibitors of ATR kinase, and thus are useful for treating or lessening the severity of a disease, condition, or disorder in a subject or patient where ATR is implicated in the disease, condition, or disorder.

As used herein, the terms "subject" and "patient" are used interchangeably. The terms "subject" and "patient" refer to an animal, and more specifically a human. In one embodiment, the subject is a non-human animal such as a rat or dog. In a preferred embodiment, the subject is a human.

Another aspect of this invention provides compounds that are useful for the treatment of diseases, disorders, and conditions characterized by excessive or abnormal cell proliferation. Such diseases include a proliferative or hyperproliferative disease. Examples of proliferative and hyperproliferative diseases include, without limitation, cancer and myeloproliferative disorders.

In some embodiments, said compounds are selected from the group consisting of a compound of formula I-A. In another aspect, said compounds are selected from the group consisting of formula I-B. In another apect, said compounds are selected from the group consisting of formula I or I-A-1. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological/Female: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from a cancer of the lung or the pancreas. In other embodiments, the cancer is selected from lung cancer, head and neck cancer, pancreatic cancer, gastric cancer, or brain cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the cancer is lung cancer. In other embodiments, the lung cancer is non-small cell lung cancer or small cell lung cancer. In another embodiment, the cancer is non-small cell lung cancer. In yet another embodiment, the non-small cell lung cancer is squamous non-small cell lung cancer.

Thus, the term "cancerous cell" as provided herein, includes a cell afflicted by any one of the above-identified conditions. In some embodiments, the cancer is selected from colorectal, thyroid, or breast cancer. In other embodiments, the cancer is triple negative breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a subject.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers. In yet other embodiments, said additional therapeutic agent is ionizing radiation.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); *Streptomyces* family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®), carboplatin (Paraplatin®); carmustine (BCNU BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/drug-listframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the dosing schedule of the compounds of the present invention may vary.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, 0 absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Alternatively, a dosage of between 0.01-50 mg/kg body weight/dose of the inhibitor can be administered to a patient receiving these compounds.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); *Streptomyces* family (Bleomycin, Mitomycin C, actinomycin) and Ultraviolet light.

Another embodiment provides administering a compound of this invention with an additional therapeutic agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly (ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I, I-A, I-A-1, and I-B.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from the cancers described herein. In some embodiments, said cancer is lung cancer, head and neck cancer, pancreatic cancer, gastric cancer, or brain cancer. In other embodiments, the cancer is selected from a cancer of the lung or the pancreas.

In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, the lung cancer is small cell lung cancer and the additional therapeutic agents are cisplatin and etoposide. In other examples, the lung cancer is non-small cell lung cancer and the additional therapeutic agents are gemcitabine and cisplatin. In yet other embodiments, the non-small cell lung cancer is squamous non-small cell lung cancer. In another embodiment, the cancer is breast cancer and the additional therapeutic agent is cisplatin. In other embodiments, the cancer is triple negative breast cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, *Streptomyces* family. Examples of Anthracyclines include doxorubicin, daunorubicin, epirubicin and other derivatives; examples of Anthracenediones include Mitoxantrone and relatives; examples of *Streptomyces* family inclue Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or *Streptomyces* family.

In some embodiments, the additional therapeutic agent is ionizing radiation. In other embodiments, the additional therapeutic agent is Cisplatin or Carboplatin. In yet other embodiments, the additional therapeutic agent is Etoposide. In yet other embodiments, the additional therapeutic agent is Temozolomide.

In certain embodiments, the additional therapeutic agent is selected from one or more of the following: Cisplatin, Carboplatin, gemcitabine, Etoposide, Temozolomide, or ionizing radiation.

Another embodiment provides methods for treating pancreatic cancer by administering a compound described herein in combination with another known pancreatic cancer treatment. One aspect of the invention includes administering a compound described herein in combination with gemcitabine. In some embodiments, the pancreatic cancer comprises one of the following cell lines: PSN-1, MiaPaCa-2 or Panc-1. According to another aspect, the cancer comprises one of the following primary tumor lines: Panc-M or MRCS.

Another aspect of the invention includes administering a compound described herein in combination with radiation therapy. Yet another aspect provides a method of abolishing radiation-induced G2/M checkpoint by administering a compound described herein in combination with radiation treatment.

Another aspect provides a method of treating pancreatic cancer by administering to pancreatic cancer cells a compound described herein in combination with one or more cancer therapies. In some embodiments, the compound is combined with chemoradiation, chemotherapy, and/or radiation therapy. As would be understood by one of skill in the art, chemoradiation refers to a treatment regime that includes both chemotherapy (such as gemcitabine) and radiation. In some embodiments, the chemotherapy is gemcitabine.

Yet another aspect provides a method of increasing the sensitivity of pancreatic cancer cells to a cancer therapy selected from gemcitabine or radiation therapy by administering a compound described herein in combination with the cancer therapy.

In some embodiments, the cancer therapy is gemcitabine. In other embodiments, the cancer therapy is radiation therapy. In yet another embodiment the cancer therapy is chemoradiation.

Another aspect provides a method of inhibiting phosphorylation of Chk1 (Ser 345) in a pancreatic cancer cell comprising administering a compound described herein after treatment with gemcitabine (100 nM) and/or radiation (6 Gy) to a pancreatic cancer cell.

Another aspect provides method of radiosensitizing hypoxic PSN-1, MiaPaCa-2 or PancM tumor cells by administering a compound described herein to the tumor cell in combination with radiation therapy.

Yet another aspect provides a method of sensitizing hypoxic PSN-1, MiaPaCa-2 or PancM tumor cells by administering a compound described herein to the tumor cell in combination with gemcitabine.

Another aspect provides a method of sensitizing PSN-1 and MiaPaCa-2 tumor cells to chemoradiation by administering a compound described herein to the tumor cells in combination with chemoradiation.

Another aspect provides a method of disrupting damage-induced cell cycle checkpoints by administering a compound described herein in combination with radiation therapy to a pancreatic cancer cell.

Another aspect provides a method of inhibiting repair of DNA damage by homologous recombination in a pancreatic cancer cell by administering a compound described herein in combination with one or more of the following treatments: chemoradiation, chemotherapy, and radiation therapy.

In some embodiments, the chemotherapy is gemcitabine. Another aspect provides a method of inhibiting repair of DNA damage by homologous recombination in a pancreatic cancer cell by administering a compound described herein in combination with gemcitabine and radiation therapy.

In some embodiments, the pancreatic cancer cells are derived from a pancreatic cell line selected from PSN-1, MiaPaCa-2 or Panc-1.

In other embodiments, the pancreatic cancer cells are in a cancer patient.

Another aspect of the invention provides a method of treating non-small cell lung cancer comprising administering to a patient a compound described herein in combination with one or more of the following additional therapeutic agents: Cisplatin or Carboplatin, Etoposide, and ionizing radiation. Some embodiments comprise administering to a patient a compound described herein in combination with Cisplatin or Carboplatin, Etoposide, and ionizing radiation. In some embodiments the combination is Cisplatin, Etoposide, and ionizing radiation. In other embodiments the combination is Carboplatin, Etoposide, and ionizing radiation.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1, H2AX, MCPH1/BRIT1, CTIP, or SMC1. In other embodiments, said defect is altered expression or activity of one or more of the following: ATM, p53, CHK2, MRE11, RAD50, NBS1, 53BP1, MDC1 or H2AX. According to another embodiment, the method is used on a cancer, cancer cell, or cell expressing DNA damaging oncogenes.

In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

According to another embodiment, the method is used on a cancer, cancer cell, or cell has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (http://www.sabiosciences.com/dna_methylation_product/HTML/MEAH-421A.html).

Finally, the expression levels of base excision repair genes can be assessed by directly quantifying levels of the mRNA and protein products of each gene using standard techniques such as quantitative reverse transcriptase-coupled polymerase chain reaction (RT-PCR) and immunhohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

In some embodiments, the base excision repair protein is PARP1, PARP2, or PolB. In other embodiments, the base excision repair protein is PARP1 or PARP2.

The methods described above (gene sequence, promoter methylation and mRNA expression) may also be used to characterize the status (e.g., expression or mutation) of other genes or proteins of interesting, such DNA-damaging oncogenes expressed by a tumor or defects in the ATM signaling cascade of a cell.

Yet another embodiment provides use of a compound described herein as a radio-sensitizer or a chemo-sensitizer.

Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

Compounds and Compositions for Use

One embodiment provides a compound or composition as described herein for use as a radio-sensitizer or a chemo-sensitizer. Another embodiment provides a compound or composition as described herein for use as a single agent (monotherapy) for treating cancer.

Another embodiment provides a compound or composition as described herein for treating patients having cancer with a DNA-damage response (DDR) defect. In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides compounds or compositions described herein for treating cancer. In some embodiments, the compound or composition is further combined with an additional therapeutic agent described herein. In some embodiments, the compound or composition is further combined with a DNA damaging agent described herein.

In some embodiments, the cancer has a defect in a pathway described herein.

Manufacture of Medicaments

One embodiment provides the use of a compound or composition described herein for the manufacture of a medicament for use as a radio-sensitizer or a chemo-sensitizer. Another embodiment provides the use of a compound or composition described herein for the manufacture of a medicament for the manufacture of a medicament for use as a single agent (monotherapy) for treating cancer.

Yet another embodiment provides the use of a compound or composition described herein for the manufacture of a medicament for the manufacture of a medicament for treating patients having cancer with a DNA-damage response (DDR) defect.

In some embodiments, said defect is a mutation or loss of ATM, p53, CHK2, MRE11, RAD50, NBS1, 53BP1, MDC1, or H2AX. In other embodiments, said defect is a mutation or loss of ATM, p53, CHK2, MRE11, RAD50, NBS1, 53BP1, MDC1, H2AX, MCPH1/BRIT1, CTIP, or SMC1.

Another embodiment provides the use of a compound or composition described herein for the manufacture of a medicament for treating cancer. In some embodiments, the compound or composition is combined with an additional therapeutic agent, such as a DNA damaging agent, described herein. In another embodiment, the cancer has a defect in a pathway described herein.

Experimental Materials and Methods

All commercially available solvents and reagents were used as received. Microwave reactions were carried out using a CEM Discovery microwave. Flash Chromatography, e.g., was carried out on an ISCO© Combiflash® Companion™ system eluting with a 0 to 100% EtOAc/petroleum ether gradient. Other methods known in the art were also utilized to perform Flash Chromotography. Samples were applied pre-absorbed on silica. Where stated, supercritical fluid chromatography (SFC) was performed on a Berger Minigram SFC machine. All $^1$HNMR spectra were recorded using a Bruker Avance III 500 instrument at 500 MHz. MS samples were analyzed on a Waters SQD mass spectrometer with electrospray ionization operating in positive and negative ion mode. Samples were introduced into the mass spectrometer using chromatography. All final products had a purity ≥95%, unless specified otherwise in the experimental details. HPLC purity was measured on a Waters Acquity UPLC system with a Waters SQD MS instrument equipped with a Waters UPLC BEH C8 1.7 μm, 2.1×50 mm column and a Vanguard BEH C8 1.7 μm, 2.1×5 mm guard column.

As used herein, the term "Rt(min)" refers to the HPLC retention time, in minutes, associated with the compound. Unless otherwise indicated, the HPLC methods utilized to obtain the reported retention times are as described below:

HPLC Method A
Instrument: Waters Acquity UPLC-MS;
Column: Waters UPLC BEH C8 1.7 μm, 2.1×50 mm with Vanguard BEH C8 1.7 μm, 2.1×5 mm guard column;
Column temperature: 45° C.;
Mobile Phase A: 10 mM ammonium formate in water: acetonitrile 95:5, pH 9;
Mobile Phase B: acetonitrile;
Detection: 210-400 nm
Gradient: initial: 2% B, 0-1.15 min: 2% B to 98% B, 1.15-1.35 min: hold at 98% B, 1.35-1.40 min: 98% B to 2% B, 1.40-1.50 min: hold at 2% B;
Flow rate: 1.0 mL/minute;

HPLC Method B
Instrument: Waters Acquity UPLC-MS;
Column: Waters UPLC BEH C8 1.7 μm, 2.1×50 mm with Vanguard BEH C8 1.7 μm, 2.1×5 mm guard column;
Column temperature: 45° C.;
Mobile Phase A: 10 mM ammonium formate in water: acetonitrile 95:5, pH 9;
Mobile Phase B: acetonitrile;
Detection: 210-400 nm;
Gradient: 0-0.40 min: 2% B, 0.40-4.85 min: 2% B to 98% B, 4.85-4.90 min: 98% B to 2% B, 4.90-5.00 min: hold at 2% B;
Flow rate: 0.6 mL/minute.

Examples and Schemes

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). The following generic schemes and examples illustrate how to prepare the compounds of the present disclosure. The examples are for the purpose of illustration only and are not to be construed as limiting the scope of the invention in any way.

It will be understood that when an inconsistency exists between the chemical structure and the corresponding name provided herein, the chemical structure will control.

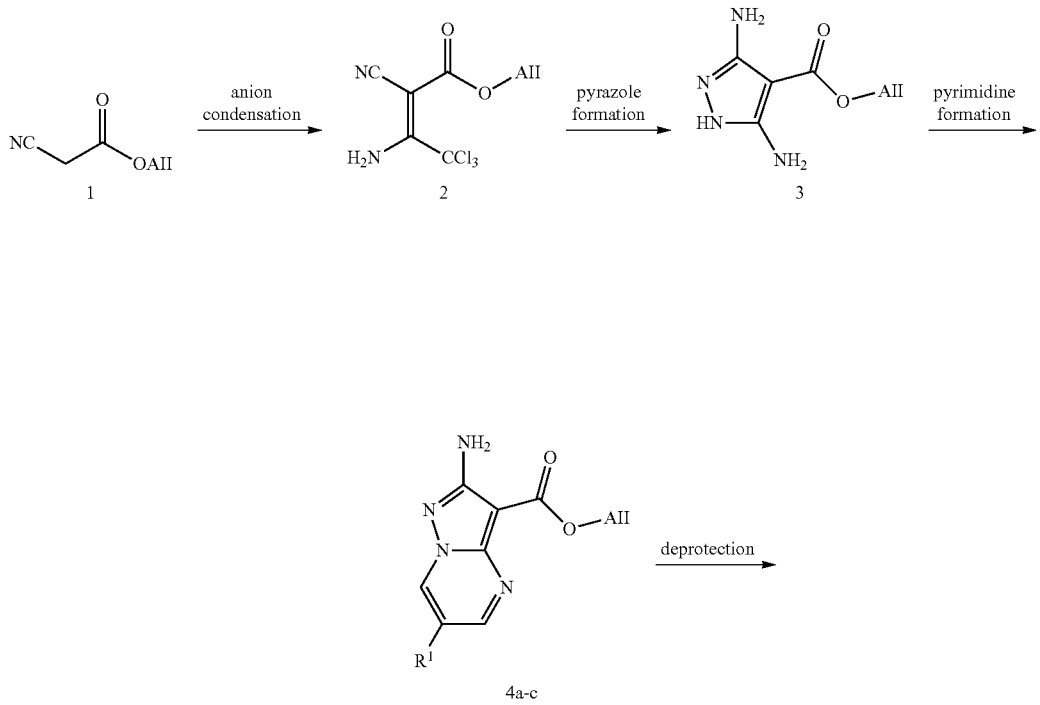

-continued

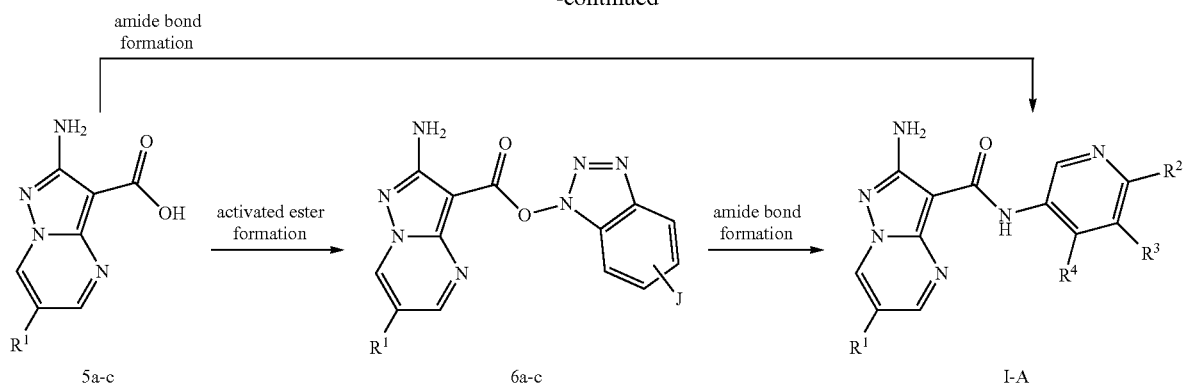

Compounds of this invention can be synthesised according to methods similar to the one depicted in Scheme 1.

The anion of commercially available allyl cyanoacetate 1 can react with trichloroacetonitrile to provide intermediate 2. In the anion condensation step, the anion of commercially available allyl cyanoacetate 1 can be generated with a base such as potassium acetate in an appropriate solvent such as an alcohol (e.g., isopropylalcohol). The anion then reacts with trichloroacetonitrile at room temperature (specific details are given in Preparation 1, Step 1 below).

Intermediate 2 then reacts with hydrazine to form the diaminopyrazole 3. In the pyrazole formation step, intermediate 2 is reacted with hydrazine (or its hydrate) in an aprotic solvent, such as DMF, to provide the diaminopyrazole 3. The reaction occurs under basic conditions (e.g., in the presence of potassium acetate or AcONa) with heating (e.g., 110° C.) to ensure complete cyclisation (specific details are given in Preparation 1, Step 2 below).

Intermediate 3 can further be condensed with a dielectrophilic coupling partner to form the pyrimidine 4a-c. In the pyrimidine formation step, intermediate 3 is reacted with a 1,3-dielectrophilic species (e.g., a 1,3-dialdehyde or a 3-(dialkylamino)-prop-2-enal) in various types of solvents (e.g., DMF or DMSO/water) to furnish the bicyclic cores 4a-c. When one or two of the electrophilic centers is protected/masked (e.g., aldehyde masked as a ketal), introduction of a sulfonic acid (e.g., PTSA) is required to liberate the reactive functional group (specific details are given in Preparation 4, Step 1 below).

Deprotection, e.g, via hydrolysis, of the allyl ester leads to the carboxylic acids 5a-c. In the deprotection step, compound 4a-c is subjected to hydrolytic conditions that are known to those skilled in the art. For example, treatment of 4a-c with phenylsilane or 4-methylbenzenesulfinate in the presence of a catalytic amount of palladium (e.g., $Pd(PPh_3)_4$) leads to the formation of the corresponding carboxylic acid 5a-c. Alternatively, compounds 4a-c could be treated with aqueous alkali (e.g., NaOH, KOH) to produce acids 5a-c (specific details are given in Preparation 4, Step 2 below).

In the activated ester formation step, the carboxylic acids 5a-c are reacted with amide coupling agents known to those skilled in the art. When the coupling agent is chosen appropriately, the reactions can proceed rapidly (~1 h) at room temperature in the presence of an organic base (e.g., triethylamine, DIPEA) to provide the activated esters 6a-c. For example, when the amide coupling agents TBTU [J=H] or TCTU [J=Cl] are used, compounds 6a-c are obtained readily by filtration of the reaction mixture (specific details are given in Preparation 4, Step 3 below).

Formation of the activated esters 6a-c prior to the amide bond formation to prepare I-A is generally preferred, although a direct conversion of 5a-c into the compounds of formula I-A of this invention is also possible. Alternative activated esters can also be utilised (isolated or formed in situ) and will be known to those skilled in the art (e.g., using TBTU, TCTU, HATU, T3P, COMU coupling agents).

In the amide bond formation step, activated esters 6a-c can react with a substituted 3-aminopyridine to provide compounds of formula I-A of this invention. The reaction conditions for the amide coupling are generally in an aprotic solvent (e.g., NMP, pyridine, DMF, etc. . . . ) with heating (e.g., ≥90° C.) (specific details are given in Example 1 below). The 3-aminopyridine may be further functionalized following amide bond formation.

Alternatively, the two steps described above can be combined: carboxylic acids 5a-c can be used as starting points for the amide bond formation, the activated esters being generated in situ, using the same amide couplings agents as those described above. Compounds I-A of this invention are isolated in a similar manner to the one described above (specific details are given in Example 3a below).

Compounds of formula I, I-A-1, and I-B can also be prepared using similar methods.

Scheme 2: Alternative approach for the preparation of compounds I-A

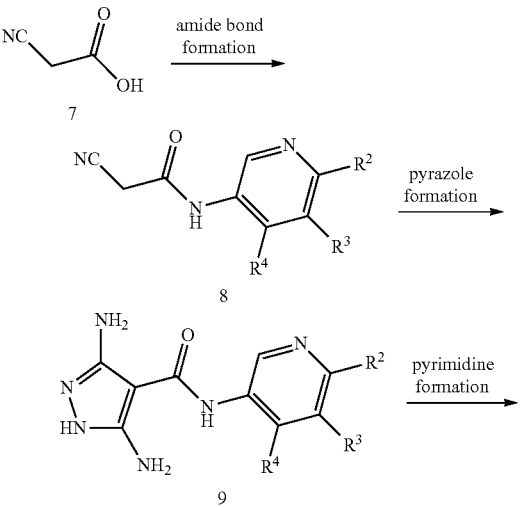

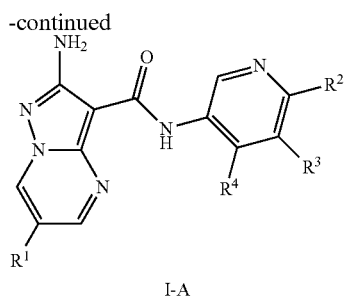

I-A

Alternatively, compounds of the present disclosure can be prepared according to methods similar to the one depicted in Scheme 2.

The amide 8 can readily be prepared from commercially available cyanoacetic acid 7. In the amide bond formation step, cyanoacetic acid 7 can react with a substituted 3-aminopyridine to provide compounds 8 of this invention. The reaction conditions for the amide coupling are generally in an aprotic solvent (e.g., DCM, NMP, DMF, etc), in the presence of an organic base, such as an aliphatic amine (e.g., triethylamine or DIPEA) and an amide coupling agent known to those skilled in the art: for example EDCI, TBTU, COMU, T3P, etc (specific details are given in Example 3e, step 1 below).

In the pyrazole formation step, the anion of cyanoamide 8 can be generated with a base (such as potassium or sodium acetate) in an appropriate solvent such as an alcohol (e.g., ethanol). The anion then reacts with trichloroacetonitrile at room temperature (specific details are given in Example 3e, step 2 below). The resulting solid, which can be collected by filtration, is then reacted with hydrazine (or its hydrate) in an aprotic solvent, such as DMF or NMP, to provide the diaminopyrazole 9, the latter being further condensed with a dielectrophilic coupling partner to form the pyrimidine portion of the compounds of formula I-A of this invention.

In the pyrimidine formation step, intermediate 9 is reacted with a 1,3-dielectrophilic species (e.g., a 1,3-dialdehyde or a 3-(dialkylamino)-prop-2-enal) in various types of solvents (e.g., iPrOH/water, DMF, or DMSO/water) to furnish the desired products I-A. When one or two of the electrophilic centers is protected/masked (e.g., aldehyde masked as a ketal), introduction of a sulfonic acid (e.g., PTSA) is required to liberate the reactive functional group. (specific details are given in Example 3e, step 3 below).

Compounds of formula I, I-A-1, and I-B can also be prepared using similar methods.

Preparation 1: Allyl 3,5-diamino-1H-pyrazole-4-carboxylate

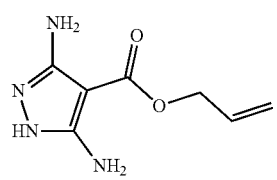

3

Step 1: allyl 3-amino-4,4,4-trichloro-2-cyanobut-2-enoate 2

To a solution of KOAc (589.4 g, 6.006 mol) in isopropanol (3 L) was added allyl cyanoacetate (429.4 g, 403.2 mL, 3.432 mol) and the reaction mixture was cooled to 5° C. Trichloroacetonitrile (495.5 g, 3.432 mol) was added in 50 mL portions, maintaining temperature below 15° C. The reaction mixture was then allowed to warm to 20° C. and stirred for 3 h. Water (~4 L) was added to dissolve the inorganic materials and precipitate out the desired product. The mixture was stirred for 20 minutes and the solid was isolated by filtration under vacuum. This solid was filtered, washed with water (2×0.5 L) and dried in a vacuum oven overnight at 40° C. to afford allyl 3-amino-4,4,4-trichloro-2-cyanobut-2-enoate 2 as an off-white powder (787 g, 85%).

Step 2: Allyl 3,5-diamino-1H-pyrazole-4-carboxylate 3

To a suspension of allyl 3-amino-4,4,4-trichloro-2-cyanobut-2-enoate 2 (619 g, 2.297 mol) and KOAc (676.3 g, 6.891 mol) in DMF (2.476 L) at 0° C. was slowly added hydrazine hydrate (172.5 g, 167.6 mL, 3.446 mol) over 15 min. The reaction mixture was then stirred at ambient temperature for 2 h, at which stage $^1$H NMR shows complete consumption of the starting material. Reaction mixture was then heated overnight at 110° C. before being allowed to cool to ambient and stirred for another 48 h. The mixture was filtered through a sintered glass funnel to remove the precipitated solid and the filtrate was evaporated under reduced pressure to give a thick liquid. DCM (approx 2 L) was added, and the mixture filtered again to remove additional solids that have precipitated. The filtrate was purified through a 1 kg silica gel plug (gradient of DCM/MeOH as an eluent), and the solvent was removed to afford an orange solid which was suspended in acetonitrile and heated at about 70° C. until all the solid went into solution, at which point the solution was allowed to cool to ambient temperature, then to 2° C. The precipitate that formed was isolated by filtration under vacuum, washed with chilled MeCN (~50 mL) and dried to constant mass in a vacuum oven to furnish the title compound as an off-white powder (171.2 g, 41%).

Preparation 2a: 1H-benzo[d][1,2,3]triazol-1-yl 2-amino-6-fluoropyrazolo[1,5-a]pyrimidine-3-carboxylate

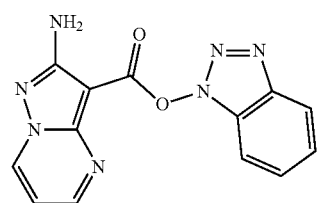

6a

Step 1: allyl 2-amino-6-fluoro-pyrazolo[1,5-a]pyrimidine-3-carboxylate 4a

To a suspension of allyl 3,5-diamino-1H-pyrazole-4-carboxylate 3 (42.72 g, 234.5 mmol) in DMSO (270.8 mL)/Water (270.8 mL), was added p-TsOH hydrate (46.72 g, 245.6 mmol) and 3-(diisopropylamino)-2-fluoro-prop-2-enal (described in Tetrahedron Letters, 33(3), 357-60; 1992) (38.69 g, 223.3 mmol). The reaction mixture was heated to 100° C. for 3 h during which time a solid slowly precipitated out of solution. The orange suspension was allowed to cool down to RT overnight. The solid was filtered, washed with water and dried under vacuum to give allyl 2-amino-6-fluoro-pyrazolo[1,5-a]pyrimidine-3-carboxylate 4a as a sand solid (45.05 g, 85% yield).

Step 2: 2-amino-6-fluoro-pyrazolo[1,5-a]pyrimidine-3-carboxylic acid 5a

To a suspension of allyl 2-amino-6-fluoro-pyrazolo[1,5-a]pyrimidine-3-carboxylate 4a (45 g, 190.5 mmol) in DCM (1.35 L) was added phenylsilane (41.23 g, 46.96 mL, 381.0 mmol), followed by Pd(PPh$_3$)$_4$ (8.805 g, 7.620 mmol). The reaction was stirred at room temperature for 2 h 30 min. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-fluoro-pyrazolo[1,5-a]pyrimidine-3-carboxylic acid 5a as a light yellow solid (37.77 g, 100% yield).

In an alternative method, 4-methylbenzenesulfinate (anhydrous, 1.2 eqv, 22.6 g, 127 mmol) was suspended in dry DMSO (20 vol, 500 ml). The stirred mixture was warmed to 30° C. under a nitrogen atmosphere. Upon complete dissolution Pd(PPh$_3$)$_4$ (2 mol %, 2.4 g, 2.1 mmol) was added. The mixture was stirred for 10 min at 25-30° C. after which time a turbid yellow solution was present. Allyl 2-amino-6-fluoro-pyrazolo[1,5-a]pyrimidine-3-carboxylate (25 g, 105.8 mmol) was added portionwise, maintaining the temperature at 25-30° C. Once addition was complete the cloudy solution was stirred until the reaction was complete by HPLC (2-3 hrs). A heavy precipitate formed after 15 minutes post addition of the substrate. The mixture became thicker as the reaction proceeded. The reaction mixture was diluted with water (125 ml) and 2M HCl (66 ml) was added slowly, maintaining the temperature at 25-30° C. The slurry was stirred for 30 minutes, then filtered. The filtration was slow (2 hrs). The resulting solid was washed with water, then dried on the sinter. The solid was slurried in DCM (8 vol) for 1 hr. The solid was filtered (rapid filtration) and washed with DCM. The solid was re-slurried in chloroform (8 vol) for 1 hr. The acid was filtered and dried on the sinter. It was further dried in a vacuum oven at 50° C. for 24 hrs. The product was obtained as an off-white solid (18.6 g, 85%); 1H NMR (500 MHz, DMSO-d6) δ 12.14 (1H, brs), 9.31 (1H, dd), 8.69 (1H, m), 6.47 (2H, brS); 19F NMR (500 MHz, DMSO-d6) δ−153.65; MS (ES+) 197.1.

Step 3: 1H-benzo[d][1,2,3]triazol-1-yl 2-amino-6-fluoropyrazolo[1,5-a]pyrimidine-3-carboxylate 6a To a suspension of 2-amino-6-fluoro-pyrazolo[1,5-a]pyrimidine-3-carboxylic acid 5a (20 g, 102.0 mmol) in chloroform (300 mL) was added Et$_3$N (11.35 g, 15.63 mL, 112.2 mmol). The suspension was stirred for ~5 mins and then (benzotriazol-1-yloxy-dimethylamino-methylene)-dimethyl-ammonium Boron Tetrafluoride was added (32.75 g, 102.0 mmol). The suspension was heated to 60° C. for 1 h before the thick suspension was allowed to cool down to RT. The resulting suspension was filtered, washed with chloroform (200 mL) and dried under vacuum overnight to afford the title compound 6a as a light yellow powder (32.5 g, 88%).

Preparation 2b: (6-chlorobenzotriazol-1-yl)-2-amino-6-fluoro-pyrazolo[1,5-a]pyrimidine-3-carboxylate 6a*

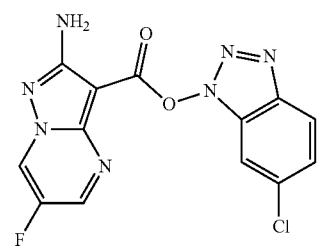

6a*

In a 2.5 L three-necked flask equipped with stirrer bar, condenser, nitrogen line and Hanna temperature probe was charged 2-amino-6-fluoro-pyrazolo[1,5-a]pyrimidine-3-carboxylic acid 5a (60 g, 305.9 mmol), chloroform (900.0 mL) and triethylamine (32.44 g, 44.68 mL, 320.6 mmol). [(6-chlorobenzotriazol-1-yl)oxy-(dimethylamino)methylene]-dimethyl-ammonium (Boron Tetrafluoride Ion (1)) (87.00 g, 244.7 mmol) was added portionwise over 5 mins (internal dropped from 22.7 to 21.5° C. on complete addition). Mixture heated at 60° C. (internal temp) for 2 h, still a cream suspension. Mixture cooled to room temperature then solid collected by filtration, washed well with chloroform (until filtrate runs essentially colourless) and dried by suction to leave product 6a* as a cream solid (82.2 g, 77% yield). $^1$H NMR (500 MHz, DMSO-d$_6$) δ 9.55 (dd, 1H), 8.91 (d, 1H), 8.22 (dd, 1H), 8.09 (dd, 1H), 7.57 (dd, 1H) and 6.87 (s, 2H). MS (ES+) 348.1.

In an alternative method, 2-Amino-6-fluoropyrazolo[1,5-a]pyrimidine-3-carboxylic acid 5a (30 g, 153 mmol) was slurried in acetonitrile (540 ml). Triethylamine (22.5 ml, 153 mmol) was added, followed by [(6-chlorobenzotriazol-1yl)oxy-(dimethylamino)methylene]-dimethylammonium tetrafluoroborate (TCTU, 54.4 g, 153 mmol). The mixture was stirred at room temperature for 2 hrs. The product was isolated by filtration—the filter cake was washed with acetonitrile (2×60 ml) (49.3 g, 93%); $^1$H NMR (500 MHz, DMSO-d6) δ 9.55 (dd, 1H), 8.91 (d, 1H), 8.22 (dd, 1H), 8.09 (dd, 1H), 7.57 (dd, 1H) and 6.87 (s, 2H); 19F NMR (500 MHz, DMSO-d6) δ−150.1; MS (ES+) 348.1.

Preparation 3: 1H-benzo[d][1,2,3]triazol-1-yl 2-amino-6-chloropyrazolo[1,5-a]pyrimidine-3-carboxylate

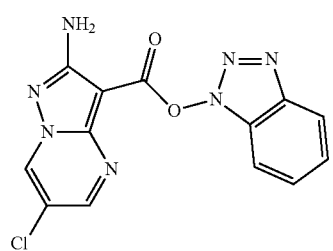

6b

Step 1: 2-amino-6-chloro-pyrazolo[1,5-a]pyrimidine-3-carboxylate 4b

To a suspension of allyl 3,5-diamino-1H-pyrazole-4-carboxylate 3 (1 g, 5.489 mmol) in DMF (5 mL) was added (Z)-2-chloro-3-dimethylamino-prop-2-enylidene]-dimethylammonium hexafluorophosphate (1.683 g, 5.489 mmol), followed by triethylamine (722.1 mg, 994.6 µL, 7.136 mmol). The reaction mixture was heated to 60° C. for 4 h during which time a solid slowly precipitated out of solution. The brown suspension was allowed to cool down to RT. The solid was filtered, washed with water and dried under vacuum to give allyl 2-amino-6-chloro-pyrazolo[1,5-a]pyrimidine-3-carboxylate 4b as a brown solid (1.092 g, 72% yield).

Step 2: 2-amino-6-chloro-pyrazolo[1,5-a]pyrimidine-3-carboxylic Acid 5b

To a suspension of allyl 2-amino-6-chloro-pyrazolo[1,5-a]pyrimidine-3-carboxylate 4b (1 g, 3.96 mmol) in DCM (15 mL) was added phenylsilane (856.6 mg, 0.9756 mL, 7.916 mmol), followed by Pd(PPh$_3$)$_4$ (182.9 mg, 0.1583 mmol). The reaction was stirred at room temperature for 7 h. The reaction mixture was filtered and the solid was washed with DCM to give a light yellow solid (43.2 g). This solid was triturated further in DCM (225 mL) at RT for 45 min, then filtered and dried overnight under vacuum to provide 2-amino-6-chloro-pyrazolo[1,5-a]pyrimidine-3-carboxylic acid 5b as a yellow solid (791 m, 94% yield).

Step 3: 1H-benzo[d][1,2,3]triazol-1-yl 2-amino-6-chloropyrazolo[1,5-a]pyrimidine-3-carboxylate 6b To a solution of 2-amino-6-chloro-pyrazolo[1,5-a]pyrimidine-3-carboxylic acid 5b (1.51 g, 7.103 mmol) in chloroform (15.1 mL) was added TBTU boron tetrafluoride (2.737 g, 8.524 mmol) and TEA (862.5 mg, 1.188 mL, 8.524 mmol). The reaction mixture was stirred at 50° C. for one hour. The resulting suspension was filtered, and the solid triturated in ethyl acetate to afford the title compound 6b as a yellow solid (2.05 g, 88%).

Preparation 4: 1H-benzo[d][1,2,3]triazol-1-yl 2-amino-6-(cyanomethyl)pyrazolo[1,5-a]pyrimidine-3-carboxylate

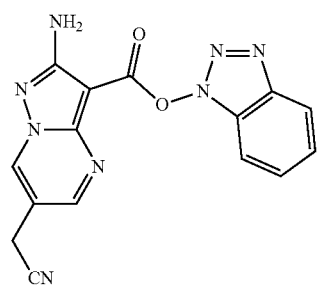

6c

Step 1: allyl 2-amino-6-(cyanomethyl)-pyrazolo[1,5-a]pyrimidine-3-carboxylate 4c To a suspension of allyl 3,5-diamino-1H-pyrazole-4-carboxylate 3 (63.49 g, 348.5 mmol) in a mixture of DMSO (340 mL) and water (340 mL), was added 3-(dimethoxymethyl)-4,4-dimethoxy-butanenitrile (Scheme 3, below) (85 g, 418.2 mmol), followed by para-toluene Sulfonic acid hydrate (1) (11.27 g, 59.24 mmol). The reaction mixture was heated to 85° C. and stirred overnight. The reaction mixture was cooled with an ice bath. The mixture was diluted with EtOAc (680 mL) and a saturated aqueous solution of NaHCO$_3$ (1.36 L). The precipitate was filtered and rinsed with water, then with a mixture of water and EtOAc. The brown solid was dried under vacuum to give allyl 2-amino-6-(cyanomethyl)-pyrazolo[1,5-a]pyrimidine-3-carboxylate 4c as a brown solid (55.94 g, 62% yield).

Step 2: 2-amino-6-(cyanomethyl)-pyrazolo[1,5-a]pyrimidine-3-carboxylic Acid 5c To a suspension of allyl 2-amino-6-(cyanomethyl)-pyrazolo[1,5-a]pyrimidine-3-carboxylate 4c (10.2 g, 39.65 mmol) in DCM (350 mL) was added phenylsilane (8.581 g, 9.773 mL, 79.3 mmol), followed by Pd(PPh$_3$)$_4$ (1.5 g, 1.298 mmol). The reaction was stirred at room temperature for 2 h. The reaction mixture was filtered and the solid was washed with DCM and dried under vacuum to provide 2-amino-6-(cyanomethyl)-pyrazolo[1,5-a]pyrimidine-3-carboxylic acid 5c as a yellow solid (8.61 g, 100% yield).

Step 3: 1H-benzo[d][1,2,3]triazol-1-yl 2-amino-6-(cyanomethyl)pyrazolo[1,5-a]pyrimidine-3-carboxylate 6c To a solution of 2-amino-6-(cyanomethyl)-pyrazolo[1,5-a]pyrimidine-3-carboxylic acid 5c (5.11 g, 23.53 mmol) in DCM (51 mL) was added TBTU boron tetrafluoride (9.067 g, 28.24 mmol) and TEA (2.858 g, 3.937 mL, 28.24 mmol). The reaction mixture was stirred at room temperature for one hour. The resulting suspension was filtered, and the solid triturated in hot chloroform to afford the title compound 6c as a beige solid (6.59 g, 84%).

Example 1: 2-amino-6-fluoro-N-(4-(4-(oxetan-3-yl)piperazin-1-yl)pyridin-3-yl)pyrazolo[1,5-a]pyrimidine-3-carboxamide (Compound I-N-1)

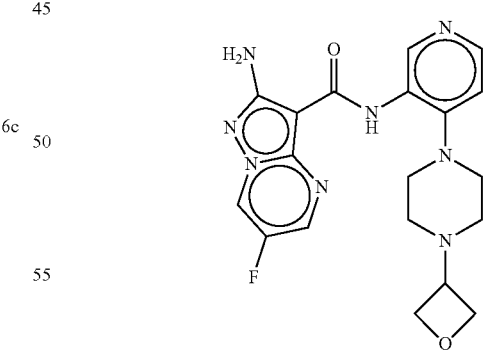

To a suspension of benzotriazol-1-yl 2-amino-6-fluoro-pyrazolo[1,5-a]pyrimidine-3-carboxylate 6a (prepared according to methods similar to the one depicted in Preparation 2a) (5 g, 15.62 mmol) in NMP (78.27 mL) was added 4-[4-(oxetan-3-yl)piperazin-1-yl]pyridin-3-amine (prepared according to methods similar to the one depicted in Preparation N-1, described below) (3.660 g, 15.62 mmol) and the resulting mixture heated at 100° C. for 18 hours. The reaction mixture was cooled to RT and then passed through a pre-wetted SCX cartridge (2×50 g cartridge) and the cartridge was washed with methanol. The product was eluted with 2M ammonia in methanol and the eluent was concentrated in vacuo to leave a dark solid that was purified by column chromatography on silica using the ISCO column companion, eluting with DCM and 90:10:1 DCM:MeOH: $NH_3$ (0-100% gradient, 40 g column). Product fractions were combined and concentrated in vacuo to leave the product as a yellow solid which was then recrystallised from methanol to leave pure product as a yellow solid. MS (ES+) 413.2.

Example 2: 2-amino-N-(4-(4-aminopiperidin-1-yl)pyridin-3-yl)-6-(cyanomethyl)pyrazolo[1,5-a]pyrimidine-3-carboxamide (Compound I-N-2)

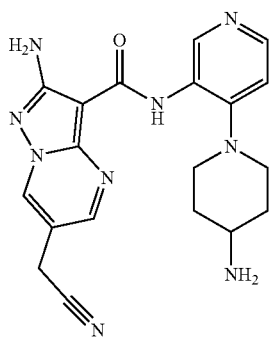 [SMILES: N#CCc1cnc2c(C(=O)Nc3cnccc3N3CCC(N)CC3)c(N)nn2c1]

To a solution of tert-butyl N-[1-[3-[[2-amino-6-(cyanomethyl)pyrazolo[1,5-a]pyrimidine-3-carbonyl]amino]-4-pyridyl]-4-piperidyl]carbamate prepared according to a method similar to the one described in Example 1 (70 mg, 0.1424 mmol) in DCM (4 mL) was added TFA (1 mL, 12.98 mmol) and the mixture was stirred at ambient temperature for 1.5 hours. The reaction mixture was evaporated to dryness and purified by HPLC: 10-90% ACN in Water (TFA modifier) and the fractions were freeze-dried. The solid residue was dissolved in methanol (1 mL) and loaded onto a pre-wetted (15 mL methanol) 2 g SCX-2 cartridge. The cartridge was washed with methanol (2×15 mL) then the product eluted as a free base using 2M ammonia in methanol solution (3×15 mL). The product-containing fractions were evaporated to dryness, re-dissolved in water/methanol and freeze-dried to afford the desired product as a yellow solid (17 mg, 31%). MS (ES+) 391.1.

Example 3a: 2-amino-6-fluoro-N-(4-(4-methylpiperazin-1-yl)pyridin-3-yl)pyrazolo[1,5-a]pyrimidine-3-carboxamide (Compound I-N-3)

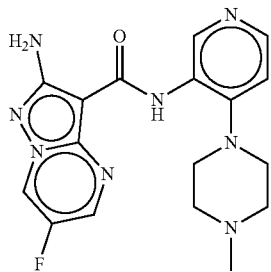

A mixture of 4-(4-methylpiperazin-1-yl)pyridin-3-amine (prepared according to methods similar to the one depicted in Preparation N-1, described below) (588.1 mg, 3.059 mmol), 2-amino-6-fluoro-pyrazolo[1,5-a]pyrimidine-3-carboxylic acid 5a (prepared according to methods similar to the ones depicted in the sequence Step 1-Step 2 of Preparation 2a) (500 mg, 2.549 mmol), TBTU (1.146 g, 3.569 mmol) and $Et_3N$ (515.9 mg, 710.6 μL, 5.098 mmol) in NMP (7 mL) was stirred at 110° C. in a sealed tube, for 20 h. The reaction mixture was diluted with EtOAc, washed with a saturated bicarbonate aqueous solution and brine. The organic was dried over $MgSO_4$ and concentrated after filtration. The solid was triturated in DCM and then filtered off. It was further purified by Fractionlynx HPLC to yield the title compound as a colourless solid. MS (ES+) 371.3.

Alternatively, compound I-N-3 can be prepared according to Scheme 2 using the procedure described in Example 3b.

Example 3b: 2-amino-6-fluoro-N-(4-(4-methylpiperazin-1-yl)pyridin-3-yl)pyrazolo[1,5-a]pyrimidine-3-carboxamide (Compound I-N-3)

Step 1: 2-cyano-N-(4-(4-methylpiperazin-1-yl)pyridin-3-yl)acetamide 8

To an ice cold solution of 2-cyanoacetic acid 7 (1.15 g, 13.52 mmol) in DCM (40 mL) was added oxalyl chloride (1.3 mL, 14.90 mmol) dropwise, followed by a catalytic amount of DMF. The reaction mixture was stirred at room temperature for 3 h and then concentrated in vacuo to remove solvent. The residue was added to a solution of 4-(4-methylpiperazin-1-yl)pyridin-3-amine (Prepared according to methods similar to the one depicted in Preparation N-1, described below) (1.3 g, 6.762 mmol) and $Et_3N$ (1.026 g, 1.413 mL, 10.14 mmol) in THF (40 mL) and the reaction mixture was stirred at room temperature for 18 h. The mixture was diluted with EtOAc, washed with a saturated bicarbonate aqueous solution and brine. The aqueous layer was further extracted with DCM (20 mL×2). The combined organic layers were dried over $Na_2SO_4$ and concentrated to give 2-cyano-N-(4-(4-methylpiperazin-1-yl)pyridin-3-yl)acetamide 8 as a yellow oil. MS (ES+) 260.1.

Step 2: 3,5-diamino-N-[4-(4-methylpiperazin-1-yl)-3-pyridyl]-1H-pyrazole-4-carboxamide 9

To a suspension of 2-cyano-N-[4-(4-methylpiperazin-1-yl)-3-pyridyl]acetamide 8 (1.6 g, 6.170 mmol) in ethanol (40 mL) was added sodium acetate (1.052 g, 12.83 mmol), followed by trichloroacetonitrile (1.042 g, 733.8 μL, 7.219 mmol) dropwise. The heterogeneous mixture was stirred at room temperature under an atmosphere of nitrogen for 18 h. The reaction mixture was concentrated under vacuum, and the residue was dissolved in NMP (30 mL). Hydrazine hydrate (803 mg, 780.4 μL, 16.04 mmol) was added and the reaction mixture was stirred at room temperature for 3 h. The solvents were removed under vacuum and the residue triturated in DCM to form a brown solid which was isolated by filtration to provide 3,5-diamino-N-[4-(4-methylpiperazin-1-yl)-3-pyridyl]-1H-pyrazole-4-carboxamide 9 (1 g, 51%). MS (ES+) 317.1.

Step 3: 2-amino-6-fluoro-N-(4-(4-methylpiperazin-1-yl)pyridin-3-yl)pyrazolo[1,5-a]pyrimidine-3-carboxamide A mixture of (Z)-3-(diisopropylamino)-2-fluoro-prop-2-enal (Tetrahedron Letters (1992), 33(3), 357-60) (22.81 mg, 0.1317 mmol), 4-methylbenzenesulfonic acid (Water (1)) (30.05 mg, 0.1580 mmol), 3,5-diamino-N-[4-(4-methylpiperazin-1-yl)-3-pyridyl]-1H-pyrazole-4-carboxamide (50 mg, 0.1580 mmol) in DMSO (1 mL)/H2O (0.5 mL) was stirred at 140° C. for 25 min. The crude mixture was purified by Fractionlynx HPLC. The aqueous fractions were combined and lyophilised to yield 2-amino-6-fluoro-N-(4-(4-methylpiperazin-1-yl)pyridin-3-yl)pyrazolo[1,5-a]pyrimidine-3-carboxamide. (10 mg, 21%).

Example 3c: 2-amino-6-fluoro-N-(5-fluoro-4-(4-(4-methylpiperazine-1-carbonyl)piperidin-1-yl)pyridin-3-yl)pyrazolo[1,5-a]pyrimidine-3-carboxamide (Compound I-G-4)

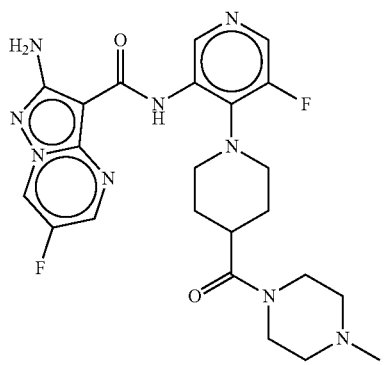

A suspension of benzotriazol-1-yl 2-amino-6-fluoro-pyrazolo[1,5-a]pyrimidine-3-carboxylate 6a (6.271 g, 20.02 mmol), [1-(3-amino-5-fluoro-4-pyridyl)-4-piperidyl]-(4-methylpiperazin-1-yl)methanone hydrobromide 17a (6.98 g, 16.68 mmol) and DIPEA (2.802 g, 3.776 mL, 21.68 mmol) in pyridine (63 mL) were placed in a sealed tube and heated at 100° C. for 24 h. The mixture cooled to room temperature then concentrated in vacuo. The resulting solid was loaded onto silica and purified by chromatography (330 g SiO2, 0.5-7.5% MeOH (containing 10% ammonium hydroxide)/DCM). The residue was stirred in ethanol for 5 mins and the solid that formed was collected by filtration, washed with minimal ethanol, dried by suction for 2 h, affording desired product as a pale yellow solid (4.71 g, 56.5%). MS (ES+) 500.2; $^1$H NMR (DMSO-d6) δ 10.63 (s, 1H), 9.67 (s, 1H), 9.47 (dd, J=4.8, 2.5 Hz, 1H), 9.25 (dd, J=2.6, 0.7 Hz, 1H), 8.25 (d, J=2.4 Hz, 1H), 6.79 (s, 2H), 3.60 (t, J=5.0 Hz, 2H), 3.55 (t, J=4.9 Hz, 2H), 3.19 (m, 2H), 3.03 (m, 2H), 2.95 (tt, J=11.7, 3.6 Hz, 1H), 2.34 (t, J=5.0 Hz, 2H), 2.29 (t, J=5.1 Hz, 2H), 2.20 (s, 3H), 2.13 (qd, J=12.4, 3.9 Hz, 2H), 1.75-1.72 (m, 2H).

Example 3d: 2-amino-6-fluoro-N-(5-fluoro-4-(4-(4-methylpiperazine-1-carbonyl)piperidin-1-yl)pyridin-3-yl)pyrazolo[1,5-a]pyrimidine-3-carboxamide (Compound I-G-4)

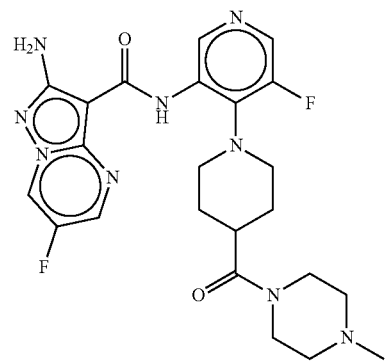

In an alternative method to the the one reported in Example 3c, compound I-G-4 can be prepared as follows:

A 2 L flask equipped with an overhead stirrer, an air condenser, a thermometer and a nitrogen line was charged with 2-amino-6-fluoro-pyrazolo[1,5-a]pyrimidine-3-carboxylic acid 5a (14.19 g, 72.36 mmol), then pyridine (353 mL) followed by [(6-chlorobenzotriazol-1-yl)oxy-(dimethylamino)methylene]-dimethyl-ammonium trifluoroborate (22.14 g, 65.78 mmol), with stirring at ambient temperature. The suspension was heated at 50° C. over 1 h period. DIPEA (17.85 g, 24.06 mL, 138.1 mmol) was then added, followed by [1-(3-amino-5-fluoro-4-pyridyl)-4-piperidyl]-(4-methylpiperazin-1-yl)methanone hydrochloride 17b (prepared according to Preparation N-14) (23.54 g, 65.78 mmol). The internal temperature was raised to 90° C. and the reaction mixture stirred at this temperature for 13 h. The mixture was then allowed to cool slowly and the solvent was evaporated in vacuo. The residue was slurried in DCM (250 ml) and the orange solid was partitioned between DCM (1 L) and 2M sodium carbonate (200 mL). The organic layer was separated, washed with 2M sodium carbonate (200 mL), dried (MgSO4), filtered and concentrated in vacuo to leave an orange solid. This solid residue was further slurried in EtOH (115 mL) for 10 mins then collected by filtration, washed with further ethanol (approx 100 mL) dried by suction to afford product as a pale yellow solid, 18.75 g, 57%).

Example 3e: 2-amino-6-fluoro-N-(5-fluoro-4-(4-(4-methylpiperazine-1-carbonyl)piperidin-1-yl)pyridin-3-yl)pyrazolo[1,5-a]pyrimidine-3-carboxamide (Compound I-G-4)

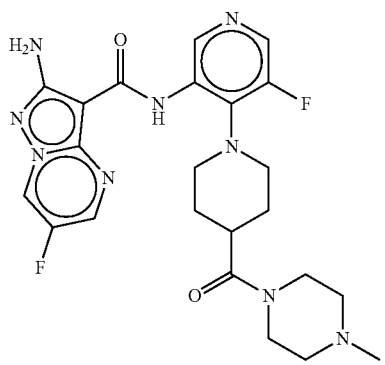

In an alternative method to the the ones reported in Example 3c and 3d, compound I-G-4 can be prepared as follows:

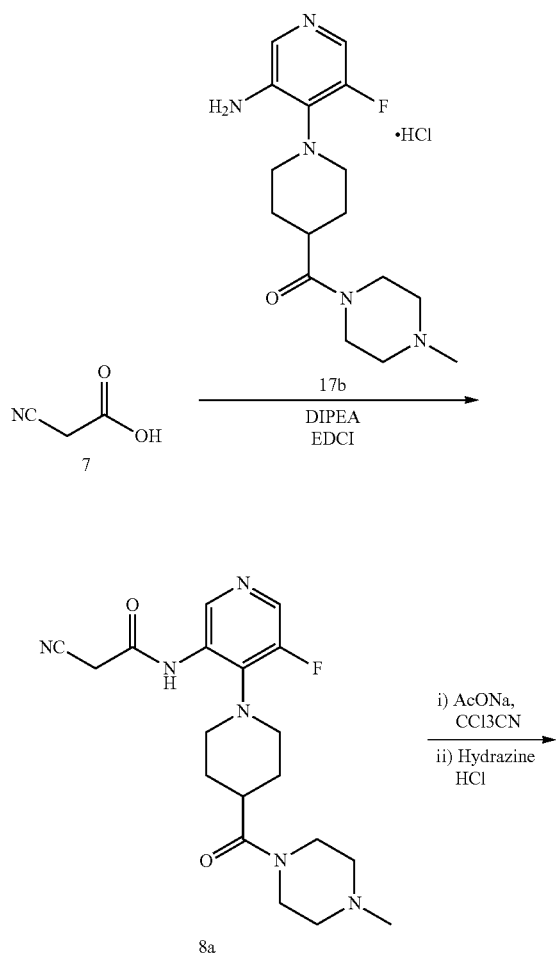

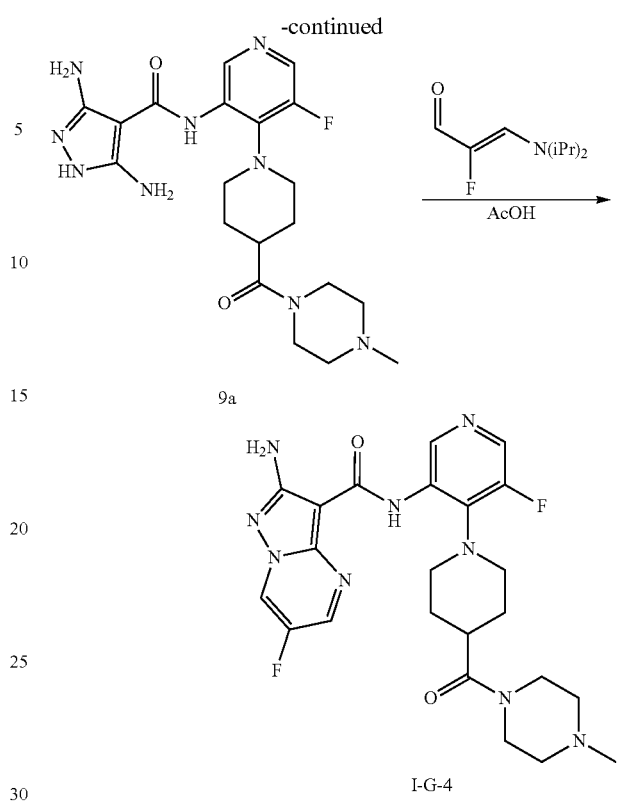

Step 1: 2-cyano-N-(5-fluoro-4-(4-(4-methylpiperazine-1-carbonyl)piperidin-1-yl)pyridin-3-yl)acetamide 8a To a solution of [1-(3-amino-5-fluoro-4-pyridyl)-4-piperidyl]-(4-methylpiperazin-1-yl)methanone hydrochloride 17b (300 mg, 0.8383 mmol) and DIPEA (541.8 mg, 730.2 µL, 4.192 mmol) in DCM (8 mL) was added cyanoacetic acid 7 (106.9 mg, 1.257 mmol). The reaction mixture was cooled on an ice bath and EDCI (241.0 mg, 1.257 mmol) was then added. The mixture was stirred at room temperature overnight, then heated under reflux for 4 h. The reaction mixture was cooled to room temperature and diluted with DCM (30 mL), washed with water (2×10 ml), then saturated sodium hydrogen carbonate solution (10 mL). The organic layer was dried (MgSO₄), filtered and concentrated in vacuo to afford the desired product 8a as an orange foam (292 mg, 90%). MS (ES+) 389.2.

Step 2: 3,5-diamino-N-(5-fluoro-4-(4-(4-methylpiperazine-1-carbonyl)piperidin-1-yl)pyridin-3-yl)-1H-pyrazole-4-carboxamide 9a 2-Cyano-N-[5-fluoro-4-[4-(4-methylpiperazine-1-carbonyl)-1-piperidyl]-3-pyridyl]acetamide 8a (290 mg, 0.7466 mmol) was slurried in ethanol (3.3 mL). Sodium acetate (127.4 mg, 1.553 mmol) was added, followed by trichloroacetonitrile (129.4 mg, 91.13 µL, 0.8959 mmol) and the reaction mixture was stirred at room temperature for 1 hr, after which time an off-white precipitate had formed. The solid was collected by filtration, washed with minimal ethanol then minimal water and dried by suction to give a white solid (155 mg). The filtrate was concentrated in vacuo to remove ethanol then residual aqueous solution was extracted with EtOAc (3×). The combined organic layers was dried (MgSO₄), filtered and concentrated to dryness in vacuo to leave a viscous oil which was triturated in EtOAc (5 mL) to form an off white precipitate that was collected by filtration, washed with minimal EtOAc and dried by suction to leave a second crop of solid (49 mg). A total of 204 mg (51%) of 3-amino-4,4,4-trichloro-2-cyano-N-[5-fluoro-4-[4-(4-methylpiperazine-1-carbonyl)-1-piperidyl]-3-pyridyl]but-2-enamide was isolated; MS (ES+) 532.0.

3-Amino-4,4,4-trichloro-2-cyano-N-[5-fluoro-4-[4-(4-methylpiperazine-1-carbonyl)-1-piperidyl]-3-pyridyl]but-2-enamide (4.1 g, 7.695 mmol) was dissolved in N-methylpyrrolidinone (40 mL). Hydrazine hydrate (1.002 g, 973.8 μL, 20.01 mmol) was added and the reaction mixture was stirred at room temperature for 10 mins, then heated at 80° C. for 3.5 h. The mixture was concentrated in vacuo and the residue was then partitioned between EtOAc/water. The organic layer was washed with water (2×), brine (1×), dried (MgSO₄), filtered and concentrated in vacuo to provide the desired compound as a white solid. (64%). MS (ES+) 446.1, ¹H NMR (500 MHz, DMSO) 11.03 (s, 1H), 9.45 (s, 1H), 8.69 (s, 1H), 8.52 (d, J=4.7 Hz, 1H), 7.36 (br s, 4H), 4.47-4.43 (m, 1H), 4.23-4.21 (m, 1H), 3.50-3.47 (m, 2H), 3.41-3.39 (m, 2H), 3.24-3.15 (m, 2H) 3.05-2.98 (m, 2H), 2.93-2.88 (m, 2H), 2.77-2.76 (m, 4H), 1.73-1.71 (m, 4H).

Step 3: 2-amino-6-fluoro-N-(5-fluoro-4-(4-(4-methylpiperazine-1-carbonyl)piperidin-1-yl)pyridin-3-yl)pyrazolo[1,5-c]pyrimidine-3-carboxamide I-G-4

To a suspension of 3,5-diamino-N-[5-fluoro-4-[4-(4-methylpiperazine-1-carbonyl)-1-piperidyl]-3-pyridyl]-1H-pyrazole-4-carboxamide 9a (106 mg, 1.19 mmol) in IPA/water (1:1, 1 mL) and acetic acid (71.46 mg, 67.67 μL, 0.1078 mmol) was added 3-(diisopropylamino)-2-fluoroprop-2-enal (41.21 mg, 0.2379 mmol). The reaction mixture was heated under reflux for 6 h and was then allowed to cool to room temperature overnight. IPA was removed in vacuo, and the resulting aqueous solution was partitioned between DCM and 2M sodium carbonate solution. The organic layer was washed with 1:1 brine/water, dried (MgSO₄) filtered and concentrated in vacuo to leave a yellow solid which was stirred as a suspension in ethanol (0.5 mL) for 2 h. The solid was collected by filtration to give the desired compound I-G-4 (63 mg, 53%).

Example 3f: 2-amino-6-fluoro-N-[5-fluoro-4-[4-[4-(oxetan-3-yl)piperazine-1-carbonyl]-1-piperidyl]-3-pyridyl]pyrazolo pyrimidine-3-carboxamide (Compound I-G-32)

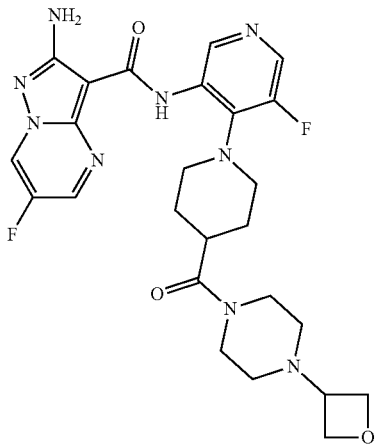 [SMILES: Nc1nn2cc(F)cnc2c1C(=O)Nc1cncc(F)c1N1CCC(C(=O)N2CCN(C3COC3)CC2)CC1]

Scheme 2b: Preparation of compound I-G-32

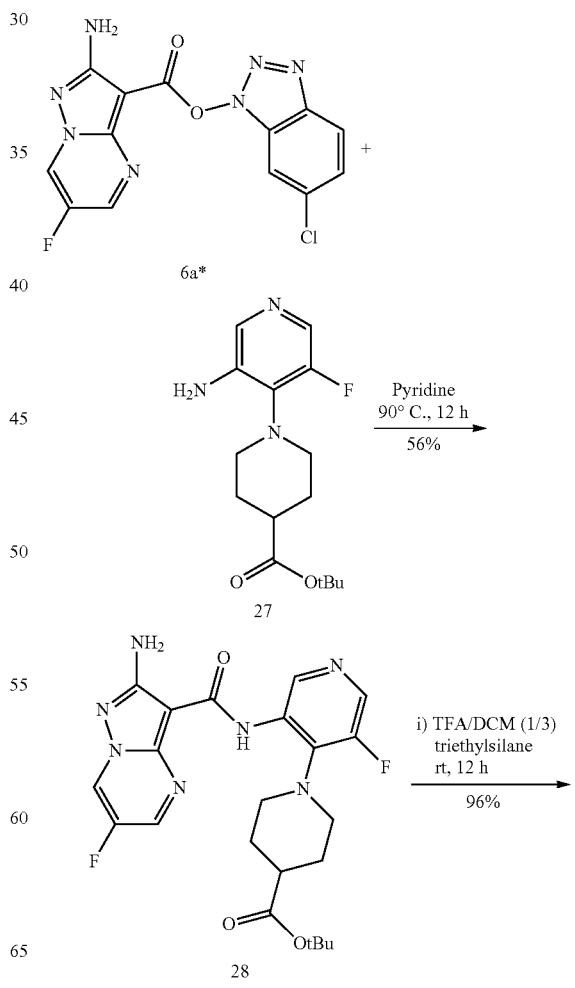

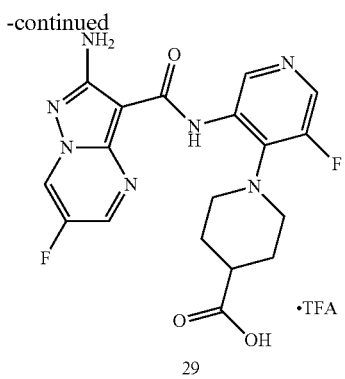

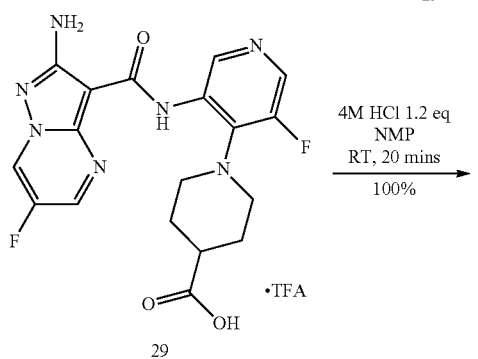

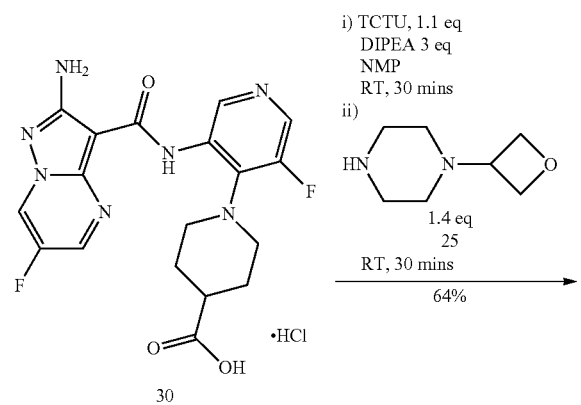

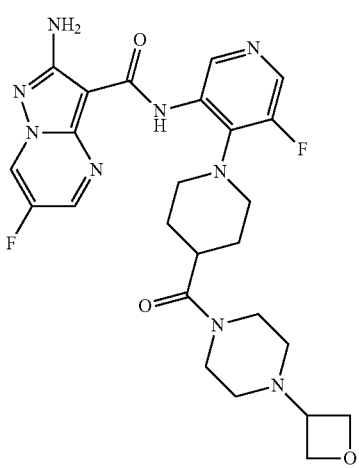

Step 1: tert-butyl 1-[3-[(2-amino-6-fluoro-pyrazolo[1,5-a]pyrimidine-3-carbonyl)amino]-5-fluoro-4-pyridyl]piperidine-4-carboxylate 28

A mixture of (6-chlorobenzotriazol-1-yl) 2-amino-6-fluoro-pyrazolo[1,5-a]pyrimidine-3-carboxylate 6a* (44.02 g, 126.6 mmol) and tert-butyl 1-(3-amino-5-fluoro-4-pyridyl)piperidine-4-carboxylate 27 (prepared according to Preparation N-15) (34 g, 115.1 mmol) in pyridine (510.0 mL) was heated at 95° C. internally overnight (18 h). Mixture was cooled to room temperature (product precipitated) then added ethanol (340.0 mL) and stirred at room temperature for 10 mins. Collected yellow solid by filtration, washed well with ethanol, dried by suction, then on high vac line for 1 h to leave product 28 as a yellow solid, (32.5 g 56% yield). $^1$H NMR (500 MHz, DMSO-d6) δ 10.45 (s, 1H), 9.58 (s, 1H), 9.51 (dd, 1H), 8.72 (dd, 1H), 8.25 (d, 1H), 6.81 (s, 2H), 3.15-2.93 (m, 4H), 2.55-2.47 (masked signal, 1H), 2.02-1.91 (m, 4H), 1.47 (s, 9H). MS (ES+) 474.2.

Step 2: 1-[3-[(2-amino-6-fluoro-pyrazolo[1,5-a]pyrimidine-3-carbonyl)amino]-5-fluoro-4-pyridyl]piperidine-4-carboxylic acid trifluorocetate 29

To a suspension of tert-butyl 1-[3-[(2-amino-6-fluoro-pyrazolo[1,5-a]pyrimidine-3-carbonyl)amino]-5-fluoro-4-pyridyl]piperidine-4-carboxylate 28 (69.7 g, 147.2 mmol) in DCM (348.5 mL) and triethylsilane (18.83 g, 25.87 mL, 161.9 mmol) was added TFA (151.1 g, 102.1 mL, 1.325 mol) (mixture sets solid on initial addition of TFA then goes into solution after complete addition). Resulting orange solution was stirred at room temperature overnight. Additional TFA (16.78 g, 11.34 mL, 147.2 mmol) was added and the mixture stirred at room temperature for 2 h. Mixture then heated at 40° C. for 20 mins to force reaction to completion. Mixture was concentrated in vacuo, chloroform (300 mL) was added and mixture again concentrated in vacuo to leave an orange solid suspension. Mixture triturated in DCM (approx. 200 mL), stirred for 20 mins then solid collected by filtration, washed with minimal DCM and dried by suction to leave a yellow solid. Filtrate was concentrated in vacuo, residue re-slurried in DCM (approx 50 mL), stirred for 20 mins then solid collected by filtration, washed with minimal DCM and dried by suction to leave a yellow solid which was combined with first crop of solid. Solid dried under vacuum overnight to leave desired product 29 as a yellow solid (82.8 g, 96%). $^1$H NMR (500 MHz, DMSO-d6) δ 10.44 (s, 1H), 9.59 (s, 1H), 9.50 (dd, 1H), 8.84 (dd, 1H), 8.33 (d, 1H), 3.13-3.10 (m, 4H), 2.57-2.47 (masked signal, 1H) and 2.08-1.93 (m, 4H). MS (ES+) 418.1.

Step 3: 1-[3-[(2-amino-6-fluoro-pyrazolo[1,5-a]pyrimidine-3-carbonyl)amino]-5-fluoro-4-pyridyl]piperidine-4-carboxylic acid hydrochloride 30

To a solution of 1-[3-[(2-amino-6-fluoro-pyrazolo[1,5-a]pyrimidine-3-carbonyl)amino]-5-fluoro-4-pyridyl]piperidine-4-carboxylic acid (Trifluoroacetic Acid) 29 (73 g, 124.7 mmol) in NMP (662.7 mL) was added hydrogen chloride (4M in 1,4-dioxane) (37.40 mL of 4 M, 149.6 mmol). After a few seconds a yellow precipitate formed. Mixture stirred at room temperature for 20 mins, then solid collected by filtration, washed with minimal NMP then MTBE, and dried by suction to leave pure product 30 as a light yellow solid, (59.7 g, quantitative yield). MS (ES+) 418.1.

Step 4: 2-amino-6-fluoro-N-[5-fluoro-4-[4-[4-(oxetan-3-yl)piperazine-1-carbonyl]-1-piperidyl]-3-pyridyl]pyrazolo[1,5-a]pyrimidine-3-carboxamide (Compound I-G-32)

To a yellow suspension of 1-[3-[(2-amino-6-fluoro-pyrazolo[1,5-a]pyrimidine-3-carbonyl)amino]-5-fluoro-4-pyridyl]piperidine-4-carboxylic acid (Hydrochloric Acid) 30 (59.7 g, 131.5 mmol) in NMP (477.6 mL) was added DIPEA (50.99 g, 68.72 mL, 394.5 mmol) then [(6-chlorobenzotriazol-1-yl)oxy-(dimethylamino)methylene]-dimethyl-ammonium (Boron Tetrafluoride Ion (1)) (51.44 g, 144.7 mmol). A yellow suspension forms after a few minutes. The mixture was sirred for 30 mins at room temperature then 1-(oxetan-3-yl)piperazine 25 (prepared according to Preparation N-32, below) (26.18 g, 184.1 mmol) was added. The cream/tan suspension turns to an orange solution (exotherms from 23.9 to 29.4° C.). The flask was placed on ice/water bath until internal temperature was at 24° C., then ice bath was removed and internal temperature steady at 24° C. thereafter.

The solution was stirred for 30 mins at room temperature then cooled on an ice/salt/water bath to 10° C. before the slow addition of water (1.015 L) in 100 mL portions. Prior to adding the next 100 mL of water, waited for exotherm to between 17° C. and 20° C. (internal) then allow to cool to between 10 and 15° C. Repeated until all water added. Once exotherm had ceased, ice/salt/water bath removed and mixture stirred at ambient temperature for 20 mins (thick yellow/cream suspension forms). Solid collected by filtration through a sinter funnel, washed well with water then dried by suction for 10 mins. Vacuum removed and solid slurried in water on sinter funnel, then vacuum reapplied and solid dried by suction overnight then dried in vacuum oven for 24 h at 40° C.<10 mBar.

Solid (54.5 g) suspended in ethanol (545 mL, 10 vol eq.) and heated under reflux for 2 h then cooled to room temperature over 2 h. Solid collected by filtration, washed with minimum ethanol and dried by suction for 1 h to leave product as a pale yellow solid. Solid placed in vacuum oven at 23.5° C. and <10 mBar overnight to leave product I-G-32 as a pale yellow solid, (51 g, 64% yield). $^1$H NMR (500 MHz, DMSO-d6) δ 10.64 (s, 1H), 9.67 (s, 1H), 9.48 (dd, 1H), 9.26 (dd, 1H), 8.26 (d, 1H), 6.79 (s, 2H), 4.55 (t, 2H), 4.47 (t, 2H), 4.34 (t, 0.7H), 3.61 (dt, 4H), 3.48-3.41 (m, 2.5H), 3.22-3.17 (m, 2H), 3.05-3.03 (m, 2H), 3.99-2.93 (m, 1H), 2.28 (dt, 4H), 2.17-2.10 (m, 2H), 1.74 (d, 2H), 1.07 (t, 2H). MS (ES+) 542.3.

Scheme 2c: Alternative approach to prepare compound I-G-32

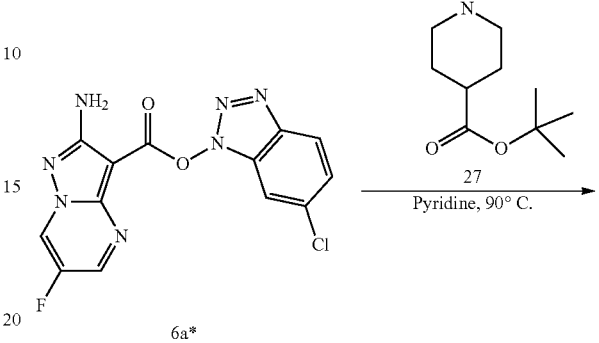

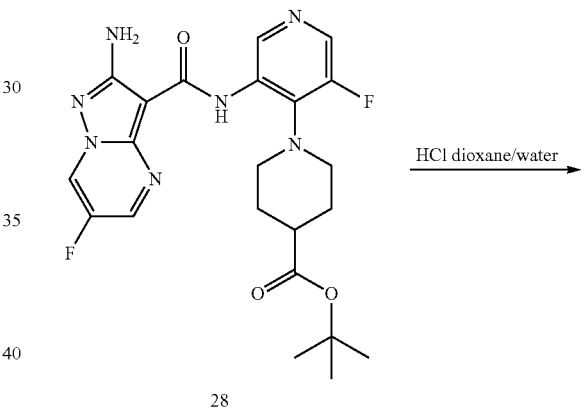

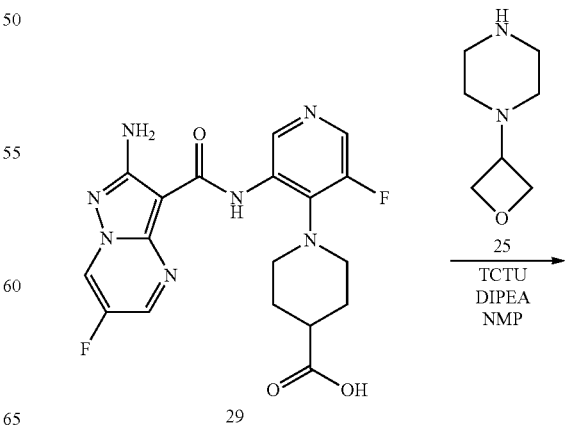

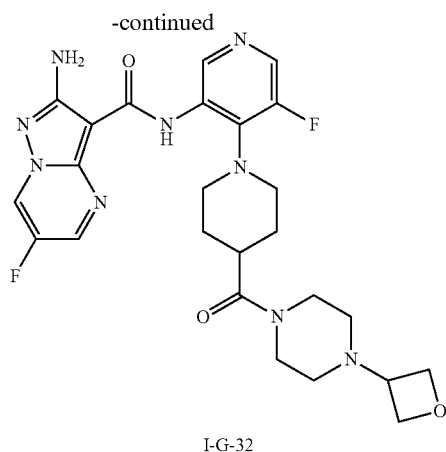

I-G-32

Step 1: tert-butyl 1-(3-(2-amino-6-fluoropyrazolo[1,5-a]pyrimidine-3-carboxamido)-5-fluoropyridin-4-yl)piperidine-4-carboxylate 28

6-chloro-1H-benzo[d][1,2,3]triazol-1-yl 2-amino-6-fluoropyrazolo[1,5-a]pyrimidine-3-carboxylate 6a* (45 g, 129.4 mmol) and tert-butyl 1-(3-amino-5-fluoropyridin-4-yl)piperidine-4-carboxylate 27 (40.1 g, 135.9 mmol) were slurried in pyridine (675 ml). The mixture was heated at 95° C. under nitrogen until the reaction was complete (determined by HPLC analysis). The mixture was cooled and ethanol (450 ml) was added dropwise. The mixture was filtered and the filter cake washed with ethanol (2×70 ml). The damp cake was dried to give the product 28 as a yellow crystalline solid (47.7 g, 78%); $^1$H NMR (500 MHz, DMSO-$d_6$) δ 10.45 (s, 1H), 9.58 (s, 1H), 9.51 (dd, 1H), 8.72 (dd, 1H), 8.25 (d, 1H), 6.81 (s, 2H), 3.15-2.93 (m, 4H), 2.55-2.47 (masked signal, 1H), 2.02-1.91 (m, 4H), 1.47 (s, 9H); 19F NMR (500 MHz, DMSO-d6) δ –153.5, –136.3; MS (ES+) 474.2.

Step 2: 1-(3-(2-amino-6-fluoropyrazolo[1,5-a]pyrimidine-3-carboxamido)-5-fluoropyridin-4-yl)piperidine-4-carboxylic Acid 29

Tert-butyl 1-(3-(2-amino-6-fluoropyrazolo[1,5-a]pyrimidine-3-carboxamido)-5-fluoropyridin-4-yl)piperidine-4-carboxylate 28 (36 g, 76 mmol) was suspended in a solution of HCl in 1,4-dioxane (4M, 670 ml). Water (36 ml) was added dropwise to the rapidly stirred slurry. The mixture was stirred under nitrogen until the reaction was complete (determined by HPLC analysis). The mixture was diluted with 1,4-dioxane (180 ml) and filtered. The filter cake was washed with TBME (2×72 ml). The damp cake was dried to give a pale brown solid (hydrochloride salt, 32.7 g, 95%); $^1$H NMR (500 MHz, DMSO-d6) δ 10.34 (s, 1H), 9.53-9.49 (m, 2H), 8.82 (m, 1H), 8.50 (m, 1H), 3.13-3.22 (m, 4H), 2.57-2.47 (masked signal, 1H) and 2.08-1.93 (m, 4H); 19F NMR (500 MHz, DMSO-d6) δ –152.9, –133.8; MS (ES+) 418.1.

Step 3: 2-amino-6-fluoro-N-(5-fluoro-4-(4-(4-(oxetan-3-yl)piperazine-1-carbonyl)piperidin-1-yl)pyridin-3-yl)pyrazolo[1,5-a]pyrimidine-3-carboxamide (compound I-G-32)

To a solution of 1-(oxetan-3-yl)piperazine (525 mg, 3.69 mmol) in THF (12 ml) was added DIPEA (1.72 ml, 9.91 mmol), followed by 1-(3-(2-amino-6-fluoropyrazolo[1,5-a]pyrimidine-3-carboxamido)-5-fluoropyridin-4-yl)piperidine-4-carboxylic acid (hydrochloride salt, 1.5 g, 3.3 mmol). [(6-chlorobenzotriazol-1-yl)oxy-(dimethylamino)methylene]-dimethyl-ammonium tetrafluoroborate (TCTU, 1.29 g, 3.64 mmol) was added and the mixture stirred under nitrogen until reaction completion (determined by HPLC analysis). The mixture was cooled and water (24 ml) was added dropwise. The mixture was allowed to warm to ambient and stirred for 3 hrs, then filtered. The filter cake was washed with (3×3 ml). The damp cake was dried under vacuum (with a nitrogen bleed) at 40° C. The product was obtained as a yellow solid (1.54 g, 86%); $^1$H NMR (500 MHz, DMSO-d6) δ 10.64 (s, 1H), 9.67 (s, 1H), 9.48 (dd, 1H), 9.26 (dd, 1H), 8.26 (d, 1H), 6.79 (s, 2H), 4.55 (t, 2H), 4.47 (t, 2H), 4.34 (t, 0.7H), 3.61 (dt, 4H), 3.48-3.41 (m, 2.5H), 3.22-3.17 (m, 2H), 3.05-3.03 (m, 2H), 3.99-2.93 (m, 1H), 2.28 (dt, 4H), 2.17-2.10 (m, 2H), 1.74 (d, 2H), 1.07 (t, 2H); 19F NMR (500 MHz, DMSO-d6) δ–152.8, –136.1; MS (ES+) 542.3.

Scheme 3-Preparation of butanenitrile intermediates

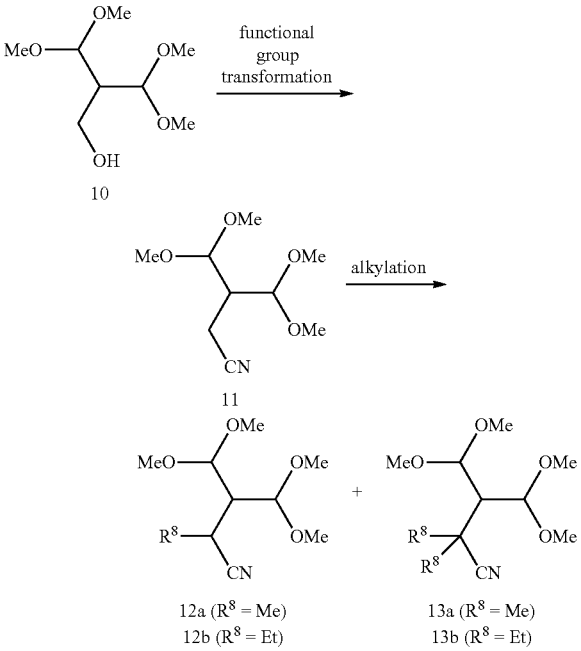

Step 1: 3-(dimethoxymethyl)-4,4-dimethoxybutanenitrile 11

2-(dimethoxymethyl)-3,3-dimethoxy-propan-1-ol 10 (Journal of the American Chemical Society (1973), 95(26), 8741) (92 g, 473.7 mmol) was dissolved in dry THF (920 mL) and the mixture was cooled down with an ice bath. Triethylamine (143.8 g, 198.1 mL, 1.421 mol) was added at once, followed by dropwise addition of methane sulfonyl chloride (59.69 g, 40.33 mL, 521.1 mmol), over 1 h and keeping the internal temperature below 5° C. The reaction mixture was stirred for 1 h and then allowed to warm to room temperature. The mixture was diluted with ethyl acetate (920 mL) and water (920 mL). The layers were separated and the organic layer was isolated, washed with a saturated solution of NaHCO$_3$, then brine. The organics were dried over MgSO$_4$, filtered and evaporated to give

[2-(dimethoxymethyl)-3,3-dimethoxypropyl]methanesulfonate as an orange oil (125.31 g, 97%) which was used directly without further purification.

Tetraethylammonium cyanide (142.3 g, 910.8 mmol) was added portionwise over 10 minutes to a solution of [2-(dimethoxymethyl)-3,3-dimethoxypropyl]methanesulfonate (124 g, 455.4 mmol) in MeCN (1.24 L). The reaction mixture was stirred at room temperature for 72 h, then portioned between ethyl acetate (1.24 L) and water (1.24 L). The layers were separated and the organic layer was isolated, washed with brine. The organics were dried over $MgSO_4$, filtered and evaporated to give 3-(dimethoxymethyl)-4,4-dimethoxybutanenitrile 11 as a dark brown oil (86.1 g).

Step 2: 3-(dimethoxymethyl)-4,4-dimethoxy-2-methylbutanenitrile 12a and 3-(dimethoxymethyl)-4,4-dimethoxy-2,2-dimethylbutanenitrile 13a To a solution of 3-(dimethoxymethyl)-4,4-dimethoxybutanenitrile 11 (250 mg, 1.205 mmol) in THF (3 mL) at −75° C. was added a solution of iodomethane (513.1 mg, 225.0 µL, 3.615 mmol) in THF (1 ml). A THF solution of (bis(trimethylsilyl)amino)sodium (1.808 mL of 2M, 3.615 mmol) was then added, keeping the temperature below −60° C. After addition, the reaction mixture was stirred at −75° C. for 2 hrs and then slowly quenched with aqueous saturated $NH_4Cl$ solution (5 ml). The mixture diluted with water and ether and layers separated. The organic layer was washed with brine, dried ($Na_2SO_4$) and concentrated in vacuo to afford a yellow oil which was purified by chromatography on silica gel, eluting with a petroleum ether:EtOAc gradient of 100:0 to 80:20. Solvents were concentrated in vacuo to afford a clear oil (194 mg). NMR proved this oil to be a mixture of 80% mono methyl compound 12a with and 20% bis methyl compound 13a. This mixture was used directly in subsequent steps.

Step 3: 3-(dimethoxymethyl)-2-ethyl-4,4-dimethoxybutanenitrile 12b and 3-(dimethoxymethyl)-2,2-diethyl-4,4-dimethoxybutanenitrile 13b When ethyl iodide was used instead of methyl iodide in a similar procedure to Scheme 3, step 2, above, a mixture of monosubstituted compound 12b and disubstituted compound 13b was isolated and used directly in subsequent steps.

Preparation N-1: 4-(4-methylpiperazin-1-yl)pyridin-3-amine 15

Scheme 4

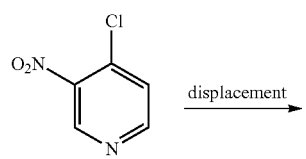

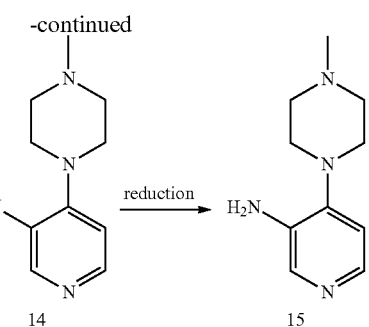

Step 1: 1-methyl-4-(3-nitro-4-pyridyl)piperazine 14

4-chloro-3-nitro-pyridine (2 g, 12.61 mmol) in dioxane (15 mL) was treated with 1-methylpiperazine (1.515 g, 1.678 mL, 15.13 mmol) and DIPEA (2.445 g, 3.295 mL, 18.92 mmol). The mixture was stirred at 80° C. for 1 hour, cooled to RT. The mixture was partioned between EtOAc and an aqueous saturated solution of $NaHCO_3$ (40 ml). Combined organic extract was dried over $MgSO_4$ and concentrated under reduced pressure to give an orange oil which was purified by chromatography on silica eluting with 5-10% MeOH/EtOAc/0.5-1% $NH_4OH$ to give 1-methyl-4-(3-nitro-4-pyridyl)piperazine 14 as a deep yellow oil which crystallised on standing. (2.56 g, 11.52 mmol, 91.36%). MS (ES+) 223.4.

Step 2: 4-(4-methylpiperazin-1-yl)pyridin-3-amine 15

1-methyl-4-(3-nitro-4-pyridyl)piperazine 14 (2.56 g, 11.52 mmol) in methanol (200 mL) was treated with palladium on carbon (10% wt % Degussa) (300 mg) and hydrogenated under balloon pressure at RT for 3 hours. The catalyst was filtered off and the filtrate was concentrated under reduced pressure to give 4-(4-methylpiperazin-1-yl)pyridin-3-amine 15 as a colourless solid (2.124 g, 11.05 mmol, 95.89%). MS (ES+) 193.1.

The following 3-aminopyridine intermediates were prepared using Preparation N-1:

4-morpholinopyridine-3-amine;

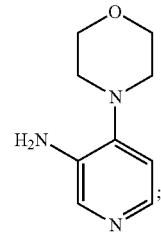

4-(pyrrolidin-1-yl)pyridin-3-amine:

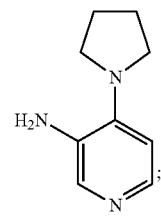

4-(piperidin-1-yl)pyridin-3-amine:

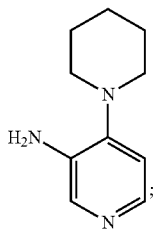

4-(azepan-1-yl)pyridin-3-amine:

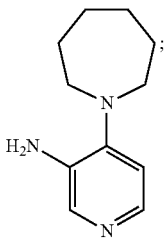

(1-(3-aminopyridin-4-yl)piperidin-4-yl)(4-methylpiperazin-1-yl)methanone:

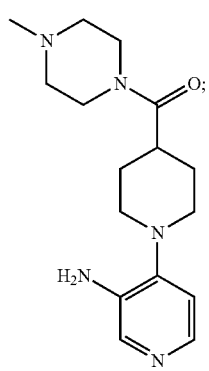

4-(1,4-dioxa-8-azaspiro[4.5]decan-8-yl)pyridin-3-amine:

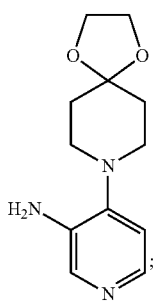

4-(3-aminopyridin-4-yl)thiomorpholine 1-oxide:

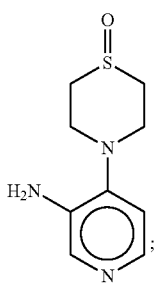

methyl 1-(3-aminopyridin-4-yl)piperidine-4-carboxylate:

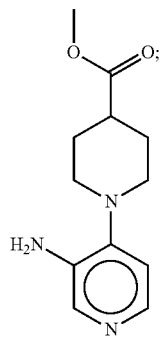

4-(4-methoxypiperidin-1-yl)pyridin-3-amine:

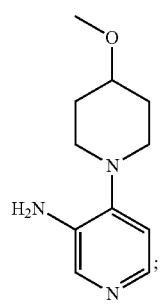

1-(3-aminopyridin-4-yl)piperidin-4-ol:

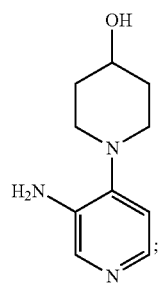

8-(3-aminopyridin-4-yl)-8-azabicyclo[3.2.1]octan-3-ol:

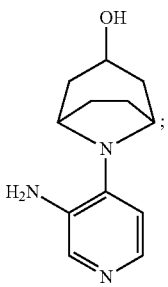

1-(3-aminopyridin-4-yl)-4-methylpiperidin-4-ol:

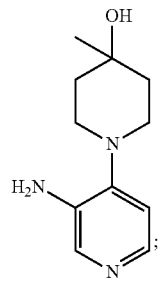

2-(1-(3-aminopyridin-4-yl)piperidin-4-yl)propan-2-ol:

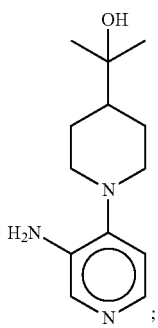

tert-butyl ((1-(3-aminopyridin-4-yl)piperidin-4-yl)methyl)carbamate:

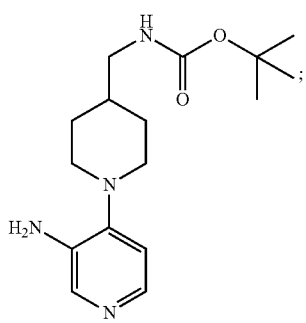

tert-butyl (1-(3-aminopyridin-4-yl)piperidin-4-yl)carbamate:

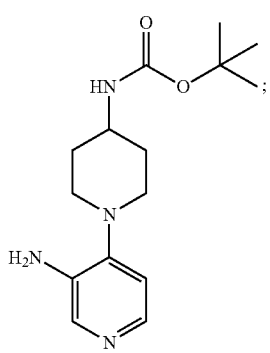

(3R,4R)-1-(3-aminopyridin-4-yl)-4-(dimethylamino)piperidin-3-ol:

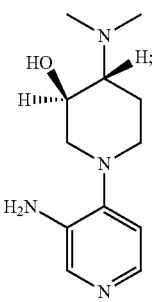

4-(4-methyl-1,4-diazepan-1-yl)pyridin-3-amine:

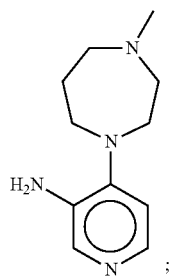

4-(1,4-diazabicyclo[3.2.2]nonan-4-yl)pyridin-3-amine:

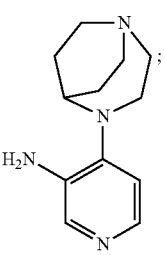

(S)-4-(hexahydropyrrolo[1,2-a]pyrazin-2(1H)-yl)pyridin-3-amine:

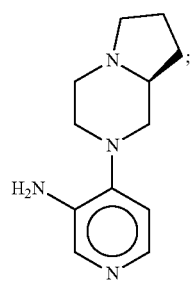

(R)-4-(hexahydropyrrolo[1,2-a]pyrazin-2(1H)-yl)pyridin-3-amine:

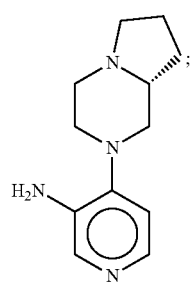

1-(3-aminopyridin-4-yl)-4-((dimethylamino)methyl)piperidin-4-ol:

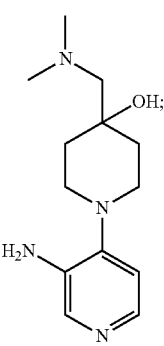

4-(3,4-dimethylpiperazin-1-yl)pyridin-3-amine:

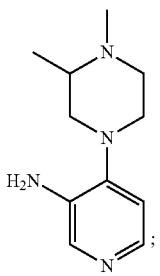

(4-(3-aminopyridin-4-yl)-1-methylpiperazin-2-yl)methanol:

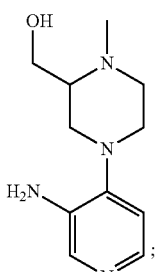

4-(4-(2,2,2-trifluoroethyl)piperazin-1-yl)pyridin-3-amine:

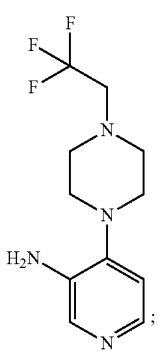

4-(4-((dimethylamino)methyl)-4-methoxypiperidin-1-yl)pyridin-3-amine:

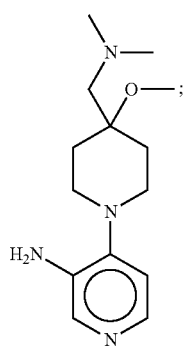

4-(4-(tert-butyl)piperazin-1-yl)pyridin-3-amine:

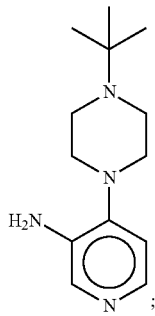

4-(4-isopropylpiperazin-1-yl)pyridin-3-amine:

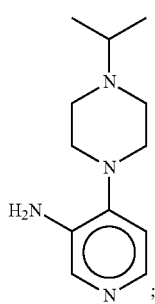

4-(5,6-dihydroimidazo[1,2-a]pyrazin-7(8H)-yl)pyridin-3-amine:

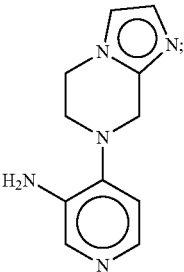

4-(4-ethylpiperazin-1-yl)pyridin-3-amine:

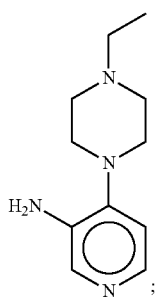

4-(5,6-dihydroimidazo[1,5-a]pyrazin-7(8H)-yl)pyridin-3-amine:

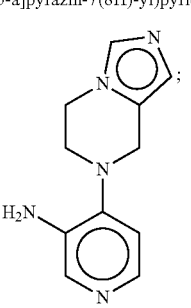

4-(3-(dimethylamino)piperidin-1-yl)pyridin-3-amine:

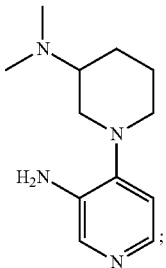

4-(4-((dimethylamino)methyl)piperidin-1-yl)pyridin-3-amine:

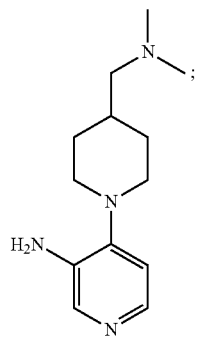

4-(3-(trifluoromethyl)piperazin-1-yl)pyridin-3-amine:

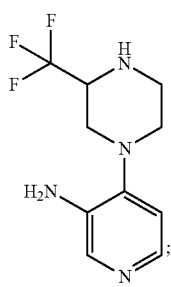

4-(4-amino-4-methylpiperidin-1-yl)pyridin-3-amine:

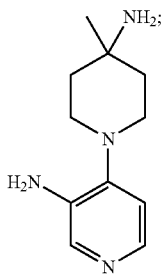

4-(4-cyclopropylpiperazin-1-yl)pyridin-3-amine:

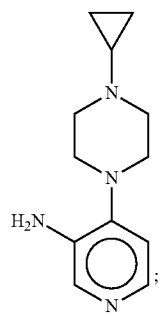

4-(4-cyclobutylpiperazin-1-yl)pyridin-3-amine:

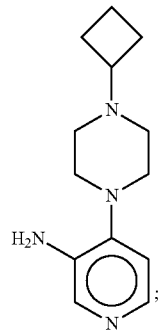

4-(4-(2-methoxyethyl)piperazin-1-yl)pyridin-3-amine:

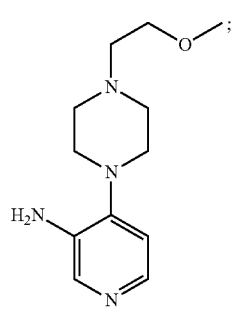

tert-butyl (1-(3-aminopyridin-4-yl)piperidin-4-yl)carbamate:

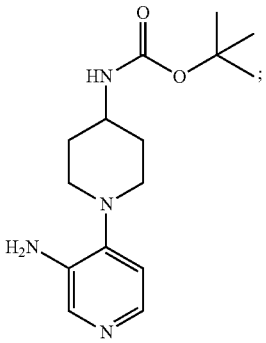

tert-butyl 4-(3-aminopyridin-4-yl)piperazine-1-carboxylate:

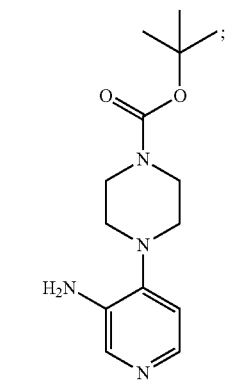

-continued tert-butyl ((4-(3-aminopyridin-4-yl)morpholin-2-yl)methyl)carbamate:

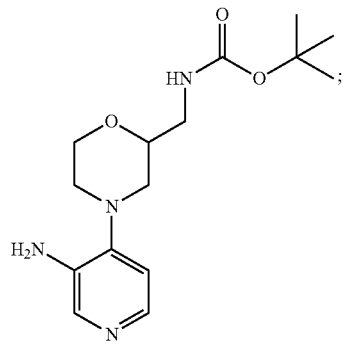

4-(4-(3-methyloxetan-3-yl)piperazin-1-yl)pyridin-3-amine:

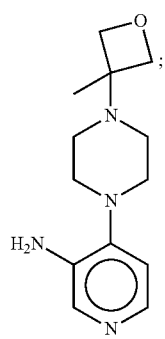

(R)-4-(hexahydropyrazino[2,1-c][1,4]oxazin-8(1H)-yl)pyridin-3-amine:

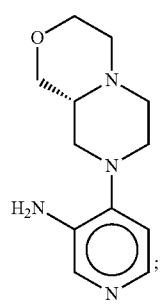

(S)-4-(hexahydropyrazino[2,1-c][1,4]oxazin-8(1H)-yl)pyridin-3-amine:

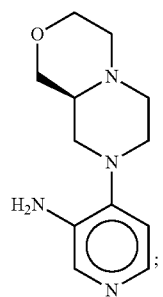

-continued 8-(3-aminopyridin-4-yl)hexahydropyrazino([2,1-c][1,4]oxazin-4(3H)-one:

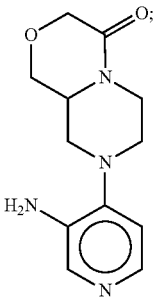

4-(4-(morpholinosulfonyl)piperidin-1-yl)pyridin-3-amine:

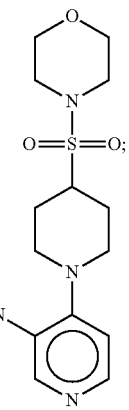

4-(4-(methylsulfonyl)piperidin-1-yl)pyridin-3-amine:

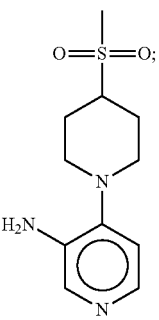

4-(4-methyl-1-oxa-4,9-diazaspiro[5.5]undecan-9-yl)pyridin-3-amine:

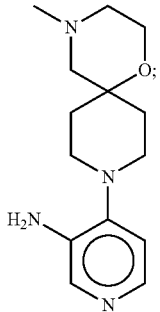

tert-butyl 8-(3-aminopyridin-4-yl)-2,8-diazaspiro[4.5]decane-2-carboxylate:

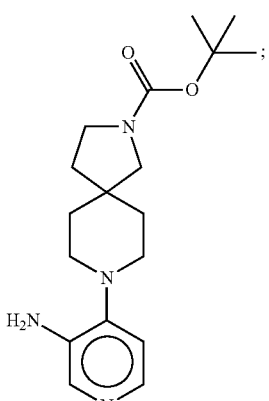

4-(2-cyclopropyl-1H-imidazol-1-yl)pyridin-3-amine:

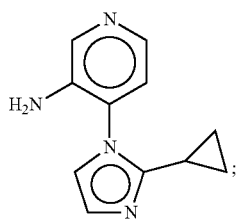

4-(3-aminopyridin-4-yl)-1-methylpiperazin-2-one:

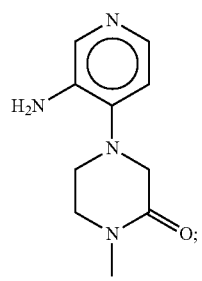

4-(3-aminopyridin-4-yl)thiomorpholine 1,1-dioxide:

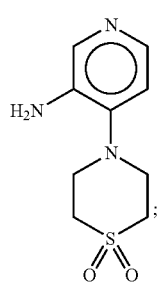

(R)-2-(3-aminopyridin-4-yl)hexahydropyrrolo[1,2-a]pyrazin-6(2H)-one:

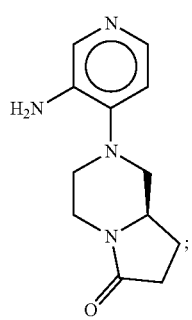

4-(3,5-dimethyl-1H-1,2,4-triazol-1-yl)pyridin-3-amine:

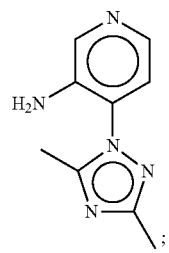

4-(2-(trifluoromethyl)-1H-imidazol-1-yl)pyridin-3-amine:

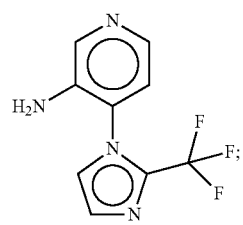

4-(2,2-dimethylpyrrolidin-1-yl)pyridin-3-amine:

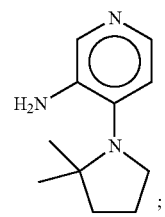

4-(3-(methylsulfonyl)piperidin-1-yl)pyridin-3-amine:

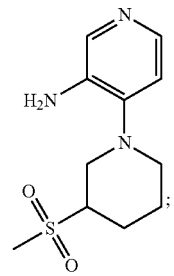

2-(3-aminopyridin-4-yl)hexahydropyrrolo[1,2-a]pyrazin-4(1H)-one:

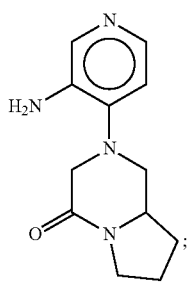

4-(2-oxa-7-azaspiro[3.5]nonan-7-yl)pyridin-3-amine:

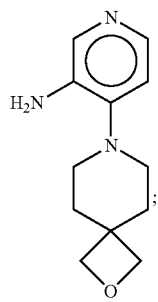

2-(3-aminopyridin-4-yl)hexahydro-1H-pyrido[1,2-a]pyrazin-6(2H)-one:

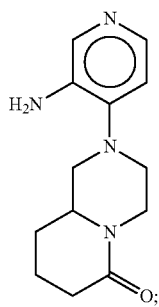

7-(3-aminopyridin-4-yl)tetrahydro-1H-oxazolo[3,4-a]pyrazin-3(5H)-one:

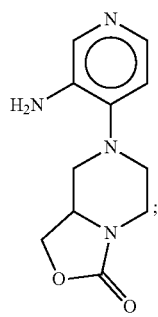

8-(3-aminopyridin-4-yl)-1-methyl-1,8-diazaspiro[4.5]decan-2-one:

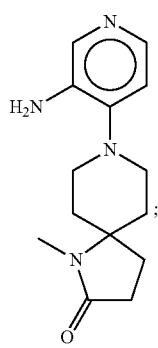

8-(3-aminopyridin-4-yl)-2-methyl-2,8-diazaspiro[4.5]decan-3-one:

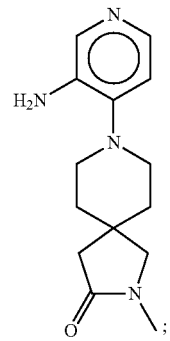

4-(3-aminopyridin-4-yl)-N,N-dimethylmorpholine-2-carboxamide:

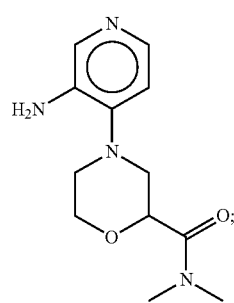

8-(3-aminopyridin-4-yl)-2-methyloctahydro-1H-pyrazino[1,2-a]pyrazin-1-one:

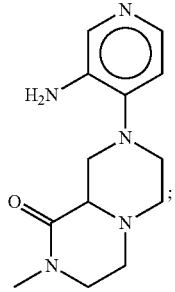

9-(3-aminopyridin-4-yl)-2-methyl-2,9-diazaspiro[5.5]undecan-3-one:

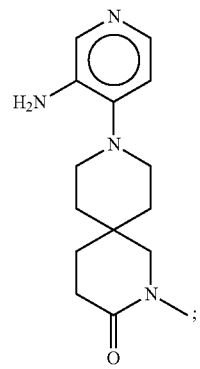

-continued 1-(1-(3-aminopyridin-4-yl)piperidin-4-yl)pyrrolidin-2-one:

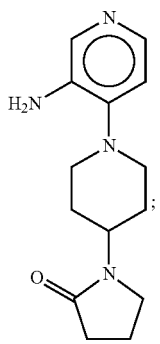

8-(3-aminopyridin-4-yl)-3-methyl-1-oxa-3,8-diazaspiro[4.5]decan-2-one:

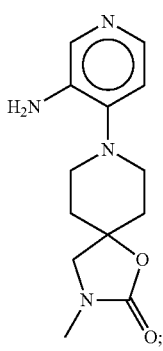

(3aS,7aS)-5-(3-aminopyridin-4-yl)-2-methylhexahydro-1H-pyrrolo[3,4-c]pyridin-3(2H)-one:

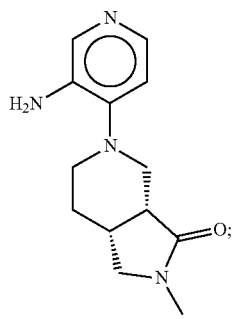

4-(4-((methylsulfonyl)methyl(piperidin-1-yl)pyridin-3-amine:

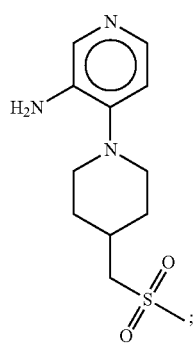

-continued 4-(3-methyl-1H-pyrazol-1-yl)pyridin-3-amine:

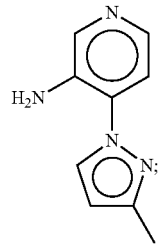

4-(5-methyl-1H-pyrazol-1-yl)pyridin-3-amine:

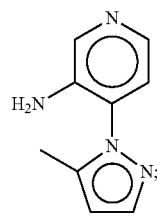

1-(3-aminopyridin-4-yl)-N,N-dimethylpiperidine-3-carboxamide:

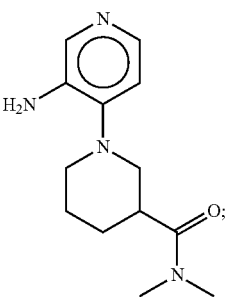

4-(4,5-dimethyl-1H-imidazol-1-yl)pyridin-3-amine:

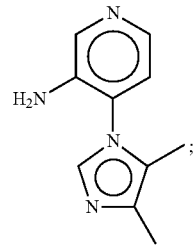

4-(4-(1,3,4-oxadiazol-2-yl)piperidin-1-yl)pyridin-3-amine:

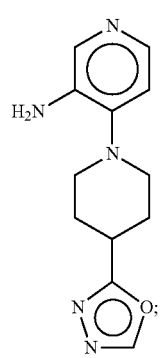

4-(4-methoxypiperidin-1-yl)pyridin-3-amine:
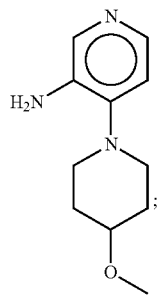
4-(4-((dimethylamino)methyl)piperidin-1-yl)pyridin-3-amine:
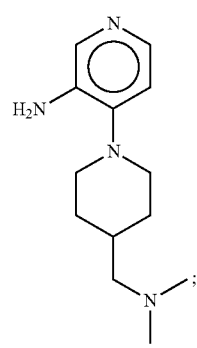
4-(4-(5-methyl-1,3,4-oxadizaol-2-yl)piperidin-1-yl)pyridin-3-amine:
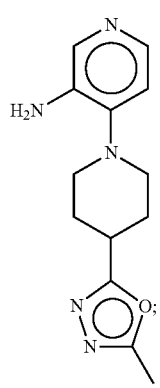
4-(4-(4-methyl-1,2,5-oxadiazol-3-yl)piperazin-1-yl)pyridin-3-amine:
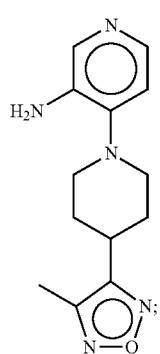
(S)-2-(3-aminopyridin-4-yl)hexahydropyrrolo[1,2-a]pyrazin-6(2H)-one:
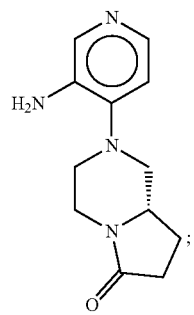
4-(4-(5-methyl-1,3,4-oxadiazol-2-yl)piperazin-1-yl)pyridin-3-amine:
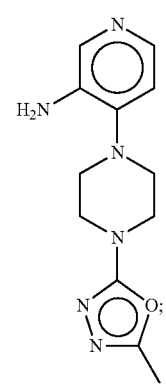
4-(2-oxa-6-azaspiro[3.5]nonan-6-yl)pyridin-3-amine:
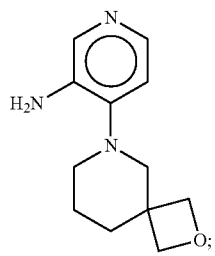
4-(4-(1,2,4-oxadiazol-3-yl)piperidin-1-yl)pyridin-3-amine:
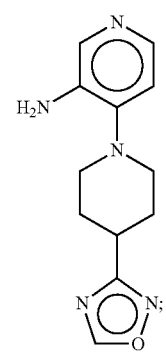

-continued 4-(3-aminopyridin-4-yl)-2,2-dimethylthiomorpholine 1,1-dioxide:

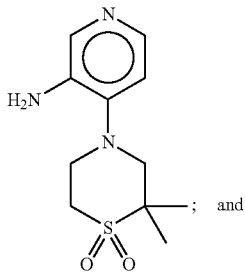

; and 4-(4-(methoxymethyl)piperidin-1-yl)pyridin-3-amine:

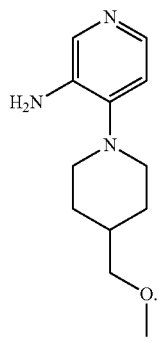

Miscellaneous Preparations of Aminopyridines

Preparation N-2: 1-(3-aminopyridin-4-yl)-N,N-dimethylpiperidine-4-carboxamide

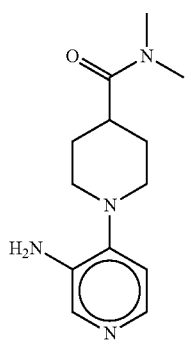

Step 1:
1-(3-amino-4-pyridyl)piperidine-4-carboxylic Acid

A microwave vial was charged with methyl 1-(3-amino-4-pyridyl)piperidine-4-carboxylate (prepared according to methods similar to the one depicted in Preparation N-1) (176 mg, 0.7106 mmol), MeOH (3 mL) and H$_2$O (0.1 mL). LiOH (51.06 mg, 2.132 mmol) was added and the mixture was stirred overnight at 50° C. The reaction was quenched by addition of an aqueous solution of HCl until pH=3-4 is reached. The reaction mixture was then concentrated under reduced pressure to yield 1-(3-amino-4-pyridyl)piperidine-4-carboxylic acid that was used without further purification. MS (ES+) 222.1.

Step 2: 1-(3-aminopyridin-4-yl)-N,N-dimethylpiperidine-4-carboxamide

A microwave vial was charged with 1-(3-amino-4-pyridyl)piperidine-4-carboxylic acid (125 mg, 0.197 mmol), TBTU (200 mg, 0.62 mmol) and N-methylmethanamine (3.5 mL, 2M in MeOH). The tube was sealed and the mixture stirred for 3 h at 120° C. The crude was redissolved in MeOH and loaded into a MeOH pre-washed SCX column, rinsed with MeOH and the product was released with methanolic ammonia. The ammonia extracts were concentrated under reduced pressure to yield 1-(3-aminopyridin-4-yl)-N,N-dimethylpiperidine-4-carboxamide. MS (ES+) 249.2.

Preparation N-3: 4-(4-(dimethylamino)piperidin-1-yl)pyridin-3-amine

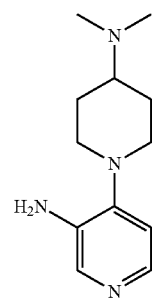 [SMILES: CN(C)C1CCN(c2ccncc2N)CC1]

Step 1: tert-butyl (1-(3-aminopyridin-4-yl)piperidin-4-yl)(methyl)carbamate

To a solution of tert-butyl N-[1-(3-nitro-4-pyridyl)-4-piperidyl]carbamate (2100 mg, 6.514 mmol) (prepared according to methods similar to the one depicted in Step 1 of Preparation N-1) and iodomethane (4.623 g, 2.028 mL, 32.57 mmol) in DMF at 0° C. was added portionwise sodium hydride (312.7 mg, 7.817 mmol). The reaction was stirred at 0° C. for 1 h, and at room temperature for 1 h. The reaction was quenched by pouring the reaction mixture onto a saturated aqueous solution of ammonium chloride, then extracted with ethyl acetate (2×50 mL). The combined organics was washed with brine (2×50 mL), dried and evaporated to leave an orange solid. To the crude solid dissolved in MeOH (50 mL) was added Pd/C (10%) (346 mg) and the mixture was stirred under a hydrogen atmosphere for 4 h. The reaction was filtered through celite and evaporated to leave tert-butyl (1-(3-aminopyridin-4-yl)piperidin-4-yl)(methyl)carbamate as a yellow oil. (600 mg, 20%) MS (ES+-tBu) 251.1.

Step 2:
4-(4-(dimethylamino)piperidin-1-yl)pyridin-3-amine

A solution of LiAlH$_4$ (49.57 mg, 1.306 mmol) was added dropwise to a solution of tert-butyl N-[1-(3-amino-4-pyridyl)-4-piperidyl]-N-methyl-carbamate (100 mg, 0.3264 mmol) in THF at room temp. The reaction was stirred at 50° C. for 3 h, then at room temperature, the reaction mixture was quenched by the dropwise addition of wet THF. The reaction mixture was partitioned between 1N NaOH (50 mL) and diethyl ether (50 mL). The combined organics was dried (MgSO₄) and evaporated to leave 4-(4-(dimethylamino)piperidin-1-yl)pyridin-3-amine as a yellow oil. MS (ES+) 221.1.

Preparation N-4: 4-(3-(methoxymethyl)-4-methylpiperazin-1-yl)pyridin-3-amine

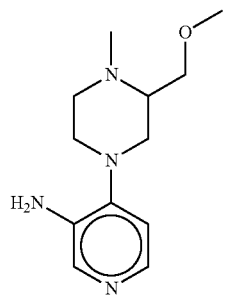

Step 1: 2-(methoxymethyl)-1-methyl-4-(3-nitropyridin-4-yl)piperazine

To (1-methyl-4-(3-nitropyridin-4-yl)piperazin-2-yl)methanol (prepared according to methods similar to the one depicted in Step 1 of Preparation N-1) (250 mg, 0.9910 mmol) in DMF (2 mL) at 0° C. was added NaH (59.43 mg, 1.486 mmol). The reaction mixture was stirred for 10 min before MeI (281.3 mg, 123.4 µL, 1.982 mmol) was added dropwise. The reaction mixture was allowed to warm to RT and was stirred for 2 hours. The reaction mixture was loaded on a pre-washed SCX column, rinsed with MeOH and the product was released with methanolic ammonia. The ammonia extracts were concentrated under reduced pressure. The residue was purified by column chromatography on silica, eluting with 1-15% MeOH:DCM yielding 2-(methoxymethyl)-1-methyl-4-(3-nitropyridin-4-yl)piperazine (84 mg, 32%). MS (ES+) 237.1.

Step 2: 4-(3-(methoxymethyl)-4-methylpiperazin-1-yl)pyridin-3-amine

To a solution of 2-(methoxymethyl)-1-methyl-4-(3-nitropyridin-4-yl)piperazine (84 mg, 0.31 mmol) in methanol was added Pd on C (10%, wet, Degussa) (10 mg) and the reaction mixture was stirred overnight at room temperature under a balloon of hydrogen. The catalyst was filtered off and and the filtrate was concentrated under reduced pressure to yield 4-(3-(methoxymethyl)-4-methylpiperazin-1-yl)pyridin-3-amine as a film. (72 mg, 96%). MS (ES+) 267.1.

Preparation N-5: 4-(2,4-dimethylpiperazin-1-yl)pyridin-3-amine

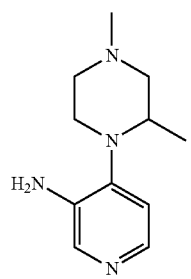

Step 1: 2-methyl-1-(3-nitro-4-pyridyl)piperazine

To a solution of tert-butyl 3-methyl-4-(3-nitropyridin-4-yl)piperazine-1-carboxylate (prepared according to methods similar to the one depicted in Step 1 of Preparation N-1) in DCM (5 mL) was added TFA (1.445 g, 976.4 µL, 12.67 mmol). The reaction mixture was stirred for 48 h at RT, then the solvent was removed under reduced pressure. The crude was redissolved in MeOH and loaded into a MeOH pre-washed SCX column, rinsed with MeOH and the product was released with methanolic ammonia. The ammonia extracts were concentrated under reduced pressure to yield 2-methyl-1-(3-nitro-4-pyridyl)piperazine (334 mg, 71%). MS (ES+) 223.1.

Step 2: 2,4-dimethyl-1-(3-nitropyridin-4-yl)piperazine

To 2-methyl-1-(3-nitro-4-pyridyl)piperazine in DMF (1.5 mL of 0.3 M, 0.4500 mmol) at 0° C. was added NaH (18.00 mg, 0.4500 mmol). The reaction was stirred for 10 mins then MeI (60.68 mg, 26.61 µL, 0.4275 mmol) was added. The reaction mixture was stirred for 4 hours at RT and quenched by the addition of water. The crude was loaded onto a MeOH pre-washed SCX column, rinsed with MeOH and the product was released with methanolic ammonia. The ammonia extracts were concentrated under reduced pressure. The residue was purified by column chromatography eluting with 1-15% MeOH:DCM to yield 2,4-dimethyl-1-(3-nitropyridin-4-yl)piperazine. MS (ES+) 237.2.

Step 3: 4-(2,4-dimethylpiperazin-1-yl)pyridin-3-amine

A solution of 2,4-dimethyl-1-(3-nitro-4-pyridyl)piperazine (89 mg, 0.3767 mmol) in methanol (4 mL) and Pd on C (10%, wet, Degussa) (20 mg) was hydrogenated overnight at RT under an atmosphere of hydrogen (balloon). The catalyst was filtered off through a Celite cartridge, washed with methanol. The filtrate was concentrated under reduced pressure yielding 4-(2,4-dimethylpiperazin-1-yl)pyridin-3-amine (71 mg, 91%). MS (ES+) 207.2.

Preparation N-6: 4-(3,3,4-trimethylpiperazin-1-yl)pyridin-3-amine

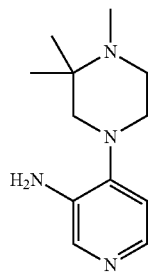 [SMILES: CN1CCN(c2ccncc2N)CC1(C)C]

To 4-(3,3-dimethylpiperazin-1-yl)pyridin-3-amine (prepared according to methods similar to the one depicted in Preparation N-1) (120 mg, 0.5817 mmol) in DMF (2 mL) at 0° C. was added NaH (20.94 mg, 0.5235 mmol). The reaction mixture was stirred for 10 mins at 0° C. then MeI (276.3 uL, 0.5526 mmol, 2M in TBDME) was added. The reaction mixture was allowed to warm to RT and was stirred for 2 hours at RT. The crude was loaded onto a MeOH pre-washed SCX column, rinsed with MeOH and the product was released with methanolic ammonia. The ammonia extracts were concentrated under reduced pressure to yield 4-(3,3,4-trimethylpiperazin-1-yl)pyridin-3-amine (128 mg, 73%). MS (ES+) 221.1.

Preparation N-7: 4-(4-(tetrahydrofuran-3-yl)piperazin-1-yl)pyridin-3-amine

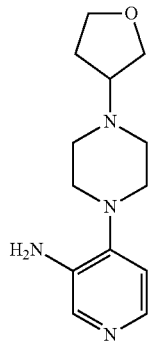 [SMILES: Nc1cnccc1N1CCN(C2CCOC2)CC1]

Step 1: 1-(3-nitropyridin-4-yl)-4-(tetrahydrofuran-3-yl)piperazine

A round-bottomed flask was charged with 1-(3-nitro-4-pyridyl)piperazine (prepared according to methods similar to the one depicted in Step 1 of Preparation N-1), dihydrofuran-3(2H)-one (98 mg, 1.13 mmol) and acetic acid (129 uL, 2.27 mmol) in MeCN (4 mL). Na(OAc)₃BH (482.4 mg, 2.27 mmol) was added and the reaction mixture was stirred at RT for 1 h. The reaction mixture was partitioned between EtOAC and an aqueous saturated solution of Na₂CO₃. The organic extracts were dried over MgSO₄, and concentrated under reduced pressure to give 1-(3-nitropyridin-4-yl)-4-(tetrahydrofuran-3-yl)piperazine as a yellow solid. MS (ES+) 279.1.

Step 2: 4-(4-(tetrahydrofuran-3-yl)piperazin-1-yl)pyridin-3-amine

A solution of 1-(3-nitropyridin-4-yl)-4-(tetrahydrofuran-3-yl)piperazine (316 mg, 1.13 mmol) in MeOH (15 mL), Pd on C (10%, wet, Degussa) (120 mg) was stirred overnight at RT under an hydrogen atmosphere (balloon). The mixture was filtered through a Celite pad and concentrated under reduced pressure. The crude was redissolved in MeOH and loaded into a MeOH pre-washed SCX column, rinsed with MeOH and the product was released with methanolic ammonia. The ammonia extracts were concentrated under reduced pressure to give 4-(4-(tetrahydrofuran-3-yl)piperazin-1-yl)pyridin-3-amine as a solid which was used in next step without further purification. (300 mg, purity 77%, yield 82%). MS (ES+) 249.2.

The following aminopyridine were prepared according to methods similar to the one depicted in Preparation N-7:

4-(4-(oxetan-3-yl)piperazin-1-yl)pyridin-3-amine:

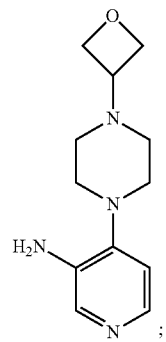 [SMILES: Nc1cnccc1N1CCN(C2COC2)CC1]

4-(4-(tetrahydro-2H-pyran-4-yl)piperazin-1-yl)pyridin-3-amine:

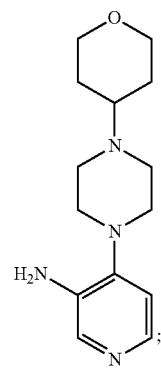 [SMILES: Nc1cnccc1N1CCN(C2CCOCC2)CC1]

and 4-(1-methyl-9-oxa-1,4-diazaspiro[5.5]undecan-4-yl)pyridin-3-amine:

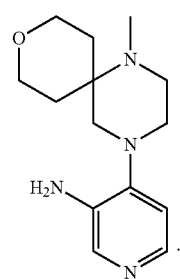

Preparation N-8: 4-(1H-pyrazol-1-yl)pyridin-3-amine

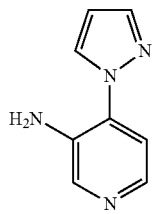 [SMILES: Nc1cnccc1-n1cccn1]

Step 1: 3-nitro-4-(1H-pyrazol-1-yl)pyridine

A suspension of pyrazole (150 mg, 2.2 mmol) and $Cs_2CO_3$ (526 mg, 1.6 mmol) in anhydrous MeCN (3.5 mL) was stirred for 20 min under an inert atmosphere. 4-chloro-3-nitro-pyridine (233 mg, 1.47 mmol) was then added and stirred overnight at 75° C. The insoluble was filtered off and the filtrate was concentrated under reduced pressure yielding 3-nitro-4-(1H-pyrazol-1-yl)pyridine that was used without further purification. (410 mg, 98%). MS (ES+) 191.1.

Step 2: 4-(1H-pyrazol-1-yl)pyridin-3-amine

To a solution of 3-nitro-4-(1H-pyrazol-1-yl)pyridine (410 mg, 2.15 mmol) in MeOH (15 mL) was added Pd on C (10%, wet, Degussa) (129 mg) and the reaction mixture was vigorously stirred overnight at RT under an atmosphere of hydrogen (balloon). The catalyst was filtered off and the filtrate was concentrated under reduced pressure yielding 4-(1H-pyrazol-1-yl)pyridin-3-amine. (285 mg, 82%). MS (ES+) 161.1.

The following aminopyridine were prepared according to methods similar to the one depicted in Preparation N-8:

4-(4-(trifluoromethyl)-1H-imidazol-1-yl)pyridin-3-amine:

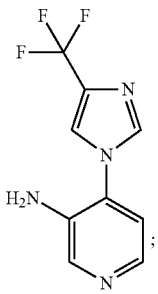

4-(2-methyl-1H-imidazol-1-yl)pyridin-3-amine:

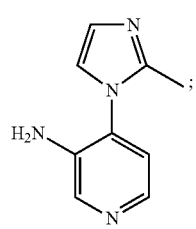

4-(1H-imidazol-1-yl)pyridin-3-amine:

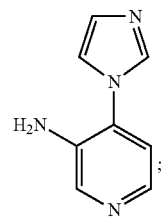

4-(2-methyl-4-(trifluoromethyl)-1H-imidazol-1-yl)pyridin-3-amine:

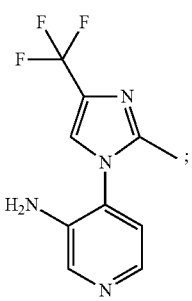

4-(3-methyl-1H-1,2,4-triazol-1-yl)pyridin-3-amine:

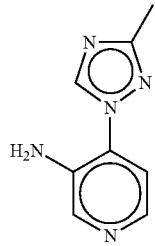; and 4-(5-methyl-1H-1,2,4-triazol-1-yl)pyridin-3-amine:

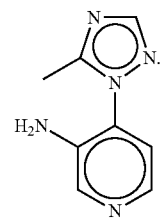

Preparation N-9: 5-fluoro-4-(4-(oxetan-3-yl)piperazin-1-yl)pyridin-3-amine

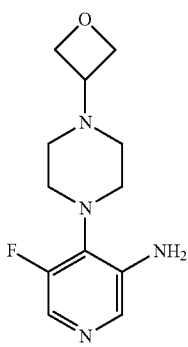

Step 1: 1-(3-chloro-5-fluoropyridin-4-yl)piperazine

In a 100 mL sealed reaction vessel/bomb, 3-chloro-5-fluoro-4-iodo-pyridine (5600 mg, 21.75 mmol) was taken up in NMP (12 mL). To the resulting clear brown solution was added DIPEA (3.373 g, 4.546 mL, 26.10 mmol) followed by piperazine (2.810 g, 32.62 mmol). The vessel was sealed and heated thermally at 120° C. for 18 hrs. The mixture was allowed to cool to RT and was concentrated in vacuo to afford a brown gum which was purified by chromatography on silica, eluting with a gradient of DCM-DCM:MeOH:NH$_3$ (90:10:1) 100-0 to 0:100. Fractions containing clean product were collected and concentrated in vacuo to afford 1-(3-chloro-5-fluoropyridin-4-yl)piperazine as a cream solid. (3.52 g, 75%). MS (ES+) 216.0.

Step 2: 1-(3-chloro-5-fluoro-4-pyridyl)-4-(oxetan-3-yl)piperazine

To a suspension of 1-(3-chloro-5-fluoropyridin-4-yl)piperazine (900 mg, 4.173 mmol) in THF (9.000 mL) was added 3-oxetanone (601.4 mg, 8.346 mmol). To this mixture, under N$_2$, was added sodium triacetoxyborohydride (2.034 g, 9.598 mmol) portionwise over 5 min and the reaction mixture was stirred at RT overnight. MeOH (2 ml) was added to the flask before the mixture was concentrated in vacuo. The residue was partitioned between water (50 ml) and EtAOc (50 ml). The aqueous phase was basified to pH 7-8 with NH$_4$OH. Combined organics washed with brine (30 ml), dried over Na$_2$SO$_4$, filtered and concentrated in vacuo to afford 1-(3-chloro-5-fluoro-4-pyridyl)-4-(oxetan-3-yl)piperazine as a cream solid that was used in next step without further purification. MS (ES+) 272.1.

Step 3: 5-fluoro-4-(4-(oxetan-3-yl)piperazin-1-yl)pyridin-3-amine

In a pressure tube containing 1-(3-chloro-5-fluoro-4-pyridyl)-4-(oxetan-3-yl)piperazine (800 mg, 2.944 mmol) was added dioxane (6 mL). To this solution was added tert-butyl carbamate (517.3 mg, 4.416 mmol), Cs$_2$CO$_3$ (1.918 g, 5.888 mmol), xantphos (85.17 mg, 0.1472 mmol) followed by Pd$_2$(dba)$_3$ (134.8 mg, 0.1472 mmol). The tube was sealed and heated thermally for 60 h at 115° C. The reaction mixture was cooled to RT and filtered on a pad of celite. The cake was washed with EtOAc and the combined filtrate was concentrated in vacuo to a black oil. The residue was taken up in DCM (2 ml) and TFA (3 ml) was added. The resulting dark brown clear solution was stirred at RT for 2 h and then concentrated in vacuo. The residue was loaded onto a SCX-2 (10 g) cartridge. Flushed with MeOH (×3, CV) before eluting the desired product with 2M NH$_3$ in MeOH (×3 CV). The basic eluent was concentrated in vacuo to afford a dark brown oil that was purified by chromatography on silica eluting with DCM-DCM:MeOH:NH$_3$ (90:10:1) a gradient of 100-0 to 30:70. Fractions containing product were collected and concentrated in vacuo to afford 5-fluoro-4-(oxetan-3-yl)piperazin-1-yl)pyridin-3-amine as a light brown solid. 295 mg: MS (ES+) 253.2.

The following aminopyridines were prepared according to methods similar to the one depicted in Preparation N-9:

4-(5-(oxetan-3-yl)-2,5-diazabicyclo[4.1.0]heptan-2-yl)pyridin-3-amine

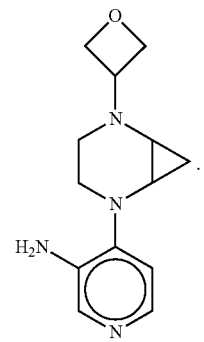

Preparation N-10: 5-fluoro-4-(4-methylpiperazin-1-yl)pyridin-3-amine

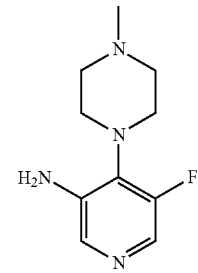

Step 1: 1-(3-chloro-5-fluoropyridin-4-yl)-4-methylpiperazine

A solution of 3-chloro-5-fluoro-4-iodo-pyridine (2.18 g, 8.468 mmol), 1-methylpiperazine (1.272 g, 1.409 mL, 12.70 mmol) and DIPEA (2.189 g, 2.950 mL, 16.94 mmol) in MeCN (13.08 mL) was heated at 130° C. in the microwave for 300 min. The reaction mixture was concentrated in vacuo and purified by column chromatography on silica eluting with 0-10% MeOH/DCM. Product fractions were combined and concentrated in vacuo to leave 1-(3-chloro-5-fluoropyridin-4-yl)-4-methylpiperazine as a yellow/brown oil. (1.16 g, 59%). MS (ES+) 230.0.

Step 2: 5-fluoro-4-(4-methylpiperazin-1-yl)pyridin-3-amine

A mixture of tert-butyl carbamate (709.9 mg, 6.060 mmol), Cs$_2$CO$_3$ (3.291 g, 10.10 mmol), xantphos (146.1 mg, 0.2525 mmol), Pd$_2$(dba)$_3$ (231.2 mg, 0.2525 mmol) and 1-(3-chloro-5-fluoro-4-pyridyl)-4-methyl-piperazine (1.16 g, 5.050 mmol) in dioxane (11.60 mL) was heated at 110° C. for 1 h. At room temperature, tert-butyl carbamate (709.9 mg, 6.060 mmol), xantphos (146.1 mg, 0.2525 mmol) and Pd$_2$(dba)$_3$ (231.2 mg, 0.2525 mmol) was added and the mixture was further heated at 120° C. in the microwave for 1 h. The reaction mixture was then filtered through a celite pad and washed with methanol and the filtrate concentrated in vacuo. The residue was purified by column chromatography on silica, using the ISCO column companion system eluting with 0-10% MeOH/DCM. Product fractions were combined and concentrated in vacuo to yield 5-fluoro-4-(4-methylpiperazin-1-yl)pyridin-3-amine as a light brown viscous oil. (642 mg, 60%). MS (ES+) 211.1.

Preparation N-11: tert-butyl 4-(3-amino-5-chloro-pyridin-4-yl)piperazine-1-carboxylate

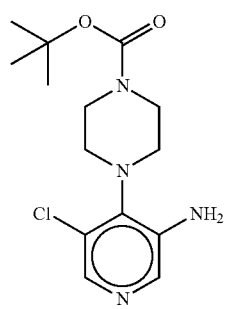

Step 1: tert-butyl 4-(3-chloro-5-nitropyridin-4-yl)piperazine-1-carboxylate

A mixture of 4-bromo-3-chloro-5-nitro-pyridine (700 mg, 2.948 mmol), tert-butyl piperazine-1-carboxylate (823.6 mg, 4.422 mmol) and DIPEA (762.0 mg, 1.027 mL, 5.896 mmol) in NMP (2.5 mL) was stirred overnight at RT. The reaction mixture was partitioned between EtOAc and water. Combined organic extract was washed with brine, dried over MgSO$_4$, concentrated under reduced pressure to yield tert-butyl 4-(3-chloro-5-nitropyridin-4-yl)piperazine-1-carboxylate which was used in next step without further purification (1 g, 99%). MS (ES+) 343.1.

Step 2: tert-butyl 4-(3-amino-5-chloropyridin-4-yl)piperazine-1-carboxylate

To a solution of tert-butyl 4-(3-chloro-5-nitropyridin-4-yl)piperazine-1-carboxylate (900 mg, 2.626 mmol) and ZnBr$_2$ (118.3 mg, 28.16 μL, 0.5252 mmol) in methanol (27.00 mL) was added Pd on C (10%, wet, Degussa) (300 mg). The reaction mixture was stirred at RT for 4 h under an atmosphere of hydrogen (balloon). The catalyst was filtered off and the filtrate was concentrated in vacuo to yield tert-butyl 4-(3-amino-5-chloropyridin-4-yl)piperazine-1-carboxylate which was used without further purification (820 mg, 99%). MS (ES+) 313.2.

The following aminopyridines were prepared according to methods similar to the one depicted in Preparation N-11:

5-chloro-4-(4-methylpiperazine-1-yl)pyridin-3-amine:

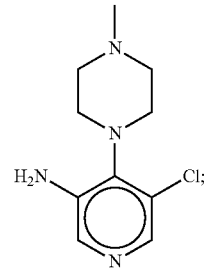

(1-(3-amino-5-chloropyridin-4-yl)piperidin-4-yl)(4-methylpiperazin-1-yl)methanone:

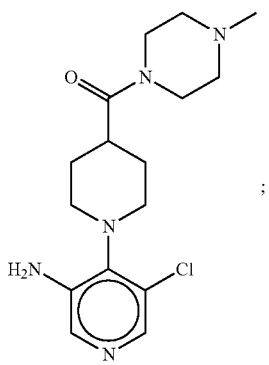

(1-(3-amino-5-chloropyridin-4-yl)piperidin-4-yl)(1,4-diazabicyclo[3.2.2]nonan-4-yl)methanone:

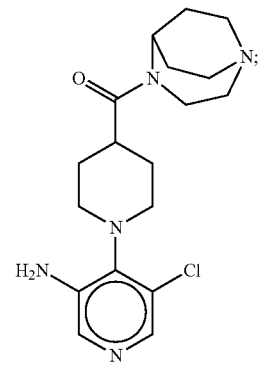

5-chloro-4-(3-(methylsulfonyl)pyrrolidin-1-yl)pyridin-3-amine:

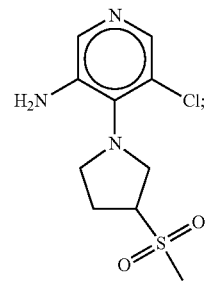

-continued 5-chloro-4-(5-methylhexahydropyrrolo[3,4-c]pyrrol-2(1H)-yl)pyridin-3-amine:

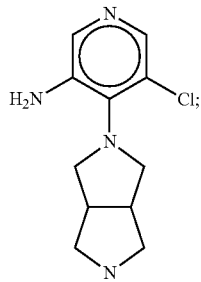

(R)-1-(3-amino-5-chloropyridin-4-yl)pyrrolidine-3-carbonitrile:

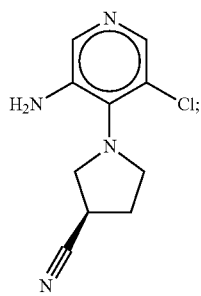

1-(3-amino-5-chloropyridin-4-yl)pyrrolidin-3-ol:

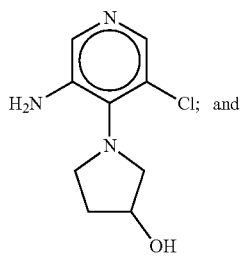

5-chloro-4-(pyrrolidin-1-yl)pyridin-3-amine:

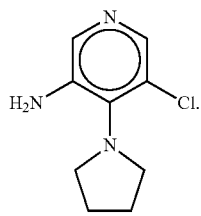

Preparation N-12: 1-methyl-4-(3-methyl-5-nitropyridin-4-yl)piperazine

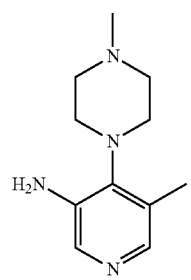

Step 1:
1-methyl-4-(3-methyl-5-nitro-4-pyridyl)piperazine

To an oven dried flask under nitrogen was added 1-(3-bromo-5-nitro-4-pyridyl)-4-methyl-piperazine (synthesized from 3-bromo-4-chloro-5-nitropyridine according to methods similar to the one depicted in Step 1 of Preparation N-1) (750 mg, 2.491 mmol), Pd$_2$dba$_3$ (34.21 mg, 0.03736 mmol) and X-Phos (35.62 mg, 0.07473 mmol). Anhydrous THF (37.50 mL) was added followed by 1,4-diazabicyclo[2.2.2]octane trimethylalumane (638.6 mg, 2.491 mmol). The reaction was heated at reflux for 2 hours then cooled to ambient temperature. The reaction mixture was partitioned between water and EtOAc. The combine organic extracts were washed with brine, dried (MgSO$_4$) and concentrated in vacuo. The residue was purified by column chromatography on silica using the ISCO column companion system (24 g column, Ethyl acetate/petroleum ether (0-100% EtOAc)) to yield 1-methyl-4-(3-methyl-5-nitro-4-pyridyl)piperazine as a yellow oil. (290 mg, 49%). MS (ES+) 237.1.

Step 2:
5-methyl-4-(4-methylpiperazin-1-yl)pyridin-3-amine

A suspension of Pd on C, (10%, wet, Degussa) (130.6 mg, 0.1227 mmol) with 1-methyl-4-(3-methyl-5-nitro-4-pyridyl)piperazine (290 mg, 1.227 mmol) in methanol (5.800 mL) was stirred at rt overnight under an atmosphere of hydrogen (balloon). The reaction mixture was filtered through a celite pad and washed with methanol and ethyl acetate and the filtrate concentrated in vacuo to leave 5-methyl-4-(4-methylpiperazin-1-yl)pyridin-3-amine as a yellow oil (243 mg, 96%). MS (ES+) 207.1.

Preparation N-13: (1-(3-amino-5-fluoropyridin-4-yl)piperidin-4-yl)(4-methylpiperazin-1-yl)methanone (hydrobromide) 17a Scheme 5

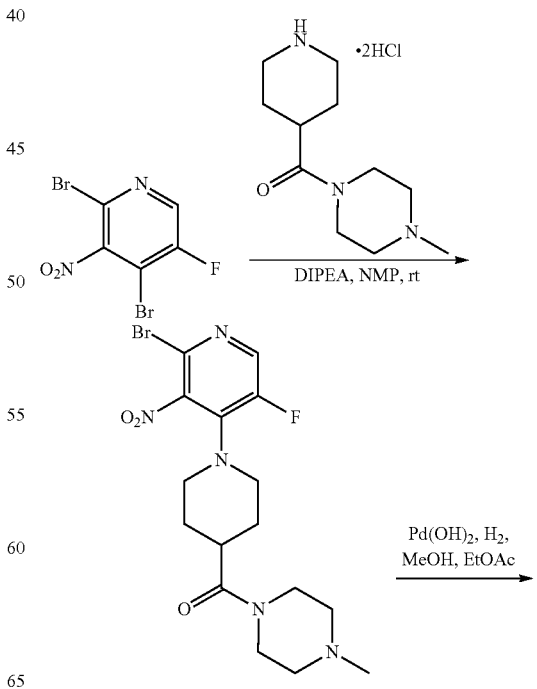

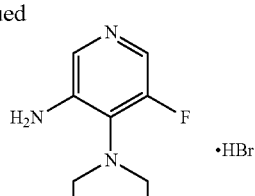

17a

Step 1: (1-(2-bromo-5-fluoro-3-nitropyridin-4-yl)piperidin-4-yl)(4-methylpiperazin-1-yl)methanone 16

A round-bottomed flask was charged with (4-methylpiperazin-1-yl)-(4-piperidyl)methanone dihydrochloride (16.45 g, 57.89 mmol) and DIPEA (23.20 g, 31.27 mL, 179.5 mmol) in NMP (160 mL). 2,4-Dibromo-5-fluoro-3-nitropyridine (17.36 g, 57.89 mmol) was added and the reaction mixture was stirred overnight at room temperature under a nitrogen atmosphere. Additional (4-methylpiperazin-1-yl)-(4-piperidyl)methanone dihydrochloride (1.65 g, 0.1 eq) and DIPEA (1 mL, 0.1 eq) was added and stirred at room temperature for a further 3 h. The mixture diluted with EtOAc, washed with water (3×). The aqueous layer was extracted with EtOAc (3×) and the combined organic extracts were combined, washed with brine, dried (sodium sulfate), filtered and concentrated in vacuo. The crude product was purified by chromatography (330 g SiO$_2$, 0 to 5% MeOH (containing 10% ammonium hydroxide)/DCM) to afford product as a yellow solid (20.24 g, 81%). MS (ES+) 432.0.

Step 2: (1-(3-amino-5-fluoropyridin-4-yl)piperidin-4-yl)(4-methylpiperazin-1-yl)methanone hydrobromide 17a

[1-(2-Bromo-5-fluoro-3-nitro-4-pyridyl)-4-piperidyl]-(4-methylpiperazin-1-yl)methanone 16 (20.24 g, 47.04 mmol) was dissolved/suspended in MeOH (389 mL)/EtOAc (78 mL) and Pd(OH)$_2$ (1.651 g, 2.352 mmol) was added. The resulting mixture was degassed by vacuum/nitrogen cycles (×5) and the atmosphere was exchanged by vacuum/hydrogen cycles (×5). The reaction mixture was stirred vigorously under a hydrogen atmosphere (balloon) for 6 hrs. Additional Pd(OH)$_2$ (4.95 g) was added and the reaction mixture was stirred overnight under hydrogen. The mixture was filtered through celite, washing through with methanol. The filtrate was concentrated in vacuo to leave an orange gum. Approx. 150 mL of ethanol was added and the mixture rotated on *buchii* for 10 mins, a yellow precipitate had formed during this time. The suspension was sonicated for 5 mins and the solid was then collected by filtration, washed with minimal ethanol and dried by suction for 1 h to afford product as a pale yellow solid. A second crop of product was obtained by concentrating the filtrate in vacuo. The residue was then slurried in minimal ethanol and sonicated for 5 mins then solid collected by filtration, dried by suction to leave second crop of product as a yellow solid. Both crops of product were combined to afford product as a yellow solid (15.8 g, 79%). MS (ES+) 322.2.

Preparation N-14: (1-(3-amino-5-fluoropyridin-4-yl)piperidin-4-yl)(4-methylpiperazin-1-yl)methanone (hydrochloride) 17b Scheme 6

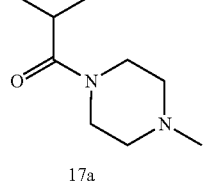

i) nBuLi, Diisopropylamine,
ii) hexachloroethane
iii) 2M HCl

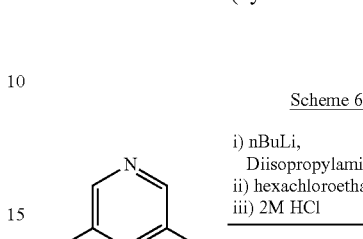

Step 1: 3-bromo-4-chloro-5-fluoropyridine hydrochloride 18

To a solution of diisopropylamine (6.899 g, 9.555 mL, 68.18 mmol) in THF (75 mL) cooled to −78° C., was added butyllithium (25 mL of 2.5 M in hexanes, 62.5 mmol). The reaction mixture was allowed to warm to −20° C. then cooled back down to −78° C. A solution of 3-bromo-5-fluoro-pyridine (10 g, 56.82 mmol) in THF (25 mL) was added dropwise keeping temperature below −70° C. (approx 30 mins). The reaction mixture was stirred at −78° C. for 30 min and a solution of 1,1,1,2,2,2-hexachloroethane (14.8 g, 62.5 mmol) in THF (20 mL) was then added dropwise, keeping temperature below −70° C. (over approx 30 mins). The mixture was stirred at −78° C. for 20 minutes, allowed to warm to room temperature, cooled back to 0° C. and quenched with water (100 mL). EtOAc (400 mL) was then added, and organic layer separated, washed with water (2×), brine (1x), dried (MgSO$_4$), filtered and concentrated in vacuo to leave a brown solid. The solid was triturated in pentane (100 mL) for 10 minutes, then filtered. The filtrate was concentrated in vacuo to afford product as a brown oil that turned to a crystalline solid on standing, 11.85 g, 89%). $^1$H NMR (DMSO-d6) δ 8.78 (s, 1H), 8.76 (s, 1H).

To a solution of 3-bromo-4-chloro-5-fluoro-pyridine (7.56 g, 32.18 mmol) in pentane (100 mL) was added hydrogen chloride (2M in ether) (17.7 mL of 2 M, 35.4 mmol). An off-white precipitate formed instantly. The mixture was stirred for 5 minutes then the solid was collected by filtration, washed with pentane and dried by suction to afford the desired product as an off-white solid (4.79 g, 60%). $^1$H NMR (DMSO-d6) δ 8.77 (s, 1H), 8.75 (s, 1H).

Step 2: (1-(3-bromo-5-fluoropyridin-4-yl)piperidin-4-yl)(4-methylpiperazin-1-yl)methanone 19

A mixture of (4-methylpiperazin-1-yl)-(4-piperidyl)methanone dihydrochloride (50.65 g, 178.2 mmol), 3-bromo-4-chloro-5-fluoro-pyridine hydrochloride 18 (40 g, 162 mmol) and dipotassium carbonate (94.04 g, 680.4 mmol) in NMP (400 mL) was heated at 150° C. overnight. The mixture was cooled to room temperature then filtered to remove inorganic salts and the filtrate was concentrated in vacuo. The residue was dissolved in EtOAc (800 mL), washed with brine (100 mL×4), dried (MgSO$_4$), filtered and concentrated in vacuo to afford a brown viscous oil. This residue was purified by silica gel column (approx 800 g of silica), product loaded onto silica in DCM, then eluting with 3% methanol (containing 10% ammonium hydroxide)/DCM to afford the desired product as a brown oil which crystallised on standing (27.44 g, 44%). MS (ES+) 387.1.

Step 3: (1-(3-amino-5-fluoropyridin-4-yl)piperidin-4-yl)(4-methylpiperazin-1-yl)methanone hydrochloride 17b Pd$_2$(dba$_3$) (3.818 g, 4.169 mmol) and Xantphos (4.824 g, 8.337 mmol) were added to a degassed (3× vacuum/N$_2$ cycles) mixture of diphenylmethanimine (16.62 g, 15.39 mL, 91.71 mmol), [1-(3-bromo-5-fluoro-4-pyridyl)-4-piperidyl]-(4-methylpiperazin-1-yl)methanone 19 (32.12 g, 83.37 mmol), tert-butyl carbamate (3.649 g, 31.15 mmol), and Cs$_2$CO$_3$ (81.49 g, 250.1 mmol) in dioxane (550 mL) in a round bottom flask under N$_2$. The reaction mixture was flushed with nitrogen via 2× vacuum/N$_2$ cycles then stirred at 100° C. overnight under N$_2$. The mixture cooled to room temperature then partitioned between EtOAc (1 L) and water (100 mL). The organic layer was separated, washed with water (2×100 mL), brine (1×100 mL), dried (MgSO$_4$), filtered and concentrated in vacuo to afford a dark orange viscous oil (56.15 g). This crude residue was then dissolved in THF (482 mL) and hydrogen chloride (300 mL of 2 M, 600 mmol) was then added and the mixture was heated at 60° C. for 30 minutes. THF was removed in vacuo and the remaining aqueous solution was washed with EtOAc (2×) then basified to pH=8 with 2M NaOH solution (approx. 310 mL), and extracted with EtOAc (3×). The combined organic extracts were washed with brine (1×), dried (MgSO$_4$), filtered and concentrated in vacuo to afford an orange solid (25.44 g). The orange solid was dissolved in dioxane (300 mL) then 4M HCl in dioxane (19.8 mL, 79.16 mmol) was added slowly over 10 mins. The mixture was stirred for 20 minutes and the precipitate that formed was collected by filtration, washed with dioxane (approx 100 mL), diethyl ether (100 mL), dried by suction to afford desired product as a white solid (25.13 g, 84%). MS (ES+) 322.2.

Step 3a: (1-(3-amino-5-fluoropyridin-4-yl)piperidin-4-yl)(4-methylpiperazin-1-yl)methanone 17

In an alternative method to Step 3, above, Tris(dibenzylideneacetone)dipalladium (1.189 g, 1.298 mmol) and xantphos (1.502 g, 2.596 mmol) were added to a degassed (3× vacuum/N$_2$ cycles) mixture of [1-(3-bromo-5-fluoro-4-pyridyl)-4-piperidyl]-(4-methylpiperazin-1-yl)methanone 19 (10 g, 25.96 mmol) and Cs$_2$CO$_3$ (16.92 g, 51.92 mmol) in dioxane (150 mL) under N$_2$. The mixture was stirred at 100° C. overnight. The reaction was cooled to ambient temperature and the precipitate was filtered off and washed with EtOAc (50 mL). The filtrate was partitioned between EtOAc and water. The combined organic layers were washed with water, brine, dried (MgSO$_4$) and concentrated in vacuo to leave tert-butyl N-[5-fluoro-4-[4-(4-methylpiperazine-1-carbonyl)-1-piperidyl]-3-pyridyl]carbamate as a red solid that was used in next step without further purification. MS (ES+) 422.2.

To a suspension of tert-butyl-N-[5-fluoro-4-[4-(4-methylpiperazine-1-carbonyl)-1-piperidyl]-3-pyridyl]carbamate (3.34 g, 7.924 mmol) in dioxane (25 mL) was added HCl (4M in dioxane) (8 mL of 4 M) and the mixture was heated at 40° C. overnight. The mixture was cooled to RT and the solid was collected by filtration, washed with dioxane (15 mL) then with EtOAc (2×20 ml) and dried in vacuo to leave a white solid which was partitioned between EtOAc (70 ml) and 1M sodium carbonate (50 ml). Combined organic extract was dried and concentrated in vacuo to yield 2.26 g of an off-white solid that was slurried in MeCN (5 mL). The solid was collected by filtration, washed with minimal MeCN (3 to 5 mL), and dried by suction to leave (1-(3-amino-5-fluoropyridin-4-yl)piperidin-4-yl)(4-methylpiperazin-1-yl)methanone as a white solid. MS (ES+) 322.1.

The following aminopyridine intermediates were prepared using a procedure similar to either Preparation N-13 or Preparation N-14:

5-fluoro-4-(4-(3-methoxypropyl)piperazin-1-yl)pyridin-3-amine:

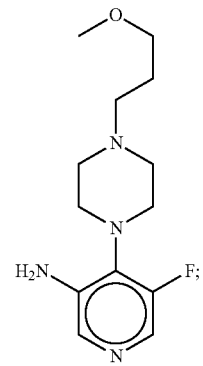

-continued (4-(3-amino-5-fluoropyridin-4-yl)piperazin-1-yl)(quinuclidin-3-yl)methanone:

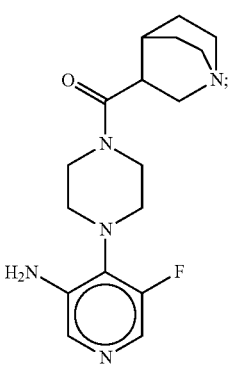

(R)-5-fluoro-4-(hexahydropyrazino[2,1-c][1,4]oxazin-8(1H)-yl)pyridin-3-amine:

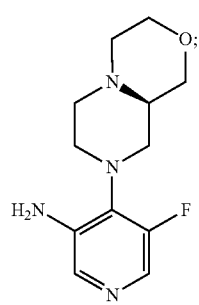

(S)-5-fluoro-4-(hexahydropyrazino[2,1-c][1,4]oxazin-8(1H)-yl)pyridin-3-amine:

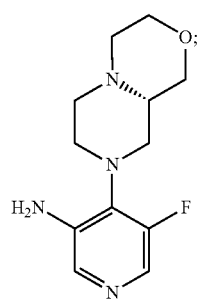

5-fluoro-4-(4-morpholinopiperidin-1-yl)pyridin-3-amine:

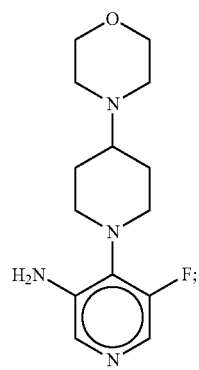

-continued 1-(4-(3-amino-5-fluoropyridin-4-yl)piperazin-1-yl)-2-methylpropan-2-ol:

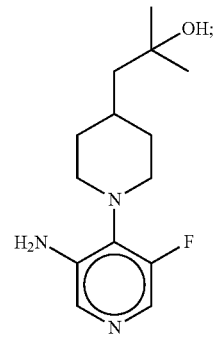

(4-(3-amino-5-fluoropyridin-4-yl)piperazin-1-yl)(4-methylpiperazin-1-yl)methanone:

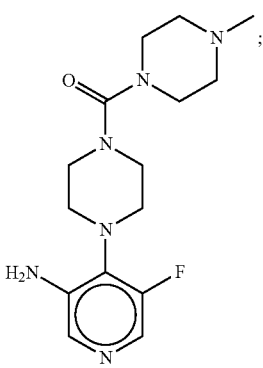

1-(3-amino-5-fluoropyridin-4-yl)-N,N-dimethylpiperidine-4-sulfonamide:

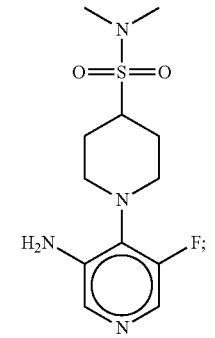

1(1-(3-amino-5-flluoropyridin-4-yl)piperidin-4-yl)pyrrolidin-2-one:

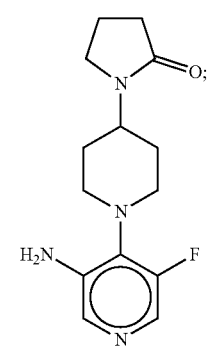

1-(3-amino-5-fluoropyridin-4-yl)-N-methyl-N-(1-methylpiperidin-4-yl)piperidine-4-sulfonamide:

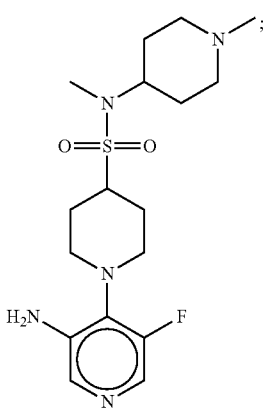

5-fluoro-4-(4-(morpholinomethyl)piperidin-1-yl)pyridin-3-amine:

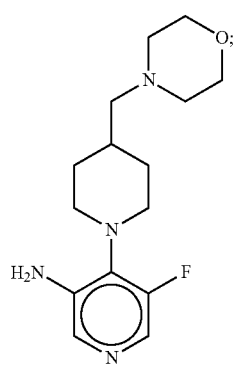

5-fluoro-4-(4-((4-methylpiperazin-1-yl)methyl)piperidin-1-yl)pyridin-3-amine:

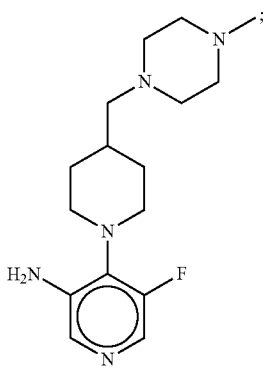

1-(1-(3-amino-5-fluoropyridin-4-yl)piperidin-4-yl)-4-methylpiperazin-2-one:

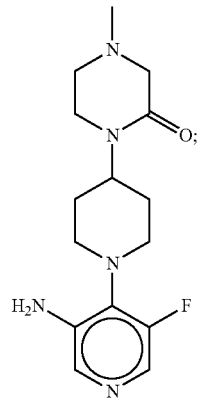

5-fluoro-4-(4-(morpholinosulfonyl)piperidin-1-yl)pyridin-3-amine:

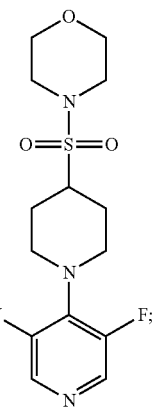

2-(3-amino-5-fluoropyridin-4-yl)hexahydropyrrolo[1,2-a]pyrazin-6(2H)-one:

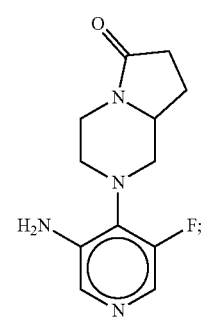

5-fluoro-4-(4-(methylsulfonyl)piperidin-1-yl)pyridin-3-amine:

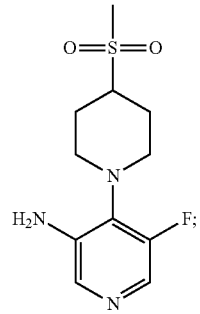

5-fluro-4-(4-(2-(pyrrolidin-1-yl)ethoxy)piperidin-1-yl)ethoxy)piperidin-1-yl)pyridin-3-amine:

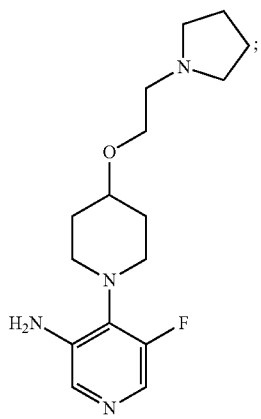

4-((1-(3-amino-5-fluoropyridin-4-yl)piperidin-4-yl)methyl)-1-methylpiperazin-2-one:

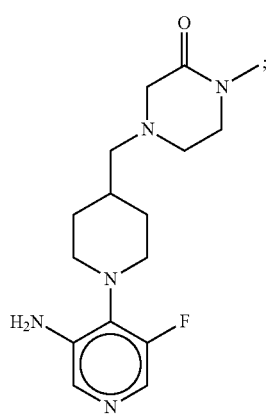

(R)-2-(3-amino-5-fluoropyridin-4-yl)hexahydropyrrolo[1,2-a]pyrazin-6(2H)-one:

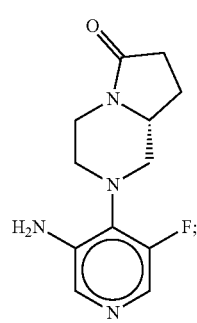

(S)-2-(3-amino-5-fluoropyridin-4-yl)hexahydropyrrolo[1,2-a]pyrazin-6(2H)-one:

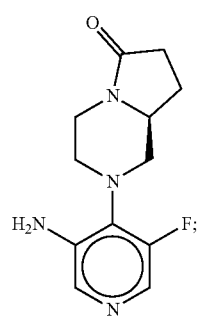

5-fluoro-4-(4-methyl-1-oxa-4,9-diazaspiro[5.5]undecan-9-yl)pyridin-3-amine:

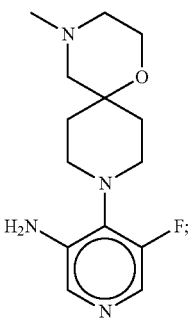

5-fluoro-4-(4-(thiazol-2-yl)piperidin-1-yl)pyridin-3-amine:

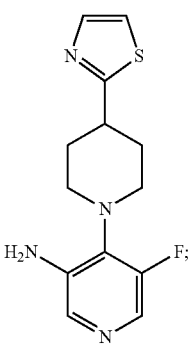

5-fluoro-4-(8-methylhexahydro-1H-pyrazino[1,2-a]pyrazin-2(6H)-yl)pyridin-3-amine:

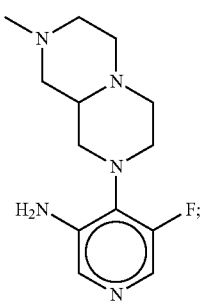

5-fluoro-4-(piperidin-1-yl)pyridin-3-amine:

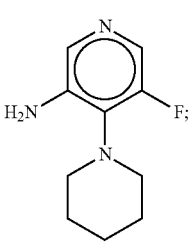

2-(3-amino-5-fluoropyridin-4-yl)hexahydro-1H-pyrido[1,2-a]pyrazin-6(2H)-one:

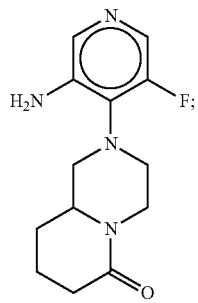

4-(3-amino-5-fluoropyridin-4-yl)thiomorpholine 1,1-dioxide:

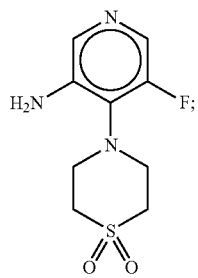

(R)-7-(3-amino-5-fluoropyridin-4-yl)tetrahydro-1H-oxazolo[3,4-a]pyrazin-3(5H)-one:

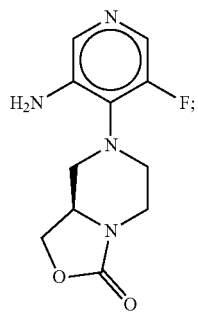

5-fluoro-4-(pyrrolidin-1-yl)pyridin-3-amine:

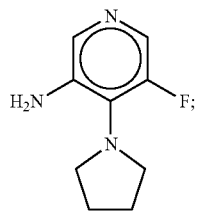

2-(3-amino-5-fluoropyridin-4-yl)hexahydro-1H-pyrido[1,2-a]pyrazin-6(2H)-one:

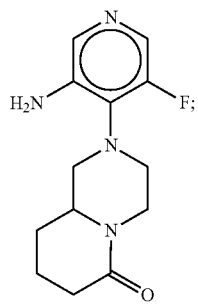

8-(3-amino-5-fluoropyridin-4-yl)-2-methyloctahydro-1H-pyrazino[1,2-a]pyrazin-1-one:

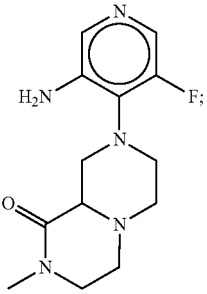

5-fluoro-4-(2-oxa-7-azaspiro[3.5]nonan-7-yl)pyridin-3-amine:

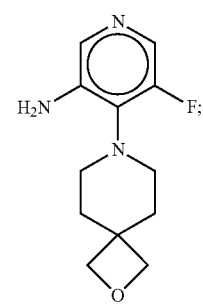

2-(3-amino-5-fluoropyridin-4-yl)hexahydropyrrolo[1,2-a]pyrazin-4(1H)-one:

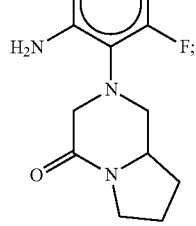

8-(3-amino-5-fluoropyridin-4-yl)-3-methyl-1-oxa-3,8-diazaspiro[4.5]decan-2-one:

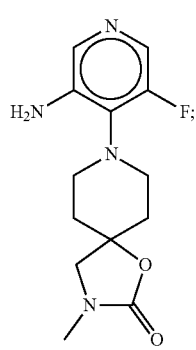

-continued
4-(3-amino-5-fluoropyridin-4-yl)-1-methylpiperazin-2-one:

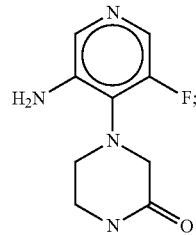

1-((1-(3-amino-5-fluoropyridin-4-yl)piperidin-4-yl)methyl)pyrrolidin-2-one:

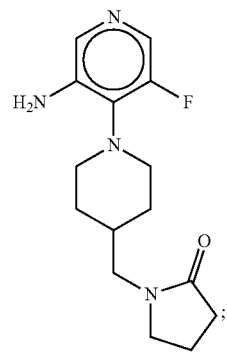

5-fluoro-4-(4-((4-methylpiperazin-1-yl)methyl)piperidin-1-yl)pyridin-3-amine:

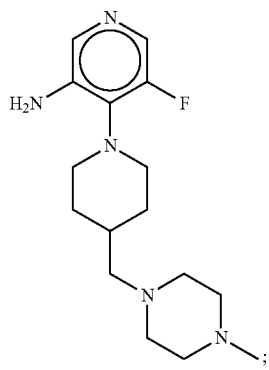

5-fluoro-4-(4-methyl-1-oxa-4,9-diazaspiro[5.5]undecan-9-yl)pyridin-3-amine:

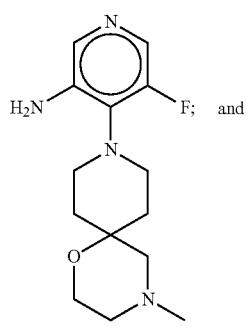

-continued
4-(4-(1H-imidazol-1-yl)piperidin-1-yl)-5-fluoropyridin-3-amine:

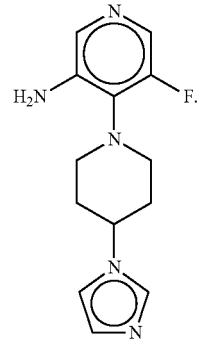

Preparation N-15: tert-butyl 1-(3-amino-5-fluoro-4-pyridyl)piperidine-4-carboxylate Scheme 7a

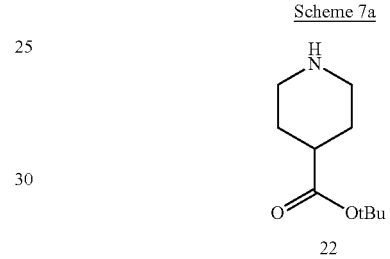

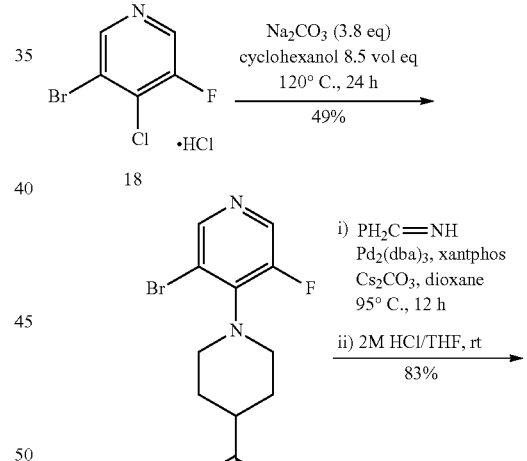

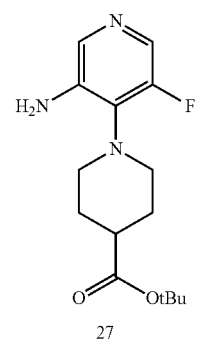

Step 1: tert-butyl 1-(3-bromo-5-fluoro-4-pyridyl)piperidine-4-carboxylate 26

A 3 L flange flask equipped with a thermometer, condenser, nitrogen line and overhead stirrer was heated at 40° C. (external) then charged with cyclohexanol (750 mL), disodium carbonate (129.8 g, 1.225 mol), 3-bromo-4-chloro-5-fluoro-pyridine (Hydrochloric Acid 18) (137.5 g, 556.8 mmol) and tert-butyl piperidine-4-carboxylate (123.8 g, 668.2 mmol) rinsed in with cyclohexanol (350 mL). Mixture was heated to 120° C. internal temperature overnight (18 h). Reaction mixture was removed from hotplate and allowed to cool to room temperature. Water (687.5 mL) and EtOAc (687.5 mL) were added, stirred for 10 mins then transferred to separating funnel. Additional EtOAc (1.238 L) was added, mixed and aqueous phase was removed. Organic phase was further washed with water (687 mL), aqueous phase removed, organic layer collected. Aqueous phases were combined and back extracted with EtOAc (687.5 mL), aqueous layer removed and organic phase combined with other organics. Organics concentrated in vacuo (water bath temp=60° C., vacuum down to 2 mBar) leaving a viscous brown oil.

Oil was dissolved in 25% EtOAc/petrol then passed through a short silica pad, eluting with 25% EtOAc/petrol until no more product came off. Filtrate was concentrated in vacuo to leave a brown oil, 127.1 g. Product re-purified by ISCO companion (1.5 Kg Silica, loaded in DCM, eluting 0 to 20% EtOAc/petrol), product fractions combined and concentrated in vacuo to leave desired product 26 as a pale yellow to cream solid, (98 g, 49% yield). $^1$H NMR (500 MHz, DMSO-d6) δ 8.47 (s, 1H), 8.41 (d, 1H), 3.39-3.36 (m, 2H), 3.12 (tt, 2H), 2.49-2.43 (m, 1H), 1.91-1.87 (m, 2H), 1.71-1.64 (m, 2H) and 1.43 (s, 9H). MS (ES+) 361.0.

Step 2: tert-butyl 1-(3-amino-5-fluoro-4-pyridyl)piperidine-4-carboxylate 27

To a solution of tert-butyl 1-(3-bromo-5-fluoro-4-pyridyl)piperidine-4-carboxylate 26 (98 g, 272.8 mmol), diphenylmethanimine (59.34 g, 54.94 mL, 327.4 mmol) and Cs$_2$CO$_3$ (177.8 g, 545.6 mmol) in Dioxane (1.274 L) was added xantphos (15.78 g, 27.28 mmol) and Pd2(dba)$_3$ (12.49 g, 13.64 mmol). The mixture was stirred under nitrogen at 95° C. overnight. The mixture was cooled to room temperature then partitioned between EtOAc (1000 mL, 10 vol eq.) and water (490 mL, 5 vol eq.), mixed and organic layer separated. Organics washed further with water (1×250 mL), brine (250 mL), dried (MgSO$_4$), filtered and concentrated in vacuo to leave crude product as a dark red viscous oil, 185.3 g.

The obtained product oil (185.3 g) was dissolved in THF (882.0 mL) and HCl (545.5 mL of 2 M, 1.091 mol) was added. The resulting mixture was stirred at room temperature for 20 mins. THF was removed in vacuo then additional (HCl (2M) (588.0 mL) was added. The aqueous was washed twice with EtOAc (294.0 mL). A large amount of a yellow precipitate formed during extraction in both organic and aqueous phase, the solid from both the organic and aqueous phase was collected by filtration and dried by suction. The mixed organic and aqueous filtrate was added to separating funnel, extracted with 2M HCl (2×200 mL). All aqueous phases plus solid collected on sinter (product) were combined to give a suspension. The pH was adjusted to 6 using 2M NaOH and extracted with DCM (3×600 mL). The organics were combined, dried (MgSO$_4$), filtered and concentrated in vacuo to leave a pale orange waxy solid, 112.2 g. This solid was slurried in MeCN (200 mL), stirred for 10 mins then solid collected by filtration, washed with minimal MeCN and dried by suction to leave product 27 as a white solid (66.8 g, 83% yield). $^1$H NMR (500 MHz, DMSO-d6) δ 7.82 (d, 1H), 7.63 (d, 1H), 5.22 (s, 2H), 3.11-3.00 (m, 2H), 2.91 (tt, 2H), 2.36 (tt, 1H), 1.88-1.83 (m, 2H), 1.79-1.71 (m, 2H), 1.43 (s, 9H). MS (ES+) 297.1.

Scheme 7B:
Alternative synthesis of tert-butyl 1-(3-amino-5-fluoro-4-pyridyl)piperidine-4-carboxylate

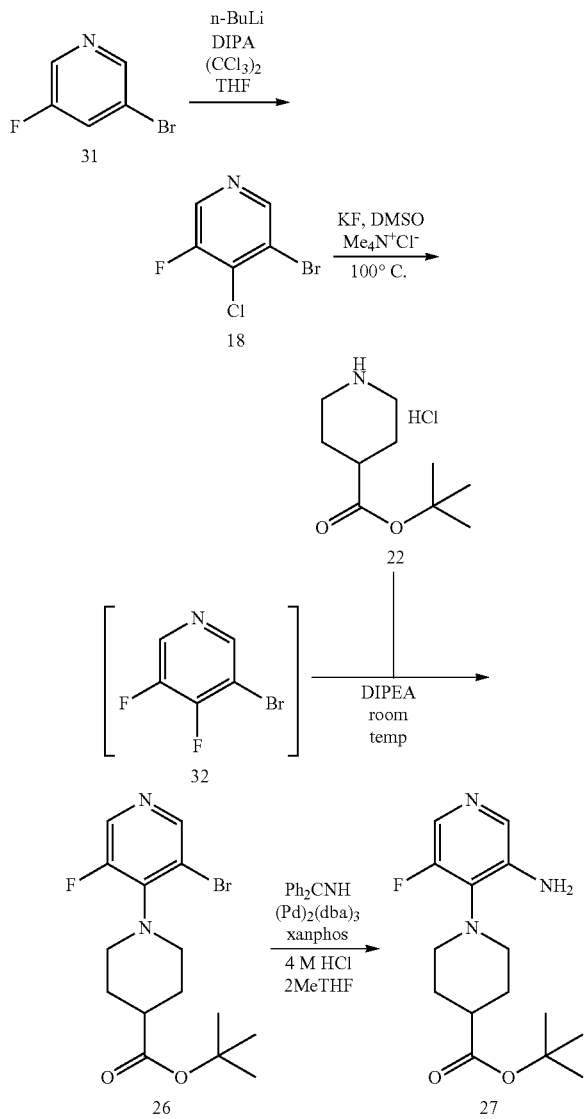

Step 1: 3-bromo-4-chloro-5-fluoropyridine hydrochloride 18

A solution of diisopropylamine (101.2 g, 140.2 mL, 1.000 mol) in tetrahydrofuran (1.148 L) was cooled to between −25° C. and −20° C. Butyllithium (2.5M in hexanes) (400 mL of 2.5 M, 1.000 mol) was added at such a rate as to maintain the reaction temperature below −20° C. (addition 20 minutes). The mixture was then allowed to warm to 4° C. over 1 hour, then re-cooled to −78° C. 3-bromo-5-fluoropyridine (153.0 g, 869.6 mmol) in tetrahydrofuran (382.5 mL) was added over 40 minutes. The mixture was stirred for 90 minutes, then a solution of 1,1,1,2,2,2-hexachloroethane (205.9 g, 869.6 mmol) in tetrahydrofuran (350.0 mL) was added dropwise over 40 minutes. Once the addition was complete the mixture was allowed to warm to ambient overnight. The mixture was cooled to 0° C. then transferred into cold water (2 L), stirred for 20 mins then MTBE (2.5 L) added and stirred vigorously for 30 mins then transferred to separating funnel and organic layer separated. Aqueous was transferred back to reaction vessel and further extracted with MTBE (2.5 L), stirred for 10 mins vigorously then transferred to separating funnel and organic layer separated. Organics were combined, dried (MgSO$_4$), filtered and concentrated to a brown oil. The oil was dissolved in pentane (500 ml) and ether (300 ml). HCl (2M in ether) (434.8 mL of 2 M, 869.6 mmol) was added slowly with stirring. On complete addition the mixture was stirred for 20 mins then solid collected by filtration, washed with ether and dried under vacuum for 1 h to leave product 18 as a beige solid (148.9 g, 69%); $^1$H NMR (500 MHz, DMSO-d6) δ 8.77 (2H, s); 19F NMR (500 MHz, DMSO-d6) δ−124.8; MS 210.8.

Step 2: tert-butyl 1-(3-bromo-5-fluoropyridin-4-yl)piperidine-4-carboxylate 26

3-bromo-4-chloro-5-fluoro-pyridine hydrochloride 18 (62 g, 251.1 mmol) was suspended in DCM (600 mL) and stirred. The mixture was cooled in an ice bath and sodium hydroxide (276.2 mL of 1 M, 276.2 mmol) was added slowly. The resulting mixture was stirred for 1 hour. The mixture was phase-separated. More DCM/water was added to aid phase separation. Some tarry particulates remained in the aqueous phase. The organic phase was washed with brine, dried (MgSO$_4$), filtered and concentrated. The residue was triturated with heptane. The heptane solution was filtered through a florsil pad, eluting with heptane. The filtrate was concentrated to an oil which solidified. This gave 41 g of free base.

A thoroughly stirred mixture of 3-bromo-4-chloro-5-fluoropyridine free base (55 g, 0.26 mol), potassium fluoride (31 g, 0.53 mol) and Me$_4$NCl (5.8 g, 53 mmol) in DMSO (400 mL) was heated to 130° C. for 2 hours. The reaction mixture was cooled to room temperature and tert-butyl piperidine-4-carboxylate hydrochloride 22 (66 g, 0.30 mol) and DIPEA (65 g, 0.50 mol) were added. The reaction mixture was stirred at room temperature overnight. The solvent was evaporated in vacuo. The residue was portioned between DCM/water. The organic layer was washed with water (3×), dried over Na$_2$SO$_4$, and filtered over silica gel using DCM as eluent. The filtrated was evaporated to give tert-butyl 1-(3-bromo-5-fluoropyridin-4-yl)piperidine-4-carboxylate 26 (61 g, 65%) as a light yellow solid; 1H NMR (500 MHz, DMSO-d$_6$) δ 8.47 (s, 1H), 8.41 (d, 1H), 3.39-3.36 (m, 2H), 3.12 (tt, 2H), 2.49-2.43 (m, 1H), 1.91-1.87 (m, 2H), 1.71-1.64 (m, 2H) and 1.43 (s, 9H); 19F NMR (500 MHz, DMSO-d6) δ−135.2; MS (ES+) 361.0.

Step 3: tert-butyl 1-(3-amino-5-fluoropyridin-4-yl)piperidine-4-carboxylate 27

Tert-butyl 1-(3-bromo-5-fluoropyridin-4-yl)piperidine-4-carboxylate 26 (800 g, 2.23 mol) was dissolved in 1,4-dioxane (7.5 L). Diphenylmethanimine (484 g, 2.67 mol) was added in one portion followed by cesium carbonate (1.45 Kg, 4.45 mol), xantphos (129 g, 223 mmol) and Pd$_2$(dba)$_3$ (102 g, 111 mmol). Additional 1,4-dioxane (2.9 L) was added and the mixture heated to 95° C. under nitrogen until the reaction was complete (determined by HPLC analysis). The mixture was cooled to 20° C. and ethyl acetate (8 L) and water (4 L) were added. The organic phase was isolated and washed with water (4 L) and brine (3.5 L) and dried over magnesium sulphate and filtered. The filtrate was concentrated to a brown oil (1.3 Kg). The oil was dissolved in 2-methyltetrahydrofuran (7.2 L) and 2M HCl was added at 20° C. and the mixture stirred for 30 minutes. The aqueous layer was isolated and the organic layer extracted with 2M HCl (1.2 L). The combined aqueous was neutralised with 2M NaOH (5.4 L, pH 8-9). The product was extracted into 2-methyltetrahydrofuran (14 L then 2×5 L). The combined extracts were washed with water (1.6 L) and the organic solution concentrated. The residue was slurried in acetonitrile (2 L), filtered and dried. This gave the product 27 as a white solid (568.7 g, 86.5%); 1H NMR (500 MHz, DMSO-d$_6$) δ 7.82 (d, 1H), 7.63 (d, 1H), 5.22 (s, 2H), 3.11-3.00 (m, 2H), 2.91 (tt, 2H), 2.36 (tt, 1H), 1.88-1.83 (m, 2H), 1.79-1.71 (m, 2H), 1.43 (s, 9H); 19F NMR (500 MHz, DMSO-d6) δ−140.0; MS (ES+) 297.1.

Preparation N-16: 5-cyclopropyl-4-(4-methylpiperazin-1-yl)pyridin-3-amine

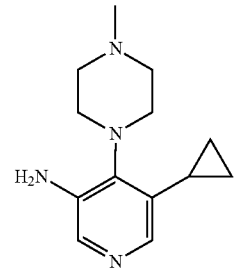 [SMILES: CN1CCN(c2c(N)cncc2C2CC2)CC1]

Step 1: 1-(3-cyclopropyl-5-nitropyridin-4-yl)-4-methylpiperazine

A mixture of 1-(3-bromo-5-nitro-4-pyridyl)-4-methylpiperazine (synthesized from 1-methylpiperazine and 3-bromo-4-chloro-5-nitropyridine using procedure Step 1 of Preparation N-1) (467.4 mg, 1.552 mmol), ferrous; dichlorobis[cyclopenta-1,4-dien-1-yl(diphenyl)phosphaniumyl]palladium(2-); dichloromethane (63.37 mg, 0.07760 mmol), potassium carbonate (429.0 mg, 3.104 mmol) and cyclopropylboronic acid (200.0 mg, 2.328 mmol) in dioxane (5 mL) was degassed and flushed with nitrogen (×2). The reaction was heated at 100° C. in a sealed tube for 18 h. At room temperature the reaction mixture was filtered through Celite and evaporated to dryness, yielding 1-(3-cyclopropyl-5-nitropyridin-4-yl)-4-methylpiperazine as a dark orange solid that was used directly in the next reaction without further purification (288 mg, 66%). MS (ES+) 263.2

Step 2: 5-cyclopropyl-4-(4-methylpiperazin-1-yl)pyridin-3-amine

To a solution of 1-(3-cyclopropyl-5-nitro-4-pyridyl)-4-methyl-piperazine (220.4 mg, 0.8403 mmol) in methanol (25 mL) was added Pd on carbon (10%, Degussa, 6.387 mg, 0.006002 mmol). The reaction mixture was stirred at room temperature under a balloon of hydrogen, for 7 h. The Preparation N-17: 6-chloro-4-(4-methylpiperazin-1-yl)pyridin-3-amine

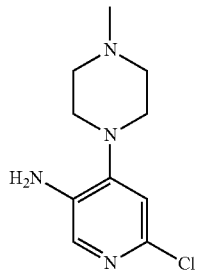

Step 1: 1-(2-chloro-5-nitropyridin-4-yl)-4-methylpiperazine 1-methylpiperazine (298.5 mg, 330.6 µL, 2.980 mmol) in THF (5 mL) was added to a stirred solution of 2,4-dichloro-5-nitro-pyridine (500 mg, 2.591 mmol) and DIPEA (401.8 mg, 541.5 µL, 3.109 mmol) in THF (10 mL) at 0° C. under an atmosphere of nitrogen. The reaction was allowed to stir at ambient temperature for 1 hour then the solvent removed in vacuo. The residue was purified by column chromatography (ISCO Companion, 40 g column, eluting with 0 to 10% MeOH/DCM solutions) to give 1-(2-chloro-5-nitropyridin-4-yl)-4-methylpiperazine as a yellow solid (638 mg, 96% Yield). MS (ES+) 257.1.

Step 2: 6-chloro-4-(4-methylpiperazin-1-yl)pyridin-3-amine 1-(2-chloro-5-nitro-4-pyridyl)-4-methyl-piperazine (580 mg, 2.260 mmol) was dissolved in AcOH (20 mL)/Water (2 mL) and Fe (2.524 g, 45.20 mmol) was added. The resulting mixture was stirred at 50° C. for 30 minutes. The reaction was cooled to ambient temperature then loaded onto 50 g SCX-2 cartridge (pre-washed with MeOH). The cartridge was washed with DCM/MeOH mixtures, before the product was eluted with 2M NH₃ in MeOH/DCM mixtures. The solvent was removed in vacuo to give 6-chloro-4-(4-methylpiperazin-1-yl)pyridin-3-amine as a purple solid (510 mg, 99% Yield). MS (ES+) 227.1.

Preparation N-18: 4-(4-methylpiperazin-1-yl)pyridine-2,5-diamine

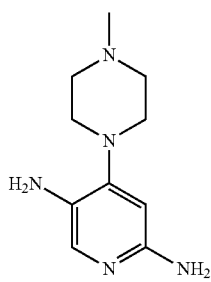

Step 1: 4-(4-methylpiperazin-1-yl)-5-nitro-pyridin-2-amine 1-methylpiperazine (265.5 mg, 294.0 µL, 2.651 mmol) in THF (5 mL) was added to a stirred suspension of 4-chloro-5-nitro-pyridin-2-amine (400 mg, 2.305 mmol) and DIPEA (357.5 mg, 481.8 µL, 2.766 mmol) in THF (10 mL) at 0° C. under an atmosphere of nitrogen. The reaction was allowed to stir at ambient temperature for 90 hours before the solvent removed in vacuo. The residue was triturated from DCM/MeOH and the resultant precipitate was washed with DCM/MeOH solutions. The filtrate was concentrated in vacuo and the residue was purified by column chromatography (ISCO Companion, 40 g column, eluting with 0 to 10% 2M NH₃ in MeOH/DCM) to give 4-(4-methylpiperazin-1-yl)-5-nitro-pyridin-2-amine as a yellow solid (355 mg, 65% Yield). MS (ES+) 238.1.

Step 2: 4-(4-methylpiperazin-1-yl)pyridine-2,5-diamine

Pd on C, (10%, wet, Degussa) (140 mg, 0.1316 mmol) was added to a stirred solution of 4-(4-methylpiperazin-1-yl)-5-nitro-pyridin-2-amine (355 mg, 1.496 mmol) in a mixture of EtOAc (5 mL) and EtOH (50 mL). The reaction was placed under an atmosphere of hydrogen and stirred at ambient temperature for 16 hours. The catalyst was removed by filtration through a pad of celite and the filtrate concentrated in vacuo to give 4-(4-methylpiperazin-1-yl)pyridine-2,5-diamine as a brown solid (291 mg, 94% Yield). MS (ES+) 208.1.

Preparation N-19: 5-(difluoromethyl)-4-(4-methylpiperazin-1-yl)pyridin-3-amine

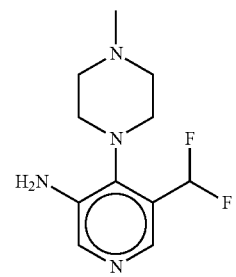

Step 1: 5-bromo-4-(4-methylpiperazin-1-yl)pyridin-3-amine 1-methylpiperazine (2.109 g, 21.06 mmol) in DCM (62.50 mL) was added to a stirred solution of 3-bromo-4-chloro-5-nitro-pyridine (5000 mg, 21.06 mmol) and DIPEA (3.266 g, 4.402 mL, 25.27 mmol) in DCM (62.50 mL) at RT. The reaction was allowed to stir at ambient temperature for 2 h, then was concentrated in vacuo. The residue was partitioned between a saturated aqueous solution of NaHCO₃ and DCM. Combined organic extract was dried and concentrated in vacuo. The orange solid was suspended in Acetic acid (60.00 mL) before iron (7.059 g, 126.4 mmol) was added. The mixture was warmed at 50° C. and stirred for 15 min. The mixture was allowed to cool to RT and DCM:EtOAc (4:1) (400 mL) was added to the reaction. The resulting brown suspension was filtered using a prewetted Celite cartridge (25 g), washing with more DCM:MeOH (4:1) (200 mL). Combined filtrate was concentrated in vacuo to afford a red/brown gum which was purified by chromatography on silica (Rf companion, 80 g cartridge), eluting with DCM-DCM:MeOH:NE3 (90:10:1) a gradient of 100-0 to 20:80. Fractions containing clean product were collected and concentrated in vacuo to afford 5-bromo-4-(4-methylpiperazin-1-yl)pyridin-3-amine as a viscous, clear light yellow oil that solidifies on standing. MS (ES+) 273.1.

Step 2: 1-(3-bromo-5-(2,5-dimethyl-1H-pyrrol-1-yl)pyridin-4-yl)-4-methylpiperazine 5-bromo-4-(4-methylpiperazin-1-yl)pyridin-3-amine (3000 mg, 11.06 mmol), hexane-2,5-dione (6.312 g, 6.487 mL, 55.30 mmol) in acetic acid (20 mL) was heated at 70° C. overnight. The reaction mixture was concentrated in vacuo and the residue was partitioned between EtOAc and an aqueous saturated solution of NaHCO₃. Combined organic extract was washed with brine, dried (MgSO₄) and concentrated in vacuo yielding an oil that was purified by filtration on silica to yield 1-(3-bromo-5-(2,5-dimethyl-1H-pyrrol-1-yl)pyridin-4-yl)-4-methylpiperazine as an off-white solid. MS (ES+) 351.1.

Step 3: 5-(2,5-dimethyl-1H-pyrrol-1-yl)-4-(4-methylpiperazin-1-yl)nicotinaldehyde A solution of 1-[3-bromo-5-(2,5-dimethylpyrrol-1-yl)-4-pyridyl]-4-methyl-piperazine (1250 mg, 3.579 mmol) in THF (35.79 mL) was cooled to −78° C. and t-BuLi (2.105 mL of 1.7 M, 3.579 mmol) was added dropwise. The mixture was stirred for 30 mins at −78° C. before DMF (261.6 mg, 277.1 µL, 3.579 mmol) was added dropwise. The mixture was stirred for 2 h at −78° C. The reaction was quenched with MeOH (5 mL) and allowed to warm to room temperature. The reaction was washed with an aqueous saturated solution of ammonium chloride (50 mL) and extracted with EtOAc (100 mL and 50 mL). The combined organics were dried (MgSO₄) and evaporated to leave an orange oil. Purification by column chromatography (EtOAc to EtOAc:MeOH 20%) yielded 5-(2,5-dimethyl-1H-pyrrol-1-yl)-4-(4-methylpiperazin-1-yl)nicotinaldehyde as a pale yellow crystalline solid. MS (ES+) 299.2.

Step 4: 1-(3-(difluoromethyl)-5-(2,5-dimethyl-1H-pyrrol-1-yl)pyridin-4-yl)-4-methylpiperazine To a solution of 5-(2,5-dimethylpyrrol-1-yl)-4-(4-methylpiperazin-1-yl)pyridine-3-carbaldehyde (100 mg, 0.3351 mmol) in methylene chloride (335.14) at RT was added 2-methoxy-N-(2-methoxyethyl)-N-(trifluoro-{4}-sulfanyl)ethanamine (370.8 mg, 1.676 mmol) and the mixture was heated at reflux for 18 h. At room temperature, the reaction was quenched with water (2 mL) and extracted with methylene chloride (2×5 mL) to yield 1-(3-(difluoromethyl)-5-(2,5-dimethyl-1H-pyrrol-1-yl)pyridin-4-yl)-4-methylpiperazine as a yellow oil. MS (ES+) 321.2.

Step 5: 5-(difluoromethyl)-4-(4-methylpiperazin-1-yl)pyridin-3-amine

A solution of 1-[3-(difluoromethyl)-5-(2,5-dimethylpyrrol-1-yl)-4-pyridyl]-4-methyl-piperazine (80 mg, 0.2497 mmol) and NH₂OH (165.0 mg, 4.994 mmol) in a mixture of triethylamine (101.1 mg, 139.3 µL, 0.9988 mmol), ethanol (1 mL) and H₂O (0.25 mL) was heated at reflux for 20 h.

After cooling to RT the reaction was quenched by loading directly onto an SCX-2 cartridge and eluted with MeOH followed by NH₃/MeOH. The basic fraction was concentrated in vacuo yielding 5-(difluoromethyl)-4-(4-methylpiperazin-1-yl)pyridin-3-amine that was used in next step without further purification. MS (ES+) 243.1.

Preparation N-20: (S)-5-fluoro-4-(4-(tetrahydrofuran-3-yl)piperazin-1-yl)pyridin-3-amine

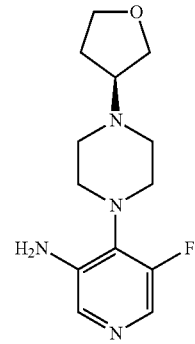

Step 1: (S)-1-(3-chloro-5-fluoropyridin-4-yl)-4-(tetrahydrofuran-3-yl)piperazine MsCl (393.3 mg, 265.7 µL, 3.433 mmol) was added to a solution of (3R)-tetrahydrofuran-3-ol (275 mg, 3.121 mmol) and Et₃N (379.0 mg, 522.0 µL, 3.745 mmol) in DCM (5 mL) at 0° C. and the resulting solution stirred at RT overnight. The reaction mixture was diluted with water (5 mL) and DCM (5 mL) and the layers separated. The aqueous layer was extracted further with DCM (2×5 mL) and the combined organic extracts washed with saturated aqueous sodium hydrogen carbonate solution (1×5 mL), dried over MgSO₄ and concentrated in vacuo. The residue was taken up in n-BuOH (5 mL) and 1-(3-chloro-5-fluoro-4-pyridyl)piperazine (1.010 g, 4.682 mmol) was added and the reaction mixture heated at 118° C. overnight. The reaction mixture was cooled to RT and concentrated in vacuo. The residue was purified by column chromatography on silica (24 g column, 0-100% EtOAc/petroleum ether). Product fractions were combined and concentrated in vacuo to leave (S)-1-(3-chloro-5-fluoropyridin-4-yl)-4-(tetrahydrofuran-3-yl)piperazine as an off white solid. MS (ES+) 288.1.

Step 2: (S)-5-fluoro-4-(4-(tetrahydrofuran-3-yl)piperazin-1-yl)pyridin-3-amine

BrettPhos pre-catalyst (4.183 mg, 0.005250 mmol) and BrettPhos (2.818 mg, 0.005250 mmol) were added to a solution of tert-butyl carbamate (153.7 mg, 1.312 mmol), sodium tert-butoxide (128.7 mg, 1.339 mmol) and 1-(3-chloro-5-fluoro-4-pyridyl)-4-[(3S)-tetrahydrofuran-3-yl]piperazine (75 mg, 0.2625 mmol) in toluene (1.500 mL) and the resulting mixture sealed (reaction in a microwave tube) and placed into a preheated drysyn block at 100° C. and heated for 6 h. Additional BrettPhos pre-catalyst (4.183 mg, 0.005250 mmol) and BrettPhos (2.818 mg, 0.005250 mmol) were added and the reaction mixture was resealed and heated at 100° C. overnight. The reaction mixture was cooled to RT and quenched by addition of saturated aqueous NH₄Cl and then filtered through a celite pad washing with ethyl acetate. The filtrate was extracted with ethyl acetate (2×5 mL) and the combined organic extracts were dried over MgSO₄ and concentrated in vacuo to leave a pale yellow oil (102 mg). The residue was taken up in DCM (2 mL) and TFA (299.3 mg, 202.2 µL, 2.625 mmol) was added and the resulting solution stirred at rt for 2 h. The mixture was concentrated in vacuo and passed through an SCX catridge eluting the product with 2M ammonia in methanol. The filtrate was concentrated in vacuo and purified by column chromatography on silica eluting with 0-20% MeOH/DCM, 4 g column. Product fractions were combined and concentrated in vacuo to leave the product as a colourless oil. MS (ES+) 267.2.

Preparation N-21: N2-methyl-4-(4-methylpiperazin-1-yl)pyridine-2,5-diamine

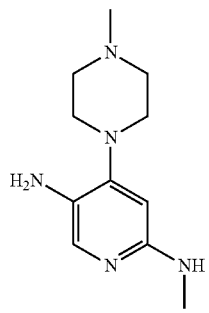 [SMILES: CNc1cc(N2CCN(C)CC2)c(N)cn1]

Step 1: 1-(2-chloro-5-nitropyridin-4-yl)-4-methylpiperazine 1-methylpiperazine (119.3 mg, 132.6 µL, 1.191 mmol) in THF (1.5 mL) was added to a stirred solution of 2,4-dichloro-5-nitro-pyridine (200 mg, 1.036 mmol) and DIPEA (160.6 mg, 216.4 µL, 1.243 mmol) in THF (3.000 mL) at 0° C. under an atmosphere of nitrogen. The reaction was allowed to stir at ambient temperature overnight. The reaction mixture was partitioned between ethyl acetate and NaHCO₃ (sat. aq. soln). The combined organics was washed with brine, dried over MgSO₄ and concentrated under reduced pressure to yield 1-(2-chloro-5-nitro-4-pyridyl)-4-methyl-piperazine. (100%) MS (ES+) 257.1.

Step 2: N-methyl-4-(4-methylpiperazin-1-yl)-5-nitro-pyridin-2-amine 1-(2-chloro-5-nitro-4-pyridyl)-4-methyl-piperazine (265.9 mg, 1.036 mmol) and methylamine 2M in THF (2.590 mL of 2 M, 5.180 mmol) were heated overnight in a sealed tube at 60° C. The mixture was purified by chromatography on silica (Companion 12 g) eluting with 0.5-15% MeOH:DCM, yielding N-methyl-4-(4-methylpiperazin-1-yl)-5-nitro-pyridin-2-amine (243 mg, 93%). MS (ES+) 252.1.

Step: 3: N2-methyl-4-(4-methylpiperazin-1-yl)pyridine-2,5-diamine

N-methyl-4-(4-methylpiperazin-1-yl)-5-nitro-pyridin-2-amine (243 mg, 0.9670 mmol) was dissolved in methanol (10 mL) and Pd on C, wet, Degussa (50 mg, 0.4698 mmol) was added. The reaction was evacuated and filled with hydrogen three times and left to stir at RT overnight. The catalyst was filtered off and the solvent was removed under reduced pressure to yield N2-methyl-4-(4-methylpiperazin-1-yl)pyridine-2,5-diamine (173 mg, 81%). MS (ES+) 222.1.

Preparation N-22: 5-fluoro-4-(4-((4-methylpiperazin-1-yl)sulfonyl)piperidin-1-yl)pyridin-3-amine

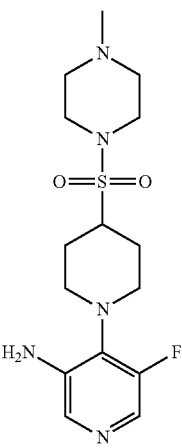 [SMILES: CN1CCN(S(=O)(=O)C2CCN(c3c(N)cncc3F)CC2)CC1]

Step 1: 1-(3-chloro-5-fluoropyridin-4-yl)piperidin-4-ol

To a solution of 3-chloro-5-fluoro-4-iodo-pyridine (1 g, 3.885 mmol) in NMP (1 mL) was added DIPEA (753.1 mg, 1.015 mL, 5.828 mmol) and piperidin-4-ol (589.4 mg, 5.828 mmol) and the mixture heated to 120° C. for 4 hours. The mixture was diluted with ethyl acetate (30 ml), washed twice with water (20 ml) and with brine. The organic layer was dried with MgSO₄ and concentrated in vacuo to a yellow solid that was purified by column chromatography using DCM and then 2% MeOH/DCM as eluent, yielding 1-(3-chloro-5-fluoro-4-pyridyl)piperidin-4-ol. MS (ES+) 231.0.

Step 2: S-(1-(3-chloro-5-fluoropyridin-4-yl)piperidin-4-yl) ethanethioate isopropyl (NE)-N-isopropoxycarbonyliminocarbamate (723.1 mg, 3.576 mmol) was added dropwise to a solution of 1-(3-chloro-5-fluoro-4-pyridyl)piperidin-4-ol (750 mg, 3.251 mmol) and Triphenylphosphine (937.9 mg, 828.5 µL, 3.576 mmol) in THF at −20° C. After stirring for 15 mins, ethanethioic S-acid (272.2 mg, 255.6 µL, 3.576 mmol) was added, the mixture was allowed to warm to room temperature and was stirred for a further 30 minutes. The mixture was then diluted with ethylacetate (30 ml), washed twice with water (20 ml) and with brine. The organic layer was dried with MgSO₄ and concentrated in vacuo to a yellow solid that was purified by column chromatography eluting with 5/95 ether/pet ether to elute side products and then 10/90 ether/pet ether. The relevant fractions were combined and concentrated in vacuo to afford S-(1-(3-chloro-5-fluoropyridin-4-yl)piperidin-4-yl) ethanethioate as a green solid. MS (ES+) 289.0.

Step 3: 1-(3-chloro-5-fluoropyridin-4-yl)piperidine-4-sulfonyl chloride

To a mixture of HCl (1.038 mL of 2 M, 2.077 mmol) and MeCN (8 mL) was added NCS (693.4 mg, 5.193 mmol) and the mixture cooled to 10° C. and stirred until most of the NCS (693.4 mg, 5.193 mmol) was dissolved. A solution of S-[1-(3-chloro-5-fluoro-4-pyridyl)-4-piperidyl] ethanethioate (500 mg, 1.731 mmol) in MeCN (8 mL) was added dropwise. The solution was stirred for 30 minutes at 10° C., diluted with ether and washed with dilute brine. The organic layer was dried with MgSO$_4$ and concentrated in vacuo to yield 1-(3-chloro-5-fluoropyridin-4-yl)piperidine-4-sulfonyl chloride as a yellow solid. MS (ES+) 313.0.

Step 4: 1-((1-(3-chloro-5-fluoropyridin-4-yl)piperidin-4-yl)sulfonyl)-4-methylpiperazine To a solution of 1-(3-chloro-5-fluoro-4-pyridyl)piperidine-4-sulfonyl chloride (400 mg, 1.277 mmol) in DCM (5 mL) was added TEA (129.2 mg, 178.0 µL, 1.277 mmol) followed by 1-methylpiperazine (255.8 mg, 2.554 mmol). The mixture was stirred at room temperature for 1 h. The mixture was diluted with ethylacetate (30 ml), washed twice with water (20 ml) and with brine. The organic layer was dried with MgSO$_4$ and concentrated in vacuo to a yellow solid. The product was purified by column chromatography eluting with 5/95 methanol/DCM. The relevant fractions were combined and concentrated in vacuo to afford the 1-((1-(3-chloro-5-fluoropyridin-4-yl)piperidin-4-yl)sulfonyl)-4-methylpiperazine as a green solid. MS (ES+) 377.1.

Step 5: 5-fluoro-4-(4-((4-methylpiperazin-1-yl)sulfonyl)piperidin-1-yl)pyridin-3-amine Tert-butyl carbamate (211.3 mg, 1.804 mmol), sodium tert-butoxide (173.4 mg, 1.804 mmol), BrettPhos Pre-catalyst (143.7 mg, 0.1804 mmol) and BrettPhos (96.83 mg, 0.1804 mmol) were degassed by vacuum/nitrogen cycles (×5). A solution of 1-[[1-(3-chloro-5-fluoro-4-pyridyl)-4-piperidyl]sulfonyl]-4-methyl-piperazine (340 mg, 0.9022 mmol) in dry toluene (9.884 mL) was added and the resulting mixture was heated to 80° C. After 5 minutes at 80° C. the reaction was cooled to RT and partitioned between ethyl acetate and water. The combined organics was dried with MgSO$_4$ and concentrated in vacuo to a yellow solid. The yellow solid was purified by column chromatography using 1% MeOH/DCM to elute side products and then 5-10% MeOH/DCM to elute product. Relevant fractions combined and concentrated in vacuo to yield a light yellow solid. It was dissolved in DCM (10 mL) followed by the addition of TFA (1.029 g, 695.3 µL, 9.022 mmol). The mixture was stirred at room temperature for 2 hours. The mixture was concentrated in vacuo to yield 5-fluoro-4-(4-((4-methylpiperazin-1-yl)sulfonyl)piperidin-1-yl)pyridin-3-amine as a light orange solid. MS (ES+) 358.1.

The following amines were prepared according to methods similar to the one depicted in Procedure N-22

4-(4-(azetidin-1-ylsulfonyl)piperidin-1-yl)-5-fluoropyridin-3-amine:

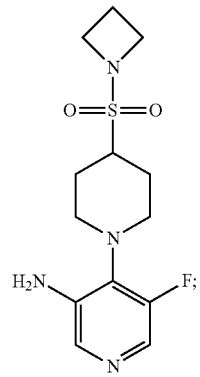

4-(4-(morpholinosulfonyl)piperidin-1-yl)pyridin-3-amine:

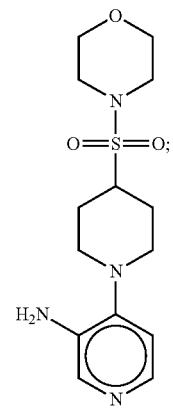

4-(4-(azetidin-1-ylsulfonyl)piperidin-1-yl)pyridin-3-amine:

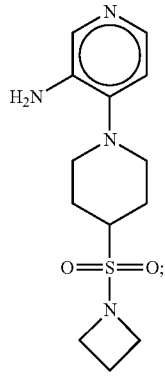

-continued 4-(4-(1,4-diazabicyclo[3.2.2]nonan-4-ylsulfonyl)piperidin-1-yl)-5-fluoropyridin-3-amine:

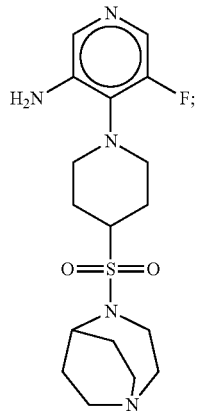

4-(4-(1,4-diazabicyclo[3.2.2]nonan-4-ylsulfonyl)piperidin-1-yl)-5-fluoropyridin-3-amine:

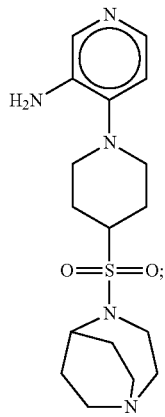

4-(4-(oxetan-3-ylsulfonyl)piperidin-1-yl)pyridin-3-amine:

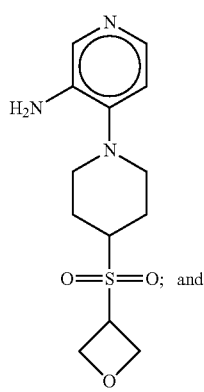

and

-continued 4-(4-((2-methoxyethyl)sulfonyl)piperidin-1-yl)pyridin-3-amine:

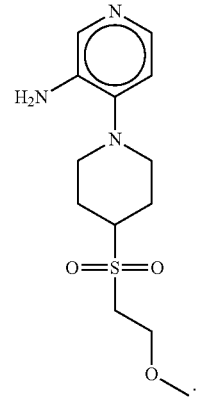

Preparation N-23: 1-((1-(3-amino-5-fluoropyridin-4-yl)piperidin-4-yl)methyl)-4-methylpiperazin-2-one

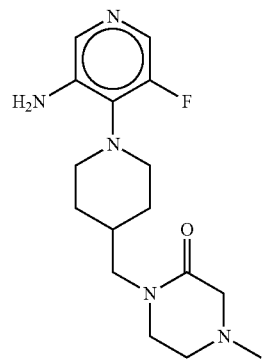

Step 1: tert-butyl 4-(((methylsulfonyl)oxy)methyl)piperidine-1-carboxylate

Methanesulfonyl chloride (186.3 mg, 125.9 µL, 1.626 mmol) was added dropwise to a stirred solution of tert-butyl 4-(hydroxymethyl)piperidine-1-carboxylate (350 mg, 1.626 mmol) and DIPEA (222.8 mg, 300.3 µL, 1.724 mmol) in DCM (5 mL) at 0° C. The reaction mixture was allowed to warm to ambient temperature over 16 hours then treated with water. The phases were separated and the aqueous phase extracted with DCM (×3). The combined organic extracts were dried (MgSO$_4$), filtered and concentrated in vacuo to give the sub-title compound as a white solid (505 mg, >100% Yield) that was used directly assuming 100% yield and purity. MS (ES+-t-Bu) 238.0.

Step 2: tert-butyl 4-((4-methyl-2-oxopiperazin-1-yl)methyl)piperidine-1-carboxylate A 60% dispersion of sodium hydride (84.55 mg, 2.114 mmol) was added to a stirred solution of 4-methylpiperazin-2-one (241.3 mg, 2.114 mmol) in DMF (10 mL) and the reaction stirred at ambient temperature for 30 minutes. Tert-butyl 4-(methylsulfonyloxymethyl)piperidine-1-carboxylate (477 mg, 1.626 mmol) in DMF (5 mL) was added dropwise and the reaction stirred at ambient temperature for a further 92 hours then at 50° C. for a further 20 hours. The reaction was cooled to ambient temperature, quenched by the addition of water and the mixture extracted with EtOAc (×3). The combined organic extracts were washed with brine (×3), dried (MgSO$_4$), filtered and concentrated in vacuo. The residue was purified by column chromatography (ISCO Companion, 40 g column, eluting with 0 to 10% MeOH/DCM, loaded in DCM) to give tert-butyl 4-((4-methyl-2-oxopiperazin-1-yl)methyl)piperidine-1-carboxylate product as a colourless oil (99 mg, 20% Yield). MS (ES+) 312.2.

Step 3:
4-methyl-1-(piperidin-4-ylmethyl)piperazin-2-one

TFA (1 mL, 12.98 mmol) was added to a stirred solution of tert-butyl 4-[(4-methyl-2-oxo-piperazin-1-yl)methyl]piperidine-1-carboxylate (98 mg, 0.3147 mmol) in DCM (2 mL) and the reaction stirred at ambient temperature for 16 hours. The solvent was removed in vacuo and the residue azeotroped with DCM (×2) and ether (×2). The residue was passed through a 5 g SCX-2 cartridge and washed with MeOH/DCM mixtures. The product was eluted by washing the cartridge with 2M NH$_3$ in MeOH/DCM mixtures. The solvent was removed in vacuo to give 4-methyl-1-(piperidin-4-ylmethyl)piperazin-2-one as a colourless oil (65 mg, 98% Yield). MS (ES+) 212.0.

Step 4: tert-butyl 4-(((methylsulfonyl)oxy)methyl)piperidine-1-carboxylate

Preparation N-13 was followed. MS (ES+) 322.1.

Preparation N-24: 4-(4-((3,3-difluoropyrrolidin-1-yl)methyl)piperidin-1-yl)pyridin-3-amine

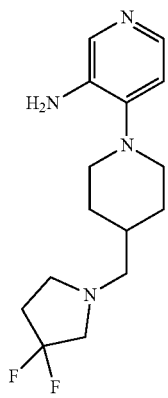

Step 1: tert-butyl 4-((3,3-difluoropyrrolidin-1-yl)methyl)piperidine-1-carboxylate A mixture of 3,3-difluoropyrrolidine (Hydrochloric Acid (1)) (965 mg, 6.722 mmol), tert-butyl 4-formylpiperidine-1-carboxylate (1.720 g, 8.066 mmol), DIPEA (955.6 mg, 1.288 mL, 7.394 mmol) and crushed 4A MS (965 mg) in DCE (30 mL) were stirred at ambient temperature for 3 hours. NaBH(OAc)$_3$ (Sodium Ion (1)) (2.848 g, 13.44 mmol) was added and the reaction stirred at ambient temperature for a further 16 hours. The mixture was filter through Celite (washing with DCM) and the filtrate concentrated in vacuo. The residue was purified by column chromatography (ISCO Companion, 80 g column, eluting with 0 to 10% MeOH/DCM, loaded in DCM) to give tert-butyl 4-((3,3-difluoropyrrolidin-1-yl)methyl)piperidine-1-carboxylate as a colourless oil that was deprotected directly assuming 100% yield and purity. MS (ES+) 305.1.

Step 2:
4-((3,3-difluoropyrrolidin-1-yl)methyl)piperidine

TFA (766.5 mg, 517.9 µL, 6.722 mmol) was added to a stirred solution of tert-butyl 4-[(3,3-difluoropyrrolidin-1-yl)methyl]piperidine-1-carboxylate (2.046 g, 6.722 mmol) in DCM (15 mL) and the reaction stirred at ambient temperature for 66 hours. The solvent was removed in vacuo and the residue azeotroped with DCM (×2) and ether (×2). The residue was passed through a 50 g SCX-2 cartridge and washed with MeOH/DCM mixtures. The product was eluted by washing the cartridge with 2M NH$_3$ in MeOH/DCM mixtures. The solvent was removed in vacuo to give 4-((3,3-difluoropyrrolidin-1-yl)methyl)piperidine as a pale yellow solid (1.15 g, 84% Yield over 2 steps). MS (ES+) 205.1.

Step 3: 4-(4-((3,3-difluoropyrrolidin-1-yl)methyl)piperidin-1-yl)pyridin-3-amine Preparation N-1 was followed. MS (ES+) 297.2.

Preparation N-25: 4-(4-methyl-4-(methylsulfonyl)piperidin-1-yl)pyridin-3-amine

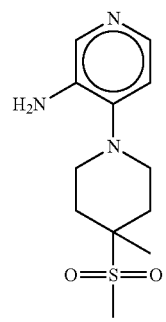

Step 1: tert-butyl 1-thia-6-azaspiro[2.5]octane-6-carboxylate

To a mixture of tert-butyl 1-oxa-8-azaspiro[2.5]octane-8-carboxylate (1 g, 4.689 mmol) and thiourea (356.9 mg, 4.689 mmol) was added water and the mixture stirred at room temperature for 72 h. the reaction mixture was partitioned between DCM and water, the organic extract was washed with brine, dried (MgSO$_4$) and concentrated to give 1-thia-6-azaspiro[2.5]octane-6-carboxylate as a pale yellow oil which solidified upon standing. (910 mg, 84%). MS (ES+-t-Bu) 173.9.

Step 2: tert-butyl 4-mercapto-4-methylpiperidine-1-carboxylate

To a solution of tert-butyl 1-thia-6-azaspiro[2.5]octane-6-carboxylate (430 mg, 1.875 mmol) in THF (5 mL) was added LiAlH₄ (Lithium Ion (1)) (0.9375 mL of 2 M, 1.875 mmol) and the solution was stirred at room temperature for 1 h. The reaction was quenched by careful dropwise addition of water (2 ml), stirred for 10 mins before the reaction mixture was partitioned between water and EtOAc. The organic extract was washed with brine, dried (MgSO₄) and concentrated to give tert-butyl 4-methyl-4-sulfanyl-piperidine-1-carboxylate as a colorless oil. (380 mg, 87%). MS (ES-) 231.0.

Step 3: tert-butyl 4-methyl-4-(methylthio)piperidine-1-carboxylate

To a solution of tert-butyl 4-methyl-4-sulfanyl-piperidine-1-carboxylate (380 mg, 1.642 mmol) in THF (5 mL) cooled to −78° C. was added LiHMDS (1.724 mL of 1 M, 1.724 mmol) and the solution stirred for 10 mins before MeI (256.3 mg, 0.1124 mL, 1.806 mmol) was added and the solution allowed to warm to 0° C. over approximately 1 h. The reaction was then quenched carefully by the addition of saturated ammonium chloride and extracted into EtOAc. The aqueous was further extracted with EtOAc and the combined organics were washed with brine, dried (MgSO₄) and concentrated to give a yellow oil (390 mg, 96%).

Step 4: tert-butyl 4-methyl-4-(methylsulfonyl)piperidine-1-carboxylate

A solution of tert-butyl 4-methyl-4-methylsulfanyl-piperidine-1-carboxylate (380 mg, 1.549 mmol) in DCM (15 mL) was cooled to 0° C. and 3-Chloroperoxybenzoic acid (867.8 mg, 3.872 mmol) was added portionwise over approx 10 mins. The solution was stirred for 30 mins and then allowed to warm to room temperature and stirred for a further 1 h. The reaction was quenched with saturated sodium hydrogen carbonate (4 ml) and saturated sodium thiosulphate (4 ml) and stirred vigorously for 5 mins. The DCM layer was removed and the aqueous further extracted with DCM. The combined organic layers were washed with saturated sodium carbonate and brine, dried (MgSO₄) and concentrated to give tert-butyl 4-methyl-4-(methylsulfonyl)piperidine-1-carboxylate as a sticky oil which solidified upon standing (450 mg, 100%).

Step 5: 4-methyl-4-(methylsulfonyl)piperidine

To a solution of tert-butyl 4-methyl-4-methylsulfonyl-piperidine-1-carboxylate (430 mg, 1.550 mmol) in DCM (10 mL) was added TFA (3 mL, 38.94 mmol) and the solution stirred at room temperature for 1 h. The reaction was concentrated and azeotroped twice with DCM to give 4-methyl-4-(methylsulfonyl)piperidine as a sticky oil that was used in next step without further purification. MS (ES+) 178.0.

Step 6: 4-(4-methyl-4-(methylsulfonyl)piperidin-1-yl)pyridin-3-amine

Preparation N-1 was followed. MS (ES+) 270.1

Preparation N-26: 8-(3-aminopyridin-4-yl)-2-isopropyloctahydro-1H-pyrazino[1,2-a]pyrazin-1-one

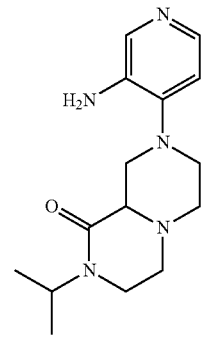 [SMILES: CC(C)N1CCN2CCN(c3ccncc3N)CC2C1=O]

Step 1: 2-isopropyl-8-(3-nitropyridin-4-yl)octahydro-1H-pyrazino[1,2-a]pyrazin-1-one NaH (15.87 mg, 0.3967 mmol) then 2-iodopropane (73.56 mg, 43.19 µL, 0.4327 mmol) were added to a solution of 2-(3-nitro-4-pyridyl)-3,4,6,7,8,9a-hexahydro-1H-pyrazino[1,2-a]pyrazin-9-one (100 mg, 0.3606 mmol) (prepared according to a procedure similar to Step 1 of Preparation N-1) in THF (5 mL) under N2. The reaction mixture was stirred at reflux for 24 h then it was partitioned between EtOAc and a saturated bicarbonate aqueous solution. Combined organic extract was washed with brine, dried over MgSO₄ and concentrated in vacuo to produce an oil that was used in next step without further purification. MS (ES+) 320.1.

Step 2: 8-(3-aminopyridin-4-yl)-2-isopropyloctahydro-1H-pyrazino[1,2-a]pyrazin-1-one Step 2 of Preparation N-1 was followed. MS (ES+) 290.2

Preparation N-27: (S)-5-(3-aminopyridin-4-yl)hexahydro-2H-isothiazolo[2,3-a]pyrazine 1,1-dioxide

Step 1: (9-ten-butyl 4-(methylsulfonyl)-3-(((methylsulfonyl)oxy)methyl)piperazine-1-carboxylate To a solution of tert-butyl (3S)-3-(hydroxymethyl)piperazine-1-carboxylate (2.5 g, 11.56 mmol) in DCM (16.25 mL) at 0° C. under a nitrogen atmosphere was added TEA (1.872 g, 2.579 mL, 18.50 mmol) and then dropwise MsCl (2.913 g, 1.968 mL, 25.43 mmol). The reaction was allowed to warm to ambient temperature and stirred thereat for 18 hours. The suspension was partitioned between DCM (2×50 mL) and water (50 mL). The combined organics were washed with brine (50 mL), dried (Na₂SO₄) and concentrated in vacuo to afford a pale honey-coloured oil (4.9 g). The residue was purified by column chromatography on ISCO Companion (ELSD) eluting with DCM (A): Methanol (B) (0-10% (B), 80 g, 16.0 CV, 60 mL/min) to afford a mixture of products (2.3 g). This oily residue was purified again by column chromatography on ISCO Companion (ELSD) eluting with DCM (A): Ethyl Acetate (B) (0-50% (B), 40 g, 25.0 CV, 40 mL/min) to afford (5)-tert-butyl 4-(methylsulfonyl)-3-(((methylsulfonyl)oxy)methyl)piperazine-1-carboxylate as a colourless oil (1.58 g, 37%). MS (ES+) 317.0.

Step 2: (9-ten-butyl tetrahydro-2H-isothiazolo[2,3-a]pyrazine-5(3H)-carboxylate 1,1-dioxide To a solution of tert-butyl (3S)-4-methylsulfonyl-3-(methylsulfonyloxymethyl)piperazine-1-carboxylate (500 mg, 1.342 mmol) in anhydrous THF (10 mL) at −78° C. was added dropwise LiHMDS (1 M in THF) (1.476 mL of 1.0 M, 1.476 mmol). The reaction mixture was stirred and allowed to slowly reach ambient temperature over 90 mins and stirred thereat for 18 hours. The reaction was cooled again to −78° C. and thereto was added dropwise LiHMDS (1 M in THF) (1.476 mL of 1.0 M, 1.476 mmol). The reaction mixture was stirred and allowed to slowly reach ambient temperature over 90 mins and stirred thereat for a further 2 hours. The reaction was quenched with water (5 mL) and partitioned between the aqueous and ethyl acetate (3×50 mL). The combined organics were dried ($Na_2SO_4$) and concentrated in vacuo to afford an orange oil (490 mg). The residue was purified by column chromatography on ISCO Companion (ELSD) eluting with petroleum ether (A): ethyl acetate (B) (0-40% (B), 12 g, 21.0 min, 30 mL/min) to afford (S)-tert-butyl tetrahydro-2H-isothiazolo[2,3-a]pyrazine-5 (3H)-carboxylate 1,1-dioxide as a pale cream solid (361 mg, 97%). MS (ES+-t-Bu) 221.0

Step 3: (S)-hexahydro-2H-isothiazolo[2,3-a]pyrazine 1,1-dioxide

To a solution of tert-butyl (3aS)-1,1-dioxo-2,3,3a,4,6,7-hexahydroisothiazolo[2,3-a]pyrazine-5-carboxylate (360 mg, 1.303 mmol) in DCM (5 mL) at 0° C. was added TFA (1.25 mL, 16.22 mmol) dropwise and the reaction was stirred and warmed slowly to ambient temperature over 45 mins. The reaction mixture was concentrated in vacuo and the residue was adsorbed onto a pre-wetted (methanol/DCM (1:1), 10 mL) SCX-2 cartridge (10 g) and flushed with DCM/methanol (1:1, 50 mL) and then the basic components eluted with 2 M ammonia in methanol (50 mL). The basic eluent was evaporated to dryness to afford (5)-hexahydro-2H-isothiazolo[2,3-a]pyrazine 1,1-dioxide as a colourless oil (192 mg, 84%).

Step 4: (S)-5-(3-aminopyridin-4-yl)hexahydro-2H-isothiazolo[2,3-c]pyrazine 1,1-dioxide Preparation N-1 was followed. MS (ES+) 269.1

Preparation N-28: 4-(3-methyl-4H-1,2,4-triazol-4-yl)pyridin-3-amine

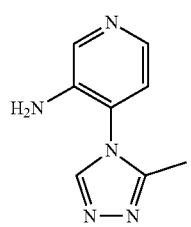

Step 1: 3-bromo-4-isothiocyanatopyridine 3-bromopyridin-4-amine (5 g, 28.90 mmol) was suspended in dry toluene (100 mL) and cooled in an ice-bath. A solution of thiophosgene (6.646 g, 4.407 mL, 57.80 mmol) in dry toluene (100 mL) was added dropwise over 25 mins. The resulting orange/red suspension was stirred at reflux overnight. The red suspension was allowed to cool to RT and concentrated under reduced pressure to give a dark brown/red solid. This material was partitioned between saturated $NaHCO_3$ and DCM. The aqueous layer was extracted with further DCM (3×50 mL) and the combined organics were dried over $Na_2SO_4$, filtered and concentrated under reduced pressure to give a dark red solid/gum. This material was suspended in MeOH/DCM, adsorbed onto silica under reduced pressure and purified by column chromatography (75% EtOAc in hexanes, ~300 mL silica) to give 3-bromo-4-isothiocyanatopyridine as a red oil which solidified on standing (3.513 g, 57% Yield). MS (ES+) 216.9.

Step 2: 2-acetyl-N-(3-bromopyridin-4-yl)hydrazinecarbothioamide 3-bromo-4-isothiocyanato-pyridine (1 g, 4.650 mmol) and acetylhydrazine (344.5 mg, 4.650 mmol) were dissolved in dry 1,4-dioxane (10 mL) and stirred at 80° C. for 0.75 hrs. The orange suspension was allowed to cool to RT. The viscous suspension was diluted with ether and the solid was collected by fitration and washed with ether (3×5 mL) to give 2-acetyl-N-(3-bromopyridin-4-yl)hydrazinecarbothioamide as a salmon-pink solid (1.2187 g, 91% Yield). MS (ES−) 288.9.

Step 3: 4-(3-bromopyridin-4-yl)-5-methyl-4H-1,2,4-triazole-3-thiol 2-acetyl-N-(3-bromopyridin-4-yl)hydrazinecarbothioamide (200 mg, 0.6917 mmol) was dissolved in sodium hydrogen carbonate (4 mL) and stirred at 50° C. for 2 hrs and at 100° C. for 5 hrs. The reaction mixture was then allowed to stand at RT for 48 h before it was carefully neutralised with dilute HCl and partitioned with 10% MeOH in DCM. The aqueous layer was extracted with further 10% MeOH in DCM (3×10 mL) and the combined organics were dried over $Na_2SO_4$, filtered and concentrated under reduced pressure to give 4-(3-bromopyridin-4-yl)-5-methyl-4H-1,2,4-triazole-3-thiol as an orange solid (152.6 mg). MS (ES+) 272.9.

Step 4: 3-bromo-4-(3-methyl-4H-1,2,4-triazol-4-yl)pyridine 4-(3-bromo-4-pyridyl)-5-methyl-1,2,4-triazole-3-thiol (145 mg, 0.5348 mmol) was suspended in dry DCM (4 mL) and cooled in an ice-bath. A solution of hydrogen peroxide (133.5 μL of 30% w/v, 1.177 mmol) in AcOH (1.5 mL) was added slowly dropwise and the resulting mixture was stirred at RT for 2 hrs. The reaction mixture was cooled with an ice bath and quenched by slow addition of 2M NaOH and partitioned with DCM. The aqueous layer was extracted with further DCM (3×10 mL) and the combined organics were dried over $Na_2SO_4$, filtered and concentrated under reduced pressure to give a yellow gum/solid (112.5 mg). This material was redissolved in MeOH/DCM, adsorbed onto silica under reduced pressure and purified by column chromatography (7.5% MeOH in DCM, ~75 mL silica) to give 3-bromo-4-(3-methyl-4H-1,2,4-triazol-4-yl)pyridine as a cream solid (82.3 mg, 64% Yield). MS (ES+) 240.9.

Step 5: 4-(3-methyl-4H-1,2,4-triazol-4-yl)pyridin-3-amine

Procedure similar to Step 3a of Preparation N-14 was used.

Preparation N-29: 5-methyl-4-(5-methyl-1H-pyrazol-1-yl)pyridin-3-amine

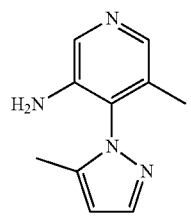

Step 1: 3-bromo-4-hydrazinyl-5-nitropyridine

A solution of 3-bromo-4-chloro-5-nitro-pyridine (500 mg, 2.106 mmol), hydrazine hydrate (158.1 mg, 153.6 µL, 3.159 mmol) in ethanol (5.000 mL) was stirred at RT for 1 h. The bright yellow precipitate was filtered, washed with methanol and dried under vacuum to leave 3-bromo-4-hydrazinyl-5-nitropyridine (390 mg, 79.5%). MS (ES−) 232.8.

Step 2: 3-bromo-4-(5-methyl-1H-pyrazol-1-yl)-5-nitropyridine 2-(2-methyl-1,3-dioxolan-2-yl)acetaldehyde (320 mg, 2.459 mmol) and (3-bromo-5-nitro-4-pyridyl)hydrazine (286.4 mg, 1.229 mmol) were heated under reflux in ethanol (2.864 mL) overnight. The reaction mixture was concentrated in vacuo and the residue was partitioned between DCM and a saturated aqueous sodium hydrogen carbonate solution. Combined organic extract was dried over $MgSO_4$ and concentrated in vacuo to leave 3-bromo-4-(5-methyl-1H-pyrazol-1-yl)-5-nitropyridine as a yellow oil. (200 mg, 85%). MS (ES+) 284.9.

Step 3: 3-methyl-4-(5-methyl-1H-pyrazol-1-yl)-5-nitropyridine

To an oven dried flask under nitrogen was added 3-bromo-4-(5-methylpyrazol-1-yl)-5-nitro-pyridine (200 mg, 0.6005 mmol), $Pd_2dba_3$ (8.249 mg, 0.009008 mmol) and X-Phos (8.590 mg, 0.01802 mmol). Anhydrous THF (1.700 mL) was added, followed by 1,4-diazabicyclo[2.2.2]octane; trimethylalumane (153 mg, 0.6005 mmol). The reaction was heated at reflux for 2 hours then cooled to ambient temperature before it was quenched by the addition of water. The mixture was extracted with EtOAc (×3) and the combined organic extract was washed with brine, dried ($MgSO_4$) and concentrated in vacuo to leave a 3/1 mixture of 3-methyl-4-(5-methyl-1H-pyrazol-1-yl)-5-nitropyridine and 4-(5-methyl-1H-pyrazol-1-yl)-3-nitropyridine, that was used in the next step without further purification. (140 mg of product isolated as a mixture). MS (ES+) 219.0.

Step 4: 5-methyl-4-(5-methyl-1H-pyrazol-1-yl)pyridin-3-amine

Reduction was run according to Step 2 of Preparation N-1. MS (ES+) 189.0.

Preparation N-30: 5-fluoro-4-(5-methyl-1H-1,2,4-triazol-1-yl)pyridin-3-amine

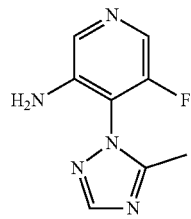

Step 1: 3-bromo-5-fluoro-4-hydrazinylpyridine 3-bromo-4-chloro-5-fluoro-pyridine (500 mg, 2.376 mmol), hydrazine (761.4 mg, 745.7 µL, 23.76 mmol), $Na_2CO_3$ (503.7 mg, 4.752 mmol) in cyclohexanol was heated at 100 C overnight. The reaction mixture was filtered on celite and loaded on a SCX column, washed with DCM/MeOH mixtures and was eluted with a 2M solution of $NH_3$ in MeOH. The filtrate was concentrated in vacuo and the 3/1 mixture of 3-bromo-5-fluoro-4-hydrazinylpyridine and 3-bromo-4-chloro-5-hydrazinylpyridine was used in next step without further purification. MS (ES+) 205.9.

Step 2: 3-bromo-5-fluoro-4-(5-methyl-1H-1,2,4-triazol-1-yl)pyridine

Acetamide (136.7 mg, 2.315 mmol), 1,1-dimethoxy-N,N-dimethyl-methanamine (382.0 mg, 425.9 µL, 3.206 mmol), in dioxane was heated at 45-50° C. under 150 mm Hg vacuum for 2 h. The reaction mixture was concentrated in vacuo. To the residue, (3-bromo-5-fluoro-4-pyridyl)hydrazine (367 mg, 1.781 mmol) and dioxane-acetic acid (1/1) was added and the mixture was heated at 130° C. for 1 h then at 160° C. for 2 h. At RT, the residue was loaded on a SCX column, washed with MeOH/DCM mixture. The filtrate is concentrated in vacuo yielding pure 3-bromo-5-fluoro-4-(5-methyl-1H-1,2,4-triazol-1-yl)pyridine as a dark oil. MS (ES+) 257.0.

Step 3: 5-fluoro-4-(5-methyl-1H-1,2,4-triazol-1-yl)pyridin-3-amine

Amination reaction was run according to a procedure similar as Step 3 of Preparation N-14. MS (ES+) 194.0.

Preparation N-31: tert-butyl piperidine-4-carboxylate

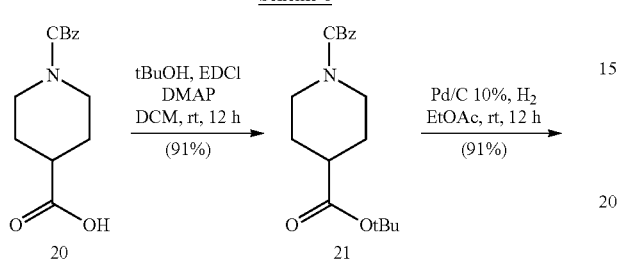

Scheme 8

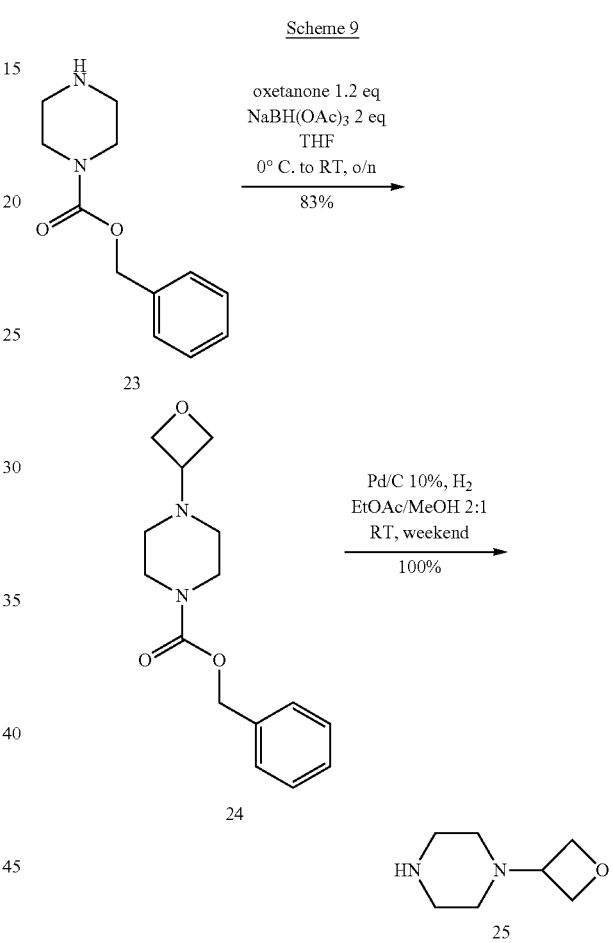

Scheme 9

Step 1: O1-benzyl O4-tert-butyl piperidine-1,4-dicarboxylate 21

In a 5 L flange flask was charged 1-benzyloxycarbonylpiperidine-4-carboxylic acid 20 (200 g, 759.6 mmol) in DCM (500.0 mL) followed by additional DCM (2.000 L), t-butanol (140.8 g, 181.7 mL, 1.899 mol) and DMAP (46.40 g, 379.8 mmol). The mixture was cooled on ice/salt/water bath (internal −3.4° C.). 3-(ethyliminomethyleneamino)-N,N-dimethyl-propan-1-amine (Hydrochloric Acid (1)) (145.6 g, 759.6 mmol) was added portionwise over 15 mins, with addition funnel rinsed with DCM (500.0 mL). Mixture was stirred on ice bath for approx. 2 h. Ice bath was then removed (internal 3° C.) and allowed to warm to room temperature overnight. Mixture was washed with 5% citric acid (2×500 mL), then saturated NaHCO₃ (500 mL), water (500 mL), and organics dried over MgSO₄, which was then filtered and concentrated in vacuo to leave product 21 as a viscous light yellow oil which turned to a white solid on standing. (246.1 g, 101%). $^1$H NMR (500 MHz, DMSO-d6) δ 7.40-7.31 (m, 5H), 5.08 (s, 2H), 3.90 (dt, 2H), 2.93 (br s, 2H), 2.43 (tt, 1H), 1.80-1.76 (m, 2H) and 1.45-1.37 (m, 11H).

Step 2: tert-butyl piperidine-4-carboxylate 22

To a 3 L florentine under nitrogen was charged Pd on C, wet, Degussa (10% Pd, 50% WATER) (8.120 g, 76.30 mmol) then EtOAc (1.706 L). The mixture was degassed via N2/vacuum cycles (3×), then a solution of O1-benzyl O4-tert-butyl piperidine-1,4-dicarboxylate 21 (243.7 g, 763.0 mmol) in EtOAc (243.7 mL) was added. Mixture was stirred under a hydrogen atmosphere overnight. Hydrogen was replenished and mixture was stirred for a further 3.5 h. Methanol (60 mL) was added to aid dissolution of precipitate then filtered through celite, washing through with methanol. Filtrate concentrated in vacuo to leave a brown oil with a slight suspension of a white solid, 138.6 g. Solid removed by filtration, and washed with minimal EtOAc. Filtrate was concentrated in vacuo to leave desired product as a light brown oil (129 g, 91%). $^1$H NMR (500 MHz, DMSO-d6) δ 2.88 (dt, 2H), 2.44 (td, 2H), 2.23 (tt, 1H), 1.69-1.64 (m, 2H) and 1.41-1.33 (m, 11H).

Preparation N-32: 1-(oxetan-3-yl)piperazine

Step 1: benzyl 4-(oxetan-3-yl)piperazine-1-carboxylate 24

Benzyl piperazine-1-carboxylate 23 (27.3 mL, 142.2 mmol) was dissolved in dry THF (313.1 mL) and oxetan-3-one (12.29 g, 10.93 mL, 170.6 mmol) was added. The resulting solution was cooled in an ice-bath. NaBH(OAc)₃ (59.99 g, 284.4 mmol) was added portionwise over 30 mins, about a quarter was added. Mixture removed from ice bath, allowed to warm to room temperature then continued adding the NaBH(OAc)₃ portionwise over 30 mins. On complete addition, an exotherm from 22° C. slowly to 32° C. was observed, whereby the mixture was subsequently cooled on an ice bath until an internal of 22° C. was reached. The ice bath was removed and the reaction mixture's internal temp was steady at 22° C. The mixture was stirred at room temperature overnight.

The resulting white suspension was quenched by addition of 2M sodium carbonate solution (approx 150 mL) (pH=8) and concentrated under reduced pressure to remove THF. Product was then extracted with EtOAc (3×250 mL). Organics were combined, dried over MgSO$_4$, filtered and concentrated under reduced pressure to leave product 24 as a white solid (32.7 g 83% yield). $^1$H NMR (500 MHz, DMSO-d6) δ 7.39-7.30 (m, 5H), 5.07 (s, 2H), 4.52 (t, 2H), 4.42 (t, 2H), 3.43-3.39 (m, 5H) and 2.22 (t, 4H). MS (ES+) 276.8.

Step 2: 1-(oxetan-3-yl)piperazine 25

In a 1 L florentine was added Pd(OH)$_2$ (1.661 g, 2.366 mmol) under nitrogen. MeOH (130.8 mL) and EtOAc (261.6 mL) were added and the mixture degassed via vacuum/nitrogen cycles (3×). Benzyl 4-(oxetan-3-yl)piperazine-1-carboxylate 24 (32.7 g, 118.3 mmol) was then added and the mixture stirred under a hydrogen atmosphere over the weekend. Mixture was filtered through a pad of celite, washing through with EtOAc then methanol. Filtrate was concentrated in vacuo to leave product 25 as an orange oil 1 (8.1 g, quantitative yield). $^1$H NMR (500 MHz, DMSO-d6) δ 4.51 (t, 2H), 4.41 (t, 2H), 3.36-3.30 (masked signal, 1H), 2.69 (t, 4H) and 2.14 (br s, 4H).

The following compounds were successfully prepared using a procedure similar to Example 1 or Examples 3a-3e:

2-amino-6-fluoro-N-(4-(4-isopropylpiperazin-1-yl)pyridin-3-yl)pyrazolo[1,5-a]pyrimidine-3-carboxamide (Compound I-N-4);

2-amino-N-(5-cyclopropyl-4-(4-methylpiperazin-1-yl)pyridin-3-yl)-6-fluoropyrazolo[1,5-a]pyrimidine-3-carboxamide (Compound I-N-5);

2-amino-N-(5-chloro-4-(8-methylhexahydro-1H-pyrazino[1,2-a]pyrazin-2(6H)-yl)pyridin-3-yl)-6-fluoropyrazolo[1,5-a]pyrimidine-3-carboxamide (Compound I-N-6);

N-(4-(1H-imidazol-1-yl)pyridin-3-yl)-2-amino-6-fluoropyrazolo[1,5-a]pyrimidine-3-carboxamide (Compound I-N-7);

2-amino-6-fluoro-N-(4-(4-(2-(methylamino)ethyl)-1H-pyrazol-1-yl)pyridin-3-yl)pyrazolo[1,5-a]pyrimidine-3-carboxamide (Compound I-N-8);

2-amino-N-(4-(4-(2-(dimethylamino)ethyl)-1H-pyrazol-1-yl)pyridin-3-yl)-6-fluoropyrazolo[1,5-a]pyrimidine-3-carboxamide (Compound I-N-9);

(R)-2-amino-6-fluoro-N-(4-(4-(tetrahydrofuran-3-yl)piperazin-1-yl)pyridin-3-yl)pyrazolo[1,5-a]pyrimidine-3-carboxamide (Compound I-N-10);

2-amino-6-fluoro-N-(4-(4-(tetrahydro-2H-pyran-4-yl)piperazin-1-yl)pyridin-3-yl)pyrazolo[1,5-a]pyrimidine-3-carboxamide (Compound I-N-11);

(S)-2-amino-6-fluoro-N-(4-(4-(tetrahydrofuran-3-yl)piperazin-1-yl)pyridin-3-yl)pyrazolo[1,5-a]pyrimidine-3-carboxamide (Compound I-N-12);

2-amino-6-fluoro-N-(5-fluoro-4-(4-(oxetan-3-yl)piperazin-1-yl)pyridin-3-yl)pyrazolo[1,5-a]pyrimidine-3-carboxamide (Compound I-N-13);

2-amino-6-chloro-N-(5-fluoro-4-(4-methylpiperazin-1-yl)pyridin-3-yl)pyrazolo[1,5-a]pyrimidine-3-carboxamide (Compound I-N-14);

2-amino-6-fluoro-N-(5-fluoro-4-(4-methylpiperazin-1-yl)pyridin-3-yl)pyrazolo[1,5-a]pyrimidine-3-carboxamide (Compound I-N-15);

2-amino-6-fluoro-N-(5-methyl-4-(4-(oxetan-3-yl)piperazin-1-yl)pyridin-3-yl)pyrazolo[1,5-a]pyrimidine-3-carboxamide (Compound I-N-16);

2-amino-N-(4-(4-ethylpiperazin-1-yl)pyridin-3-yl)-6-fluoropyrazolo[1,5-a]pyrimidine-3-carboxamide (Compound I-N-17);

N-(4-(1,4-diazabicyclo[3.2.2]nonan-4-yl)pyridin-3-yl)-2-amino-6-fluoropyrazolo[1,5-a]pyrimidine-3-carboxamide (Compound I-N-18);

(R,S)-2-amino-6-fluoro-N-(4-(4-(tetrahydrofuran-3-yl)piperazin-1-yl)pyridin-3-yl)pyrazolo[1,5-a]pyrimidine-3-carboxamide (Compound I-N-19);

2-amino-6-fluoro-N-(4-(4-(2,2,2-trifluoroethyl)piperazin-1-yl)pyridin-3-yl)pyrazolo[1,5-a]pyrimidine-3-carboxamide (Compound I-N-20);

(S)-2-amino-6-fluoro-N-(4-(hexahydropyrrolo[1,2-a]pyrazin-2(1H)-yl)pyridin-3-yl)pyrazolo[1,5-a]pyrimidine-3-carboxamide (Compound I-N-21);

2-amino-6-fluoro-N-(4-(4-(2-methoxyethyl)piperazin-1-yl)pyridin-3-yl)pyrazolo[1,5-a]pyrimidine-3-carboxamide (Compound I-N-22);

(R)-2-amino-6-fluoro-N-(4-(2-methyl-4-(oxetan-3-yl)piperazin-1-yl)pyridin-3-yl)pyrazolo[1,5-a]pyrimidine-3-carboxamide (Compound I-N-23);

(S)-2-amino-6-fluoro-N-(4-(2-methyl-4-(oxetan-3-yl)piperazin-1-yl)pyridin-3-yl)pyrazolo[1,5-a]pyrimidine-3-carboxamide (Compound I-N-24);

2-amino-6-chloro-N-(4-(4-(3-methyloxetan-3-yl)piperazin-1-yl)pyridin-3-yl)pyrazolo[1,5-a]pyrimidine-3-carboxamide (Compound I-N-25);

N-(4-(1H-pyrazol-1-yl)pyridin-3-yl)-2-amino-6-fluoropyrazolo[1,5-a]pyrimidine-3-carboxamide (Compound I-N-26);

2-amino-6-fluoro-N-(4-(4-(trifluoromethyl)-1H-imidazol-1-yl)pyridin-3-yl)pyrazolo[1,5-a]pyrimidine-3-carboxamide (Compound I-N-27);

2-amino-6-fluoro-N-(4-(2-methyl-1H-imidazol-1-yl)pyridin-3-yl)pyrazolo[1,5-a]pyrimidine-3-carboxamide (Compound I-N-28);

N-(4-(1H-imidazol-1-yl)pyridin-3-yl)-2-amino-6-chloropyrazolo[1,5-a]pyrimidine-3-carboxamide (Compound I-N-29);

2-amino-6-fluoro-N-(4-(2-methyl-4-(trifluoromethyl)-1H-imidazol-1-yl)pyridin-3-yl)pyrazolo[1,5-a]pyrimidine-3-carboxamide (Compound I-N-30);

2-amino-6-fluoro-N-(4-(5-(oxetan-3-yl)-2,5-diazabicyclo[4.1.0]heptan-2-yl)pyridin-3-yl)pyrazolo[1,5-a]pyrimidine-3-carboxamide (Compound I-N-31);

2-amino-N-(5-cyclopropyl-4-(4-(oxetan-3-yl)piperazin-1-yl)pyridin-3-yl)-6-fluoropyrazolo[1,5-a]pyrimidine-3-carboxamide (Compound I-N-32);

2-amino-N-(4-(4-cyclopropylpiperazin-1-yl)pyridin-3-yl)-6-fluoropyrazolo[1,5-a]pyrimidine-3-carboxamide (Compound I-N-33);

2-amino-N-(4-(4-(tert-butyl)piperazin-1-yl)pyridin-3-yl)-6-chloropyrazolo[1,5-a]pyrimidine-3-carboxamide (Compound I-N-34);

2-amino-6-chloro-N-(4-((3S,4S)-4-(dimethylamino)-3-hydroxypiperidin-1-yl)pyridin-3-yl)pyrazolo[1,5-a]pyrimidine-3-carboxamide (Compound I-N-35);

2-amino-6-chloro-N-(4-(4-((dimethylamino)methyl)-4-hydroxypiperidin-1-yl)pyridin-3-yl)pyrazolo[1,5-a]pyrimidine-3-carboxamide (Compound I-N-36);

2-amino-6-chloro-N-(4-(4-(dimethylamino)piperidin-1-yl)pyridin-3-yl)pyrazolo[1,5-a]pyrimidine-3-carboxamide (Compound I-N-37);

2-amino-6-chloro-N-(4-(4-isopropylpiperazin-1-yl)pyridin-3-yl)pyrazolo[1,5-a]pyrimidine-3-carboxamide (Compound I-N-39);

2-amino-6-chloro-N-(4-(3-(dimethylamino)piperidin-1-yl)pyridin-3-yl)pyrazolo[1,5-a]pyrimidine-3-carboxamide (Compound I-N-40);
2-amino-6-chloro-N-(5-chloro-4-(4-methylpiperazin-1-yl)pyridin-3-yl)pyrazolo[1,5-a]pyrimidine-3-carboxamide (Compound I-N-41);
2-amino-6-chloro-N-(4-(3-hydroxy-8-azabicyclo[3.2.1]octan-8-yl)pyridin-3-yl)pyrazolo[1,5-a]pyrimidine-3-carboxamide (Compound I-N-42);
2-amino-6-chloro-N-(4-(4-methyl-1,4-diazepan-1-yl)pyridin-3-yl)pyrazolo[1,5-a]pyrimidine-3-carboxamide (Compound I-N-43);
2-amino-6-chloro-N-(4-(5,6-dihydroimidazo[1,2-a]pyrazin-7(8H)-yl)pyridin-3-yl)pyrazolo[1,5-a]pyrimidine-3-carboxamide (Compound I-N-44);
2-amino-6-chloro-N-(4-(4-((dimethylamino)methyl)piperidin-1-yl)pyridin-3-yl)pyrazolo[1,5-a]pyrimidine-3-carboxamide (Compound I-N-45);
2-amino-6-chloro-N-(4-(4-((dimethylamino)methyl)-4-methoxypiperidin-1-yl)pyridin-3-yl)pyrazolo[1,5-a]pyrimidine-3-carboxamide (Compound I-N-46);
2-amino-6-chloro-N-(4-(3-(methoxymethyl)-4-methylpiperazin-1-yl)pyridin-3-yl)pyrazolo[1,5-a]pyrimidine-3-carboxamide (Compound I-N-47);
2-amino-6-chloro-N-(4-(4-cyclobutylpiperazin-1-yl)pyridin-3-yl)pyrazolo[1,5-a]pyrimidine-3-carboxamide (Compound I-N-48);
2-amino-6-chloro-N-(4-(4-(2-(dimethylamino)ethyl)piperazin-1-yl)pyridin-3-yl)pyrazolo[1,5-a]pyrimidine-3-carboxamide (Compound I-N-49);
2-amino-N-(6-amino-4-(4-methylpiperazin-1-yl)pyridin-3-yl)-6-chloropyrazolo[1,5-a]pyrimidine-3-carboxamide (Compound I-N-50);
2-amino-6-chloro-N-(4-(4-ethylpiperazin-1-yl)pyridin-3-yl)pyrazolo[1,5-a]pyrimidine-3-carboxamide (Compound I-N-51);
2-amino-6-chloro-N-(6-chloro-4-(4-methylpiperazin-1-yl)pyridin-3-yl)pyrazolo[1,5-a]pyrimidine-3-carboxamide (Compound I-N-52);
2-amino-6-chloro-N-(4-(3,3,4-trimethylpiperazin-1-yl)pyridin-3-yl)pyrazolo[1,5-a]pyrimidine-3-carboxamide (Compound I-N-53);
2-amino-6-chloro-N-(4-(3,4-dimethylpiperazin-1-yl)pyridin-3-yl)pyrazolo[1,5-a]pyrimidine-3-carboxamide (Compound I-N-54);
2-amino-N-(4-(3-aminopiperidin-1-yl)pyridin-3-yl)-6-chloropyrazolo[1,5-a]pyrimidine-3-carboxamide (Compound I-N-55);
N-(4-(1,4-diazabicyclo[3.2.2]nonan-4-yl)pyridin-3-yl)-2-amino-6-chloropyrazolo[1,5-a]pyrimidine-3-carboxamide (Compound I-N-56);
2-amino-6-chloro-N-(5-methyl-4-(4-methylpiperazin-1-yl)pyridin-3-yl)pyrazolo[1,5-a]pyrimidine-3-carboxamide (Compound I-N-57);
2-amino-6-chloro-N-(4-(4-(oxetan-3-yl)piperazin-1-yl)pyridin-3-yl)pyrazolo[1,5-a]pyrimidine-3-carboxamide (Compound I-N-58);
2-amino-6-chloro-N-(4-(4-methylpiperazin-1-yl)pyridin-3-yl)pyrazolo[1,5-a]pyrimidine-3-carboxamide (Compound I-N-59);
2-amino-6-chloro-N-(4-(4-(2-methoxyethyl)piperazin-1-yl)pyridin-3-yl)pyrazolo[1,5-a]pyrimidine-3-carboxamide (Compound I-N-60);
2-amino-6-chloro-N-(4-(8-methylhexahydro-1H-pyrazino[1,2-a]pyrazin-2(6H)-yl)pyridin-3-yl)pyrazolo[1,5-a]pyrimidine-3-carboxamide (Compound I-N-61);
2-amino-6-fluoro-N-(4-(4-(3-methyloxetan-3-yl)piperazin-1-yl)pyridin-3-yl)pyrazolo[1,5-a]pyrimidine-3-carboxamide (Compound I-N-62);
2-amino-6-chloro-N-(4-(3-(hydroxymethyl)-4-methylpiperazin-1-yl)pyridin-3-yl)pyrazolo[1,5-a]pyrimidine-3-carboxamide (Compound I-N-63);
2-amino-6-chloro-N-(4-(4-cyclopropylpiperazin-1-yl)pyridin-3-yl)pyrazolo[1,5-a]pyrimidine-3-carboxamide (Compound I-N-64);
(R)-2-amino-6-chloro-N-(4-(hexahydropyrrolo[1,2-a]pyrazin-2(1H)-yl)pyridin-3-yl)pyrazolo[1,5-a]pyrimidine-3-carboxamide (Compound I-N-65);
2-amino-6-chloro-N-(4-(4-hydroxy-4-methylpiperidin-1-yl)pyridin-3-yl)pyrazolo[1,5-a]pyrimidine-3-carboxamide (Compound I-N-66);
2-amino-6-chloro-N-(4-(4-(2,2,2-trifluoroethyl)piperazin-1-yl)pyridin-3-yl)pyrazolo[1,5-a]pyrimidine-3-carboxamide (Compound I-N-67);
2-amino-6-chloro-N-(4-(1-oxidothiomorpholino)pyridin-3-yl)pyrazolo[1,5-a]pyrimidine-3-carboxamide (Compound I-N-68);
2-amino-6-chloro-N-(4-(4-(2-hydroxypropan-2-yl)piperidin-1-yl)pyridin-3-yl)pyrazolo[1,5-a]pyrimidine-3-carboxamide (Compound I-N-69);
2-amino-6-chloro-N-(4-(3-(trifluoromethyl)piperazin-1-yl)pyridin-3-yl)pyrazolo[1,5-a]pyrimidine-3-carboxamide (Compound I-N-70);
(S)-2-amino-6-chloro-N-(4-(hexahydropyrrolo[1,2-a]pyrazin-2(1H)-yl)pyridin-3-yl)pyrazolo[1,5-a]pyrimidine-3-carboxamide (Compound I-N-71);
2-amino-6-chloro-N-(4-(2,4-dimethylpiperazin-1-yl)pyridin-3-yl)pyrazolo[1,5-a]pyrimidine-3-carboxamide (Compound I-N-72);
2-amino-6-chloro-N-(4-(4-methoxypiperidin-1-yl)pyridin-3-yl)pyrazolo[1,5-a]pyrimidine-3-carboxamide (Compound I-N-73);
methyl-1-(3-(2-amino-6-chloropyrazolo[1,5-a]pyrimidine-3-carboxamido)pyridin-4-yl)piperidine-4-carboxylate (Compound I-N-74);
2-amino-6-chloro-N-(4-(5,6-dihydroimidazo[1,5-a]pyrazin-7(8H)-yl)pyridin-3-yl)pyrazolo[1,5-a]pyrimidine-3-carboxamide (Compound I-N-75);
2-amino-6-(2-cyanopropan-2-yl)-N-(4-(4-methylpiperazin-1-yl)pyridin-3-yl)pyrazolo[1,5-a]pyrimidine-3-carboxamide (Compound I-N-76);
2-amino-6-(cyanomethyl)-N-(4-(pyrrolidin-1-yl)pyridin-3-yl)pyrazolo[1,5-a]pyrimidine-3-carboxamide (Compound I-N-77);
2-amino-6-(1-cyanoethyl)-N-(4-(4-methylpiperazin-1-yl)pyridin-3-yl)pyrazolo[1,5-a]pyrimidine-3-carboxamide (Compound I-N-78);
2-amino-N-(4-(azepan-1-yl)pyridin-3-yl)-6-(cyanomethyl)pyrazolo[1,5-a]pyrimidine-3-carboxamide (Compound I-N-79);
2-amino-6-(cyanomethyl)-N-(5-fluoro-4-(4-methylpiperazin-1-yl)pyridin-3-yl)pyrazolo[1,5-a]pyrimidine-3-carboxamide (Compound I-N-80);
2-amino-6-(cyanomethyl)-N-(4-morpholinopyridin-3-yl)pyrazolo[1,5-a]pyrimidine-3-carboxamide (Compound I-N-81);
2-amino-6-(cyanomethyl)-N-(4-(4-methylpiperazin-1-yl)pyridin-3-yl)pyrazolo[1,5-a]pyrimidine-3-carboxamide (Compound I-N-82);
2-amino-6-(cyanomethyl)-N-(4-(4-hydroxypiperidin-1-yl)pyridin-3-yl)pyrazolo[1,5-a]pyrimidine-3-carboxamide (Compound I-N-83);

2-amino-6-(cyanomethyl)-N-(4-(piperidin-1-yl)pyridin-3-yl)pyrazolo[1,5-a]pyrimidine-3-carboxamide (Compound I-N-84);

2-amino-N-(5-chloro-4-(4-methylpiperazin-1-yl)pyridin-3-yl)-6-fluoropyrazolo[1,5-a]pyrimidine-3-carboxamide (Compound I-N-85);

2-amino-N-(5-(difluoromethyl)-4-(4-methylpiperazin-1-yl)pyridin-3-yl)-6-fluoropyrazolo[1,5-a]pyrimidine-3-carboxamide (Compound I-N-111)

2-amino-6-fluoro-N-(4-(5-(oxetan-3-yl)-2,5-diazabicyclo[4.1.0]heptan-2-yl)pyridin-3-yl)pyrazolo[1,5-a]pyrimidine-3-carboxamide (Compound I-N-112);

2-amino-6-fluoro-N-(5-fluoro-4-(8-methylhexahydro-1H-pyrazino[1,2-a]pyrazin-2(6H)-yl)pyridin-3-yl)pyrazolo[1,5-a]pyrimidine-3-carboxamide (Compound I-N-114);

(S)-2-amino-6-fluoro-N-(4-(hexahydropyrazino[2,1-c][1,4]oxazin-8(1H)-yl)pyridin-3-yl)pyrazolo[1,5-a]pyrimidine-3-carboxamide (Compound I-N-115);

(R)-2-amino-6-fluoro-N-(4-(hexahydropyrazino[2,1-c][1,4]oxazin-8(1H)-yl)pyridin-3-yl)pyrazolo[1,5-a]pyrimidine-3-carboxamide (Compound I-N-116);

2-amino-6-chloro-N-(5-fluoro-4-(4-(oxetan-3-yl)piperazin-1-yl)pyridin-3-yl)pyrazolo[1,5-a]pyrimidine-3-carboxamide (Compound I-N-117);

(S)-2-amino-6-fluoro-N-(5-fluoro-4-(4-(tetrahydrofuran-3-yl)piperazin-1-yl)pyridin-3-yl)pyrazolo[1,5-a]pyrimidine-3-carboxamide (Compound I-N-125);

2-amino-6-fluoro-N-(5-fluoro-4-(4-(2-methoxyethyl)piperazin-1-yl)pyridin-3-yl)pyrazolo[1,5-a]pyrimidine-3-carboxamide (Compound I-N-127);

2-amino-6-fluoro-N-(5-fluoro-4-(4-(quinuclidine-3-carbonyl)piperazin-1-yl)pyridin-3-yl)pyrazolo[1,5-a]pyrimidine-3-carboxamide (Compound I-N-130);

2-amino-6-fluoro-N-(4-(1-methyl-9-oxa-1,4-diazaspiro[5.5]undecan-4-yl)pyridin-3-yl)pyrazolo[1,5-a]pyrimidine-3-carboxamide (Compound I-N-133);

(R)-2-amino-6-fluoro-N-(5-fluoro-4-(hexahydropyrazino[2,1-c][1,4]oxazin-8(1H)-yl)pyridin-3-yl)pyrazolo[1,5-a]pyrimidine-3-carboxamide (Compound I-N-135);

2-amino-6-fluoro-N-(4-(4-oxohexahydropyrazino[2,1-c][1,4]oxazin-8(1H)-yl)pyridin-3-yl)pyrazolo[1,5-a]pyrimidine-3-carboxamide (Compound I-N-136);

(S)-2-amino-6-fluoro-N-(5-fluoro-4-(hexahydropyrazino[2,1-c][1,4]oxazin-8(1H)-yl)pyridin-3-yl)pyrazolo[1,5-a]pyrimidine-3-carboxamide (Compound I-N-137);

2-amino-6-(2-cyanopropan-2-yl)-N-(5-fluoro-4-(4-methylpiperazin-1-yl)pyridin-3-yl)pyrazolo[1,5-a]pyrimidine-3-carboxamide (Compound I-N-138);

2-amino-6-fluoro-N-(5-fluoro-4-(4-(2-hydroxy-2-methylpropyl)piperazin-1-yl)pyridin-3-yl)pyrazolo[1,5-a]pyrimidine-3-carboxamide (Compound I-N-139);

2-amino-6-fluoro-N-(5-fluoro-4-(4-(4-methylpiperazine-1-carbonyl)piperazin-1-yl)pyridin-3-yl)pyrazolo[1,5-a]pyrimidine-3-carboxamide (Compound I-N-140);

2-amino-6-fluoro-N-(4-morpholinopyridin-3-yl)pyrazolo[1,5-a]pyrimidine-3-carboxamide (Compound I-N-141);

2-amino-6-(2-cyanopropan-2-yl)-N-(4-(4-(oxetan-3-yl)piperazin-1-yl)pyridin-3-yl)pyrazolo[1,5-a]pyrimidine-3-carboxamide (Compound I-N-142);

2-amino-6-(1-cyanoethyl)-N-(4-(4-(oxetan-3-yl)piperazin-1-yl)pyridin-3-yl)pyrazolo[1,5-a]pyrimidine-3-carboxamide (Compound I-N-143);

2-amino-6-(1-cyanoethyl)-N-(4-(4-(oxetan-3-yl)piperazin-1-yl)pyridin-3-yl)pyrazolo[1,5-a]pyrimidine-3-carboxamide (Compound I-N-144);

2-amino-6-(2-cyanopropan-2-yl)-N-(5-fluoro-4-(4-(oxetan-3-yl)piperazin-1-yl)pyridin-3-yl)pyrazolo[1,5-a]pyrimidine-3-carboxamide (Compound I-N-145);

2-amino-N-(4-(4-(N,N-dimethylsulfamoyl)piperidin-1-yl)-5-fluoropyridin-3-yl)-6-fluoropyrazolo[1,5-a]pyrimidine-3-carboxamide (Compound I-N-146);

2-amino-6-fluoro-N-(5-fluoro-4-(4-(2-oxopyrrolidin-1-yl)piperidin-1-yl)pyridin-3-yl)pyrazolo[1,5-a]pyrimidine-3-carboxamide (Compound I-N-147);

2-amino-6-fluoro-N-(5-fluoro-4-(4-(N-methyl-N-(1-methylpiperidin-4-yl)sulfamoyl)piperidin-1-yl)pyridin-3-yl)pyrazolo[1,5-a]pyrimidine-3-carboxamide (Compound I-N-148);

2-amino-6-fluoro-N-(5-fluoro-4-(4-(morpholinomethyl)piperidin-1-yl)pyridin-3-yl)pyrazolo[1,5-a]pyrimidine-3-carboxamide (Compound I-N-149);

2-amino-6-fluoro-N-(5-fluoro-4-(4-((4-methylpiperazin-1-yl)methyl)piperidin-1-yl)pyridin-3-yl)pyrazolo[1,5-a]pyrimidine-3-carboxamide (Compound I-N-150);

2-amino-6-fluoro-N-(5-fluoro-4-(4-(4-methyl-2-oxopiperazin-1-yl)piperidin-1-yl)pyridin-3-yl)pyrazolo[1,5-a]pyrimidine-3-carboxamide (Compound I-N-151);

2-amino-6-fluoro-N-(4-(piperidin-1-yl)pyridin-3-yl)pyrazolo[1,5-a]pyrimidine-3-carboxamide (Compound I-N-152);

2-amino-6-fluoro-N-(5-fluoro-4-(4-(morpholinosulfonyl)piperidin-1-yl)pyridin-3-yl)pyrazolo[1,5-a]pyrimidine-3-carboxamide (Compound I-N-155);

2-amino-6-fluoro-N-(4-(3-methyl-1H-1,2,4-triazol-1-yl)pyridin-3-yl)pyrazolo[1,5-a]pyrimidine-3-carboxamide (Compound I-N-161);

2-amino-6-fluoro-N-(4-(5-methyl-1H-1,2,4-triazol-1-yl)pyridin-3-yl)pyrazolo[1,5-a]pyrimidine-3-carboxamide (Compound I-N-162);

2-amino-6-fluoro-N-(5-fluoro-4-(6-oxohexahydropyrrolo[1,2-a]pyrazin-2(1H)-yl)pyridin-3-yl)pyrazolo[1,5-a]pyrimidine-3-carboxamide (Compound I-N-163);

2-amino-6-fluoro-N-(5-fluoro-4-(4-(methylsulfonyl)piperidin-1-yl)pyridin-3-yl)pyrazolo[1,5-a]pyrimidine-3-carboxamide (Compound I-N-165);

2-amino-6-fluoro-N-(5-fluoro-4-(4-((4-methylpiperazin-1-yl)sulfonyl)piperidin-1-yl)pyridin-3-yl)pyrazolo[1,5-a]pyrimidine-3-carboxamide (Compound I-N-166);

2-amino-6-fluoro-N-(5-fluoro-4-(4-(2-(pyrrolidin-1-yl)ethoxy)piperidin-1-yl)pyridin-3-yl)pyrazolo[1,5-a]pyrimidine-3-carboxamide (Compound I-N-167);

2-amino-N-(4-(4-(azetidin-1-ylsulfonyl)piperidin-1-yl)-5-fluoropyridin-3-yl)-6-fluoropyrazolo[1,5-a]pyrimidine-3-carboxamide (Compound I-N-169);

2-amino-6-fluoro-N-(4-(4-(morpholinosulfonyl)piperidin-1-yl)pyridin-3-yl)pyrazolo[1,5-a]pyrimidine-3-carboxamide (Compound I-N-170);

2-amino-6-fluoro-N-(5-fluoro-4-(4-((4-methyl-3-oxopiperazin-1-yl)methyl)piperidin-1-yl)pyridin-3-yl)pyrazolo[1,5-a]pyrimidine-3-carboxamide (Compound I-N-171);

2-amino-6-(1-cyanocyclopropyl)-N-(5-fluoro-4-(4-(oxetan-3-yl)piperazin-1-yl)pyridin-3-yl)pyrazolo[1,5-a]pyrimidine-3-carboxamide (Compound I-N-180);

(R)-2-amino-6-fluoro-N-(5-fluoro-4-(6-oxohexahydropyrrolo[1,2-a]pyrazin-2(1H)-yl)pyridin-3-yl)pyrazolo[1,5-a]pyrimidine-3-carboxamide (Compound I-N-182);

2-amino-6-fluoro-N-(4-(4-methyl-1-oxa-4,9-diazaspiro[5.5]undecan-9-yl)pyridin-3-yl)pyrazolo[1,5-a]pyrimidine-3-carboxamide (Compound I-N-183);

2-amino-6-fluoro-N-(5-fluoro-4-(4-(thiazol-2-yl)piperidin-1-yl)pyridin-3-yl)pyrazolo[1,5-a]pyrimidine-3-carboxamide (Compound I-N-184);

(R)-2-amino-6-fluoro-N-(5-fluoro-4-(6-oxohexahydropyrrolo[1,2-a]pyrazin-2(1H)-yl)pyridin-3-yl)pyrazolo[1,5-a]pyrimidine-3-carboxamide (Compound I-N-186);

2-amino-6-fluoro-N-(5-fluoro-4-(4-(2-(pyrrolidin-1-yl)acetyl)piperazin-1-yl)pyridin-3-yl)pyrazolo[1,5-a]pyrimidine-3-carboxamide (Compound I-N-187);

2-amino-6-fluoro-N-(5-fluoro-4-(4-morpholinopiperidin-1-yl)pyridin-3-yl)pyrazolo[1,5-a]pyrimidine-3-carboxamide (Compound I-N-189);

2-amino-6-fluoro-N-(4-(4-(methylsulfonyl)piperidin-1-yl)pyridin-3-yl)pyrazolo[1,5-a]pyrimidine-3-carboxamide (Compound I-N-190);

2-amino-6-fluoro-N-(5-fluoro-4-(3-(4-methylpiperazine-1-carbonyl)pyrrolidin-1-yl)pyridin-3-yl)pyrazolo[1,5-a]pyrimidine-3-carboxamide (Compound I-N-191);

2-amino-6-(1-cyanocyclopropyl)-N-(5-fluoro-4-(4-((4-methylpiperazin-1-yl)methyl)piperidin-1-yl)pyridin-3-yl)pyrazolo[1,5-a]pyrimidine-3-carboxamide (Compound I-N-192);

2-amino-6-fluoro-N-(5-fluoro-4-(4-((4-methyl-2-oxopiperazin-1-yl)methyl)piperidin-1-yl)pyridin-3-yl)pyrazolo[1,5-a]pyrimidine-3-carboxamide (Compound I-N-193);

N-(4-(4-(1,4-diazabicyclo[3.2.2]nonan-4-ylsulfonyl)piperidin-1-yl)pyridin-3-yl)-2-amino-6-fluoropyrazolo[1,5-a]pyrimidine-3-carboxamide (Compound I-N-196);

2-amino-N-(4-(4-((3,3-difluoropyrrolidin-1-yl)methyl)piperidin-1-yl)pyridin-3-yl)-6-fluoropyrazolo[1,5-a]pyrimidine-3-carboxamide (Compound I-N-197);

2-amino-6-fluoro-N-(4-(4-(oxetan-3-ylsulfonyl)piperidin-1-yl)pyridin-3-yl)pyrazolo[1,5-a]pyrimidine-3-carboxamide (Compound I-N-200);

2-amino-N-(4-(2-cyclopropyl-1H-imidazol-1-yl)pyridin-3-yl)-6-fluoropyrazolo[1,5-a]pyrimidine-3-carboxamide (Compound I-N-202);

2-amino-6-fluoro-N-(4-(4-((2-methoxyethyl)sulfonyl)piperidin-1-yl)pyridin-3-yl)pyrazolo[1,5-a]pyrimidine-3-carboxamide (Compound I-N-208);

2-amino-6-fluoro-N-(4-(4-methyl-3-oxopiperazin-1-yl)pyridin-3-yl)pyrazolo[1,5-a]pyrimidine-3-carboxamide (Compound I-N-209);

2-amino-N-(4-(1,1-dioxidothiomorpholino)pyridin-3-yl)-6-fluoropyrazolo[1,5-a]pyrimidine-3-carboxamide (Compound I-N-210);

2-amino-6-fluoro-N-(5-fluoro-4-(4-methyl-3-oxopiperazin-1-yl)pyridin-3-yl)pyrazolo[1,5-a]pyrimidine-3-carboxamide (Compound I-N-212);

2-amino-6-fluoro-N-(5-fluoro-4-(4-((2-oxopyrrolidin-1-yl)methyl)piperidin-1-yl)pyridin-3-yl)pyrazolo[1,5-a]pyrimidine-3-carboxamide (Compound I-N-213);

2-amino-6-fluoro-N-(4-(4-((methylsulfonyl)methyl)piperidin-1-yl)pyridin-3-yl)pyrazolo[1,5-a]pyrimidine-3-carboxamide (Compound I-N-215);

2-amino-6-fluoro-N-(4-(3-methyl-2-oxo-1-oxa-3,8-diazaspiro[4.5]decan-8-yl)pyridin-3-yl)pyrazolo[1,5-a]pyrimidine-3-carboxamide (Compound I-N-216);

(S)-2-amino-6-fluoro-N-(4-(6-oxohexahydropyrrolo[1,2-a]pyrazin-2(1H)-yl)pyridin-3-yl)pyrazolo[1,5-a]pyrimidine-3-carboxamide (Compound I-N-217);

2-amino-N-(4-(3,5-dimethyl-1H-1,2,4-triazol-1-yl)pyridin-3-yl)-6-fluoropyrazolo[1,5-a]pyrimidine-3-carboxamide (Compound I-N-218);

2-amino-6-fluoro-N-(4-(2-(trifluoromethyl)-1H-imidazol-1-yl)pyridin-3-yl)pyrazolo[1,5-a]pyrimidine-3-carboxamide (Compound I-N-219);

2-amino-N-(4-(2,2-dimethylpyrrolidin-1-yl)pyridin-3-yl)-6-fluoropyrazolo[1,5-a]pyrimidine-3-carboxamide (Compound I-N-220);

2-amino-6-fluoro-N-(4-(3-(methylsulfonyl)piperidin-1-yl)pyridin-3-yl)pyrazolo[1,5-a]pyrimidine-3-carboxamide (Compound I-N-221);

2-amino-6-fluoro-N-(4-(4-oxohexahydropyrrolo[1,2-a]pyrazin-2(1H)-yl)pyridin-3-yl)pyrazolo[1,5-a]pyrimidine-3-carboxamide (Compound I-N-222);

2-amino-6-fluoro-N-(4-(5-methyl-1H-pyrazol-1-yl)pyridin-3-yl)pyrazolo[1,5-a]pyrimidine-3-carboxamide (Compound I-N-223);

2-amino-6-fluoro-N-(4-((3aR,7aR)-2-methyl-3-oxohexahydro-1H-pyrrolo[3,4-c]pyridin-5(6H)-yl)pyridin-3-yl)pyrazolo[1,5-a]pyrimidine-3-carboxamide (Compound I-N-224);

2-amino-6-fluoro-N-(4-(3-methyl-1H-pyrazol-1-yl)pyridin-3-yl)pyrazolo[1,5-a]pyrimidine-3-carboxamide (Compound I-N-225);

N-(4-(2-oxa-7-azaspiro[3.5]nonan-7-yl)pyridin-3-yl)-2-amino-6-fluoropyrazolo[1,5-a]pyrimidine-3-carboxamide (Compound I-N-226);

2-amino-6-fluoro-N-(5-fluoro-4-(3-methyl-2-oxo-1-oxa-3,8-diazaspiro[4.5]decan-8-yl)pyridin-3-yl)pyrazolo[1,5-a]pyrimidine-3-carboxamide (Compound I-N-229);

2-amino-6-fluoro-N-(4-(4-(2-oxopyrrolidin-1-yl)piperidin-1-yl)pyridin-3-yl)pyrazolo[1,5-a]pyrimidine-3-carboxamide (Compound I-N-230);

2-amino-6-fluoro-N-(4-(2-methyl-3-oxo-2,9-diazaspiro[5.5]undecan-9-yl)pyridin-3-yl)pyrazolo[1,5-a]pyrimidine-3-carboxamide (Compound I-N-231);

2-amino-6-fluoro-N-(5-fluoro-4-(4-oxohexahydropyrrolo[1,2-a]pyrazin-2(1H)-yl)pyridin-3-yl)pyrazolo[1,5-a]pyrimidine-3-carboxamide (Compound I-N-232);

2-amino-6-fluoro-N-(4-(8-methyl-9-oxohexahydro-1H-pyrazino[1,2-a]pyrazin-2(6H)-yl)pyridin-3-yl)pyrazolo[1,5-a]pyrimidine-3-carboxamide (Compound I-N-233);

4-(3-(2-amino-6-fluoropyrazolo[1,5-a]pyrimidine-3-carboxamido)pyridin-4-yl)-N,N-dimethylmorpholine-2-carboxamide (Compound I-N-234);

2-amino-6-fluoro-N-(4-(1-methyl-2-oxo-1,8-diazaspiro[4.5]decan-8-yl)pyridin-3-yl)pyrazolo[1,5-a]pyrimidine-3-carboxamide (Compound I-N-235);

2-amino-6-fluoro-N-(4-(2-methyl-3-oxo-2,8-diazaspiro[4.5]decan-8-yl)pyridin-3-yl)pyrazolo[1,5-a]pyrimidine-3-carboxamide (Compound I-N-236);

2-amino-6-fluoro-N-(4-(3-oxotetrahydro-1H-oxazolo[3,4-a]pyrazin-7(3H)-yl)pyridin-3-yl)pyrazolo[1,5-a]pyrimidine-3-carboxamide (Compound I-N-238);

2-amino-6-fluoro-N-(5-fluoro-4-(2-oxa-7-azaspiro[3.5]nonan-7-yl)pyridin-3-yl)pyrazolo[1,5-a]pyrimidine-3-carboxamide (Compound I-N-239);

2-amino-6-fluoro-N-(5-fluoro-4-(8-methyl-9-oxohexahydro-1H-pyrazino[1,2-a]pyrazin-2(6H)-yl)pyridin-3-yl)pyrazolo[1,5-a]pyrimidine-3-carboxamide (Compound I-N-240);

N-(4-(4-(1,2,4-oxadiazol-3-yl)piperidin-1-yl)pyridin-3-yl)-2-amino-6-fluoropyrazolo[1,5-a]pyrimidine-3-carboxamide (Compound I-N-241);

2-amino-N-(4-(5-fluoro-4-(5-methyl-1H-1,2,4-triazol-1-yl)pyridin-3-yl)pyrazolo[1,5-a]pyrimidine-3-carboxamide (Compound I-N-242);

2-amino-6-fluoro-N-(4-(4-methyl-4-(methylsulfonyl)piperidin-1-yl)pyridin-3-yl)pyrazolo[1,5-a]pyrimidine-3-carboxamide (Compound I-N-243);

2-amino-6-fluoro-N-(4-(6-oxohexahydro-1H-pyrido[1,2-a]pyrazin-2(6H)-yl)pyridin-3-yl)pyrazolo[1,5-a]pyrimidine-3-carboxamide (Compound I-N-244);

2-amino-6-fluoro-N-(4-(8-isopropyl-9-oxohexahydro-1H-pyrazino[1,2-a]pyrazin-2(6H)-yl)pyridin-3-yl)pyrazolo[1,5-a]pyrimidine-3-carboxamide (Compound I-N-245);

2-amino-6-fluoro-N-(5-fluoro-4-(pyrrolidin-1-yl)pyridin-3-yl)pyrazolo[1,5-a]pyrimidine-3-carboxamide (Compound I-N-246);

(S)-2-amino-N-(4-(1,1-dioxidotetrahydro-2H-isothiazolo[2,3-a]pyrazin-5(3H)-yl)pyridin-3-yl)-6-fluoropyrazolo[1,5-a]pyrimidine-3-carboxamide (Compound I-N-247);

(S)-2-amino-6-fluoro-N-(5-fluoro-4-(3-oxotetrahydro-1H-oxazolo[3,4-a]pyrazin-7(3H)-yl)pyridin-3-yl)pyrazolo[1,5-a]pyrimidine-3-carboxamide (Compound I-N-248);

2-amino-N-(4-(1,1-dioxidothiomorpholino)-5-fluoropyridin-3-yl)-6-fluoropyrazolo[1,5-a]pyrimidine-3-carboxamide (Compound I-N-250);

2-amino-N-(4-(2,2-dimethyl-1,1-dioxidothiomorpholino)pyridin-3-yl)-6-fluoropyrazolo[1,5-a]pyrimidine-3-carboxamide (Compound I-N-252);

N-(4-(2-oxa-6-azaspiro[3.5]nonan-6-yl)pyridin-3-yl)-2-amino-6-fluoropyrazolo[1,5-a]pyrimidine-3-carboxamide (Compound I-N-253);

2-amino-6-fluoro-N-(4-(4-(5-methyl-1,3,4-oxadiazol-2-yl)piperazin-1-yl)pyridin-3-yl)pyrazolo[1,5-a]pyrimidine-3-carboxamide (Compound I-N-256);

(R)-2-amino-6-fluoro-N-(4-(6-oxohexahydropyrrolo[1,2-a]pyrazin-2(1H)-yl)pyridin-3-yl)pyrazolo[1,5-a]pyrimidine-3-carboxamide (Compound I-N-258);

2-amino-6-fluoro-N-(1-methyl-1H-pyrrolo[3,2-c]pyridin-7-yl)pyrazolo[1,5-a]pyrimidine-3-carboxamide (Compound I-N-259);

2-amino-6-fluoro-N-(4-(4-(4-methyl-1,2,5-oxadiazol-3-yl)piperazin-1-yl)pyridin-3-yl)pyrazolo[1,5-a]pyrimidine-3-carboxamide (Compound I-N-260);

2-amino-6-fluoro-N-(4-(3-methyl-4H-1,2,4-triazol-4-yl)pyridin-3-yl)pyrazolo[1,5-a]pyrimidine-3-carboxamide (Compound I-N-263);

2-amino-N-(4-(azepan-1-yl)pyridin-3-yl)-6-fluoropyrazolo[1,5-a]pyrimidine-3-carboxamide (Compound I-N-264);

2-amino-6-fluoro-N-(4-(4-(5-methyl-1,3,4-oxadiazol-2-yl)piperidin-1-yl)pyridin-3-yl)pyrazolo[1,5-a]pyrimidine-3-carboxamide (Compound I-N-265);

2-amino-6-fluoro-N-(4-(4-methoxypiperidin-1-yl)pyridin-3-yl)pyrazolo[1,5-a]pyrimidine-3-carboxamide (Compound I-N-266);

2-amino-N-(4-(4-((dimethylamino)methyl)piperidin-1-yl)pyridin-3-yl)-6-fluoropyrazolo[1,5-a]pyrimidine-3-carboxamide (Compound I-N-267);

N-(4-(4-(1,3,4-oxadiazol-2-yl)piperidin-1-yl)pyridin-3-yl)-2-amino-6-fluoropyrazolo[1,5-a]pyrimidine-3-carboxamide (Compound I-N-268);

2-amino-N-(4-(4,5-dimethyl-1H-imidazol-1-yl)pyridin-3-yl)-6-fluoropyrazolo[1,5-a]pyrimidine-3-carboxamide (Compound I-N-269);

2-amino-6-fluoro-N-(5-fluoro-4-(piperidin-1-yl)pyridin-3-yl)pyrazolo[1,5-a]pyrimidine-3-carboxamide (Compound I-N-270);

2-amino-N-(4-(4-(azetidin-1-ylsulfonyl)piperidin-1-yl)pyridin-3-yl)-6-fluoropyrazolo[1,5-a]pyrimidine-3-carboxamide (Compound I-N-271);

2-amino-6-fluoro-N-(5-fluoro-4-(4-methyl-1-oxa-4,9-diazaspiro[5.5]undecan-9-yl)pyridin-3-yl)pyrazolo[1,5-a]pyrimidine-3-carboxamide (Compound I-N-272);

N-(4-(4-(1,4-diazabicyclo[3.2.2]nonan-4-ylsulfonyl)piperidin-1-yl)-5-fluoropyridin-3-yl)-2-amino-6-fluoropyrazolo[1,5-a]pyrimidine-3-carboxamide (Compound I-N-273);

2-amino-6-fluoro-N-(5-fluoro-4-(6-oxohexahydro-1H-pyrido[1,2-a]pyrazin-2(6H)-yl)pyridin-3-yl)pyrazolo[1,5-a]pyrimidine-3-carboxamide (Compound I-N-277);

(S)-2-amino-6-fluoro-N-(5-fluoro-4-(6-oxohexahydro-1H-pyrido[1,2-a]pyrazin-2(6H)-yl)pyridin-3-yl)pyrazolo[1,5-a]pyrimidine-3-carboxamide (Compound I-N-279);

(R)-2-amino-6-fluoro-N-(5-fluoro-4-(6-oxohexahydro-1H-pyrido[1,2-a]pyrazin-2(6H)-yl)pyridin-3-yl)pyrazolo[1,5-a]pyrimidine-3-carboxamide (Compound I-N-280);

2-amino-N-(5-chloro-4-(pyrrolidin-1-yl)pyridin-3-yl)-6-fluoropyrazolo[1,5-a]pyrimidine-3-carboxamide (Compound I-N-281);

2-amino-6-fluoro-N-(4-(4-(methoxymethyl)piperidin-1-yl)pyridin-3-yl)pyrazolo[1,5-a]pyrimidine-3-carboxamide (Compound I-N-282);

2-amino-6-fluoro-N-(4-(5-methyl-1H-imidazol-1-yl)pyridin-3-yl)pyrazolo[1,5-a]pyrimidine-3-carboxamide (Compound I-N-283);

2-amino-N-(5-chloro-4-(3-hydroxypyrrolidin-1-yl)pyridin-3-yl)-6-fluoropyrazolo[1,5-a]pyrimidine-3-carboxamide (Compound I-N-284);

(R)-2-amino-N-(5-chloro-4-(3-cyanopyrrolidin-1-yl)pyridin-3-yl)-6-fluoropyrazolo[1,5-a]pyrimidine-3-carboxamide (Compound I-N-285);

2-amino-N-(5-chloro-4-(5-methylhexahydropyrrolo[3,4-c]pyrrol-2(1H)-yl)pyridin-3-yl)-6-fluoropyrazolo[1,5-a]pyrimidine-3-carboxamide (Compound I-N-286);

2-amino-N-(5-chloro-4-(3-(methylsulfonyl)pyrrolidin-1-yl)pyridin-3-yl)-6-fluoropyrazolo[1,5-a]pyrimidine-3-carboxamide (Compound I-N-287);

N-(4-(4-(1H-imidazol-1-yl)piperidin-1-yl)-5-fluoropyridin-3-yl)-2-amino-6-fluoropyrazolo[1,5-a]pyrimidine-3-carboxamide (Compound I-N-288)

2-amino-6-fluoro-N-(5-fluoro-4-(3-(4-methylpiperazine-1-carbonyl)piperidin-1-yl)pyridin-3-yl)pyrazolo[1,5-a]pyrimidine-3-carboxamide (Compound I-N-289);

2-amino-N-(4-(3-(dimethylcarbamoyl)piperidin-1-yl)pyridin-3-yl)-6-fluoropyrazolo[1,5-a]pyrimidine-3-carboxamide (Compound I-N-290);

2-amino-6-fluoro-N-(5'-methoxy-[3,4'-bipyridin]-3'-yl)pyrazolo[1,5-a]pyrimidine-3-carboxamide (Compound I-C-82);

2-amino-6-fluoro-N-(4-(1-(2-methoxyethyl)-1H-imidazol-5-yl)pyridin-3-yl)pyrazolo[1,5-a]pyrimidine-3-carboxamide (Compound I-C-83);

2-amino-N-(4-cyclopropyl-5-methoxypyridin-3-yl)-6-fluoropyrazolo[1,5-a]pyrimidine-3-carboxamide (Compound I-C-84);

2-amino-6-fluoro-N-(4-(4-(4-methylpiperazine-1-carbonyl)piperidin-1-yl)pyridin-3-yl)pyrazolo[1,5-a]pyrimidine-3-carboxamide (Compound I-G-1);

2-amino-N-(4-(4-(dimethylcarbamoyl)piperidin-1-yl)pyridin-3-yl)-6-fluoropyrazolo[1,5-a]pyrimidine-3-carboxamide (Compound I-G-2);

2-amino-N-(5-chloro-4-(4-(4-methylpiperazine-1-carbonyl)piperidin-1-yl)pyridin-3-yl)-6-fluoropyrazolo[1,5-a]pyrimidine-3-carboxamide (Compound I-G-3);

2-amino-6-fluoro-N-(5-fluoro-4-(4-(4-methylpiperazine-1-carbonyl)piperidin-1-yl)pyridin-3-yl)pyrazolo[1,5-a]pyrimidine-3-carboxamide (Compound I-G-4);

2-amino-6-chloro-N-(5-fluoro-4-(4-(4-methylpiperazine-1-carbonyl)piperidin-1-yl)pyridin-3-yl)pyrazolo[1,5-a]pyrimidine-3-carboxamide (Compound I-G-5);

2-amino-6-fluoro-N-(5-fluoro-4-(4-(4-methyl-1,4-diazepane-1-carbonyl)piperidin-1-yl)pyridin-3-yl)pyrazolo[1,5-a]pyrimidine-3-carboxamide (Compound I-G-6);

N-(4-(4-(1,4-diazabicyclo[3.2.2]nonane-4-carbonyl)piperi-
din-1-yl)-5-fluoropyridin-3-yl)-2-amino-6-fluoropyra-
zolo[1,5-a]pyrimidine-3-carboxamide (Compound I-G-
7);

2-amino-N-(4-(4-(4-cyclopropylpiperazine-1-carbonyl)pip-
eridin-1-yl)-5-fluoropyridin-3-yl)-6-fluoropyrazolo[1,5-
a]pyrimidine-3-carboxamide (Compound I-G-13);

2-amino-6-fluoro-N-(5-fluoro-4-(4-(3,3,4-trimethylpipera-
zine-1-carbonyl)piperidin-1-yl)pyridin-3-yl)pyrazolo[1,
5-a]pyrimidine-3-carboxamide (Compound I-G-15);

2-amino-N-(4-(4-cyano-4-(4-methylpiperazine-1-carbonyl)
piperidin-1-yl)-5-fluoropyridin-3-yl)-6-fluoropyrazolo[1,
5-a]pyrimidine-3-carboxamide (Compound I-G-25);

2-amino-6-fluoro-N-(5-fluoro-4-(4-methyl-4-(4-methylpip-
erazine-1-carbonyl)piperidin-1-yl)pyridin-3-yl)pyrazolo
[1,5-a]pyrimidine-3-carboxamide (Compound I-G-54);

2-amino-6-fluoro-N-(5-fluoro-4-(4-(5-methyl-2,5-diazabi-
cyclo[4.1.0]heptane-2-carbonyl)piperidin-1-yl)pyridin-3-
yl)pyrazolo[1,5-a]pyrimidine-3-carboxamide (Compound
I-G-65); and N-(4-(4-(1,4-diazabicyclo[3.2.2]nonane-4-carbonyl)piperi-
din-1-yl)-5-chloropyridin-3-yl)-2-amino-6-fluoropyra-
zolo[1,5-a]pyrimidine-3-carboxamide (Compound I-G-
66).

The following compounds were prepared according to methods similar to the one depicted in the procedure described in Example 2:

2-amino-N-(4-(4-aminopiperidin-1-yl)pyridin-3-yl)-6-chlo-
ropyrazolo[1,5-a]pyrimidine-3-carboxamide (Compound
I-N-86);

2-amino-6-chloro-N-(4-(4-(methylamino)piperidin-1-yl)
pyridin-3-yl)pyrazolo[1,5-a]pyrimidine-3-carboxamide
(Compound I-N-87);

2-amino-6-chloro-N-(4-(piperazin-1-yl)pyridin-3-yl)pyra-
zolo[1,5-a]pyrimidine-3-carboxamide (Compound I-N-
88);

2-amino-6-(cyanomethyl)-N-(4-(piperazin-1-yl)pyridin-3-
yl)pyrazolo[1,5-a]pyrimidine-3-carboxamide (Compound
I-N-89);

2-amino-N-(4-(2-(aminomethyl)morpholino)pyridin-3-yl)-
6-(cyanomethyl)pyrazolo[1,5-a]pyrimidine-3-carboxam-
ide (Compound I-N-90);

2-amino-N-(4-(4-(aminomethyl)piperidin-1-yl)pyridin-3-
yl)-6-chloropyrazolo[1,5-a]pyrimidine-3-carboxamide
(Compound I-N-91);

2-amino-6-fluoro-N-(5-fluoro-4-(piperazin-1-yl)pyridin-3-
yl)pyrazolo[1,5-a]pyrimidine-3-carboxamide (Compound
I-N-118);

2-amino-N-(5-chloro-4-(piperazin-1-yl)pyridin-3-yl)-6-
fluoropyrazolo[1,5-a]pyrimidine-3-carboxamide (Com-
pound I-N-126);

2-amino-6-fluoro-N-(6-(methylamino)-4-(4-methylpiper-
azin-1-yl)pyridin-3-yl)pyrazolo[1,5-a]pyrimidine-3-car-
boxamide (Compound I-N-129); and N-(4-(2,8-diazaspiro[4.5]decan-8-yl)pyridin-3-yl)-2-amino-
6-fluoropyrazolo[1,5-a]pyrimidine-3-carboxamide (Com-
pound I-N-255).

Example 4: 2-amino-N-(4-(4-(4-ethylpiperazine-1-
carbonyl)piperidin-1-yl)-5-fluoropyridin-3-yl)-6-
fluoropyrazolo[1,5-a]pyrimidine-3-carboxamide
(compound I-G-9)

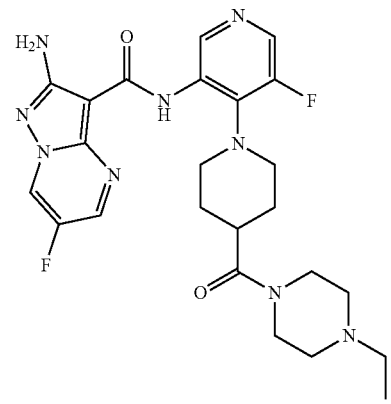 [SMILES: CCN1CCN(C(=O)C2CCN(c3c(F)cncc3NC(=O)c3c(N)nn4cc(F)cnc34)CC2)CC1]

Step 1: 1-(3-(2-amino-6-fluoropyrazolo[1,5-a]py-
rimidine-3-carboxamido)-5-fluoropyridin-4-yl)pip-
eridine-4-carboxylic acid (Compound I-N-92)

tert-butyl 1-(3-(2-amino-6-fluoropyrazolo[1,5-a]pyrimi-
dine-3-carboxamido)pyridin-4-yl)piperidine-4-carboxylate
prepared according to methods similar to the one depicted in
Example 1 was dissolved in DCM (5 mL). TFA (1 mL, 12.98
mmol) was added and the mixture was stirred at RT for 5 hr.
The reaction mixture was concentrated to give 1-(3-(2-
amino-6-fluoropyrazolo[1,5-a]pyrimidine-3-carboxamido)-
5-fluoropyridin-4-yl)piperidine-4-carboxylic acid as a beige
solid that was used in next step without further purification.
MS (ES+) 418.1.

Step 2: 2-amino-N-(4-(4-(4-ethylpiperazine-1-carbo-
nyl)piperidin-1-yl)-5-fluoropyridin-3-yl)-6-fluoropy-
razolo[1,5-a]pyrimidine-3-carboxamide A mixture of 1-(3-(2-amino-6-fluoropyrazolo[1,5-a]py-
rimidine-3-carboxamido)pyridin-4-yl)piperidine-4-carbox-
ylic acid (Trifluoroacetic Acid (2)) (30 mg), (benzotriazol-
1-yloxy-dimethylamino-methylene)-dimethyl-ammonium
(Boron Tetrafluoride Ion (1)) (46.17 mg, 0.1438 mmol) and
TEA (33.07 mg, 45.55 µL, 0.3268 mmol) in DMF was
stirred at room temperature for 5 minutes followed by the
addition of 1-ethylpiperazine (13.68 mg, 0.1198 mmol). The
mixture was stirred at room temperature for 1 hour. The
mixture was filtered and purified directly by fractionlynx
yielding 2-amino-N-(4-(4-(4-ethylpiperazine-1-carbonyl)pi-
peridin-1-yl)-5-fluoropyridin-3-yl)-6-fluoropyrazolo[1,5-a]
pyrimidine-3-carboxamide. yield 38% MS (ES+) 514.0.

The following compounds were successfully prepared
using a procedure similar to Example 4:

2-amino-N-(4-(4-(azetidine-1-carbonyl)piperidin-1-yl)-5-
fluoropyridin-3-yl)-6-fluoropyrazolo[1,5-a]pyrimidine-3-
carboxamide (Compound I-G-8);

2-amino-6-fluoro-N-(5-fluoro-4-(4-(octahydropyrrolo[1,2-
a]pyrazine-2-carbonyl)piperidin-1-yl)pyridin-3-yl)pyra-
zolo[1,5-a]pyrimidine-3-carboxamide (Compound I-G-
10);

(R)-2-amino-N-(4-(4-(3-(dimethylamino)pyrrolidine-1-carbonyl)piperidin-1-yl)-5-fluoropyridin-3-yl)-6-fluoropyrazolo[1,5-a]pyrimidine-3-carboxamide (Compound I-G-11);
N-(4-(4-(2-oxa-6-azaspiro[3.3]heptane-6-carbonyl)piperidin-1-yl)-5-fluoropyridin-3-yl)-2-amino-6-fluoropyrazolo[1,5-a]pyrimidine-3-carboxamide (Compound I-G-14);
2-amino-N-(4-(4-((3-(dimethylamino)propyl)(methyl)carbamoyl)piperidin-1-yl)-5-fluoropyridin-3-yl)-6-fluoropyrazolo[1,5-a]pyrimidine-3-carboxamide (Compound I-G-16);
2-amino-6-fluoro-N-(5-fluoro-4-(4-(5-methyloctahydropyrrolo[3,4-c]pyrrole-2-carbonyl)piperidin-1-yl)pyridin-3-yl)pyrazolo[1,5-a]pyrimidine-3-carboxamide (Compound I-G-18);
2-amino-N-(4-(4-(tert-butylcarbamoyl)piperidin-1-yl)-5-fluoropyridin-3-yl)-6-fluoropyrazolo[1,5-a]pyrimidine-3-carboxamide (Compound I-G-19);
2-amino-6-fluoro-N-(5-fluoro-4-(4-((1-methylpiperidin-4-yl)carbamoyl)piperidin-1-yl)pyridin-3-yl)pyrazolo[1,5-a]pyrimidine-3-carboxamide (Compound I-G-20);
2-amino-6-fluoro-N-(5-fluoro-4-(4-(3-methoxyazetidine-1-carbonyl)piperidin-1-yl)pyridin-3-yl)pyrazolo[1,5-a]pyrimidine-3-carboxamide (Compound I-G-21);
2-amino-N-(4-(4-(3-(dimethylamino)azetidine-1-carbonyl)piperidin-1-yl)-5-fluoropyridin-3-yl)-6-fluoropyrazolo[1,5-a]pyrimidine-3-carboxamide (Compound I-G-22);
2-amino-6-fluoro-N-(5-fluoro-4-(4-((1-methylazetidin-3-yl)carbamoyl)piperidin-1-yl)pyridin-3-yl)pyrazolo[1,5-a]pyrimidine-3-carboxamide (Compound I-G-23);
2-amino-6-fluoro-N-(5-fluoro-4-(4-((1-methylpyrrolidin-3-yl)carbamoyl)piperidin-1-yl)pyridin-3-yl)pyrazolo[1,5-a]pyrimidine-3-carboxamide (Compound I-G-24);
2-amino-N-(4-(4-((3-(dimethylamino)propyl)carbamoyl)piperidin-1-yl)-5-fluoropyridin-3-yl)-6-fluoropyrazolo[1,5-a]pyrimidine-3-carboxamide (Compound I-G-26);
2-amino-N-(4-(4-(dimethylcarbamoyl)piperidin-1-yl)-5-fluoropyridin-3-yl)-6-fluoropyrazolo[1,5-a]pyrimidine-3-carboxamide (Compound I-G-29);
2-amino-N-(4-(4-((2-(dimethylamino)ethyl)carbamoyl)piperidin-1-yl)-5-fluoropyridin-3-yl)-6-fluoropyrazolo[1,5-a]pyrimidine-3-carboxamide (Compound I-G-30);
2-amino-N-(4-(4-((2-(dimethylamino)ethyl)(methyl)carbamoyl)piperidin-1-yl)-5-fluoropyridin-3-yl)-6-fluoropyrazolo[1,5-a]pyrimidine-3-carboxamide (Compound I-G-31);
2-amino-6-fluoro-N-(5-fluoro-4-(4-(4-(oxetan-3-yl)piperazine-1-carbonyl)piperidin-1-yl)pyridin-3-yl)pyrazolo[1,5-a]pyrimidine-3-carboxamide (Compound I-G-32);
2-amino-6-fluoro-N-(5-fluoro-4-(4-(methylcarbamoyl)piperidin-1-yl)pyridin-3-yl)pyrazolo[1,5-a]pyrimidine-3-carboxamide (Compound I-G-33);
2-amino-N-(4-(4-(4-cyclobutylpiperazine-1-carbonyl)piperidin-1-yl)-5-fluoropyridin-3-yl)-6-fluoropyrazolo[1,5-a]pyrimidine-3-carboxamide (Compound I-G-35);
2-amino-6-fluoro-N-(5-fluoro-4-(4-(morpholine-4-carbonyl)piperidin-1-yl)pyridin-3-yl)pyrazolo[1,5-a]pyrimidine-3-carboxamide (Compound I-G-36);
2-amino-6-fluoro-N-(5-fluoro-4-(4-(oxetan-3-ylcarbamoyl)piperidin-1-yl)pyridin-3-yl)pyrazolo[1,5-a]pyrimidine-3-carboxamide (Compound I-G-37);
2-amino-6-fluoro-N-(5-fluoro-4-(4-(4-methyl-4,7-diazaspiro[2.5]octane-7-carbonyl)piperidin-1-yl)pyridin-3-yl)pyrazolo[1,5-a]pyrimidine-3-carboxamide (Compound I-G-38);
2-amino-6-fluoro-N-(5-fluoro-4-(4-((2-methoxyethyl)(methyl)carbamoyl)piperidin-1-yl)pyridin-3-yl)pyrazolo[1,5-a]pyrimidine-3-carboxamide (Compound I-G-40);
2-amino-6-fluoro-N-(5-fluoro-4-(4-(3-hydroxyazetidine-1-carbonyl)piperidin-1-yl)pyridin-3-yl)pyrazolo[1,5-a]pyrimidine-3-carboxamide (Compound I-G-41);
2-amino-N-(4-(4-((2-(azetidin-1-yl)ethyl)carbamoyl)piperidin-1-yl)-5-fluoropyridin-3-yl)-6-fluoropyrazolo[1,5-a]pyrimidine-3-carboxamide (Compound I-G-42);
2-amino-6-fluoro-N-(5-fluoro-4-(4-(3-(pyrrolidin-1-yl)azetidine-1-carbonyl)piperidin-1-yl)pyridin-3-yl)pyrazolo[1,5-a]pyrimidine-3-carboxamide (Compound I-G-43);
N-(4-(4-(1,4-diazabicyclo[3.2.1]octane-4-carbonyl)piperidin-1-yl)-5-fluoropyridin-3-yl)-2-amino-6-fluoropyrazolo[1,5-a]pyrimidine-3-carboxamide (Compound I-G-46);
(S)-2-amino-N-(4-(4-(3,4-dimethylpiperazine-1-carbonyl)piperidin-1-yl)-5-fluoropyridin-3-yl)-6-fluoropyrazolo[1,5-a]pyrimidine-3-carboxamide (Compound I-G-47);
N-(4-(4-([1,3'-biazetidine]-1'-carbonyl)piperidin-1-yl)-5-fluoropyridin-3-yl)-2-amino-6-fluoropyrazolo[1,5-a]pyrimidine-3-carboxamide (Compound I-G-49);
(R)-2-amino-N-(4-(4-(3,4-dimethylpiperazine-1-carbonyl)piperidin-1-yl)-5-fluoropyridin-3-yl)-6-fluoropyrazolo[1,5-a]pyrimidine-3-carboxamide (Compound I-G-50);
2-amino-6-fluoro-N-(5-fluoro-4-(4-(8-methyl-3,8-diazabicyclo[3.2.1]octane-3-carbonyl)piperidin-1-yl)pyridin-3-yl)pyrazolo[1,5-a]pyrimidine-3-carboxamide (Compound I-G-52);
2-amino-6-fluoro-N-(5-fluoro-4-(4-(5-methyl-2,5-diazabicyclo[2.2.1]heptane-2-carbonyl)piperidin-1-yl)pyridin-3-yl)pyrazolo[1,5-a]pyrimidine-3-carboxamide (Compound I-G-53);
2-amino-6-fluoro-N-(5-methyl-4-(4-(4-methylpiperazine-1-carbonyl)piperidin-1-yl)pyridin-3-yl)pyrazolo[1,5-a]pyrimidine-3-carboxamide (Compound I-G-55);
2-amino-6-fluoro-N-(5-fluoro-4-(4-(3-(piperidin-1-yl)azetidine-1-carbonyl)piperidin-1-yl)pyridin-3-yl)pyrazolo[1,5-a]pyrimidine-3-carboxamide (Compound I-G-57);
(S)—N-(4-(4-([1,3'-bipyrrolidine]-1'-carbonyl)piperidin-1-yl)-5-fluoropyridin-3-yl)-2-amino-6-fluoropyrazolo[1,5-a]pyrimidine-3-carboxamide (Compound I-G-58);
2-amino-6-fluoro-N-(5-fluoro-4-(4-(4-(pyrrolidin-1-yl)piperidine-1-carbonyl)piperidin-1-yl)pyridin-3-yl)pyrazolo[1,5-a]pyrimidine-3-carboxamide (Compound I-G-59);
N-(4-(4-([1,4'-bipiperidine]-1'-carbonyl)piperidin-1-yl)-5-fluoropyridin-3-yl)-2-amino-6-fluoropyrazolo[1,5-a]pyrimidine-3-carboxamide (Compound I-G-60);
2-amino-6-fluoro-N-(5-fluoro-4-(4-(3-hydroxy-3-methylazetidine-1-carbonyl)piperidin-1-yl)pyridin-3-yl)pyrazolo[1,5-a]pyrimidine-3-carboxamide (Compound I-G-63);
2-amino-6-fluoro-N-(5-fluoro-4-(4-(3-(piperidin-1-yl)pyrrolidine-1-carbonyl)piperidin-1-yl)pyridin-3-yl)pyrazolo[1,5-a]pyrimidine-3-carboxamide (Compound I-G-64);
2-amino-6-fluoro-N-(5-fluoro-4-(4-(3-fluoroazetidine-1-carbonyl)piperidin-1-yl)pyridin-3-yl)pyrazolo[1,5-a]pyrimidine-3-carboxamide (Compound I-G-67);
2-amino-N-(4-(4-(4-(azetidin-1-yl)piperidine-1-carbonyl)piperidin-1-yl)-5-fluoropyridin-3-yl)-6-fluoropyrazolo[1,5-a]pyrimidine-3-carboxamide (Compound I-G-68);
N-(4-(4-(1,4-diazabicyclo[3.2.1]octane-4-carbonyl)piperidin-1-yl)-5-chloropyridin-3-yl)-2-amino-6-fluoropyrazolo[1,5-a]pyrimidine-3-carboxamide (Compound I-G-69);

N-(4-(4-((5S)-1,4-diazabicyclo[3.2.1]octane-4-carbonyl)pi-peridin-1-yl)-5-fluoropyridin-3-yl)-2-amino-6-fluoropy-razolo[1,5-a]pyrimidine-3-carboxamide (Compound I-G-70);

N-(4-(4-((5R)-1,4-diazabicyclo[3.2.1]octane-4-carbonyl)pi-peridin-1-yl)-5-fluoropyridin-3-yl)-2-amino-6-fluoropy-razolo[1,5-a]pyrimidine-3-carboxamide (Compound I-G-71);

N-(4-(4-(2-oxa-6-azaspiro[3.3]heptane-6-carbonyl)piperi-din-1-yl)-5-fluoropyridin-3-yl)-2-amino-6-fluoropyra-zolo[1,5-a]pyrimidine-3-carboxamide (Compound I-G-72);

2-amino-N-(4-(4-(3,3-difluoroazetidine-1-carbonyl)piperi-din-1-yl)-5-fluoropyridin-3-yl)-6-fluoropyrazolo[1,5-a]pyrimidine-3-carboxamide (Compound I-G-73);

2-amino-6-fluoro-N-(5-fluoro-4-(4-(3-fluoroazetidine-1-carbonyl)piperidin-1-yl)pyridin-3-yl)pyrazolo[1,5-a]py-rimidine-3-carboxamide (Compound I-G-74);

2-amino-6-fluoro-N-(5-fluoro-4-(4-(3-methoxy-3-methyl-azetidine-1-carbonyl)piperidin-1-yl)pyridin-3-yl)pyra-zolo[1,5-a]pyrimidine-3-carboxamide (Compound I-G-75);

2-amino-N-(4-(4-(3-cyanoazetidine-1-carbonyl)piperidin-1-yl)-5-fluoropyridin-3-yl)-6-fluoropyrazolo[1,5-a]pyrimi-dine-3-carboxamide (Compound I-G-76);

2-amino-N-(4-(4-(azetidine-1-carbonyl)piperidin-1-yl)pyri-din-3-yl)-6-fluoropyrazolo[1,5-a]pyrimidine-3-carbox-amide (Compound I-G-77);

2-amino-6-fluoro-N-(4-(4-(3-methoxyazetidine-1-carbonyl)piperidin-1-yl)pyridin-3-yl)pyrazolo[1,5-a]pyrimidine-3-carboxamide (Compound I-G-78);

2-amino-6-fluoro-N-(4-(4-(3-methoxy-3-methylazetidine-1-carbonyl)piperidin-1-yl)pyridin-3-yl)pyrazolo[1,5-a]pyrimidine-3-carboxamide (Compound I-G-79);

2-amino-N-(4-(4-(3,3-difluoroazetidine-1-carbonyl)piperi-din-1-yl)pyridin-3-yl)-6-fluoropyrazolo[1,5-a]pyrimi-dine-3-carboxamide (Compound I-G-80);

2-amino-N-(4-(4-(3-cyanoazetidine-1-carbonyl)piperidin-1-yl)pyridin-3-yl)-6-fluoropyrazolo[1,5-a]pyrimidine-3-carboxamide (Compound I-G-81);

2-amino-6-fluoro-N-(4-(4-(3-fluoroazetidine-1-carbonyl)pi-peridin-1-yl)pyridin-3-yl)pyrazolo[1,5-a]pyrimidine-3-carboxamide (Compound I-G-82);

2-amino-6-fluoro-N-(4-(4-(pyrrolidine-1-carbonyl)piperi-din-1-yl)pyridin-3-yl)pyrazolo[1,5-a]pyrimidine-3-car-boxamide (Compound I-G-83);

N-(4-(4-(2-oxa-6-azaspiro[3.4]octane-6-carbonyl)piperidin-1-yl)pyridin-3-yl)-2-amino-6-fluoropyrazolo[1,5-a]py-rimidine-3-carboxamide (Compound I-G-84);

2-amino-6-fluoro-N-(4-(4-(morpholine-4-carbonyl)piperi-din-1-yl)pyridin-3-yl)pyrazolo[1,5-a]pyrimidine-3-car-boxamide (Compound I-G-85);

2-amino-6-fluoro-N-(5-fluoro-4-(4-(3-(methylsulfonyl)aze-tidine-1-carbonyl)piperidin-1-yl)pyridin-3-yl)pyrazolo[1,5-a]pyrimidine-3-carboxamide (Compound I-G-86);

N-(4-(4-(1,4-diazabicyclo[3.2.2]nonane-4-carbonyl)piperi-din-1-yl)-5-fluoropyridin-3-yl)-2-amino-6-chloropyra-zolo[1,5-a]pyrimidine-3-carboxamide (Compound I-G-87);

N-(4-(4-(2-oxa-6-azaspiro[3.3]heptane-6-carbonyl)piperi-din-1-yl)pyridin-3-yl)-2-amino-6-fluoropyrazolo[1,5-a]pyrimidine-3-carboxamide (Compound I-G-88);

2-amino-6-fluoro-N-(4-(4-(3-(methylsulfonyl)azetidine-1-carbonyl)piperidin-1-yl)pyridin-3-yl)pyrazolo[1,5-a]py-rimidine-3-carboxamide (Compound I-G-89);

N-(4-(4-(1-oxa-6-azaspiro[3.3]heptane-6-carbonyl)piperi-din-1-yl)pyridin-3-yl)-2-amino-6-fluoropyrazolo[1,5-a]pyrimidine-3-carboxamide (Compound I-G-90);

2-amino-N-(4-(4-(3-ethoxyazetidine-1-carbonyl)piperidin-1-yl)pyridin-3-yl)-6-fluoropyrazolo[1,5-a]pyrimidine-3-carboxamide (Compound I-G-91);

2-amino-6-fluoro-N-(5-fluoro-4-(4-(4-(3-methyloxetan-3-yl)piperazine-1-carbonyl)piperidin-1-yl)pyridin-3-yl)pyrazolo[1,5-a]pyrimidine-3-carboxamide (Compound I-G-92);

(R)-2-amino-6-fluoro-N-(4-(4-(3-methoxypyrrolidine-1-carbonyl)piperidin-1-yl)pyridin-3-yl)pyrazolo[1,5-a]py-rimidine-3-carboxamide (Compound I-G-93);

(S)-2-amino-6-fluoro-N-(4-(4-(3-methoxypyrrolidine-1-carbonyl)piperidin-1-yl)pyridin-3-yl)pyrazolo[1,5-a]py-rimidine-3-carboxamide (Compound I-G-94);

4-(1-(3-(2-amino-6-fluoropyrazolo[1,5-a]pyrimidine-3-car-boxamido)-5-fluoropyridin-4-yl)piperidine-4-carbonyl)-1-methylpiperazine 1-oxide (Compound I-G-95);

2-amino-6-fluoro-N-(5-fluoro-4-(4-(4-(1-methylazetidin-3-yl)piperazine-1-carbonyl)piperidin-1-yl)pyridin-3-yl)pyrazolo[1,5-a]pyrimidine-3-carboxamide (Compound I-G-96);

2-amino-6-fluoro-N-(5-fluoro-4-(4-(3-(methoxymethyl)azetidine-1-carbonyl)piperidin-1-yl)pyridin-3-yl)pyra-zolo[1,5-a]pyrimidine-3-carboxamide (Compound I-G-98); and (S)-2-amino-6-fluoro-N-(5-fluoro-4-(4-(3-methoxypyrroli-dine-1-carbonyl)piperidin-1-yl)pyridin-3-yl)pyrazolo[1,5-a]pyrimidine-3-carboxamide (Compound I-G-99).

Example 5: 2-amino-6-fluoro-N-(5-fluoro-4-(4-(pip-erazine-1-carbonyl)piperidin-1-yl)pyridin-3-yl)pyra-zolo[1,5-a]pyrimidine-3-carboxamide (Compound I-G-12)

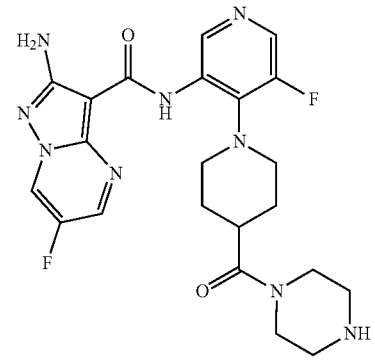 [SMILES: Nc1nn2cc(F)cnc2c1C(=O)Nc1cncc(F)c1N1CCC(C(=O)N2CCNCC2)CC1]

tert-butyl 4-(1-(3-(2-amino-6-fluoropyrazolo[1,5-a]py-rimidine-3-carboxamido)-5-fluoropyridin-4-yl)piperidine-4-carbonyl)piperazine-1-carboxylate prepared using proce-dure similar to Example 4 was dissolved in a mixture of DCM (5 mL)/TFA (1 mL, 12.98 mmol) and stirred at RT for 90 min. then concentrated in vacuo. The residue was purified by fractionlynx. Clean fractions were freeze dried to yield 2-amino-6-fluoro-N-(5-fluoro-4-(4-(piperazine-1-carbonyl)piperidin-1-yl)pyridin-3-yl)pyrazolo[1,5-a]pyrimidine-3-carboxamide. MS (ES+) 486.2.

The following compounds were successfully prepared using a procedure similar to Example 5:

2-amino-N-(4-(4-(3,3-dimethylpiperazine-1-carbonyl)pip-eridin-1-yl)-5-fluoropyridin-3-yl)-6-fluoropyrazolo[1,5-a]pyrimidine-3-carboxamide (Compound I-G-27);

N-(4-(4-(4,7-diazaspiro[2.5]octane-7-carbonyl)piperidin-1-yl)-5-fluoropyridin-3-yl)-2-amino-6-fluoropyrazolo[1,5-a]pyrimidine-3-carboxamide (Compound I-G-28);

2-amino-6-fluoro-N-(5-fluoro-4-(4-(3-(methylamino)azetidine-1-carbonyl)piperidin-1-yl)pyridin-3-yl)pyrazolo[1,5-a]pyrimidine-3-carboxamide (Compound I-G-34);

N-(4-(4-(3,8-diazabicyclo[3.2.1]octane-3-carbonyl)piperidin-1-yl)-5-fluoropyridin-3-yl)-2-amino-6-fluoropyrazolo[1,5-a]pyrimidine-3-carboxamide (Compound I-G-44);

(R)-2-amino-6-fluoro-N-(5-fluoro-4-(4-(3-methylpiperazine-1-carbonyl)piperidin-1-yl)pyridin-3-yl)pyrazolo[1,5-a]pyrimidine-3-carboxamide (Compound I-G-45);

2-amino-N-(5-chloro-4-(4-(piperazine-1-carbonyl)piperidin-1-yl)pyridin-3-yl)-6-fluoropyrazolo[1,5-a]pyrimidine-3-carboxamide (Compound I-G-48);

2-amino-6-fluoro-N-(5-fluoro-4-(4-(octahydropyrrolo[3,4-c]pyrrole-2-carbonyl)piperidin-1-yl)pyridin-3-yl)pyrazolo[1,5-a]pyrimidine-3-carboxamide (Compound I-G-51);

2-amino-6-fluoro-N-(5-methyl-4-(4-(piperazine-1-carbonyl)piperidin-1-yl)pyridin-3-yl)pyrazolo[1,5-a]pyrimidine-3-carboxamide (Compound I-G-56);

(S)-2-amino-6-fluoro-N-(5-fluoro-4-(4-(3-methylpiperazine-1-carbonyl)piperidin-1-yl)pyridin-3-yl)pyrazolo[1,5-a]pyrimidine-3-carboxamide (Compound I-G-61); and N-(4-(4-(2,5-diazabicyclo[4.1.0]heptane-2-carbonyl)piperidin-1-yl)-5-fluoropyridin-3-yl)-2-amino-6-fluoropyrazolo[1,5-a]pyrimidine-3-carboxamide (Compound I-G-62).

Example 6: 2-amino-N-(4-(4-(azetidin-1-yl)piperidin-1-yl)pyridin-3-yl)-6-chloropyrazolo[1,5-a]pyrimidine-3-carboxamide (Compound I-N-93)

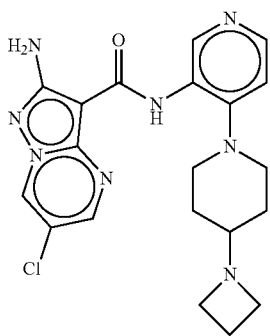

Step 1: 2-amino-6-chloro-N-(4-(4-oxopiperidin-1-yl)pyridin-3-yl)pyrazolo[1,5-a]pyrimidine-3-carboxamide To a solution of 2-amino-6-chloro-N-[4-(1,4-dioxa-8-azaspiro[4.5]decan-8-yl)-3-pyridyl]pyrazolo[1,5-a]pyrimidine-3-carboxamide (prepared according to a procedure similar to Example 1) (420 mg, 0.9771 mmol) in tetrahydrofuran (10 mL) was added HCl (4.886 mL of 2 M, 9.771 mmol). The resulting mixture was stirred at room temperature overnight. The resulting reaction mixture was diluted with water (100 mL), made basic with 2.5 N aqueous sodium hydroxide, and extracted three times with dichloromethane (100 mL). The combined organic layers were dried over anhydrous sodium sulfate, filtered, and concentrated under reduced pressure to give 2-amino-6-chloro-N-(4-(4-oxopiperidin-1-yl)pyridin-3-yl)pyrazolo[1,5-a]pyrimidine-3-carboxamide as a pale yellow solid which was used without further purification. MS (ES+) 386.1.

Step 2: 2-amino-N-(4-(4-(azetidin-1-yl)piperidin-1-yl)pyridin-3-yl)-6-chloropyrazolo[1,5-c]pyrimidine-3-carboxamide A solution of 2-amino-6-chloro-N-[4-(4-oxo-1-piperidyl)-3-pyridyl]pyrazolo[1,5-a]pyrimidine-3-carboxamide (50 mg, 0.1296 mmol), azetidine (Hydrochloric Acid (1)) (12.12 mg, 0.1296 mmol) and ammonium formate (8.172 mg, 0.1296 mmol) in toluene was heated at reflux for 1 h with a Dean-Stark apparatus. The reaction was cooled to room temperature and evaporated. The resulting yellow solid was dissolved in DMSO and purified by fractionlynx to yield 2-amino-N-(4-(4-(azetidin-1-yl)piperidin-1-yl)pyridin-3-yl)-6-chloropyrazolo[1,5-a]pyrimidine-3-carboxamide as a white solid. (27 mg, 31%). MS (ES+) 427.2.

The following compounds were successfully prepared using a procedure similar to Example 6:

2-amino-6-chloro-N-(4-(4-(3-(dimethylamino)azetidin-1-yl)piperidin-1-yl)pyridin-3-yl)pyrazolo[1,5-a]pyrimidine-3-carboxamide (Compound I-N-94);

2-amino-6-chloro-N-(4-(4-(3-methoxypyrrolidin-1-yl)piperidin-1-yl)pyridin-3-yl)pyrazolo[1,5-a]pyrimidine-3-carboxamide (Compound I-N-95);

N-(4-(4-(2-oxa-6-azaspiro[3.3]heptan-6-yl)piperidin-1-yl)pyridin-3-yl)-2-amino-6-chloropyrazolo[1,5-a]pyrimidine-3-carboxamide (Compound I-N-96);

2-amino-6-chloro-N-(4-(4-(4-methylpiperazin-1-yl)piperidin-1-yl)pyridin-3-yl)pyrazolo[1,5-a]pyrimidine-3-carboxamide (Compound I-N-97);

(R)-2-amino-6-chloro-N-(4-(4-(3-fluoropyrrolidin-1-yl)piperidin-1-yl)pyridin-3-yl)pyrazolo[1,5-a]pyrimidine-3-carboxamide (Compound I-N-98);

N-(4-(4-(2-oxa-6-azaspiro[3.4]octan-6-yl)piperidin-1-yl)pyridin-3-yl)-2-amino-6-chloropyrazolo[1,5-a]pyrimidine-3-carboxamide (Compound I-N-99);

2-amino-6-chloro-N-(4-(4-(1-oxidothiomorpholino)piperidin-1-yl)pyridin-3-yl)pyrazolo[1,5-a]pyrimidine-3-carboxamide (Compound I-N-100);

2-amino-6-chloro-N-(4-(4-(5,6-dihydroimidazo[1,5-a]pyrazin-7(8H)-yl)piperidin-1-yl)pyridin-3-yl)pyrazolo[1,5-a]pyrimidine-3-carboxamide (Compound I-N-101);

2-amino-6-chloro-N-(4-(4-(5,6-dihydroimidazo[1,2-a]pyrazin-7(8H)-yl)piperidin-1-yl)pyridin-3-yl)pyrazolo[1,5-a]pyrimidine-3-carboxamide (Compound I-N-102);

(S)-2-amino-6-chloro-N-(4-(4-(3-fluoropyrrolidin-1-yl)piperidin-1-yl)pyridin-3-yl)pyrazolo[1,5-a]pyrimidine-3-carboxamide (Compound I-N-103);

2-amino-6-chloro-N-(4-(4-morpholinopiperidin-1-yl)pyridin-3-yl)pyrazolo[1,5-a]pyrimidine-3-carboxamide (Compound I-N-104);

2-amino-6-chloro-N-(4-(4-(pyrrolidin-1-yl)piperidin-1-yl)pyridin-3-yl)pyrazolo[1,5-a]pyrimidine-3-carboxamide (Compound I-N-105);

2-amino-6-chloro-N-(4-(4-(3-(dimethylamino)pyrrolidin-1-yl)piperidin-1-yl)pyridin-3-yl)pyrazolo[1,5-a]pyrimidine-3-carboxamide (Compound I-N-106);

2-amino-6-chloro-N-(4-(4-(3-methoxyazetidin-1-yl)piperidin-1-yl)pyridin-3-yl)pyrazolo[1,5-a]pyrimidine-3-carboxamide (Compound I-N-107);

2-amino-6-chloro-N-(4-(4-(3,3-difluoroazetidin-1-yl)piperidin-1-yl)pyridin-3-yl)pyrazolo[1,5-a]pyrimidine-3-carboxamide (Compound I-N-108); and

303

N-(4-(4-(6-oxa-1-azaspiro[3.3]heptan-1-yl)piperidin-1-yl)pyridin-3-yl)-2-amino-6-chloropyrazolo[1,5-a]pyrimidine-3-carboxamide (Compound I-N-109).

Example 7: 2-amino-N-(5-chloro-4-(4-(oxetan-3-yl)piperazin-1-yl)pyridin-3-yl)-6-fluoropyrazolo[1,5-a]pyrimidine-3-carboxamide (Compound I-N-110)

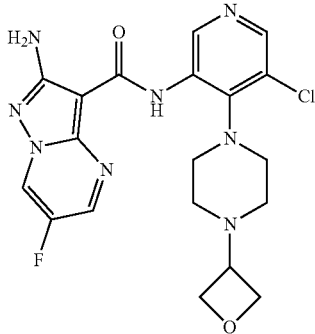 [SMILES: Nc1nn2cc(F)cnc2c1C(=O)Nc1cncc(Cl)c1N1CCN(C2COC2)CC1]

To a solution of 2-amino-N-(5-chloro-4-(piperazin-1-yl)pyridin-3-yl)-6-fluoropyrazolo[1,5-a]pyrimidine-3-carboxamide (51 mg, 0.13 mmol) (synthesized according to a procedure similar to Example 2) in THF (4 mL) was added oxetan-3-one (14.31 mg, 11.63 μL, 0.1986 mmol) and triacetoxyborohydride (Sodium Ion (1)) (56.12 mg, 0.2648 mmol), and the mixture was stirred at rt for 4 h. The reaction mixture was partitioned between an aqueous saturated solution of $NaHCO_3$ and ethyl acetate. The organic extract was washed with brine, dried over $MgSO_4$ and concentrated under reduced pressure. The residue was purified by fractionlynx to yield 2-amino-N-(5-chloro-4-(4-(oxetan-3-yl)piperazin-1-yl)pyridin-3-yl)-6-fluoropyrazolo[1,5-a]pyrimidine-3-carboxamide. MS (ES+) 447.2.

The following compounds were synthesized according to a procedure similar to Example 7:

2-amino-N-(5-chloro-4-(8-(oxetan-3-yl)hexahydro-1H-pyrazino[1,2-a]pyrazin-2(6H)-yl)pyridin-3-yl)-6-fluoropyrazolo[1,5-a]pyrimidine-3-carboxamide (Compound I-N-38);

(R)-2-amino-N-(5-cyclopropyl-4-(4-(tetrahydrofuran-3-yl)piperazin-1-yl)pyridin-3-yl)-6-fluoropyrazolo[1,5-a]pyrimidine-3-carboxamide (Compound I-N-119);

(S)-2-amino-N-(5-cyclopropyl-4-(4-(tetrahydrofuran-3-yl)piperazin-1-yl)pyridin-3-yl)-6-fluoropyrazolo[1,5-a]pyrimidine-3-carboxamide (Compound I-N-120);

2-amino-6-fluoro-N-(5-fluoro-4-(4-(tetrahydro-2H-pyran-4-yl)piperazin-1-yl)pyridin-3-yl)pyrazolo[1,5-a]pyrimidine-3-carboxamide (Compound I-N-121);

2-amino-6-fluoro-N-(5-fluoro-4-(4-(tetrahydrofuran-3-yl)piperazin-1-yl)pyridin-3-yl)pyrazolo[1,5-a]pyrimidine-3-carboxamide (Compound I-N-122);

2-amino-6-fluoro-N-(5-methyl-4-(4-(tetrahydro-2H-pyran-4-yl)piperazin-1-yl)pyridin-3-yl)pyrazolo[1,5-a]pyrimidine-3-carboxamide (Compound I-N-123); and 2-amino-N-(5-chloro-4-(4-(tetrahydrofuran-3-yl)piperazin-1-yl)pyridin-3-yl)-6-fluoropyrazolo[1,5-a]pyrimidine-3-carboxamide (Compound I-N-124).

304

Example 8: 2-amino-6-fluoro-N-(5-fluoro-4-(4-(1-methylpiperidine-4-carbonyl)piperazin-1-yl)pyridin-3-yl)pyrazolo[1,5-a]pyrimidine-3-carboxamide (Compound I-N-128)

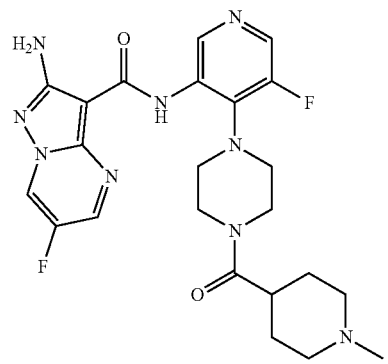 [SMILES: CN1CCC(C(=O)N2CCN(c3c(F)cncc3NC(=O)c3c(N)nn4cc(F)cnc34)CC2)CC1]

A microwave vial was charged with 2-amino-6-fluoro-N-(5-fluoro-4-piperazin-1-yl-3-pyridyl)pyrazolo[1,5-a]pyrimidine-3-carboxamide (79 mg, 0.2110 mmol) (synthesized according to a procedure similar to Example 2), 1-methylpiperidine-4-carboxylic acid (Hydrochloric Acid (1)) (37.90 mg, 0.2110 mmol), TBTU (74.52 mg, 0.2321 mmol), $Et_3N$ (46.97 mg, 64.70 μL, 0.4642 mmol) in NMP (0.5 mL), the tube sealed and stirred at 100° C. overnight. The mixture was cooled to RT and was loaded into a MeOH pre-washed SCX column, rinsed with MeOH and released with methanolic ammonia. The ammonia extracts were concentrated under reduced pressure to give 110 mg of a brown oil/gum, which was purified by Fraction Lynx reverse phase column chromatography. The clean fractions were combined and freeze dried, yielding 2-amino-6-fluoro-N-(5-fluoro-4-(4-(1-methylpiperidine-4-carbonyl)piperazin-1-yl)pyridin-3-yl)pyrazolo[1,5-a]pyrimidine-3-carboxamide. MS (ES+) 500.2.

The following compounds were synthesized according to a procedure similar to Example 8:

2-amino-6-fluoro-N-(5-fluoro-4-(4-(quinuclidine-4-carbonyl)piperazin-1-yl)pyridin-3-yl)pyrazolo[1,5-a]pyrimidine-3-carboxamide (Compound I-N-134);

2-amino-N-(4-(4-(2-(dimethylamino)acetyl)piperazin-1-yl)-5-fluoropyridin-3-yl)-6-fluoropyrazolo[1,5-a]pyrimidine-3-carboxamide (Compound I-N-153);

2-amino-6-fluoro-N-(5-fluoro-4-(4-(1-methylpyrrolidine-3-carbonyl)piperazin-1-yl)pyridin-3-yl)pyrazolo[1,5-a]pyrimidine-3-carboxamide (Compound I-N-156);

(S)-2-amino-6-fluoro-N-(5-fluoro-4-(4-(1-methylpyrrolidine-2-carbonyl)piperazin-1-yl)pyridin-3-yl)pyrazolo[1,5-a]pyrimidine-3-carboxamide (Compound I-N-157);

2-amino-N-(4-(4-(2-(azetidin-1-yl)acetyl)piperazin-1-yl)-5-fluoropyridin-3-yl)-6-fluoropyrazolo[1,5-a]pyrimidine-3-carboxamide (Compound I-N-160);

2-amino-6-fluoro-N-(5-fluoro-4-(4-(1-methylpiperidine-2-carbonyl)piperazin-1-yl)pyridin-3-yl)pyrazolo[1,5-a]pyrimidine-3-carboxamide (Compound I-N-173);

2-amino-6-fluoro-N-(5-fluoro-4-(4-(4-methylmorpholine-2-carbonyl)piperazin-1-yl)pyridin-3-yl)pyrazolo[1,5-a]pyrimidine-3-carboxamide (Compound I-N-174);

(R)-2-amino-6-fluoro-N-(5-fluoro-4-(4-(1-methylpyrrolidine-2-carbonyl)piperazin-1-yl)pyridin-3-yl)pyrazolo[1,5-a]pyrimidine-3-carboxamide (Compound I-N-181);

2-amino-N-(4-(4-(1-ethylpyrrolidine-2-carbonyl)piperazin-1-yl)-5-fluoropyridin-3-yl)-6-fluoropyrazolo[1,5-a]pyrimidine-3-carboxamide (Compound I-N-185);

2-amino-6-fluoro-N-(5-fluoro-4-(4-(2-(pyrrolidin-1-yl)acetyl)piperazin-1-yl)pyridin-3-yl)pyrazolo[1,5-a]pyrimidine-3-carboxamide (Compound I-N-187);

(S)-2-amino-6-fluoro-N-(4-(4-(1-methylpyrrolidine-2-carbonyl)piperazin-1-yl)pyridin-3-yl)pyrazolo[1,5-a]pyrimidine-3-carboxamide (Compound I-N-198);

(R)-2-amino-6-fluoro-N-(4-(4-(1-methylpyrrolidine-2-carbonyl)piperazin-1-yl)pyridin-3-yl)pyrazolo[1,5-a]pyrimidine-3-carboxamide (Compound I-N-199);

2-amino-6-fluoro-N-(5-fluoro-4-(4-(octahydroindolizine-2-carbonyl)piperazin-1-yl)pyridin-3-yl)pyrazolo[1,5-a]pyrimidine-3-carboxamide (Compound I-N-203);

2-amino-N-(4-(4-(1-ethylpiperidine-2-carbonyl)piperazin-1-yl)-5-fluoropyridin-3-yl)-6-fluoropyrazolo[1,5-a]pyrimidine-3-carboxamide (Compound I-N-204);

2-amino-6-fluoro-N-(5-fluoro-4-(4-(1-isopropylpyrrolidine-2-carbonyl)piperazin-1-yl)pyridin-3-yl)pyrazolo[1,5-a]pyrimidine-3-carboxamide (Compound I-N-205);

2-amino-6-fluoro-N-(5-fluoro-4-(4-(1-isopropylpyrrolidine-3-carbonyl)piperazin-1-yl)pyridin-3-yl)pyrazolo[1,5-a]pyrimidine-3-carboxamide (Compound I-N-206);

2-amino-N-(4-(4-(1-ethylpyrrolidine-3-carbonyl)piperazin-1-yl)-5-fluoropyridin-3-yl)-6-fluoropyrazolo[1,5-a]pyrimidine-3-carboxamide (Compound I-N-207);

2-amino-6-fluoro-N-(5-fluoro-4-(4-(1-(oxetan-3-yl)piperidine-4-carbonyl)piperazin-1-yl)pyridin-3-yl)pyrazolo[1,5-a]pyrimidine-3-carboxamide (Compound I-N-211);

2-amino-6-fluoro-N-(5-fluoro-4-(4-(1-methylpiperidine-2-carbonyl)piperazin-1-yl)pyridin-3-yl)pyrazolo[1,5-a]pyrimidine-3-carboxamide (Compound I-N-214);

2-amino-6-fluoro-N-(5-fluoro-4-(4-(4-methylmorpholine-3-carbonyl)piperazin-1-yl)pyridin-3-yl)pyrazolo[1,5-a]pyrimidine-3-carboxamide (Compound I-N-227);

2-amino-6-fluoro-N-(4-(4-(oxetane-3-carbonyl)piperazin-1-yl)pyridin-3-yl)pyrazolo[1,5-a]pyrimidine-3-carboxamide (Compound I-N-254);

N-(4-(2-acetyl-2,7-diazaspiro[3.5]nonan-7-yl)pyridin-3-yl)-2-amino-6-fluoropyrazolo[1,5-a]pyrimidine-3-carboxamide (Compound I-N-251);

N-(4-(4-acetylpiperazin-1-yl)pyridin-3-yl)-2-amino-6-fluoropyrazolo[1,5-a]pyrimidine-3-carboxamide (Compound I-N-254);

N-(4-(2-acetyl-2,8-diazaspiro[4.5]decan-8-yl)pyridin-3-yl)-2-amino-6-fluoropyrazolo[1,5-a]pyrimidine-3-carboxamide (Compound I-N-257);

methyl-4-(3-(2-amino-6-fluoropyrazolo[1,5-a]pyrimidine-3-carboxamido)-5-fluoropyridin-4-yl)piperazine-1-carboxylate (Compound I-N-261);

N-(4-(1-acetyl-1,8-diazaspiro[4.5]decan-8-yl)pyridin-3-yl)-2-amino-6-fluoropyrazolo[1,5-a]pyrimidine-3-carboxamide (Compound I-N-262);

N-(4-(1-acetylpiperidin-4-yl)pyridin-3-yl)-2-amino-6-fluoropyrazolo[1,5-a]pyrimidine-3-carboxamide (Compound I-C-69);

2-amino-N-(4-(1-(cyclopropanecarbonyl)piperidin-4-yl)pyridin-3-yl)-6-fluoropyrazolo[1,5-a]pyrimidine-3-carboxamide (Compound I-C-70);

2-amino-N-(4-(1-(1-cyanocyclopropanecarbonyl)piperidin-4-yl)pyridin-3-yl)-6-fluoropyrazolo[1,5-a]pyrimidine-3-carboxamide (Compound I-C-71);

2-amino-6-fluoro-N-(5-fluoro-4-(4-(tetrahydrofuran-3-carbonyl)piperazin-1-yl)pyridin-3-yl)pyrazolo[1,5-a]pyrimidine-3-carboxamide (Compound I-N-274);

N-(4-(4-acetylpiperazin-1-yl)-5-fluoropyridin-3-yl)-2-amino-6-fluoropyrazolo[1,5-a]pyrimidine-3-carboxamide (Compound I-N-275);

2-amino-N-(4-(4-(cyclopropanecarbonyl)piperazin-1-yl)-5-fluoropyridin-3-yl)-6-fluoropyrazolo[1,5-a]pyrimidine-3-carboxamide (Compound I-N-276); and 2-amino-6-fluoro-N-(5-fluoro-4-(4-(oxetane-3-carbonyl)piperazin-1-yl)pyridin-3-yl)pyrazolo[1,5-a]pyrimidine-3-carboxamide (Compound I-N-278).

Example 9: 2-amino-N-(4-(4-(azetidine-3-carbonyl)piperazin-1-yl)-5-fluoropyridin-3-yl)-6-fluoropyrazolo[1,5-a]pyrimidine-3-carboxamide (Compound I-N-168)

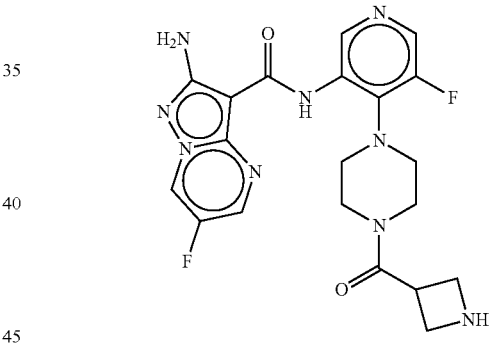

Tert-butyl 3-(4-(3-(2-amino-6-fluoropyrazolo[1,5-a]pyrimidine-3-carboxamido)-5-fluoropyridin-4-yl)piperazine-1-carbonyl)azetidine-1-carboxylate (73 mg, 0.1309 mmol) (prepared using a procedure similar to Example 8) was dissolved in DCM (219.0 µL). TFA (298.5 mg, 201.7 µL, 2.618 mmol) was added and the mixture was stirred at RT for 2 hr. The reaction mixture was concentrated in vacuo and the residue was purified by fractionlynx yielding 2-amino-N-(4-(4-(azetidine-3-carbonyl)piperazin-1-yl)-5-fluoropyridin-3-yl)-6-fluoropyrazolo[1,5-a]pyrimidine-3-carboxamide as a cream solid. MS (ES+) 458.1.

The following compounds were synthesized according to the procedure similar to Example 9:

2-amino-6-fluoro-N-(5-fluoro-4-(4-(morpholine-2-carbonyl)piperazin-1-yl)pyridin-3-yl)pyrazolo[1,5-a]pyrimidine-3-carboxamide (Compound I-N-172).

Example 10: 2-amino-6-fluoro-N-(5-fluoro-4-(4-((tetrahydro-2H-pyran-4-yl)sulfonyl)piperazin-1-yl)pyridin-3-yl)pyrazolo[1,5-a]pyrimidine-3-carboxamide (Compound I-N-158)

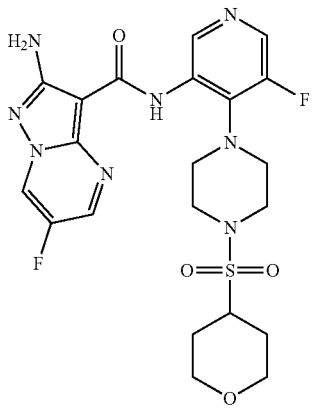 [SMILES: Nc1nn2cc(F)cnc2c1C(=O)Nc1cncc(F)c1N1CCN(S(=O)(=O)C2CCOCC2)CC1]

Tetrahydropyran-4-sulfonyl chloride (16.28 mg, 0.08815 mmol) was added to a suspension of 2-amino-6-fluoro-N-(5-fluoro-4-piperazin-1-yl-3-pyridyl)pyrazolo[1,5-a]pyrimidine-3-carboxamide (30 mg, 0.08014 mmol) (synthesized according to the procedure similar to Example 2) and Et₃N (12.16 mg, 16.75 µL, 0.1202 mmol) in DMF (0.2 mL). The crude mixture was purified by Fractionlynx HPLC. The clean aqueous fractions were combined and lyophilised, yielding 2-amino-6-fluoro-N-(5-fluoro-4-(4-((tetrahydro-2H-pyran-4-yl)sulfonyl)piperazin-1-yl)pyridin-3-yl)pyrazolo[1,5-a]pyrimidine-3-carboxamide. MS (ES+) 523.1.

The following compounds were synthesized according to methods similar to the one depicted in the procedure described in Example 10:

2-amino-N-(4-(4-(cyclopropylsulfonyl)piperazin-1-yl)-5-fluoropyridin-3-yl)-6-fluoropyrazolo[1,5-a]pyrimidine-3-carboxamide (Compound I-N-159);

2-amino-6-fluoro-N-(5-fluoro-4-(4-((1-methylpiperidin-4-yl)sulfonyl)piperazin-1-yl)pyridin-3-yl)pyrazolo[1,5-a]pyrimidine-3-carboxamide (Compound I-N-175);

2-amino-N-(4-(4-(cyclopropylsulfonyl)piperazin-1-yl)pyridin-3-yl)-6-fluoropyrazolo[1,5-a]pyrimidine-3-carboxamide (Compound I-N-176);

2-amino-6-fluoro-N-(4-(4-((tetrahydro-2H-pyran-4-yl)sulfonyl)piperazin-1-yl)pyridin-3-yl)pyrazolo[1,5-a]pyrimidine-3-carboxamide (Compound I-N-177);

2-amino-6-fluoro-N-(4-(4-(methylsulfonyl)piperazin-1-yl)pyridin-3-yl)pyrazolo[1,5-a]pyrimidine-3-carboxamide (Compound I-N-178);

2-amino-6-fluoro-N-(4-(4-((tetrahydrofuran-3-yl)sulfonyl)piperazin-1-yl)pyridin-3-yl)pyrazolo[1,5-a]pyrimidine-3-carboxamide (Compound I-N-179);

2-amino-6-fluoro-N-(4-(4-((1-methylpiperidin-4-yl)sulfonyl)piperazin-1-yl)pyridin-3-yl)pyrazolo[1,5-a]pyrimidine-3-carboxamide (Compound I-N-188);

2-amino-6-fluoro-N-(4-(4-(oxetan-3-ylsulfonyl)piperazin-1-yl)pyridin-3-yl)pyrazolo[1,5-a]pyrimidine-3-carboxamide (Compound I-N-195); and 2-amino-6-fluoro-N-(5-fluoro-4-(4-(oxetan-3-ylsulfonyl)piperazin-1-yl)pyridin-3-yl)pyrazolo[1,5-a]pyrimidine-3-carboxamide (Compound I-N-202).

Example 11: 2-amino-6-fluoro-N-(5-fluoro-4-(4-((tetrahydro-2H-pyran-4-yl)sulfonyl)piperazin-1-yl)pyridin-3-yl)pyrazolo[1,5-a]pyrimidine-3-carboxamide (Compound I-N-131)

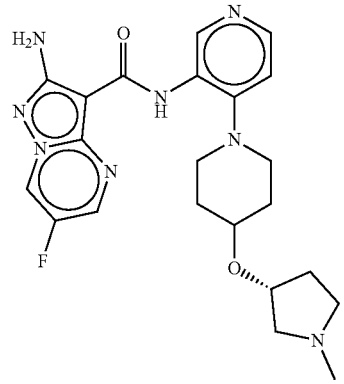

To a solution of (R)-2-amino-6-fluoro-N-(4-(4-(pyrrolidin-3-yloxy)piperidin-1-yl)pyridin-3-yl)pyrazolo[1,5-a]pyrimidine-3-carboxamide (synthesized according to a procedure similar to Example 2) was dissolved in a mixture of DCE (5.0 mL) and AcOH (0.050 mL). Formaldehyde (37% in water, 47.46 mg, 0.5848 mmol) was added and the mixture was stirred at RT for 30 mins. Triacetoxyboranuide (Sodium Ion (1)) (186 mg, 0.8772 mmol) was added portionwise. The mixture was stirred at RT for 1 hour and was quenched by the addition of water and methanol. The mixture was concentrated under reduced pressure and the residue was purified by fractionlynx to yield 2-amino-6-fluoro-N-(5-fluoro-4-(4-((tetrahydro-2H-pyran-4-yl)sulfonyl)piperazin-1-yl)pyridin-3-yl)pyrazolo[1,5-a]pyrimidine-3-carboxamide. MS (ES+) 455.2.

The following compounds were synthesized according to a procedure similar to Example 11:

(R)-2-amino-6-fluoro-N-(5-fluoro-4-(4-((1-methylpyrrolidin-3-yl)oxy)piperidin-1-yl)pyridin-3-yl)pyrazolo[1,5-a]pyrimidine-3-carboxamide (Compound I-N-132);

2-amino-6-fluoro-N-(4-(4-((1-methylpiperidin-4-yl)oxy)piperidin-1-yl)pyridin-3-yl)pyrazolo[1,5-a]pyrimidine-3-carboxamide (Compound I-N-154); and 2-amino-6-fluoro-N-(4-(4-((1-methylazetidin-3-yl)oxy)piperidin-1-yl)pyridin-3-yl)pyrazolo[1,5-a]pyrimidine-3-carboxamide (Compound I-N-164).

Example 12: 2-amino-N-(5-cyano-4-(4-methylpiperazin-1-yl)pyridin-3-yl)-6-fluoropyrazolo[1,5-a]pyrimidine-3-carboxamide (Compound I-N-113)

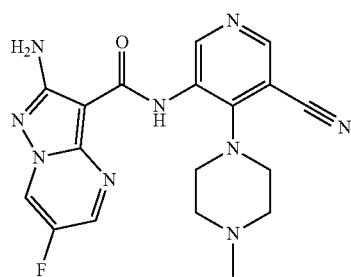 [SMILES: CN1CCN(c2c(C#N)cncc2NC(=O)c2c(N)nn3cc(F)cnc23)CC1]

A mixture of 2-amino-N-[5-bromo-4-(4-methylpiperazin-1-yl)-3-pyridyl]-6-fluoro-pyrazolo[1,5-a]pyrimidine-3-carboxamide (80.4 mg, 0.1790 mmol) synthesized according to a procedure similar to Example 1, Pd$_2$(dba)$_3$ (6.557 mg, 0.007160 mmol), zinc cyanide (18.92 mg, 10.23 µL, 0.1611 mmol) and xantphos (8.286 mg, 0.01432 mmol) was placed in a sealed microwave tube and evacuated and flushed with nitrogen. Solvent DMF (1.6 mL) was added and nitrogen bubbled through the reaction (with needle as outlet and inlet) for 5 mins. The reaction was heated at 120° C. for 1 h. LCMS shows reaction near completion, so cooled to room temperature and loaded onto an SCX-2 cartidge, eluting with MeOH and then NH$_3$/MeOH. The basic fraction was evaporated and purified by fractionlynx and lyophilize to yield 2-amino-N-(5-cyano-4-(4-methylpiperazin-1-yl)pyridin-3-yl)-6-fluoropyrazolo[1,5-a]pyrimidine-3-carboxamide as a white solid. MS (ES+) 396.2.

Example 13: 2-amino-N-(4-(4-(azetidine-3-carbonyl)piperazin-1-yl)-5-fluoropyridin-3-yl)-6-fluoropyrazolo[1,5-a]pyrimidine-3-carboxamide (Compound I-N-194)

A solution of 2-amino-N-[4-[4-(azetidine-3-carbonyl)piperazin-1-yl]-5-fluoro-3-pyridyl]-6-fluoro-pyrazolo[1,5-a]pyrimidine-3-carboxamide (Trifluoroacetic Acid (2)) (20 mg, 0.02918 mmol), (synthesized according to Example 9), and formaldehyde (3.552 µL of 37% w/v, 0.04377 mmol) in DMF (1 mL) was stirred for 1 h at RT. Triacetoxyboranuide (Sodium Ion (1)) (9.277 mg, 0.04377 mmol) was added and the reaction mixture was stirred at RT for 2 hr before it was quenched by the addition of methanol. The crude mixture was purified by Fractionlynx HPLC. The aqueous fractions were combined and lyophilised, yielding 2-amino-N-(4-(4-(azetidine-3-carbonyl)piperazin-1-yl)-5-fluoropyridin-3-yl)-6-fluoropyrazolo[1,5-a]pyrimidine-3-carboxamide (3 mg, 21%). MS (ES+) 472.1.

Example 14: 2-amino-N-(4-(4-(2-(azetidin-1-yl)-2-oxoethyl)piperazin-1-yl)-5-fluoropyridin-3-yl)-6-fluoropyrazolo[1,5-a]pyrimidine-3-carboxamide (Compound I-N-228)

1-(azetidin-1-yl)-2-chloro-ethanone (12.03 mg, 0.09003 mmol) was added to a solution of 2-amino-6-fluoro-N-(5-fluoro-4-piperazin-1-yl-3-pyridyl)pyrazolo[1,5-a]pyrimidine-3-carboxamide (Trifluoroacetic Acid (3)) (50 mg, 0.06002 mmol) (synthesized according to a procedure similar to Example 2) and Et$_3$N (30.37 mg, 41.83 µL, 0.3001 mmol) in DMF (2 mL). The solution was stirred at RT for 18 hr.

The crude mixture was purified by Fractionlynx HPLC. The aqueous fractions were combined and lyophilised yielding 2-amino-N-(4-(4-(2-(azetidin-1-yl)-2-oxoethyl)piperazin-1-yl)-5-fluoropyridin-3-yl)-6-fluoropyrazolo[1,5-a]pyrimidine-3-carboxamide (30 mg, 71%). MS (ES+) 472.1.

| | | | Compound Analytical Data |
|---|---|---|---|
| Cmpd No. | LCMS ES+ | LCMS (Rt min) | HNMR |
| I-N-1 | 413.3 | 0.58 | $^1$H NMR (500 MHz, DMSO-d6) δ 9.77 (s, 1H), 9.46 (dd, J = 4.8, 2.5 Hz, 1H), 9.42 (s, 1H), 8.82 (d, J = 2.5 Hz, 1H), 8.23 (d, J = 5.3 Hz, 1H), 7.19 (d, J = 5.2 Hz, 1H), 6.76 (s, 2H), 4.58 (t, J = 6.5 Hz, 2H), 4.46 (t, J = 6.1 Hz, 2H), 3.60 (p, J = 6.3 Hz, 1H), 2.98 (t, J = 4.7 Hz, 4H), 2.50 (t, J = 3.5 Hz, 4H). |
| I-N-2 | 392.1 | 0.51 | $^1$H NMR (500 MHz, DMSO-d6) δ 9.94 (s, 1H), 9.47 (s, 1H), 9.06 (d, J = 2.1 Hz, 1H), 8.73 (d, J = 2.1 Hz, 1H), 8.20 (d, J = 5.1 Hz, 1H), 7.18 (d, J = 5.3 Hz), 6.77 (s, 3H), 4.14 (s, 2H), 3.14 (dt, J = 12.9, 3.5 Hz, 2H), 2.77 (dd, J = 9.8, 5.2 Hz, 1H), 2.72 (td, J = 11.8, 11.4, 2.8 Hz, 2H), 1.91-1.82 (m, 2H), 1.67-1.55 (m, 2H). |
| I-N-3 | 371.2 | 1.82* | $^1$H NMR (500 MHz, Methanol-d4) δ 2.43 (3H, s), 2.75-2.75 (4H, m), 3.1-3.13 (4H, m), 7.22-7.23 (1H, d), 8.21-8.22 (1H, d), 8.72-8.73 (1H, d), 9.02-9.04 (1H, dd), 9.42 91H, s). |
| I-N-4 | 399.2 | 2.16* | — |
| I-N-5 | 411.3 | 2.16* | $^1$H NMR (500 MHz, DMSO-d6) δ 9.82 (s, 1H), 9.54 (s, 1H), 9.27 (s, 1H), 8.96 (s, 1H), 8.17 (s, 1H), 6.80 (br, 2H), 3.23 (m, 4H), 2.93 (s, 3H), 2.52 (br, 4H), 2.13 (m, 1H), 1.09 (m, 2H), 0.92 (m, 2H). |
| I-N-6 | 460.2 | 0.67 | $^1$H NMR (500 MHz, Methanol-d4) δ 9.64 (s, 2H), 9.00 (s, 1H), 8.23 (s, 1H), 3.82 (td, J = 11.5, 2.9 Hz, 1H), 3.53-3.43 (m, 1H), 3.04-2.88 (m, 5H), 2.90-2.74 (m, 3H), 2.64-2.54 (m, 1H), 2.42-2.36 (m, 1H), 2.35 (s, 3H), 2.02-1.92 (m, 1H). |
| I-N-7 | 339.2 | 0.51 | $^1$H NMR (500 MHz, Methanol-d4) δ 9.62 (d, J = 0.6 Hz, 1H), 9.35 (t, J = 1.4 Hz, 1H), 9.03 (dd, J = 4.4, 2.5 Hz, 1H), 8.62 (d, J = 5.3 Hz, 1H), 8.47 (dd, J = 2.6, 0.5 Hz, 1H), 7.98 (dd, J = 1.9, 1.5 Hz, 1H), 7.86 (dd, J = 1.9, 1.3 Hz, 1H), 7.74 (dd, J = 5.2, 0.6 Hz, 1H). |
| I-N-8 | 396.3 | 0.55 | $^1$H NMR (500 MHz, Methanol-d4) δ 10.04 (d, J = 0.8 Hz, 1H), 8.89 (dd, J = 4.4, 2.6 Hz, 1H), 8.63 (d, J = 2.5 Hz, 1H), 8.48 (dd, J = 6.1, 0.8 Hz, 1H), 8.45 (d, J = 0.9 Hz, 1H), 8.06 (d, J = 0.7 Hz, 1H), 8.02 (d, J = 6.3 Hz, 1H), 3.35 (dd, J = 8.3, 7.0 Hz, 2H), 3.05 (dd, J = 8.0, 7.2 Hz, 2H), 2.78 (s, 3H). |
| I-N-9 | 410.3 | 0.67 | $^1$H NMR (500 MHz, Methanol-d4) δ 10.06 (d, J = 0.9 Hz, 1H), 8.93-8.87 (m, 1H), 8.64 (dd, J = 2.6, 0.7 Hz, 1H), 8.49 (dd, J = 6.2, 0.8 Hz, 1H), 8.46 (d, J = 0.9 Hz, 1H), 8.07 (s, 1H), 8.02 (d, J = 6.2 Hz, 1H), 3.51-3.44 (m, 2H), 3.15-3.08 (m, 2H), 2.99 (s, 6H). |

-continued

| Compound Analytical Data | | | |
|---|---|---|---|
| Cmpd No. | LCMS ES+ | LCMS (Rt min) | HNMR |
| I-N-10 | 427.3 | 0.59 | $^1$H NMR (500 MHz, Methanol-d4) δ 9.42 (s, 1H), 9.06-8.98 (m, 1H), 8.77-8.70 (m, 1H), 8.22 (d, J = 5.4 Hz, 1H), 8.09 (d, J = 2.4 Hz, 1H), 7.21 (d, J = 5.4 Hz, 1H), 5.53 (s, 2H), 4.00 (td, J = 8.6, 4.1 Hz, 1H), 3.94 (dd, J = 8.8, 6.8 Hz, 1H), 3.83 (td, J = 8.5, 7.2 Hz, 1H), 3.73 (dd, J = 8.8, 6.5 Hz, 1H), 3.22-3.15 (m, 1H), 3.15-3.06 (m, 4H), 2.90-2.80 (m, 2H), 2.78-2.69 (m, 2H), 2.24-2.15 (m, 1H), 1.97-1.85 (m, 1H). |
| I-N-11 | | | $^1$H NMR (500 MHz, Methanol-d4) δ 9.39 (d, J = 0.5 Hz, 1H), 9.05 (dd, J = 4.4, 2.6 Hz, 1H), 8.74-8.68 (m, 1H), 8.23 (d, J = 5.5 Hz, 1H), 7.23 (dd, J = 5.5, 0.5 Hz, 1H), 4.10-4.00 (m, 2H), 3.53-3.43 (m, 2H), 3.18-3.09 (m, 4H), 2.93-2.83 (m, 4H), 2.60 (tt, J = 11.3, 3.8 Hz, 1H), 1.93 (dm, 2H), 1.60 (qd, J = 12.2, 4.5 Hz, 2H). |
| I-N-12 | 427.3 | 0.59 | $^1$H NMR (500 MHz, Methanol-d4) δ 9.42 (s, 1H), 9.06-8.98 (m, 1H), 8.77-8.70 (m, 1H), 8.22 (d, J = 5.4 Hz, 1H), 8.09 (d, J = 2.4 Hz, 1H), 7.21 (d, J = 5.4 Hz, 1H), 5.53 (s, 2H), 4.00 (td, J = 8.6, 4.1 Hz, 1H), 3.94 (dd, J = 8.8, 6.8 Hz, 1H), 3.83 (td, J = 8.5, 7.2 Hz, 1H), 3.73 (dd, J = 8.8, 6.5 Hz, 1H), 3.22-3.15 (m, 1H), 3.15-3.06 (m, 4H), 2.90-2.80 (m, 2H), 2.78-2.69 (m, 2H), 2.24-2.15 (m, 1H), 1.97-1.85 (m, 1H). |
| I-N-13 | 431.0 | 0.62 | $^1$H NMR (500 MHz, DMSO-d6) δ 10.26 (s, 1H), 9.49 (q, J = 2.3 Hz, 2H), 8.80 (d, J = 2.5 Hz, 1H), 8.27 (d, J = 2.8 Hz, 1H), 6.79 (s, 2H), 4.60 (t, J = 6.5 Hz, 2H), 4.47 (t, J = 6.0 Hz, 2H), 3.63 (p, J = 6.3 Hz, 1H), 3.13 (m, 4H), 2.50 (m, 4H). |
| I-N-14 | 405.1 | 0.7 | $^1$H NMR (500 MHz, DMSO-d6) δ 2.97 (3H, s), 3.21 (2H, m), 3.41 (4H, m), 3.60 (masked signal), 6.86 (2H, br s), 8.32 (1H, d), 8.83 (1H, m), 9.47 (2H, m) and 10.00 (2H, m) ppm. |
| I-N-15 | 389.0 | 0.65 | $^1$H NMR (500 MHz, DMSO-d6) δ 10.27 (s, 1H), 9.50 (dd, J = 4.8, 2.5 Hz, 1H), 9.49 (s, 1H), 8.77 (d, J = 2.5 Hz, 1H), 8.25 (d, J = 2.8 Hz, 1H), 6.80 (s, 2H), 3.10 (t, J = 4.6 Hz, 4H), 2.59 (t, J = 4.8 Hz, 4H), 2.33 (s, 3H). |
| I-N-16 | 427.2 | 1.87* | $^1$H NMR (500 MHz, DMSO-d6) δ 10.1 (s, 1H), 9.47 (s, 1H), 9.36 (s, 1H), 8.80, (s, 1H), 8.05 (s, 1H), 6.78 (br, 2H), 4.59 (m, 2H), 4.45 (m, 2H), 3.57 (m, 1H), 3.12 (br, 4H) 2.52 (br, 4H), 2.40 (s, 3H). |
| I-N-17 | 385.2 | 1.99* | $^1$H NMR (500 MHz, DMSO-d6) δ1.26-1.28 (3H, m), 3.20-3.40 (4H, masked), 3.60-3.80 (6H, m), 6.80 (2H, s), 7.49-7.51 (1H, d), 8.44-8.45 (1H, d), 9.01-9.02 (1H, dd), 9.42 (1H, s), 9.54-9.55 (1H, dd), 9.65 (1H, s), 9.90-10.05 (1H, br s). |
| I-N-18 | 397.0 | 1.74* | — |
| I-N-19 | | | $^1$H NMR (500 MHz, Methanol-d4) δ 9.43 (d, J = 1.1 Hz, 1H), 9.14 (dd, J = 4.3, 2.5 Hz, 1H), 8.84 (dd, J = 2.6, 0.6 Hz, 1H), 8.43 (dd, J = 6.6, 1.1 Hz, 1H), 7.61 (d, J = 6.7 Hz, 1H), 4.23 (dd, J = 11.0, 3.4 Hz, 1H), 4.11 (td, J = 8.7, 4.3 Hz, 1H), 4.04 (d, J = 6.2 Hz, 1H), 3.92 (dd, J = 10.8, 6.1 Hz, 1H), 3.87-3.70 (m, 5H), 3.57-3.43 (m, 4H), 2.52-2.39 (m, 1H), 2.24 (ddd, J = 10.5, 6.2, 2.9 Hz, 1H). |
| I-N-20 | 439.2 | 2.52* | — |
| I-N-21 | 397.2 | 2.04* | — |
| I-N-22 | 415.4 | 0.62 | $^1$H NMR (500 MHz, DMSO-d6) δ 2.61 (2H, t), 2.68 (4H, m), 2.95 (4H, m), 3.26 (3H, s), 3.48 (2H, t), 6.77 (2H, br s), 7.17 (1H, m), 8.22 (1H, d), 8.81 (1H, m), 9.42 (1H, s), 9.48 (1H, dd) and 9.79 (1H, s) ppm. |
| I-N-23 | 427.3 | 0.61 | $^1$H NMR (500 MHz, DMSO-d6) δ 10.33 (s, 1H), 9.65 (s, 1H), 9.47 (dd, J = 4.8, 2.5 Hz, 1H), 8.79 (d, J = 2.5 Hz, 1H), 8.27 (d, J = 5.2 Hz, 1H), 7.38 (d, J = 5.2 Hz, 1H), 6.76 (s, 2H), 4.61 (dt, J = 17.9, 6.5 Hz, 2H), 4.52 (t, J = 6.0 Hz, 1H), 4.44 (t, J = 6.0 Hz, 1H), 3.61 (p, J = 6.3 Hz, 1H), 2.95 (d, J = 11.1 Hz, 1H), 2.86-2.73 (m, 2H), 2.71-2.59 (m, 1H), 2.41-2.27 (m, 1H), 2.12-2.02 (m, 1H), 0.83 (d, J = 6.2 Hz, 3H). 1H multiplet hidden under water peak. |
| I-N-24 | 427.3 | 0.64 | $^1$H NMR (500 MHz, DMSO-d6) δ 10.33 (s, 1H), 9.65 (s, 1H), 9.47 (dd, J = 4.8, 2.5 Hz, 1H), 8.79 (d, J = 2.5 Hz, 1H), 8.27 (d, J = 5.2 Hz, 1H), 7.38 (d, J = 5.2 Hz, 1H), 6.76 (s, 2H), 4.61 (dt, J = 17.9, 6.5 Hz, 2H), 4.52 (t, J = 6.0 Hz, 1H), 4.44 (t, J = 6.0 Hz, 1H), 3.61 (p, J = 6.3 Hz, 1H), 2.95 (d, J = 11.2 Hz, 1H), 2.88-2.73 (m, 2H), 2.71-2.58 (m, 1H), 2.41-2.26 (m, 1H), 2.06 (t, J = 9.8 Hz, 1H), 0.82 (d, J = 6.1 Hz, 3H). 1H multiplet hidden under water peak. |

Compound Analytical Data

| Cmpd No. | LCMS ES+ | LCMS (Rt min) | HNMR |
|---|---|---|---|
| I-N-25 | 443.0 | 0.68 | ¹H NMR (500 MHz, DMSO-d6) δ 9.60 (s, 1H), 9.49 (d, J = 2.2 Hz, 1H), 9.21 (d, J = 1.1 Hz, 1H), 8.66 (d, J = 2.2 Hz, 1H), 8.46 (dd, J = 6.5, 1.0 Hz, 1H), 7.55 (d, J = 6.5 Hz, 1H), 6.82 (s, 2H), 4.69 (d, J = 6.8 Hz, 2H), 4.31 (d, J = 6.9 Hz, 2H), 3.59 (s, 4H), 3.01 (s, 4H), 1.54 (s, 3H). |
| I-N-26 | 339.1 | 0.61 | ¹H NMR (500 MHz, Acetone-d6) δ 11.17 (s, 2H), 9.80 (t, J = 0.5 Hz, 1H), 8.99 (dd, J = 4.6, 2.6 Hz, 1H), 8.70 (d, J = 2.6 Hz, 1H), 8.41 (d, J = 5.2 Hz, 1H), 8.30 (dd, J = 2.5, 0.6 Hz, 1H), 8.05 (dd, J = 1.9, 0.6 Hz, 1H), 7.57 (dd, J = 5.3, 0.5 Hz, 1H), 6.65 (dd, J = 2.5, 1.8 Hz, 1H), 6.37 (s, 1H). |
| I-N-27 | 407.1 | 0.69 | ¹H NMR (500 MHz, Methanol-d4) δ 9.79 (s, 1H), 9.02 (dd, J = 4.4, 2.5 Hz, 1H), 8.52 (d, J = 5.2 Hz, 1H), 8.30 (d, J = 2.5 Hz, 1H), 8.26 (dd, J = 1.2, 0.7 Hz, 1H), 8.10 (t, J = 1.3 Hz, 1H), 7.61 (d, J = 5.2 Hz, 1H). |
| I-N-28 | 353.2 | 0.55 | ¹H NMR (500 MHz, Methanol-d4) δ 9.66 (d, J = 0.6 Hz, 1H), 9.08 (dd, J = 4.4, 2.5 Hz, 1H), 8.67 (d, J = 5.2 Hz, 1H), 8.49 (dd, J = 2.5, 0.5 Hz, 1H), 7.79 (d, J = 2.1 Hz, 1H), 7.77 (d, J = 2.1 Hz, 1H), 7.72 (dd, J = 5.2, 0.6 Hz, 1H), 2.62 (s, 3H). |
| I-N-29 | 355.1 | 0.56 | ¹H NMR (500 MHz, Methanol-d4) δ 9.63 (d, J = 0.6 Hz, 1H), 9.14 (s, 1H), 9.03 (d, J = 2.2 Hz, 1H), 8.61 (d, J = 5.2 Hz, 1H), 8.36 (d, J = 2.2 Hz, 1H), 7.90 (t, J = 1.7 Hz, 1H), 7.77 (t, J = 1.6 Hz, 1H), 7.71 (dd, J = 5.3, 0.6 Hz, 1H). |
| I-N-30 | 421.2 | 0.72 | ¹H NMR (500 MHz, Methanol-d4) δ 10.01-9.94 (m, 1H), 9.65 (s, 1H), 9.03 (dd, J = 4.4, 2.5 Hz, 1H), 8.52 (d, J = 5.1 Hz, 1H), 8.27 (ddd, J = 2.6, 1.2, 0.5 Hz, 1H), 7.89 (q, J = 1.4 Hz, 1H), 7.59 (dt, J = 5.1, 0.6 Hz, 1H), 2.32 (s, 3H). |
| I-N-31 | 425.3 | 0.54 | ¹H NMR (500 MHz, DMSO-d6) δ 9.45 (dd, J = 4.8, 2.6 Hz, 1H), 9.18 (s, 1H), 8.80 (dd, J = 2.5, 0.5 Hz, 1H), 8.50 (s, 1H), 8.13 (d, J = 5.7 Hz, 1H), 7.02 (d, J = 5.7 Hz, 1H), 6.65 (s, 2H), 4.60-4.50 (m, 4H), 3.70 (p, J = 6.4 Hz, 1H), 3.42-3.27 (m, 1H), 3.17 (ddd, J = 12.6, 10.4, 2.7 Hz, 1H), 2.76 (ddd, J = 8.1, 6.6, 4.2 Hz, 1H), 2.66 (ddd, J = 11.0, 4.1, 2.5 Hz, 1H), 2.59-2.51 (m, 1H), 2.31-2.16 (m, 1H), 0.61 (td, J = 5.6, 4.2 Hz, 1H), 0.37 (td, J = 6.8, 5.8 Hz, 1H). |
| I-N-32 | 453.3 | 0.66 | ¹H NMR (500 MHz, DMSO-d6) δ 10.07 (s, 1H), 9.48 (dd, J = 4.8, 2.5 Hz, 1H), 9.31 (s, 1H), 8.81 (d, J = 2.5 Hz, 1H), 7.97 (d, J = 0.6 Hz, 1H), 6.77 (s, 2H), 4.59 (t, J = 6.5 Hz, 2H), 4.45 (t, J = 6.1 Hz, 2H), 3.66-3.51 (m, 1H), 3.31-3.18 (m, 4H), 2.51 (p, J = 1.9 Hz, 4H), 2.13 (tt, J = 8.4, 5.4 Hz, 1H), 1.11-1.01 (m, 2H), 0.90-0.78 (m, 2H). |
| I-N-33 | 397.2 | 2.25* | ¹H NMR (500 MHz, DMSO-d6) δ 9.65 (s, 1H), 9.55 (d, J = 4.0 Hz, 1H), 9.38 (s, 1H), 9.02 (s, 1H), 8.45 (d, J = 8.8 Hz, 1H), 7.52 (d, J = 4.0 Hz, 1H), 6.80 (br, 2H), 2.90 (br, 8H), 0.87 (m, 2H), 0.80 (m, 2H). |
| I-N-34 | 429.3 | 0.8 | ¹H NMR (500 MHz, DMSO-d6) δ 9.81 (s, 1H), 9.43 (d, J = 2.2 Hz, 1H), 9.37 (s, 1H), 8.53 (d, J = 2.2 Hz, 1H), 8.22 (d, J = 5.3 Hz, 1H), 7.16 (dd, J = 5.3, 0.5 Hz, 1H), 6.81 (s, 2H), 2.93 (t, J = 4.6 Hz, 4H), 2.72 (t, J = 4.7 Hz, 4H), 1.07 (s, 9H). |
| I-N-35 | 431.2 | 0.6 | ¹H NMR (500 MHz, DMSO-d6) δ 9.65 (s, 1H), 9.44 (d, J = 2.2 Hz, 1H), 9.29 (s, 1H), 8.58 (d, J = 2.2 Hz, 1H), 8.21 (d, J = 5.3 Hz, 1H), 7.15 (dd, J = 5.3, 0.5 Hz, 1H), 6.82 (s, 2H), 4.52-4.42 (m, 1H), 3.77 (t, J = 4.7 Hz, 1H), 3.31-3.22 (m, 1H), 3.18 (d, J = 11.0 Hz, 1H), 2.76-2.60 (m, 1H), 2.59-2.53 (m, 1H), 2.48-2.40 (m, 1H), 2.32 (s, 6H), 1.81-1.57 (m, 2H). |
| I-N-36 | 445.2 | 0.7 | ¹H NMR (500 MHz, DMSO-d6) δ 10.07 (s, 1H), 9.53 (s, 1H), 9.43 (d, J = 2.2 Hz, 1H), 8.73 (d, J = 2.2 Hz, 1H), 8.21 (d, J = 5.2 Hz, 1H), 7.22 (dd, J = 5.3, 0.6 Hz, 1H), 6.81 (s, 2H), 4.24 (s, 1H), 3.02 (td, J = 11.5, 10.3, 3.9 Hz, 2H), 2.87 (dd, J = 11.3, 4.2 Hz, 2H), 2.33 (s, 6H), 2.31 (s, 2H), 2.07 (td, J = 12.5, 4.2 Hz, 2H), 1.50 (d, J = 12.8 Hz, 2H). |
| I-N-37 | 415.2 | 0.7 | — |
| I-N-38 | 502.2 | 1.97* | ¹H NMR (500 MHz, CDCl₃) δ 10.30 (s, 1H), 9.73 (s, 1H), 8.74 (s, 1H), 8.51 (dd, J = 3.8, 2.5 Hz, 1H), 8.25 (s, 1H), 5.92 (s, 2H), 4.66 (dt, J = 19.3, 6.5 Hz, 2H), 4.57 (s, 1H), 3.87 (s, 1H), 3.62-3.39 (m, 2H), 2.92 (s, 2H), 2.79 (s, 2H), 2.65-2.44 (m, 2H), 2.28 (s, 1H), 1.89 (s, 1H), 1.67 (s, 2H). |
| I-N-39 | 415.2 | 0.75 | H NMR (500 MHz, DMSO-d6) δ 9.77 (s, 1H), 9.43 (d, J = 2.2 Hz, 1H), 9.37 (s, 1H), 8.56 (d, J = 2.2 Hz, 1H), 8.22 (d, J = 5.2 Hz, 1H), 7.17 (d, J = 5.3 Hz, 1H), 6.81 (s, 2H), 2.95 (t, J = 4.7 Hz, 4H), 2.76 (s, 2H), 2.72-2.63 (m, 3H), 1.04 (d, J = 6.5 Hz, 6H). |

-continued

Compound Analytical Data

| Cmpd No. | LCMS ES+ | LCMS (Rt min) | HNMR |
|---|---|---|---|
| I-N-40 | 415.2 | 0.72 | $^1$H NMR (500 MHz, DMSO-d6) δ 9.68 (s, 1H), 9.44 (d, J = 2.2 Hz, 1H), 9.34 (s, 1H), 8.70 (d, J = 2.2 Hz, 1H), 8.22 (d, J = 5.3 Hz, 1H), 7.18 (d, J = 5.3 Hz, 1H), 6.82 (s, 2H), 3.34-3.19 (m, 1H), 3.09 (d, J = 11.5 Hz, 1H), 2.69-2.47 (m, 3H), 2.09 (d, J = 5.2 Hz, 6H), 1.99 (d, J = 12.3 Hz, 1H), 1.90-1.70 (m, 2H), 1.28 (dd, J = 11.2, 6.4 Hz, 1H). |
| I-N-41 | 421.1 | 0.75 | $^1$H NMR (500 MHz, DMSO-d6) δ 2.32 (3H, s), 2.60 (4H, m), 3.25 (4H, m), 6.85 (2H, br s), 8.26 (1H, s), 8.59 (1H, m), 9.44 (1H, m), 9.53 (1H, s) and 10.28 (1H, br s) ppm. |
| I-N-42 | 414.1 | 0.65 | $^1$H NMR (500 MHz, Methanol-d4) δ 9.05 (d, J = 2.2 Hz, 1H), 8.59 (d, J = 2.2 Hz, 1H), 8.34 (d, J = 1.3 Hz, 1H), 8.09 (dd, J = 7.3, 1.4 Hz, 1H), 7.25 (d, J = 7.3 Hz, 1H), 4.92 (d, J = 2.4 Hz, 2H), 4.05-4.01 (m, 1H), 2.45-2.37 (m, 2H), 2.22-2.14 (m, 2H), 2.10-2.03 (m, 2H), 1.89-1.82 (m, 2H). |
| I-N-43 | 401.1 | 0.63 | $^1$H NMR (500 MHz, Methanol-d4) δ 8.89 (d, J = 2.2 Hz, 1H), 8.62 (s, 1H), 8.49 (d, J = 2.2 Hz, 1H), 8.01 (d, J = 5.8 Hz, 1H), 6.96 (d, J = 5.8 Hz, 1H), 3.45-3.39 (m, 2H), 2.72-2.67 (m, 2H), 2.66-2.60 (m, 2H), 2.26 (s, 3H), 1.93-1.85 (m, 2H). |
| I-N-44 | 410.1 | 0.6 | $^1$H NMR (500 MHz, DMSO-d6) δ 10.15 (s, 1H), 9.54 (s, 1H), 9.36 (d, J = 2.2 Hz, 1H), 8.29 (d, J = 5.2 Hz, 1H), 7.56 (d, J = 2.2 Hz, 1H), 7.33-7.21 (m, 2H), 6.93 (d, J = 1.3 Hz, 1H), 6.78 (s, 2H), 4.24-4.10 (m, 4H), 3.62-3.50 (m, 2H). |
| I-N-45 | 429.2 | 2.29* | — |
| I-N-46 | 459.2 | 0.8 | $^1$H NMR (500 MHz, DMSO-d6) δ 10.02 (s, 1H), 9.50 (s, 1H), 9.43 (d, J = 2.2 Hz, 1H), 8.69 (d, J = 2.2 Hz, 1H), 8.21 (d, J = 5.2 Hz, 1H), 7.21 (d, J = 5.3 Hz, 1H), 6.81 (s, 2H), 3.16 (s, 3H), 2.94-2.83 (m, 4H), 2.40 (s, 2H), 2.31 (s, 6H), 2.06-1.95 (m, 2H), 1.84-1.73 (m, 2H). |
| I-N-47 | 431.2 | 0.66 | $^1$H NMR (500 MHz, DMSO-d6) δ 9.71 (s, 1H), 9.43 (d, J = 2.2 Hz, 1H), 9.38 (s, 1H), 8.63 (d, J = 2.2 Hz, 1H), 8.23 (d, J = 5.3 Hz, 1H), 7.17 (dd, J = 5.4, 0.5 Hz, 1H), 6.82 (s, 2H), 3.50 (dd, J = 9.9, 4.1 Hz, 1H), 3.28-3.23 (m, 1H), 3.18 (dd, J = 11.0, 2.3 Hz, 1H), 3.12 (s, 3H), 3.07-3.00 (m, 1H), 2.89-2.77 (m, 2H), 2.61-2.53 (m, 1H), 2.50-2.45 (m, 2H), 2.31 (s, 3H). |
| I-N-48 | 427.2 | 0.79 | $^1$H NMR (500 MHz, DMSO-d6) δ 9.76 (s, 1H), 9.42 (d, J = 2.2 Hz, 1H), 9.40 (s, 1H), 8.58 (d, J = 2.2 Hz, 1H), 8.22 (d, J = 5.3 Hz, 1H), 7.17 (d, J = 5.3 Hz, 1H), 6.81 (s, 2H), 2.94 (t, J = 4.8 Hz, 4H), 2.91-2.82 (m, 1H), 2.50-2.46 (m, 4H), 1.99 (ddtd, J = 11.2, 8.7, 4.5, 2.6 Hz, 2H), 1.88-1.74 (m, 2H), 1.66 (tdd, J = 10.9, 6.0, 2.1 Hz, 2H). |
| I-N-49 | 444.2 | 0.66 | $^1$H NMR (500 MHz, DMSO-d6) δ 9.74 (s, 1H), 9.46-9.36 (m, 2H), 8.63 (d, J = 2.2 Hz, 1H), 8.22 (d, J = 5.3 Hz, 1H), 7.17 (d, J = 5.3 Hz, 1H), 6.81 (s, 2H), 2.94 (t, J = 4.7 Hz, 4H), 2.69-2.62 (m, 4H), 2.53 (d, J = 6.9 Hz, 2H), 2.38 (dd, J = 7.8, 5.8 Hz, 2H), 2.17 (s, 6H). |
| I-N-50 | 402.1 | 0.61 | $^1$H NMR (500 MHz, DMSO-d6) δ 9.39 (d, J = 2.2 Hz, 1H), 9.28 (s, 1H), 8.61 (d, J = 2.2 Hz, 1H), 8.60 (s, 1H), 6.75 (s, 2H), 6.20 (s, 1H), 5.66 (s, 2H), 2.92-2.84 (m, 4H), 2.50 (s, 4H), 2.24 (s, 3H). |
| I-N-51 | 401.1 | 0.71 | $^1$H NMR (500 MHz, DMSO-d6) δ 9.75 (s, 1H), 9.42 (d, J = 2.2 Hz, 1H), 9.40 (s, 1H), 8.62 (d, J = 2.3 Hz, 1H), 8.23 (d, J = 5.3 Hz, 1H), 7.18 (d, J = 5.3 Hz, 1H), 6.81 (s, 2H), 2.97 (t, J = 4.8 Hz, 4H), 2.64 (d, J = 9.5 Hz, 4H), 2.50-2.43 (m, 2H), 1.05 (t, J = 7.1 Hz, 3H). |
| I-N-52 | 421.0 | 0.75 | $^1$H NMR (500 MHz, DMSO-d6) δ 9.70 (s, 1H), 9.53 (s, 1H), 9.47 (d, J = 2.2 Hz, 1H), 9.25 (s, 1H), 8.92 (d, J = 2.2 Hz, 1H), 7.34 (s, 1H), 6.84 (s, 2H), 3.65-3.48 (m, 4H), 3.32-3.21 (m, 2H), 3.15-3.04 (m, 2H), 2.97 (s, 3H). |
| I-N-53 | 415.2 | 0.71 | $^1$H NMR (500 MHz, DMSO-d6) δ 9.52 (s, 1H), 9.44 (d, J = 2.2 Hz, 1H), 9.31 (s, 1H), 8.48 (d, J = 2.2 Hz, 1H), 8.22 (d, J = 5.3 Hz, 1H), 7.12 (dd, J = 5.4, 0.5 Hz, 1H), 6.84 (s, 2H), 2.88-2.81 (m, 2H), 2.77 (s, 2H), 2.61 (t, J = 5.0 Hz, 2H), 2.19 (s, 3H), 1.14 (s, 6H). |
| I-N-54 | 401.2 | 0.39 | $^1$H NMR (500 MHz, DMSO-d6) δ 9.74 (s, 1H), 9.43 (d, J = 2.2 Hz, 1H), 9.41 (s, 1H), 8.60 (d, J = 2.2 Hz, 1H), 8.22 (d, J = 5.3 Hz, 1H), 7.17 (d, J = 5.3 Hz, 1H), 6.82 (s, 2H), 3.11-2.99 (m, 2H), 2.90-2.75 (m, 2H), 2.60-2.52 (m, 1H), 2.49-2.42 (m, 1H), 2.43-2.34 (m, 1H), 2.27 (s, 3H), 0.99 (d, J = 6.2 Hz, 3H). |
| I-N-55 | 387.1 | 1.92* | $^1$H NMR (500 MHz, Methanol-d4) δ 9.27 (d, J = 0.9 Hz, 1H), 9.00 (d, J = 2.2 Hz, 1H), 8.54 (d, J = 2.2 Hz, 1H), 8.25 (dd, J = 6.3, 0.9 Hz, 1H), 7.39 (d, J = 6.3 Hz, 1H), 3.74 (d, |

Compound Analytical Data

| Cmpd No. | LCMS ES+ | LCMS (Rt min) | HNMR |
|---|---|---|---|
| | | | J = 11.8 Hz, 1H), 3.59-3.50 (m, 1H), 3.46 (d, J = 12.5 Hz, 1H), 3.38-3.22 (m, 2H), 3.13-3.02 (m, 1H), 2.95 (dd, J = 11.9, 9.7 Hz, 1H), 2.20-2.06 (m, 2H), 1.95-1.80 (m, 3H), 1.57 (dtd, J = 12.9, 10.5, 5.0 Hz, 2H). |
| I-N-56 | 413.1 | 0.65 | $^1$H NMR (500 MHz, Methanol-d4) δ 9.10 (d, J = 2.2 Hz, 1H), 8.88 (d, J = 1.2 Hz, 1H), 8.67 (d, J = 2.2 Hz, 1H), 8.36 (dd, J = 6.9, 1.2 Hz, 1H), 7.50 (d, J = 6.9 Hz, 1H), 4.59 (ddd, J = 5.8, 3.8, 1.9 Hz, 1H), 4.14-4.04 (m, 2H), 3.74-3.67 (m, 2H), 3.67-3.57 (m, 2H), 3.50 (ddd, J = 14.3, 11.3, 6.4 Hz, 2H), 2.51-2.41 (m, 2H), 2.35-2.24 (m, 2H). |
| I-N-57 | 401.2 | 0.68 | $^1$H NMR (500 MHz, DMSO-d6) δ 2.30 (3H, s), 2.38 (3H, s), 2.57 (4H, m), 3.09 (4H, m), 6.83 (2H, br s), 8.05 (1H, s), 8.60 (1H, m), 9.34 (1H, s), 9.43 (1H, s) and 10.12 (1H, br s) ppm |
| I-N-58 | 429.1 | 0.62 | $^1$H NMR (500 MHz, Methanol-d4) δ 9.40 (d, J = 0.5 Hz, 1H), 9.03 (d, J = 2.2 Hz, 1H), 8.62 (d, J = 2.2 Hz, 1H), 8.23 (d, J = 5.5 Hz, 1H), 7.25 (dd, J = 5.5, 0.5 Hz, 1H), 4.76 (t, J = 6.7 Hz, 2H), 4.65 (dd, J = 6.5, 5.9 Hz, 2H), 3.72-3.63 (m, 1H), 3.15 (t, J = 4.9 Hz, 5H), 2.65 (t, J = 4.8 Hz, 5H). |
| I-N-59 | 387.0 | 0.67 | $^1$H NMR (500 MHz, DMSO-d6) δ 9.73 (s, 1H), 9.43 (d, J = 2.2 Hz, 1H), 9.40 (s, 1H), 8.64 (d, J = 2.2 Hz, 1H), 8.22 (d, J = 5.3 Hz, 1H), 7.18 (dd, J = 5.3, 0.5 Hz, 1H), 6.82 (s, 2H), 2.96 (t, J = 4.8 Hz, 4H), 2.56 (t, J = 4.5 Hz, 4H), 2.28 (s, 3H). |
| I-N-60 | 431.2 | 0.68 | $^1$H NMR (500 MHz, DMSO-d6) δ 9.75 (s, 1H), 9.44-9.39 (m, 2H), 8.63 (d, J = 2.3 Hz, 1H), 8.22 (d, J = 5.3 Hz, 1H), 7.17 (d, J = 5.3 Hz, 1H), 6.81 (s, 2H), 3.49 (t, J = 5.6 Hz, 2H), 3.26 (s, 3H), 2.95 (t, J = 4.7 Hz, 4H), 2.68 (d, J = 4.2 Hz, 4H), 2.61 (t, J = 5.6 Hz, 2H). |
| I-N-61 | 442.3 | 0.59 | $^1$H NMR (500 MHz, Methanol-d4) δ 9.39 (s, 1H), 9.13 (d, J = 2.2 Hz, 1H), 8.66 (d, J = 2.2 Hz, 1H), 8.40 (dd, J = 6.7, 1.2 Hz, 1H), 7.60 (d, J = 6.7 Hz, 1H), 3.92 (d, J = 12.7 Hz, 2H), 3.79 (d, J = 12.1 Hz, 2H), 3.60 (d, J = 12.3 Hz, 2H), 3.10-2.97 (m, 2H), 2.95 (s, 3H), 2.86-2.58 (m, 5H). |
| I-N-62 | 427.0 | 0.63 | $^1$H NMR (500 MHz, DMSO-d6) δ 9.60 (s, 1H), 9.54 (dd, J = 4.8, 2.5 Hz, 1H), 9.21 (d, J = 0.9 Hz, 1H), 8.80 (d, J = 2.5 Hz, 1H), 8.46 (dd, J = 6.5, 1.0 Hz, 1H), 7.54 (d, J = 6.5 Hz, 1H), 6.78 (s, 2H), 4.68 (t, J = 7.0 Hz, 2H), 4.30 (d, J = 6.8 Hz, 2H), 3.58 (s, 4H), 2.98 (s, 4H), 1.54 (s, 3H). |
| I-N-63 | 417.1 | 0.47 | $^1$H NMR (500 MHz, DMSO-d6) δ 9.77 (s, 1H), 9.43 (d, J = 2.2 Hz, 1H), 9.40 (s, 1H), 8.61 (d, J = 2.2 Hz, 1H), 8.23 (d, J = 5.3 Hz, 1H), 7.17 (dd, J = 5.3, 0.5 Hz, 1H), 6.81 (s, 2H), 4.43 (t, J = 5.5 Hz, 1H), 3.63 (ddd, J = 11.0, 5.6, 3.9 Hz, 1H), 3.28-3.20 (m, 1H), 3.08-2.97 (m, 1H), 2.93-2.75 (m, 2H), 2.54 (ddd, J = 11.1, 3.6, 1.8 Hz, 2H), 2.37 (h, J = 1.7 Hz, 1H), 2.31 (s, 3H). |
| I-N-64 | 413.2 | 0.77 | $^1$H NMR (500 MHz, DMSO-d6) δ 9.77 (s, 1H), 9.41 (d, J = 2.2 Hz, 1H), 9.39 (s, 1H), 8.67 (d, J = 2.3 Hz, 1H), 8.20 (d, J = 5.4 Hz, 1H), 7.14 (d, J = 5.4 Hz, 1H), 6.80 (s, 2H), 2.90 (t, J = 4.9 Hz, 4H), 2.77 (d, J = 5.3 Hz, 4H), 1.80 (pd, J = 6.6, 4.2, 3.4 Hz, 1H), 0.45 (dq, J = 6.6, 4.3, 3.8 Hz, 2H), 0.36-0.29 (m, 2H). |
| I-N-65 | 413.1 | 1.61* | $^1$H NMR (500 MHz, DMSO-d6) δ 9.75 (s, 1H), 9.46-9.39 (m, 2H), 8.58 (d, J = 2.3 Hz, 1H), 8.22 (d, J = 5.3 Hz, 1H), 7.20 (d, J = 5.4 Hz, 1H), 6.82 (s, 2H), 3.26-3.20 (m, 1H), 3.14 (d, J = 11.5 Hz, 1H), 3.05-2.96 (m, 2H), 2.78 (td, J = 11.4, 3.1 Hz, 1H), 2.63 (t, J = 10.3 Hz, 1H), 2.48-2.43 (m, 1H), 2.33 (d, J = 7.7 Hz, 1H), 2.20 (q, J = 7.9 Hz, 1H), 1.79-1.66 (m, 3H), 1.35 (tt, J = 14.8, 7.2 Hz, 1H). |
| I-N-66 | 402.1 | 0.67 | $^1$H NMR (500 MHz, Methanol-d4) δ 9.42 (d, J = 0.5 Hz, 1H), 9.04 (d, J = 2.2 Hz, 1H), 8.62 (d, J = 2.2 Hz, 1H), 8.22 (d, J = 5.4 Hz, 1H), 7.27 (dd, J = 5.5, 0.5 Hz, 1H), 3.24-3.14 (m, 2H), 3.06 (dd, J = 11.1, 5.6 Hz, 2H), 1.94 (ddd, J = 13.6, 9.8, 4.0 Hz, 2H), 1.85 (d, J = 13.2 Hz, 2H), 1.37 (s, 3H). |
| I-N-67 | 455.1 | 0.84 | $^1$H NMR (500 MHz, DMSO-d6) δ 2.89 (4H, m), 2.97 (4H, m), 3.37 masked signal, 6.82 (2H, br s), 7.20 (1H, m), 8.22 (1H, m), 8.70 (1H, m), 9.43 (2H, m) and 9.75 (1H, s) ppm. |
| I-N-68 | 406.2 | 0.53 | $^1$H NMR (500 MHz, Methanol-d4) δ 9.45 (d, J = 1.1 Hz, 1H), 9.11 (d, J = 2.2 Hz, 1H), 8.76 (d, J = 2.2 Hz, 1H), 8.41 (dd, J = 6.6, 1.1 Hz, 1H), 7.68 (d, J = 6.6 Hz, 1H), 4.02 (ddd, J = 13.6, 11.1, 2.0 Hz, 2H), 3.83-3.75 (m, 2H), 3.33-3.28 (m, 2H), 3.16-3.08 (m, 2H). |

Compound Analytical Data

| Cmpd No. | LCMS ES+ | LCMS (Rt min) | HNMR |
|---|---|---|---|
| I-N-69 | 430.2 | 0.75 | $^1$H NMR (500 MHz, Methanol-d4) δ 9.23 (d, J = 1.3 Hz, 1H), 9.10 (d, J = 2.2 Hz, 1H), 8.68 (d, J = 2.2 Hz, 1H), 8.30 (dd, J = 6.8, 1.3 Hz, 1H), 7.52 (d, J = 6.8 Hz, 1H), 4.00 (dt, J = 13.0, 2.8 Hz, 2H), 3.15-3.03 (m, 2H), 2.00-1.90 (m, 2H), 1.74 (qd, J = 12.6, 3.8 Hz, 2H), 1.66-1.60 (m, 1H), 1.25 (s, 6H). |
| I-N-70 | 441.1 | 0.71 | $^1$H NMR (500 MHz, DMSO-d6) δ 9.77 (s, 1H), 9.50-9.40 (m, 2H), 8.77 (d, J = 2.2 Hz, 1H), 8.25 (d, J = 5.3 Hz, 1H), 7.25 (dd, J = 5.3, 0.5 Hz, 1H), 6.82 (s, 2H), 3.84-3.65 (m, 1H), 3.22 (d, J = 11.0 Hz, 1H), 3.12-2.90 (m, 3H), 2.81 (dd, J = 10.9, 10.1 Hz, 1H), 2.76-2.59 (m, 1H). |
| I-N-71 | 413.1 | 0.72 | $^1$H NMR (500 MHz, DMSO-d6) δ 9.75 (s, 1H), 9.44-9.38 (m, 2H), 8.58 (d, J = 2.2 Hz, 1H), 8.22 (d, J = 5.3 Hz, 1H), 7.20 (dd, J = 5.4, 0.5 Hz, 1H), 6.82 (s, 2H), 3.31-3.20 (m, 2H), 3.14 (dd, J = 10.8, 2.9 Hz, 1H), 3.07-2.96 (m, 2H), 2.78 (td, J = 11.4, 2.9 Hz, 1H), 2.66-2.60 (m, 1H), 2.34 (s, 1H), 2.19 (q, J = 8.4 Hz, 1H), 1.73 (tdd, J = 13.4, 7.9, 4.2 Hz, 3H), 1.35 (td, J = 10.5, 5.8 Hz, 1H). |
| I-N-72 | 401.2 | 0.69 | $^1$H NMR (500 MHz, DMSO-d6) δ 10.29 (s, 1H), 9.62 (s, 1H), 9.43 (d, J = 2.2 Hz, 1H), 8.58 (d, J = 2.2 Hz, 1H), 8.26 (d, J = 5.1 Hz, 1H), 7.34 (d, J = 5.2 Hz, 1H), 6.82 (s, 2H), 3.00-2.89 (m, 1H), 2.90-2.81 (m, 1H), 2.81-2.73 (m, 1H), 2.72-2.62 (m, 1H), 2.47-2.39 (m, 1H), 2.30 (s, 3H), 2.24-2.11 (m, 1H), 0.82 (d, J = 6.2 Hz, 3H). (One proton hidden under DMSO peak). |
| I-N-73 | 402.1 | 0.76 | $^1$H NMR (500 MHz, DMSO-d6) δ 9.83 (s, 1H), 9.50-9.35 (m, 2H), 8.58 (d, J = 2.2 Hz, 1H), 8.21 (d, J = 5.2 Hz, 1H), 7.18 (d, J = 5.3 Hz, 1H), 6.82 (s, 2H), 3.44 (dt, J = 7.9, 4.0 Hz, 1H), 3.30 (s, 3H), 3.12-3.03 (m, 2H), 2.79 (ddd, J = 11.8, 8.8, 3.1 Hz, 2H), 2.07-1.98 (m, 2H), 1.75 (dtd, J = 12.2, 8.5, 3.4 Hz, 2H). |
| I-N-74 | 430.2 | 0.8 | $^1$H NMR (500 MHz, Methanol-d4) δ 9.44 (d, J = 1.2 Hz, 1H), 9.10 (d, J = 2.2 Hz, 1H), 8.71 (d, J = 2.2 Hz, 1H), 8.34 (dd, J = 6.7, 1.2 Hz, 1H), 7.56 (d, J = 6.7 Hz, 1H), 3.84-3.79 (m, 2H), 3.78 (s, 3H), 3.23-3.14 (m, 2H), 2.80-2.72 (m, 1H), 2.22-2.06 (m, 4H). |
| I-N-75 | 410.1 | 0.57 | $^1$H NMR (500 MHz, DMSO-d6) δ 10.13 (s, 1H), 9.54 (s, 1H), 9.36 (d, J = 2.2 Hz, 1H), 8.28 (d, J = 5.2 Hz, 1H), 7.72 (d, J = 1.0 Hz, 1H), 7.57 (d, J = 2.2 Hz, 1H), 7.29 (dd, J = 5.3, 0.5 Hz, 1H), 6.78 (s, 2H), 6.66 (d, J = 1.0 Hz, 1H), 4.34-4.11 (m, 4H), 3.59-3.44 (m, 2H). |
| I-N-76 | 420.2 | 0.67 | $^1$H NMR (500 MHz, DMSO-d6) δ 1.85 (6H, s), 2.95 (3H, s), 3.2-3.4 (4H, m), 3.6-3.8 (4H, m), 6.8 (1H, brs) 7.47 (1H, d), 8.47 (1H, d), 9.05 (1H, s), 9.15 (1H, s), 9.45 (1H, s), 9.75 (1H, s), 10.0 (1H, brs). |
| I-N-77 | 363.1 | 1.89* | — |
| I-N-78 | 406.2 | 0.62 | $^1$H NMR (500 MHz, DMSO-d6) δ 1.7 (3H, d), 2.95 (3H, s), 3.2-3.4 (4H, m), 3.6-3.8 (4H, m), 4.5 (1H, q), 6.8 (1H, brs), 7.49 (1H, d), 8.47 (1H, d), 8.95 (1H, s), 9.18 (1H, s), 9.40 (1H, s), 9.75 (1H, s), 10.1 (1H, brs). |
| I-N-79 | 391.2 | 2.32* | — |
| I-N-80 | 410.1 | 0.65 | $^1$H NMR (500 MHz, DMSO-d6) δ 2.99 (3H, br s), 3.18 (2H, m), 3.37-3.44 (4H, m), 3.67 (2H, m), 4.15 (2H, s), 6.80 (2H, br s), 8.32 (1H, d), 8.76 (1H, d), 9.12 (1H, d), 9.51 (1H, s), 9.86 (1H, br s) and 10.19 (1H, s) ppm. |
| I-N-81 | 379.2 | 1.79* | $^1$H NMR (500 MHz, DMSO-d6) δ 9.79 (s, 1H), 9.36 (s, 1H), 9.10 (d, J = 2.0 Hz, 1H), 8.77 (d, J = 2.0 Hz, 1H), 8.44 (d, J = 6.4 Hz, 1H), 7.49 (d, J = 6.4 Hz, 1H), 6.78 (s, 2H), 4.15 (s, 2H), 3.87-3.83 (m, 4H), 3.33-3.29 (m, 4H). |
| I-N-82 | 92.2 | 1.74* | $^1$H NMR (500 MHz, DMSO-d6) δ 9.71 (s, 1H), 9.42 (s, 1H), 9.12 (d, J = 1.9 Hz, 1H), 8.84 (d, J = 2.0 Hz, 1H), 8.45 (d, J = 6.2 Hz, 1H), 7.52 (d, J = 6.2 Hz, 1H), 6.80 (s, 2H), 4.15 (s, 2H), 3.90-3.68 (m, 4H), 3.68-3.55 (m, 3H), 2.96 (s, 3H). |
| I-N-83 | 393.2 | 0.53 | $^1$H NMR (500 MHz, DMSO-d6) δ 9.92 (s, 1H), 9.46 (s, 1H), 9.06 (dt, J = 2.0, 0.8 Hz, 1H), 8.64 (d, J = 2.1 Hz, 1H), 8.21 (d, J = 5.3 Hz, 1H), 7.21-7.16 (m, 1H), 6.77 (s, 2H), 4.73 (d, J = 4.3 Hz, 1H), 4.14 (d, J = 0.7 Hz, 2H), 3.71 (s, 1H), 3.12 (d, J = 11.5 Hz, 2H), 2.77 (t, J = 9.6 Hz, 2H), 1.92 (s, 2H), 1.73 (t, J = 9.2 Hz, 2H). |
| I-N-84 | 377.2 | 2.38* | — |
| I-N-85 | 405.2 | 0.69 | $^1$H NMR (500 MHz, Methanol-d4) δ 9.56 (s, 1H), 9.07 (dd, J = 4.3, 2.6 Hz, 1H), 8.82-8.77 (m, 1H), 8.25 (s, 1H), 3.38-3.36 (m, 4H), 2.84 (d, J = 4.4 Hz, 4H), 2.50 (s, 3H). |

Compound Analytical Data

| Cmpd No. | LCMS ES+ | LCMS (Rt min) | HNMR |
|---|---|---|---|
| I-N-86 | 387.1 | 0.56 | ¹H NMR (500 MHz, Methanol-d4) δ 9.30 (s, 1H), 8.90 (d, J = 2.2 Hz, 1H), 8.69 (d, J = 2.2 Hz, 1H), 8.08 (d, J = 5.5 Hz, 1H), 7.10 (d, J = 5.5 Hz, 1H), 2.81 (td, J = 10.9, 5.5 Hz, 1H), 2.71 (td, J = 12.0, 2.4 Hz, 2H), 1.87 (d, J = 12.4 Hz, 2H), 1.66 (qd, J = 12.1, 3.8 Hz, 2H), 3.26-3.23 (m, 2H). |
| I-N-87 | 401.1 | 1.85* | — |
| I-N-88 | 373.0 | 1.16* | ¹H NMR (500 MHz, DMSO-d6) δ 9.82 (s, 1H), 9.43 (d, J = 2.2 Hz, 1H), 9.41 (s, 1H), 8.67 (d, J = 2.2 Hz, 1H), 8.23 (d, J = 5.3 Hz, 1H), 7.16 (d, J = 5.3 Hz, 1H), 6.82 (s, 2H), 2.93 (dd, J = 6.2, 3.3 Hz, 4H), 2.85 (dd, J = 6.1, 3.2 Hz, 4H). |
| I-N-89 | 378.1 | 0.97 | ¹H NMR (500 MHz, DMSO-d6) δ 9.90 (s, 1H), 9.44 (s, 1H), 9.06 (d, J = 1.9 Hz, 1H), 8.66 (d, J = 2.0 Hz, 1H), 8.22 (d, J = 5.2 Hz, 1H), 7.16 (d, J = 5.3 Hz, 1H), 6.77 (s, 2H), 4.15 (s, 2H), 2.95 (d, J = 4.7 Hz, 4H), 2.88-2.85 (m, 4H). |
| I-N-90 | 408.2 | 0.51 | ¹H NMR (500 MHz, DMSO-d6) δ 9.90 (d, J = 14.9 Hz, 1H), 9.51 (d, J = 4.6 Hz, 1H), 9.04 (dd, J = 22.0, 2.2 Hz, 1H), 8.67 (dd, J = 24.9, 2.2 Hz, 1H), 8.24 (d, J = 5.3 Hz, 1H), 7.19 (dd, J = 13.7, 5.3 Hz, 1H), 6.76 (d, J = 10.4 Hz, 2H), 4.14 (d, J = 7.0 Hz, 2H), 3.99-3.79 (m, 2H), 3.77-3.68 (m, 1H), 3.20 (d, J = 11.4 Hz, 1H), 3.16-3.00 (m, 1H), 2.90-2.73 (m, 1H), 2.71-2.53 (m, 3H). |
| I-N-91 | 401.1 | 0.6 | ¹H NMR (500 MHz, DMSO-d6) δ 1.47 (2H, m), 1.82 (3H, m), 2.85 (2H, m), 2.96 (2H, m), 3.66 (2H, m), 6.83 (2H, br s), 7.46 (1H, d), 7.90 (3H, br s), 8.40 (1H, m), 8.76 (1H, s), 9.27 (1H, s), 9.47 (1H, m) and 9.57 (1H, s) ppm. |
| I-N-92 | | | ¹H NMR (500 MHz, DMSO-d6) δ 12.39 (s, 1H), 9.81 (s, 1H), 9.45 (d, J = 2.2 Hz, 1H), 9.41 (s, 1H), 8.65 (d, J = 2.2 Hz, 1H), 8.35 (d, J = 5.5 Hz, 1H), 3.45-3.40 (m, 2H), 7.40 (d, J = 6.1 Hz, 1H), 6.83 (s, 2H), 3.04-2.86 (m, 2H), 2.60-2.55 (m, 1H), 2.05-1.85 (m, 4H). |
| I-N-93 | 427.2 | 2.2* | — |
| I-N-94 | 470.2 | 2.15* | — |
| I-N-95 | 471.2 | 2.27* | — |
| I-N-96 | 469.3 | 0.66 | ¹H NMR (500 MHz, DMSO-d6) δ 9.86 (s, 1H), 9.52-9.31 (m, 2H), 8.62 (d, J = 2.2 Hz, 1H), 8.21 (d, J = 5.3 Hz, 1H), 7.17 (dd, J = 5.3, 0.5 Hz, 1H), 6.81 (s, 2H), 4.63 (s, 4H), 3.27 (s, 4H), 3.13-3.02 (m, 2H), 2.76-2.66 (m, 2H), 2.14 (dq, J = 8.3, 4.4, 3.8 Hz, 1H), 1.84-1.70 (m, 2H), 1.57-1.41 (m, 2H). |
| I-N-97 | 470.3 | 0.64 | ¹H NMR (500 MHz, DMSO-d6) δ 9.56 (s, 1H), 9.49 (d, J = 2.2 Hz, 1H), 9.14 (s, 1H), 8.69 (d, J = 2.2 Hz, 1H), 8.39 (dd, J = 6.5, 1.1 Hz, 1H), 7.46 (d, J = 6.6 Hz, 1H), 6.82 (s, 2H), 3.77 (d, J = 12.8 Hz, 2H), 3.25-3.11 (m, 3H), 3.11-3.00 (m, 3H), 3.00-2.89 (m, 2H), 2.77 (s, 3H), 2.58-2.53 (m, 2H), 2.49-2.45 (m, 1H), 1.99-1.85 (m, 2H), 1.77-1.59 (m, 2H). |
| I-N-98 | 459.2 | 2.43* | — |
| I-N-99 | 483.3 | 0.69 | ¹H NMR (500 MHz, DMSO-d6) δ 10.43 (s, 1H), 9.53-9.46 (m, 2H), 9.34-9.23 (m, 1H), 8.83 (d, J = 2.2 Hz, 1H), 8.43 (dd, J = 6.5, 1.0 Hz, 1H), 7.50 (d, J = 6.5 Hz, 1H), 6.84 (s, 2H), 4.70-4.42 (m, 3H), 4.04-3.90 (m, 2H), 3.89-3.74 (m, 3H), 3.24-3.09 (m, 1H), 3.10-2.90 (m, 2H), 2.46-2.39 (m, 1H), 2.33-2.12 (m, 3H), 2.00-1.73 (m, 2H). 2 proton signals hidden by water. |
| I-N-100 | 489.2 | 0.61 | ¹H NMR (500 MHz, Methanol-d4) δ 9.35 (s, 1H), 9.06 (d, J = 2.2 Hz, 1H), 8.70 (d, J = 2.2 Hz, 1H), 8.22 (d, J = 5.4 Hz, 1H), 7.27-7.20 (m, 1H), 3.12-3.00 (m, 2H), 3.00-2.90 (m, 2H), 2.90-2.79 (m, 2H), 2.74-2.63 (m, 2H), 2.11-2.04 (m, 1H), 2.04-1.86 (m, 4H), 1.36 (d, J = 19.8 Hz, 4H). |
| I-N-101 | 493.2 | 1.4* | ¹H NMR (500 MHz, Methanol-d4) δ 9.18 (d, J = 1.3 Hz, 1H), 9.08 (d, J = 2.2 Hz, 1H), 8.86 (d, J = 1.3 Hz, 1H), 8.69 (d, J = 2.2 Hz, 1H), 8.32 (dd, J = 6.8, 1.4 Hz, 1H), 7.54 (d, J = 6.9 Hz, 1H), 7.38 (d, J = 1.5 Hz, 1H), 4.44-4.35 (m, 2H), 4.10-3.98 (m, 4H), 3.29-3.17 (m, 4H), 3.03-2.92 (m, 1H), 2.19-2.10 (m, 2H), 1.99-1.88 (m, 2H), 1.39-1.26 (m, 1H), 0.92 (d, J = 7.0 Hz, 1H). |
| I-N-102 | 493.2 | 1.4* | ¹H NMR (500 MHz, Methanol-d4) δ 9.16 (d, J = 1.3 Hz, 1H), 9.12 (d, J = 2.2 Hz, 1H), 8.67 (d, J = 2.2 Hz, 1H), 8.32 (dd, J = 6.9, 1.3 Hz, 1H), 7.56 (q, J = 2.1 Hz, 2H), 7.54 (d, J = 6.9 Hz, 1H), 4.28 (t, J = 5.3 Hz, 2H), 4.06 (dm, J = 13.0 Hz, 2H), 3.33-3.19 (m, 4H), 2.99-2.93 (m, 1H), 2.14 (d, J = 12.4 Hz, 2H), 1.98-1.87 (m, 2H), 1.39-1.29 (m, 3H), 0.95-0.89 (m, 1H). |

Compound Analytical Data

| Cmpd No. | LCMS ES+ | LCMS (Rt min) | HNMR |
|---|---|---|---|
| I-N-103 | 459.2 | 2.42* | — |
| I-N-104 | 457.3 | 0.67 | $^1$H NMR (500 MHz, DMSO-d6) δ 10.25 (s, 1H), 9.55 (s, 1H), 9.49 (d, J = 2.2 Hz, 1H), 9.23 (d, J = 0.9 Hz, 1H), 8.79 (d, J = 2.2 Hz, 1H), 8.43 (dd, J = 6.4, 1.0 Hz, 1H), 7.49 (d, J = 6.5 Hz, 1H), 6.83 (s, 2H), 4.20-3.93 (m, 2H), 3.91-3.79 (m, 2H), 3.30-3.09 (m, 1H), 3.03 (t, J = 12.1 Hz, 2H), 2.27-2.13 (m, 2H), 1.86 (qd, J = 12.5, 3.7 Hz, 2H). Remaining signals for 6 protons under water peak. |
| I-N-105 | 441.0 | 2.26* | — |
| I-N-106 | 484.3 | 2.29* | — |
| I-N-107 | 457.2 | 2.24* | — |
| I-N-108 | 463.2 | 2.55* | — |
| I-N-109 | 469.3 | 0.69 | $^1$H NMR (500 MHz, DMSO-d6) δ 9.54-9.45 (m, 2H), 9.31 (d, J = 1.1 Hz, 1H), 8.82 (d, J = 2.2 Hz, 1H), 8.43 (dd, J = 6.4, 1.0 Hz, 1H), 7.49 (d, J = 6.5 Hz, 1H), 6.94-6.73 (m, 2H), 5.51-4.98 (m, 1H), 4.85 (d, J = 9.2 Hz, 2H), 4.83-4.51 (m, 1H), 3.93-3.66 (m, 6H), 3.09 (t, J = 12.3 Hz, 2H), 2.76-2.54 (m, 1H), 2.32-1.57 (m, 4H). (Aliphatic signals broad and undefined). |
| I-N-110 | 447.2 | 0.67 | $^1$H NMR (500 MHz, DMSO-d6) δ 10.31 (s, 1H), 9.56 (s, 1H), 9.50 (dd, J = 4.8, 2.5 Hz, 1H), 8.80 (d, J = 2.5 Hz, 1H), 8.27 (s, 1H), 6.80 (s, 2H), 4.61 (t, J = 6.4 Hz, 2H), 4.47 (t, J = 6.0 Hz, 2H), 3.70-3.51 (m, 1H), 3.44-3.20 (m, 4H), 2.60-2.45 (m, 4H). |
| I-N-111 | 421.2 | 2.1* | $^1$H NMR (500 MHz, DMSO-d6) δ 9.73 (1H, br), 9.68 (1H, s), 9.54 (1H, d, J = 5.0 Hz), 8.95 (1 H, d, J = 5.0 Hz), 8.55 (1 H, s), 7.37 (1H, t, J = 55 Hz), 6.79 (2H, br), 2.88 (3H, s) 3.47-3.22 (8 H, br). |
| I-N-112 | 425.3 | 1.67* | $^1$H NMR (500 MHz, DMSO-d6) δ 9.45 (dd, J = 4.8, 2.6 Hz, 1H), 9.18 (s, 1H), 8.80 (dd, J = 2.5, 0.5 Hz, 1H), 8.50 (s, 1H), 8.13 (d, J = 5.7 Hz, 1H), 7.02 (d, J = 5.7 Hz, 1H), 6.65 (s, 2H), 4.60-4.50 (m, 4H), 3.70 (p, J = 6.4 Hz, 1H), 3.42-3.27 (m, 1H), 3.17 (ddd, J = 12.6, 10.4, 2.7 Hz, 1H), 2.76 (ddd, J = 8.1, 6.6, 4.2 Hz, 1H), 2.66 (ddd, J = 11.0, 4.1, 2.5 Hz, 1H), 2.59-2.51 (m, 1H), 2.31-2.16 (m, 1H), 0.61 (td, J = 5.6, 4.2 Hz, 1H), 0.37 (td, J = 6.8, 5.8 Hz, 1H). |
| I-N-113 | 396.2 | 1.93* | $^1$H NMR (500 MHz, DMSO-d6) δ 9.82 (1H, br), 9.71 (1 H, d, J = 2.2 Hz), 9.54 (1H, dd, J = 5.0, 2.2 Hz), 9.46 (1 H, s), 8.98 (1H, s), 8.66 (1 H, s), 6.77 (2 H, br), 3.63-3.41 (6 H, br), 3.17 (2 H, br), 2.92 (3 H, s). |
| I-N-114 | 444.3 | 1.96* | $^1$H NMR (500 MHz, methanol-d4) δ 10.41 (s, 1H), 9.57 (d, J = 1.6 Hz, 1H), 9.08 (dd, J = 4.4, 2.4 Hz, 1H), 8.87 (d, J = 2.5 Hz, 1H), 8.20 (d, J = 3.0 Hz, 1H), 3.53-3.44 (m, 1H), 3.43-3.39 (m, 1H), 3.26-3.18 (m, 1H), 3.18-3.06 (m, 3H), 3.02 (dt, J = 11.3, 2.5 Hz, 1H), 2.99-2.92 (m, 1H), 2.92-2.85 (m, 1H), 2.85-2.78 (m, 1H), 2.74 (s, 3H), 2.71-2.66 (m, 1H), 2.63 (d, J = 17.2 Hz, 1H). |
| I-N-115 | 413.2 | 1.82* | $^1$H NMR (500 MHz, methanol-d4) δ 9.49 (s, 1H), 9.06 (d, J = 4.5 Hz, 1H), 8.77 (s, 1H), 8.24 (d, J = 5.6 Hz, 1H), 7.24 (d, J = 5.7 Hz, 1H), 3.93 (d, J = 11.2 Hz, 1H), 3.83-3.62 (m, 2H), 3.46-3.25 (m, 2H), 3.24-3.00 (m, 2H), 2.94 (d, J = 11.2 Hz, 1H), 2.83 (d, J = 11.6 Hz, 1H), 2.80-2.66 (m, 2H), 2.65-2.48 (m, 2H). |
| I-N-116 | 413.2 | 1.82* | $^1$H NMR (500 MHz, DMSO-d6) δ 9.77 (s, 1H), 9.48 (dd, J = 4.8, 2.5 Hz, 1H), 9.45 (s, 1H), 8.83-8.78 (m, 1H), 8.21 (d, J = 5.3 Hz, 1H), 7.17 (dd, J = 5.3, 0.5 Hz, 1H), 6.77 (s, 2H), 3.79 (dm, J = 10.9 Hz, 1H), 3.59 (dd, J = 10.8, 2.8 Hz, 1H), 3.53 (td, 1H), 3.16-3.08 (m, 2H), 2.97 (dm, 1H), 2.86 (td, 1H), 2.78 (dm, J = 11.1 Hz, 1H), 2.68 (dm, J = 11.5 Hz, 1H), 2.63 (p, J = 1.8 Hz, 1H), 2.59-2.53 (m, 1H), 2.40 (dd, J = 11.5, 3.3 Hz, 1H), 2.36 (p, J = 1.9 Hz, 1H). |
| I-N-117 | 447.1 | 2.10* | $^1$H NMR (500 MHz, DMSO-d6) δ 10.22 (s, 1H), 2.54-2.51 (m, 2H), 9.47 (s, 1H), 9.43 (d, J = 2.2 Hz, 1H), 8.60 (d, J = 2.2 Hz, 1H), 8.26 (d, J = 2.8 Hz, 1H), 6.83 (s, 2H), 4.60 (t, J = 6.5 Hz, 2H), 4.47 (t, J = 6.1 Hz, 2H), 4.08 (q, J = 5.3 Hz, 2H), 3.62-3.54 (m, 1H), 3.15-3.08 (m, 4H). |
| I-N-118 | 375.1 | 1.84* | $^1$H NMR (500 MHz, DMSO-d6) δ 3.34 (m, 8H), 6.83 (2H, br s), 8.32 (1H, m), 8.74 (2H, br s), 8.94 (1H, m), 9.55 (1H, m), 9.61 (1H, s) and 10.32 (1H, s) ppm. |
| I-N-119 | 467.3 | 2.18* | $^1$H NMR (500 MHz, DMSO-d6) δ 10.07 (s, 1H), 9.48 (dd, J = 4.8, 2.5 Hz, 1H), 9.28 (s, 1H), 8.83 (d, J = 2.5 Hz, 1H), 7.96 (d, J = 0.6 Hz, 1H), 6.78 (s, 2H), 3.91-3.76 (m, 2H), 3.75-3.65 (m, 1H), 3.48 (t, J = 7.7 Hz, 1H), 3.32-3.12 (m, 4H), 3.09-2.92 (m, 1H), 2.80-2.66 (m, 2H), 2.65-2.54 |

Compound Analytical Data

| Cmpd No. | LCMS ES+ | LCMS (Rt min) | HNMR |
|---|---|---|---|
| | | | (m, 2H), 2.19-1.97 (m, 2H), 1.84-1.63 (m, 1H), 1.09-0.97 (m, 2H), 0.90-0.77 (m, 2H). |
| I-N-120 | 467.3 | 2.18* | $^1$H NMR (500 MHz, DMSO-d6) δ 10.07 (s, 1H), 9.48 (dd, J = 4.8, 2.5 Hz, 1H), 9.28 (s, 1H), 8.83 (d, J = 2.5 Hz, 1H), 7.96 (d, J = 0.6 Hz, 1H), 6.77 (s, 2H), 3.90-3.76 (m, 2H), 3.76-3.63 (m, 1H), 3.55-3.42 (m, 1H), 3.31-3.12 (m, 4H), 2.99 (t, J = 7.2 Hz, 1H), 2.77-2.66 (m, 2H), 2.63-2.54 (m, 2H), 2.17-1.95 (m, 2H), 1.79-1.64 (m, 1H), 1.08-0.99 (m, 2H), 0.89-0.78 (m, 2H). |
| I-N-121 | 459.2 | 2.13* | $^1$H NMR (500 MHz, DMSO-d6) δ 1.65-1.73 (2H, m), 2.09 (2H, m), 3.16 (2H, m), 3.38 (5H, m), 3.49 (3H, m), 3.72 (1H, m), 4.02 (2H, m), 6.80 (2H, br s), 8.33 (1H, d), 8.96 (1H, d), 9.46 (1H, s), 9.54 (1H, m), 9.78 (1H, br s) and 10.09 (1H, s) ppm. |
| I-N-122 | 445.2 | 1.99* | $^1$H NMR (500 MHz, DMSO-d6) δ 2.12-2.17 (1H, m), 2.35-2.42 (1H, m), 3.22-3.47 (6H, m), 3.73 masked signal, 3.95-4.09 (5H, m), 6.81 (2H, br s), 8.33 (1H, d), 8.97 (1H, m), 9.50 (1H, s), 9.54 (1H, d) and 10.09 (2H, m) ppm. |
| I-N-123 | 455.3 | 1.97* | $^1$H NMR (500 MHz, DMSO-d6) δ 10.05 (1 H, br), 9.48 (1 H, d, J = 5.2 Hz), 9.24 (1 H, m), 8.79 (1 H, br), 8.06 (1 H, d, J = 5.2 Hz), 6.77 (2 H, br), 3.92 (2 H, br), 3.35-3.32 (7 H, br), 2.70 (4 H, br), 2.39 (3 H, s), 1.78 (2 H, br), 1.55 (2 H, br). |
| I-N-124 | 461.2 | 2.11* | $^1$H NMR (500 MHz, DMSO-d6) δ 2.1-2.12 (1H, m), 2.4-2.5 (1H, m), 3.2-3.4 (4H, m), 3.6-3.85 (5H, m), 3.9-4.1 (4H, m), 6.78 (2H, brs), 8.35 (1H, d), 8.92 (1H, s), 9.5-9.6 (2H, m), 10.0-10.15 (2H, m). |
| I-N-125 | 445.2 | 1.99* | $^1$H NMR (500 MHz, DMSO-d6) δ 2.12-2.17 (1H, m), 2.35-2.42 (1H, m), 3.22-3.47 (6H, m), 3.73 masked signal, 3.95-4.09 (5H, m), 6.81 (2H, br s), 8.32 (1H, d), 8.98 (1H, m), 9.50 (1H, s), 9.54 (1H, d) and 10.09 (2H, m) ppm. |
| I-N-126 | 391.1 | 1.97* | $^1$H NMR (500 MHz, DMSO-d6) δ 10.35 (s, 1H), 9.72 (s, 1H), 9.55 (dd, J = 4.7, 2.5 Hz, 1H), 8.93 (dd, J = 2.5, 0.7 Hz, 1H), 8.85 (s, 2H), 8.32 (s, 1H), 6.85 (s, 2H), 3.43-3.27 (m, 4H), 2.58-2.45 (m, 4H). |
| I-N-127 | 433.2 | 2.11* | $^1$H NMR (500 MHz, DMSO-d6) δ 2.64 (2H, t), 2.70 (4H, m), 3.09 (4H, m), 3.27 (3H, s), 3.51 (2H, t, J = 5 Hz), 6.80 (2H, br s), 8.25 (1H, d), 8.77 (1H, m), 9.50 (2H, m) and 10.30 (1H, s) ppm. |
| I-N-128 | 500.1 | 2.13* | $^1$H NMR (500 MHz, methanol-d4) δ 9.54 (bs, 1H), 9.07 (dd, J = 4.3, 2.5 Hz, 1H), 8.71 (d, J = 2.5 Hz, 1H), 8.34 (bs, 1H), 4.02-3.85 (m, 4H), 3.62 (dm, J = 12.6 Hz, 2H), 3.50-3.42 (m, 1H), 3.41-3.35 (m, 2H), 3.32-3.21 (m, 2H), 3.17-3.03 (m, 2H), 2.91 (s, 3H), 2.05 (2m, 4H). |
| I-N-129 | 400.2 | 1.88* | $^1$H NMR (500 MHz, DMSO-d6) δ 10.36 (s, 1H), 9.52 (dd, J = 4.8, 2.5 Hz, 1H), 9.32 (s, 1H), 9.05 (dd, J = 2.6, 0.6 Hz, 1H), 8.66 (s, 1H), 8.21 (s, 1H), 6.75 (s, 2H), 6.55 (s, 1H), 3.86-3.03 (m, 8H, under water peak), 2.95 (s, 3H), 2.94 (s, 3H). |
| I-N-130 | 512.2 | 2.18* | $^1$H NMR (500 MHz, methanol-d4) δ 10.26 (s, 1H), 9.50 (s, 1H), 9.03 (dd, J = 4.3, 2.5 Hz, 1H), 8.68 (dd, J = 2.5, 0.5 Hz, 1H), 8.35 (d, J = 4.1 Hz, 1H), 4.03-3.82 (m, 5H), 3.58-3.51 (m, 1H), 3.49-3.37 (m, 5H), 3.30-3.27 (m, 3H), 2.35 (d, J = 3.1 Hz, 1H), 2.18-2.09 (m, 1H), 2.09-2.01 (m, 2H), 2.01-1.87 (m, 2H). |
| I-N-131 | 455.2 | 2.23* | $^1$H NMR (500 MHz, DMSO-d6) δ 9.88 (s, 1H), 9.49 (dd, J = 4.8, 2.5 Hz, 1H), 9.43 (s, 1H), 8.73 (d, J = 2.5 Hz, 1H), 8.21 (d, J = 5.3 Hz, 1H), 7.17 (d, J = 5.3 Hz, 1H), 6.77 (s, 2H), 4.18 (ddt, J = 7.6, 6.3, 3.7 Hz, 1H), 3.56 (tt, J = 7.9, 3.8 Hz, 1H), 3.13-3.01 (m, 2H), 2.79 (ddt, J = 12.2, 8.4, 3.1 Hz, 2H), 2.67 (dd, J = 9.7, 6.3 Hz, 1H), 2.54-2.51 (m, 1H), 2.44-2.31 (m, 2H), 2.23 (s, 3H), 2.13-1.94 (m, 3H), 1.83-1.70 (m, 2H), 1.70-1.61 (m, 1H). |
| I-N-132 | 473.2 | 2.52* | $^1$H NMR (500 MHz, DMSO-d6) δ 10.50 (s, 1H), 9.55 (s, 1H), 9.54-9.46 (m, 1H), 8.70 (d, J = 2.5 Hz, 1H), 8.24 (d, J = 2.4 Hz, 1H), 6.80 (s, 2H), 4.23 (ddt, J = 7.4, 6.3, 3.6 Hz, 1H), 3.64 (dt, J = 8.8, 4.5 Hz, 1H), 3.19-3.08 (m, 2H), 3.07-2.97 (m, 2H), 2.72 (dd, J = 9.7, 6.2 Hz, 1H), 2.60-2.53 (m, 1H), 2.47-2.34 (m, 2H), 2.26 (s, 3H), 2.15-1.98 (m, 3H), 1.91-1.79 (m, 2H), 1.75-1.64 (m, 1H). |
| I-N-133 | 441.2 | 1.78* | $^1$H NMR (500 MHz, DMSO-d6) δ 10.35 (s, 2H), 9.55 (dd, J = 4.7, 2.5 Hz, 1H), 9.50 (s, 1H), 9.44 (s, 1H), 8.83 (d, J = 2.5 Hz, 1H), 8.49 (d, J = 6.0 Hz, 1H), 7.59 (d, J = 6.0 Hz, 1H), 4.00-3.81 (m, 4H), 3.54 (d, J = 28.4 Hz, 4H), 3.29 (d, |

Compound Analytical Data

| Cmpd No. | LCMS ES+ | LCMS (Rt min) | HNMR |
|---|---|---|---|
| | | | J = 65.1 Hz, 2H), 2.96 (s, 3H), 2.15 (dd, J = 58.8, 17.3 Hz, 4H). |
| I-N-134 | 512.2 | 1.84* | ¹H NMR (500 MHz, DMSO-d6) δ 10.36 (s, 1H), 9.54 (s, 1H), 9.51 (dd, J = 4.8, 2.5 Hz, 1H), 9.30 (s, 1H), 8.87 (d, J = 2.5 Hz, 1H), 8.29 (d, J = 2.6 Hz, 1H), 6.81 (s, 2H), 3.98-3.81 (m, 4H), 3.38-3.25 (m, 6H), 3.09 (t, J = 4.9 Hz, 4H), 2.22-2.11 (m, 6H). |
| I-N-135 | 431.2 | 1.94* | ¹H NMR (500 MHz, DMSO-d6) δ 10.29 (s, 1H), 9.54-9.48 (m, 2H), 8.74 (d, J = 2.5 Hz, 1H), 8.25 (d, J = 2.7 Hz, 1H), 6.80 (s, 2H), 4.07 (q, J = 5.3 Hz, 1H), 3.80 (dd, J = 11.4, 2.9 Hz, 1H), 3.64-3.49 (m, 2H), 3.29-3.24 (m, 1H), 3.19-3.08 (m, 2H), 2.99 (dm, J = 11.9 Hz, 1H), 2.90-2.77 (m, 2H), 2.73 (dm, J = 11.8 Hz, 2H), 2.63-2.57 (m, 1H), 2.41 (td, J = 11.6, 3.3 Hz, 1H). |
| I-N-136 | 427.2 | 1.12* | ¹H NMR (500 MHz, DMSO-d6) δ 9.90 (s, 1H), 9.51 (s, 1H), 9.47 (dd, J = 4.8, 2.5 Hz, 1H), 8.99-8.94 (m, 1H), 8.23 (d, J = 5.3 Hz, 1H), 7.21 (d, J = 5.3 Hz, 1H), 6.76 (s, 2H), 4.51-4.43 (m, 1H), 4.07 (s, 2H), 3.98 (dd, J = 11.8, 4.7 Hz, 1H), 3.96-3.87 (m, 1H), 3.57 (dd, J = 11.8, 7.0 Hz, 1H), 3.25-3.15 (m, 2H), 3.04 (td, J = 12.5, 2.9 Hz, 1H), 2.73-2.65 (m, 2H). |
| I-N-137 | 431.2 | 1.94* | ¹H NMR (500 MHz, DMSO-d6) δ 10.29 (s, 1H), 9.54-9.48 (m, 2H), 8.74 (d, J = 2.5 Hz, 1H), 8.25 (d, J = 2.7 Hz, 1H), 6.80 (s, 2H), 4.07 (q, J = 5.3 Hz, 1H), 3.80 (dd, J = 11.4, 2.9 Hz, 1H), 3.64-3.49 (m, 2H), 3.29-3.24 (m, 1H), 3.19-3.08 (m, 2H), 2.99 (dm, J = 11.9 Hz, 1H), 2.90-2.77 (m, 2H), 2.73 (dm, J = 11.8 Hz, 2H), 2.63-2.57 (m, 1H), 2.41 (td, J = 11.6, 3.3 Hz, 1H). |
| I-N-138 | 438.2 | 2.21* | ¹H NMR (500 MHz, DMSO-d6) δ 1.84 (6H, s), 2.33 (3H, s), 2.64 (4H, br d), 3.11 (4H, br s), 6.81 (2H, s), 8.26 (1H, d), 8.815 (1H, d), 9.16 (1H, d), 9.52 (1H, d), 10.46 (1H, s). |
| I-N-139 | 447.1 | 2.35* | — |
| I-N-140 | 501.1 | 2.04* | ¹H NMR (500 MHz, DMSO-d6) δ 2.10-2.15 (3H, s), 2.35-2.40 (2H, m), 2.50-2.60 (2H, masked), 2.66 (2H, br s), 2.81 (4H, br s), 3.15 (2H, br s), 7.51-7.52 (1H, d), 7.88-7.89 (1H, s), 8.21-8.23 (1H, d), 8.77 (1H, s). |
| I-N-141 | 357.0 | 1.89* | ¹H NMR (500 MHz, DMSO-d6) δ 9.65 (s, 1H), 9.52 (dd, J = 4.7, 2.5 Hz, 1H), 9.31 (d, J = 1.1 Hz, 1H), 8.97 (dd, J = 2.5, 0.5 Hz, 1H), 8.47 (dd, J = 6.6, 1.1 Hz, 1H), 7.53 (d, J = 6.6 Hz, 1H), 6.78 (s, 2H), 3.86-3.81 (m, 4H), 3.39-3.33 (m, 4H). |
| I-N-142 | 463.1 | 1.94* | ¹H NMR (500 MHz, DMSO-d6) δ 9.69 (s, 1H), 9.34 (s, 1H), 9.13 (d, J = 2.2 Hz, 1H), 8.92 (d, J = 2.3 Hz, 1H), 8.56-8.43 (m, 1H), 7.57 (d, J = 6.5 Hz, 1H), 6.80 (s, 2H), 4.79-4.59 (m, 4H), 4.20 (s, 1H), 3.57 (d, J = 6.0 Hz, 5H), 3.08 (s, 4H), 1.85 (s, 6H). |
| I-N-143 | 448.2 | 1.81* | ¹H NMR (500 MHz, DMSO-d6) δ 9.71 (s, 1H), 9.32 (d, J = 1.0 Hz, 1H), 9.16 (dd, J = 2.1, 0.6 Hz, 1H), 8.81 (d, J = 2.1 Hz, 1H), 8.46 (dd, J = 6.5, 1.0 Hz, 1H), 7.55 (d, J = 6.4 Hz, 1H), 6.88-6.70 (m, 2H), 4.65-4.69 (m, 5H), 4.51 (q, J = 7.2 Hz, 1H), 3.51 (s, 4H), 2.96 (br s, 3H), 1.71 (d, J = 7.2 Hz, 3H). |
| I-N-144 | 480.2 | 2.12* | ¹H NMR (500 MHz, DMSO-d6) δ 10.13 (s, 1H), 9.45 (s, 1H), 9.15 (d, J = 2.2 Hz, 1H), 8.88 (d, J = 2.3 Hz, 1H), 8.33 (d, J = 2.6 Hz, 1H), 6.81 (s, 2H), 4.87-4.67 (m, 4H), 4.42-4.27 (br m, 9H), 1.87 (s, 6H). |
| I-N-145 | 466.1 | 2.00* | ¹H NMR (500 MHz, DMSO-d6) δ 10.20 (s, 1H), 9.48 (s, 1H), 9.19 (dd, J = 2.1, 0.6 Hz, 1H), 8.78 (d, J = 2.1 Hz, 1H), 8.33 (d, J = 2.5 Hz, 1H), 6.81 (s, 2H), 4.86-4.70 (m, 4H), 4.52 (q, J = 7.2 Hz, 1H), 3.71 (5H), 3.41 (s, 4H), 1.73 (d, J = 7.3 Hz, 3H). |
| I-N-146 | 481.1 | 2.44* | ¹H NMR (500 MHz, DMSO-d6) δ 2.05-2.12 (4H, m), 2.9 (6H, s), 3.15-3.22 (4H, m), 3.55-3.62 (1H, m), 8.29 (1H, d), 8.96 (1H, d), 9.50-9.53 (1H, m), 9.65 (1H, s), 10.42 (1H, s). |
| I-N-147 | 457.1 | 2.1* | — |
| I-N-148 | 564.2 | 2.42* | ¹H NMR (500 MHz, DMSO-d6) δ 1.88-1.92 (2H, m), 1.96-2.05 (2H, m), 2.06-2.15 (4H, m), 2.77-2.83 (6H, m), 3.1-3.22 (6H, m), 3.47-3.60 (3H, m), 3.85-3.95 (1H, m), 8.29 (1H, d), 8.96 (1H, d), 9.40 (1H, d), 9.50-9.53 (1H, m), 9.65 (1H, s), 10.42 (1H, s). |
| I-N-149 | 473.2 | 2.60* | ¹H NMR (500 MHz, DMSO-d6) δ 10.22 (s, 1H), 9.53 (dd, J = 4.9, 2.5 Hz, 1H), 9.51 (s, 1H), 9.40 (s, 1H), 8.80 (d, J = 2.5 Hz, 1H), 8.28 (d, J = 2.8 Hz, 1H), 6.82 (s, 2H), 4.01 (d, J = 12.9 Hz, 2H), 3.73 (t, J = 12.0 Hz, 2H), 3.56 (d, J = 12.4 |

-continued

Compound Analytical Data

| Cmpd No. | LCMS ES+ | LCMS (Rt min) | HNMR |
|---|---|---|---|
| | | | Hz, 2H), 3.21 (t, J = 6.1 Hz, 2H), 3.13 (d, J = 7.7 Hz, 5H), 2.08 (d, J = 5.7 Hz, 2H), 1.90 (d, J = 11.8 Hz, 2H), 1.56 (q, J = 18.7, 14.9 Hz, 2H). |
| I-N-150 | 486.2 | 2.41* | ¹H NMR (500 MHz, DMSO-d6) δ 10.22 (s, 1H), 9.52 (dd, J = 4.8, 2.5 Hz, 1H), 9.49 (s, 1H), 8.75 (d, J = 2.6 Hz, 1H), 8.28 (d, J = 2.9 Hz, 1H), 6.82 (s, 2H), 3.47 (br s, 6H), 3.19-2.94 (m, 5H), 2.86-2.78 (m, 2H), 2.82 (s, 3H), 1.86 (d, J = 12.8 Hz, 4H), 1.52 (dd, J = 16.7, 8.1 Hz, 2H). |
| I-N-151 | 486.2 | 1.96* | — |
| I-N-152 | 354.0 | 2.59* | ¹H NMR (500 MHz, DMSO-d6) δ 9.61 (s, 1H), 9.52 (dd, J = 4.8, 2.5 Hz, 1H), 9.20 (s, 1H), 8.90 (d, J = 2.5 Hz, 1H), 8.38 (d, J = 6.7 Hz, 1H), 7.46 (d, J = 6.6 Hz, 1H), 6.77 (s, 2H), 3.32 (t, J = 5.4 Hz, 4H), 1.77-1.69 (m, 4H), 1.65 (td, J = 6.3, 3.5 Hz, 2H). |
| I-N-153 | 460.2 | 2.01* | — |
| I-N-154 | 469.2 | 2.16* | ¹H NMR (500 MHz, DMSO-d6) δ 1.42-1.50 (2H, m), 1.72-1.81 (4H, m), 1.96-2.04 (5H, m), 2.14 (3H, s), 2.61 (2H, m), 2.81 (2H, m), 3.07 (2H, m), 3.40-3.47 (1H, m), 3.67-3.72 (1H, m), 6.77 (2H, br s), 7.17 (1H, d), 8.20 (1H, d), 8.73 (1H, d), 9.44 (1H, s), 9.49 (1H, m) and 9.91 (1H, br s) ppm. |
| I-N-155 | 523.2 | 2.37* | ¹H NMR (500 MHz, DMSO-d6) δ 2.02-2.18 (4H, m), 3.12-3.22 (4H, m), 3.26-3.40 (8H, m), 3.57-3.63 (1H, m), 3.62-3.68 (4H, m), 8.27 (1H, d), 8.95 (1H, d), 9.48-9.52 (1H, m), 9.64 (1H, s), 10.42 (1H, s). |
| I-N-156 | 486.2 | 1.97* | ¹H NMR (500 MHz, methanol-d4) δ 2.09-2.20 (2H, m), 2.41 (2H, s), 2.52-2.57 (1H, m), 2.70-2.82 (2H, m), 2.93-2.97 (1H, m), 3.17-3.22 (3H, m), 3.40-3.45 (1H, m), 3.88-3.97 (1H, m), 8.18 (1H, d), 8.71 (1H, dd), 9.58 (1H, s), |
| I-N-157 | 486.2 | 2.03* | — |
| I-N-158 | 523.1 | 2.25* | ¹H NMR (500 MHz, CDCl3) δ 1.92-2.05 (3H, m), 2.07-2.12 (2H, m), 3.26-3.28 (4H, m), 3.45 (2H, m), 3.61-3.63 (4H, m), 5.89 (2H, s), 8.25 (1H, d), 8.54 (1H, dd), 8.61 (1H, d), 9.70 (1H, s), 10.25 (1H, s). |
| I-N-159 | 479.1 | 2.34* | — |
| I-N-160 | 472.1 | 1.96* | — |
| I-N-161 | 354.0 | 1.70* | — |
| I-N-162 | 354.0 | 1.63* | — |
| I-N-163 | 429.1 | 1.93* | ¹H NMR (500 MHz, DMSO-d6) δ 1.52-1.62 (2H, m), 1.12-1.18 (1H, m), 2.22-2.25 (1H, m), 2.32-2.37 (1H, m), 2.85-2.92 (1H, m), 2.94-2.98 (1H, m), 3.03-3.18 (2H, m), 3.22-3.27 (1H, m), 3.95 (1H, masked), 6.85 (2H, br s), 8.29 (1H, d), 8.81 (1H, d), 9.48 (1H, dd), 9.55 (1H, s), 10.42 (1H, s). |
| I-N-164 | 441.2 | 2.02* | ¹H NMR (500 MHz, DMSO-d6) δ 1.70-1.76 (2H, m), 1.94-1.97 (2H, m), 2.24 (3H, s), 2.75-2.81 (4H, m), 3.04-3.08 (2H, m), 3.53-3.57 (3H, m), 4.10-4.15 (1H, m), 6.77 (2H, br s), 7.18 (1H, d), 8.21 (1H, d), 8.75 (1H, d), 9.42 (1H, s), 9.49 (1H, m) and 9.86 (1H, br s) ppm. |
| I-N-165 | 452.0 | 1.48* | ¹H NMR (500 MHz, DMSO-d6) δ 10.42 (s, 1H), 9.64 (s, 1H), 9.49 (dd, J = 4.7, 2.5 Hz, 1H), 8.96 (d, J = 2.3 Hz, 1H), 8.27 (d, J = 2.6 Hz, 1H), 7.16 (s, 1H), 6.80 (s, 2H), 3.45 (ddt, J = 12.2, 7.5, 3.8 Hz, 1H), 3.25-3.10 (m, 4H), 3.07 (s, 3H), 2.23-2.16 (m, 2H), 2.10-1.98 (m, 2H). |
| I-N-166 | 536.1 | 2.33* | ¹H NMR (500 MHz, DMSO-d6) δ 2.02-2.18 (5H, m), 2.47 (3H, s), 3.12-3.32 (7H, m), 3.48-3.53 (2H, m), 3.65-3.71 (1H, m), 3.85-3.92 (4H, m), 8.27 (1H, d), 8.91 (1H, d), 9.51-9.53 (1H, m), 9.65 (1H, s), 9.72 (1H, brs), 10.43 (1H, s). |
| I-N-167 | 487.2 | 2.38* | ¹H NMR (500 MHz, methanol-d4) δ 9.60 (s, 1H), 9.05 (dd, J = 4.4, 2.5 Hz, 1H), 8.75 (d, J = 2.4 Hz, 1H), 8.14 (d, J = 2.9 Hz, 1H), 3.76 (t, J = 5.8 Hz, 2H), 3.65 (dt, J = 9.1, 4.8 Hz, 1H), 3.28-3.22 (m, 2H), 3.16 (dt, J = 11.4, 2.6 Hz, 2H), 2.83 (t, J = 5.8 Hz, 2H), 2.72 (d, J = 6.9 Hz, 4H), 2.19 (dt, J = 13.0, 4.0 Hz, 2H), 2.07-1.96 (m, 2H), 1.90-1.84 (m, 4H). |
| I-N-168 | 458.2 | 1.70* | ¹H NMR (500 MHz, DMSO-d6) δ 10.39 (s, 1H), 9.56 (s, 1H), 9.51 (dd, J = 4.8, 2.5 Hz, 1H), 8.87 (d, J = 2.5 Hz, 1H), 8.62 (s, 1H), 8.29 (d, J = 2.5 Hz, 1H), 6.81 (s, 2H), 4.30-4.08 (m, 4H), 4.07-3.92 (m, 1H), 3.77 (s, 2H), 3.08 (dt, J = 10.8, 4.7 Hz, 4H). |
| I-N-169 | 493.1 | 2.51* | ¹H NMR (500 MHz, DMSO-d6) δ 2.01-2.12 (2H, m), 2.12-2.18 (2H, m), 2.22-2.28 (2H, m), 3.16-3.21 (4H, m), 3.38-3.46 (1H, m), 3.92-3.97 (4H, m), 5.8 (2H, brs), 8.29 (1H, d), 8.93 (1H, d), 9.50-9.53 (1H, m), 9.63 (1H, s), 10.41 (1H, s). |
| I-N-170 | 505.1 | 2.12* | ¹H NMR (500 MHz, DMSO-d6) δ 2.02-2.18 (3H, m), 2.98-3.08 (2H, m), 3.25-3.31 (4H, m), 3.57-3.71 (8H, m), 6.82 |

-continued

Compound Analytical Data

| Cmpd No. | LCMS ES+ | LCMS (Rt min) | HNMR |
|---|---|---|---|
| | | | (2H, brs), 7.5 (1H, d), 8.42 (1H, d), 8.81 (1H, d), 9.44 (1H, s), 9.54-9.57 (1H, m), 9.80 (1H, s). |
| I-N-171 | 500.1 | 2.31* | $^1$H NMR (500 MHz, DMSO-d6) δ 10.24 (s, 1H), 9.57-9.47 (m, 2H), 8.80 (d, J = 2.5 Hz, 1H), 8.27 (d, J = 2.8 Hz, 1H), 6.82 (s, 2H), 4.12 (s, 2H), 3.86 (s, 2H), 3.56 (s, 2H), 3.42 (s, 1H), 3.24 (s, 1H), 3.12 (s, 4H), 2.92 (s, 3H), 2.11 (s, 1H), 1.88 (s, 2H), 1.63-1.45 (m, 2H). |
| I-N-172 | 488.1 | 1.8* | — |
| I-N-173 | 501.0 | 2.26* | — |
| I-N-174 | 502.2 | 1.94* | $^1$H NMR (500 MHz, DMSO-d6) δ 2.15-2.30 (4H, m), 2.65-2.75 (1H, br s), 2.78-2.88 (1H, br s), 3.02-3.14 (5H, m), 3.55-3.65 (2H, br s), 3.70-3.75 (1H, br s), 3.82-3.90 (3H, br s), 4.30-4.38 (1H, br s), 6.80 (2H, s), 8.27 (1H, d), 8.82 (1H, d), 9.49 (1H, dd), 9.55 (1H, d), 10.40 (1H, s). |
| I-N-175 | 536.0 | 2.26* | — |
| I-N-176 | 461.0 | 2.14* | $^1$H NMR (500 MHz, DMSO-d6) δ 0.94-1.03 (4H, m), 2.80-2.83 (1H, m), 3.37 (4H, m), 3.42 (4H, m), 6.79 (2H, s), 7.51-7.52 (1H, d), 8.44-8.45 (1H, d), 8.88 (1H, d), 9.32 (1H, s), 9.55 (1H, dd), 9.77 (1H, s). |
| I-N-177 | 505.0 | 2.08* | — |
| I-N-178 | 435.0 | 1.9* | — |
| I-N-179 | 491.0 | 2.03* | — |
| I-N-180 | 478.0 | 1.87* | $^1$H NMR (500 MHz, DMSO-d6) δ 1.66-1.70 (2H, m), 1.80-1.85 (2H, m), 2.59 (4H, brs), 3.12 (4H, brs), 3.58-3.64 (1H, m), 4.48-4.52 (2H, m), 3.58-3.62 (2H, m), 6.78 (2H, s), 8.24 (1H, s), 8.71 (1H, s), 9.08 (1H, s), 9.49 (1H, s), 10.36 (1H, s). |
| I-N-181 | 486.0 | 2.07* | $^1$H NMR (500 MHz, DMSO-d6) δ 1.85-2.03 (2H, m), 2.06-2.13 (1H, m), 2.86 (3H, d), 3.11-3.13 (4H, m), 3.19-3.24 (1H, m), 3.63-3.68 (3H, m), 3.75-3.80 (1H, m), 3.82-3.85 (1H, m), 4.63-4.65 (2H, m), 6.80 (2H, br s), 8.30 (1H, d), 8.90 (1H, d), 9.51-9.53 (1H, dd), 9.56 (2H, m), 10.37 (1H, s). |
| I-N-182 | 429.0 | 1.97* | $^1$H NMR (500 MHz, DMSO-d6) δ 1.52-1.62 (2H, m), 1.12-1.18 (1H, m), 2.22-2.25 (1H, m), 2.32-2.37 (1H, m), 2.85-2.92 (1H, m), 2.94-2.98 (1H, m), 3.03-3.18 (2H, m), 3.22-3.27 (1H, m), 3.95 (1H, masked), 6.85 (2H, br s), 8.29 (1H, d), 8.81 (1H, d), 9.48 (1H, dd), 9.55 (1H, s), 10.42 (1H, s). |
| I-N-183 | 441.4 | 2.12* | $^1$H NMR (500 MHz, DMSO-d6) δ 1.77-1.82 (2H, m), 1.99 (2H, m), 2.23 (3H, m), 2.37 (3H, m), 2.93 (4H, m), 3.68 (2H, m), 6.77 (2H, br s), 7.19 (1H, d, J = 5Hz), 8.20 (1H, d), 8.80 (1H, m), 9.41 (1H, s), 9.41 (1H, m) and 9.79 (1H, br s) ppm. |
| I-N-184 | 457.1 | 2.74* | $^1$H NMR (500 MHz, DMSO-d6) δ 10.52 (s, 1H), 9.60 (s, 1H), 9.49 (dd, J = 4.7, 2.5 Hz, 1H), 8.99 (dd, J = 2.6, 0.7 Hz, 1H), 8.27 (d, J = 2.6 Hz, 1H), 7.83 (d, J = 3.3 Hz, 1H), 7.68 (d, J = 3.3 Hz, 1H), 6.80 (s, 2H), 3.40-3.32 (m, 1H), 3.27-3.22 (m, 2H), 3.16 (d, J = 11.7 Hz, 2H), 2.30-2.20 (m, 2H), 2.12 (d, J = 12.5 Hz, 2H). |
| I-N-185 | 500.0 | 2.16* | — |
| I-N-186 | 429.0 | 1.97* | $^1$H NMR (500 MHz, DMSO-d6) δ 1.52-1.62 (1H, m), 2.11-2.17 (1H, m), 2.22-2.25 (1H, m), 2.32-2.37 (1H, m), 2.85-2.88 (1H, m), 2.90-2.92 (1H, m), 3.02-3.05 (1H, m), 3.10-3.13 (1H, m), 3.22-3.27 (1H, m), 3.93-3.95 (2H, m), 6.79 (2H, br s), 8.29 (1H, d), 8.81 (1H, d), 9.48 (1H, dd), 9.55 (1H, s), 10.42 (1H, s). |
| I-N-187 | 486.0 | 2.19* | $^1$H NMR (500 MHz, CDCl3) δ 10.34 (s, 1H), 9.69 (s, 1H), 8.54-8.55 (dd, 1H), 8.46 (d, 1H), 8.23 (d, 1H), 5.89 (s, 2H), 3.90 (s, 4H), 3.48 (s, 2H), 3.18 (s, 4H), 2.71 (s, 4H). 1.86 (s, 4H). |
| I-N-188 | 518.0 | 2.05* | $^1$H NMR (500 MHz, DMSO-d6) δ 1.80-1.87 (2H, m), 2.20-2.25 (2H, m), 2.81 (3H, s), 2.92-2.97 (2H, m), 3.33 (3H, s), 3.48-3.56 (8H, m), 6.80 (2H, s), 7.45 (1H, m), 8.41 (1H, d), 8.90 (1H, d), 9.31 (1H, s), 9.53-9.55 (1H, m), 9.73 (1H, s). |
| I-N-189 | 459.0 | 2.36* | $^1$H NMR (500 MHz, DMSO-d6) δ 1.85-1.88 (2H, m), 2.17-2.19 (2H, m), 3.14-3.21 (3H, m), 3.27-3.30 (2H, m), 3.53-3.55 (2H, m), 3.73-3.76 (2H, m), 4.04-4.07 (2H, m), 6.75-6.6.85 (2H, s), 7.41-7.44 (1H, m), 7.54-7.56 (1H, m), 7.72-7.74 (1H, d), 7.99-8.00 (1H, d), 8.29 (1H, d), 8.94 (1H, d), 9.41 (1H, s), 9.52-9.54 (1H, m), 9.60-9.80 (1H, m), 10.05 (1H, s). |
| I-N-190 | 434.0 | 0.6 | $^1$H NMR (500 MHz, Methanol-d4) δ 9.90 (s, 0.5H), 9.62 (d, 1H), 9.1-9.07 (m, 1H), 8.88 (d, 1H), 8.38 (d, 1H), 7.62 (d, 1H), 3.92-3.85 (m, 2H), 3.51-3.45 (m, 1H), 3.15-3.08 (m, 2H), 3.06 (s, 3H), 2.35-2.26 (m, 4H) |

-continued

Compound Analytical Data

| Cmpd No. | LCMS ES+ | LCMS (Rt min) | HNMR |
|---|---|---|---|
| I-N-191 | 486.2 | 1.89* | — |
| I-N-192 | 533.0 | 2.44* | ¹H NMR (500 MHz, DMSO-d6) δ 10.37 (1H, s), 9.48 (1H, s), 9.08 (1H, d), 8.68 (1H, d), 8.28 (1H, d), 6.77 (2H, brs), 3.08-3.19 (6H, m), 2.80 (3H, s), 1.85-1.88 (2H, m), 1.76-1.81 (2H, m), 1.70-1.73 (2H, m), 1.52-1.55 (2H, m) (n.b some signals masked by broad water peak). |
| I-N-193 | 500.1 | 2.24* | ¹H NMR (500 MHz, DMSO-d6) δ 10.31 (s, 1H), 9.53 (s, 1H), 9.51 (dd, J = 4.7, 2.5 Hz, 1H), 8.94 (d, J = 2.4 Hz, 1H), 8.27 (d, J = 2.6 Hz, 1H), 6.81 (s, 2H), 3.92 (s, 2H), 3.59 (d, J = 4.7 Hz, 4H), 3.45 (s, 2H), 3.17-3.00 (m, 4H), 2.88 (s, 3H), 1.93 (dtd, J = 15.7, 8.3, 7.6, 3.8 Hz, 1H), 1.74 (d, J = 12.1 Hz, 2H), 1.55 (qd, J = 12.1, 4.4 Hz, 2H). |
| I-N-194 | 472.1 | 1.85* | ¹H NMR (500 MHz, DMSO-d6) δ 9.57 (s, 1H), 9.04-9.05 (dd, 1H), 9.70 (d, 1H), 8.18 (d, 1H), 3.92 (s, 2H), 3.68-3.71 (m, 5H), 3.49 (m, 2H), 3.18-3.20 (m, 4H), 2.42 (s, 3H). |
| I-N-195 | 477.1 | 1.97* | ¹H NMR (500 MHz, DMSO-d6) δ 9.80 (s, 1H), 9.50-9.51 (dd, 1H), 9.39 (s, 1H), 8.91 (d, 1H), 8.26 (d, 1H), 7.23-7.24 (d, 1H), 6.76 (s, 2H), 4.93-4.97 (m, 1H), 4.84-4.88 (m, 2H), 4.73-4.76 (m, 2H), 3.35 (s, 4H), 3.03 (s, 4H). |
| I-N-196 | 544.1 | 2.04* | ¹H NMR (500 MHz, DMSO-d6) δ 1.97-2.18 (9H, m), 2.92-3.00 (2H, m), 3.30-3.50 (5H, m), 3.55-3.65 (3H, m), 3.67-3.72 (2H, m), 4.22-4.26 (1H, m), 6.70-6.88 (2H, m), 7.45 (1H, d), 8.40 (1H, d), 8.78 (1H, s), 9.45 (1H, s), 9.52-9.54 (1H, m), 9.8 (1H, brs), 10.35 (1H, s). |
| I-N-197 | 475.1 | 2.83* | ¹H NMR (500 MHz, Methanol-d4) δ 9.69 (s, 1H), 9.20 (dd, 1H), 9.11 (dd, 1H), 8.76 (dd, 1H), 8.36-8.22 (m, 1H), 7.51 (dd, 1H), 3.98 (d, 2H), 3.71 (br t, 2H), 3.52 (s, 2H), 3.19-3.16 (m, 2H), 3.13 (dd, 2H), 2.59 (tt, 2H), 2.11-2.05 (m, 1H), 1.98 (d, 2H), 1.62 (qd, 2H). |
| I-N-198 | 468.1 | 1.83* | ¹H NMR (500 MHz, DMSO-d6) δ 9.88 (s, 1H), 9.46-9.49 (m, 2H), 8.94 (d, 1H), 7.20 (d, 1H), 6.76 (s, 2H), 3.90-3.95 (m, 1H), 3.80-3.87 (m, 2H), 3.60-3.67 (m, 1H), 3.29 (s, 3H), 3.15-3.25 (m, 1H), 2.85-3.00 (m, 4H), 2.20-2.30 (m, 2H), 2.10-2.15 (m, 1H), 1.80-1.90 (m, 2H). |
| I-N-199 | 468.2 | 1.83* | ¹H NMR (500 MHz, DMSO-d6) δ 9.88 (s, 1H), 9.46-9.49 (m, 2H), 8.94 (d, 1H), 7.20 (d, 1H), 6.76 (s, 2H), 3.90-3.95 (m, 1H), 3.80-3.87 (m, 2H), 3.60-3.67 (m, 1H), 3.29 (s, 3H), 3.15-3.25 (m, 1H), 2.85-3.00 (m, 4H), 2.20-2.30 (m, 2H), 2.10-2.15 (m, 1H), 1.80-1.90 (m, 2H). |
| I-N-200 | 476.1 | 1.9* | ¹H NMR (500 MHz, DMSO-d6) δ 1.97-2.12 (4H, m), 2.92-3.00 (2H, m), 3.44-3.56 (1H, m), 3.60-3.67 (2H, m), 4.75-4.79 (2H, m), 4.83-4.86 (2H, m), 6.80 (2H, brs), 7.50 (1H, d), 8.42 (1H, d), 8.81-8.83 (1H, m), 9.47 (1H, s), 9.54-9.58 (1H, m), 9.8 (1H, brs). |
| I-N-201 | 495.0 | 2.13* | ¹H NMR (500 MHz, DMSO-d6) δ 10.24 (s, 1H), 9.52 (dd, J = 4.8, 2.5 Hz, 1H), 9.46 (s, 1H), 8.84-8.80 (m, 1H), 8.30 (d, J = 2.6 Hz, 1H), 6.79 (s, 2H), 5.07-4.97 (m, 1H), 4.85 (dd, J = 8.1, 7.0 Hz, 2H), 4.75 (dd, J = 7.1, 6.1 Hz, 2H), 3.45 (dd, J = 6.1, 3.4 Hz, 4H), 3.18-3.12 (m, 4H). |
| I-N-202 | 379.1 | 1.88* | ¹H NMR (500 MHz, DMSO-d6) δ 9.80 (s, 1H), 9.49 (dd, J = 4.8, 2.5 Hz, 1H), 9.42 (s, 1H), 8.61 (d, J = 5.1 Hz, 1H), 8.39 (d, J = 2.5 Hz, 1H), 7.83 (dd, J = 18.1, 2.1 Hz, 2H), 7.79 (d, J = 5.1 Hz, 1H), 6.74 (s, 2H), 1.87 (ddd, J = 10.6, 8.2, 5.3 Hz, 1H), 1.11-0.93 (m, 4H). |
| I-N-203 | 526.1 | 2.26* | — |
| I-N-204 | 514.0 | 2.41* | ¹H NMR (500 MHz, DMSO-d6) δ 10.35 (s, 1H), 9.55 (s, 1H), 9.51-9.52 (dd, 1H), 9.38-9.46 (m, 1H), 8.88 (d, 1H), 8.30 (d, 1H), 6.80 (s, 2H), 4.56-4.61 (m, 1H), 3.92-3.95 (m, 1H), 3.82-3.85 (m, 1H), 3.70-3.80 (m, 2H), 3.55-3.58 (m, 1H), 3.08-3.20 (m, 5H), 2.98-3.05 (m, 1H), 2.89-2.95 (m, 1H), 212-2.15 (m, 1H), 1.78-1.90 (m, 3H), 1.50-1.65 (m, 2H), .25-1.28 (t, 3H). |
| I-N-205 | 514.0 | 2.23* | — |
| I-N-206 | 514.1 | 2.18* | — |
| I-N-207 | 500.1 | 2.09* | — |
| I-N-208 | 478.2 | 2.04* | ¹H NMR (500 MHz, DMSO-d6) δ 1.99-2.10 (2H, m), 2.18-2.25 (2H, m), 2.95-3.05 (2H, m), 3.32 (3H, s), 3.40-3.50 (4H, m), 3.62-3.68 (2H, m), 3.75-3.78 (2H, m), 6.80 (2H, brs), 7.55 (1H, d), 8.43 (1H, d), 8.81-8.82 (1H, m), 9.48 (1H, s), 9.54-9.57 (1H, m), 9.8 (1H, brs). |
| I-N-209 | 385.1 | 1.61* | ¹H NMR (500 MHz, DMSO-d6) δ 9.62 (s, 1H), 9.53 (dd, 1H), 9.09 (s, 1H), 8.74 (d, 1H), 8.40 (dd, 1H), 7.42 (d, 1H), 6.75 (s, 2H), 4.02 (s, 2H), 3.75 (br t, 2H), 3.48 (br t, 1H), 2.94 (s, 3H). |

-continued

| Compound Analytical Data | | | |
|---|---|---|---|
| Cmpd No. | LCMS ES+ | LCMS (Rt min) | HNMR |
| I-N-210 | 406.0 | 1.65* | $^1$H NMR (500 MHz, DMSO-d6) δ 9.77 (s, 1H), 9.55 (dd, J = 4.8, 2.5 Hz, 1H), 9.33 (d, J = 0.9 Hz, 1H), 8.86-8.81 (m, 1H), 8.47 (dd, J = 6.2, 0.9 Hz, 1H), 7.64 (d, J = 6.3 Hz, 1H), 6.80 (s, 2H), 3.77-3.71 (m, 4H), 3.46-3.40 (m, 8H). |
| I-N-211 | 542.1 | 2.02* | |
| I-N-212 | 403.1 | 1.8* | $^1$H NMR (500 MHz, DMSO-d6) δ 10.35 (s, 1H), 9.51 (s, 1H), 9.50 (t, 1H), 8.54 (d, 1H), 8.31 (d, 1H), 6.76 (br s, 2H), 3.71 (s, 2H), 3.53-3.50 (m, 2H), 3.46-3.44 (m, 2H), 3.01 (s, 3H). |
| I-N-213 | 471.1 | 2.44* | $^1$H NMR (500 MHz, DMSO-d6) δ 10.26 (s, 1H), 9.52 (s, 1H), 9.50 (dd, 1H), 8.99 (d, 1H), 8.28 (d, 1H), 6.79 (br s, 2H), 3.38 (t, 2H), 3.22 (d, 2H), 3.12-3.02 (m, 4H), 2.26 (t, 2H), 1.98-1.92 (m, 2H), 1.89-1.82 (m, 1H), 1.68 (dd, 2H), 1.52 (qd, 2H). |
| I-N-214 | 500.1 | 2.49* | $^1$H NMR (500 MHz, DMSO-d6) δ 10.38 (s, 1H), 9.49-9.56 (m, 2H), 8.77 (d, 1H), 8.27 (d, 1H), 6.80 (s, 2H), 4.02-4.25 (m, 2H), 3.80-3.90 (m, 1H), 3.70-3.80 (m, 2H), 3.35-3.45 (m, 1H), 3.05-3.20 (m, 4H), 2.88-2.90 (m, 1H), 2.19 (s, 2H), 1.90-205 (m, 2H), 1.60-1.80 (m, 3H), 1.50-1.55 (s, 1H), 1.30-1.40 (m, 1H). |
| I-N-215 | 448.1 | 1.91* | $^1$H NMR (500 MHz, DMSO-d6) δ 1.62-1.70 (2H, m), 1.96-2.03 (2H, m), 2.20-2.28 (1H, m), 3.00-3.08 (5H, m), 3.28 (2H, d), 3.62-3.68 (2H, m), 6.80 (2H, brs), 7.48 (1H, d), 8.42 (1H, d), 8.97 (1H, d), 9.32 (1H, s), 9.53-9.56 (1H, m), 9.63 (1H, brs). |
| I-N-216 | 441.0 | 1.95* | $^1$H NMR (500 MHz, DMSO-d6) δ 9.65 (s, 1H), 9.53 (dd, 1H), 9.29 (s, 1H), 8.88 (d, 1H), 8.43-8.45 (dd, 1H), 7.57-7.58 (d, 1H), 6.79 (s, 2H), 3.45-3.50 (m, 2H), 3.45 (s, 2H), 3.30-3.45 (m, 2H), 2.78 (s, 3H), 1.97-2.08 (m, 4H). |
| I-N-217 | 411.1 | 1.74* | $^1$H NMR (500 MHz, DMSO-d6) δ 9.78 (s, 1H), 9.52 (dd, J = 4.8, 2.5 Hz, 1H), 9.40-9.34 (m, 1H), 8.99-8.92 (m, 1H), 8.43 (dd, J = 6.3, 0.9 Hz, 1H), 7.52 (d, J = 6.4 Hz, 1H), 6.78 (s, 2H), 3.95-3.85 (m, 2H), 3.77-3.70 (m, 1H), 3.62 (d, J = 12.5 Hz, 1H), 3.15-3.05 (m, 1H), 2.87 (td, J = 12.3, 3.5 Hz, 1H), 2.77 (dd, J = 12.1, 10.9 Hz, 1H), 2.37-2.21 (m, 2H), 2.09 (dddd, J = 12.8, 9.8, 7.7, 4.0 Hz, 1H), 1.63-1.52 (m, 1H). |
| I-N-218 | 368.1 | 1.66* | $^1$H NMR (500 MHz, DMSO-d6) δ 9.81 (s, 1H), 9.73 (s, 1H), 9.45 (dd, J = 4.8, 2.5 Hz, 1H), 8.51 (d, J = 5.1 Hz, 1H), 8.46 (d, J = 2.5 Hz, 1H), 7.67 (dd, J = 5.1, 0.6 Hz, 1H), 2.38 (s, 3H), 2.36 (s, 3H). |
| I-N-219 | 407.0 | 2.1* | $^1$H NMR (500 MHz, DMSO-d6) δ 9.85 (s, 1H), 9.48 (s, 1H), 9.45 (dd, J = 4.8, 2.5 Hz, 1H), 8.52 (d, J = 5.0 Hz, 1H), 8.24 (d, J = 2.5 Hz, 1H), 7.87 (d, J = 1.3 Hz, 1H), 7.71 (d, J = 5.1 Hz, 1H), 7.59 (d, J = 1.3 Hz, 1H), 6.66 (s, 2H). |
| I-N-220 | 370.1 | 2.63* | $^1$H NMR (500 MHz, DMSO-d6) δ 9.48 (dd, J = 4.8, 2.6 Hz, 1H), 9.26 (d, J = 0.9 Hz, 1H), 8.79 (d, J = 2.5 Hz, 1H), 8.30 (dd, J = 1.5, 0.7 Hz, 1H), 8.10 (dd, J = 7.4, 1.4 Hz, 1H), 7.30 (d, J = 7.4 Hz, 1H), 6.65 (s, 2H), 3.80 (t, J = 6.5 Hz, 2H), 1.90-1.77 (m, 4H), 1.54 (s, 6H). |
| I-N-221 | 434.0 | 1.88* | $^1$H NMR (500 MHz, DMSO-d6) δ 9.69 (1H, s), 9.53 (1H, dd), 9.35 (1H, s), 9.00 (1H, dd), 8.45 (1H, dd), 7.57 (1H, d), 6.79 (2H, brs), 3.92 (1H, d), 3.52-3.58 (2H, m), 3.16-3.21 (1H, t), 2.99 (3H, s), 2.88-2.93 (1H, m), 2.30-2.33 (1H, m), 1.83-1.93 (2H, m), 1.67-1.71 (1H, m). |
| I-N-222 | 411.1 | 1.8* | $^1$H NMR (500 MHz, DMSO-d6) δ 9.60 (s, 1H), 9.52 (dd, 1H), 9.01 (s, 1H), 8.74 (d, 1H), 8.38 (dd, 1H), 7.44 (d, 1H), 6.74 (s, 2H), 4.24 (d, 1H), 4.20 (d, 1H), 3.87 (d, 1H), 3.84-3.78 (m, 1H), 3.53-3.48 (m, 1H), 3.41-3.36 (m, 1H), 3.18 (dd, 1H), 1.95-1.90 (m, 2H), 1.84-1.74 (m, 1H), 1.47-1.38 (m, 1H). |
| I-N-223 | 353.1 | 1.97* | $^1$H NMR (500 MHz, DMSO-d6) δ 2.26 (3H, s), 6.47 (1H, m), 6.70 (2H, br s), 7.59 (1H, m), 7.94 (1H, m), 8.48 (1H, m), 8.60 (1H, m), 9.41 (1H, m), 9.79 (1H, s) and 10.14 (1H, s) ppm. |
| I-N-224 | 425.1 | 1.81* | $^1$H NMR (500 MHz, DMSO-d6) δ 9.51 (dd, J = 4.8, 2.5 Hz, 1H), 9.45 (s, 1H), 8.92 (d, J = 1.1 Hz, 1H), 8.71 (d, J = 2.5 Hz, 1H), 8.33 (dd, J = 6.9, 1.2 Hz, 1H), 7.45 (d, J = 6.9 Hz, 1H), 6.73 (s, 2H), 3.97-3.90 (m, 1H), 3.72-3.63 (m, 1H), 3.50 (ddd, J = 13.8, 11.4, 5.6 Hz, 2H), 3.10 (ddd, J = 13.4, 10.7, 2.7 Hz, 1H), 3.00 (dd, J = 9.9, 1.7 Hz, 1H), 2.74 (d, J = 0.7 Hz, 3H), 2.71 (dt, J = 7.5, 4.1 Hz, 1H), 2.63-2.53 (m, 1H), 1.94-1.84 (m, 1H), 1.59 (dtd, J = 13.7, 10.1, 3.6 Hz, 1H). |

Compound Analytical Data

| Cmpd No. | LCMS ES+ | LCMS (Rt min) | HNMR |
|---|---|---|---|
| I-N-225 | 352.9 | 2.07* | $^1$H NMR (500 MHz, DMSO-d6) δ 2.32 (3H, s), 6.46 (1H, m), 6.73 (2H, br s), 7.64 (1H, m), 8.37-8.40 (2H, m), 8.76 (1H, m), 9.40-9.42 (2H, m) and 11.10 (1H, s) ppm. |
| I-N-226 | 398.1 | 2.0* | $^1$H NMR (500 MHz, DMSO-d6) δ 9.81 (s, 1H), 9.47 (dd, J = 4.8, 2.5 Hz, 1H), 9.44 (s, 1H), 8.77 (d, J = 2.5 Hz, 1H), 8.20 (d, J = 5.2 Hz, 1H), 7.14 (d, J = 5.3 Hz, 1H), 6.77 (s, 2H), 4.39 (s, 4H), 2.86-2.80 (m, 4H), 2.02 (t, J = 5.5 Hz, 4H). |
| I-N-227 | 502.0 | 1.99* | $^1$H NMR (500 MHz, DMSO-d6) δ 10.37 (s, 1H), 10.20 (s, 1H), 9.56 (s, 1H), 9.51 (dd, 1H), 8.91 (d, 1H), 8.30 (d, 1H), 6.80 (br s, 2H), 4.80-4.85 (m, 1H), 4.32 (m, 1H), 4.01-4.09 (m, 2H), 3.88-3.91 (m, 1H), 3.70-3.76 (m, 2H), 3.57-3.62 (m, 1H), 3.49-3.53 (t, 1H), 3.42-3.45 (d, 1H), 3.20 (m, 3H), 3.11 (s, 2H), 2.83 (s, 3H). |
| I-N-228 | 472.0 | 2.06* | $^1$H NMR (500 MHz, DMSO-d6) δ 10.11 (s, 1H), 9.52-9.54 (m, 2H), 9.07 (dd, 1H), 8.32 (d, 1H), 6.80 (br s, 2H), 4.22-4.24 (m, 2H), 4.15 (s, 2H), 3.99-4.00 (t, 2H), 3.25-3.70 (m, 8H), 2.29-237 (s, 2H). |
| I-N-229 | 459.0 | 2.18* | $^1$H NMR (500 MHz, DMSO-d6) δ 10.31 (s, 1H), 9.51-9.52 (dd, 2H), 8.67 (d, 1H), 8.30 (d, 1H), 6.80 (br s, 2H), 3.54 (s, 2H), 3.22-3.28 (m, 2H), 3.02-3.08 (m, 2H), 2.81 (s, 3H), 2.02-2.07 (m, 4H). |
| I-N-230 | 439.0 | 1.92* | $^1$H NMR (500 MHz, DMSO-d6) δ 9.76 (s, 1H), 9.49 (dd, J = 4.8, 2.5 Hz, 1H), 9.36 (s, 1H), 8.93-8.88 (m, 1H), 8.22 (d, J = 5.3 Hz, 1H), 7.19 (d, J = 5.4 Hz, 1H), 6.76 (d, J = 4.5 Hz, 2H), 4.34 (t, J = 5.1 Hz, 1H), 3.84 (tt, J = 12.1, 3.9 Hz, 1H), 3.48-3.44 (m, 1H), 3.27-3.21 (m, 2H), 2.80 (td, J = 12.2, 2.2 Hz, 2H), 2.25 (dd, J = 8.6, 7.5 Hz, 2H), 2.09-1.91 (m, 4H), 1.69-1.62 (m, 2H). |
| I-N-231 | 453.1 | 2.01* | 1H NMR (500 MHz, DMSO-d6) δ 9.52-9.55 (m, 2H), 9.15 (d, 1H), 8.90 (d, 1H), 8.41-8.43 (m, 1H), 7.50 (d, 1H), 6.77 (s, 2H), 3.40 (m, 4H), 3.23 (s, 2H), 2.80 (s, 3H), 2.20-2.25 (m, 2H), 1.74-1.77 (m, 2H), 1.63-1.71 (m, 4H). |
| I-N-232 | 429.1 | 2.02* | $^1$H NMR (500 MHz, DMSO-d6) δ 10.39 (s, 1H), 9.54 (s, 1H), 9.50 (dd, 1H), 8.48 (d, 1H), 8.30 (d, 1H), 6.76 (s, 2H), 3.78-3.56 (m, 5H), 3.50-3.45 (m, 1H), 3.29-3.23 (m, 1H), 2.02-1.94 (m, 2H), 1.92-1.84 (m, 1H), 1.54-1.45 (m, 1H). |
| I-N-233 | 440.1 | 1.7* | $^1$H NMR (500 MHz, DMSO-d6) δ 9.68 (s, 1H), 9.52-9.53 (dd, 1H), 9.32 (d, 1H), 8.93 (d, 1H), 8.47-8.48 (dd, 1H), 7.57-7.58 (d, 1H), 6.80 (s, 2H), 4.03-4.06 (dd, 1H), 3.66-3.69 (m, 1H), 3.45-3.50 (m, 1H), 3.23-3.26 (m, 1H), 3.06-3.15 (m, 4H), 2.97-3.03 (m, 1H), 2.95-2.97 (m, 4H), 2.62-2.65 (m, 1H). |
| I-N-234 | 429.1 | 1.75* | $^1$H NMR (500 MHz, DMSO-d6) δ 9.66 (s, 1H), 9.52-9.53 (dd, 1H), 9.24 (d, 1H), 8.96-8.97 (dd, 1H), 8.40-8.42 (dd, 1H), 7.51-7.52 (d, 1H), 6.80 (s, 2H), 4.51-4.54 (dd, 1H), 3.96-3.98 (m, 1H), 3.56-3.58 (m 2H), 3.18-3.23 (m, 2H), 3.02 (s, 3H), 2.77 (s, 3H). |
| I-N-235 | 439.1 | 1.83* | $^1$H NMR (500 MHz, DMSO-d6) δ 9.65 (s, 1H), 9.50 (dd, J = 4.8, 2.5 Hz, 1H), 9.26 (s, 1H), 8.85 (dd, J = 2.6, 0.5 Hz, 1H), 8.23 (d, J = 5.3 Hz, 1H), 7.21 (dd, J = 5.3, 0.5 Hz, 1H), 6.77 (s, 2H), 3.23-3.16 (m, 2H), 2.89 (dd, J = 13.1, 11.0 Hz, 2H), 2.72 (t, J = 0.7 Hz, 3H), 2.26 (dd, J = 8.4, 7.4 Hz, 2H), 2.14 (td, J = 12.7, 4.2 Hz, 2H), 1.97 (t, J = 7.9 Hz, 2H), 1.47 (d, J = 12.4 Hz, 2H). |
| I-N-236 | 439.1 | 1.88* | $^1$H NMR (500 MHz, DMSO-d6) δ 9.61 (s, 1H), 9.53 (dd, J = 4.8, 2.5 Hz, 1H), 9.21 (d, J = 1.1 Hz, 1H), 8.89 (d, J = 2.5 Hz, 1H), 8.42 (dd, J = 6.7, 1.1 Hz, 1H), 7.51 (d, J = 6.7 Hz, 1H), 6.78 (s, 2H), 3.41-3.32 (m, 4H), 3.27 (s, 2H), 2.73 (s, 3H), 2.29 (d, J = 1.1 Hz, 2H), 1.77 (dtdd, J = 17.2, 10.7, 7.1, 3.8 Hz, 4H). |
| I-N-237 | 367.1 | 2.11* | — |
| I-N-238 | 413.1 | 1.72* | $^1$H NMR (500 MHz, DMSO-d6) δ 9.84 (s, 1H), 9.53 (dd, J = 4.7, 2.5 Hz, 1H), 9.47-9.40 (m, 1H), 9.00 (dd, J = 2.6, 0.6 Hz, 1H), 8.45 (dd, J = 6.2, 0.9 Hz, 1H), 7.52 (d, J = 6.2 Hz, 1H), 6.78 (s, 2H), 4.42-4.34 (m, 1H), 4.18 (dddd, J = 10.9, 8.6, 5.0, 3.7 Hz, 1H), 3.98-3.94 (m, 1H), 3.75-3.64 (m, 2H), 3.52 (d, J = 12.4 Hz, 1H), 3.35 (ddd, J = 13.3, 12.0, 3.5 Hz, 1H), 3.02-2.89 (m, 2H). |
| I-N-239 | 416.1 | 2.27* | $^1$H NMR (500 MHz, DMSO-d6) δ 10.26 (s, 1H), 9.49 (q, J = 2.3 Hz, 2H), 8.61 (d, J = 2.5 Hz, 1H), 8.28 (d, J = 3.0 Hz, 1H), 6.79 (s, 2H), 4.44 (s, 4H), 3.00 (dd, J = 6.8, 4.1 Hz, 4H), 2.04 (t, J = 5.4 Hz, 4H). |

-continued

| Cmpd No. | LCMS ES+ | LCMS (Rt min) | HNMR |
|---|---|---|---|
| I-N-240 | 458.1 | 1.88* | ¹H NMR (500 MHz, Methanol-d4) δ 9.48 (s, 1H0, 9.07-9.09 (d, 1H), 8.77 (d, 1H), 8.43-8.44 (d, 1H), 3.91-3.96 (m, 1H), 3.62-3.68 (m, 1H), 3.53-3.56 (m, 1H), 3.30-3.45 (m, 4H), 3.25-3.28 (m, 1H), 2.88-3.04 (m, 5H). |
| I-N-241 | 424.1 | 2.24* | ¹H NMR (500 MHz, DMSO-d6) δ 2.05-2.15 (4H, m), 3.15-3.20 (2H, m), 3.23-3.32 (1H, m), 3.62-3.68 (2H, m), 6.80 (2H, brs), 7.52 (1H, d), 8.42 (1H, d), 8.87 (1H, d), 9.38 (1H, s), 9.53-9.56 (1H, m), 9.63 (1H, brs), 9.79 (1H, s). |
| I-N-242 | 372.0 | 1.85* | — |
| I-N-243 | 448.0 | 1.96* | ¹H NMR (500 MHz, DMSO-d6) δ 9.71 (1H, s), 9.54 (1H, dd), 9.44 (1H, s), 8.88 (1H, d), 8.50 (1H, dd), 7.62 (1H, d), 6.81 (2H, brs), 3.59-3.63 (2H, m), 3.17-3.22 (2H, m), 2.97 (3H, s), 2.37-2.42 (2H, m), 1.78-1.81 (2H, m), 1.53 (3H, s). |
| I-N-244 | 425.0 | 1.93* | ¹H NMR (500 MHz, DMSO-d6) δ 9.70 (s, 1H), 9.52-9.53 (dd, 1H), 9.34 (s, 1H), 8.99 (d, 1H), 8.43-8.44 (d, 1H), 7.50-7.52 (d, 1H), 6.78 (s, 2H), 4.47-4.50 (m, 1H), 3.62-3.78 (m, 2H), 2.94-2.97 (m, 2H), 2.86 (t, 1H), 2.18-2.22 (m, 2H), 2.81-2.83 (m, 1H), 2.64-2.78 (m, 2H), 1.35-1.47 (m, 1H). |
| I-N-245 | 468.1 | 2.05* | ¹H NMR (500 MHz, DMSO-d6) δ 9.67 (s, 1H), 9.51-9.53 (dd, 1H), 9.31 (d, 1H), 8.94 (d, 1H), 8.44-8.45 (dd, 1H), 7.54-7.55 (d, 1H), 4.50-4.55 (m, 1H) 3.91-3.96 (m, 1H), 3.62-3.68 (m, 1H), 3.25-3.30 (m, 1H), 2.90-3.15 (m, 4H), 2.50-2.80 (m, 4H). 1.03-1.06 (t, 6H). |
| I-N-246 | 360.1 | 2.44* | ¹H NMR (500 MHz, DMSO-d6) δ 1.82-1.92 (4H, m), 3.6-3.7 (4H, m), 6.85 (2H, s), 8.45 (1H, d), 8.59 (1H, s), 8.80-8.82 (1H, m), 9.48-9.53 (2H, m). |
| I-N-247 | 447.1 | 1.89* | ¹H NMR (500 MHz, DMSO-d6) δ 9.86 (s, 1H), 9.54 (dd, J = 4.8, 2.5 Hz, 1H), 9.48 (s, 1H), 8.74 (d, J = 2.5 Hz, 1H), 8.44 (dd, J = 6.1, 0.7 Hz, 1H), 7.54 (d, J = 6.1 Hz, 1H), 6.81 (s, 2H), 3.70-3.63 (m, 1H), 3.57 (d, J = 12.1 Hz, 1H), 3.47 (tdd, J = 9.8, 6.7, 3.0 Hz, 1H), 3.40-3.33 (m, 2H), 3.33-3.29 (m, 1H), 3.12 (td, J = 11.5, 3.0 Hz, 1H), 3.02 (td, J = 12.0, 3.0 Hz, 1H), 2.95 (dd, J = 12.0, 10.2 Hz, 1H), 2.36 (dddd, J = 12.6, 9.3, 5.8, 3.6 Hz, 1H), 1.97 (dtd, J = 12.5, 10.3, 8.2 Hz, 1H). |
| I-N-248 | 431.0 | 1.91* | ¹H NMR (500 MHz, DMSO-d6) δ 10.41 (s, 1H), 9.55 (s, 1H), 9.50 (dd, J = 4.8, 2.5 Hz, 1H), 8.90 (d, J = 2.5 Hz, 1H), 8.30 (d, J = 2.5 Hz, 1H), 6.79 (s, 2H), 4.43 (t, J = 8.6 Hz, 1H), 4.20 (ddd, J = 12.1, 9.5, 4.4 Hz, 1H), 3.99 (dd, J = 8.9, 5.0 Hz, 1H), 3.73 (dt, J = 13.0, 2.6 Hz, 1H), 3.42-3.31 (m, 1H), 3.23 (m, J = 11.4, 3.9 Hz, 1H), 3.07-2.99 (m, 3H). |
| I-N-249 | 441.0 | 1.76* | — |
| I-N-250 | 424.0 | 1.90* | ¹H NMR (500 MHz, DMSO-d6) δ 10.32 (s, 1H), 9.58 (s, 1H), 9.55 (dd, J = 4.7, 2.5 Hz, 1H), 8.68 (d, J = 2.5 Hz, 1H), 8.32 (d, J = 1.8 Hz, 1H), 6.85 (s, 2H), 3.60-3.42 (m, 8H). |
| I-N-251 | 439.0 | 1.94* | ¹H NMR (500 MHz, DMSO-d6) δ 9.82 (s, 1H), 9.47-9.48 (dd, 1H), 9.45 (s, 1H), 8.80 (d, 1H), 8.22 (d, 1H), 7.17 (d, 1H), 6.77 (s, 2H), 3.93 (s, 2H), 3.63 (s, 2H), 2.87 (m, 4H), 1.93-1.95 (m, 4H), 1.78 (s, 3H). |
| I-N-252 | 434.1 | 1.91* | ¹H NMR (500 MHz, DMSO-d6) δ 9.55 (dd, J = 4.7, 2.5 Hz, 1H), 9.51 (s, 1H), 9.26 (s, 1H), 8.66 (d, J = 2.5 Hz, 1H), 8.41 (d, J = 6.1 Hz, 1H), 7.54 (d, J = 6.2 Hz, 1H), 6.81 (s, 2H), 3.51 (m, 6H), 1.46 (s, 6H). |
| I-N-253 | 397.9 | 2.05* | ¹H NMR (500 MHz, DMSO-d6) δ 9.51-9.52 (d, 1H), 9.48 (s, 1H), 9.25 (s, 1H), 8.83 (d, 1H), 7.51-7.53 (d, 1H), 6.78 (s, 2H), 4.43 (d, 2H), 4.31 (d, 2H), 3.55 (s, 2H), 3.08 (m, 2H), 1.87-1.89 (m, 2H), 1.65-1.67 (m, 2H). |
| I-N-254 | 399.1 | 1.72* | — |
| I-N-255 | 411.2 | 1.8* | ¹H NMR (500 MHz, DMSO-d6) δ 9.62 (s, 1H), 9.54 (dd, 1H), 9.27 (s, 1H), 8.90 (d, 1H), 8.88 (br s, 2H), 8.40 (dd, 1H), 7.46 (d, 1H), 6.80 (s, 2H), 3.34-3.25 (m, 6H), 3.12 (t, 2H), 1.91 (t, 2H), 1.83-1.73 (m, 4H). |
| I-N-256 | 439.1 | 1.89* | 1H NMR (500 MHz, DMSO-d6) (TFA salt) δ 2.37 (3H, s), 3.43-3.48 (4H, m), 3.63-3.67 (4H, m), 6.80 (2H, brs), 7.57 (1H, d), 8.48 (1H, d), 9.02 (1H, d), 9.37 (1H, s), 9.53-9.56 (1H, m), 9.63 (1H, brs), 9.77 (1H, s). |
| I-N-257 | 453.1 | 2.05* | ¹H NMR (500 MHz, DMSO) δ 9.60 (d, 1H), 9.53 (ddd, 1H), 9.19 (t, 1H), 8.90 (t, 1H), 8.41 (dt, 1H), 7.50 (dd, 1H), 6.78 (s, 2H), 3.50 (t, 1H), 3.43-3.31 (m, 6H), 3.27 (s, 1H), 1.94 (d, 3H), 1.90 (t, 1H), 1.81 (t, 1H), 1.74-1.70 (m, 4H). |
| I-N-258 | 411.1 | 1.8* | ¹H NMR (500 MHz, DMSO) δ 9.79 (s, 1H), 9.52 (dd, 1H), 9.37 (s, 1H), 8.96 (d, 1H), 8.43 (d, 1H), 7.51 (d, 1H), 6.78 |

Compound Analytical Data

| Cmpd No. | LCMS ES+ | LCMS (Rt min) | HNMR |
|---|---|---|---|
| | | | (s, 2H), 3.92-3.87 (m, 2H), 3.72 (d, 1H), 3.60 (d, 1H), 3.10 (td, 1H), 2.87 (td, 1H), 2.77 (t, 1H), 2.35-2.23 (m, 2H), 2.13-2.06 (m, 1H), 1.61-1.54 (m, 1H). |
| I-N-259 | 326.1 | 1.81* | $^1$H NMR (500 MHz, DMSO-d6) δ 9.99 (s, 1H), 9.52-9.54 (d, 1H), 9.16 (d, 1H), 8.87 (m, 1H), 8.81 (s, 1H), 7.90 (d, 1H), 7.08 (d, 1H), 6.74 (s, 2H), 4.22 (d, 3H). |
| I-N-260 | 439.1 | 2.4* | $^1$H NMR (500 MHz, DMSO-d6) δ 2.41 (3H, s), 3.43-3.47 (4H, m), 3.53-3.57 (4H, m), 6.80 (2H, brs), 7.51 (1H, d), 8.45 (1H, d), 8.87 (1H, d), 9.37 (1H, s), 9.52-9.56 (1H, m), 9.63 (1H, brs), 9.77 (1H, s). |
| I-N-261 | 433.1 | 2.29* | $^1$H NMR (500 MHz, DMSO-d6) δ 10.37 (s, 1H), 9.53 (s, 1H), 9.47-9.49 (dd, 1H), 8.86 (d, 1H), 8.27 (s, 1H), 6.79 (s, 2H), 3.64-3.66 (m, 7H), 3.05-3.07 (m, 4H). |
| I-N-262 | 453.2 | 2.29* | $^1$H NMR (500 MHz, DMSO-d6) δ 9.67 (s, 1H), 9.51 (dd, J = 4.7, 2.6 Hz, 1H), 9.40 (d, J = 1.1 Hz, 1H), 9.19 (dd, J = 2.6, 0.8 Hz, 1H), 8.44 (dd, J = 6.7, 1.1 Hz, 1H), 7.53 (d, J = 6.7 Hz, 1H), 6.79 (s, 2H), 3.71-3.60 (m, 2H), 3.51 (t, J = 6.7 Hz, 2H), 3.21 (td, J = 12.8, 3.9 Hz, 2H), 3.08-2.94 (m, 2H), 2.01 (d, J = 6.9 Hz, 5H), 1.81 (p, J = 6.8 Hz, 2H), 1.42 (dd, J = 12.6, 2.2 Hz, 2H). |
| I-N-263 | 354.1 | 1.34* | $^1$H NMR (500 MHz, DMSO) δ 9.74 (s, 1H), 9.60 (s, 1H), 9.46 (dd, J = 4.8, 2.5 Hz, 1H), 8.84 (s, 1H), 8.55 (d, J = 5.1 Hz, 1H), 8.27 (d, J = 2.5 Hz, 1H), 7.68 (d, J = 5.1 Hz, 1H), 6.67 (s, 1H), 2.27 (s, 3H). |
| I-N-264 | 371.0 | 2.49* | run in d6-DMSO |
| I-N-265 | 438.1 | 2.02* | $^1$H NMR (500 MHz, DMSO-d6) δ 2.02-2.18 (4H, m), 2.37 (3H, s), 3.21-3.27 (2H, m), 3.30-3.37 (1H, m), 3.68-3.75 (2H, m), 6.80 (2H, brs), 7.58 (1H, d), 8.48 (1H, d), 8.87 (1H, d), 9.33 (1H, s), 9.53-9.56 (1H, m), 9.72 (1H, brs). |
| I-N-266 | 387.2 | 2.18* | $^1$H NMR (500 MHz, DMSO-d6) δ 9.63 (s, 1H), 9.52 (dd, J = 4.8, 2.5 Hz, 1H), 9.22 (d, J = 1.1 Hz, 1H), 8.82 (d, J = 2.5 Hz, 1H), 8.40 (dd, J = 6.6, 1.1 Hz, 1H), 7.49 (d, J = 6.6 Hz, 1H), 6.77 (s, 2H), 3.49 (dtt, J = 11.8, 7.5, 3.6 Hz, 3H), 3.26 (s, 3H), 3.26-3.12 (m, 2H), 2.09-1.92 (m, 2H), 1.80-1.61 (m, 2H). |
| I-N-267 | 413.1 | 2.14* | $^1$H NMR (500 MHz, DMSO-d6) δ 9.79 (s, 1H), 9.48 (dd, J = 4.8, 2.5 Hz, 1H), 9.41 (s, 1H), 8.79 (d, J = 2.5 Hz, 1H), 8.21 (d, J = 5.3 Hz, 1H), 7.16 (d, J = 5.3 Hz, 1H), 6.77 (s, 2H), 3.32 (s, 2H), 3.16 (dt, J = 12.0, 3.3 Hz, 2H), 2.68 (td, J = 11.8, 2.4 Hz, 2H), 2.18 (s, 6H), 1.79 (dd, J = 13.3, 3.6 Hz, 2H), 1.63 (s, 1H), 1.49-1.41 (m, 2H). |
| I-N-268 | 424.1 | 1.93* | $^1$H NMR (500 MHz, DMSO-d6) δ 2.02-2.13 (2H, m), 2.14-2.24 (2H, m), 3.21-3.27 (2H, m), 3.38-3.42 (1H, m), 3.68-3.75 (2H, m), 6.80 (2H, brs), 7.58 (1H, d), 8.48 (1H, d), 8.85 (1H, d), 9.22 (1H, s), 9.33 (1H, s), 9.53-9.55 (1H, m), 9.72 (1H, brs). |
| I-N-269 | 367.1 | 1.89* | $^1$H NMR (500 MHz, DMSO-d6) δ 9.75 (s, 1H), 9.50 (dd, J = 4.8, 2.5 Hz, 1H), 9.36 (s, 1H), 9.33 (s, 1H), 8.61 (d, J = 5.1 Hz, 1H), 8.40 (d, J = 2.5 Hz, 1H), 7.73 (d, J = 5.1 Hz, 1H), 6.74 (s, 2H), 2.38 (d, J = 1.0 Hz, 3H), 2.04 (d, J = 1.0 Hz, 3H). |
| I-N-270 | 374.1 | 2.88* | $^1$H NMR (500 MHz, DMSO-d6) δ 10.41 (s, 1H), 9.51 (s, 1H), 9.49 (dd, 1H), 8.77 (d, 1H), 8.24 (d, 1H), 6.79 (s, 2H), 3.03 (br t, 4H), 1.80-1.76 (m, 4H), 1.669-1.65 (m, 2H). |
| I-N-271 | 475.1 | 2.21* | $^1$H NMR (500 MHz, DMSO-d6) δ 2.01-2.12 (2H, m), 2.12-2.18 (2H, m), 2.22-2.28 (2H, m), 2.92-3.02 (2H, m), 3.38-3.46 (2H, m), 3.52-3.60 (3H, m), 3.92-3.97 (4H, m), 6.82 (2H, brs), 7.45-7.48 (1H, m), 8.40 (1H, brs), 8.80 (1H, d), 9.45-9.50 (1H, m), 9.53-9.56 (1H, m), 9.83 (1H, s). |
| I-N-272 | 459.1 | 2.38* | $^1$H NMR (500 MHz, DMSO-d6) δ 1.83 (2H, m), 2.02 (2H, m), 3.19 (3H, s), 2.30 (4H, m), 2.89-2.91 (2H, m), 3.25 (2H, m), 3.70 (2H, m), 6.80 (2H, br s), 8.24 (1H, d), 8.71 (1H, d), 9.49 (2H, m) and 10.31 (1H, br s) ppm. |
| I-N-273 | 562.1 | 2.25* | $^1$H NMR (500 MHz, DMSO-d6) δ 2.0-2.2 (10H, m), 2.90-3.05 (3H, m), 3.35-3.42 (2H, m), 3.42-3.53 (3H, m), 3.60-3.68 (1H, m), 3.75-3.79 (2H, m), 4.30-4.33 (1H, m), 8.28 (1H, d), 8.94 (1H, d), 9.50-9.53 (1H, m), 9.66 (1H, s), 10.23 (1H, brs), 10.43 (1H, s). |
| I-N-274 | 473.0 | 2.03* | — |
| I-N-275 | 417.1 | 1.96* | $^1$H NMR (500 MHz, Methanol-d4) δ1.03 (s, 1H), 9.52 (d, 1H), 9.05 (d, 1H), 8.72 (d, 1H), 8.36 (d, 1H), 3.85-3.91 (m, 4H), 3.35-3.40 (masked, 4H), 2.15 (s, 3H). |

-continued

Compound Analytical Data

| Cmpd No. | LCMS ES+ | LCMS (Rt min) | HNMR |
|---|---|---|---|
| I-N-276 | 443.0 | 2.24* | — |
| I-N-277 | 443.1 | 2.1* | $^1$H NMR (500 MHz, DMSO-d6) δ 10.39 (s, 1H), 9.56 (s, 1H), 9.49 (dd, J = 4.8, 2.5 Hz, 1H), 8.86 (d, J = 2.5 Hz, 1H), 8.27 (d, J = 2.7 Hz, 1H), 6.80 (s, 2H), 4.60 (dd, J = 12.1, 2.7 Hz, 1H), 3.75 (d, J = 8.1 Hz, 1H), 3.15-3.06 (m, 2H), 3.05-2.89 (m, 3H), 2.33-2.26 (m, 2H), 1.93 (dt, J = 13.5, 4.7 Hz, 1H), 1.75 (p, J = 4.1 Hz, 2H), 1.51-1.40 (m, 1H). |
| I-N-278 | 459.0 | 1.94* | $^1$H NMR (500 MHz, DMSO-d6) δ 10.35 (s, 1H), 9.53-9.55 (d, 1H), 9.48-9.49 (dd, 1H), 8.88 (d, 1H), 8.29 (d, 1H), 6.80 (s, 2H), 4.71-4.76 (m, 4H), 4.17-4.23 (m, 1H), 3.75(m, 2H), 3.741-3.43 (m, 2H), 3.05-3.07 (m, 2H). |
| I-N-279 | 443.1 | 2.09* | $^1$H NMR (500 MHz, DMSO) δ 10.39 (s, 1H), 9.56 (s, 1H), 9.49 (dd, J = 4.8, 2.5 Hz, 1H), 8.86 (d, J = 2.5 Hz, 1H), 8.28 (d, J = 2.7 Hz, 1H), 6.84-6.74 (m, 2H), 4.63-4.56 (m, 1H), 3.74 (d, J = 11.3 Hz, 1H), 3.15-3.06 (m, 2H), 3.05-2.89 (m, 3H), 2.29 (dd, J = 9.7, 4.8 Hz, 2H), 1.93 (dt, J = 13.5, 4.6 Hz, 1H), 1.75 (dq, J = 10.2, 4.4 Hz, 2H), 1.51-1.40 (m, 1H). |
| I-N-280 | 443.1 | 2.1* | $^1$H NMR (500 MHz, DMSO) δ 10.38 (s, 1H), 9.56 (s, 1H), 9.49 (dd, J = 4.8, 2.5 Hz, 1H), 8.86 (d, J = 2.5 Hz, 1H), 8.29 (d, J = 2.7 Hz, 1H), 6.78 (s, 2H), 4.63-4.56 (m, 1H), 3.75 (q, J = 8.5 Hz, 1H), 3.17-3.06 (m, 2H), 3.06-2.89 (m, 3H), 2.29 (t, J = 7.3 Hz, 2H), 1.93 (dq, J = 13.4, 4.5, 4.0 Hz, 1H), 1.81-1.71 (m, 2H), 1.45 (dtd, J = 14.2, 9.5, 4.7 Hz, 1H). |
| I-N-281 | 376.0 | 2.87* | $^1$H NMR (500 MHz, DMSO-d6) δ 10.28 (s, 1H), 9.53 (dd, J = 4.8, 2.5 Hz, 1H), 9.35 (s, 1H), 8.83 (d, J = 2.5 Hz, 1H), 8.41 (s, 1H), 3.52-3.45 (m, 4H), 2.12-2.04 (m, 4H). |
| I-N-282 | 400.0 | 2.46* | $^1$H NMR (500 MHz, DMSO-d6) δ 9.68 (s, 1H), 9.52 (dd, J = 4.8, 2.5 Hz, 1H), 9.28 (d, J = 1.1 Hz, 1H), 8.83 (d, J = 2.5 Hz, 1H), 8.39 (dd, J = 6.6, 1.0 Hz, 1H), 7.48 (d, J = 6.5 Hz, 1H), 6.78 (s, 2H), 3.65 (dt, J = 13.2, 3.4 Hz, 2H), 3.30 (d, J = 13.4 Hz, 6H), 2.98 (td, J = 12.5, 2.5 Hz, 2H), 1.91-1.67 (m, 3H), 1.66-1.46 (m, 2H). |
| I-N-283 | 353.1 | 1.75* | $^1$H NMR (500 MHz, DMSO-d6) δ 9.82 (d, J = 0.6 Hz, 1H), 9.58 (s, 1H), 9.42 (dd, J = 4.8, 2.5 Hz, 1H), 8.47 (d, J = 5.0 Hz, 1H), 8.31 (d, J = 2.5 Hz, 1H), 7.80 (d, J = 1.1 Hz, 1H), 7.50 (dd, J = 5.0, 0.6 Hz, 1H), 7.08 (t, J = 1.1 Hz, 1H), 6.70 (s, 2H), 2.01 (d, J = 1.1 Hz, 3H). |
| I-N-284 | 392.1 | 2.03* | $^1$H NMR (500 MHz, DMSO-d6) δ 10.13 (s, 1H), 9.48-9.49 (m, 1H), 9.19 (s, 1H), 8.78 (d, 1H), 8.36 (s, 1H), 6.80 (s, 2H), 4.45-4.48 (m, 1H), 3.78-3.80 (m, 1H), 3.70-3.73 (m, 1H), 3.41-3.45 (m, 1H), 3.35-3.37 (m, 1H), 2.10-2.15 (m, 1H), 1.88-1.93 (m, 1H). |
| I-N-285 | 401.0 | 2.4* | — |
| I-N-286 | 431.1 | 2.25* | — |
| I-N-287 | 454.0 | 2.11* | — |
| I-N-288 | 440.3 | 2.16* | — |
| I-N-289 | 500.0 | 2.2* | $^1$H NMR (500 MHz, DMSO-d6) δ 1.50-1.60 (1H, m), 1.75-1.95 (2H, m), 2.01-2.12 (2H, m), 2.70-2.90 (5H, m), 3.00-3.15 (5H, m), 3.20-3.45 (2H, m), 3.85-3.97 (2H, m), 4.40-4.45 (1H, m), 6.85-6.93 (2H, br s), 8.28 (1H, d), 8.94 (1H, d), 9.51-9.53 (2H, dd), 9.60-9.70 (1H, s), 10.30-10.33 (1H, s). |
| I-N-290 | 427.0 | 2.02* | $^1$H NMR (500 MHz, DMSO-d6) δ 9.60 (s, 1H), 9.52-9.54 (dd, 1H), 9.09 (d, 1H), 8.94 (dd, 1H), 8.36-8.38 (dd, 1H), 6.77 (s, 2H), 3.74-3.77 (m, 2H), 3.11-3.18 (m, 1H), 2.90-3.05 (m, 2H), 2.71 (s, 3H), 2.55 (s, 3H), 1.95-1.98 (m, 1H), 1.77-1.79 (m, 2H), 1.46-1.51 (m, 1H). |
| I-G-1 | 482.3 | 0.63 | $^1$H NMR (500 MHz, MeOD) δ 9.52 (d, J = 1.2 Hz, 1H), 9.06 (dd, J = 4.3, 2.5 Hz, 1H), 8.88 (dd, J = 2.6, 0.5 Hz, 1H), 8.34 (dd, J = 6.6, 1.2 Hz, 1H), 7.56 (d, J = 6.7 Hz, 1H), 4.77 (s, 2H), 4.36 (s, 2H), 3.78 (dm, J = 13.0 Hz, 2H), 3.57 (s, 2H), 3.22-3.01 (m, 5H), 2.95 (s, 3H), 2.20 (dm, J = 12.2 Hz, 2H), 1.91 (dm, 2H). |
| I-G-2 | 427.2 | 0.65 | $^1$H NMR (500 MHz, MeOD) δ 9.60 (s, 1H), 9.02 (dd, J = 2.6, 0.6 Hz, 1H), 9.00 (dd, J = 4.3, 2.5 Hz, 1H), 8.21 (d, J = 5.4 Hz, 1H), 7.25 (d, J = 5.4 Hz, 1H), 3.29 (dt, J = 11.6, 2.6 Hz, 2H), 3.20 (s, 3H), 3.03 (s, 3H), 2.95 (tt, J = 11.7, 3.8 Hz, 1H), 2.87 (td, J = 12.1, 2.3 Hz, 2H), 2.25 (qd, 2H), 1.87 (dm, 2H). |
| I-G-3 | 516.2 | 0.77 | $^1$H NMR (500 MHz, MeOD) δ 10.65 (s, 1H), 9.81 (d, J = 1.3 Hz, 1H), 9.21 (dd, J = 2.6, 0.8 Hz, 1H), 9.04 (dd, J = 4.3, 2.6 Hz, 1H), 8.30 (s, 1H), 4.57-4.28 (m, 2H), 3.75-3.65 (m, 2H), 3.69-3.45 (m, 4H), 3.25-3.07 (m, 4H), 3.03 |

Compound Analytical Data

| Cmpd No. | LCMS ES+ | LCMS (Rt min) | HNMR |
|---|---|---|---|
| | | | (dt, J = 12.2, 3.6 Hz, 1H), 3.00 (s, 3H), 2.40-2.23 (m, 2H), 1.91 (dm, J = 12.7 Hz, 2H). |
| I-G-4 | 500.2 | 0.72 | $^1$H NMR (500 MHz, MeOD) δ 10.67 (s, 1H), 9.69 (d, J = 0.6 Hz, 1H), 9.20 (dd, J = 2.7, 0.6 Hz, 1H), 9.01 (dd, J = 4.3, 2.6 Hz, 1H), 8.16 (d, J = 3.0 Hz, 1H), 7.58 (d, J = 2.8 Hz, 1H), 3.74 (t, J = 5.1 Hz, 2H), 3.72-3.65 (m, 2H), 3.34-3.28 (m, 2H), 3.18 (tt, J = 12.0, 2.4 Hz, 2H), 3.06-2.95 (m, 1H), 2.60-2.45 (m, 4H), 2.38 (s, 3H), 2.36-2.25 (m, 2H), 1.91-1.79 (m, 2H). |
| I-G-5 | 516.2 | 2.34* | $^1$H NMR (500 MHz, DMSO-d6) δ 10.59 (s, 1H), 9.66 (s, 1H), 9.44 (d, J = 2.2 Hz, 1H), 9.03 (d, J = 2.2 Hz, 1H), 8.32-8.24 (m, 1H), 6.85 (s, 2H), 4.47 (dd, J = 115.4, 12.9 Hz, 2H), 3.48 (d, J = 10.4 Hz, 2H), 3.40 (t, J = 13.5 Hz, 1H), 3.20 (d, J = 10.8 Hz, 2H), 3.10-2.94 (m, 6H), 2.85 (d, J = 2.9 Hz, 3H), 2.12 (dd, J = 43.1, 13.1 Hz, 2H), 1.84-1.73 (m, 2H). |
| I-G-6 | 514.2 | 2.28* | $^1$H NMR (500 MHz, DMSO-d6) δ 1.7-1.8 (2H, m), 2.1-2.25 (4H, m), 2.85-3.0 (4H, m), 3.05-3.12 (3H, m), 3.2-3.3 (3H, m), 3.4-3.55 (3H, m), 3.6-3.75 (2H, m), 4.05-4.15 (1H, m), 6.8 (2H, brs), 8.28 (1H, d), 9.25 (1H, d), 9.5-9.6 (2H, m), 9.7 (1H, d), 10.63-10.66 (1H, m). |
| I-G-7 | 526.2 | 2.21* | $^1$H NMR (500 MHz, DMSO-d6, 370 K) δ 10.50 (s, 1H), 9.62 (s, 1H), 9.27 (dd, J = 4.7, 2.4 Hz, 1H), 8.19 (d, J = 2.7 Hz, 1H), 6.53 (s, 2H), 3.78-3.67 (m, 2H), 3.22 (tm, J = 11.6 Hz, 2H), 3.09 (dm, 2H), 3.02-2.83 (m, 8H), 2.29-2.14 (m, 3H), 1.96-1.84 (m, 2H), 1.83-1.64 (m, 2H). |
| I-G-8 | 457.1 | 2.35* | $^1$H NMR (500 MHz, DMSO-d6) δ 1.7-1.75 (2H, m), 2.05-2.15 (2H, m), 2.2-2.28 (2H, m), 2.4-2.5 (1H, m), 3.03-3.18 (4H, m), 3.95 (2H, t), 4.25 (2H, t), 8.28 (1H, d), 9.38 (1H, d), 9.47-9.50 (1H, m), 9.7 (1H, s), 10.65 (1H, s). |
| I-G-9 | 514.0 | 2.40* | $^1$H NMR (500 MHz, DMSO-d6) δ 1.23 (3H, t), 1.75-1.81 (2H, m), 2.05-2.20 (2H, m), 2.97-3.1 (5H, m), 3.15-3.25 (4H, m), 3.4-3.57 (3H, m), 4.35-4.4 (1H, m), 4.6-4.65 (1H, m), 8.28 (1H, d), 9.18 (1H, d), 9.48-9.56 (2H, m), 9.68 (1H, s), 10.65 (1H, s). |
| I-G-10 | 526.2 | 2.46* | $^1$H NMR (500 MHz, DMSO-d6) δ 1.5-1.6 (1H, m), 1.70-1.81 (3H, m), 1.90-2.25 (5H, m), 2.90-3.1 (4H, m), 3.18-3.37 (4H, m), 3.4-3.5 (1H, m), 3.6-3.9 (3H, m), 3.9-4.0 (1H, m), 6.6-6.85 (2H, m), 8.26 (1H, d), 9.1-9.2 (1H, m), 9.47-9.51 (2H, m), 9.68 (1H, s), 10.1 (1H, brs), 10.67 (1H, s). |
| I-G-11 | 514.2 | 2.30* | $^1$H NMR (500 MHz, DMSO-d6) δ 1.78-1.84 (2H, m), 2.00-2.18 (4H, m), 2.28-2.4 (2H, m), 2.45-2.55 (1H, m), 2.70-2.80 (1H, m), 2.80-2.90 (6H, m), 3.05-3.12 (2H, m), 3.12-3.22 (3H, m), 4.35-4.4 (1H, m), 4.6-4.65 (1H, m), 6.78 (2H, brs), 8.28 (1H, d), 9.35 (1H, d), 9.48-9.50 (1H, m), 9.70 (1H, s), 9.75-9.85 (1H, m), 10.67-10.69 (1H, m). |
| I-G-12 | 486.2 | 1.99* | $^1$H NMR (500 MHz, DMSO-d6) δ 1.75-1.80 (2H, m), 2.08-2.15 (2H, m), 2.92-3.00 (1H, m), 3.05-3.25 (8H, m), 3.72-3.78 (2H, m), 3.80-3.85 (2H, m), 6.79 (2H, brs), 8.23 (1H, d), 8.72 (2H, brs), 9.15 (1H, d), 9.48 (1H, d), 9.65 (1H, s), 10.63 (1H, s). |
| I-G-13 | 526.1 | 2.62* | $^1$H NMR (500 MHz, CDCl3) δ 0.57 (4H, br s), 1.82-1.85 (2H, d), 2.03 (21H, s), 2.33-2.35 (2H, m), 2.60-2.85 (4H, m), 3.13-3.15 (2H, m), 3.24-3.29 (2H, m), 3.70 (4H, br s), 5.84 (2H, s), 8.20 (2H, d), 8.48-8.49 (1H, d), 9.34 (1H, d), 9.80 (1H, s), 10.6 (1H, s). |
| I-G-14 | 498.4 | 2.13* | $^1$H NMR (500 MHz, DMSO-d6) δ 10.63 (s, 1H), 9.68 (s, 1H), 9.47-9.48 (dd, 1H), 9.35 (dd, 1H), 8.25-8.26 (d, 1H), 6.79 (s, 2H), 4.69 (s, 4H), 4.41 (s, 2H), 4.10 (s, 2H), 3.10-3.13 (m, 2H), 3.02-3.05 (m, 2H), 2.45-2.50 (m, 2H), 2.04-2.08 (m, 2H), 1.72-1.75 (m, 2H). |
| I-G-15 | 528.2 | 2.43* | — |
| I-G-16 | 516.3 | 2.29* | $^1$H NMR (500 MHz, DMSO-d6) δ 1.75-1.95 (3H, m), 2.10-2.25 (2H, m), 2.78-2.85 (5H, m), 2.90-3.00 (1H, m), 3.02-3.15 (5H, m), 3.17-3.26 (2H, m), 3.43-3.52 (2H, m), 8.27-8.29 (1H, m), 9.22 (1H, s), 9.27 (1H, d), 9.48-9.53 (1H, m), 9.68-9.71 (1H, m), 10.64-10.68 (1H, s). |
| I-G-18 | 526.2 | 2.30* | $^1$H NMR (500 MHz, DMSO-d6) δ 1.75-1.90 (2H, m), 2.10-2.22 (2H, m), 2.70-2.82 (1H, m), 2.85-2.93 (4H, m), 2.96-3.12 (3H, m), 3.12-3.22 (2H, m), 3.23-3.35 (2H, m), 3.40-3.55 (2H, m), 3.59-3.75 (2H, m), 3.78-3.90 (2H, m), 6.75-6.90 (1H, m), 8.28 (1H, d), 9.37 (1H, d), 9.48-9.53 (1H, m), 9.69 (1H, s), 9.74-9.88 (1H, m), 10.66 (1H, s). |

-continued

Compound Analytical Data

| Cmpd No. | LCMS ES+ | LCMS (Rt min) | HNMR |
|---|---|---|---|
| I-G-19 | 473.2 | 2.78* | — |
| I-G-20 | 514.2 | 2.14* | — |
| I-G-21 | 487.1 | 2.31* | $^1$H NMR (500 MHz, DMSO-d6) δ 1.68-1.75 (2H, m), 2.01-2.14 (2H, m), 2.35-2.40 (1H, masked), 3.05-3.15 (4H, m), 3.24 (3H, s), 3.71-3.74 (1H, m), 4.05-4.12 (2H, m), 4.22-4.24 (1H, m), 4.41-4.44 (1H, m), 6.70-7.00 (2H, br s), 8.29 (1H, d), 9.36 (1H, dd), 9.47-9.49 (1H, dd), 9.67 (1H, s), 10.62 (1H, s). |
| I-G-22 | 500.2 | 2.23* | — |
| I-G-23 | 486.1 | 2.04* | — |
| I-G-24 | 500.2 | 2.14* | — |
| I-G-25 | 525.2 | 2.35* | $^1$H NMR (500 MHz, DMSO-d6) δ 2.22-2.25 (2H, m), 2.35-2.50 (6H, masked), 2.87 (3H, s), 3.05-3.25 (4H, m), 3.30-3.35 (2H, m), 4.70-4.80 (2H, m), 6.77-6.92 (2H, br s), 8.32 (1H, d), 8.69 (1H, dd), 9.51-9.53 (1H, dd), 9.64 (1H, s), 9.80-9.95 (1H, br s), 10.37 (1H, s). |
| I-G-26 | 502.0 | 2.07* | $^1$H NMR (500 MHz, DMSO-d6) δ 1.77-1.83 (4H, m), 2.10-2.18 (2H, m), 2.36-2.42 (1H, m), 2.78-2.80 (6H, m), 3.05-3.09 (6H, m), 3.18-3.22 (2H, m), 6.80 (2H, br s), 8.16-8.18 (1H, m), 8.27 (1H, d), 9.34-9.36 (2H, m), 9.49-9.50 (1H, d), 9.67 (1H, s), 10.62 (1H, s). |
| I-G-27 | 514.2 | 2.19* | — |
| I-G-28 | 512.2 | 2.2* | — |
| I-G-29 | 445.0 | 2.37* | $^1$H NMR (500 MHz, DMSO-d6) δ 1.74-1.77 (2H, m), 2.05-2.15 (2H, m), 2.88-2.91 (4H, m), 3.03-3.05 (2H, m), 3.11 (3H, s), 3.15-3.22 (2H, m), 6.79 (1H, s), 8.25 (1H, d), 9.34 (1H, dd), 9.47-9.49 (1H, dd), 9.68 (1H, s), 10.66 (1H, s). |
| I-G-30 | 489.2 | 2.12* | — |
| I-G-31 | 502.1 | 2.33* | — |
| I-G-32 | 542.3 | 2.14* | $^1$H NMR (500 MHz, methanol-d4) δ 1.87 (2H, m), 2.27-2.33 (2H, m), 2.55 (4H, m), 2.97-3.03 (1H, m), 3.18 (2H, m), 3.70-3.85 (4H, m), 4.67-4.70 (2H, m), 4.75-4.78 (2H, m), 8.16 (1H, d), 9.00 (1H, dd), 9.17 (1H, dd), 9.68 (1H, s), 10.65 (1H, s). |
| I-G-33 | 432.1 | 2.07* | — |
| I-G-34 | 486.1 | 2.07* | — |
| I-G-35 | 540.2 | 2.74* | — |
| I-G-36 | 487.0 | 2.34* | — |
| I-G-37 | 473.1 | 2.04* | — |
| I-G-38 | 526.2 | 2.39* | — |
| I-G-40 | 489.2 | 2.45* | — |
| I-G-41 | 473.1 | 1.97* | $^1$H NMR (500 MHz, DMSO-d6) δ 1.87 (2H, m), 2.25 (2H, m), 2.61 (1H, m), 3.84 (1H, m), 4.10 (1H, m), 4.28 (1H, m), 4.55 (1H, m), 4.62 (1H, m), 4.80 (3H, masked), 8.32 (1H, d), 9.05 (1H, dd), 9.24 (1H, dd), 9.69 (1H, s), 10.56 (1H, s). |
| I-G-42 | 500.2 | 2.11* | — |
| I-G-43 | 526.0 | 2.43* | — |
| I-G-44 | 512.0 | 2.18* | — |
| I-G-45 | 500.0 | 2.14* | $^1$H NMR (500 MHz, DMSO-d6) δ 1.14-1.17 (3H, m), 1.83-1.86 (2H, m), 2.22-2.34 (2H, m), 2.37-2.45 (1H, m), 2.75-2.88 (3H, m), 2.92-3.12 (2H, m), 3.11-3.20 (3H, m), 3.28-3.335 (1H, masked), 4.01-4.08 (1H, m), 4.46-4.54 (1H, m), 8.14 (1H, s), 8.99-9.00 (1H, m), 9.19 (1H, m), 9.67 (1H, s). |
| I-G-46 | 512.1 | 2.15* | — |
| I-G-47 | 514.2 | 2.37* | — |
| I-G-48 | 504.1 | 2.15* | $^1$H NMR (500 MHz, DMSO-d6) δ 10.69 (s, 1H), 9.81 (s, 1H), 9.46 (dd, J = 4.7, 2.5 Hz, 1H), 9.35 (s, 1H), 8.24 (s, 1H), 6.79 (s, 2H), 3.58-3.44 (m, 6H), 2.95-2.84 (m, 3H), 2.68 (dt, J = 22.8, 4.7 Hz, 4H), 2.40 (s, 1H), 2.21-2.11 (m, 2H), 1.77-1.70 (m, 2H). |
| I-G-49 | 512.1 | 2.29* | — |
| I-G-50 | 514.2 | 2.38* | — |
| I-G-51 | 512.1 | 2.03* | — |
| I-G-52 | 526.2 | 2.46* | $^1$'H NMR (500 MHz, DMSO-d6) δ 1.72-1.76 (1H, m), 1.83-1.85 (1H, m), 1.92-1.98 (3H, m), 2.05-2.12 (2H, m), 2.15-2.25 (1H, m), 2.80 (3H, s), 2.89 (1H, m), 3.05-3.25 (7H, m), 3.45-3.47 (2H, m), 4.78-4.80 (2H, m), 6.82 (2H, br s), 8.27 (1H, d), 9.27 (1H, d), 9.49-9.51 (1H, dd), 9.68 (1H, s), 10.65 (1H, s). |
| I-G-53 | 512.1 | 2.18* | — |
| I-G-54 | 514.2 | 2.29* | $^1$H NMR (500 MHz, DMSO-d6) δ 10.35 (s, 1H), 9.81 (s, 1H), 9.53 (s, 1H), 9.51 (dd, J = 4.8, 2.5 Hz, 1H), 8.64 (d, J = 2.4 Hz, 1H), 8.27 (d, J = 2.7 Hz, 1H), 6.81 (s, 2H), 4.50 (d, J = 14.0 Hz, 2H), 3.46 (d, J = 11.7 Hz, 2H), 3.28-3.10 (m, |

-continued

| Cmpd No. | LCMS ES+ | LCMS (Rt min) | HNMR |
|---|---|---|---|
| | | | 4H), 3.10-2.89 (m, 4H), 2.83 (s, 3H), 2.30 (ddd, J = 13.1, 8.9, 3.4 Hz, 2H), 1.86-1.67 (m, 2H), 1.40 (s, 3H). |
| I-G-55 | 496.2 | 2.17* | $^1$H NMR (500 MHz, DMSO-d6) δ 10.57 (s, 1H), 9.67 (s, 1H), 9.45 (dd, J = 4.8, 2.5 Hz, 1H), 9.25 (s, 1H), 8.04 (s, 1H), 6.78 (s, 2H), 3.64 (d, J = 37.4 Hz, 4H), 3.16-3.07 (m, 1H), 3.01-2.87 (m, 3H), 2.70-2.56 (m, 5H), 2.41 (s, 6H), 2.23-2.09 (m, 2H), 1.77-1.67 (m, 2H), 1.19 (t, J = 7.3 Hz, 1H). |
| I-G-56 | 482.2 | 1.94* | $^1$H NMR (500 MHz, DMSO-d6) δ 10.63 (s, 1H), 9.73 (s, 1H), 9.50 (dd, J = 4.8, 2.6 Hz, 1H), 9.38-9.30 (m, 1H), 8.08 (d, J = 0.8 Hz, 1H), 6.83 (s, 2H), 3.61 (dt, J = 26.1, 5.2 Hz, 4H), 2.97 (tt, J = 11.8, 3.6 Hz, 3H), 2.85 (dt, J = 23.8, 5.0 Hz, 4H), 2.46 (s, 5H), 2.28-2.15 (m, 2H), 1.77 (dd, J = 12.2, 3.4 Hz, 2H). |
| I-G-57 | 540.0 | 2.69* | — |
| I-G-58 | 540.0 | 2.57* | — |
| I-G-59 | 554.0 | 2.45* | — |
| I-G-60 | 568.0 | 2.58* | — |
| I-G-61 | 500.2 | 2.14* | — |
| I-G-62 | 498.0 | 2.17* | — |
| I-G-63 | 487.0 | 2.17* | — |
| I-G-64 | 554.0 | 2.75* | — |
| I-G-65 | 512.0 | 2.41* | $^1$H NMR (500 MHz, DMSO-d6) δ 0.64-0.78 (2H, m), 1.75-1.88 (2H, m), 2.05-2.24 (3H, m), 2.34-2.35 (3H, m), 2.50-2.55 (1H, masked), 2.61-2.63 (1H, m), 2.71-2.74 (1H, m), 3.05-3.20 (6H, m), 4.07-4.09 (1H, m), 6.79 (2H, s), 8.26 (1H, d), 9.45 (1H, d), 9.48 (1H, dd), 9.69 (1H, s), 10.68 (1H, s). |
| I-G-66 | 542.1 | 2.41* | $^1$H NMR (500 MHz, DMSO) δ 10.71 (d, J = 19.7 Hz, 1H), 9.82 (d, J = 12.7 Hz, 1H), 9.47 (dt, J = 4.7, 2.9 Hz, 1H), 9.31 (s, 1H), 8.24 (d, J = 1.0 Hz, 1H), 6.80 (s, 2H), 4.54-4.23 (m, 1H), 3.73 (dt, J = 31.9, 5.7 Hz, 2H), 3.59-3.50 (m, 2H), 2.96-2.79 (m, 9H), 2.20 (dd, J = 26.6, 13.3 Hz, 2H), 1.87 (d, J = 13.8 Hz, 3H), 1.76 (d, J = 12.7 Hz, 2H), 1.65 (tt, J = 10.1, 4.8 Hz, 1H). |
| I-G-67 | 474.4 | 2.42* | — |
| I-G-68 | 542.0 | 2.42* | $^1$H NMR (500 MHz, DMSO-d6) δ 1.05-1.25 (2H, m), 1.71-1.78 (2H, m), 1.95-1.98 (2H, m), 2.05-2.25 (3H, m), 2.340-2.45 (2H, masked), 2.60 (1H, m), 2.95-3.10 (4H, m), 3.15-3.22 (2H, m), 3.35-3.40 (1H, m), 4.04-4.08 (2H, m), 4.15-4.27 (3H, m), 4.52-4.55 (1H, m), 6.80 (2H, br s), 8.27 (1H, d), 9.22 (1H, dd), 9.48-9.50 (1H, dd), 9.67 (1H, s), 9.90-10.00 (1H, s), 10.62 (1H, s). |
| I-G-69 | 528.1 | 2.30* | $^1$H NMR (500 MHz, DMSO) δ 10.54 (s, 1H), 9.75 (s, 1H), 9.33-9.28 (m, 2H), 8.22 (s, 1H), 6.58 (s, 2H), 3.55 (t, J = 11.6 Hz, 2H), 2.26-2.11 (m, 4H), 3.01-2.93 (m, 3H), 2.80 (s, 2H), 2.47 (d, J = 11.4 Hz, 2H), 1.96 (s, 1H), 1.77 (d, J = 13.6 Hz, 3H), 2.39-2.34 (m, 1H), 2.68-2.60 (m, 2H). |
| I-G-70 | 512.0 | 2.11* | $^1$H NMR (500 MHz, DMSO-d6) δ 1.70-1.80 (2H, m), 1.81-1.97 (2H, m), 2.05-2.15 (2H, m), 2.40-2.50 (2H, masked), 2.55-2.60 (1H, m), 2.78-2.83 (2H, m), 2.85-3.05 (2H, m), 3.10-3.20 (2H, m), 3.72-3.74 (1H, m), 3.96-3.98 (1H, m), 4.51 (1H, m), 5.05 (1H, m), 6.79 (2H, s), 8.25 (1H, m), 9.31 (1H, d), 9.35 (1H, d), 9.45 (1H, m), 9.67 (1H, d), 10.60 (1H, d). |
| I-G-71 | 512.0 | 2.11* | $^1$H NMR (500 MHz, DMSO-d6) δ 1.70-1.80 (2H, m), 1.81-1.97 (2H, m), 2.05-2.15 (2H, m), 2.40-2.50 (1H, masked), 2.55-2.60 (1H, m), 2.78-2.83 (2H, m), 2.85-3.05 (2H, m), 3.72-3.74 (1H, m), 3.96-3.98 (1H, m), 4.51 (1H, m), 5.05 (1H, m), 6.79 (2H, s), 8.25 (1H, m), 9.31 (1H, d), 9.35 (1H, d), 9.45 (1H, m), 9.67 (1H, d), 10.60 (1H, d). |
| I-G-72 | 499.1 | 2.13* | $^1$H NMR (500 MHz, DMSO-d6) δ 10.63 (s, 1H), 9.68 (s, 1H), 9.47-9.48 (dd, 1H), 9.35 (dd, 1H), 8.25-8.26 (d, 1H), 6.79 (s, 2H), 4.69 (s, 4H), 4.41 (s, 2H), 4.10 (s, 2H), 3.10-3.13 (m, 2H), 3.02-3.05 (m, 2H), 2.45-2.50 (m, 2H), 2.04-2.08 (m, 2H), 1.72-1.75 (m, 2H). |
| I-G-73 | 493.0 | 2.63* | $^1$H NMR (500 MHz, DMSO-d6) δ 10.62 (s, 1H), 9.67 (s, 1H), 9.48-9.50 (dd, 1H), 9.27 (dd, 1H), 8.28 (d, 1H), 6.80 (be s, 2H), 4.76 (m, 2H), 4.38 (m, 2H), 3.14 (m, 2H), 3.08-3.11 (m, 2H), 2.55-2.60 (m, 1H), 2.03-2.15 (m, 2H), 1.82-1.84 (m, 2H). |

-continued

Compound Analytical Data

| Cmpd No. | LCMS ES+ | LCMS (Rt min) | HNMR |
|---|---|---|---|
| I-G-74 | 475.1 | 2.42* | — |
| I-G-75 | 501.0 | 2.5* | — |
| I-G-76 | 482.1 | 2.22* | ¹H NMR (500 MHz, DMSO-d6) δ 10.61 (s, 1H), 9.67 (s, 1H), 9.48-9.50 (dd, 1H), 9.30 (dd, 1H), 8.28 (d, 1H), 6.80 (br s, 2H), 4.55-4.56 (m, 1H), 4.46-4.49 (m, 1H), 4.21-4.25 (m, 1H), 4.07-4.11 (m, 1H), 3.81-3.85 (m, 1H), 3.05-3.17 (m, 4H), 2.50-2.55 (masked, 1H), 2.03-2.09 (m, 2H), 1.75-1.81 (m, 2H). |
| I-G-77 | 439.1 | 2.02* | ¹H NMR (500 MHz, DMSO-d6) δ 9.86 (s, 1H), 9.53 (dd, J = 4.7, 2.5 Hz, 1H), 9.45 (d, J = 1.0 Hz, 1H), 9.02 (dd, J = 2.6, 0.6 Hz, 1H), 8.44 (dd, J = 6.5, 1.1 Hz, 1H), 7.55 (d, J = 6.5 Hz, 1H), 6.80 (s, 2H), 4.21 (t, J = 7.6 Hz, 2H), 3.89 (t, J = 7.7 Hz, 2H), 3.58 (dt, J = 12.3, 3.2 Hz, 2H), 3.02 (td, J = 12.5, 2.5 Hz, 2H), 2.59-2.52 (m, 1H), 2.26-2.16 (m, 2H), 2.06-1.94 (m, 2H), 1.80-1.72 (m, 2H). |
| I-G-78 | 469.1 | 1.99* | — |
| I-G-79 | 483.0 | 2.12* | ¹H NMR (500 MHz, DMSO-d6) δ 9.83 (s, 1H), 9.53 (dd, J = 4.8, 2.5 Hz, 1H), 9.45 (d, J = 1.0 Hz, 1H), 9.00 (dd, J = 2.5, 0.6 Hz, 1H), 8.46 (dd, J = 6.5, 1.1 Hz, 1H), 7.58 (d, J = 6.5 Hz, 1H), 6.80 (s, 2H), 4.17-4.11 (m, 1H), 4.00 (dd, J = 8.8, 1.2 Hz, 1H), 3.80 (d, J = 9.9 Hz, 1H), 3.68 (d, J = 10.0, 1.2 Hz, 1H), 3.60 (dt, J = 12.5, 3.3 Hz, 2H), 3.18 (s, 3H), 3.06-2.98 (m, 2H), 2.57 (ddt, J = 11.7, 8.3, 4.2 Hz, 1H), 2.06-1.94 (m, 2H), 1.83-1.75 (m, 2H), 1.42 (s, 3H). |
| I-G-80 | 475.1 | 2.24* | — |
| I-G-81 | 464.1 | 1.92* | ¹H NMR (500 MHz, DMSO-d6) δ 9.82 (s, 1H), 9.54 (dd, J = 4.7, 2.5 Hz, 1H), 9.44 (d, J = 1.0 Hz, 1H), 8.96 (dd, J = 2.5, 0.5 Hz, 1H), 8.46 (dd, J = 6.5, 1.1 Hz, 1H), 7.57 (d, J = 6.5 Hz, 1H), 6.80 (s, 2H), 4.55-4.41 (m, 2H), 4.19 (t, J = 9.4 Hz, 1H), 4.05 (dd, J = 9.6, 6.1 Hz, 1H), 3.81 (tt, J = 9.1, 6.1 Hz, 1H), 3.64-3.56 (m, 2H), 3.02 (td, J = 12.4, 2.6 Hz, 2H), 2.61-2.52 (m, 1H), 2.04-1.90 (m, 2H), 1.80 (dd, J = 30.8, 12.9 Hz, 2H). |
| I-G-82 | 457.1 | 2.04* | — |
| I-G-83 | 453.1 | 2.21* | ¹H NMR (500 MHz, DMSO-d6) δ 9.86 (d, J = 1.5 Hz, 1H), 9.53 (ddd, J = 4.9, 2.6, 1.0 Hz, 1H), 9.46 (dd, J = 2.5, 1.1 Hz, 1H), 9.06-9.01 (m, 1H), 8.46 (ddd, J = 6.4, 2.5, 1.1 Hz, 1H), 7.57 (dd, J = 6.6, 1.7 Hz, 1H), 6.80 (s, 2H), 3.62 (dt, J = 12.8, 3.2 Hz, 2H), 3.53 (t, J = 6.8 Hz, 2H), 3.33 (t, J = 6.9 Hz, 2H), 3.05 (td, J = 12.5, 2.4 Hz, 2H), 2.77 (tt, J = 11.5, 3.9 Hz, 1H), 2.05 (qd, J = 12.7, 3.9 Hz, 2H), 1.96-1.86 (m, 2H), 1.85-1.75 (m, 4H). |
| I-G-84 | 495.1 | 1.94* | ¹H NMR (500 MHz, DMSO-d6) δ 9.84 (q, J = 1.7 Hz, 1H), 9.54 (ddd, J = 4.7, 2.6, 2.0 Hz, 1H), 9.45 (q, J = 1.6 Hz, 1H), 9.06-8.96 (m, 1H), 8.46 (ddd, J = 6.5, 2.6, 1.2 Hz, 1H), 7.61-7.52 (m, 1H), 6.80 (s, 2H), 4.55 (d, J = 6.1 Hz, 1H), 4.52-4.34 (m, 2H), 3.82 (s, 1H), 3.71-3.24 (m, 6H), 3.11-2.99 (m, 2H), 2.76 (dddd, J = 21.0, 17.3, 12.3, 6.9 Hz, 1H), 2.21 (t, J = 6.9 Hz, 1H), 2.13-1.97 (m, 3H), 1.82 (td, J = 13.2, 6.7 Hz, 2H). |
| I-G-85 | 469.1 | 1.97* | ¹H NMR (500 MHz, DMSO-d6) δ 9.79 (s, 1H), 9.54 (dd, J = 4.8, 2.5 Hz, 1H), 9.41 (d, J = 1.1 Hz, 1H), 8.97-8.90 (m, 1H), 8.45 (dd, J = 6.6, 1.1 Hz, 1H), 7.56 (d, J = 6.6 Hz, 1H), 6.80 (s, 2H), 3.68-3.54 (m, 8H), 3.50 (t, J = 4.5 Hz, 2H), 3.16-2.94 (m, 3H), 2.07-1.96 (m, 2H), 1.81-1.71 (m, 2H). |
| I-G-86 | 535.0 | 2.12* | — |
| I-G-87 | 542.0 | 2.33* | ¹H NMR (500 MHz, DMSO-d6) δ 11.28 (1H, brs), 10.56 (0.4H, s), 10.52 (0.6H, s), 9.66 0.4H, s), 9.63 (0.6H, s), 9.44 (1H, d), 9.22 (0.4H, d), 8.99 (0.6H, d), 8.38 (1H, dd), 4.72 (0.6H, brs), 4.58 (0.4H, brs), 3.96-3.99 (2H, m), 3.20-3.40 (8H, m), 3.11-3.12 (2H, m), 1.98-2.15 (7H, m), 1.77-1.80 (2H, m). |
| I-G-88 | 481.1 | 1.86* | — |
| I-G-89 | 517.1 | 1.81* | ¹H NMR (500 MHz, DMSO-d6) δ 10.16 (s, 1H), 9.64 (s, 1H), 9.47 (dd, J = 4.8, 2.5 Hz, 1H), 9.06 (dd, J = 2.5, 0.6 Hz, 1H), 8.23 (d, J = 5.2 Hz, 1H), 7.21 (dd, J = 5.2, 0.6 Hz, 1H), 6.77 (s, 2H), 4.59-4.52 (m, 1H), 4.43 (dd, J = 9.5, 4.9 Hz, 1H), 4.31 (tt, J = 8.4, 5.0 Hz, 1H), 4.20 (d, J = 10.4, 8.5 Hz, 1H), 4.14-4.07 (m, 1H), 3.14-3.08 (m, 2H), 3.07 (s, 3H), 2.75 (tdd, J = 11.9, 6.5, 2.4 Hz, 2H), 2.48 (dt, J = 11.8, 4.0 Hz, 1H), 2.14-2.00 (m, 2H), 1.76 (dt, J = 12.5, 3.0 Hz, 2H). |
| I-G-90 | 481.1 | 1.96* | ¹H NMR (500 MHz, DMSO-d6) δ 9.83 (s, 1H), 9.52 (dd, J = 4.7, 2.5 Hz, 1H), 9.44 (d, J = 1.1 Hz, 1H), 8.98 (d, J = 2.5 |

Compound Analytical Data

| Cmpd No. | LCMS ES+ | LCMS (Rt min) | HNMR |
|---|---|---|---|
| | | | Hz, 1H), 8.44 (dd, J = 6.5, 1.1 Hz, 1H), 7.55 (d, J = 6.5 Hz, 1H), 6.80 (s, 2H), 4.49-4.38 (m, 3H), 4.33 (dd, J = 10.0, 1.7 Hz, 1H), 4.14 (dd, J = 11.3, 1.7 Hz, 1H), 3.96 (dd, J = 11.2, 1.7 Hz, 1H), 3.61-3.54 (m, 2H), 3.01 (tt, J = 12.5, 3.2 Hz, 2H), 2.84 (t, J = 7.5 Hz, 2H), 2.59-2.52 (m, 1H), 1.97 (qq, J = 12.5, 4.8, 4.3 Hz, 2H), 1.81-1.73 (m, 2H). |
| I-G-91 | 483.1 | 2.18* | $^1$H NMR (500 MHz, DMSO-d6) δ 9.86 (s, 1H), 9.53 (dd, J = 4.8, 2.5 Hz, 1H), 9.45 (d, J = 0.9 Hz, 1H), 9.04-8.98 (m, 1H), 8.43 (dd, J = 6.4, 1.0 Hz, 1H), 7.54 (d, J = 6.4 Hz, 1H), 6.80 (s, 2H), 4.40 (ddd, J = 9.1, 6.5, 1.3 Hz, 1H), 4.30 (tt, J = 6.5, 4.0 Hz, 1H), 4.11-3.99 (m, 2H), 3.70-3.66 (m, 1H), 3.56 (d, J = 12.5 Hz, 2H), 3.43 (qd, J = 7.0, 2.3 Hz, 2H), 3.05-2.96 (m, 2H), 2.61-2.52 (m, 1H), 1.99 (qt, J = 12.6, 3.5 Hz, 2H), 1.79 (q, J = 12.8, 11.8 Hz, 2H), 1.14 (t, J = 7.0 Hz, 3H). |
| I-G-92 | 556.0 | 2.37* | $^1$H NMR (500 MHz, DMSO-d6) δ 10.62 (s, 1H), 9.67 (s, 1H), 9.49-9.50 (dd, 1H), 9.19 (d, 1H), 8.28 (d, 1H), 6.81 (s, 2H), 4.30-4.90 (m, 7H), 2.98-3.21 (m, 10H), 2.15-2.20 (m, 2H), 1.78-1.80 (m, 2H), 1.58 (m, 3H). |
| I-G-93 | 483.1 | 2.07* | $^1$H NMR (500 MHz, DMSO-d6) δ 9.88-9.83 (m, 1H), 9.53 (dd, J = 4.8, 2.5 Hz, 1H), 9.45 (dd, J = 2.2, 1.1 Hz, 1H), 9.02 (t, J = 2.5 Hz, 1H), 8.44 (dd, J = 6.4, 1.1 Hz, 1H), 7.56 (dd, J = 6.5, 1.6 Hz, 1H), 6.79 (s, 2H), 3.99 (dtt, J = 37.7, 4.6, 2.3 Hz, 1H), 3.71-3.43 (m, 5H), 3.41-3.27 (m, 1H), 3.25 (d, J = 11.0 Hz, 3H), 3.05 (tq, J = 12.4, 2.5 Hz, 2H), 2.78 (qt, J = 11.6, 3.9 Hz, 1H), 2.12-1.76 (m, 6H). |
| I-G-94 | 483.0 | 2.07* | $^1$H NMR (500 MHz, DMSO-d6) δ 9.87 (d, J = 1.5 Hz, 1H), 9.54 (dd, J = 4.7, 2.5 Hz, 1H), 9.46 (dd, J = 2.2, 1.0 Hz, 1H), 9.02 (t, J = 2.7 Hz, 1H), 8.44 (dd, J = 6.4, 1.0 Hz, 1H), 7.55 (dd, J = 6.5, 1.6 Hz, 1H), 6.80 (s, 2H), 3.99 (dtt, J = 37.8, 4.5, 2.3 Hz, 1H), 3.71-3.43 (m, 5H), 3.40-3.27 (m, 1H), 3.25 (d, J = 10.9 Hz, 3H), 3.03 (dddd, J = 12.9, 8.3, 3.9, 2.3 Hz, 2H), 2.77 (qt, J = 11.0, 3.7 Hz, 1H), 2.12-1.86 (m, 4H), 1.80 (dt, J = 13.6, 6.9 Hz, 2H). |
| I-G-95 | 516.1 | 1.79* | $^1$H NMR (500 MHz, DMSO-d6) δ 12.48 (s, 1H), 10.64 (s, 1H), 9.68 (s, 1H), 9.50 (dd, 1H), 9.17 (dd, 1H), 8.28 (d, 1H), 6.81 (s, 2H), 4.54 (d, 1H), 4.31 (d, 1H), 3.79-3.69 (m, 5H), 3.53 (s, 3H), 3.36-3.30 (m, 1H), 3.24-3.18 (m, 2H), 3.09-3.01 (m, 3H), 2.21-2.07 (m, 2H), 1.79 (br d, 2H). |
| I-G-96 | 555.2 | 2.13* | $^1$H NMR (500 MHz, DMSO-d6) δ 10.64 (s, 1H), 9.67 (s, 1H), 9.48 (dd, J = 4.8, 2.5 Hz, 1H), 9.29-9.18 (m, 1H), 8.26 (d, J = 2.4 Hz, 1H), 6.79 (s, 2H), 3.65-3.50 (m, 4H), 3.38 (s, 1H), 3.19 (t, J = 11.7 Hz, 2H), 3.04 (t, J = 7.6 Hz, 2H), 2.95 (t, J = 11.7 Hz, 1H), 2.82 (d, J = 31.4 Hz, 3H), 2.65 (p, J = 1.9 Hz, 1H), 2.55 (s, 1H), 2.37 (p, J = 1.9 Hz, 1H), 2.30-2.19 (m, 7H), 2.18-2.06 (m, 2H), 1.78-1.69 (m, 2H), 1.25 (s, 2H). |
| I-G-98 | 501.0 | 2.44* | $^1$H NMR (500 MHz, DMSO-d6) δ 10.63 (s, 1H), 9.67 (s, 1H), 9.47-9.49 (dd, 1H), 9.38 (dd, 1H), 8.28 (d, 1H), 6.80 (s, 2H), 4.27-4.30 (m, 1H), 3.93-3.97 (m, 2H), 3.61-3.64 (m, 1H), 3.49-3.51 (m, 2H), 3.30 (s, 3H), 3.15-3.16 (m, 2H), 3.10-3.11 (m, 2H), 2.80-2.83 (m, 1H), 2.35-2.40 (masked, 1H), 2.00-2.10 (m, 2H), 1.70-1.80 (m, 2H). |
| I-G-99 | 501.1 | 2.45* | — |

Retention times measured using HPLC Method B, described in the Experimental Methods and Materials section, above., are designated by (*). For all other compounds, the retention time was measured using the HPLC Method A.

Preparation O-1: (S)-tert-butyl 3-((3-aminopyridin-4-yl)oxy)piperidine-1-carboxylate Scheme 7

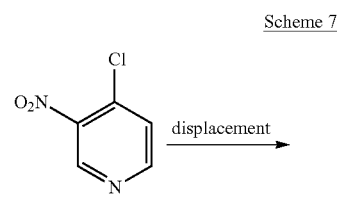

displacement →

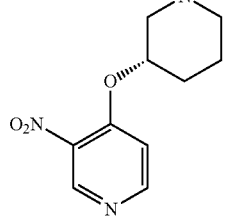

-continued

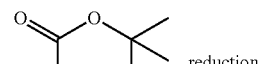

reduction →

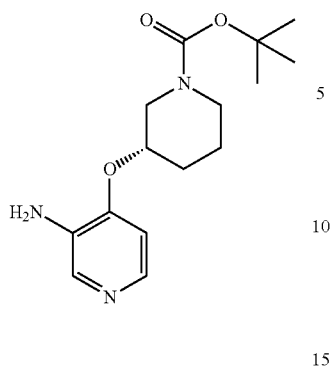

Step 1: tert-butyl (3S)-3-[(3-nitro-4-pyridyl)oxy]piperidine-1-carboxylate

Sodium hydride (492.0 mg, 12.30 mmol) was added to a solution of tert-butyl (3S)-3-hydroxypiperidine-1-carboxylate (2.095 g, 10.41 mmol) in THF (20 mL) and the reaction stirred at 0° C. for 15 minutes. A suspension of 4-chloro-3-nitro-pyridine (1.5 g, 9.461 mmol) in THF (10 mL) was added and the reaction allowed to warm slowly to ambient temperature over 2 hours. The reaction was quenched with water and the mixture was partitioned between EtOAc and brine. The combined organic extract was washed with brine, dried ($MgSO_4$), filtered and concentrated in vacuo. The residue was purified by column chromatography (ISCO Companion, 80 g column, eluting with 0 to 100% EtOAc/Petroleum Ether) to give tert-butyl (3S)-3-[(3-nitro-4-pyridyl)oxy]piperidine-1-carboxylate as a pale yellow solid (2.65 g, 87% Yield, 93% ee). MS (ES+) 324.1.

Step 2: (9-ten-butyl 3-((3-aminopyridin-4-yl)oxy)piperidine-1-carboxylate

Pd on C, (10%, wet, Degussa) (1 g, 0.9397 mmol) was added to a stirred solution of tert-butyl (3S)-3-[(3-nitro-4-pyridyl)oxy]piperidine-1-carboxylate (2.65 g, 8.196 mmol) in EtOAc (30 mL)/EtOH (15 mL). The reaction was placed under an atmosphere of hydrogen and stirred at ambient temperature for 16 hours. The catalyst was removed by filtration through a pad of celite and the filtrate concentrated in vacuo to give the sub-title compound as an off-white solid (2.46 g, >100% Yield). MS (2ES+) 587.3.

The following aminopyridines were prepared using Preparation O-1:

(R)-4-((1-methylpyrrolidin-3-yl)oxy)pyridin-3-amine

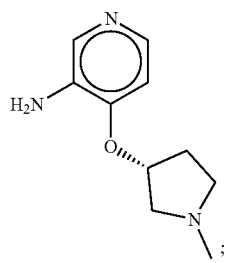

4-((1-methylpiperidin-4-yl)oxy)pyridin-3-amine

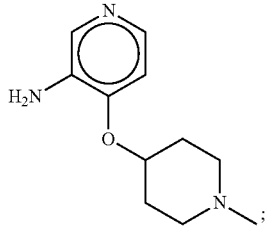

(R)-4-(quinuclidin-3-yloxy)pyridin-3-amine

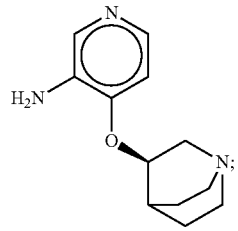

(S)-4-(quinuclidin-3-yloxy)pyridin-3-amine

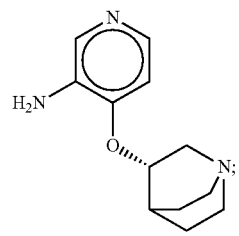

4-(quinuclidin-3-yloxy)pyridin-3-amine

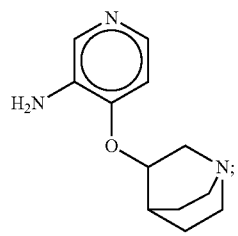

4-(2-methyoxyethoxy)pyridin-3-amine

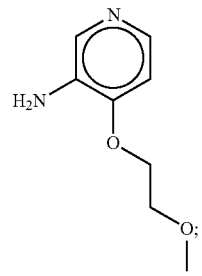

2-((3-aminopyridin-4-yl)oxy)ethanol

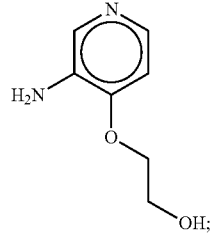

3-((3-aminopyridin-4-yl)oxy)propan-1-ol

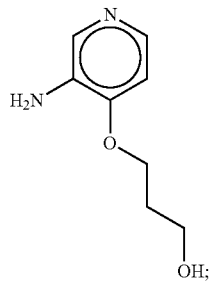

4-(2-(dimethylamino)ethoxy)pyridin-3-amine

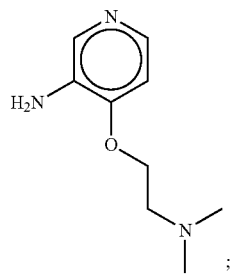

4-(2-morpholinoethoxy)pyridin-3-amine

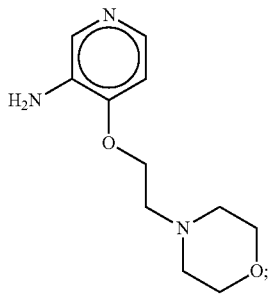

(R)-4-((1-(2-methoxyethyl)piperidin-3-yl)oxy)pyridin-3-amine

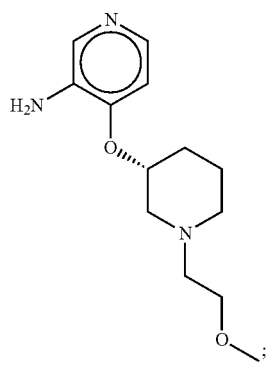

6-chloro-4-(2-(dimethylamino)ethoxy)pyridin-3-amine

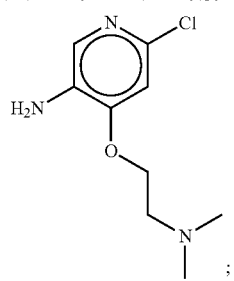

4-(2-(2-(dimethylamino)ethoxy)ethoxy)pyridin-3-amine

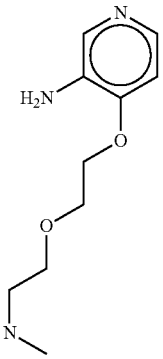

4-(3-(dimethylamino)propoxy)pyridin-3-amine

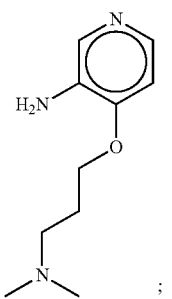

4-(2-(dimethylamino)ethoxy)-6-(trifluoromethyl)pyridin-3-amine

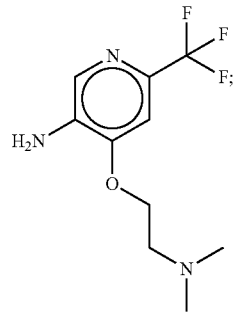

5-chloro-4-((1-methylpiperidin-4-yl)oxy)pyridin-3-amine

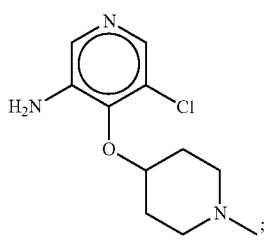

(R)-4-((1-methylpyrrolidin-2-yl)methoxy)pyridin-3-amine

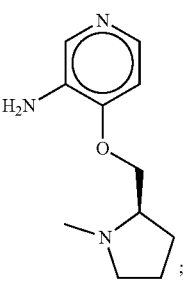

(1s,4s)-methyl 4-((3-aminopyridin-4-yl)oxy)cyclohexanecarboxylate

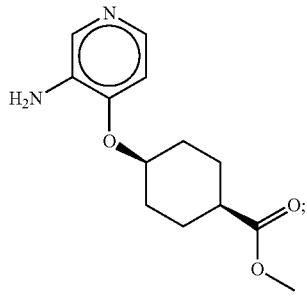

(1r,4r)-methyl 4-((3-aminopyridin-4-yl)oxy)cyclohexanecarboxylate

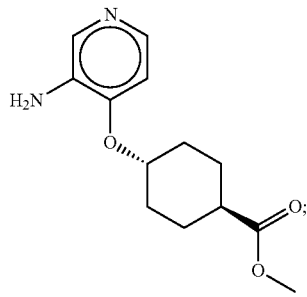

(S)-4-((1-methylpyrrolidin-2-yl)methoxy)pyridin-3-amine

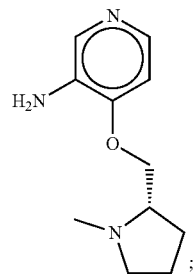

4-((1-(oxetan-3-yl)piperidin-4-yl)oxy)pyridin-3-amine

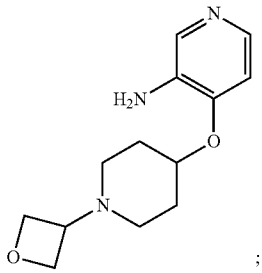

(S)-4-((1-(-oxetan-3-yl)piperidin-4-yl)oxy)pyridin-3-amine

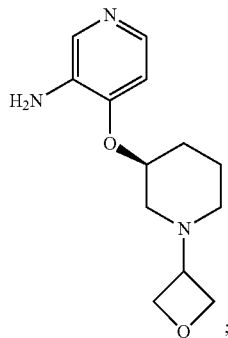

4-(2,2,2-trifluoroethoxy)pyridin-3-amine

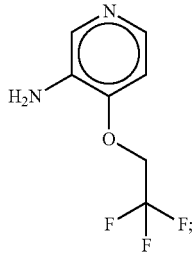

4-ethoxypyridin-3-amine

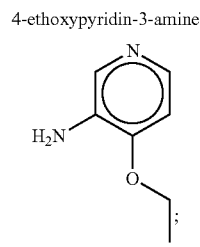

4-methoxypyridin-3-amine

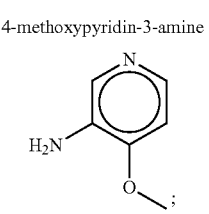

4-isopropoxypyridin-3-amine

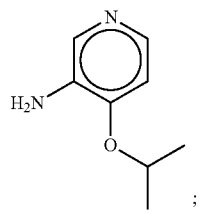

4-cyclobutoxypyridin-3-amine

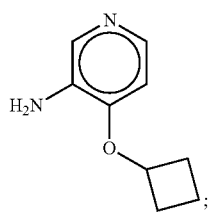

4-(cyclopentyloxy)pyridin-3-amine

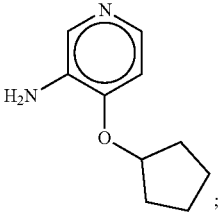

4-(oxetan-3-yloxy)pyridin-3-amine

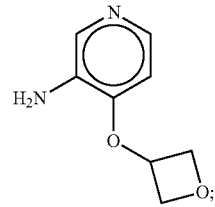

4-(cyclopropylmethoxy)pyridin-3-amine

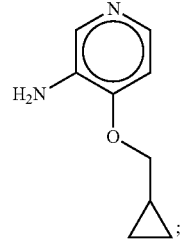

4-(cyclohexyloxy)pyridin-3-amine

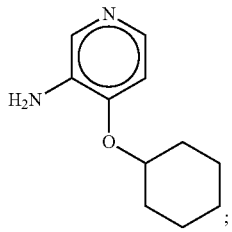

4-((tetrahydrofuran-3-yl)oxy)pyridin-3-amine

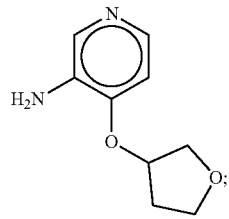

(R)-4-((tetrahydrofuran-3-yl)oxy)pyridin-3-amine

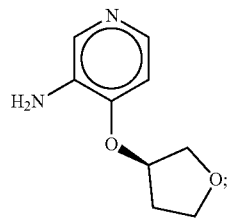

(S)-4-((tetrahydrofuran-3-yl)oxy)pyridin-3-amine

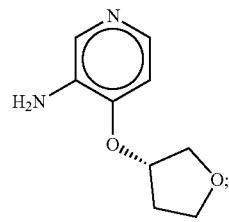

4-((tetrahydro-2H-pyran-4-yl)oxy)pyridin-3-amine

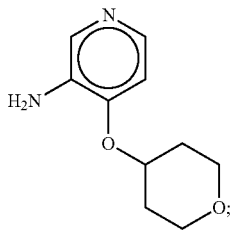

4-((tetrahydro-2H-pyran-3-yl)oxy)pyridin-3-amine

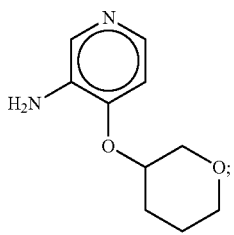

(R)-tert-butyl 3-((3-aminopyridin-4-yl)oxy)piperidine-1-carboxylate

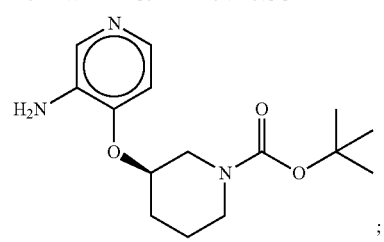

tert-butyl (2-((3-aminopyridin-4-yl)oxy)ethyl)carbamate

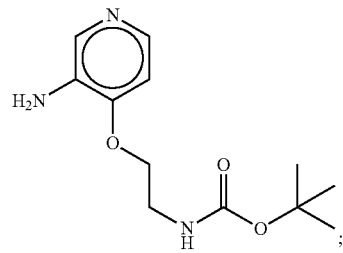

(4r,6s)-tert-butyl 6-((3-aminopyridin-4-yl)oxy)-1-azaspiro[3.3]heptane-1-carboxylate

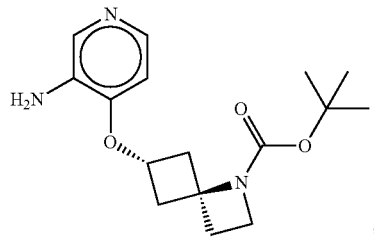

(4s,6r)-tert-butyl 6-((3-aminopyridin-4-yl)oxy)-1-azaspiro[3.3]heptane-1-carboxylate

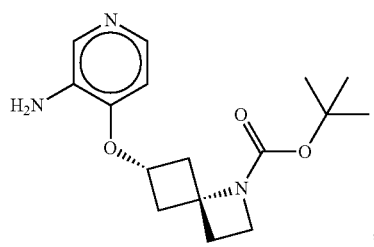

4-((tetrahydro-2H-thiopyran-4-yl)oxy)pyridin-3-amine

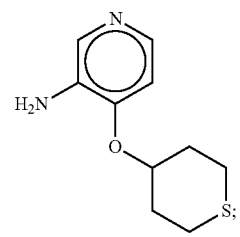

tert-butyl 6-((3-aminopyridin-4-yl)oxy)-2-azaspiro[3.3]heptane-2-carboxylate

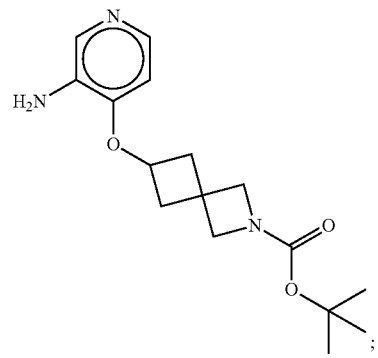

-continued 6-chloro-4-methoxypyridin-3-amine

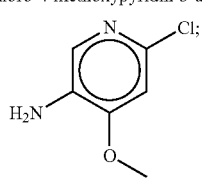

tert-butyl 3-((3-aminopyridin-4-yl)oxy)azetidine-1-carboxylate

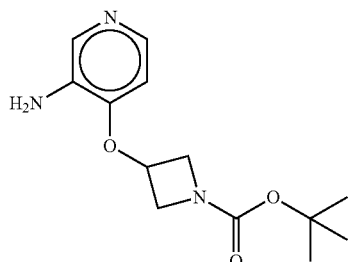

(R)-4-((6,7-dihydro-5H-pyrrolo[1,2-a]imidazol-6-yl)oxy)pyridin-3-amine

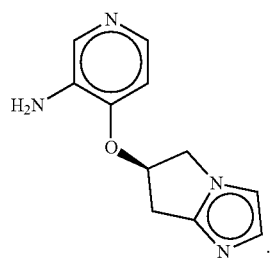

Miscellaneous Preparation of Aminopyridines

Preparation O-2: 4-((6-((dimethylamino)methyl)pyridin-3-yl)oxy)pyridin-3-amine

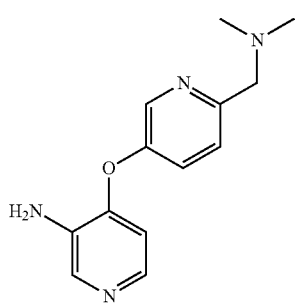 [SMILES: CN(C)Cc1ccc(Oc2ccncc2N)cn1]

Step 1: 6-((dimethylamino)methyl)pyridin-3-ol 6-(aminomethyl)pyridin-3-ol (150 mg, 1.208 mmol), formic acid (1 mL, 26.51 mmol), formaldehyde (1 mL, 36.30 mmol) was heated at 100° C. overnight. The mixture was concentrated in vacuo to yield 6-((dimethylamino)methyl)pyridin-3-ol that was used in next step without further purification.

Step 2: N,N-dimethyl-1-(5-((3-nitropyridin-4-yl)oxy)pyridin-2-yl)methanamine

To a solution of 6-((dimethylamino)methyl)pyridin-3-ol in DMF (5 mL) was added, K$_2$CO$_3$ (834.8 mg, 6.040 mmol) and the mixture was stirred at RT for 10 min before 4-chloro-3-nitro-pyridine (191.5 mg, 1.208 mmol) was added. The mixture was stirred at RT for 60 h. The reaction mixture was partitioned between EtOAc and NH$_4$Cl aq satd. Combined organic extract was washed with brine, dried (MgSO$_4$) and concentrated in vacuo yielding an oil that purified by SCX column, yielding N,N-dimethyl-1-(5-((3-nitropyridin-4-yl)oxy)pyridin-2-yl)methanamine as a colourless oil. MS (ES+) 275.1.

Step 3: 4-((6-((dimethylamino)methyl)pyridin-3-yl)oxy)pyridin-3-amine

N,N-dimethyl-1-(5-((3-nitropyridin-4-yl)oxy)pyridin-2-yl)methanamine (150 mg, 0.5469 mmol), Pd/C (10%) (58.20 mg, 0.5469 mmol) in MeOH (15 mL) was stirred overnight at RT under hydrogen (balloon). The catalyst was filtered off and the filtrate was concentrated in vacuo to yield the title product as a clear oil. MS (ES+) 245.2.

The following aminopyridine synthesized using Step 2 and Step 3 of Preparation O-2:

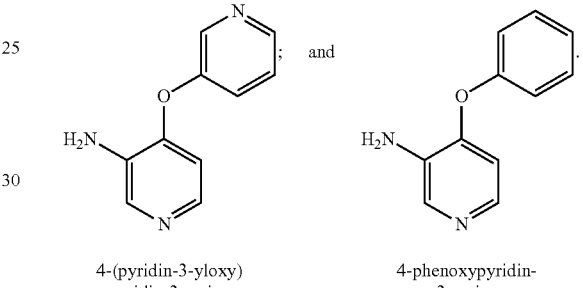

4-(pyridin-3-yloxy)pyridin-3-amine 4-phenoxypyridin-3-amine

Preparation O-3: (1s,4s)-4-((3-aminopyridin-4-yl)oxy)-N,N-dimethylcyclohexanecarboxamide

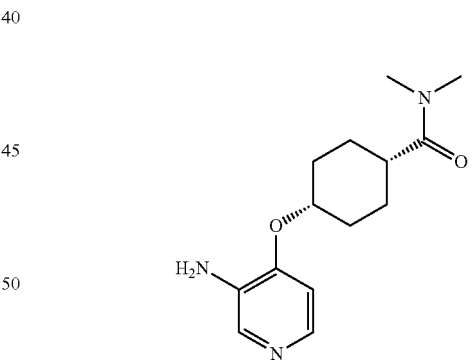

Step 1: 4-[(3-nitro-4-pyridyl)oxy]cyclohexanecarboxylic acid

Methyl 4-[(3-nitro-4-pyridyl)oxy]cyclohexanecarboxylate (250.0 mg, 0.8920 mmol) (prepared according to methods similar to the one depicted in Step 1 of preparation 0-1) in THF (2.748 mL), Water (2.748 mL) and MeOH (1.5 mL) solution was stirred at RT and treated with Lithium hydroxide monohydrate (Water (1)) (224.6 mg, 5.352 mmol). The mixture was stirred at RT overnight, then was concentrated under reduced pressure to remove the organics. The aqueous solution was cooled in an ice bath then acidified with HCl (5.352 mL of 1 M, 5.352 mmol) to pH 4-5. Ethyl acetate was then added and the layers separated. Aqueous layer was extracted further with ethyl acetate (2×5 mL) and the combined organic layers were dried over MgSO$_4$ and concentrated in vacuo to leave the 4-[(3-nitro-4-pyridyl)oxy]cyclohexanecarboxylic acid as a yellow oil. Used in the next step without further purification. MS (ES+) 267.0.

Step 2: N,N-dimethyl-4-[(3-nitro-4-pyridyl)oxy]cyclohexanecarboxamide

TBTU (630.0 mg, 1.962 mmol) and dimethylamine (1.784 mL of 2 M, 3.568 mmol) were added to a solution of 4-[(3-nitro-4-pyridyl)oxy]cyclohexanecarboxylic acid (475 mg, 1.784 mmol) and DIPEA (253.6 mg, 341.8 μL, 1.962 mmol) in THF (9.500 mL) and the resulting solution was stirred at RT overnight. The reaction mixture was partitioned between EtOAc and water, and the combined organic extracts were dried over MgSO$_4$ and concentrated in vacuo. The residue was purified by column chromatography on silica eluting with 0-100% EtOAc/petroleum ether using the ISCO column companion system (12 g column). Clean fractions were combined and concentrated in vacuo to yield N,N-dimethyl-4-[(3-nitro-4-pyridyl)oxy]cyclohexanecarboxamide as a pale yellow oil. (180 mg, 34%). MS (ES+) 294.3.

Step 3: (1s,4s)-4-((3-aminopyridin-4-yl)oxy)-N,N-dimethylcyclohexanecarboxamide

Pd on C, (10%, wet, Degussa) (65.31 mg, 0.06137 mmol) was added to a solution of N,N-dimethyl-4-[(3-nitro-4-pyridyl)oxy]cyclohexanecarboxamide (180 mg, 0.6137 mmol) in methanol (6.300 mL) and the reaction mixture was stirred under a hydrogen atmosphere overnight. The catalyst was filtered off and the filtrate was concentrated in vacuo to leave the title product as a yellow oil. (160 mg, 99%), MS (ES+) 264.3.

The following aminopyridine was synthesized according to methods similar to the one depicted in Preparation O-3:

((1s,4s)-4-((3-aminopyridin-4-yl)oxy)cyclohexyl)(4-methylpiperazin-1-yl)methanone:

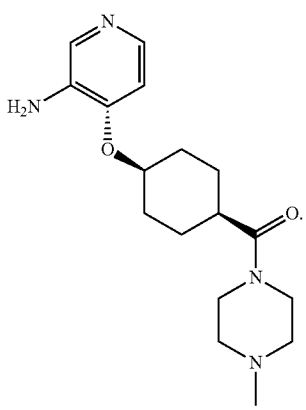

Preparation O-4: 4-((3-aminopyridin-4-yl)oxy)tetrahydro-2H-thiopyran 1-oxide and 4-((3-aminopyridin-4-yl)oxy)tetrahydro-2H-thiopyran 1,1-dioxide

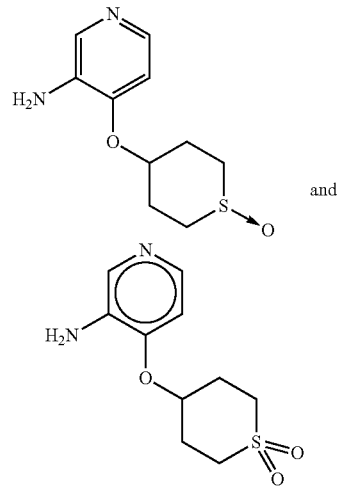

An amount of mCPBA (513.0 mg, 2.081 mmol) was added to a solution of 3-nitro-4-((tetrahydro-2H-thiopyran-4-yl)oxy)pyridine (prepared according to methods similar to the one depicted in Preparation O-1) (400 mg, 1.665 mmol) in DCM (10 mL) at RT. The mixture was stirred at RT overnight before 5 mL of an aqueous saturated solution of NaHCO$_3$ and 5 mL of an aqueous saturated solution of Na$_2$S$_2$O$_3$ was added. The mixture was stirred at RT for 30 min, partitioned between DCM and water. Combined organic extract was washed with brine, dried (MgSO$_4$) and concentrated in vacuo yielding an oil that was dissolved in MeOH (15 mL). Pd/C 10% (177.2 mg, 1.665 mmol) was added and the mixture was hydrogenated (H$^2$ balloon) overnight. The catalyst was filtered off and the filtrate was concentrated in vacuo to yield a 1/1 mixture of "sulfoxide and sulfone aminopyridine" intermediates that was used in next step without further purification.

MS (ES+) 227.1 (sulfoxide); and
MS (ES+) 243.1 (sulfone).

Preparation O-5: 5-fluoro-4-((1-methylpiperidin-4-yl)oxy)pyridin-3-amine

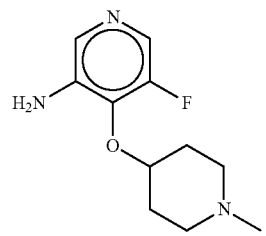

Step 1: 2-bromo-5-fluoro-4-((1-methylpiperidin-4-yl)oxy)-3-nitropyridine

NaH (86.67 mg, 2.167 mmol) was added portionwise to a solution of 1-methylpiperidin-4-ol (192.0 mg, 1.667 mmol) in THF (5.000 mL) at 0° C. and the resulting solution stirred for 15 min and then 2,4-dibromo-5-fluoro-3-nitro-pyridine (500 mg, 1.667 mmol) in THF (5.000 mL) was added and the reaction mixture stirred at RT overnight. The reaction mixture was partitioned between water (10 mL) and ethyl acetate (10 mL). Combined organic extracts was dried over MgSO₄ and concentrated in vacuo. The residue was purified by column chromatograph on silica eluting with ethyl acetate/petroleum ether (24 g column, 0-100% EtOAc) using the ISCO column companion system. Product fractions were combined and concentrated in vacuo to leave the product as a yellow oil that solidified on standing. (125 mg). MS (ES+) 334.0 336.0.

Step 2: 5-fluoro-4-((1-methylpiperidin-4-yl)oxy)pyridin-3-amine

A solution of 2-bromo-5-fluoro-4-[(1-methyl-4-piperidyl)oxy]-3-nitro-pyridine (96 mg, 0.2873 mmol), ZnBr₂ (12.94 mg, 3.080 µL, 0.05746 mmol) and Pd on C, wet, Degussa (31 mg) in methanol (5 mL) was flushed with hydrogen and evacuated (3×) and then stirred under a hydrogen atmosphere overnight. The catalyst was filtered off through a celite pad and washed with methanol and ethyl acetate mixtures and the filtrate was concentrated in vacuo to leave a pale yellow oil that was used in next step without further purification. MS (ES+) 226.1.

The following aminopyridine was prepared using Step 1 and Step 2 of Preparation O-5:
5-fluoro-4-((1-(oxetan-3-yl)piperidin-4-yl)oxy)pyridin-3-amine:

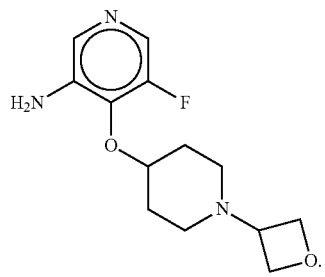

Preparation O-6: tert-butyl (5-amino-4-methoxy-pyridin-2-yl)(methyl)carbamate

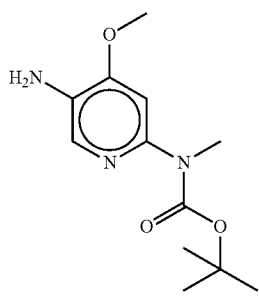

Step 1: tert-butyl (5-iodo-4-methoxypyridin-2-yl)(methyl)carbamate

Sodium hydride (37.70 mg, 0.9425 mmol) was added to a stirred suspension of tert-butyl N-(5-iodo-4-methoxy-2-pyridyl)carbamate (300 mg, 0.8568 mmol) in DMF (3 mL) and the reaction was stirred at 0° C. for 15 minutes. MeI (145.9 mg, 63.99 µL, 1.028 mmol) was added and the reaction allowed to warm to ambient temperature over 1 hour. The mixture was quenched by the addition of water, diluted with EtOAc and the layers separated. The organic layer washed with saturated aqueous NaHCO₃ (×1), brine (×2), dried (MgSO₄) filtered and concentrated in vacuo. The residue was purified by column chromatography (ISCO Companion, 40 g column, eluting with 0 to 30% EtOAc/Petroleum Ether, loaded in DCM) to give tert-butyl (5-iodo-4-methoxypyridin-2-yl)(methyl)carbamate as a colourless oil (269 mg, 86% Yield). MS (ES+-t-Bu) 309.4.

Step 2: tert-butyl (5-((diphenylmethylene)amino)-4-methoxypyridin-2-yl)(methyl)carbamate Pd₂(dba)₃ (33.70 mg, 0.03680 mmol) and Xantphos (42.58 mg, 0.07359 mmol) were added to a sealed tube containing tert-butyl N-(5-iodo-4-methoxy-2-pyridyl)-N-methyl-carbamate (268 mg, 0.7359 mmol), diphenylmethanimine (173.4 mg, 160.6 µL, 0.9567 mmol) and Cs₂CO₃ (719.4 mg, 2.208 mmol) in dioxane (2.5 mL). The reaction was placed under an atmosphere of nitrogen and heated at 100° C. for 4 hours. At RT, the reaction mixture was filtered through celite and the filtrate concentrated in vacuo. The residue was purified by column chromatography (ISCO Companion, 40 g column, eluting with 0 to 30% EtOAc/Petroleum Ether, loaded in DCM) to give tert-butyl (5-((diphenylmethylene)amino)-4-methoxypyridin-2-yl)(methyl)carbamate as a yellow solid (213 mg, 69% Yield). MS (ES+) 418.2.

Step 3: tert-butyl (5-amino-4-methoxypyridin-2-yl)(methyl)carbamate

HCl (100 µL of 2 M, 0.2000 mmol) was added to a stirred solution of tert-butyl N-[5-(benzhydrylideneamino)-4-methoxy-2-pyridyl]-N-methyl-carbamate (212 mg, 0.5078 mmol) in THF (2 mL) and the reaction was stirred at ambient temperature for 18 hours. The resultant precipitate was isolated by filtration and the filtrate stirred at ambient temperature for a further 6 hours. The reaction was diluted with 1M HCl and extracted with Et₂O (×3). The aqueous layer was made basic by the addition of saturated aqueous NaHCO₃ and extracted with DCM (×3). The combined organic extratcs were dried (MgSO₄), filtered and concentrated in vacuo to give tert-butyl (5-amino-4-methoxypyridin-2-yl)(methyl)carbamate as a red oil (98.2 mg, 76% Yield). MS (ES+) 254.1.

The following compounds were synthesized using a procedure similar to Example 1 or Example 3a:
(S)-2-amino-6-fluoro-N-(4-((1-methylpyrrolidin-3-yl)oxy)pyridin-3-yl)pyrazolo[1,5-a]pyrimidine-3-carboxamide (Compound I-O-1);
(R,S)-2-amino-6-(cyanomethyl)-N-(4-(piperidin-3-yloxy)pyridin-3-yl)pyrazolo[1,5-a]pyrimidine-3-carboxamide (Compound I-O-2);
2-amino-N-(4-((6-((dimethylamino)methyl)pyridin-3-yl)oxy)pyridin-3-yl)-6-fluoropyrazolo[1,5-a]pyrimidine-3-carboxamide (Compound I-O-3);
2-amino-6-fluoro-N-(4-methoxypyridin-3-yl)pyrazolo[1,5-a]pyrimidine-3-carboxamide (Compound I-O-4);
(R)-2-amino-6-fluoro-N-(4-(quinuclidin-3-yloxy)pyridin-3-yl)pyrazolo[1,5-a]pyrimidine-3-carboxamide (Compound I-O-5);

(R,S)-2-amino-6-fluoro-N-(4-(quinuclidin-3-yloxy)pyridin-3-yl)pyrazolo[1,5-a]pyrimidine-3-carboxamide (Compound I-O-6);

2-amino-6-fluoro-N-(4-(pyridin-3-yloxy)pyridin-3-yl)pyrazolo[1,5-a]pyrimidine-3-carboxamide (Compound I-O-7);

4-((3-(2-amino-6-fluoropyrazolo[1,5-a]pyrimidine-3-carboxamido)pyridin-4-yl)oxy)cyclohexanecarboxylic acid (Compound I-O-8);

(S)-2-amino-6-fluoro-N-(4-((1-(oxetan-3-yl)piperidin-3-yl)oxy)pyridin-3-yl)pyrazolo[1,5-a]pyrimidine-3-carboxamide (Compound I-O-9);

(S)-2-amino-6-fluoro-N-(4-(quinuclidin-3-yloxy)pyridin-3-yl)pyrazolo[1,5-a]pyrimidine-3-carboxamide (Compound I-O-10);

2-amino-6-fluoro-N-(4-((1-(oxetan-3-yl)piperidin-4-yl)oxy)pyridin-3-yl)pyrazolo[1,5-a]pyrimidine-3-carboxamide (Compound I-O-11);

2-amino-6-fluoro-N-(4-((1-methylpiperidin-4-yl)oxy)pyridin-3-yl)pyrazolo[1,5-a]pyrimidine-3-carboxamide (Compound I-O-12);

(1r,4r)-methyl 4-((3-(2-amino-6-fluoropyrazolo[1,5-a]pyrimidine-3-carboxamido)pyridin-4-yl)oxy)cyclohexanecarboxylate (Compound I-O-13);

2-amino-N-(4-ethoxypyridin-3-yl)-6-fluoropyrazolo[1,5-a]pyrimidine-3-carboxamide (Compound I-O-14);

(R,S)-2-amino-6-fluoro-N-(4-((tetrahydrofuran-3-yl)oxy)pyridin-3-yl)pyrazolo[1,5-a]pyrimidine-3-carboxamide (Compound I-O-15);

(S)-2-amino-N-(4-((6,7-dihydro-5H-pyrrolo[1,2-a]imidazol-6-yl)oxy)pyridin-3-yl)-6-fluoropyrazolo[1,5-a]pyrimidine-3-carboxamide (Compound I-O-16);

2-amino-N-(4-(((1s,4s)-4-(dimethylcarbamoyl)cyclohexyl)oxy)pyridin-3-yl)-6-fluoropyrazolo[1,5-a]pyrimidine-3-carboxamide (Compound I-O-17);

(1s,4s)-methyl 4-((3-(2-amino-6-fluoropyrazolo[1,5-a]pyrimidine-3-carboxamido)pyridin-4-yl)oxy)cyclohexanecarboxylate (Compound I-O-18);

2-amino-6-fluoro-N-(4-(((1s,4s)-4-(4-methylpiperazine-1-carbonyl)cyclohexyl)oxy)pyridin-3-yl)pyrazolo[1,5-a]pyrimidine-3-carboxamide (Compound I-O-19);

2-amino-6-(1-cyanopropyl)-N-(4-methoxypyridin-3-yl)pyrazolo[1,5-a]pyrimidine-3-carboxamide (Compound I-O-20);

2-amino-6-(1-cyanoethyl)-N-(4-methoxypyridin-3-yl)pyrazolo[1,5-a]pyrimidine-3-carboxamide (Compound I-O-21);

(R,S)-2-amino-6-(cyanomethyl)-N-(4-(quinuclidin-3-yloxy)pyridin-3-yl)pyrazolo[1,5-a]pyrimidine-3-carboxamide (Compound I-O-22);

2-amino-6-(cyanomethyl)-N-(4-((1-methylpiperidin-4-yl)oxy)pyridin-3-yl)pyrazolo[1,5-a]pyrimidine-3-carboxamide (Compound I-O-23);

2-amino-6-(cyanomethyl)-N-(4-(2-(dimethylamino)ethoxy)pyridin-3-yl)pyrazolo[1,5-a]pyrimidine-3-carboxamide (Compound I-O-24);

2-amino-6-(cyanomethyl)-N-(4-phenoxypyridin-3-yl)pyrazolo[1,5-a]pyrimidine-3-carboxamide (Compound I-O-25);

2-amino-6-(cyanomethyl)-N-(4-methoxypyridin-3-yl)pyrazolo[1,5-a]pyrimidine-3-carboxamide (Compound I-O-26);

2-amino-N-(6-chloro-4-methoxypyridin-3-yl)-6-(cyanomethyl)pyrazolo[1,5-a]pyrimidine-3-carboxamide (Compound I-O-27);

2-amino-6-(cyanomethyl)-N-(4-ethoxypyridin-3-yl)pyrazolo[1,5-a]pyrimidine-3-carboxamide (Compound I-O-28);

2-amino-6-(cyanomethyl)-N-(4-(2-methoxyethoxy)pyridin-3-yl)pyrazolo[1,5-a]pyrimidine-3-carboxamide (Compound I-O-29);

2-amino-6-(cyanomethyl)-N-(4-((tetrahydro-2H-pyran-4-yl)oxy)pyridin-3-yl)pyrazolo[1,5-a]pyrimidine-3-carboxamide (Compound I-O-30);

(R)-2-amino-6-(cyanomethyl)-N-(4-((tetrahydrofuran-3-yl)oxy)pyridin-3-yl)pyrazolo[1,5-a]pyrimidine-3-carboxamide (Compound I-O-31);

2-amino-6-(cyanomethyl)-N-(4-(cyclopropylmethoxy)pyridin-3-yl)pyrazolo[1,5-a]pyrimidine-3-carboxamide (Compound I-O-32);

2-amino-6-(cyanomethyl)-N-(4-(2-hydroxyethoxy)pyridin-3-yl)pyrazolo[1,5-a]pyrimidine-3-carboxamide (Compound I-O-33);

2-amino-6-(cyanomethyl)-N-(4-(2,2,2-trifluoroethoxy)pyridin-3-yl)pyrazolo[1,5-a]pyrimidine-3-carboxamide (Compound I-O-34);

2-amino-6-(cyanomethyl)-N-(4-isopropoxypyridin-3-yl)pyrazolo[1,5-a]pyrimidine-3-carboxamide (Compound I-O-35);

2-amino-6-(cyanomethyl)-N-(4-cyclobutoxypyridin-3-yl)pyrazolo[1,5-a]pyrimidine-3-carboxamide (Compound I-O-36);

(R,S)-2-amino-6-(cyanomethyl)-N-(4-((tetrahydrofuran-3-yl)oxy)pyridin-3-yl)pyrazolo[1,5-a]pyrimidine-3-carboxamide (Compound I-O-37);

2-amino-6-(cyanomethyl)-N-(4-(oxetan-3-yloxy)pyridin-3-yl)pyrazolo[1,5-a]pyrimidine-3-carboxamide (Compound I-O-38);

2-amino-6-(cyanomethyl)-N-(4-(cyclohexyloxy)pyridin-3-yl)pyrazolo[1,5-a]pyrimidine-3-carboxamide (Compound I-O-39);

2-amino-6-(cyanomethyl)-N-(4-(3-hydroxypropoxy)pyridin-3-yl)pyrazolo[1,5-a]pyrimidine-3-carboxamide (Compound I-O-40);

2-amino-6-(cyanomethyl)-N-(4-((tetrahydro-2H-pyran-3-yl)oxy)pyridin-3-yl)pyrazolo[1,5-a]pyrimidine-3-carboxamide (Compound I-O-41);

(S)-2-amino-6-(cyanomethyl)-N-(4-((tetrahydrofuran-3-yl)oxy)pyridin-3-yl)pyrazolo[1,5-a]pyrimidine-3-carboxamide (Compound I-O-42);

2-amino-6-(cyanomethyl)-N-(4-(cyclopentyloxy)pyridin-3-yl)pyrazolo[1,5-a]pyrimidine-3-carboxamide (Compound I-O-43);

2-amino-6-fluoro-N-(4-((1-oxidotetrahydro-2H-thiopyran-4-yl)oxy)pyridin-3-yl)pyrazolo[1,5-a]pyrimidine-3-carboxamide (Compound I-O-44);

2-amino-N-(4-((1,1-dioxidotetrahydro-2H-thiopyran-4-yl)oxy)pyridin-3-yl)-6-fluoropyrazolo[1,5-a]pyrimidine-3-carboxamide (Compound I-O-45);

2-amino-6-chloro-N-(5-chloro-4-((1-methylpiperidin-4-yl)oxy)pyridin-3-yl)pyrazolo[1,5-a]pyrimidine-3-carboxamide (Compound I-O-46);

2-amino-6-chloro-N-(4-(2-(2-(dimethylamino)ethoxy)ethoxy)pyridin-3-yl)pyrazolo[1,5-a]pyrimidine-3-carboxamide (Compound I-O-47);

2-amino-6-chloro-N-(4-(2-(dimethylamino)ethoxy)pyridin-3-yl)pyrazolo[1,5-a]pyrimidine-3-carboxamide (Compound I-O-48);

(R)-2-amino-6-chloro-N-(4-((1-methylpyrrolidin-2-yl)methoxy)pyridin-3-yl)pyrazolo[1,5-a]pyrimidine-3-carboxamide (Compound I-O-49);

(S)-2-amino-6-chloro-N-(4-((1-methylpyrrolidin-2-yl)methoxy)pyridin-3-yl)pyrazolo[1,5-a]pyrimidine-3-carboxamide (Compound I-O-50);

2-amino-6-chloro-N-(4-((1-methylpiperidin-3-yl)oxy)pyridin-3-yl)pyrazolo[1,5-a]pyrimidine-3-carboxamide (Compound I-O-51);

2-amino-6-chloro-N-(4-(3-(dimethylamino)propoxy)pyridin-3-yl)pyrazolo[1,5-a]pyrimidine-3-carboxamide (Compound I-O-52);

2-amino-6-chloro-N-(4-(3-hydroxypropoxy)pyridin-3-yl)pyrazolo[1,5-a]pyrimidine-3-carboxamide (Compound I-O-53);

(R)-2-amino-6-chloro-N-(4-((tetrahydrofuran-3-yl)oxy)pyridin-3-yl)pyrazolo[1,5-a]pyrimidine-3-carboxamide (Compound I-O-54);

2-amino-6-chloro-N-(4-(2-methoxyethoxy)pyridin-3-yl)pyrazolo[1,5-a]pyrimidine-3-carboxamide (Compound I-O-55);

2-amino-6-chloro-N-(4-ethoxypyridin-3-yl)pyrazolo[1,5-a]pyrimidine-3-carboxamide (Compound I-O-56);

2-amino-6-chloro-N-(4-methoxypyridin-3-yl)pyrazolo[1,5-a]pyrimidine-3-carboxamide (Compound I-O-57);

(S)-2-amino-6-chloro-N-(4-((tetrahydrofuran-3-yl)oxy)pyridin-3-yl)pyrazolo[1,5-a]pyrimidine-3-carboxamide (Compound I-O-58);

2-amino-6-chloro-N-(4-(2,2,2-trifluoroethoxy)pyridin-3-yl)pyrazolo[1,5-a]pyrimidine-3-carboxamide (Compound I-O-59);

2-amino-6-chloro-N-(4-(2-morpholinoethoxy)pyridin-3-yl)pyrazolo[1,5-a]pyrimidine-3-carboxamide (Compound I-O-60);

2-amino-6-chloro-N-(4-((tetrahydro-2H-pyran-4-yl)oxy)pyridin-3-yl)pyrazolo[1,5-a]pyrimidine-3-carboxamide (Compound I-O-61);

2-amino-6-chloro-N-(4-(quinuclidin-3-yloxy)pyridin-3-yl)pyrazolo[1,5-a]pyrimidine-3-carboxamide (Compound I-O-62);

(R)-2-amino-6-chloro-N-(4-((1-methylpyrrolidin-3-yl)oxy)pyridin-3-yl)pyrazolo[1,5-a]pyrimidine-3-carboxamide (Compound I-O-63);

2-amino-6-chloro-N-(4-((1-methylpiperidin-4-yl)oxy)pyridin-3-yl)pyrazolo[1,5-a]pyrimidine-3-carboxamide (Compound I-O-64);

2-amino-6-chloro-N-(4-((tetrahydro-2H-pyran-3-yl)oxy)pyridin-3-yl)pyrazolo[1,5-a]pyrimidine-3-carboxamide (Compound I-O-65);

2-amino-6-chloro-N-(4-(2-hydroxyethoxy)pyridin-3-yl)pyrazolo[1,5-a]pyrimidine-3-carboxamide (Compound I-O-66);

(S)-2-amino-6-chloro-N-(4-((1-(2-methoxyethy)piperidin-3-yl)oxy)pyridin-3-yl)pyrazolo[1,5-a]pyrimidine-3-carboxamide (Compound I-O-67);

2-amino-6-chloro-N-(6-chloro-4-(2-(dimethylamino)ethoxy)pyridin-3-yl)pyrazolo[1,5-a]pyrimidine-3-carboxamide (Compound I-O-68);

(S)-2-amino-6-chloro-N-(4-((1-methylpyrrolidin-3-yl)oxy)pyridin-3-yl)pyrazolo[1,5-a]pyrimidine-3-carboxamide (Compound I-O-69);

2-amino-6-chloro-N-(4-(pyridin-3-yloxy)pyridin-3-yl)pyrazolo[1,5-a]pyrimidine-3-carboxamide (Compound I-O-70);

2-amino-6-chloro-N-(4-(2-(dimethylamino)ethoxy)-6-(trifluoromethyl)pyridin-3-yl)pyrazolo[1,5-a]pyrimidine-3-carboxamide (Compound I-O-71);

2-amino-N-(4-(tert-butoxy)pyridin-3-yl)-6-fluoropyrazolo[1,5-a]pyrimidine-3-carboxamide (Compound I-O-88);

2-amino-6-fluoro-N-(5-fluoro-4-((1-methylpiperidin-4-yl)oxy)pyridin-3-yl)pyrazolo[1,5-a]pyrimidine-3-carboxamide (Compound I-O-89);

2-amino-6-fluoro-N-(5-fluoro-4-((1-(oxetan-3-yl)piperidin-4-yl)oxy)pyridin-3-yl)pyrazolo[1,5-a]pyrimidine-3-carboxamide (Compound I-O-91); and 2-amino-6-fluoro-N-(4-(oxetan-3-yloxy)pyridin-3-yl)pyrazolo[1,5-a]pyrimidine-3-carboxamide (Compound I-O-92).

The following compounds were prepared using a procedure similar to Example 2:

N-(4-(2-azaspiro[3.3]heptan-6-yloxy)pyridin-3-yl)-2-amino-6-chloropyrazolo[1,5-a]pyrimidine-3-carboxamide (Compound I-O-72);

2-amino-N-(4-(azetidin-3-yloxy)pyridin-3-yl)-6-chloropyrazolo[1,5-a]pyrimidine-3-carboxamide (Compound I-O-73);

(S)-2-amino-6-chloro-N-(4-(piperidin-3-yloxy)pyridin-3-yl)pyrazolo[1,5-a]pyrimidine-3-carboxamide (Compound I-O-74);

2-amino-6-chloro-N-(4-(piperidin-3-yloxy)pyridin-3-yl)pyrazolo[1,5-a]pyrimidine-3-carboxamide (Compound I-O-75);

(S)-2-amino-6-chloro-N-(4-(pyrrolidin-3-yloxy)pyridin-3-yl)pyrazolo[1,5-a]pyrimidine-3-carboxamide (Compound I-O-76);

(R)-2-amino-6-chloro-N-(4-(pyrrolidin-3-yloxy)pyridin-3-yl)pyrazolo[1,5-a]pyrimidine-3-carboxamide (Compound I-O-77);

N-(4-((4s,6r)-1-azaspiro[3.3]heptan-6-yloxy)pyridin-3-yl)-2-amino-6-chloropyrazolo[1,5-a]pyrimidine-3-carboxamide (Compound I-O-78);

N-(4-44r,6s)-1-azaspiro[3.3]heptan-6-yloxy)pyridin-3-yl)-2-amino-6-chloropyrazolo[1,5-a]pyrimidine-3-carboxamide (Compound I-O-79);

2-amino-6-chloro-N-(4-(piperidin-4-yloxy)pyridin-3-yl)pyrazolo[1,5-a]pyrimidine-3-carboxamide (Compound I-O-80);

(R)-2-amino-6-chloro-N-(4-(piperidin-3-yloxy)pyridin-3-yl)pyrazolo[1,5-a]pyrimidine-3-carboxamide (Compound I-O-81);

2-amino-N-(4-(azetidin-3-yloxy)pyridin-3-yl)-6-(cyanomethyl)pyrazolo[1,5-a]pyrimidine-3-carboxamide (Compound I-O-82);

2-amino-N-(4-(2-aminoethoxy)pyridin-3-yl)-6-(cyanomethyl)pyrazolo[1,5-a]pyrimidine-3-carboxamide (Compound I-O-83);

2-amino-6-(cyanomethyl)-N-(4-(piperidin-4-yloxy)pyridin-3-yl)pyrazolo[1,5-a]pyrimidine-3-carboxamide (Compound I-O-84);

(S)-2-amino-6-fluoro-N-(4-(piperidin-3-yloxy)pyridin-3-yl)pyrazolo[1,5-a]pyrimidine-3-carboxamide (Compound I-O-85);

(S)-2-amino-6-(cyanomethyl)-N-(4-(pyrrolidin-3-yloxy)pyridin-3-yl)pyrazolo[1,5-a]pyrimidine-3-carboxamide (Compound I-O-86);

(R)-2-amino-6-(cyanomethyl)-N-(4-(pyrrolidin-3-yloxy)pyridin-3-yl)pyrazolo[1,5-a]pyrimidine-3-carboxamide (Compound I-O-87); and 2-amino-6-fluoro-N-(4-methoxy-6-(methylamino)pyridin-3-yl)pyrazolo[1,5-a]pyrimidine-3-carboxamide (Compound I-O-90).

Compound Analytical Data

| Cmpd No. | LCMS ES+ | LCMS (Rt min) | HNMR |
|---|---|---|---|
| I-O-1 | 372.2 | 0.60 | $^1$H NMR (500 MHz, DMSO-d6) δ 10.4-10.6 (s, 1H), 10.05-10.15 (s, 1H), 9.64 (s, 1H), 9.54-9.56 (dd, 1H), 8.91 (s, 1H), 8.47-8.48 (d, 1H), 7.52 (s, 1H), 6.79 (s, 2H), 5.50-5.60 (m, 1H), 4.10-4.15 (s < 1H), 3.85-3.95 (s, 2H), 3.20-3.60 (m, 3H), 2.93 (s, 3H), 2.80-2.90 (s, 1H). |
| I-O-2 | 393.1 | 0.56 | $^1$H NMR (500 MHz, DMSO-d6) δ 10.05 (s, 1H), 9.55 (s, 1H), 9.06 (dt, J = 2.0, 0.7 Hz, 1H), 8.58 (d, J = 2.0 Hz, 1H), 8.17 (d, J = 5.5 Hz, 1H), 7.20 (d, J = 5.6 Hz, 1H), 6.75 (s, 2H), 4.63-4.53 (m, 1H), 4.15 (d, J = 0.7 Hz, 2H), 3.20-3.11 (m, 1H), 2.85-2.75 (m, 2H), 2.69-2.61 (m, 1H), 2.17-2.05 (m, 1H), 1.86-1.70 (m, 2H), 1.59-1.44 (m, 1H). |
| I-O-3 | 423.0 | 0.62 | $^1$H NMR (500 MHz, DMSO-d6) δ 10.20 (s, 1H), 9.71 (s, 1H), 9.50 (dd, J = 4.7, 2.5 Hz, 1H), 8.77 (dd, J = 2.9, 0.6 Hz, 1H), 8.73-8.66 (m, 1H), 8.39 (d, J = 5.8 Hz, 1H), 7.91 (dd, J = 8.5, 2.9 Hz, 1H), 7.69 (dd, J = 8.6, 0.7 Hz, 1H), 7.22 (d, J = 5.8 Hz, 1H), 6.77 (s, 2H), 4.50 (s, 2H), 2.84 (s, 6H). |
| I-O-4 | 303.1 | 0.60 | $^1$H NMR (500 MHz, DMSO-d6) δ 4.03 (2H, s), 6.71 (2H, s), 7.15-7.16 (1H, dd), 8.22-8.23 (1H, s), 8.87 (1H, d), 9.44 91H, s), 9.45-9.46 (1H, m), 9.96 (1H, s). |
| I-O-5 | 398.0 | 0.61 | $^1$H NMR (500 MHz, DMSO-d6) δ 10.13 (s, 1H), 9.97 (s, 1H), 9.68 (s, 1H), 9.55 (dd, J = 4.7, 2.5 Hz, 1H), 8.83-8.79 (m, 1H), 8.50 (d, J = 6.0 Hz, 1H), 7.54 (d, J = 6.0 Hz, 1H), 6.82 (s, 2H), 5.30 (d, J = 4.2 Hz, 1H), 3.98 (ddd, J = 14.0, 8.3, 2.2 Hz, 1H), 3.50-3.24 (m, 5H), 2.68-2.63 (m, 1H), 2.28 (s, 1H), 2.10-2.01 (m, 1H), 1.95 (d, J = 7.2 Hz, 2H). |
| I-O-6 | 398.2 | 0.64 | — |
| I-O-7 | 366.1 | 0.63 | $^1$H NMR (500 MHz, DMSO-d6) δ 6.80-6.90 (2H, s), 7.23-7.24 (1H, d), 7.62-7.65 (1H, dd), 7.87-7.89 (1H, m), 8.43-8.44 (1H, m), 8.61-8.63 (1H, m), 8.72-8.76 (1H, m), 9.50 (1H, d), 8.78 (1H, (1H, s), 10.48 (1H, s) |
| I-O-8 | 415.3 | 0.43 | $^1$H NMR (500 MHz, DMSO-d6) δ 12.20 (s, 1H), 10.34 (s, 1H), 9.62 (d, J = 0.9 Hz, 1H), 9.53 (dd, J = 4.8, 2.5 Hz, 1H), 8.92 (d, J = 2.5 Hz, 1H), 8.50 (d, J = 6.3 Hz, 1H), 7.74 (d, J = 6.3 Hz, 1H), 6.76 (s, 2H), 6.51 (s, 1H), 4.90 (s, 1H), 2.22 (dd, J = 12.4, 4.0 Hz, 2H), 2.15-2.01 (m, 2H), 1.81-1.53 (m, 4H). |
| I-O-9 | 428.3 | 0.63 | $^1$H NMR (500 MHz, DMSO-d6) δ 10.19 (s, 1H), 9.68 (s, 1H), 9.55 (dd, J = 4.8, 2.5 Hz, 1H), 8.82 (d, J = 2.4 Hz, 1H), 8.57 (d, J = 6.5 Hz, 1H), 7.77 (d, J = 6.8 Hz, 1H), 6.80 (s, 2H), 5.16 (s, 1H), 4.68-4.65 (m, 5H), 4.57 (s, 1H), 4.15 (s, 1H), 3.30 (s, 1H), 2.96 (s, 1H), 2.20 (s, 2H), 1.92 (s, 2H) |
| I-O-10 | 398.0 | 0.61 | $^1$H NMR (500 MHz, DMSO-d6) δ 9.90 (s, 1H), 9.54 (s, 1H), 9.48 (dd, J = 4.8, 2.5 Hz, 1H), 8.59 (d, J = 2.5 Hz, 1H), 8.16 (d, J = 5.5 Hz, 1H), 7.07 (d, J = 5.5 Hz, 1H), 6.76 (s, 2H), 4.72 (dt, J = 7.3, 3.1 Hz, 1H), 3.38 (ddd, J = 14.3, 7.9, 2.1 Hz, 1H), 2.92-2.82 (m, 1H), 2.82-2.64 (m, 3H), 2.22 (q, J = 3.2 Hz, 1H), 2.01 (ddt, J = 13.0, 9.8, 4.0 Hz, 1H), 1.75-1.66 (m, 1H), 1.66-1.55 (m, 1H), 1.51-1.42 (m, 1H). |
| I-O-11 | 428.2 | 0.59 | $^1$H NMR (500 MHz, DMSO-d6) δ 2.2-2.36 (4H, m), 3.25 masked signal, 4.39 (1H, m), 4.73-4.78 (4H, m), 5.18 (1H, m), 6.81 (2H, br s), 7.71 (1H, m), 8.55 (1H, m), 8.78 (1H, m), 9.56 (1H, m), 9.66 (1H, m) and 10.18 (1H, br s) ppm |
| I-O-12 | 386.1 | 0.59 | — |
| I-O-13 | 429.2 | 0.78 | $^1$H NMR (500 MHz, DMSO-d6) δ 1.40-1.76 (4H, m), 2.07 (2H, m), 2.21 (2H, m), 2.63 (1H, m), 3.65 (3H, s), 4.91 (1H, m), 6.76 (2H, br s), 7.73 (1H, m), 8.50 (1H, m), 8.92 (1H, s), 9.52 (1H, m), 9.62 (1H, m) and 10.34 (1H, s) ppm |
| I-O-14 | 317.1 | 0.60 | — |
| I-O-15 | 359.1 | 1.86* | — |
| I-O-16 | 395.0 | 0.55 | $^1$H NMR (500 MHz, DMSO-d6) δ 10.03 (s, 1H), 9.67 (s, 1H), 9.57-9.43 (m, 1H), 8.76 (d, J = 2.5 Hz, 1H), 8.52 (dd, J = 6.1, 2.5 Hz, 1H), 7.79 (d, J = 1.9 Hz, 1H), 7.69-7.59 (m, 2H), 6.77 (s, 2H), 6.09 (d, J = 5.7 Hz, 1H), 4.82 (dd, J = 13.3, 5.3 Hz, 1H), 4.62 (dd, J = 13.4, 1.1 Hz, 1H), 3.94 (dd, J = 18.2, 6.2 Hz, 1H), 3.53 (d, J = 18.2 Hz, 1H). |
| I-O-17 | 442.2 | 0.69 | $^1$H NMR (500 MHz, DMSO-d6) δ 1.67 (2H, m), 1.85-2.00 (4H, m), 2.12 (2H, m), 2.84 (4H, m), 3.09 (3H, s), 5.22 (1H, m), 6.80 (2H, br s), 7.75 (1H, m), 8.56 (1H, m), 9.11 (1H, m), 9.52 (1H, m), 9.69 (1H, s) and 10.09 (1H, s) ppm |
| I-O-18 | 429.2 | 0.76 | $^1$H NMR (500 MHz, DMSO-d6) δ 1.75-1.84 (4H, m), 1.91-2.03 (4H, m), 2.57 masked signal, 3.58 (3H, s), 4.92 (1H, s), 6.54 (1H, s), 6.78 (2H, br s), 7.26 (1H, m), 8.21 (1H, m), 8.68 (1H, m), 9.51 (2H, m) and 9.81 (1H, s) ppm |

-continued

| Cmpd No. | LCMS ES+ | LCMS (Rt min) | HNMR |
|---|---|---|---|
| I-O-19 | 497.3 | 0.66 | $^1$H NMR (500 MHz, DMSO-d6) δ 1.68 (2H, m), 1.85-1.98 (4H, m), 2.12 (2H, m), 2.84 (3H, s), 2.91 (1H, m), 4.42 masked signal, 5.24 (1H, m), 6.81 (2H, br s), 7.72 (1H, m), 8.57 (1H, m), 9.03 (1H, m), 9.53 (1H, m), 9.70 (1H, s) and 10.05 (1H, s) ppm |
| I-O-20 | 352.1 | 0.69 | $^1$H NMR (500 MHz, Methanol-d4) δ 1.2 (3H, t), 1.2-2.0 (2H, m), 3.8 (1H, t), 4.45 (3H, s), 7.7 (1H, d), 8.4-8.6 (3H, m), 8.7 (1H, s), 8.9 (1H, s), 9.7 (1H, s), |
| I-O-21 | 338.1 | 1.97* | $^1$H NMR (500 MHz, DMSO-d6) δ 1.7 (3H, d), 4.3 (3H, s), 4.55 (1H, q), 6.68-6.8 (2H, m), 7.2 (0.5H, d), 7.5 (0.5H, d), 7.7 (1H, d), 8.15 (1H, d), 8.8 (1H, s), 9.2 (1H, s), 9.7 (1H, s), 10.5 (1H, s). |
| I-O-22 | 419.0 | 0.63 | $^1$H NMR (500 MHz, DMSO-d6) δ 10.27 (s, 1H), 10.07 (d, J = 2.7 Hz, 1H), 9.70 (s, 1H), 9.13 (dd, J = 1.6, 0.9 Hz, 1H), 8.61 (d, J = 1.9 Hz, 1H), 8.54 (d, J = 6.4 Hz, 1H), 7.56 (d, J = 6.6 Hz, 1H), 6.81 (s, 2H), 5.33 (d, J = 5.4 Hz, 1H), 4.13 (s, 2H), 4.03-3.93 (m, 1H), 3.48 (d, J = 13.8 Hz, 1H), 3.39 (m, 3H), 3.31-3.22 (m, 1H), 2.65 (m, 1H), 2.44 (m, 1H), 2.14-1.90 (m, 3H). |
| I-O-23 | 407.2 | 0.58 | $^1$H NMR (500 MHz, DMSO-d6) δ 10.05 (s, 1H), 9.55 (s, 1H), 9.06 (dt, J = 1.9, 0.8 Hz, 1H), 8.59 (d, J = 2.0 Hz, 1H), 8.17 (d, J = 5.5 Hz, 1H), 7.22 (d, J = 5.6 Hz, 1H), 6.74 (s, 2H), 4.68 (dq, J = 8.5, 4.6, 4.2 Hz, 1H), 4.20-4.10 (m, 2H), 2.81-2.66 (m, 2H), 2.35-2.24 (m, 2H), 2.21 (s, 3H), 2.12-2.00 (m, 2H), 1.89-1.76 (m, 2H). |
| I-O-24 | 381.1 | 0.57 | $^1$H NMR (500 MHz, DMSO-d6) δ 10.07 (s, 1H), 9.60 (s, 1H), 9.12 (d, J = 2.0 Hz, 1H), 8.75 (d, J = 2.0 Hz, 1H), 8.53 (d, J = 6.1 Hz, 1H), 7.58 (d, J = 5.7 Hz, 1H), 6.79 (s, 2H), 4.80 (d, J = 4.6 Hz, 2H), 4.14 (s, 2H), 3.77-3.70 (m, 2H), 2.94 (s, 6H). |
| I-O-25 | 386.1 | 0.74 | $^1$H NMR (500 MHz, DMSO-d6) δ 10.56 (s, 1H), 9.76 (d, J = 0.8 Hz, 1H), 9.08 (dd, J = 1.9, 0.8 Hz, 1H), 8.53 (d, J = 2.0 Hz, 1H), 8.42 (dd, J = 6.3, 0.8 Hz, 1H), 7.67-7.54 (m, 2H), 7.49-7.37 (m, 3H), 7.12 (d, J = 6.3 Hz, 1H), 6.79 (s, 2H), 4.07 (s, 2H). |
| I-O-26 | 324.1 | 0.56 | $^1$H NMR (500 MHz, DMSO-d6) δ 10.40 (s, 1H), 9.62 (s, 1H), 9.09 (d, J = 2.0 Hz, 1H), 8.74 (d, J = 2.0 Hz, 1H), 8.59 (d, J = 6.7 Hz, 1H), 7.67 (d, J = 6.5 Hz, 1H), 6.76 (s, 2H), 4.27 (s, 3H), 4.14 (s, 2H). |
| I-O-27 | 358.0 | 0.68 | $^1$H NMR (500 MHz, DMSO-d6) δ 10.06 (s, 1H), 9.27 (s, 1H), 9.05 (d, J = 2.0 Hz, 1H), 8.68 (d, J = 2.0 Hz, 1H), 7.29 (s, 1H), 6.71 (s, 2H), 4.12 (s, 2H), 4.08 (s, 3H). |
| I-O-28 | 338.1 | 0.62 | $^1$H NMR (500 MHz, DMSO-d6) δ 10.51 (s, 1H), 9.63 (s, 1H), 9.11 (d, J = 2.0 Hz, 1H), 8.65 (d, J = 2.0 Hz, 1H), 8.57 (d, J = 6.4 Hz, 1H), 7.64 (d, J = 6.5 Hz, 1H), 6.77 (s, 2H), 4.51 (q, J = 7.0 Hz, 2H), 4.14 (s, 2H), 1.63 (t, J = 7.0 Hz, 3H). |
| I-O-29 | 368.2 | 0.57 | $^1$H NMR (500 MHz, DMSO-d6) δ 10.47 (s, 1H), 9.64 (d, J = 1.0 Hz, 1H), 9.10 (dt, J = 1.5, 0.7 Hz, 1H), 8.65 (d, J = 2.0 Hz, 1H), 8.57 (dd, J = 6.4, 1.0 Hz, 1H), 7.68 (d, J = 6.4 Hz, 1H), 6.77 (s, 2H), 4.72-4.53 (m, 2H), 4.22-4.11 (m, 2H), 4.02-3.86 (m, 2H), 3.42 (s, 3H). |
| I-O-30 | 394.2 | 0.60 | $^1$H NMR (500 MHz, DMSO-d6) δ 10.37 (s, 1H), 9.68 (d, J = 1.0 Hz, 1H), 9.11 (dt, J = 1.6, 0.7 Hz, 1H), 8.63 (d, J = 2.0 Hz, 1H), 8.58 (dd, J = 6.6, 1.1 Hz, 1H), 7.83 (d, J = 6.7 Hz, 1H), 6.78 (s, 2H), 5.23 (tt, J = 7.9, 3.9 Hz, 1H), 4.15 (s, 2H), 4.02 (ddd, J = 11.4, 5.9, 3.9 Hz, 2H), 3.66 (ddd, J = 11.5, 8.3, 3.1 Hz, 2H), 2.23-2.10 (m, 2H), 1.88 (dtd, J = 12.2, 8.1, 3.8 Hz, 2H). |
| I-O-31 | 380.1 | 0.57 | $^1$H NMR (500 MHz, DMSO-d6) δ 10.42 (s, 1H), 9.63 (d, J = 1.0 Hz, 1H), 9.08 (dt, J = 1.6, 0.8 Hz, 1H), 8.60-8.53 (m, 2H), 7.68 (d, J = 6.5 Hz, 1H), 6.75 (s, 2H), 5.56 (ddd, J = 5.7, 3.7, 1.8 Hz, 1H), 4.16 (d, J = 0.8 Hz, 2H), 4.13-3.98 (m, 3H), 3.93 (td, J = 8.4, 4.3 Hz, 1H), 2.50-2.40 (m, 1H), 2.29-2.18 (m, 1H). |
| I-O-32 | 364.1 | 0.69 | $^1$H NMR (500 MHz, DMSO-d6) δ 10.52 (s, 1H), 9.65 (d, J = 1.0 Hz, 1H), 9.11 (dd, J = 1.9, 0.8 Hz, 1H), 8.65 (d, J = 2.0 Hz, 1H), 8.59-8.48 (m, 1H), 7.60 (d, J = 6.5 Hz, 1H), 6.77 (s, 2H), 4.34 (d, J = 7.2 Hz, 2H), 4.14 (s, 2H), 1.50 (pt, J = 7.5, 4.7 Hz, 1H), 0.86-0.74 (m, 2H), 0.58-0.46 (m, 2H). |
| I-O-33 | 354.1 | 0.49 | $^1$H NMR (500 MHz, DMSO-d6) δ 10.58 (s, 1H), 9.63 (d, J = 0.9 Hz, 1H), 9.10 (dd, J = 1.9, 0.8 Hz, 1H), 8.68 (d, J = 2.0 Hz, 1H), 8.55 (d, J = 6.4 Hz, 1H), 7.67 (d, J = 6.4 Hz, |

Compound Analytical Data

| Cmpd No. | LCMS ES+ | LCMS (Rt min) | HNMR |
|---|---|---|---|
| | | | 1H), 6.76 (s, 2H), 5.07 (s, 1H), 4.50 (t, J = 4.8 Hz, 2H), 4.15 (s, 2H), 4.00 (t, J = 4.7 Hz, 2H). |
| I-O-34 | 392.1 | 0.65 | $^1$H NMR (500 MHz, DMSO-d6) δ 10.41 (s, 1H), 9.72 (d, J = 0.7 Hz, 1H), 9.09 (dt, J = 2.0, 0.7 Hz, 1H), 8.58 (dd, J = 6.2, 0.8 Hz, 1H), 8.50 (d, J = 2.0 Hz, 1H), 7.65 (d, J = 6.3 Hz, 1H), 6.77 (s, 2H), 5.27 (q, J = 8.4 Hz, 2H), 4.22-4.14 (m, 2H). |
| I-O-35 | 352.2 | 0.67 | $^1$H NMR (500 MHz, DMSO-d6) δ 10.69-10.33 (m, 1H), 9.64 (d, J = 5.6 Hz, 1H), 9.23-9.02 (m, 1H), 8.80-8.64 (m, 1H), 8.55 (t, J = 6.5 Hz, 1H), 7.72 (t, J = 5.7 Hz, 1H), 6.76 (s, 2H), 5.19 (hept, J = 6.6 Hz, 1H), 4.29-4.03 (m, 2H), 1.67-1.44 (m, 6H). |
| I-O-36 | 364.1 | 0.71 | $^1$H NMR (500 MHz, DMSO-d6) δ 10.48 (s, 1H), 9.63 (d, J = 0.9 Hz, 1H), 9.11 (dt, J = 1.6, 0.7 Hz, 1H), 8.69 (d, J = 2.0 Hz, 1H), 8.51 (dd, J = 6.4, 1.0 Hz, 1H), 7.46 (d, J = 6.4 Hz, 1H), 6.77 (s, 2H), 5.29-5.13 (m, 1H), 4.14 (s, 2H), 2.73-2.59 (m, 2H), 2.40-2.27 (m, 2H), 2.03-1.91 (m, 1H), 1.80 (dtt, J = 10.9, 9.8, 8.3 Hz, 1H). |
| I-O-37 | 380.2 | 0.57 | $^1$H NMR (500 MHz, DMSO-d6) δ 10.44 (s, 1H), 9.64 (d, J = 0.9 Hz, 1H), 9.10 (dd, J = 1.9, 0.8 Hz, 1H), 8.60 (d, J = 2.0 Hz, 1H), 8.58-8.52 (m, 1H), 7.66 (d, J = 6.4 Hz, 1H), 6.77 (s, 2H), 5.57 (ddd, J = 5.6, 3.5, 1.7 Hz, 1H), 4.16 (d, J = 0.9 Hz, 2H), 4.13-4.00 (m, 3H), 3.93 (td, J = 8.4, 4.3 Hz, 1H), 2.49-2.40 (m, 1H), 2.32-2.19 (m, 1H). |
| I-O-38 | 366.0 | 0.54 | $^1$H NMR (500 MHz, DMSO-d6) δ 10.49 (s, 1H), 9.67 (d, J = 0.8 Hz, 1H), 9.11 (dt, J = 1.9, 0.7 Hz, 1H), 8.74 (d, J = 2.0 Hz, 1H), 8.51 (dd, J = 6.3, 0.9 Hz, 1H), 7.32 (d, J = 6.3 Hz, 1H), 6.77 (s, 2H), 5.75 (tt, J = 5.8, 4.4 Hz, 1H), 5.14 (ddd, J = 7.8, 5.9, 1.1 Hz, 2H), 4.80 (ddd, J = 7.8, 4.4, 1.0 Hz, 2H), 4.16-4.11 (m, 2H). |
| I-O-39 | 392.2 | 0.79 | $^1$H NMR (500 MHz, DMSO-d6) δ 10.36 (s, 1H), 9.67 (d, J = 1.0 Hz, 1H), 9.12 (dt, J = 2.0, 0.7 Hz, 1H), 8.61 (d, J = 2.0 Hz, 1H), 8.55 (dd, J = 6.6, 1.1 Hz, 1H), 7.77 (d, J = 6.6 Hz, 1H), 6.78 (s, 2H), 5.03 (tt, J = 8.0, 3.6 Hz, 1H), 4.20-4.12 (m, 2H), 2.15-2.01 (m, 2H), 1.96-1.83 (m, 2H), 1.83-1.69 (m, 2H), 1.66-1.38 (m, 4H). |
| I-O-40 | 368.1 | 0.52 | $^1$H NMR (500 MHz, DMSO-d6) δ 10.38 (s, 1H), 9.64 (d, J = 1.0 Hz, 1H), 9.09 (dd, J = 1.9, 0.9 Hz, 1H), 8.69-8.47 (m, 2H), 7.68 (d, J = 6.5 Hz, 1H), 6.77 (s, 2H), 4.52 (t, J = 5.8 Hz, 2H), 4.15 (d, J = 0.8 Hz, 2H), 3.81 (q, J = 7.0, 6.5 Hz, 2H), 2.14 (p, J = 6.0 Hz, 2H). |
| I-O-41 | 394.1 | 0.62 | $^1$H NMR (500 MHz, DMSO-d6) δ 10.46 (s, 1H), 9.69 (d, J = 1.0 Hz, 1H), 9.10 (dt, J = 1.6, 0.7 Hz, 1H), 8.64 (d, J = 2.0 Hz, 1H), 8.55 (dd, J = 6.5, 1.1 Hz, 1H), 7.76 (d, J = 6.6 Hz, 1H), 6.78 (s, 2H), 5.03 (h, J = 3.7, 3.2 Hz, 1H), 4.16 (d, J = 0.7 Hz, 2H), 3.97-3.85 (m, 2H), 3.83-3.74 (m, 1H), 3.69 (ddd, J = 11.3, 8.1, 3.1 Hz, 1H), 2.16 (tt, J = 9.2, 4.7 Hz, 1H), 2.11-1.92 (m, 2H), 1.73-1.59 (m, 1H). |
| I-O-42 | 380.1 | 0.57 | $^1$H NMR (500 MHz, DMSO-d6) δ 10.43 (s, 1H), 9.63 (d, J = 0.9 Hz, 1H), 9.09 (dd, J = 2.0, 0.8 Hz, 1H), 8.59-8.55 (m, 2H), 7.68 (d, J = 6.5 Hz, 1H), 6.75 (s, 2H), 5.57 (ddd, J = 5.9, 3.8, 1.7 Hz, 1H), 4.16 (d, J = 0.9 Hz, 2H), 4.13-3.99 (m, 3H), 3.93 (td, J = 8.4, 4.3 Hz, 1H), 2.50-2.41 (m, 1H), 2.27-2.21 (m, 1H). |
| I-O-43 | 378.1 | 0.74 | $^1$H NMR (500 MHz, DMSO-d6) δ 10.37 (s, 1H), 9.64 (d, J = 1.0 Hz, 1H), 9.11 (dt, J = 1.9, 0.7 Hz, 1H), 8.63-8.49 (m, 2H), 7.68 (d, J = 6.6 Hz, 1H), 6.78 (s, 2H), 5.39 (dq, J = 5.8, 3.7, 2.9 Hz, 1H), 4.20-4.12 (m, 2H), 2.20-2.07 (m, 2H), 2.07-1.95 (m, 2H), 1.96-1.84 (m, 2H), 1.83-1.66 (m, 2H). |
| I-O-44 | 405.0 | 0.5 | $^1$H NMR (500 MHz, DMSO-d6) δ 9.95 (s, 1H), 9.69 (d, J = 1.0 Hz, 1H), 9.54 (dd, J = 4.7, 2.5 Hz, 1H), 8.77-8.69 (m, 1H), 8.58 (dd, J = 6.5, 1.1 Hz, 1H), 7.77 (d, J = 6.6 Hz, 1H), 6.82 (s, 2H), 5.34-5.26 (m, 1H), 3.10 (td, J = 13.7, 12.2, 3.0 Hz, 2H), 3.01-2.90 (m, 2H), 2.55 (m, 2H), 2.14 (dd, J = 15.1, 4.3 Hz, 2H). |
| I-O-45 | 421.0 | 0.56 | $^1$H NMR (500 MHz, DMSO-d6) δ 9.93 (s, 1H), 9.68 (d, J = 0.9 Hz, 1H), 9.55 (dd, J = 4.7, 2.5 Hz, 1H), 8.83 (dd, J = 2.5, 0.7 Hz, 1H), 8.58 (dd, J = 6.5, 1.0 Hz, 1H), 7.76 (d, J = 6.6 Hz, 1H), 6.82 (s, 2H), 5.34-5.27 (m, 1H), 3.50 (ddd, J = 14.4, 10.8, 3.7 Hz, 2H), 3.39-3.32 (m, 2H), 2.50-2.34 (m, 4H). |

Compound Analytical Data

| Cmpd No. | LCMS ES+ | LCMS (Rt min) | HNMR |
|---|---|---|---|
| I-O-46 | 436.1 | 0.8 | $^1$H NMR (500 MHz, Methanol-d4) δ 2.10 (6H, m), 2.27 (3H, s), 2.90 (2H, m), 4.75 (1H, m), 8.28 (1H, s), 8.75 (1H, d), 9.02 (1H, m) and 9.61 (1H, s) ppm |
| I-O-47 | 420.1 | 0.65 | $^1$H NMR (500 MHz, DMSO-d6) δ 10.03 (s, 1H), 9.48 (s, 1H), 9.43 (d, J = 2.2 Hz, 1H), 8.67 (d, J = 2.2 Hz, 1H), 8.20 (d, J = 5.5 Hz, 1H), 7.17 (d, J = 5.5 Hz, 1H), 6.77 (s, 2H), 4.37-4.31 (m, 2H), 3.95-3.89 (m, 2H), 3.60 (t, J = 6.0 Hz, 2H), 2.36 (t, J = 6.0 Hz, 2H), 2.07 (s, 6H). |
| I-O-48 | 376.1 | 0.66 | $^1$H NMR (500 MHz, DMSO-d6) δ 9.93 (s, 1H), 9.48 (s, 1H), 9.42 (d, J = 2.3 Hz, 1H), 8.62-8.56 (m, 1H), 8.20 (d, J = 5.6 Hz, 1H), 7.19 (d, J = 5.6 Hz, 1H), 6.78 (s, 2H), 4.30 (t, J = 5.6 Hz, 2H), 2.84 (t, J = 5.6 Hz, 2H), 2.26 (s, 6H). |
| I-O-49 | 402.1 | 0.73 | $^1$H NMR (500 MHz, DMSO-d6) δ 1.72 (3H, m), 2.09 (1H, m), 2.28 (1H, m), 2.39 (3H, s), 2.79 (1H, m), 2.97 (1H, m), 4.00 (1H, m), 4.25 (1H, m), 6.79 (2H, br s), 7.18 (1H, m), 8.19 (1H, m), 8.54 (1H, m), 9.42 (1H, d), 9.47 (1H, s) and 9.81 (1H, s) ppm |
| I-O-50 | 402.2 | 0.76 | $^1$H NMR (500 MHz, DMSO-d6) δ 1.72 (3H, m), 2.11 (1H, m), 2.27 (1H, m), 2.39 (3H, s), 2.78 (1H, m), 2.97 (1H, m), 4.00 (1H, m), 4.25 (1H, m), 6.79 (2H, br s), 7.19 (1H, m), 8.20 (1H, m), 8.54 (1H, m), 9.42 (1H, m), 9.47 (1H, s) and 9.81 (1H, s) ppm |
| I-O-51 | 402.1 | 0.74 | $^1$H NMR (500 MHz, DMSO-d6) δ 9.98 (s, 1H), 9.53 (s, 1H), 9.43 (d, J = 2.2 Hz, 1H), 8.55 (d, J = 2.2 Hz, 1H), 8.18 (d, J = 5.5 Hz, 1H), 7.23 (d, J = 5.6 Hz, 1H), 6.78 (s, 2H), 4.69 (s, 1H), 2.92 (s, 1H), 2.59-2.47 (m, 1H), 2.35-2.12 (m, 2H), 2.33 (s, 3H), 2.07 (d, J = 5.5 Hz, 1H), 1.91 (s, 1H), 1.73-1.51 (m, 2H). |
| I-O-52 | 390.1 | 0.68 | $^1$H NMR (500 MHz, DMSO-d6) δ 10.06 (s, 1H), 9.51 (s, 1H), 9.43 (d, J = 2.2 Hz, 1H), 8.66 (d, J = 2.2 Hz, 1H), 8.19 (d, J = 5.4 Hz, 1H), 7.13 (d, J = 5.5 Hz, 1H), 6.78 (s, 2H), 4.22 (t, J = 5.9 Hz, 2H), 2.16 (s, 6H), 2.06 (p, J = 6.6 Hz, 2H). |
| I-O-53 | 365.1 | 0.59 | $^1$H NMR (500 MHz, DMSO-d6) δ 10.24 (s, 1H), 9.61 (s, 1H), 9.47 (d, J = 2.2 Hz, 1H), 8.63 (d, J = 2.2 Hz, 1H), 8.52 (d, J = 6.4 Hz, 1H), 7.60 (d, J = 6.4 Hz, 1H), 6.81 (s, 2H), 4.47 (t, J = 5.9 Hz, 2H), 3.77 (s, 2H), 2.12 (p, J = 6.2 Hz, 2H). |
| I-O-54 | 375.0 | 0.66 | $^1$H NMR (500 MHz, Methanol-d4) δ 10.29 (s, 1H), 9.61 (s, 1H), 8.88 (d, J = 2.2 Hz, 1H), 8.38 (d, J = 2.2 Hz, 1H), 8.36 (d, J = 6.5 Hz, 1H), 7.56 (d, J = 6.6 Hz, 1H), 5.47 (t, J = 4.9 Hz, 1H), 4.20 (dt, J = 11.0, 1.0 Hz, 1H), 4.08-4.00 (m, 2H), 3.93 (td, J = 8.5, 4.2 Hz, 1H), 2.47-2.36 (m, 1H), 2.27-2.18 (m, 1H). |
| I-O-55 | 363.0 | 0.67 | $^1$H NMR (500 MHz, Methanol-d4) δ 10.44 (s, 1H), 9.70 (d, J = 1.2 Hz, 1H), 8.95 (d, J = 2.2 Hz, 1H), 8.49 (d, J = 2.2 Hz, 1H), 8.36 (dd, J = 6.7, 1.2 Hz, 1H), 7.59 (d, J = 6.7 Hz, 1H), 4.60-4.55 (m, 2H), 3.96-3.90 (m, 2H), 3.39 (s, 3H). |
| I-O-56 | 333.0 | 0.74 | $^1$H NMR (500 MHz, DMSO-d6) δ 10.06 (s, 1H), 9.49 (s, 1H), 9.42 (d, J = 2.2 Hz, 1H), 8.60 (d, J = 2.2 Hz, 1H), 8.19 (d, J = 5.4 Hz, 1H), 7.13 (d, J = 5.5 Hz, 1H), 6.77 (s, 2H), 4.25 (q, J = 6.9 Hz, 2H), 1.54 (t, J = 7.0 Hz, 3H). |
| I-O-57 | 319.1 | 0.67 | $^1$H NMR (500 MHz, DMSO-d6) δ 4.28 (3H, s), 6.81 (2H, br s), 7.68 (1H, d), 8.60 (1H, d), 8.81 (1H, d), 9.47 (1H, d), 9.61 (1H, s) and 10.34 (1H, s) ppm |
| I-O-58 | 375.0 | 0.66 | $^1$H NMR (500 MHz, Methanol-d4) δ 10.31 (s, 1H), 9.62 (s, 1H), 8.89 (d, J = 2.2 Hz, 1H), 8.39 (d, J = 2.2 Hz, 1H), 8.36 (d, J = 6.6 Hz, 1H), 7.57 (d, J = 6.6 Hz, 1H), 5.51-5.45 (m, 1H), 4.20 (d, J = 10.9 Hz, 1H), 4.08-4.00 (m, 2H), 3.93 (td, J = 8.5, 4.2 Hz, 1H), 2.47-2.36 (m, 1H), 2.29-2.18 (m, 1H). |
| I-O-59 | 387.0 | 0.78 | $^1$H NMR (500 MHz, Methanol-d4) δ 10.41 (s, 1H), 9.79 (d, J = 1.1 Hz, 1H), 8.94 (dd, J = 2.1, 0.4 Hz, 1H), 8.42 (dd, J = 6.6, 1.1 Hz, 1H), 8.32 (d, J = 2.2 Hz, 1H), 7.61 (d, J = 6.6 Hz, 1H), 5.10-5.01 (m, 2H) |
| I-O-60 | 418.1 | 0.63 | $^1$H NMR (500 MHz, DMSO-d6) δ 9.91 (s, 1H), 9.47 (s, 1H), 9.43 (d, J = 2.2 Hz, 1H), 8.60 (d, J = 2.2 Hz, 1H), 8.20 (d, J = 5.5 Hz, 1H), 7.20 (d, J = 5.5 Hz, 1H), 6.78 (s, 2H), 4.35 (t, J = 5.9 Hz, 2H), 3.53 (t, J = 4.6 Hz, 4H), 2.90 (t, J = 5.8 Hz, 2H), 2.52-2.50 (masked signal, 4H). |
| I-O-61 | 389.0 | 0.68 | $^1$H NMR (500 MHz, Methanol-d4) δ 10.28 (s, 1H), 9.75 (d, J = 1.2 Hz, 1H), 8.97 (d, J = 2.2 Hz, 1H), 8.48 (d, J = 2.2 Hz, 1H), 8.35 (dd, J = 6.7, 1.3 Hz, 1H), 7.66 (d, J = 6.8 Hz, 1H), 5.15 (dt, J = 7.9, 4.0 Hz, 1H), 4.05 (ddd, J = 10.8, 6.1, |

Compound Analytical Data

| Cmpd No. | LCMS ES+ | LCMS (Rt min) | HNMR |
|---|---|---|---|
| | | | 3.9 Hz, 2H), 3.66 (ddd, J = 11.6, 8.2, 3.3 Hz, 2H), 2.22-2.14 (m, 2H), 1.92 (ddt, J = 13.2, 8.5, 4.0 Hz, 2H). |
| I-O-62 | 414.0 | 0.69 | $^1$H NMR (500 MHz, DMSO-d6) δ 9.86 (s, 1H), 9.53 (s, 1H), 9.41 (d, J = 2.2 Hz, 1H), 8.40 (d, J = 2.2 Hz, 1H), 8.16 (d, J = 5.5 Hz, 1H), 7.06 (d, J = 5.5 Hz, 1H), 6.80 (s, 2H), 4.75-4.66 (m, 1H), 3.38 (d, J = 4.0 Hz, 0H), 2.92-2.82 (m, 1H), 2.82-2.64 (m, 4H), 2.21 (dd, J = 4.9, 1.8 Hz, 1H), 1.97 (ddd, J = 14.8, 11.1, 3.5 Hz, 1H), 1.76-1.66 (m, 1H), 1.66-1.55 (m, 1H), 1.48-1.39 (m, 1H). |
| I-O-63 | 388.0 | 0.69 | $^1$H NMR (500 MHz, DMSO-d6) δ 10.00 (s, 1H), 9.51 (s, 1H), 9.42 (d, J = 2.2 Hz, 1H), 8.51 (d, J = 2.2 Hz, 1H), 8.17 (d, J = 5.5 Hz, 1H), 7.06 (d, J = 5.5 Hz, 1H), 6.78 (s, 2H), 5.11-5.07 (m, 1H), 2.93 (dd, J = 10.7, 6.0 Hz, 1H), 2.79-2.76 (m, 2H), 2.45-2.40 (m, 2H), 2.32 (s, 3H), 2.02-1.96 (m, 1H). |
| I-O-64 | 402.0 | 0.66 | $^1$H NMR (500 MHz, DMSO-d6) δ 9.93 (s, 1H), 9.52 (s, 1H), 9.43 (d, J = 2.2 Hz, 1H), 8.56 (d, J = 2.2 Hz, 1H), 8.17 (d, J = 5.5 Hz, 1H), 7.21 (d, J = 5.6 Hz, 1H), 6.79 (s, 2H), 4.66 (dq, J = 8.3, 4.1 Hz, 1H), 2.71 (q, J = 5.5 Hz, 2H), 2.26 (t, J = 10.3 Hz, 2H), 2.20 (s, 3H), 2.12-2.01 (m, 2H), 1.82 (dtd, J = 12.6, 8.8, 3.6 Hz, 2H). |
| I-O-65 | 389.0 | 0.73 | $^1$H NMR (500 MHz, Methanol-d4) δ 10.47 (s, 1H), 9.74 (d, J = 1.2 Hz, 1H), 8.91 (d, J = 2.2 Hz, 1H), 8.47 (d, J = 2.2 Hz, 1H), 8.37-8.32 (m, 1H), 7.59 (dd, J = 6.8, 2.1 Hz, 1H), 4.95-4.88 (m, 1H), 4.00 (dd, J = 12.6, 3.8 Hz, 1H), 3.89 (dd, J = 12.5, 2.3 Hz, 1H), 3.82 (dt, J = 11.1, 4.0 Hz, 1H), 3.64 (ddd, J = 11.3, 9.4, 2.8 Hz, 1H), 2.10 (dt, J = 9.1, 4.3 Hz, 2H), 2.06-1.99 (m, 1H), 1.59 (dddd, J = 12.8, 7.6, 4.6, 2.7 Hz, 1H). |
| I-O-66 | 349.0 | 0.56 | $^1$H NMR (500 MHz, DMSO-d6) δ 10.18 (s, 1H), 9.50 (s, 1H), 9.42 (d, J = 2.2 Hz, 1H), 8.62 (d, J = 2.2 Hz, 1H), 8.19 (d, J = 5.5 Hz, 1H), 7.16 (d, J = 5.5 Hz, 1H), 6.76 (s, 2H), 4.92 (t, J = 5.1 Hz, 1H), 4.24 (t, J = 4.8 Hz, 2H), 3.94 (q, J = 4.9 Hz, 2H). |
| I-O-67 | 446.2 | 0.74 | $^1$H NMR (500 MHz, DMSO-d6) δ 10.00 (s, 1H), 9.53 (s, 1H), 9.43 (s, 1H), 8.56 (s, 1H), 8.17 (d, J = 5.5 Hz, 1H), 7.22 (d, J = 5.6 Hz, 1H), 6.78 (s, 2H), 4.71-4.56 (m, 1H), 3.44 (dd, J = 6.5, 4.8 Hz, 1H), 3.21 (s, 3H), 3.11 (dd, J = 12.8, 2.5 Hz, 1H), 2.76-2.46 (m, 4H), 2.37 (d, J = 5.6 Hz, 1H), 2.30-2.20 (m, 1H), 2.13 (d, J = 11.0 Hz, 1H), 1.86 (d, J = 8.5 Hz, 1H), 1.71-1.57 (m, 1H), 1.57-1.45 (m, 1H). |
| I-O-68 | 410.0 | 0.76 | $^1$H NMR (500 MHz, DMSO-d6) δ 9.80 (s, 1H), 9.71 (s, 1H), 9.46 (d, J = 2.2 Hz, 1H), 9.30 (s, 1H), 8.76 (d, J = 2.2 Hz, 1H), 7.40 (s, 1H), 6.81 (s, 1H), 4.74-4.61 (m, 2H), 3.69 (s, 2H), 2.92 (s, 6H). |
| I-O-69 | 388.0 | 0.69 | $^1$H NMR (500 MHz, DMSO-d6) δ 10.00 (s, 1H), 9.51 (s, 1H), 9.42 (d, J = 2.2 Hz, 1H), 8.51 (d, J = 2.2 Hz, 1H), 8.17 (d, J = 5.5 Hz, 1H), 7.06 (d, J = 5.5 Hz, 1H), 6.78 (s, 2H), 5.11-5.07 (m, 1H), 2.93 (dd, J = 10.7, 6.0 Hz, 1H), 2.79-2.76 (m, 2H), 2.45-2.40 (m, 2H), 2.32 (s, 3H), 2.02-1.96 (m, 1H). |
| I-O-70 | 382.0 | 0.67 | $^1$H NMR (500 MHz, DMSO-d6) δ 10.29 (s, 1H), 9.73 (s, 1H), 9.44 (d, J = 2.2 Hz, 1H), 8.71 (dd, J = 2.9, 0.6 Hz, 1H), 8.66-8.55 (m, 2H), 8.41 (d, J = 6.0 Hz, 1H), 7.84 (ddd, J = 8.4, 2.9, 1.3 Hz, 1H), 7.61 (ddd, J = 8.4, 4.8, 0.6 Hz, 1H), 7.20 (d, J = 6.0 Hz, 1H), 6.82 (s, 2H). |
| I-O-71 | 444.1 | 0.84 | $^1$H NMR (500 MHz, DMSO-d6) δ 10.01 (s, 1H), 9.70 (br s, 1H), 9.68 (s, 1H), 9.48 (d, J = 2.2 Hz, 1H), 8.79 (d, J = 2.2 Hz, 1H), 7.72 (s, 1H), 6.85 (s, 2H), 4.84-4.69 (m, 2H), 3.71 (s, 2H), 2.92 (s, 6H). |
| I-O-72 | 400.0 | 0.54 | $^1$H NMR (500 MHz, DMSO-d6) δ 10.18 (s, 1H), 9.63 (s, 1H), 9.49 (dt, J = 2.8, 1.4 Hz, 1H), 8.77 (s, 2H), 8.72 (dd, J = 2.1, 0.7 Hz, 1H), 8.52 (d, J = 5.0 Hz, 1H), 7.38 (s, 1H), 6.83 (s, 2H), 5.06 (t, J = 6.3 Hz, 1H), 4.09 (d, J = 3.1 Hz, 4H), 2.99 (dd, J = 13.8, 6.7 Hz, 2H), 2.55 (d, J = 5.6 Hz, 2H). |
| I-O-73 | 360.0 | 0.56 | $^1$H NMR (500 MHz, DMSO-d6) δ 10.07 (s, 1H), 9.57 (s, 1H), 9.46 (d, J = 2.2 Hz, 1H), 8.77 (d, J = 2.2 Hz, 1H), 8.22 (d, J = 5.4 Hz, 1H), 6.99 (d, J = 5.5 Hz, 1H), 6.80 (s, 2H), 5.32 (tt, J = 6.5, 4.5 Hz, 1H), 4.64-4.56 (m, 2H), 4.22-4.15 (m, 2H). |
| I-O-74 | 388.2 | 0.62 | $^1$H NMR (500 MHz, Methanol-d4) δ 9.90 (d, J = 1.2 Hz, 1H), 9.11 (d, J = 2.2 Hz, 1H), 8.64 (d, J = 2.2 Hz, 1H), 8.56 (dd, J = 6.7, 1.2 Hz, 1H), 7.84 (d, J = 6.7 Hz, 1H), 5.37 (dt, |

Compound Analytical Data

| Cmpd No. | LCMS ES+ | LCMS (Rt min) | HNMR |
|---|---|---|---|
| | | | J = 7.8, 4.0 Hz, 1H), 3.69 (d, J = 4.1 Hz, 2H), 3.44-3.36 (m, 2H), 2.49 (ddq, J = 13.6, 8.9, 4.5 Hz, 1H), 2.35 (ddt, J = 25.5, 11.3, 5.0 Hz, 2H), 2.22-2.06 (m, 1H). |
| I-O-75 | 388.1 | 0.65 | ¹H NMR (500 MHz, Methanol-d4) δ 9.78 (d, J = 1.2 Hz, 1H), 8.97 (d, J = 2.2 Hz, 1H), 8.48 (d, J = 2.2 Hz, 1H), 8.42 (dd, J = 6.7, 1.3 Hz, 1H), 7.69 (d, J = 6.7 Hz, 1H), 5.24 (td, J = 5.1, 2.7 Hz, 1H), 3.63-3.50 (m, 2H), 3.37-3.28 (m, 1H), 3.24-3.18 (m, 1H), 2.40 (dd, J = 9.5, 4.7 Hz, 1H), 2.29-2.14 (m, 2H), 2.01 (dd, J = 10.3, 4.2 Hz, 1H). |
| I-O-76 | 374.2 | 0.56 | ¹H NMR (500 MHz, Methanol-d4) δ 9.90 (d, J = 1.2 Hz, 1H), 9.11 (d, J = 2.2 Hz, 1H), 8.71 (d, J = 2.2 Hz, 1H), 8.57 (dd, J = 6.7, 1.2 Hz, 1H), 7.82 (d, J = 6.8 Hz, 1H), 5.79 (q, J = 4.4, 3.5 Hz, 1H), 3.91 (dd, J = 13.8, 4.7 Hz, 1H), 3.87-3.69 (m, 3H), 2.75-2.64 (m, 2H). |
| I-O-77 | 374.0 | 0.58 | ¹H NMR (500 MHz, DMSO-d6) δ 10.01 (s, 1H), 9.51 (s, 1H), 9.43 (d, J = 2.2 Hz, 1H), 8.56 (d, J = 2.2 Hz, 1H), 8.19 (d, J = 5.5 Hz, 1H), 7.13 (d, J = 5.5 Hz, 1H), 6.78 (s, 2H), 5.17-5.10 (m, 1H), 3.30-3.18 (m, 2H), 3.12-2.99 (m, 2H), 2.90 (ddd, J = 10.8, 8.0, 4.4 Hz, 1H), 2.16-2.05 (m, 1H), 1.99-1.90 (m, 1H). |
| I-O-78 | 400.0 | 0.6 | ¹H NMR (500 MHz, DMSO-d6) δ 10.00 (s, 1H), 9.50 (s, 1H), 9.42 (d, J = 2.1 Hz, 1H), 8.63 (d, J = 2.2 Hz, 1H), 8.16 (d, J = 5.4 Hz, 1H), 6.99 (d, J = 5.4 Hz, 1H), 6.77 (s, 2H), 4.64 (p, J = 6.9 Hz, 1H), 3.33 (m, 2H), 2.93 (ddd, J = 9.9, 6.7, 3.3 Hz, 2H), 2.32 (t, J = 7.1 Hz, 2H), 2.24 (ddd, J = 10.0, 7.2, 3.5 Hz, 2H). |
| I-O-79 | 400.0 | 0.6 | ¹H NMR (500 MHz, DMSO-d6) δ 9.55 (s, 1H), 9.45 (dd, J = 2.2, 0.6 Hz, 1H), 9.02 (s, 2H), 8.71 (d, J = 2.2 Hz, 1H), 8.23 (d, J = 5.4 Hz, 1H), 6.92 (d, J = 5.5 Hz, 1H), 6.80 (d, J = 3.6 Hz, 2H), 5.04 (tt, J = 6.7, 4.7 Hz, 1H), 3.83 (t, J = 8.2 Hz, 2H), 3.27 (dd, J = 14.7, 6.8 Hz, 2H), 2.66-2.56 (m, 4H). |
| I-O-80 | 388.0 | 0.56 | ¹H NMR (500 MHz, DMSO-d6) δ 9.98 (s, 1H), 9.52 (s, 1H), 9.42 (d, J = 2.2 Hz, 1H), 8.60 (d, J = 2.3 Hz, 1H), 8.16 (d, J = 5.5 Hz, 1H), 7.21 (d, J = 5.6 Hz, 1H), 6.78 (s, 2H), 4.77 (tt, J = 7.9, 3.5 Hz, 1H), 3.11-3.03 (m, 2H), 2.65 (ddd, J = 12.4, 9.0, 3.1 Hz, 2H), 1.98 (ddt, J = 12.9, 6.5, 3.6 Hz, 2H), 1.65 (dtt, J = 12.4, 9.2, 3.4 Hz, 2H). |
| I-O-81 | 388.2 | 0.62 | ¹H NMR (500 MHz, Methanol-d4) δ 9.90 (d, J = 1.2 Hz, 1H), 9.11 (d, J = 2.2 Hz, 1H), 8.64 (d, J = 2.2 Hz, 1H), 8.55 (dd, J = 6.7, 1.2 Hz, 1H), 7.83 (d, J = 6.7 Hz, 1H), 5.42-5.31 (m, 1H), 3.69 (d, J = 4.1 Hz, 2H), 3.48-3.35 (m, 2H), 2.49 (ddq, J = 13.5, 8.8, 4.5 Hz, 1H), 2.43-2.25 (m, 2H), 2.21-2.08 (m, 1H). |
| I-O-82 | 365.1 | 0.49 | ¹H NMR (500 MHz, DMSO-d6) δ 10.34 (s, 1H), 9.66 (s, 1H), 9.33 (s, 1H), 9.20-9.01 (m, 2H), 8.76 (d, J = 2.0 Hz, 1H), 8.46 (d, J = 6.0 Hz, 1H), 7.31 (d, J = 5.9 Hz, 1H), 6.79 (s, 2H), 5.56-5.38 (m, 1H), 4.66 (p, J = 6.5, 6.1 Hz, 2H), 4.25 (dd, J = 13.6, 6.9 Hz, 2H), 4.14 (s, 2H). |
| I-O-83 | 353.1 | 0.49 | ¹H NMR (500 MHz, DMSO-d6) δ 10.25 (s, 1H), 9.60 (s, 1H), 9.11 (dd, J = 1.9, 0.9 Hz, 1H), 8.71 (d, J = 2.0 Hz, 1H), 8.51 (d, J = 6.1 Hz, 1H), 8.15 (s, 3H), 7.59 (d, J = 6.1 Hz, 1H), 6.77 (s, 2H), 4.61 (t, J = 4.9 Hz, 2H), 4.12 (s, 2H), 3.49 (q, J = 5.2, 4.6 Hz, 2H). |
| I-O-84 | 393.1 | 0.52 | ¹H NMR (500 MHz, DMSO-d6) δ 10.09 (s, 1H), 9.55 (s, 1H), 9.06 (dt, J = 1.5, 0.7 Hz, 1H), 8.60 (d, J = 2.1 Hz, 1H), 8.16 (d, J = 5.5 Hz, 1H), 7.20 (d, J = 5.6 Hz, 1H), 6.74 (s, 2H), 4.77 (tt, J = 7.7, 3.5 Hz, 1H), 4.14 (s, 2H), 3.13-3.02 (m, 2H), 2.74-2.62 (m, 2H), 2.06-1.95 (m, 2H), 1.74-1.61 (m, 2H). |
| I-O-85 | 372.2 | 0.60 | — |
| I-O-86 | 377.1 | 0.51 | ¹H NMR (500 MHz, DMSO-d6) δ 10.08 (s, 1H), 9.52 (s, 1H), 9.04 (dd, J = 2.0, 0.9 Hz, 1H), 8.55 (d, J = 2.0 Hz, 1H), 8.17 (d, J = 5.5 Hz, 1H), 7.11 (d, J = 5.5 Hz, 1H), 6.72 (s, 2H), 5.12 (ddt, J = 6.7, 4.6, 2.0 Hz, 1H), 4.14 (s, 2H), 3.20 (dd, J = 12.6, 5.1 Hz, 1H), 3.12-3.01 (m, 2H), 2.90 (ddd, J = 10.9, 8.1, 4.5 Hz, 1H), 2.12 (dtd, J = 14.0, 8.0, 6.2 Hz, 1H), 1.97 (dqd, J = 13.4, 4.3, 2.0 Hz, 1H). |
| I-O-87 | 379.1 | 0.51 | ¹H NMR (500 MHz, DMSO-d6) δ 10.07 (s, 1H), 9.53 (s, 1H), 9.04 (d, J = 2.0 Hz, 1H), 8.56 (d, J = 2.1 Hz, 1H), 8.17 (d, J = 5.4 Hz, 1H), 7.12 (d, J = 5.5 Hz, 1H), 6.72 (s, 2H), 5.18-5.07 (m, 1H), 4.15 (s, 2H), 3.28-3.17 (m, 1H), 3.15-3.02 (m, 2H), 2.99-2.86 (m, 1H), 2.21-2.07 (m, 1H), 2.02-1.93 (m, 1H). |

Compound Analytical Data

| Cmpd No. | LCMS ES+ | LCMS (Rt min) | HNMR |
|---|---|---|---|
| I-O-88 | 345.0 | 1.16* | ¹H NMR (500 MHz, DMSO-d6) δ 1.74 (9H, s), 6.79 (2H, s), 7.82-7.83 (1H, d), 8.45-8.46 (1H, d), 8.74-8.75 (1H, d), 9.53-9.54 (1H, dd), 9.68-9.69 (1H, d), 10.29 (1H, s). |
| I-O-89 | 404.1 | 2.23* | ¹H NMR (500 MHz, DMSO-d6) δ 1.99-2.15 (2H, m), 2.27-2.37 (2H, m), 2-76-2.79 (3H, m), 3.09-3.30 (2H, m), 3.46-3.57 (2H, m), 4.74 (1H, m), 6.78 (2H, br s), 8.36 (1H, d), 8.83-8.88 (1H, m), 9.45-9.54 (2H, m), 9.77 (1H, m) and 10.09 (1H, s) ppm rotamers observed. |
| I-O-90 | 332.1 | 1.88* | ¹H NMR (500 MHz, DMSO-d6) δ 12.47 (s, 1H), 9.91 (s, 1H), 9.50 (dd, J = 4.8, 2.6 Hz, 1H), 8.89 (d, J = 2.5 Hz, 1H), 8.74 (s, 1H), 6.69 (s, 2H), 6.50 (s, 1H), 4.12 (s, 3H), 2.94 (d, J = 4.7 Hz, 3H). |
| I-O-91 | 446.1 | 2.06* | ¹H NMR (500 MHz, DMSO-d6) δ 1.85 (2H, m), 1.92-2.08 (4H, m), 2.67 (2H, m), 4.40 (2H, m), 4.49 (2H, m), 4.61 (1H, m), 6.77 (2H, br s), 8.30 (1H, m), 8.82 (1H, m), 9.47 (1H, s), 9.52 (1H, m) and 10.03 (1H, s) ppm Oxetane CH not observed. |
| I-O-92 | 345.0 | 1.76* | ¹H NMR (500 MHz, DMSO-d6) δ 10.34 (s, 1H), 9.68 (s, 1H), 9.53 (dd, J = 4.8, 2.5 Hz, 1H), 8.96-8.85 (m, 1H), 8.48 (s, 1H), 7.25 (s, 1H), 6.78 (s, 2H), 5.71 (tt, J = 5.9, 4.5 Hz, 1H), 5.10 (ddd, J = 7.8, 5.9, 1.1 Hz, 2H), 4.79 (ddd, J = 7.9, 4.5, 1.0 Hz, 2H). |

Retention times measured using HPLC Method B, described in the Experimental Methods and Materials section, above., are designated by (*). For all other compounds, the retention time was measured using the HPLC Method A.

Preparation C-1: 4-(1-methylpiperidin-4-yl)pyridin-3-amine

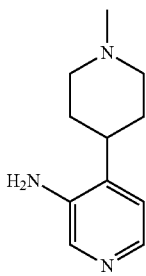

Step 1: 4-(1-methyl-3,6-dihydro-2H-pyridin-4-yl)-3-nitro-pyridine

To a solution of 4-chloro-3-nitro-pyridine (350 mg, 2.208 mmol) in Toluene (7.00 mL), Ethanol (1.75 mL) and sodium carbonate solution (aq) (2.21 mL of 1 M, 2.21 mmol) was added 1-methyl-4-(4,4,5,5-tetramethyl-1,3,2-dioxaborolan-2-yl)-3,6-dihydro-2H-pyridine (985.3 mg, 4.416 mmol), Pd$_2$(dba)$_3$ (60.66 mg, 0.07 mmol) and triphenyl phosphine (115.8 mg, 102.3 μL, 0.44 mmol). The mixture was stirred at 75° C. (reflux) for 18 hours. The reaction mixture was evaporated to dryness and the residue was partitioned between water (30 mL) and DCM (2×30 mL). The combined organics were washed with water (30 mL) and brine (30 mL), dried and evaporated to dryness to afford a dark brown oil which was purified by column chromatography on silica gel eluting with petroleum ether (A): ethyl acetate (B) (20-100% (B), 24 g, 30.0 CV, 35 mL/min) then ethyl acetate (A): methanol (B) (0-10% (B)) to afford 4-(1-methyl-3,6-dihydro-2H-pyridin-4-yl)-3-nitro-pyridine as a red oil (305 mg, 63%). MS (ES+) 220.1.

Step 2: 4-(1-methylpiperidin-4-yl)pyridin-3-amine

To a solution of 4-(1-methyl-3,6-dihydro-2H-pyridin-4-yl)-3-nitro-pyridine (300 mg, 1.37 mmol) in Methanol (3.00 mL) was added Pd on C, (10%, wet, Degussa) (29.12 mg, 0.274 mmol) and the mixture was stirred at ambient temperature under an atmosphere of hydrogen, for 18 hours. The catalyst was filtered off and the filtrate was concentrated in vacuo to afford 4-(1-methylpiperidin-4-yl)pyridin-3-amine. MS (ES+) 192.1.

The following aminopyridine were synthesized according to Preparation C-1:

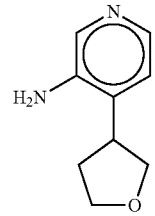

4-(tetrahydrofuran-3-yl)pyridin-3-amine

Preparation C-2: tert-butyl 5-amino-3,4-dihydro-2,7-naphthyridine-2(1H)-carboxylate

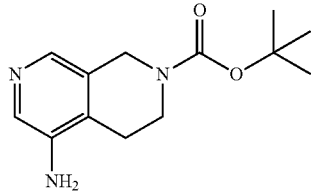 [SMILES: CC(C)(C)OC(=O)N1CCc2c(N)cncc2C1]

Step 1: 7-tert-butoxycarbonyl-6,8-dihydro-5H-2,7-naphthyridine-4-carboxylic acid To a solution of 5,6,7,8-tetrahydro-2,7-naphthyridine-4-carboxylic acid (Hydrochloric Acid (2)) (1 g, 3.982 mmol) in a mixture of $NaHCO_3$ (1.673 g, 19.91 mmol) in water (20.00 mL) and dioxane (20.00 mL), was added $Boc_2O$ (869.1 mg, 914.8 μL, 3.982 mmol), and the mixture was stirred overnight at RT. The reaction mixture was concentrated in vacuo. The residue was dissolved in ethyl acetate and water mixture and the pH of the aqueous phase was adjusted to pH4 using a sodium bisulfate solution. The organic and aqueous layers were separated, the organic layer washed with brine, dried over $MgSO_4$, and concentrated under reduced pressure to yield 7-tert-butoxycarbonyl-6,8-dihydro-5H-2,7-naphthyridine-4-carboxylic acid (440 mg, 40%). MS (ES+) 279.2.

Step 2: tert-butyl 5-amino-3,4-dihydro-2,7-naphthyridine-2(1H)-carboxylate

To a solution of 7-tert-butoxycarbonyl-6,8-dihydro-5H-2,7-naphthyridine-4-carboxylic acid (440 mg, 1.581 mmol) in NMP (6 mL) was added TEA (207.9 mg, 286.4 μL, 2.055 mmol) followed by diphenylphosphoryl azide (478.6 mg, 374.8 μL, 1.739 mmol) at rt under nitrogen. The reaction was heated to 90° C. for 2 hours. At RT, the reaction mixture was partitioned between an aqueous saturated solution of $NaHCO_3$ and EtOAc. Combined organic extract was washed with brine, dried over $MgSO_4$ and concentrated under reduced pressure. The residue was purified by chromatography on silica, eluting with 1-15% MeOH:DCM to yield tert-butyl 5-amino-3,4-dihydro-2,7-naphthyridine-2(1H)-carboxylate. (397 mg, 100.7%). MS (2ES+) 501.2.

Preparation C-3: [4,4'-bipyridin]-3-amine

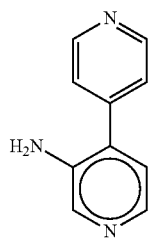

4-chloro-3-nitro-pyridine (100 mg, 0.6307 mmol), 4-pyridylboronic acid (77.52 mg, 0.6307 mmol), palladium; triphenylphosphane (36.45 mg, 0.03154 mmol), $K_3PO_4$ (946.0 μL, of 2 M, 1.892 mmol) in dioxane (3 mL) was heated at 130° C. for 30 min in a microwave. The mixture was loaded on a SCX column, washed with MeOH. The product was eluted with a 2M $NH_3$ in MeOH. The filtrate was concentrated in vacuo. The residue was dissolved in MeOH (20 mL), Pd/C 10% (42.04 mg, 0.3950 mmol) was added and the mixture was hydrogenated ($H_2$ balloon) overnight. The catalyst was filtered off and the filtrate was concentrated in vacuo yielding [4,4'-bipyridin]-3-amine that was used in next step without further purification. MS (ES+) 172.1.

Preparation C-4: 3'-methyl-[4,4'-bipyridin]-3-amine

[3-(tert-butoxycarbonylamino)-4-pyridyl]boronic acid (100 mg, 0.4201 mmol), palladium; triphenylphosphane (48.55 mg, 0.04201 mmol), 4-bromo-3-methyl-pyridine (113.9 mg, 0.5461 mmol), $K_3PO_4$ (630.0 μL of 2 M, 1.260 mmol), in dioxane (4.000 mL) was heated at 130° C. for 30 min in a MW. The reaction mixture was partitioned between water and DCM. Combined organic extract was dried and concentrated in vacuo. The residue was dissolved in DCM (10 mL) and TFA (2 mL) was added. After 1 h, the reaction mixture was concentrated in vacuo. The residue was loaded on a SCX column, washed with MeOH. The product was eluted with a 2M $NH_3$ in MeOH, filtrate was concentrated in vacuo yielding 3'-methyl-[4,4'-bipyridin]-3-amine that was used in next reaction w/o further purification (90 mg). MS (ES+) 172.1.

The following amino pyridine were prepared using procedures similar to Preparation C-3 or Preparation C-4:

[3,4'-bipyridin]-3'-amine:

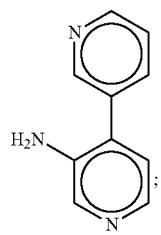

2-methyl-[3,4'-bipyridin]-3'-amine:

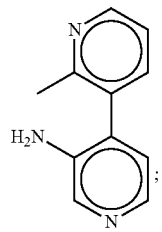

6-methyl-[3,4'-bipyridin]-3'-amine:

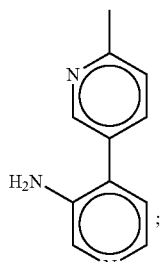

(4-(3-aminopyridin-4-yl)phenyl)(4-methylpiperazin-1-yl)methanone:

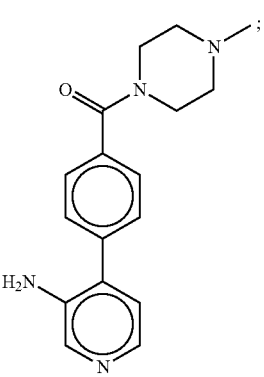

-continued
4-(pyridazin-4-yl)pyridin-3-amine:
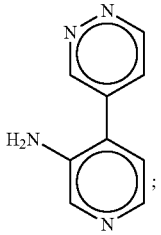
6-methoxy-[3,4'-bipyridin]-3'-amine:
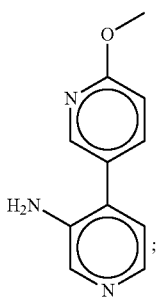
4-(pyrimidin-5-yl)pyridin-3-amine:
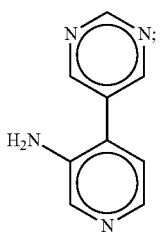
4-methyl-[3,4'-bipyridin]-3'-amine:
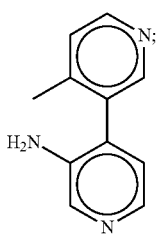
4-(3-methylpyridazin-4-yl)pyridin-3-amine:
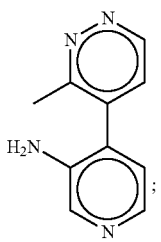
3'-amino[3,4'-bipyridin]-2-ol:
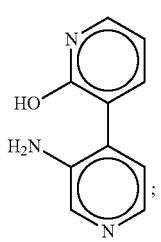
-continued
4-(4-methylpyridazin-3-yl)pyridin-3-amine:
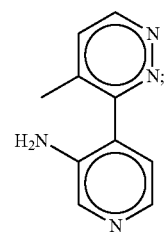
6-fluoro-2-methyl-[3,4'-bipyridin]-3'-amine:
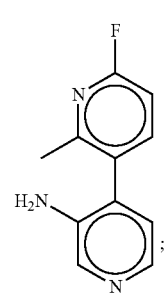
2-fluoro-[3,4'-bipyridin]-3'-amine:
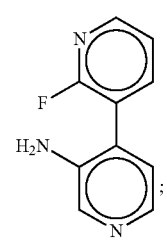
3-methyl-[2,4'-bipyridin]-3'-amine:
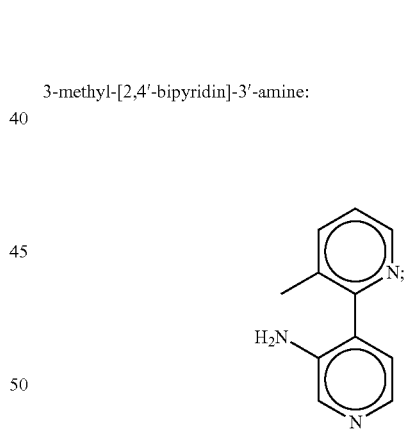
2-chloro-[3,4'-bipyridin]-3'-amine:
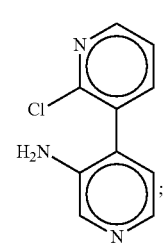

-continued tert-butyl 4-(4-(3-aminopyridin-4-yl)benzoyl)piperazine-1-carboxylate:

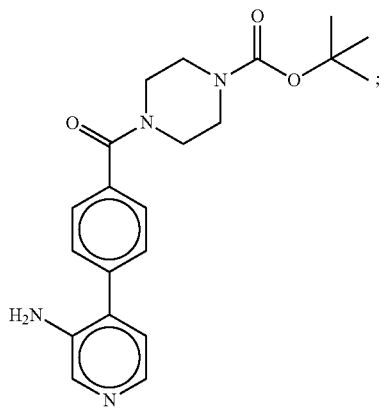

(4-(3-aminopyridin-4-yl)-3-methylphenyl)(4-methylpiperazin-1-yl)methanone:

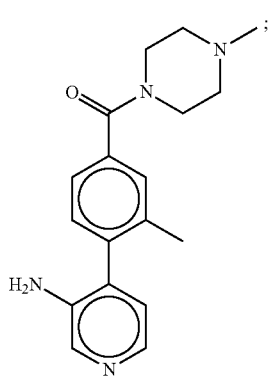

(3'-amino-3-chloro-[2,4'-bipyridin]-5-yl)(4-methylpiperazin-1-yl)methanone:

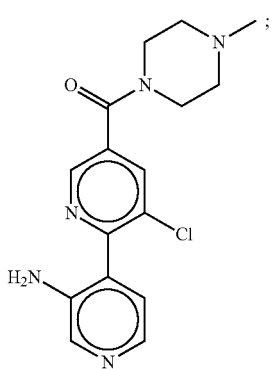

(3'-amino-2-methyl-[3,4'-bipyridin]-6-yl)(4-methylpiperazin-1-yl)methanone:

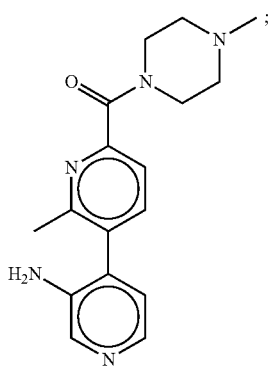

-continued 2-methyl-6-(4-methylpiperazin-1-yl)-[3,4'-bipyridin]-3'-amine:

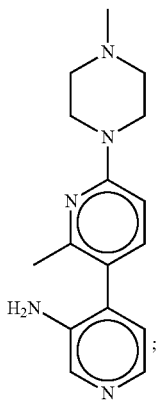

(S)-2-methyl-6-((1-methylpyrrolidin-3-yl)oxy)-[3,4'-bipyridin]-3'-amine:

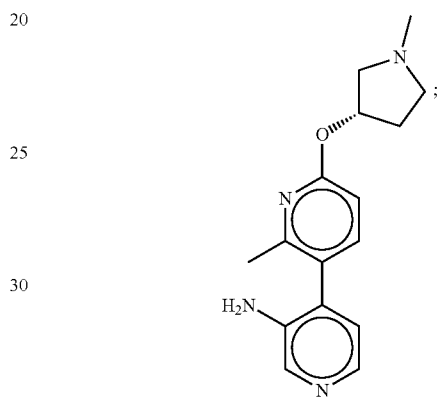

(3'-amino-[3,4'-bipyridin]-6-yl)(4-methylpiperazin-1-yl)methanone:

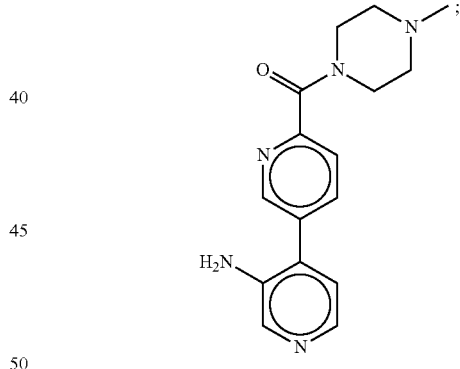

6-(4-methylpiperazin-1-yl)-[3,4'-bipyridin]-3'-amine:

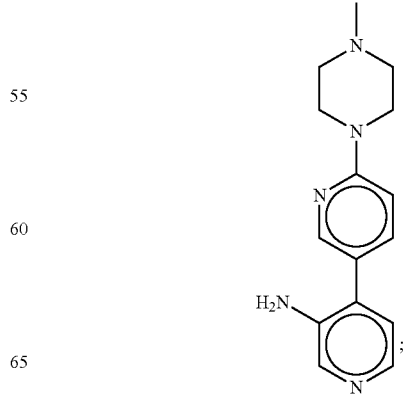

-continued 4-(1-methyl-1H-imidazol-2-yl)pyridin-3-amine:

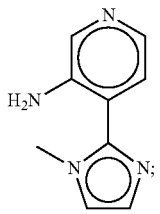

4-(1-methyl-1H-imidazol-5-yl)pyridin-3-amine:

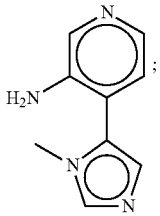

4-(1-methyl-1H-pyrazol-5-yl)pyridin-3-amine:

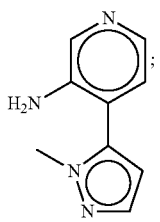

3'-amino-1-methyl-[2,4'-bipyridin]-6(1H)-one:

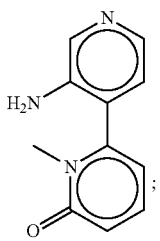

3'-amino-1-methyl-[3,4'-bipyridin]-6(1H)-one:

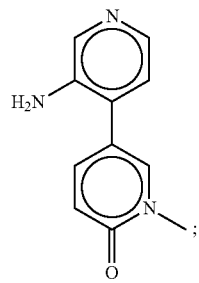

[2,4'-bipyridin]-3'-amine:

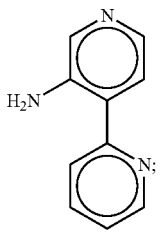

-continued 4-(4-(methylsulfonyl)phenyl)pyridin-3-amine:

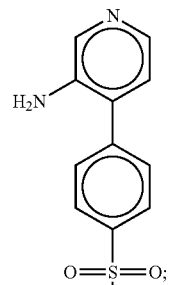

4-(3-methylpyrazin-2-yl)pyridin-3-amine:

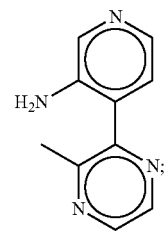

4-(1,3-dimethyl-1H-pyrazol-4-yl)pyridin-3-amine:

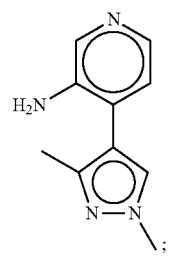

4-(1-methyl-1H-1,2,4-triazol-5-yl)pyridin-3-amine:

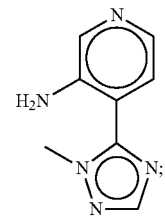

4-(4-(azetidin-1-ylsulfonyl)phenyl)pyridin-3-amine:

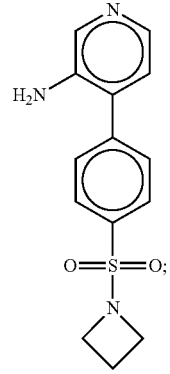

-continued 4-(5-methylpyrimidin-4-yl)pyridin-3-amine:

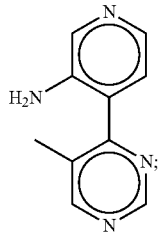

4-(1-methyl-1H-pyrazol-3-yl)pyridin-3-amine:

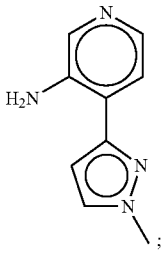

4-(1,2-dimethyl-1H-imidazol-5-yl)pyridin-3-amine:

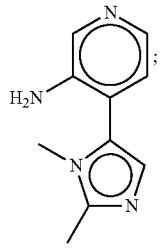

4-(1,4-dimethyl-1H-imidazol-5-yl)pyridin-3-amine:

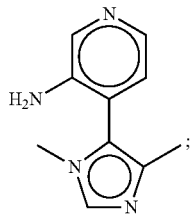

4-(1-ethyl-1H-imidazol-5-yl)pyridin-3-amine:

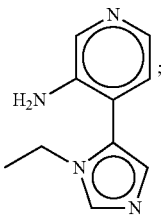

-continued 5-methoxy-4-(1-methyl-1H-imidazol-5-yl)pyridin-3-amine:

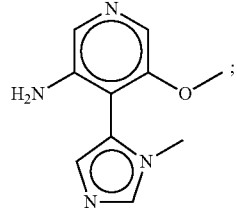

4-(1-methyl-1H-1,2,3-triazol-5-yl)pyridin-3-amine:

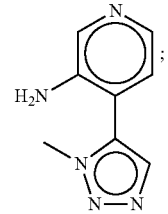

(S)-4-(4-(4-methylmorpholin-3-yl)phenyl)pyridin-3-amine:

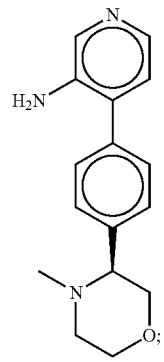

5-fluoro-4-(1-methyl-1H-imidazol-5-yl)pyridin-3-amine:

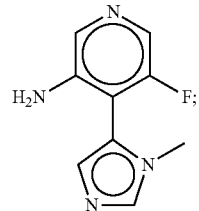

(4-(3-aminopyridin-4-yl)phenyl)(1,4-diazabicyclo[3.2.2]nonan-4-yl)methanone:

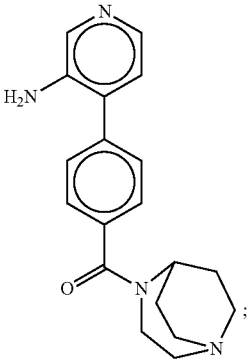

(4-(3-aminopyridin-4-yl)phenyl)(4-(oxetan-3-yl)piperazin-1-yl)methanone:

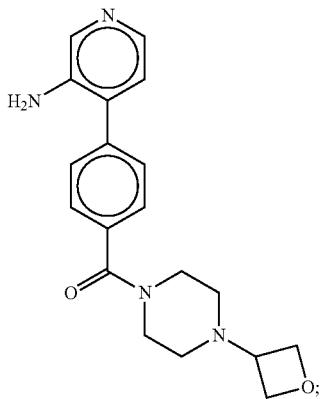

(4-(3-aminopyridin-4-yl)-3-fluorophenyl)(1,4-diazabicyclo[3.2.2]nonan-4-yl)methanone:

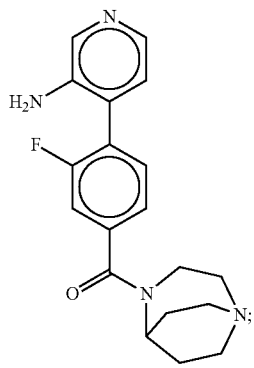

(4-(3-aminopyridin-4-yl)-3-fluorophenyl)(4-oxetan-3-yl)piperazin-1-yl)methanone:

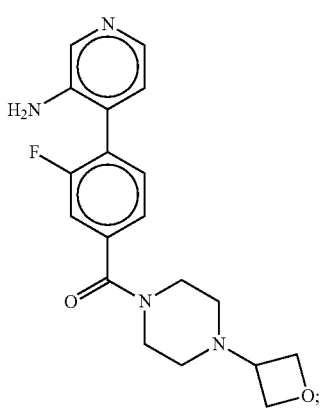

(3'-amino-[3,4'-bipyridin]-6-yl)(4-(oxetan-3-yl)piperazin-1-yl)methanone:

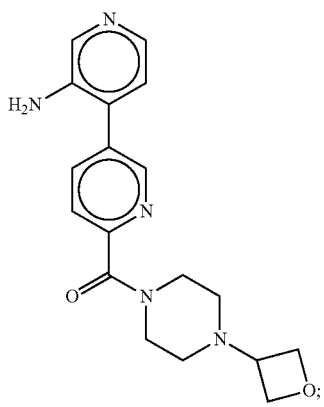

(3'-amino-[3,4'-bipyridin]-6-yl)(4-(pyrrolidin-1-yl)piperidin-1-yl)methanone:

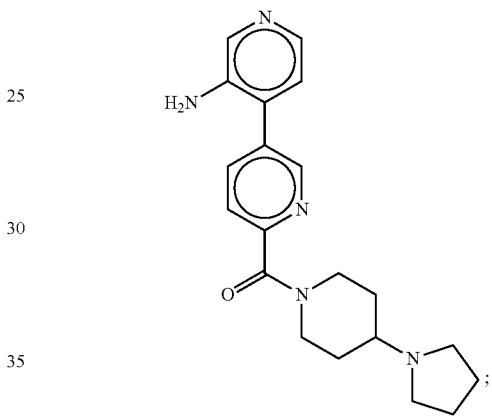

(3'-amino-[3,4'-bipyridin]-6-yl)(4-(azetidin-1-yl)piperidin-1-yl)methanone:

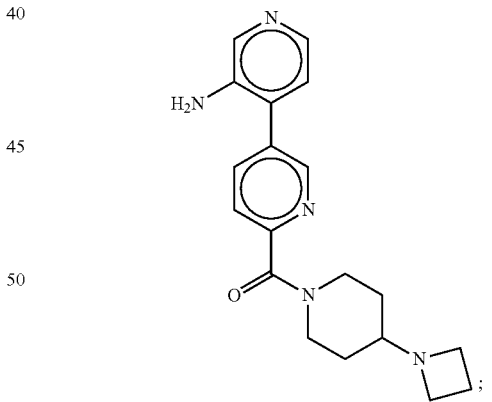

5'-methoxy-[3,4'-bipyridin]-3'-amine:

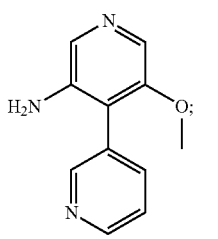

-continued 4-cyclopropyl-5-methoxypryidin-3-amine:

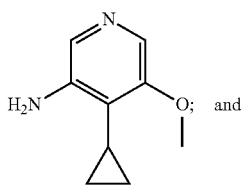

4-(1-(2-methoxyethyl)-1H-imidazol-5-yl)pyridin-3-amine:

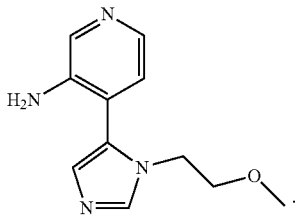

Preparation C-5: 4-(1-(oxetan-3-yl)piperidin-4-yl)pyridin-3-amine

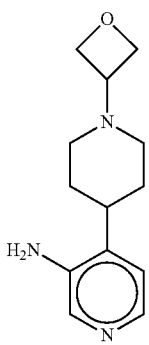

Step 1: tert-butyl 3'-nitro-5,6-dihydro-[4,4'-bipyridine]-1(2H)-carboxylate 4-chloro-3-nitro-pyridine (1 g, 6.307 mmol), tert-butyl 4-(4,4,5,5-tetramethyl-1,3,2-dioxaborolan-2-yl)-3,6-dihydro-2H-pyridine-1-carboxylate (2.145 g, 6.938 mmol) and PdCl$_2$(PPh$_3$)$_2$ (221.4 mg, 0.3154 mmol) in DME (20.00 mL) were degassed using 3× vacuum/nitrogen cycles. Na$_2$CO$_3$ (9.460 mL of 2 M, 18.92 mmol) was added followed by further degassing and the reaction heated at 80° C. for 18 hours. The reaction was cooled to ambient temperature and diluted with EtOAc/water. The layers were separated and the aqueous layer was extracted with EtOAc (×3). The combined organic extracts were washed with brine (×1), dried (MgSO$_4$), filtered and concentrated in vacuo. The residue was purified by column chromatography (ISCO Companion, 120 g column, eluting with 0 to 70% EtOAc/Petroleum Ether, dry loaded) to give tert-butyl 3'-nitro-5,6-dihydro-[4,4'-bipyridine]-1(2H)-carboxylate as a pale yellow solid (884 mg, 46% Yield). MS (ES Na+) 328.1.

Step 2: 3'-nitro-1,2,3,6-tetrahydro-4,4'-bipyridine

TFA (2 mL, 25.96 mmol) was added to a stirred solution of tert-butyl 4-(3-nitro-4-pyridyl)-3,6-dihydro-2H-pyridine-1-carboxylate (883 mg, 2.892 mmol) in DCM (10 mL) and the reaction stirred at ambient temperature for 15 hours. The solvent was removed in vacuo and the residue azeotroped with DCM (×2) and ether (×2). The residue was passed through a 25 g SCX-2 cartridge and washed with MeOH/DCM mixtures. The product was eluted by washing the cartridge with 2M NH$_3$ in MeOH/DCM mixtures and concentrated in vacuo to give 3'-nitro-1,2,3,6-tetrahydro-4,4'-bipyridine as an orange oil (523 mg, 88% Yield). MS (ES+) 206.1.

Step 3: 3'-nitro-1-(oxetan-3-yl)-1,2,3,6-tetrahydro-4,4'-bipyridine

Sodium triacetoxyborohydride (Sodium Ion (1)) (1.189 g, 5.608 mmol) was added in portions to a stirred solution of 3-nitro-4-(1,2,3,6-tetrahydropyridin-4-yl)pyridine (523 mg, 2.549 mmol) and 3-oxetanone (312.2 mg, 277.8 µL, 4.333 mmol) in THF (10 mL) at 0° C. under an atmosphere of nitrogen. The reaction was allowed to warm to ambient temperature and was stirred for 16 hours. MeOH (2 mL) was added dropwise and the mixture stirred at ambient temperature for 30 minutes. The mixture was concentrated in vacuo and the residue was partitioned between water and EtAOc. The pH of the aqueous layer was adjusted to pH 7-8 by the addition of NH$_4$OH and the layers separated. The aqueous layer was extracted with EtOAc (×3) and the combined organic extracts washed with brine (×1), dried (MgSO$_4$), filtered and concentrated in vacuo to give 3'-nitro-1-(oxetan-3-yl)-1,2,3,6-tetrahydro-4,4'-bipyridine as a red oil (615 mg, 92% Yield). MS (ES+) 262.1.

Step 4: 4-(1-(oxetan-3-yl)piperidin-4-yl)pyridin-3-amine

Pd on C, wet, Degussa (240 mg, 0.2255 mmol) was added to a stirred solution of 3-nitro-4-[1-(oxetan-3-yl)-3,6-dihydro-2H-pyridin-4-yl]pyridine (614 mg, 2.350 mmol) in EtOAc (20 mL)/EtOH (20 mL). The reaction was placed under an atmosphere of hydrogen and stirred at ambient temperature for 15 hours. The catalyst was removed by filtration through a pad of celite and the filtrate concentrated in vacuo to give the 4-(1-(oxetan-3-yl)piperidin-4-yl)pyridin-3-amine as a pale yellow solid (518 mg, 95% Yield). MS (ES+) 234.2.

Preparation C-6: 5-fluoro-4-(1-methylpiperidin-4-yl)pyridin-3-amine

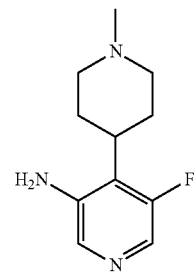

Step 1: 3'-chloro-5'-fluoro-1-methyl-1,2,3,6-tetrahydro-4,4'-bipyridine 3-chloro-5-fluoro-4-iodo-pyridine (500 mg, 1.942 mmol), 1-methyl-4-(4,4,5,5-tetramethyl-1,3,2-dioxaborolan-2-yl)-

3,6-dihydro-2H-pyridine (476.6 mg, 2.136 mmol) and Pd(PPh₃)₂Cl₂ (68.15 mg, 0.09710 mmol) in DME (10.00 mL) were degassed using 3× vacuum/nitrogen cycles. Na₂CO₃ (2.913 mL of 2 M, 5.826 mmol) was added followed by further degassing and the reaction heated at 80° C. for 18 hours. The reaction was cooled to ambient temperature and diluted with EtOAc/water. The layers were separated and the aqueous layer extracted with EtOAc (×3). The combined organic extracts were washed with brine (×1), dried (MgSO₄), filtered and concentrated in vacuo. The residue was passed through a 10 g SCX-2 cartridge and washed with MeOH/DCM mixtures. The product was eluted by washing the cartridge with 2M NH₃ in MeOH/DCM mixtures and concentrated in vacuo. The residue was purified by column chromatography (ISCO Companion, 40 g column, eluting with 0 to 10% MeOH/DCM+1% NH₄OH, loaded in DCM) to give 3'-chloro-5'-fluoro-1-methyl-1,2,3,6-tetrahydro-4,4'-bipyridine as a red solid (378 mg, 86% Yield). MS (ES+) 227.1.

Step 2: tert-butyl (5-fluoro-1'-methyl-1',2',3',6'-tetrahydro-[4,4'-bipyridin]-3-yl)carbamate 3-chloro-5-fluoro-4-(1-methyl-3,6-dihydro-2H-pyridin-4-yl)pyridine (377 mg, 1.663 mmol), tert-butyl carbamate (974.1 mg, 8.315 mmol), sodium tert-butoxide (815.1 mg, 8.481 mmol), BrettPhos pre-catalyst (66.25 mg, 0.08315 mmol) and BrettPhos (44.63 mg, 0.08315 mmol) were placed in a sealable tube an degassed by vacuum/nitrogen cycles (×5). Dry dioxane (10 mL) was added and the resulting mixture was placed into a pre-heated block at 100° C. and stirred at this temperature for 16 hours. Further portions of BrettPhos pre-catalyst (66.25 mg, 0.08315 mmol) and BrettPhos (44.63 mg, 0.08315 mmol) were added and the reaction heated at 100° C. for 8 hours. The reaction mixture was cooled to ambient temperature and quenched with saturated NH₄Cl. The mixture was passed through a pre-wetted (EtOAc) celite cartridge (2.5 g). The cartridge was washed with EtOAc/saturated NH₄Cl and the layers of the filtrate separated. The aqueous layer was extracted with EtOAc (×3) and the combined organic extracts were washed with brine (×1), dried (MgSO₄), filtered and concentrated in vacuo. The residue was purified by column chromatography (ISCO Companion, 40 g column, eluting with 0 to 10% MeOH/DCM, loaded in DCM) to give tert-butyl (5-fluoro-1'-methyl-1',2',3',6'-tetrahydro-[4,4'-bipyridin]-3-yl)carbamate. MS (ES+) 308.2.

Step 3: 5-fluoro-1'-methyl-1',2',3',6'-tetrahydro-[4,4'-bipyridin]-3-amine

TFA (2 mL, 25.96 mmol) was added to a stirred solution of tert-butyl N-[5-fluoro-4-(1-methyl-3,6-dihydro-2H-pyridin-4-yl)-3-pyridyl]carbamate (483 mg, 1.571 mmol) in DCM (10 mL) and the reaction stirred at ambient temperature for 6 hours. The solvent was removed in vacuo and the residue azeotroped with DCM (×2) and ether (×2). The residue was passed through a 10 g SCX-2 cartridge and washed with MeOH/DCM mixtures. The product was eluted by washing the cartridge with 2M NH₃ in MeOH/DCM mixtures and concentrated in vacuo. The residue was purified by column chromatography (ISCO Companion, 40 g column, eluting with 0 to 10% MeOH/DCM+1% NH₄OH, loaded in DCM) to give 5-fluoro-1'-methyl-1',2',3',6'-tetrahydro-[4,4'-bipyridin]-3-amine as an off-white solid (61 mg, 19% Yield over 2 steps). MS (ES+) 208.1.

Step 4: 5-fluoro-4-(1-methylpiperidin-4-yl)pyridin-3-amine

Pd on C, wet, Degussa (25 mg, 0.1175 mmol) was added to a stirred solution of 5-fluoro-4-(1-methyl-3,6-dihydro-2H-pyridin-4-yl)pyridin-3-amine (61 mg, 0.2943 mmol) in EtOAc (5 mL)/EtOH (5 mL). The reaction was placed under an atmosphere of hydrogen and stirred at ambient temperature for 15 hours. A further portion of Pd on C, wet, Degussa (25 mg, 0.1175 mmol) was added and the reaction was placed under an atmosphere of hydrogen and stirred at ambient temperature for 24 hours. The catalyst was removed by filtration through a pad of celite and the filtrate concentrated in vacuo to give 5-fluoro-4-(1-methylpiperidin-4-yl)pyridin-3-amine as an off-white solid (58 mg, 95% Yield). MS (ES+) 210.1.

Preparation C-7: 5-fluoro-4-(1-(oxetan-3-yl)piperidin-4-yl)pyridin-3-amine

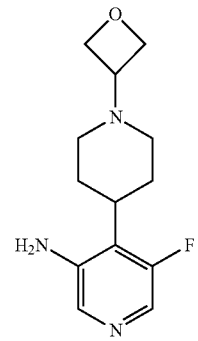

Step 1: tert-butyl 3'-chloro-5'-fluoro-5,6-dihydro-[4,4'-bipyridine]-1(2H)-carboxylate 3-chloro-5-fluoro-4-iodo-pyridine (750 mg, 2.913 mmol), tert-butyl 4-(4,4,5,5-tetramethyl-1,3,2-dioxaborolan-2-yl)-3,6-dihydro-2H-pyridine-1-carboxylate (990.7 mg, 3.204 mmol) and Pd(PPh₃)₂Cl₂ (102.2 mg, 0.1456 mmol) in DME (15 mL) were degassed using 3× vacuum/nitrogen cycles. Na₂CO₃ (4.370 mL of 2 M, 8.739 mmol) was added followed by further degassing and the reaction heated at 90° C. for 2 hours. The reaction was cooled to ambient temperature and diluted with EtOAc/water. The layers were separated and the aqueous layer extracted with EtOAc (×3). The combined organic extracts were washed with brine (×1), dried (MgSO₄), filtered and concentrated in vacuo. The residue was purified by column chromatography (ISCO Companion, 80 g column, eluting with 0 to 20% EtOAc/Petroleum Ether, loaded in DCM) to give tert-butyl 3'-chloro-5'-fluoro-5,6-dihydro-[4,4'-bipyridine]-1(2H)-carboxylate as an off-white solid (708 mg, 78% Yield). MS (ES+) 313.1.

Step 2: 3'-chloro-5'-fluoro-1,2,3,6-tetrahydro-4,4'-bipyridine

TFA (2 mL, 25.96 mmol) was added to a stirred solution of tert-butyl 4-(3-chloro-5-fluoro-4-pyridyl)-3,6-dihydro-2H-pyridine-1-carboxylate (708 mg, 2.264 mmol) in DCM (10 mL) and the reaction stirred at ambient temperature for 2 hours. The solvent was removed in vacuo and the residue azeotroped with DCM (×2) and ether (×2). The residue was passed through a 10 g SCX-2 cartridge and washed with MeOH/DCM mixtures. The product was eluted by washing the cartridge with 2M NH$_3$ in MeOH/DCM mixtures and concentrated in vacuo to give 3'-chloro-5'-fluoro-1,2,3,6-tetrahydro-4,4'-bipyridine as an off-white solid (468 mg, 97% Yield). MS (ES+) 213.1.

Step 3: 3'-chloro-5'-fluoro-1-(oxetan-3-yl)-1,2,3,6-tetrahydro-4,4'-bipyridine

Sodium triacetoxyborohydride (Sodium Ion (1)) (1.026 g, 4.842 mmol) was added in portions to a stirred solution of 3-chloro-5-fluoro-4-(1,2,3,6-tetrahydropyridin-4-yl)pyridine (468 mg, 2.201 mmol) and 3-oxetanone (269.7 mg, 239.9 μL, 3.742 mmol) in THF (10 mL) at 0° C. under an atmosphere of nitrogen. The reaction was allowed to warm to ambient temperature over 16 hours. MeOH (2 mL) was added dropwise and the mixture stirred at ambient temperature for 30 minutes. The mixture was concentrated in vacuo and partitioned between water and EtAOc. The pH of the aqueous layer was adjusted to pH 7-8 by the addition of NH$_4$OH and the layers separated. The aqueous layer was extracted with EtOAc (×3) and the combined organic extracts washed with brine (×1), dried (MgSO$_4$), filtered and concentrated in vacuo to give 3'-chloro-5'-fluoro-1-(oxetan-3-yl)-1,2,3,6-tetrahydro-4,4'-bipyridine as a white solid (573 mg, 97% Yield). MS (ES+) 269.1.

Step 4: tert-butyl (5-fluoro-1'-(oxetan-3-yl)-1',2',3',6'-tetrahydro-[4,4'-bipyridin]-3-yl)carbamate 3-chloro-5-fluoro-4-[1-(oxetan-3-yl)-3,6-dihydro-2H-pyridin-4-yl]pyridine (572 mg, 2.129 mmol), tert-butyl carbamate (1.246 g, 10.64 mmol), sodium tert-butoxide (1.044 g, 10.86 mmol), BrettPhos pre-catalyst (84.78 mg, 0.1064 mmol) and BrettPhos (57.11 mg, 0.1064 mmol) were placed in a sealable tube and degassed by vacuum/nitrogen cycles (×5). Dry dioxane (10 mL) was added and the resulting mixture was placed into a pre-heated block at 100° C. and stirred at this temperature for 16 hours. The reaction mixture was cooled to ambient temperature and quenched with saturated NH$_4$Cl. The mixture was passed through a pre-wetted (EtOAc) celite cartridge (2.5 g). The cartridge was washed with EtOAc/saturated NH$_4$Cl and the layers of the filtrate separated. The aqueous layer was extracted with EtOAc (×3) and the combined organic extracts were dried (Na$_2$SO$_4$), filtered and concentrated in vacuo. The residue was purified by column chromatography (ISCO Companion, 80 g column, eluting with 0 to 100% EtOAc/Petroleum Ether, loaded in DCM) to give tert-butyl (5-fluoro-1'-(oxetan-3-yl)-1',2',3',6'-tetrahydro-[4,4'-bipyridin]-3-yl)carbamate as a pale yellow solid (180 mg, 24% Yield). Also isolate 197 mg of a mixture of SM and product. MS (ES+) 350.2.

Step 5: tert-butyl (5-fluoro-4-(1-(oxetan-3-yl)piperidin-4-yl)pyridin-3-yl)carbamate Pd on C, wet, Degussa (70 mg, 0.06578 mmol) was added to a stirred solution of tert-butyl N-[5-fluoro-4-[1-(oxetan-3-yl)-3,6-dihydro-2H-pyridin-4-yl]-3-pyridyl]carbamate (180 mg, 0.5152 mmol) in EtOH (5 mL)/EtOAc (5 mL). The reaction was placed under an atmosphere of hydrogen and stirred at ambient temperature for 46 hours. The catalyst was removed by filtration through a pad of celite and the filtrate concentrated in vacuo to give tert-butyl (5-fluoro-4-(1-(oxetan-3-yl)piperidin-4-yl)pyridin-3-yl)carbamate as an off-white solid (175 mg, 97% Yield). MS (ES+) 352.2.

Step 6: 5-fluoro-4-(1-(oxetan-3-yl)piperidin-4-yl)pyridin-3-amine

TFA (1 mL, 12.98 mmol) was added to a stirred solution of tert-butyl N-[5-fluoro-4-[1-(oxetan-3-yl)-4-piperidyl]-3-pyridyl]carbamate (174 mg, 0.4951 mmol) in DCM (5 mL) and the reaction stirred at ambient temperature for 4 hours. The solvent was removed in vacuo and the residue azeotroped with DCM (×2) and ether (×2). The residue was passed through a 5 g SCX-2 cartridge and washed with MeOH/DCM mixtures. The product was eluted by washing the cartridge with 2M NH$_3$ in MeOH/DCM mixtures and concentrated in vacuo to give 5-fluoro-4-(1-(oxetan-3-yl)piperidin-4-yl)pyridin-3-amine as a yellow oil (109 mg, 88% Yield). MS (ES+) 252.1.

Preparation C-8: (3'-amino-5'-fluoro-5,6-dihydro-[4,4'-bipyridin]-1(2H)-yl)(1-methylpiperidin-4-yl)methanone

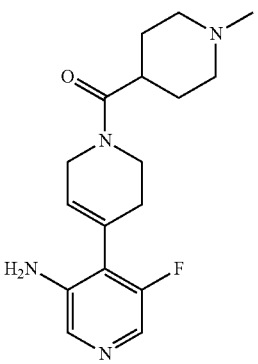 [SMILES: CN1CCC(C(=O)N2CC=C(c3c(N)cncc3F)CC2)CC1]

Step 1: (3'-chloro-5'-fluoro-5,6-dihydro-[4,4'-bipyridin]-1(2H)-yl)(1-methylpiperidin-4-yl)methanone To a solution of 3-chloro-5-fluoro-4-(1,2,3,6-tetrahydropyridin-4-yl)pyridine (540 mg, 2.539 mmol) (prepared according to methods similar to the ones depicted in step 1 and step 2 of Preparation C-7) in NMP (5 mL) was added TBTU (1.223 g, 3.809 mmol), 1-methylpiperidine-4-carboxylic acid (Hydrochloric Acid (1)) (547.4 mg, 3.047 mmol) and DIPEA (656.3 mg, 884.5 μL, 5.078 mmol) and the reaction was stirred at ambient temperature for 2 hours. The reaction mixture was adsorbed onto a pre-wetted (methanol, 20 mL) SCX-2 cartridge (10 g) and flushed with DCM/methanol (1:1, 2×20 mL) and then the basic components eluted with 2 M ammonia in methanol (2×20 mL). The basic eluent was evaporated to dryness to afford a pale orange oil (744 mg). The residue was triturated in DCM (2 mL) and a white solid was filtered off. The filtrate was purified by column chromatography on silica gel eluting with DCM (A): DCM/Methanol/NH$_4$OH (90:10:1, (B)) (0-100% (B), 40 g, 20.0 CV, 40 mL/min) to afford (3'-chloro-5'-fluoro-5,6-dihydro-[4,4'-bipyridin]-1(2H)-yl)(1-methylpiperidin-4-yl)methanone as a pale orange oil (410 mg, 48%). MS (ES+) 338.5.

Step 2: (3'-amino-5'-fluoro-5,6-dihydro-[4,4'-bipyridin]-1(2H)-yl)(1-methylpiperidin-4-yl)methanone

[4-(3-chloro-5-fluoro-4-pyridyl)-3,6-dihydro-2H-pyridin-1-yl]-(1-methyl-4-piperidyl)methanone (400 mg, 1.184 mmol), tert-butyl carbamate (693.5 mg, 5.920 mmol), Brett-Phos (63.55 mg, 0.1184 mmol), BrettPhos pre-catalyst (94.34 mg, 0.1184 mmol) and sodium tert-butoxide (580.3 mg, 6.038 mmol) were added to a Schlenk tube under a nitrogen atmosphere. The solid mixture was degassed by vacuum/nitrogen cycles (×5) then was added anhydrous Toluene (8.000 mL) and the resulting mixture was placed into a pre-heated block at 100° C. and was stirred for 4 hours. The reaction mixture was cooled to ambient temperature, quenched with saturated $NH_4Cl$ solution and partitioned between DCM/MeOH (9:1, 2×50 mL) and water (50 mL). The combined organics were washed with brine (50 mL), dried and concentrated in vacuo to afford a pale orange oil (456 mg). The residue was purified by column chromatography on silica gel eluting with DCM (A): DCM/MeOH/NH 4 OH (90:10:1, (B)) (0-100% (B), 40 g, 20.0 CV, 40 mL/min) to afford (3'-amino-5'-fluoro-5,6-dihydro-[4,4'-bipyridin]-1(2H)-yl)(1-methylpiperidin-4-yl)methanone (200 mg). It was dissolved in DCM (2.000 mL) and TFA (1.0 mL) was added and the mixture was stirred at ambient temperature overnight. The reaction mixture was concentrated in vacuo and the residue was loaded onto a pre-wetted (DCM/methanol, (1:1) 10 mL) SCX-2 cartridge (5 g) and flushed with DCM/methanol (1:1, 25 mL) and then the basic components was eluted with 2 M ammonia in methanol (20 mL). The basic eluent was evaporated to dryness to afford a pale yellow oil (325 mg) that was purified by column chromatography on silica gel eluting with DCM (A): DCM/Methanol/$NH_4OH$ (90:10:1, (B)) (50-100% (B), 2 4 g, 20.0 CV, 35 mL/min) to afford (3'-amino-5'-fluoro-5,6-dihydro-[4,4'-bipyridin]-1(2H)-yl)(1-methylpiperidin-4-yl)methanone as a colourless oil (55 mg, 12%). MS (ES+) 319.2.

Preparation C-9: 4-(3-aminopyridin-4-yl)-1-methylpiperidin-2-one

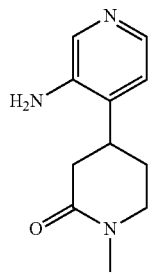

Step 1: tert-butyl (1'-methyl-2'-oxo-1',2'-dihydro-[4,4'-bipyridin]-3-yl)carbamate To a suspension of [3-(tert-butoxycarbonylamino)-4-pyridyl]boronic acid (200 mg, 0.8402 mmol), 4-bromo-1-methyl-pyridin-2-one (158.0 mg, 0.8402 mmol) and $Pd(PPh_3)_4$ (48.55 mg, 0.04201 mmol) in Dioxane (2 mL) was added $Na_2CO_3$ (840.0 μL of 2 M, 1.680 mmol) and was heated at 80° C. overnight. The reaction mixture was cooled to ambient temperature and filtered through a prewetted (methanol, 5 mL) Celite cartridge (2.5 g) and washed with methanol (35 mL). The filtrate was concentrated in vacuo to afford a pale brown oil (500 mg). The residue was partitioned between DCM (2×30 mL) and saturated sodium bicarbonate solution (30 mL). The combined organics were dried (phase sep cartridge) and concentrated in vacuo to afford an orange oil (280 mg). The residue was purified by column chromatography on ISCO Companion eluting with DCM (A): DCM/Methanol/$NH_4OH$ (90:10:1, (B)) (0-100% (B), 12 g, 16.0 CV, 30 mL/min) to afford tert-butyl (1'-methyl-2'-oxo-1',2'-dihydro-[4,4'-bipyridin]-3-yl)carbamate as a pale yellow oil (121 mg, 48%). MS (ES+) 302.1.

Step 2: tert-butyl (4-(1-methyl-2-oxopiperidin-4-yl)pyridin-3-yl)carbamate

A 0.05 M solution of tert-butyl N-[4-(1-methyl-2-oxo-4-pyridyl)-3-pyridyl]carbamate (120 mg, 0.3982 mmol) in Ethanol (8 mL) was passed through a Pd/C CatCart in the H-cube at a flow rate of 0.5 mL/min at 50 C and 50 bar. The procedure was repeated 3 more time. The product solution was concentrated in vacuo to afford tert-butyl (4-(1-methyl-2-oxopiperidin-4-yl)pyridin-3-yl)carbamate as a colourless oil (74 mg, 61%). MS (ES+) 306.1.

Step 3: 4-(3-aminopyridin-4-yl)-1-methylpiperidin-2-one

TFA (0.75 mL, 9.735 mmol) was added to a solution of tert-butyl N-[4-(1-methyl-2-oxo-4-piperidyl)-3-pyridyl]carbamate (74 mg, 0.2423 mmol) in DCM (2 mL) and was stirred at ambient temperature for 2 hours. The reaction mixture was adsorbed onto a pre-wetted (methanol/DCM (1:1), 2 mL) SCX-2 cartridge (2 g) and flushed with DCM/methanol (1:1, 20 mL) and then the basic components eluted with 2 M ammonia in methanol (20 mL). The basic eluent was evaporated to dryness to afford 4-(3-aminopyridin-4-yl)-1-methylpiperidin-2-one as a pale yellow oil (50 mg, 97%). MS (ES+) 206.1.

Preparation C-10: 1-((3-aminopyridin-4-yl)methyl)pyrrolidin-2-one

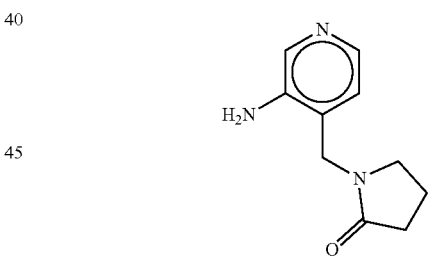

Step 1: 1-((3-bromopyridin-4-yl)methyl)pyrrolidin-2-one

Solution A: Sodium hydride (141.5 mg, 3.537 mmol) was added to a solution of pyrrolidin-2-one (316.1 mg, 282.2 μL, 3.714 mmol) in THF (5 mL) and the solution was stirred for 30 mins.

Solution B: To a solution of (3-bromo-4-pyridyl)methanol (665 mg, 3.537 mmol) in DCM (20 mL) at 0° C. was added triethylamine (0.467 mL, 3.351 mmol) and methanesulfonyl chloride (0.287 mL, 3.708 mmol) and the solution allowed to warm to room temperature and stirred for 1 h.

Solution B was added to Solution A and the mixture was stirred for 2 h. The reaction mixture was partitioned between water and EtOAc. Combined organic extract was washed with brine, dried ($MgSO_4$) and concentrated in vacuo (at RT)

to give a oil that was purified by chromatography on silica (eluting with 2-4% MeOH in EtOAc) to give 1-((3-bromopyridin-4-yl)methyl)pyrrolidin-2-one as a yellow oil. MS (ES+) 211.0.

Step 2:
1-((3-aminopyridin-4-yl)methyl)pyrrolidin-2-one

Prepared according to a procedure similar to Step 3 of Preparation N-14. MS (ES+) 192.0.

The following amides were formed using a procedure similar to Example 1 or Example 3a:
- 2-amino-6-fluoro-N-(4-(1-methylpiperidin-4-yl)pyridin-3-yl)pyrazolo[1,5-a]pyrimidine-3-carboxamide (Compound I-C-1);
- 2-amino-6-chloro-N-(4-methylpyridin-3-yl)pyrazolo[1,5-a]pyrimidine-3-carboxamide (Compound I-C-2);
- 2-amino-6-(cyanomethyl)-N-(4-methylpyridin-3-yl)pyrazolo[1,5-a]pyrimidine-3-carboxamide (Compound I-C-3);
- 2-amino-6-fluoro-N-(4-methylpyridin-3-yl)pyrazolo[1,5-a]pyrimidine-3-carboxamide (Compound I-C-4);
- 2-amino-6-fluoro-N-(4-phenylpyridin-3-yl)pyrazolo[1,5-a]pyrimidine-3-carboxamide (Compound I-C-5);
- 2-amino-6-(cyanomethyl)-N-(4-phenylpyridin-3-yl)pyrazolo[1,5-a]pyrimidine-3-carboxamide (Compound I-C-6);
- 2-amino-6-fluoro-N-(5,6,7,8-tetrahydro-2,7-naphthyridin-4-yl)pyrazolo[1,5-a]pyrimidine-3-carboxamide (Compound I-C-7);
- 2-amino-6-fluoro-N-(4-(1-(oxetan-3-yl)piperidin-4-yl)pyridin-3-yl)pyrazolo[1,5-a]pyrimidine-3-carboxamide (Compound I-C-10);
- 2-amino-6-chloro-N-(4-(1-(oxetan-3-yl)piperidin-4-yl)pyridin-3-yl)pyrazolo[1,5-a]pyrimidine-3-carboxamide (Compound I-C-11);
- 2-amino-6-fluoro-N-(5-fluoro-1'-(oxetan-3-yl)-1',2',3',6'-tetrahydro-[4,4'-bipyridin]-3-yl)pyrazolo[1,5-a]pyrimidine-3-carboxamide (Compound I-C-12);
- 2-amino-6-fluoro-N-(5-fluoro-4-(1-(oxetan-3-yl)piperidin-4-yl)pyridin-3-yl)pyrazolo[1,5-a]pyrimidine-3-carboxamide (Compound I-C-13);
- 2-amino-6-fluoro-N-(5-fluoro-4-(1-methylpiperidin-4-yl)pyridin-3-yl)pyrazolo[1,5-a]pyrimidine-3-carboxamide (Compound I-C-14);
- N-([3,4'-bipyridin]-3'-yl)-2-amino-6-fluoropyrazolo[1,5-a]pyrimidine-3-carboxamide (Compound I-C-15);
- 2-amino-6-fluoro-N-(6-(4-methylpiperazine-1-carbonyl)-[3,4'-bipyridin]-3'-yl)pyrazolo[1,5-a]pyrimidine-3-carboxamide (Compound I-C-19);
- 2-amino-6-fluoro-N-(2-methyl-[3,4'-bipyridin]-3'-yl)pyrazolo[1,5-a]pyrimidine-3-carboxamide (Compound I-C-20)
- 2-amino-6-fluoro-N-(6-(4-methylpiperazin-1-yl)-[3,4'-bipyridin]-3'-yl)pyrazolo[1,5-a]pyrimidine-3-carboxamide (Compound I-C-21);
- 2-amino-6-fluoro-N-(6-methyl-[3,4'-bipyridin]-3'-yl)pyrazolo[1,5-a]pyrimidine-3-carboxamide (Compound I-C-22);
- 2-amino-6-(2-cyanopropan-2-yl)-N-(4-(1-methylpiperidin-4-yl)pyridin-3-yl)pyrazolo[1,5-a]pyrimidine-3-carboxamide (Compound I-C-23);
- N-([4,4'-bipyridin]-3-yl)-2-amino-6-fluoropyrazolo[1,5-a]pyrimidine-3-carboxamide (Compound I-C-24);
- 2-amino-6-fluoro-N-(4-(4-(4-methylpiperazine-1-carbonyl)phenyl)pyridin-3-yl)pyrazolo[1,5-a]pyrimidine-3-carboxamide (Compound I-C-25);
- 2-amino-6-fluoro-N-(4-(pyridazin-4-yl)pyridin-3-yl)pyrazolo[1,5-a]pyrimidine-3-carboxamide (Compound I-C-26);
- 2-amino-6-fluoro-N-(6-methoxy-[3,4'-bipyridin]-3'-yl)pyrazolo[1,5-a]pyrimidine-3-carboxamide (Compound I-C-27);
- 2-amino-6-fluoro-N-(4-(pyrimidin-5-yl)pyridin-3-yl)pyrazolo[1,5-a]pyrimidine-3-carboxamide (Compound I-C-28);
- 2-amino-6-fluoro-N-(3'-methyl-[4,4'-bipyridin]-3-yl)pyrazolo[1,5-a]pyrimidine-3-carboxamide I-C-29);
- 2-amino-6-fluoro-N-(4-methyl-[3,4'-bipyridin]-3'-yl)pyrazolo[1,5-a]pyrimidine-3-carboxamide (Compound I-C-30);
- 2-amino-6-fluoro-N-(4-(3-methylpyridazin-4-yl)pyridin-3-yl)pyrazolo[1,5-a]pyrimidine-3-carboxamide (Compound I-C-31);
- 2-amino-6-fluoro-N-(2-hydroxy-[3,4'-bipyridin]-3'-yl)pyrazolo[1,5-a]pyrimidine-3-carboxamide (Compound I-C-32);
- 2-amino-6-fluoro-N-(4-(4-methylpyridazin-3-yl)pyridin-3-yl)pyrazolo[1,5-a]pyrimidine-3-carboxamide (Compound I-C-33);
- 2-amino-6-fluoro-N-(6-fluoro-2-methyl-[3,4'-bipyridin]-3'-yl)pyrazolo[1,5-a]pyrimidine-3-carboxamide (Compound I-C-34);
- 2-amino-6-fluoro-N-(2-fluoro-[3,4'-bipyridin]-3'-yl)pyrazolo[1,5-a]pyrimidine-3-carboxamide (Compound I-C-35);
- 2-amino-6-fluoro-N-(3-methyl-[2,4'-bipyridin]-3'-yl)pyrazolo[1,5-a]pyrimidine-3-carboxamide (Compound I-C-36);
- 2-amino-N-(2-chloro-[3,4'-bipyridin]-3'-yl)-6-fluoropyrazolo[1,5-a]pyrimidine-3-carboxamide (Compound I-C-37);
- 2-amino-6-fluoro-N-(5-fluoro-1'-(1-methylpiperidine-4-carbonyl)-1',2',3',6'-tetrahydro-[4,4'-bipyridin]-3-yl)pyrazolo[1,5-a]pyrimidine-3-carboxamide (Compound I-C-38);
- 2-amino-6-fluoro-N-(2-methyl-6-(4-methylpiperazine-1-carbonyl)-[3,4'-bipyridin]-3'-yl)pyrazolo[1,5-a]pyrimidine-3-carboxamide (Compound I-C-39);
- 2-amino-6-fluoro-N-(2-methyl-6-(4-methylpiperazin-1-yl)-[3,4'-bipyridin]-3'-yl)pyrazolo[1,5-a]pyrimidine-3-carboxamide (Compound I-C-40);
- (R)-2-amino-6-fluoro-N-(2-methyl-6-((1-methylpyrrolidin-3-yl)oxy)-[3,4'-bipyridin]-3'-yl)pyrazolo[1,5-a]pyrimidine-3-carboxamide (Compound I-C-41);
- 2-amino-N-(4-cyclopropylpyridin-3-yl)-6-fluoropyrazolo[1,5-a]pyrimidine-3-carboxamide (Compound I-C-42);
- 2-amino-6-fluoro-N-(5-fluoro-4-(4-(4-methylpiperazine-1-carbonyl)phenyl)pyridin-3-yl)pyrazolo[1,5-a]pyrimidine-3-carboxamide (Compound I-C-43);
- 2-amino-6-fluoro-N-(4-(4-(piperazine-1-carbonyl)phenyl)pyridin-3-yl)pyrazolo[1,5-a]pyrimidine-3-carboxamide (Compound I-C-44);
- 2-amino-6-fluoro-N-(4-(2-methyl-4-(4-methylpiperazine-1-carbonyl)phenyl)pyridin-3-yl)pyrazolo[1,5-a]pyrimidine-3-carboxamide (Compound I-C-45);
- 2-amino-N-(3-chloro-5-(4-methylpiperazine-1-carbonyl)-[2,4'-bipyridin]-3'-yl)-6-fluoropyrazolo[1,5-a]pyrimidine-3-carboxamide (Compound I-C-46); and
- 2-amino-N-(4-(1-(cyclopropylsulfonyl)piperidin-4-yl)pyridin-3-yl)-6-fluoropyrazolo[1,5-a]pyrimidine-3-carboxamide (Compound I-C-47);

N-(4-(4-(1,4-diazabicyclo[3.2.2]nonane-4-carbonyl)phenyl)pyridin-3-yl)-2-amino-6-fluoropyrazolo[1,5-a]pyrimidine-3-carboxamide (Compound I-C-48);

2-amino-6-fluoro-N-(4-(4-(4-(oxetan-3-yl)piperazine-1-carbonyl)phenyl)pyridin-3-yl)pyrazolo[1,5-a]pyrimidine-3-carboxamide (Compound I-C-49);

N-(4-(4-(1,4-diazabicyclo[3.2.2]nonane-4-carbonyl)-2-fluorophenyl)pyridin-3-yl)-2-amino-6-fluoropyrazolo[1,5-a]pyrimidine-3-carboxamide (Compound I-C-50);

2-amino-6-fluoro-N-(4-(2-fluoro-4-(4-(oxetan-3-yl)piperazine-1-carbonyl)phenyl)pyridin-3-yl)pyrazolo[1,5-a]pyrimidine-3-carboxamide (Compound I-C-51);

2-amino-6-fluoro-N-(6-(4-(oxetan-3-yl)piperazine-1-carbonyl)-[3,4'-bipyridin]-3'-yl)pyrazolo[1,5-a]pyrimidine-3-carboxamide (Compound I-C-52);

2-amino-6-fluoro-N-(6-(4-(pyrrolidin-1-yl)piperidine-1-carbonyl)-[3,4'-bipyridin]-3'-yl)pyrazolo[1,5-a]pyrimidine-3-carboxamide (Compound I-C-53);

2-amino-N-(6-(4-(azetidin-1-yl)piperidine-1-carbonyl)-[3,4'-bipyridin]-3'-yl)-6-fluoropyrazolo[1,5-a]pyrimidine-3-carboxamide (Compound I-C-54);

2-amino-6-fluoro-N-(4-(1-methyl-1H-imidazol-2-yl)pyridin-3-yl)pyrazolo[1,5-a]pyrimidine-3-carboxamide (Compound I-C-55);

2-amino-6-fluoro-N-(4-(1-methyl-1H-imidazol-5-yl)pyridin-3-yl)pyrazolo[1,5-a]pyrimidine-3-carboxamide (Compound I-C-56);

2-amino-6-fluoro-N-(4-(1-methyl-1H-pyrazol-5-yl)pyridin-3-yl)pyrazolo[1,5-a]pyrimidine-3-carboxamide (Compound I-C-57);

2-amino-6-fluoro-N-(1-methyl-6-oxo-1,6-dihydro-[2,4'-bipyridin]-3'-yl)pyrazolo[1,5-a]pyrimidine-3-carboxamide (Compound I-C-58);

2-amino-6-fluoro-N-(1-methyl-6-oxo-1,6-dihydro-[3,4'-bipyridin]-3'-yl)pyrazolo[1,5-a]pyrimidine-3-carboxamide (Compound I-C-59);

N-([2,4'-bipyridin]-3'-yl)-2-amino-6-fluoropyrazolo[1,5-a]pyrimidine-3-carboxamide (Compound I-C-60);

2-amino-6-fluoro-N-(4-(4-(methylsulfonyl)phenyl)pyridin-3-yl)pyrazolo[1,5-a]pyrimidine-3-carboxamide (Compound I-C-61);

2-amino-6-fluoro-N-(4-(3-methylpyrazin-2-yl)pyridin-3-yl)pyrazolo[1,5-a]pyrimidine-3-carboxamide (Compound I-C-62);

2-amino-N-(4-(1,3-dimethyl-1H-pyrazol-4-yl)pyridin-3-yl)-6-fluoropyrazolo[1,5-a]pyrimidine-3-carboxamide (Compound I-C-63);

2-amino-N-(4-(4-(azetidin-1-ylsulfonyl)phenyl)pyridin-3-yl)-6-fluoropyrazolo[1,5-a]pyrimidine-3-carboxamide (Compound I-C-64);

2-amino-6-fluoro-N-(4-(1-methyl-1H-1,2,4-triazol-5-yl)pyridin-3-yl)pyrazolo[1,5-a]pyrimidine-3-carboxamide (Compound I-C-65);

(S)-2-amino-6-fluoro-N-(4-(4-(4-methylmorpholin-3-yl)phenyl)pyridin-3-yl)pyrazolo[1,5-a]pyrimidine-3-carboxamide (Compound I-C-66);

2-amino-6-fluoro-N-(4-(5-methylpyrimidin-4-yl)pyridin-3-yl)pyrazolo[1,5-a]pyrimidine-3-carboxamide (Compound I-C-67);

2-amino-6-fluoro-N-(4-(1-methyl-1H-pyrazol-3-yl)pyridin-3-yl)pyrazolo[1,5-a]pyrimidine-3-carboxamide (Compound I-C-68);

2-amino-6-fluoro-N-(4-(1-methyl-1H-1,2,3-triazol-5-yl)pyridin-3-yl)pyrazolo[1,5-a]pyrimidine-3-carboxamide (Compound I-C-72);

2-amino-6-fluoro-N-(4-(1-methyl-2-oxopiperidin-4-yl)pyridin-3-yl)pyrazolo[1,5-a]pyrimidine-3-carboxamide (Compound I-C-73);

2-amino-6-fluoro-N-(4-(tetrahydrofuran-3-yl)pyridin-3-yl)pyrazolo[1,5-a]pyrimidine-3-carboxamide (Compound I-C-75);

2-amino-6-fluoro-N-(4-((2-oxopyrrolidin-1-yl)methyl)pyridin-3-yl)pyrazolo[1,5-a]pyrimidine-3-carboxamide (Compound I-C-76);

2-amino-N-(4-(1,2-dimethyl-1H-imidazol-5-yl)pyridin-3-yl)-6-fluoropyrazolo[1,5-a]pyrimidine-3-carboxamide (Compound I-C-77);

2-amino-N-(4-(1,4-dimethyl-1H-imidazol-5-yl)pyridin-3-yl)-6-fluoropyrazolo[1,5-a]pyrimidine-3-carboxamide (Compound I-C-78);

2-amino-6-fluoro-N-(5-fluoro-4-(1-methyl-1H-imidazol-5-yl)pyridin-3-yl)pyrazolo[1,5-a]pyrimidine-3-carboxamide (Compound I-C-79);

2-amino-N-(4-(1-ethyl-1H-imidazol-5-yl)pyridin-3-yl)-6-fluoropyrazolo[1,5-a]pyrimidine-3-carboxamide (Compound I-C-80);

2-amino-6-fluoro-N-(5-methoxy-4-(1-methyl-1H-imidazol-5-yl)pyridin-3-yl)pyrazolo[1,5-a]pyrimidine-3-carboxamide (Compound I-C-81);

2-amino-6-fluoro-N-(5'-methoxy-[3,4'-bipyridin]-3'-yl)pyrazolo[1,5-a]pyrimidine-3-carboxamide (Compound I-C-82);

2-amino-6-fluoro-N-(4-(1-(2-methoxyethyl)-1H-imidazol-5-yl)pyridin-3-yl)pyrazolo[1,5-a]pyrimidine-3-carboxamide (Compound I-C-83); and 2-amino-N-(4-cyclopropyl-5-methoxypyridin-3-yl)-6-fluoropyrazolo[1,5-a]pyrimidine-3-carboxamide (Compound I-C-84).

Example 15: 2-amino-6-fluoro-N-(7-methyl-5,6,7,8-tetrahydro-2,7-naphthyridin-4-yl)pyrazolo[1,5-a]pyrimidine-3-carboxamide (Compound I-C-8)

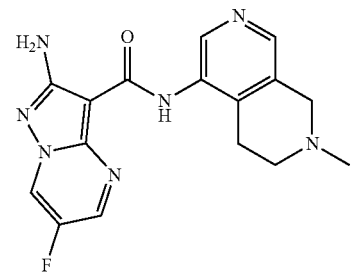 [SMILES: CN1CCc2c(cncc2NC(=O)c2c(N)nn3cc(F)cnc23)C1]

tert-butyl 5-(2-amino-6-fluoropyrazolo[1,5-a]pyrimidine-3-carboxamido)-3,4-dihydro-2,7-naphthyridine-2(1H)-carboxylate was dissolved in MeOH (8 mL). Acetic acid (91.88 mg, 87.01 µL, 1.530 mmol), formaldehyde (37% solution in water, 99.33 mg, 91.13 µL, 1.224 mmol) and NaBH(OAc)$_3$ (324.3 mg, 1.530 mmol) was sequentially added and the mixture was stirred for 1 hour at RT. The reaction mixture was partitioned between an aqueous saturated solution of NaHCO$_3$ and DCM. The insoluble was filtered off and the combined organic extract was dried and concentrated in vacuo. The insoluble and the residue were combined and purified by fractionlynx to yield 2-amino-6-fluoro-N-(7-methyl-5,6,7,8-tetrahydro-2,7-naphthyridin-4-yl)pyrazolo[1,5-a]pyrimidine-3-carboxamide. MS (ES+) 342.2.

Example 16: 5-(2-amino-6-fluoropyrazolo[1,5-a]pyrimidine-3-carboxamido)-2-methyl-1,2,3,4-tetrahydro-2,7-naphthyridine 2-oxide (Compound I-C-9)

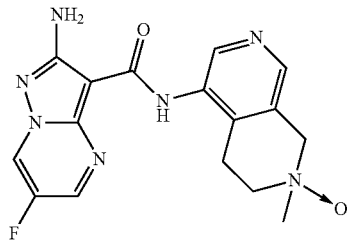 [SMILES: C[N+]1([O-])CCc2c(cncc2NC(=O)c2c(N)nn3cc(F)cnc23)C1]

To 2-amino-6-fluoro-N-(7-methyl-5,6,7,8-tetrahydro-2,7-naphthyridin-4-yl)pyrazolo[1,5-a]pyrimidine-3-carboxamide (12 mg, 0.03516 mmol) in DCM (2 mL) was added mCPBA (5.764 mg, 0.03340 mmol) and the mixture was stirred at RT for 2 h before the solvent was removed in vacuo. The residue was purified by FractionLynx to yield 5-(2-amino-6-fluoropyrazolo[1,5-a]pyrimidine-3-carboxamido)-2-methyl-1,2,3,4-tetrahydro-2,7-naphthyridine 2-oxide. MS (ES+) 358.2.

Example 17: 2-amino-6-fluoro-N-(4-(1-(1-methylpiperidine-4-carbonyl)piperidin-4-yl)pyridin-3-yl)pyrazolo[1,5-a]pyrimidine-3-carboxamide (Compound I-C-16)

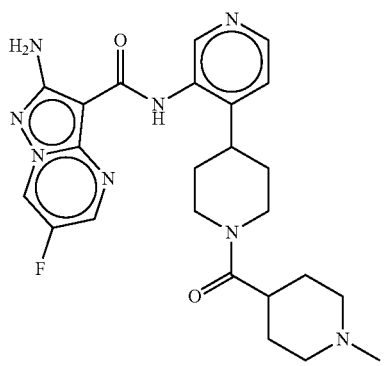

Step 1: 2-amino-6-fluoro-N-(4-(piperidin-4-yl)pyridin-3-yl)pyrazolo[1,5-a]pyrimidine-3-carboxamide To a solution of tert-butyl 4-[3-[(2-amino-6-fluoro-pyrazolo[1,5-a]pyrimidine-3-carbonyl)amino]-4-pyridyl]piperidine-1-carboxylate (555 mg, 1.218 mmol) (prepared using a procedure similar to example 2) in MeOH (2.135 mL) and DCM (2.135 mL) was added TFA (6.2 g, 4.2 mL, 54 mmol) and the resulting solution stirred at rt for 96 h. The reaction mixture was concentrated in vacuo and taken up in methanol and DCM and passed through an 25 g SCX cartridge flushing with methanol (3 column volumes) followed by 2M ammonia in methanol (3 column volumes) to elute the product. The filtrate was concentrated in vacuo to leave 2-amino-6-fluoro-N-(4-(piperidin-4-yl)pyridin-3-yl)pyrazolo[1,5-a]pyrimidine-3-carboxamide as a yellow solid that was used directly in the next step without further purification. MS (ES+) 356.1.

Step 2: 2-amino-6-fluoro-N-(4-(1-(1-methylpiperidine-4-carbonyl)piperidin-4-yl)pyridin-3-yl)pyrazolo[1,5-a]pyrimidine-3-carboxamide pyrimidine-3-carboxamide TBTU (154.5 mg, 0.4812 mmol) and DIPEA (82.92 mg, 111.8 µL, 0.6416 mmol) were added to a solution of 2-amino-6-fluoro-N-[4-(4-piperidyl)-3-pyridyl]pyrazolo[1,5-a]pyrimidine-3-carboxamide (114 mg, 0.3208 mmol) and 1-methylpiperidine-4-carboxylic acid (Hydrochloric Acid (1)) (69.16 mg, 0.3850 mmol) in NMP (2.280 mL) and the resulting solution stirred at RT for 2 h. Passed through an SCX cartridge flushing the desired product with 2M ammonia in methanol and the filtrate concentrated in vacuo. The residue was purified by fractionlynx HPLC and the product fractions combined and freeze dried to leave 2-amino-6-fluoro-N-(4-(1-(1-methylpiperidine-4-carbonyl)piperidin-4-yl)pyridin-3-yl)pyrazolo[1,5-a]pyrimidine-3-carboxamide as a yellow crystalline solid. MS (ES+) 481.3.

The following compounds were formed using a procedure similar to Example 17:
2-amino-6-fluoro-N-(4-(1-(4-methylpiperazine-1-carbonyl)piperidin-4-yl)pyridin-3-yl)pyrazolo[1,5-a]pyrimidine-3-carboxamide (Compound I-C-17); and
2-amino-6-fluoro-N-(4-(1-(quinuclidine-4-carbonyl)piperidin-4-yl)pyridin-3-yl)pyrazolo[1,5-a]pyrimidine-3-carboxamide (Compound I-C-18).

Example 18: 2-amino-6-fluoro-N-(1-methyl-1H-pyrrolo[2,3-c]pyridin-4-yl)pyrazolo[1,5-a]pyrimidine-3-carboxamide (Compound I-C-74)

NaH (3.958 mg, 0.09894 mmol) was added to a suspension of 2-amino-6-fluoro-N-(1H-pyrrolo[2,3-c]pyridin-4-yl)pyrazolo[1,5-a]pyrimidine-3-carboxamide (28 mg, 0.08995 mmol) (synthesized according to a procedure similar to Example 1 or Example 3a) and MeI (11.49 mg, 5.039 µL, 0.08096 mmol) in DMF (3 mL) under N2. The suspension was stirred at RT for 5 h before water (2 drops) was added. The crude mixture was purified by fractionlynx HPLC. Clean fractions were liophilized to yield 2-amino-6-fluoro-N-(1-methyl-1H-pyrrolo[2,3-c]pyridin-4-yl)pyrazolo[1,5-a]pyrimidine-3-carboxamide (5 mg, 16%). MS (ES+) 326.1.

| Compound Analytical Data | | | |
|---|---|---|---|
| Cmpd No. | LCMS ES+ | LCMS (Rt min) | HNMR |
| I-C-1 | 370.2 | 0.57 | $^1$H NMR (500 MHz, DMSO-d6) δ 9.55 (s, 1H), 9.49 (dd, J = 4.7, 2.5 Hz, 1H), 9.24 (s, 1H), 8.78 (d, J = 2.6 Hz, 1H), 8.29 (d, J = 5.1 Hz, 1H), 7.34 (d, J = 5.1 Hz, 1H), 6.71 (s, 2H), 2.93 (dt, J = 12.0, 2.9 Hz, 2H), 2.81 (tq, J = 7.4, 3.8, 3.4 Hz, 1H), 2.23 (s, 3H), 2.04 (td, J = 11.7, 2.6 Hz, 2H), 1.82-1.66 (m, 4H). |

-continued

Compound Analytical Data

| Cmpd No. | LCMS ES+ | LCMS (Rt min) | HNMR |
|---|---|---|---|
| I-C-2 | 303.1 | 0.94 | $^1$H NMR (500 MHz, DMSO-d6) δ 9.81 (s, 1H), 9.51 (s, 1H), 9.48 (d, J = 2.2 Hz, 1H), 8.76 (d, J = 2.2 Hz, 1H), 8.44 (d, J = 5.4 Hz, 1H), 7.74 (d, J = 5.3 Hz, 1H), 6.80 (s, 2H), 2.57 (s, 3H). |
| I-C-3 | 308.1 | 0.58 | — |
| I-C-4 | 287.1 | 0.62 | $^1$H NMR (500 MHz, DMSO-d6) δ 9.89 (s, 1H), 9.57 (s, 1H), 9.55 (dd, J = 4.8, 2.5 Hz, 1H), 8.91 (dd, J = 2.6, 0.5 Hz, 1H), 8.48 (d, J = 5.5 Hz, 1H), 7.91-7.73 (m, 1H), 6.77 (s, 2H), 2.61 (s, 3H). |
| I-C-5 | 349.0 | 2.48* | $^1$H NMR (500 MHz, CDCl3) δ7.53-7.55 (2H, m), 7.67-7.73 (3H, m), 7.87 (1H, s), 8.45-8.46 (1H, d), 7.61-8.62 (1H, d), 9.96 91H, s), 10.28 (1H, s). |
| I-C-6 | 370.0 | 0.74 | $^1$H NMR (500 MHz, DMSO-d6) δ 9.68 (s, 1H), 9.64 (s, 1H), 8.97-8.93 (m, 1H), 8.38 (d, J = 4.8 Hz, 1H), 8.03 (d, J = 2.0 Hz, 1H), 7.62-7.55 (m, 3H), 7.54-7.50 (m, 2H), 7.33 (dd, J = 4.8, 0.7 Hz, 1H), 6.68 (s, 2H), 4.06 (s, 2H). |
| I-C-7 | 328.1 | 0.49 | $^1$H NMR (500 MHz, DMSO-d6) δ 9.56 (s, 1H), 9.53 (dd, J = 4.8, 2.6 Hz, 1H), 9.24 (s, 1H), 9.16 (s, 2H), 8.85 (dd, J = 2.6, 0.5 Hz, 1H), 8.30 (s, 1H), 6.73 (s, 2H), 4.49-4.34 (m, 2H), 3.57-3.49 (m, 2H), 3.04 (t, J = 6.2 Hz, 2H). |
| I-C-8 | 342.2 | 0.58 | $^1$H NMR (500 MHz, DMSO-d6) δ 10.05 (s, 1H), 9.59-9.47 (m, 2H), 9.24 (s, 1H), 8.83 (dd, J = 2.6, 0.5 Hz, 1H), 8.26 (s, 1H), 6.73 (s, 2H), 4.74-4.58 (m, 1H), 4.45-4.32 (m, 1H), 3.91-3.71 (m, 1H), 3.51-3.37 (m, 1H), 3.24-3.12 (m, 1H), 3.12-3.03 (m, 1H), 3.00 (s, 3H). |
| I-C-9 | 358.2 | 0.38 | $^1$H NMR (500 MHz, DMSO-d6) δ 9.54 (s, 1H), 9.50 (dd, J = 4.8, 2.5 Hz, 1H), 9.24 (s, 1H), 8.82 (d, J = 2.5 Hz, 1H), 8.10 (s, 1H), 6.75-6.67 (m, 3H), 4.77 (d, J = 14.9 Hz, 1H), 4.36 (d, J = 14.9 Hz, 1H), 3.73 (td, J = 11.5, 5.1 Hz, 1H), 3.61-3.49 (m, 1H), 3.25-3.15 (m, 1H), 3.02-2.90 (m, 1H). Methyl singlet hidden under water peak. |
| I-C-10 | 412.2 | 1.78* | $^1$H NMR (500 MHz, DMSO-d6) δ 10.55 (s, 1H), 9.62 (s, 1H), 9.55 (dd, J = 4.8, 2.5 Hz, 1H), 9.32 (s, 1H), 8.94 (d, J = 2.5 Hz, 1H), 8.46 (d, J = 5.2 Hz, 1H), 7.44 (d, J = 5.1 Hz, 1H), 6.75 (s, 2H), 4.89-4.71 (m, 4H), 4.51 (s, 1H), 3.59 (d, J = 11.8 Hz, 2H), 3.37-3.09 (m, 1H), 3.08-2.84 (m, 2H), 2.17 (d, J = 14.0 Hz, 2H), 1.97 (q, J = 13.2 Hz, 2H). |
| I-C-11 | 428.1 | 1.95* | $^1$H NMR (500 MHz, DMSO-d6) δ 10.37 (s, 1H), 9.53 (s, 1H), 9.48 (d, J = 2.2 Hz, 1H), 9.27 (s, 1H), 8.77 (d, J = 2.2 Hz, 1H), 8.44 (d, J = 5.2 Hz, 1H), 7.39 (d, J = 6.1 Hz, 1H), 6.78 (s, 2H), 4.79 (p, J = 8.0 Hz, 4H), 4.51 (s, 1H), 3.59 (s, 2H), 3.27-3.15 (m, 1H), 2.98 (d, J = 15.4 Hz, 2H), 2.16 (d, J = 14.0 Hz, 2H), 1.95 (q, J = 10.6, 8.2 Hz, 2H). |
| I-C-12 | 428.2 | 1.99* | $^1$H NMR (500 MHz, DMSO-d6) δ 9.56-9.52 (m, 2H), 9.45 (s, 1H), 8.93 (d, J = 2.5 Hz, 1H), 8.39 (s, 1H), 6.78 (s, 1H), 6.16 (s, 2H), 4.79 (s, 4H), 4.40-3.35 (very broad m, 7H). |
| I-C-13 | 430.2 | 1.82* | $^1$H NMR (500 MHz, DMSO-d6) δ 9.64 (s, 1H), 9.51 (dd, J = 4.8, 2.5 Hz, 1H), 9.03 (s, 1H), 8.83 (d, J = 2.5 Hz, 1H), 8.32 (d, J = 2.2 Hz, 1H), 6.71 (s, 2H), 4.55 (t, J = 6.5 Hz, 2H), 4.46 (t, J = 6.0 Hz, 2H), 3.52-3.43 (m, 1H), 3.09-2.91 (m, 1H), 2.86 (d, J = 10.9 Hz, 2H), 2.11 (q, J = 13.0, 12.4 Hz, 2H), 1.85 (t, J = 11.5 Hz, 2H), 1.77 (d, J = 12.3 Hz, 2H). |
| I-C-14 | 388.2 | 1.82* | $^1$H NMR (500 MHz, DMSO-d6) δ 9.57 (s, 1H), 9.53 (dd, J = 4.7, 2.5 Hz, 1H), 9.41 (s, 1H), 8.91 (d, J = 2.6 Hz, 1H), 8.86 (s, 1H), 8.40 (d, J = 2.3 Hz, 1H), 6.71 (s, 2H), 3.56 (d, J = 13.0 Hz, 2H), 3.16 (t, J = 12.2 Hz, 1H), 3.03 (q, J = 12.0, 11.5 Hz, 2H), 2.82 (d, J = 4.6 Hz, 3H), 2.26 (q, J = 13.8, 12.8 Hz, 2H), 2.08 (d, J = 13.7 Hz, 2H). |
| I-C-15 | 350.0 | 1.84* | $^1$H NMR (500 MHz, DMSO-d6) δ 6.8 (2H, br s), 7.68-7.69 (1H, d), 7.75-7.77 (1H, dd), 8.14-8.16 (1H, dd), 8.21-8.22 (1H, d), 8.56-8.57 (1H, dd), 8.82-8.83 (1H, d), 8.87-8.88 1H, d), 9.41-9.42 (1H, d), 9.67 (1H, s), 9.77 (1H, s). |
| I-C-16 | 481.3 | 1.80* | $^1$H NMR (DMSO-d6, 500 MHz) δ 1.42-1.65 (6H, m), 1.91 (2H, m), 2.10 (1H, m), 2.29 (3H, br s), 2.64-2.71 (2H, m), 2.89 (2H, m), 3.12-3.21 (3H, m), 4.09 (1H, m), 4.63 (1H, m), 6.72 (2H, br s), 7.34 (1H, d, J = 5 Hz), 8.29 (1H, d, J = 5 Hz), 8.93 (1H, m), 9.28 (1H, s), 9.51 (1H, dd) and 9.62 (1H, s) ppm. |
| I-C-17 | 482.2 | 1.85* | $^1$H NMR (500 MHz, DMSO-d6) δ 1.67-1.75 (2H, m), 1.87 (2H, m), 2.85 (3H, s), 3.01-3.22 (7H, m), 3.41 (2H, m), 3.69 (2H, m), 3.86 (2H, m), 6.77 (2H, br s), 7.65 (1H, d, J = 5 Hz), 8.47 (1H, d), 8.95 (1H, d), 9.49 (1H, s), 9.55 (1H, m), 9.83 (1H, s) and 9.95 (1H, br s) ppm. |

-continued

| Cmpd No. | LCMS ES+ | LCMS (Rt min) | HNMR |
|---|---|---|---|
| I-C-18 | 493.2 | 1.69* | $^1$H NMR (500 MHz, DMSO-d6) δ 1.50-1.59 (2H, m), 1.73 (6H, m), 1.87 (2H, m), 2.76 (6H, m), 2.93 (2H, m), 3.15 (1H, m), 4.61 (2H, m), 6.72 (2H, br s), 7.34 (1H, d), 8.29 (1H, d), 8.93 (1H, d), 9.26 (1H, s), 9.50 (1H, dd) and 9.62 (1H, s) ppm. |
| I-C-19 | 476.0 | 1.74* | $^1$H NMR (500 MHz, DMSO-d6) δ 9.93 (s, 1H), 9.70 (s, 1H), 9.53 (s, 1H), 9.42 (dd, J = 4.8, 2.5 Hz, 1H), 8.75 (dd, J = 2.2, 0.9 Hz, 1H), 8.49 (d, J = 4.9 Hz, 1H), 8.36-8.32 (m, 1H), 8.22 (dd, J = 8.0, 2.2 Hz, 1H), 7.90 (dd, J = 8.0, 0.9 Hz, 1H), 7.48 (dd, J = 4.9, 0.7 Hz, 1H), 6.70 (m, 2H), 4.68 (m, 1H), 4.07 (m, 1H), 3.59 (m, 1H), 3.44 (m, 2H), 3.16 (m, 3H), 2.87 (s, 3H). |
| I-C-20 | 364.0 | 1.92* | $^1$H NMR (500 MHz, DMSO-d6) δ 9.80 (s, 0H), 9.42 (dd, J = 4.8, 2.5 Hz, 0H), 9.35 (s, 0H), 8.86 (dd, J = 5.2, 1.6 Hz, 0H), 8.57 (d, J = 5.1 Hz, 0H), 8.07 (d, J = 2.5 Hz, 0H), 7.99 (d, J = 7.5 Hz, 0H), 7.68 (dd, J = 7.7, 5.2 Hz, 0H), 7.63 (d, J = 5.1 Hz, 0H), 2.35 (s, 1H). |
| I-C-21 | 448.0 | 1.94* | $^1$H NMR (500 MHz, DMSO-d6) δ 10.15 (s, 1H), 9.90 (s, 1H), 9.67 (s, 1H), 9.47 (dd, J = 4.8, 2.5 Hz, 1H), 8.55 (d, J = 5.4 Hz, 1H), 8.42 (dd, J = 2.5, 0.7 Hz, 1H), 8.30 (d, J = 2.5 Hz, 1H), 7.94 (dd, J = 8.8, 2.5 Hz, 1H), 7.69 (d, J = 5.4 Hz, 1H), 7.21 (dd, J = 9.0, 0.9 Hz, 1H), 4.60 (s, 2H), 3.59 (s, 2H), 3.28 (s, 2H), 3.13 (s, 2H), 2.89 (s, 3H). |
| I-C-22 | 364.0 | 1.97* | $^1$H NMR (500 MHz, DMSO-d6) δ 9.72 (s, 1H), 9.68 (s, 1H), 9.44 (dd, J = 4.8, 2.5 Hz, 1H), 8.81 (dd, J = 2.4, 0.9 Hz, 1H), 8.58 (d, J = 5.2 Hz, 1H), 8.25 (d, J = 2.5 Hz, 1H), 8.21 (dd, J = 8.1, 2.3 Hz, 1H), 7.76-7.72 (m, 1H), 7.69 (dd, J = 5.2, 0.6 Hz, 1H), 2.72 (s, 3H). |
| I-C-23 | 419.1 | 2.01* | $^1$H NMR (500 MHz, DMSO-d6) δ 1.86 (6H, s), 1.90-2.00 (2H, br m), 2.07 (2H, d), 2.79 (3H, s), 3.0-3.1 (1H, m), 3.52 (2H, br s), 6.63 (2H, s), 7.32 (1H, s), 8.40 (1H, d), 8.81 (1H, d), 9.09 (2H, d), 9.51 (1H, s). |
| I-C-24 | 350.0 | 1.80* | $^1$H NMR (500 MHz, DMSO-d6) δ 9.62 (s, 1H), 9.58 (s, 1H), 9.43 (dd, J = 4.8, 2.5 Hz, 1H), 8.91-8.86 (m, 2H), 8.54 (d, J = 5.1 Hz, 1H), 8.25 (d, J = 2.5 Hz, 1H), 7.77-7.72 (m, 2H), 7.59 (d, J = 5.0 Hz, 1H). |
| I-C-25 | 475.0 | 1.99* | $^1$H NMR (500 MHz, DMSO-d6) δ 10.34 (s, 1H), 9.80 (s, 1H), 9.66 (s, 1H), 9.40 (dd, J = 4.8, 2.5 Hz, 1H), 8.52 (d, J = 5.1 Hz, 1H), 8.36 (d, J = 2.5 Hz, 1H), 7.75-7.69 (m, 2H), 7.68-7.63 (m, 2H), 7.56 (d, J = 5.0 Hz, 1H), 6.72 (s, 2H), 4.65 (s, 2H), 3.0 to 4.0 (m, 6H), 2.86 (s, 3H). |
| I-C-26 | 351.0 | 1.47* | $^1$H NMR (500 MHz, DMSO-d6) δ 9.49 (s, 1H), 9.49 (s, 1H), 9.48 (dd, J = 5.3, 1.3 Hz, 1H), 9.44 (dd, J = 2.4, 1.2 Hz, 1H), 9.42 (dd, J = 4.8, 2.5 Hz, 1H), 8.50 (d, J = 4.9 Hz, 1H), 8.26 (d, J = 2.5 Hz, 1H), 7.98 (dd, J = 5.3, 2.4 Hz, 1H), 7.52 (dd, J = 5.0, 0.7 Hz, 1H), 6.66 (s, 1H). |
| I-C-27 | 380.0 | 2.23* | $^1$H NMR (500 MHz, DMSO-d6) δ 9.78 (s, 1H), 9.69 (s, 1H), 9.45 (dd, J = 4.8, 2.5 Hz, 1H), 8.55 (d, J = 5.3 Hz, 1H), 8.41 (dd, J = 2.6, 0.8 Hz, 1H), 8.18 (d, J = 2.5 Hz, 1H), 7.98 (dd, J = 8.6, 2.5 Hz, 1H), 7.69 (dd, J = 5.2, 0.6 Hz, 1H), 7.12 (dd, J = 8.6, 0.8 Hz, 1H), 3.99 (s, 3H). |
| I-C-28 | 351.0 | 1.58* | $^1$H NMR (500 MHz, DMSO-d6) δ 9.54 (s, 1H), 9.42 (dd, J = 4.8, 2.5 Hz, 1H), 9.40 (s, 1H), 9.05 (s, 2H), 8.26 (d, J = 2.5 Hz, 1H), 7.53 (d, J = 4.7 Hz, 1H), 6.68 (s, 2H). |
| I-C-29 | 364.0 | 1.95* | $^1$H NMR (500 MHz, DMSO-d6) δ 9.75 (s, 1H), 9.41 (dd, J = 4.8, 2.5 Hz, 1H), 9.22 (s, 1H), 8.80 (s, 1H), 8.71 (d, J = 5.0 Hz, 1H), 8.51 (d, J = 5.0 Hz, 1H), 8.03 (d, J = 2.6 Hz, 1H), 7.50-7.44 (m, 2H), 6.70 (bs, 1h), 2.12 (s, 3H). |
| I-C-30 | 364.0 | 1.97* | $^1$H NMR (500 MHz, DMSO-d6) δ 9.80 (d, J = 0.7 Hz, 1H), 9.41 (dd, J = 4.8, 2.5 Hz, 1H), 9.29 (s, 1H), 8.79 (d, J = 5.3 Hz, 1H), 8.59 (s, 1H), 8.52 (d, J = 5.0 Hz, 1H), 8.11 (d, J = 2.5 Hz, 1H), 7.75-7.68 (m, 1H), 7.54 (dd, J = 5.1, 0.7 Hz, 1H), 6.71 (s, 2H), 2.19 (d, J = 0.7 Hz, 3H). |
| I-C-31 | 365.0 | 1.58* | $^1$H NMR (500 MHz, DMSO-d6) δ 9.73 (d, J = 0.6 Hz, 1H), 9.41 (dd, J = 4.8, 2.5 Hz, 1H), 9.38 (d, J = 5.0 Hz, 1H), 9.21 (s, 1H), 8.53 (d, J = 5.0 Hz, 1H), 2.45 (s, 3H). |
| I-C-32 | 366.0 | 1.53* | $^1$H NMR (500 MHz, DMSO-d6) δ 12.15 (s, 1H), 9.61 (s, 1H), 9.52 (s, 1H), 9.43 (dd, J = 4.8, 2.6 Hz, 1H), 8.46 (s, 1H), 8.42 (d, J = 5.0 Hz, 1H), 7.78-7.60 (m, 2H), 7.45 (d, J = 5.1 Hz, 1H), 6.70 (s, 2H), 6.43 (t, J = 6.6 Hz, 1H). |

-continued

Compound Analytical Data

| Cmpd No. | LCMS ES+ | LCMS (Rt min) | HNMR |
|---|---|---|---|
| I-C-33 | 365.0 | 1.58* | $^1$H NMR (500 MHz, DMSO-d6) δ 9.82 (s, 1H), 9.59 (s, 1H), 9.40 (dd, J = 4.8, 2.5 Hz, 1H), 9.37 (d, J = 5.3 Hz, 1H), 8.56 (d, J = 5.0 Hz, 1H), 8.19 (d, J = 2.5 Hz, 1H), 7.87 (dd, J = 5.1, 1.0 Hz, 1H), 7.71-7.62 (m, 1H), 2.21 (d, J = 0.8 Hz, 3H). |
| I-C-34 | 382.0 | 2.24* | $^1$H NMR (500 MHz, DMSO-d6) δ 9.77 (s, 1H), 9.44 (dd, J = 4.8, 2.5 Hz, 1H), 9.35 (s, 1H), 8.53 (d, J = 5.1 Hz, 1H), 8.03 (d, J = 2.5 Hz, 1H), 7.98 (t, J = 8.2 Hz, 1H), 7.57 (d, J = 5.1 Hz, 1H), 7.33-7.26 (m, 1H), 2.23 (s, 3H). |
| I-C-35 | 368.0 | 2.03* | $^1$H NMR (500 MHz, DMSO-d6) δ 9.71 (s, 1H), 9.47 (s, 1H), 9.43 (dd, J = 4.8, 2.5 Hz, 1H), 8.55 (ddd, J = 4.9, 1.9, 1.0 Hz, 1H), 8.51 (d, J = 5.0 Hz, 1H), 8.19 (ddd, J = 9.6, 7.4, 2.0 Hz, 1H), 8.15 (d, J = 2.5 Hz, 1H), 7.65 (ddd, J = 7.1, 4.9, 1.9 Hz, 1H), 7.59 (d, J = 5.0 Hz, 1H). |
| I-C-36 | 364.0 | 2.03* | $^1$H NMR (500 MHz, DMSO-d6) δ 9.94 (s, 1H), 9.78 (s, 1H), 9.40 (dd, J = 4.8, 2.5 Hz, 1H), 8.77 (ddd, J = 4.8, 1.7, 0.8 Hz, 1H), 8.55 (d, J = 5.2 Hz, 1H), 8.36 (d, J = 2.5 Hz, 1H), 7.95 (ddd, J = 7.8, 1.6, 0.8 Hz, 1H), 7.71 (d, J = 5.1 Hz, 1H), 7.60 (dd, J = 7.8, 4.8 Hz, 1H), 2.22 (s, 3H). |
| I-C-37 | 384.0 | 2.08* | $^1$H NMR (500 MHz, DMSO-d6) δ 9.77 (s, 1H), 9.42 (dd, J = 4.8, 2.5 Hz, 1H), 9.34 (s, 1H), 8.74 (dd, J = 4.8, 1.9 Hz, 1H), 8.51 (d, J = 5.0 Hz, 1H), 8.07-8.00 (m, 2H), 7.72 (dd, J = 7.5, 4.8 Hz, 1H), 7.55 (d, J = 5.0 Hz, 1H). |
| I-C-38 | 497.2 | 2.02* | $^1$H NMR (500 MHz, DMSO-d6) δ 9.58 (s, 1H), 9.46 (s, 1H), 9.32 (dd, J = 4.7, 2.5 Hz, 1H), 8.61 (s, 1H), 8.31 (s, 1H), 6.08 (dt, J = 3.3, 1.9 Hz, 1H), 4.29 (q, J = 2.9 Hz, 2H), 3.82 (t, J = 5.6 Hz, 2H), 3.49 (s, 1H), 3.01 (s, 3H), 2.80 (s, 3H), 2.44 (d, J = 6.3 Hz, 3H), 1.90 (s, 4H). |
| I-C-39 | 490.0 | 1.89* | $^1$H NMR (500 MHz, DMSO-d6) δ 10.13 (s, 1H), 9.86 (s, 1H), 9.39 (dd, J = 4.8, 2.5 Hz, 1H), 9.31 (s, 1H), 8.51 (s, 1H), 8.29 (s, 1H), 7.96 (d, J = 7.8 Hz, 1H), 7.72 (d, J = 7.7 Hz, 1H), 7.46 (d, J = 4.8 Hz, 1H), 6.72 (s, 2H), 4.70 (s, 1H), 4.02 (s, 1H), 3.33 (d, J = 118.2 Hz, 5H), 2.87 (s, 3H), 2.28 (s, 3H). |
| I-C-40 | 462.0 | 2.33* | $^1$H NMR (500 MHz, DMSO-d6) δ 9.72 (s, 1H), 9.47 (s, 1H), 9.40 (dd, J = 4.8, 2.5 Hz, 1H), 8.35 (d, J = 4.8 Hz, 1H), 7.98 (d, J = 2.5 Hz, 1H), 7.39 (d, J = 8.6 Hz, 1H), 7.27 (dd, J = 4.8, 0.7 Hz, 1H), 6.84 (d, J = 8.4 Hz, 1H), 6.70 (s, 2H), 3.63 (d, J = 33.6 Hz, 4H), 2.47 (s, 4H), 2.28 (s, 3H), 2.08 (s, 3H). |
| I-C-41 | 463.0 | 2.35* | $^1$H NMR (500 MHz, DMSO-d6) δ 9.68 (s, 1H), 9.41 (dd, J = 4.8, 2.5 Hz, 1H), 9.32 (s, 1H), 8.38 (d, J = 4.8 Hz, 1H), 7.95 (d, J = 2.5 Hz, 1H), 7.59 (d, J = 8.3 Hz, 1H), 7.31 (dd, J = 4.8, 0.7 Hz, 1H), 6.85 (dd, J = 8.4, 0.8 Hz, 1H), 6.71 (s, 2H), 2.86 (dd, J = 10.5, 6.1 Hz, 1H), 2.73 (td, J = 8.2, 5.7 Hz, 1H), 2.69-2.62 (m, 1H), 2.41 (td, J = 7.9, 6.1 Hz, 1H), 2.37-2.31 (m, 0H), 2.29 (s, 3H), 2.15 (s, 3H), 1.93-1.83 (m, 1H). |
| I-C-42 | 313.0 | 2.22* | $^1$H NMR (500 MHz, DMSO-d6) δ 10.29 (s, 1H), 9.61 (s, 1H), 9.52 (dd, J = 4.7, 2.5 Hz, 1H), 8.92 (d, J = 2.5 Hz, 1H), 8.51-8.40 (m, 1H), 7.58 (d, J = 5.6 Hz, 1H), 6.77 (s, 2H), 2.18 (tt, J = 8.4, 5.2 Hz, 1H), 1.39-1.33 (m, 2H), 1.01-0.94 (m, 2H). |
| I-C-43 | 493.0 | 2.22* | $^1$H NMR (500 MHz, DMSO-d6) δ 9.64 (s, 1H), 9.39 (s, 1H), 9.22 (dd, J = 4.7, 2.5 Hz, 1H), 8.42 (s, 1H), 8.35 (dd, J = 2.5, 0.6 Hz, 1H), 7.69-7.54 (m, 4H), 6.49 (s, 2H), 3.66 (s, 4H), 2.74 (s, 4H), 2.48 (s, 3H). |
| I-C-44 | 461.0 | 1.79* | $^1$H NMR (500 MHz, DMSO-d6) δ 9.70 (s, 1H), 9.54 (s, 1H), 9.37 (dd, J = 4.8, 2.5 Hz, 1H), 8.41-8.38 (m, 2H), 7.59 (d, J = 8.4 Hz, 2H), 7.57-7.53 (m, 2H), 7.37 (dd, J = 4.8, 0.7 Hz, 1H), 6.69 (s, 2H), 3.62 (s, 2H), 2.73 (d, J = 55.4 Hz, 4H). |
| I-C-45 | 489.0 | 2.16* | $^1$H NMR (500 MHz, DMSO-d6) δ 9.82 (s, 1H), 9.34 (dd, J = 4.8, 2.5 Hz, 1H), 9.27 (s, 1H), 8.39 (s, 1H), 8.39 (d, J = 1.9 Hz, 1H), 7.54-7.48 (m, 1H), 7.41 (dd, J = 7.7, 1.6 Hz, 1H), 7.33 (d, J = 7.7 Hz, 1H), 7.30 (dd, J = 4.7, 0.7 Hz, 1H), 6.68 (s, 2H), 3.73 (bs, 2H), 3.42 (bs, 2H), 2.45-2.30 (m, 4H), 2.08 (s, 3H). |
| I-C-46 | 510.0 | 2.00* | $^1$H NMR (500 MHz, DMSO-d6) δ 9.78 (d, J = 0.7 Hz, 1H), 9.61 (s, 1H), 9.41 (dd, J = 4.8, 2.5 Hz, 1H), 8.93 (d, J = 1.8 Hz, 1H), 8.53 (dd, J = 2.6, 0.6 Hz, 1H), 8.50 (d, J = 4.9 Hz, 1H), 8.36 (d, J = 1.8 Hz, 1H), 7.53 (dd, J = 5.0, 0.7 Hz, 1H), 6.71 (s, 2H), 2.86 (s, 3H). |
| I-C-47 | 460.1 | 2.13* | $^1$H NMR (500 MHz, methanol-d4) δ 1.09-1.15 (4H, m), 1.99 (2H, m), 2.15-2.17 (2H, m), 2.64-2.69 (1H, m), 3.17-3.19 (2H, m), 3.31-3.34 (1H, masked), 4.03-4.06 (2H, m), |

Compound Analytical Data

| Cmpd No. | LCMS ES+ | LCMS (Rt min) | HNMR |
|---|---|---|---|
| | | | 7.94-7.95 (1H, d), 8.50-8.51 (1H, d), 8.78 (1H, dd), 9.13-9.14 (1H, dd), 9.74 (1H, s). |
| I-C-48 | 501.0 | 2.01* | ¹H NMR (500 MHz, DMSO-d6) δ 10.27 (s, 1H), 9.77 (s, 1H), 9.61 (s, 1H), 9.40 (dd, J = 4.8, 2.5 Hz, 1H), 8.46 (d, J = 4.9 Hz, 1H), 8.41 (s, 1H), 7.71 (d, J = 7.7 Hz, 2H), 7.63 (d, J = 8.4 Hz, 2H), 7.46 (d, J = 5.0 Hz, 1H), 6.72 (bs, 2H), 4.85 (s, 1H), 4.09 (s, 1H), 3.77 (t, J = 5.6 Hz, 1H), 3.58 (s, 1H), 3.45 (s, 2H), 3.33 (s, 1H), 2.20 (d, J = 69.6 Hz, 4H), 1.96 (s, 1H). |
| I-C-49 | 517.0 | 1.93* | ¹H NMR (500 MHz, DMSO-d6) δ 9.69 (s, 1H), 9.53 (s, 1H), 9.38 (dd, J = 4.8, 2.5 Hz, 1H), 8.44-8.32 (m, 2H), 7.64-7.59 (m, 2H), 7.59-7.53 (m, 2H), 7.37 (dd, J = 4.8, 0.7 Hz, 1H), 6.69 (s, 2H), 4.56 (t, J = 6.5 Hz, 2H), 4.46 (t, J = 6.0 Hz, 2H), 3.73 (s, 2H), 3.47 (t, J = 6.2 Hz, 1H), 3.40 (d, J = 5.8 Hz, 2H), 2.38 (d, J = 6.0 Hz, 2H), 2.27 (s, 2H). |
| I-C-50 | 519.0 | 2.08* | ¹H NMR (500 MHz, DMSO-d6) δ 9.73 (s, 1H), 9.42 (s, 1H), 9.39 (dd, J = 4.8, 2.5 Hz, 1H), 8.46-8.38 (m, 2H), 7.63-7.54 (m, 2H), 7.45 (dd, J = 7.8, 1.5 Hz, 1H), 7.42 (dd, J = 4.8, 0.7 Hz, 1H), 6.70 (s, 2H), 4.57 (t, J = 6.5 Hz, 2H), 4.47 (t, J = 6.1 Hz, 2H), 3.73 (s, 2H), 3.49 (m, 2H), 3.39 (m, 2H), 2.46-2.35 (m, 3H), 2.29 (m, 2H). |
| I-C-51 | 535.0 | 2.00* | ¹H NMR (500 MHz, DMSO-d6) δ 9.73 (s, 1H), 9.42 (s, 1H), 9.39 (dd, J = 4.8, 2.5 Hz, 1H), 8.46-8.39 (m, 2H), 7.62-7.55 (m, 2H), 7.48-7.40 (m, 2H), 6.70 (s, 2H), 4.57 (t, J = 6.5 Hz, 2H), 4.47 (t, J = 6.0 Hz, 2H), 3.73 (s, 2H), 3.49 (s, 1H), 3.39 (s, 2H), 2.40 (s, 2H), 2.29 (s, 2H). |
| I-C-52 | 518.0 | 1.7* | ¹H NMR (500 MHz, DMSO-d6) δ 9.67 (s, 1H), 9.49 (s, 1H), 9.39 (dd, J = 4.8, 2.5 Hz, 1H), 8.71 (dd, J = 2.1, 0.8 Hz, 1H), 8.44 (d, J = 4.9 Hz, 1H), 8.38 (d, J = 2.5 Hz, 1H), 8.13 (dd, J = 8.0, 2.2 Hz, 1H), 7.80 (dd, J = 8.0, 0.9 Hz, 1H), 7.45 (d, J = 4.9 Hz, 1H), 6.69 (s, 2H), 4.56 (t, J = 6.5 Hz, 2H), 4.47 (t, J = 6.1 Hz, 2H), 3.76 (s, 2H), 3.58-3.40 (m, 3H), 2.42 (s, 2H), 2.29 (s, 2H). |
| I-C-53 | 530.0 | 1.98* | ¹H NMR (500 MHz, DMSO-d6) δ 9.68 (s, 1H), 9.50 (s, 1H), 9.40 (dd, J = 4.8, 2.5 Hz, 1H), 8.70 (dd, J = 2.2, 0.9 Hz, 1H), 8.43 (d, J = 4.8 Hz, 1H), 8.41-8.40 (m, 1H), 8.12 (dd, J = 8.0, 2.2 Hz, 1H), 7.78 (dd, J = 8.0, 0.9 Hz, 1H), 7.45 (dd, J = 4.8, 0.7 Hz, 1H), 6.69 (s, 2H), 4.37 (d, J = 12.1 Hz, 1H), 3.64 (d, J = 12.6 Hz, 1H), 3.18-3.03 (m, 2H), 2.56 (s, 4H), 2.37 (s, 1H), 1.98 (d, J = 12.1 Hz, 1H), 1.80 (d, J = 10.1 Hz, 1H), 1.71 (d, J = 6.2 Hz, 4H), 1.47 (td, J = 20.6, 17.0, 10.5 Hz, 2H). |
| I-C-54 | 516.2 | 1.98* | ¹H NMR (500 MHz, DMSO-d6) δ 11.57 (s, 1H), 10.33 (s, 1H), 9.68 (s, 1H), 9.43 (dd, J = 4.8, 2.6 Hz, 1H), 8.96 (dd, J = 2.2, 0.9 Hz, 1H), 8.87 (d, J = 2.5 Hz, 1H), 8.52 (d, J = 5.2 Hz, 1H), 8.09 (dd, J = 8.1, 2.2 Hz, 1H), 8.04 (dd, J = 8.1, 0.9 Hz, 1H), 7.85 (d, J = 5.2 Hz, 1H), 6.73 (s, 2H), 4.60 (s, 1H), 4.16 (s, 2H), 4.06 (s, 2H), 3.69 (s, 1H), 3.55-3.38 (m, 1H), 3.17 (d, J = 7.9 Hz, 1H), 2.90 (s, 1H), 2.45 (dt, J = 11.6, 9.3 Hz, 1H), 2.24 (ddd, J = 12.4, 7.8, 4.6 Hz, 1H), 2.07 (d, J = 11.5 Hz, 1H), 1.89 (s, 1H), 1.37 (s, 2H). |
| I-C-55 | 353.0 | 1.66* | ¹H NMR (500 MHz, DMSO-d6) δ 10.81 (s, 1H), 9.72 (d, J = 0.6 Hz, 1H), 9.40 (dd, J = 4.9, 2.6 Hz, 1H), 8.67 (d, J = 2.6 Hz, 1H), 8.42 (d, J = 4.9 Hz, 1H), 7.59 (dd, J = 5.0, 0.7 Hz, 1H), 7.48 (d, J = 1.2 Hz, 1H), 7.37 (d, J = 1.2 Hz, 1H), 6.71 (s, 2H), 3.72 (s, 3H). |
| I-C-56 | 353.0 | 1.66* | ¹H NMR (500 MHz, DMSO-d6) δ 9.86-9.70 (m, 1H), 9.35-9.28 (m, 1H), 8.52 (d, J = 4.9 Hz, 1H), 8.50 (dd, J = 2.5, 0.5 Hz, 1H), 8.08 (d, J = 1.5 Hz, 1H), 7.60 (dd, J = 5.0, 0.7 Hz, 1H), 3.69 (d, J = 0.6 Hz, 3H). |
| I-C-57 | 353.1 | 1.88* | ¹H NMR (500 MHz, DMSO-d6) δ 3.65 (3H, s), 6.55 (1H, d), 6.71 (2H, br s), 7.44 (1H, m), 7.75 (1H, m), 8.35 (1H, m), 8.42 (1H, m), 9.41 (1H, m), 9.56 (1H, s) and 9.77 (1H, s) ppm. |
| I-C-58 | 380.0 | 1.67* | ¹H NMR (500 MHz, DMSO-d6) δ 3.16 (3H, s), 6.34 (1H, m), 6.70 (1H, m), 7.53 (1H, m), 7.59-7.62 (1H, m), 8.24 (1H, m), 8.49 (1H, d), 9.39 (1H, s), 9.45 (1H, m) and 9.79 (1H, s) ppm. |
| I-C-59 | 380.1 | 1.52* | ¹H NMR (500 MHz, DMSO-d6) δ 3.47 (3H, s), 6.57 (1H, m), 6.72 (2H, br s), 7.36 (1H, m), 7.58 (1H, m), 8.06 (1H, m), 8.26 (1H, m), 8.36 (1H, m), 9.44 (1H, m) and 9.52 (1H, s) ppm. |
| I-C-60 | 350.0 | 1.98* | ¹H NMR (500 MHz, DMSO-d6) δ 6.73 (2H, br s), 7.54 (1H, m), 7.72 (1H, m), 7.96 (1H, m), 8.04 (1H, m), 8.42 (1H, m), |

-continued

Compound Analytical Data

| Cmpd No. | LCMS ES+ | LCMS (Rt min) | HNMR |
|---|---|---|---|
| | | | 8.89 (1H, m), 9.40 (1H, m), 9.58 (1H, s) and 11.85 (1H, s) ppm. |
| I-C-61 | 427.0 | 1.98* | $^1$H NMR (500 MHz, DMSO-d6) δ 3.37 (3H, s), 6.70 (2H, br s), 7.40 (1H, m), 7.81 (2H, m), 8.14-8.17 (2H, m), 8.43 (1H, m), 9.39 (1H, m), 9.47 (1H, s) and 9.64 (1H, s) ppm. |
| I-C-62 | 365.0 | 1.74* | $^1$H NMR (500 MHz, DMSO-d6) δ 9.92 (s, 1H), 9.83 (s, 1H), 9.43 (dd, J = 4.8, 2.5 Hz, 1H), 8.88 (dd, J = 2.5, 0.8 Hz, 1H), 8.86 (d, J = 2.5 Hz, 1H), 8.66 (d, J = 5.4 Hz, 1H), 8.40 (d, J = 2.5 Hz, 1H), 7.96 (d, J = 5.3 Hz, 1H), 6.67 (s, 2H), 2.46 (d, J = 0.7 Hz, 3H). |
| I-C-63 | 367.8 | 1.83* | $^1$H NMR (500 MHz, DMSO-d6) δ 2.06 (3H, s), 3.88 (3H, s), 6.72 (2H, br s), 7.27 (1H, m), 7.91 (1H, s), 8.30 (1H, m), 8.37 (1H, m), 9.42 (1H, m) and 9.59 (2H, m) ppm. |
| I-C-64 | 468.0 | 2.29* | $^1$H NMR (500 MHz, DMSO-d6) δ 2.02-2.08 (2H, m), 3.78 (4H, m), 6.69 (2H, br s), 7.44 (1H, m), 7.82 (2H, m), 8.01 (2H, m), 8.21 (1H, m), 8.44 (1H, m), 9.40 (1H, m), 9.48 (1H, s) and 9.57 (1H, s) ppm. |
| I-C-65 | 354.0 | 1.51* | $^1$H NMR (500 MHz, DMSO-d6) δ 10.41 (s, 1H), 9.82 (d, J = 0.7 Hz, 1H), 9.43 (dd, J = 4.9, 2.5 Hz, 1H), 8.67 (d, J = 2.5 Hz, 1H), 8.55 (d, J = 5.1 Hz, 1H), 8.44 (s, 1H), 7.84-7.79 (m, 1H), 6.75 (s, 1H), 3.91 (s, 3H). |
| I-C-66 | 448.1 | 2.26* | $^1$H NMR (500 MHz, DMSO-d6) δ 9.59 (s, 1H), 9.52 (s, 1H), 9.40 (dd, J = 4.8, 2.5 Hz, 1H), 8.37 (d, J = 4.8 Hz, 1H), 8.23 (d, J = 2.5 Hz, 1H), 7.58-7.53 (m, 2H), 7.49 (d, J = 8.2 Hz, 2H), 7.34 (dd, J = 4.8, 0.7 Hz, 1H), 6.70 (s, 2H), 3.90-3.80 (m, 1H), 3.72-3.62 (m, 2H), 3.17 (dd, J = 10.2, 3.3 Hz, 1H), 2.85 (dt, J = 11.8, 1.9 Hz, 1H), 2.32 (td, J = 11.7, 3.4 Hz, 1H), 1.98 (d, J = 11.0 Hz, 3H). |
| I-C-67 | 365.1 | 1.69* | $^1$H NMR (500 MHz, DMSO-d6) δ 9.90 (s, 1H), 9.76 (s, 1H), 9.46-9.39 (m, 2H), 9.00 (d, J = 0.9 Hz, 1H), 8.61 (d, J = 5.2 Hz, 1H), 8.41 (d, J = 2.5 Hz, 1H), 7.82 (d, J = 5.2 Hz, 1H), 6.68 (s, 2H), 2.23 (t, J = 0.7 Hz, 3H). |
| I-C-68 | 353.1 | 1.93* | 1H NMR (500 MHz, DMSO-d6) δ 11.31 (s, 1H), 9.49-9.36 (m, 2H), 8.86 (d, J = 2.6 Hz, 1H), 8.32 (d, J = 5.1 Hz, 1H), 7.90 (d, J = 2.3 Hz, 1H), 7.74 (d, J = 5.1 Hz, 1H), 6.93 (d, J = 2.3 Hz, 1H), 6.74 (s, 2H), 3.92 (s, 3H). |
| I-C-69 | 398.0 | 1.76* | $^1$H NMR (500 MHz, DMSO-d6) δ 9.88 (s, 1H), 9.53-9.55 (m, 2H), 8.99 (dd, 1H), 8.50 (d, 1H), 7.71-7.73 (d, 1H), 6.80 3(s, 2H), 4.63-4.66 (m, 1H), 4.03-4.05 (m, 1H), 3.25-3.28 (m, 2H), 2.70-2.75 (m, 1H), 2.06 (s, 3H), 1.85-1.95 (m, 2H), 1.75-1.80 (m, 1H), 1.55-1.60 (m, 1H). |
| I-C-70 | 424.0 | 2.04* | $^1$H NMR (500 MHz, DMSO-d6) δ 9.90 (s, 1H), 9.53-9.55 (m, 2H), 9.00 (dd, 1H), 8.50 (dd, 1H), 7.73-7.74 (d, 1H), 6.80 3(s, 2H), 4.65-4.70 (m, 1H), 4.50-4.55 (m, 1H), 3.25-3.33 (m, 2H), 2.85-2.88 (m, 1H), 1.85-2.06 (m, 3H), 1.55-1.80 (m, 2H), 0.71-0.77 (m, 4H). |
| I-C-71 | 449.0 | 2.07* | — |
| I-C-72 | 354.1 | 1.61* | $^1$H NMR (500 MHz, DMSO-d6) δ 9.72 (d, J = 0.7 Hz, 1H), 9.48 (s, 1H), 9.45 (dd, J = 4.8, 2.6 Hz, 1H), 8.49 (d, J = 4.9 Hz, 1H), 8.24 (d, J = 2.5 Hz, 1H), 8.06 (s, 1H), 7.56 (dd, J = 4.9, 0.7 Hz, 1H), 6.71 (s, 2H), 3.91 (s, 3H). |
| I-C-73 | 384.1 | 1.58* | $^1$H NMR (500 MHz, DMSO-d6) δ 9.72 (s, 1H), 9.53 (dd, J = 4.8, 2.5 Hz, 1H), 9.34 (s, 1H), 8.69 (d, J = 2.5 Hz, 1H), 8.47 (d, J = 5.4 Hz, 1H), 7.58 (d, J = 5.2 Hz, 1H), 6.73 (s, 2H), 3.38 (dt, J = 12.4, 4.5 Hz, 2H), 2.91 (s, 3H), 2.70-2.62 (m, 1H), 2.49-2.45 (m, 1H), 2.15-2.08 (m, 2H). |
| I-C-74 | 326.1 | 1.97* | $^1$H NMR (500 MHz, DMSO-d6) δ 10.02 (s, 1H), 9.51-9.52 (dd, 1H), 9.11 (s, 1H), 9.00 (dd, 1H), 8.70 (s, 1H), 7.70 (s, 1H), 6.74-6.75 (m, 3H), 3.97 (s, 3H). |
| I-C-75 | 343.1 | 1.81* | $^1$H NMR (500 MHz, DMSO-d6) δ 9.87 (s, 1H), 9.53 (dd, 1H), 9.39 (s, 1H), 8.91 (dd, 1H), 8.48 (d, 1H), 7.68 (d, 1H), 6.74 (s, 2H), 4.09 (dd, 1H), 3.97-3.88 (m, 3H), 3.81-3.76 (m, 1H), 2.61-2.53 (m, 1H), 2.04-1.97 (m, 1H). |
| I-C-76 | 370.0 | 1.53* | run in D6-DMSO |
| I-C-77 | 367.1 | 1.68* | $^1$H NMR (500 MHz, DMSO) δ 15.03 (s, 1H), 9.76 (d, J = 0.7 Hz, 1H), 9.52-9.46 (m, 2H), 8.55 (d, J = 2.5 Hz, 1H), 8.51 (d, J = 4.8 Hz, 1H), 8.02 (s, 1H), 7.52 (dd, J = 4.9, 0.7 Hz, 1H), 6.75 (s, 2H), 3.49 (s, 3H), 2.72 (s, 3H). |
| I-C-78 | 367.1 | 1.71* | $^1$H NMR (500 MHz, DMSO) δ? 9.80 (d, J = 0.7 Hz, 1H), 9.56 (s, 1H), 9.42 (dd, J = 4.8, 2.6 Hz, 1H), 8.40 (d, J = 4.8 Hz, 1H), 8.33 (d, J = 2.5 Hz, 1H), 7.91 (s, 1H), 7.39 (dd, J = 4.8, 0.7 Hz, 1H), 6.71 (s, 2H), 3.40 (s, 3H), 1.97 (s, 3H). |

-continued

Compound Analytical Data

| Cmpd No. | LCMS ES+ | LCMS (Rt min) | HNMR |
|---|---|---|---|
| I-C-79 | 371.0 | 1.84* | $^1$H NMR (500 MHz, DMSO-d6) 9.70 (s, 2H), 09.44 (dd, 1H), 8.47 (s, 1H), 8.32 (d, 1H), 8.08 (dd, 1H), 7.26 (d, 1H), 6.79-6.64 (m, 2H), 3.47 (s, 3H). |
| I-C-80 | 367.1 | 1.76* | $^1$H NMR (500 MHz, DMSO-d6) 9.76 (s, 1H), 9.59 (s, 1H), 9.41-9.43 (m, 1H), 8.40 (d, 1H), 8.33 (d, 1H), 8.07 (d, 1H), 7.40 (m, 1H), 7.13 (d, 1H), 6.71 (s, 2H), 3.79-3.83 (qd, 2H), 1.09-1.12 (t, 3H). |
| I-C-81 | 383.1 | 1.7* | $^1$H NMR (500 MHz, Methanol-d4) 3.90 (d, 1H), 9.08 (s, 1H), 8.91 (d, 1H), 8.30 (s, 1H), 8.24 (s, 1H), 7.78 (s, 1H), 3.91 (s, 3H), 3.65 (s, 3H). |
| I-C-82 | 380.1 | 1.92* | $^1$H NMR (500 MHz, DMSO-d6) δ 9.49 (s, 1H0, 9.39-9.40 (d, 1H), 9.32 (s, 1H), 8.87-8.89 (d, 1H), 8.69 (dd, 1H), 8.41 (s, 1H), 8.08 (d, 1H0, 8.02-8.05 (m, 1H0, 7.78-7.80 (m, 1H0, 6.80 (br s, 2H), 3.89 (s, 3H). |
| I-C-83 | 397.1 | 1.69* | $^1$H NMR (500 MHz, CDCl3) δ 9.95 (s, 1H), 9.60 (s, 1H), 8.53 (m, 1H0, 8.47-8.48 (m, 1H), 8.43-8.44 (m, 1H), 8.38 (m, 1H), 7.93 (s, 1H), 7.20-7.30 (masked, 2H), 5.73 (s, 2H), 3.91-3.93 (t, 2H), 3.40-3.42 (t, 2H), 3.14 (s, 3H). |
| I-C-84 | 343.1 | 2.3* | — |

Retention times measured using HPLC Method B, described in the Experimental Methods and Materials section, above., are designated by (*). For all other compounds, the retention time was measured using the HPLC Method A.

Example 19: Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum ($J^R$ H Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0 cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 20: ATR Inhibition Assay

Compounds were screened for their ability to inhibit ATR kinase using a radioactive-phosphate incorporation assay. Assays were carried out in a mixture of 50 mM Tris/HCl (pH 7.5), 10 mM $MgCl_2$ and 1 mM DTT. Final substrate concentrations were 10 µM [γ-33P]ATP (3 mCi 33P ATP/mmol ATP, Perkin Elmer) and 800 µM target peptide (ASEL-PASQPQPFSAKKK) (SEQ ID NO:1).

Assays were carried out at 25° C. in the presence of 5 nM full-length ATR. An assay stock buffer solution was prepared containing all of the reagents listed above, with the exception of ATP and the test compound of interest. 13.5 µL of the stock solution was placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate was pre-incubated for 10 minutes at 25° C. and the reaction initiated by addition of 15 µL [γ-33P]ATP (final concentration 10 µM).

The reaction was stopped after 24 hours by the addition of 30 µM phosphoric acid containing 2 mM ATP. A multiscreen phosphocellulose filter 96-well plate (Millipore, Cat no. MAPHNOB50) was pretreated with 100 µL 0.2M phosphoric acid prior to the addition of 45⍴ of the stopped assay mixture. The plate was washed with 5×200⍴ 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0 cx for Macintosh, GraphPad Software, San Diego Calif., USA).

Table 5, below, shows the ATR Inhibition Ki values of compounds of the disclosure. Compounds with a Ki value of <0.01 µM are marked with "+++." Compounds with a Ki value >0.01 µM but <1 µM are marked with "++." Compounds with a Ki value >1 µM but <5 µM are marked with "+."

TABLE 5

| Cmpd. # | ATR Ki |
| --- | --- |
| I-N-1 | ++ |
| I-N-2 | ++ |
| I-N-3 | ++ |
| I-N-4 | ++ |
| I-N-5 | ++ |
| I-N-6 | ----- |
| I-N-7 | ++ |
| I-N-8 | + |
| I-N-9 | + |
| I-N-10 | ++ |
| I-N-11 | ++ |
| I-N-12 | ++ |
| I-N-13 | ++ |
| I-N-14 | ++ |
| I-N-15 | ++ |
| I-N-16 | ++ |
| I-N-17 | ++ |
| I-N-18 | ++ |
| I-N-19 | ++ |
| I-N-20 | ++ |
| I-N-21 | ++ |
| I-N-22 | ++ |
| I-N-23 | ++ |
| I-N-24 | ++ |
| I-N-25 | ++ |
| I-N-26 | ++ |
| I-N-27 | ++ |
| I-N-28 | ++ |
| I-N-29 | ++ |
| I-N-30 | ++ |
| I-N-31 | + |
| I-N-32 | ++ |
| I-N-33 | ++ |
| I-N-34 | + |
| I-N-35 | + |
| I-N-36 | + |
| I-N-37 | + |
| I-N-38 | ++ |
| I-N-39 | ++ |
| I-N-40 | ++ |
| I-N-41 | ++ |
| I-N-42 | ++ |
| I-N-43 | ++ |
| I-N-44 | ++ |
| I-N-45 | ++ |
| I-N-46 | ++ |
| I-N-47 | ++ |
| I-N-48 | ++ |
| I-N-49 | ++ |
| I-N-50 | ++ |
| I-N-51 | ++ |
| I-N-52 | + |
| I-N-53 | ++ |
| I-N-54 | ++ |
| I-N-55 | ++ |
| I-N-56 | ++ |
| I-N-57 | ++ |
| I-N-58 | ++ |
| I-N-59 | ++ |
| I-N-60 | ++ |
| I-N-61 | ++ |
| I-N-62 | ++ |
| I-N-63 | ++ |
| I-N-64 | ++ |
| I-N-65 | ++ |
| I-N-66 | ++ |
| I-N-67 | ++ |
| I-N-68 | ++ |
| I-N-69 | ++ |
| I-N-70 | ++ |
| I-N-71 | ++ |
| I-N-72 | ++ |
| I-N-73 | ++ |
| I-N-74 | ++ |
| I-N-75 | ++ |
| I-N-76 | + |
| I-N-77 | ++ |
| I-N-78 | ++ |
| I-N-79 | ++ |
| I-N-80 | ++ |
| I-N-81 | ++ |
| I-N-82 | +++ |
| I-N-83 | +++ |
| I-N-84 | +++ |
| I-N-85 | ++ |
| I-N-86 | ++ |
| I-N-87 | ++ |
| I-N-88 | ++ |
| I-N-89 | ++ |
| I-N-90 | ++ |
| I-N-91 | +++ |
| I-N-92 | + |
| I-N-93 | ++ |
| I-N-94 | ++ |
| I-N-95 | ++ |
| I-N-96 | ----- |
| I-N-97 | ++ |
| I-N-98 | ++ |
| I-N-99 | ++ |
| I-N-100 | ++ |
| I-N-101 | ++ |
| I-N-102 | ++ |
| I-N-103 | ++ |
| I-N-104 | ++ |
| I-N-105 | ++ |
| I-N-106 | ++ |
| I-N-107 | ++ |
| I-N-108 | ++ |
| I-N-109 | ++ |
| I-N-110 | ----- |
| I-N-111 | + |
| I-N-112 | + |
| I-N-113 | + |
| I-N-114 | ----- |
| I-N-115 | ++ |
| I-N-116 | ++ |
| I-N-117 | ++ |
| I-N-118 | ++ |
| I-N-119 | ++ |
| I-N-120 | ++ |
| I-N-121 | ++ |
| I-N-122 | ++ |

TABLE 5-continued

| Cmpd. # | ATR Ki |
|---|---|
| I-N-123 | ++ |
| I-N-124 | ++ |
| I-N-125 | ++ |
| I-N-126 | ++ |
| I-N-127 | ++ |
| I-N-128 | ++ |
| I-N-129 | ++ |
| I-N-130 | ++ |
| I-N-131 | ++ |
| I-N-132 | ++ |
| I-N-133 | ++ |
| I-N-134 | ++ |
| I-N-135 | ++ |
| I-N-136 | ++ |
| I-N-137 | ++ |
| I-N-138 | + |
| I-N-139 | ++ |
| I-N-140 | ++ |
| I-N-141 | ++ |
| I-N-142 | + |
| I-N-143 | ++ |
| I-N-144 | + |
| I-N-145 | ++ |
| I-N-146 | ++ |
| I-N-147 | ++ |
| I-N-148 | ++ |
| I-N-149 | ++ |
| I-N-150 | ++ |
| I-N-151 | + |
| I-N-152 | ++ |
| I-N-153 | ----- |
| I-N-154 | ++ |
| I-N-155 | ++ |
| I-N-156 | ++ |
| I-N-157 | ++ |
| I-N-158 | ++ |
| I-N-159 | ++ |
| I-N-160 | ++ |
| I-N-161 | ++ |
| I-N-162 | ++ |
| I-N-163 | ++ |
| I-N-164 | ++ |
| I-N-165 | ++ |
| I-N-166 | ++ |
| I-N-167 | ++ |
| I-N-168 | ++ |
| I-N-169 | ++ |
| I-N-170 | ++ |
| I-N-171 | ++ |
| I-N-172 | ++ |
| I-N-173 | ++ |
| I-N-174 | ++ |
| I-N-175 | ++ |
| I-N-176 | ++ |
| I-N-177 | ++ |
| I-N-178 | ++ |
| I-N-179 | ++ |
| I-N-180 | ++ |
| I-N-181 | ++ |
| I-N-182 | ++ |
| I-N-183 | ++ |
| I-N-184 | ++ |
| I-N-185 | ++ |
| I-N-186 | ++ |
| I-N-187 | ++ |
| I-N-188 | ++ |
| I-N-189 | ++ |
| I-N-190 | ++ |
| I-N-191 | + |
| I-N-192 | ++ |
| I-N-193 | ++ |
| I-N-194 | ++ |
| I-N-195 | ++ |
| I-N-196 | ++ |
| I-N-197 | ++ |
| I-N-198 | ++ |
| I-N-199 | ++ |
| I-N-200 | ++ |
| I-N-201 | ++ |
| I-N-202 | ++ |
| I-N-203 | ++ |
| I-N-204 | ++ |
| I-N-205 | ++ |
| I-N-206 | ++ |
| I-N-207 | ++ |
| I-N-208 | ++ |
| I-N-209 | ++ |
| I-N-210 | ++ |
| I-N-211 | ++ |
| I-N-212 | ++ |
| I-N-213 | ++ |
| I-N-214 | ++ |
| I-N-215 | ++ |
| I-N-216 | ++ |
| I-N-217 | ++ |
| I-N-218 | ++ |
| I-N-219 | ++ |
| I-N-220 | ++ |
| I-N-221 | ++ |
| I-N-222 | ++ |
| I-N-223 | ++ |
| I-N-224 | ++ |
| I-N-225 | ++ |
| I-N-226 | ++ |
| I-N-227 | ++ |
| I-N-228 | ++ |
| I-N-229 | ++ |
| I-N-230 | ++ |
| I-N-231 | ++ |
| I-N-232 | ++ |
| I-N-233 | ++ |
| I-N-234 | ++ |
| I-N-235 | ++ |
| I-N-236 | ++ |
| I-N-237 | ++ |
| I-N-238 | ++ |
| I-N-239 | ++ |
| I-N-240 | ++ |
| I-N-241 | ++ |
| I-N-242 | ----- |
| I-N-243 | ++ |
| I-N-244 | ++ |
| I-N-245 | ----- |
| I-N-246 | ++ |
| I-N-247 | ++ |
| I-N-248 | ++ |
| I-N-249 | ++ |
| I-N-250 | ++ |
| I-N-251 | ++ |
| I-N-252 | ++ |
| I-N-253 | ++ |
| I-N-254 | ++ |
| I-N-255 | ++ |
| I-N-256 | ++ |
| I-N-257 | ++ |
| I-N-258 | ++ |
| I-N-259 | + |
| I-N-260 | ++ |
| I-N-261 | ++ |
| I-N-262 | ++ |
| I-N-263 | ++ |
| I-N-264 | + |
| I-N-265 | ++ |
| I-N-266 | ++ |
| I-N-267 | ++ |
| I-N-268 | ++ |
| I-N-269 | ++ |
| I-N-270 | ++ |
| I-N-271 | ++ |
| I-N-272 | ++ |
| I-N-273 | ++ |
| I-N-274 | ++ |
| I-N-275 | ++ |
| I-N-276 | ++ |
| I-N-277 | ++ |
| I-N-278 | ++ |

TABLE 5-continued

| Cmpd. # | ATR Ki |
|---|---|
| I-N-279 | ++ |
| I-N-280 | ++ |
| I-N-281 | ++ |
| I-N-282 | ++ |
| I-N-283 | ++ |
| I-N-284 | ++ |
| I-N-285 | ++ |
| I-N-286 | ++ |
| I-N-287 | ++ |
| I-N-288 | ++ |
| I-N-289 | + |
| I-N-290 | ++ |
| I-O-1 | ++ |
| I-O-2 | +++ |
| I-O-3 | ++ |
| I-O-4 | ++ |
| I-O-5 | ++ |
| I-O-6 | ++ |
| I-O-7 | ++ |
| I-O-8 | ++ |
| I-O-9 | ++ |
| I-O-10 | ++ |
| I-O-11 | ++ |
| I-O-12 | ++ |
| I-O-13 | ++ |
| I-O-14 | ++ |
| I-O-15 | ++ |
| I-O-16 | ++ |
| I-O-17 | ++ |
| I-O-18 | ++ |
| I-O-19 | ++ |
| I-O-20 | ++ |
| I-O-21 | ++ |
| I-O-22 | ++ |
| I-O-23 | ++ |
| I-O-24 | +++ |
| I-O-25 | +++ |
| I-O-26 | +++ |
| I-O-27 | +++ |
| I-O-28 | +++ |
| I-O-29 | +++ |
| I-O-30 | +++ |
| I-O-31 | +++ |
| I-O-32 | +++ |
| I-O-33 | +++ |
| I-O-34 | +++ |
| I-O-35 | +++ |
| I-O-36 | +++ |
| I-O-37 | +++ |
| I-O-38 | +++ |
| I-O-39 | +++ |
| I-O-40 | +++ |
| I-O-41 | +++ |
| I-O-42 | +++ |
| I-O-43 | +++ |
| I-O-44 | ++ |
| I-O-45 | ++ |
| I-O-46 | + |
| I-O-47 | ++ |
| I-O-48 | ++ |
| I-O-49 | ++ |
| I-O-50 | ++ |
| I-O-51 | ++ |
| I-O-52 | + |
| I-O-53 | ++ |
| I-O-54 | ++ |
| I-O-55 | ++ |
| I-O-56 | ++ |
| I-O-57 | ++ |
| I-O-58 | ++ |
| I-O-59 | ++ |
| I-O-60 | ++ |
| I-O-61 | ++ |
| I-O-62 | ++ |
| I-O-63 | ++ |
| I-O-64 | ++ |
| I-O-65 | ++ |
| I-O-66 | ++ |
| I-O-67 | ++ |
| I-O-68 | ++ |
| I-O-69 | ++ |
| I-O-70 | ++ |
| I-O-71 | ++ |
| I-O-72 | ++ |
| I-O-73 | ++ |
| I-O-74 | ++ |
| I-O-75 | ++ |
| I-O-76 | ++ |
| I-O-77 | ++ |
| I-O-78 | ++ |
| I-O-79 | ----- |
| I-O-80 | ++ |
| I-O-81 | ++ |
| I-O-82 | +++ |
| I-O-83 | +++ |
| I-O-84 | +++ |
| I-O-85 | ++ |
| I-O-86 | +++ |
| I-O-87 | ++ |
| I-O-88 | ++ |
| I-O-89 | ++ |
| I-O-90 | ++ |
| I-O-91 | ++ |
| I-O-92 | ++ |
| I-C-1 | + |
| I-C-2 | + |
| I-C-3 | ++ |
| I-C-4 | ++ |
| I-C-5 | ++ |
| I-C-6 | ++ |
| I-C-7 | ++ |
| I-C-8 | ++ |
| I-C-9 | ++ |
| I-C-10 | ++ |
| I-C-11 | ++ |
| I-C-12 | ++ |
| I-C-13 | + |
| I-C-14 | + |
| I-C-15 | ++ |
| I-C-16 | ++ |
| I-C-17 | ++ |
| I-C-18 | ++ |
| I-C-19 | ++ |
| I-C-20 | ++ |
| I-C-21 | ++ |
| I-C-22 | ++ |
| I-C-23 | + |
| I-C-24 | ++ |
| I-C-25 | ++ |
| I-C-26 | ++ |
| I-C-27 | ++ |
| I-C-28 | ++ |
| I-C-29 | ++ |
| I-C-30 | ++ |
| I-C-31 | ++ |
| I-C-32 | ++ |
| I-C-33 | ++ |
| I-C-34 | ++ |
| I-C-35 | ++ |
| I-C-36 | ++ |
| I-C-37 | + |
| I-C-38 | ++ |
| I-C-39 | ++ |
| I-C-40 | ++ |
| I-C-41 | ++ |
| I-C-42 | ++ |
| I-C-43 | ++ |
| I-C-44 | ++ |
| I-C-45 | ++ |
| I-C-46 | ++ |
| I-C-47 | ++ |
| I-C-48 | ++ |
| I-C-49 | ++ |
| I-C-50 | ++ |
| I-C-51 | ++ |
| I-C-52 | ++ |

TABLE 5-continued

| Cmpd. # | ATR Ki |
|---|---|
| I-C-53 | ++ |
| I-C-54 | ++ |
| I-C-55 | ++ |
| I-C-56 | ++ |
| I-C-57 | ++ |
| I-C-58 | ++ |
| I-C-59 | ++ |
| I-C-60 | ++ |
| I-C-61 | ++ |
| I-C-62 | ++ |
| I-C-63 | ++ |
| I-C-64 | ++ |
| I-C-65 | ++ |
| I-C-66 | ++ |
| I-C-67 | ++ |
| I-C-68 | ++ |
| I-C-69 | ++ |
| I-C-70 | ++ |
| I-C-71 | ++ |
| I-C-72 | ++ |
| I-C-73 | ++ |
| I-C-74 | ++ |
| I-C-75 | ++ |
| I-C-76 | + |
| I-C-77 | ++ |
| I-C-78 | ++ |
| I-C-79 | ++ |
| I-C-80 | ++ |
| I-C-81 | +++ |
| I-C-82 | ++ |
| I-C-83 | ++ |
| I-C-84 | ++ |
| I-G-1 | ++ |
| I-G-2 | ++ |
| I-G-3 | ++ |
| I-G-4 | ++ |
| I-G-5 | ++ |
| I-G-6 | ++ |
| I-G-7 | ++ |
| I-G-8 | ++ |
| I-G-9 | ++ |
| I-G-10 | ++ |
| I-G-11 | ++ |
| I-G-12 | ++ |
| I-G-13 | ++ |
| I-G-14 | +++ |
| I-G-15 | ++ |
| I-G-16 | ++ |
| I-G-17 | + |
| I-G-18 | ++ |
| I-G-19 | ++ |
| I-G-20 | ++ |
| I-G-21 | ++ |
| I-G-22 | ++ |
| I-G-23 | ++ |
| I-G-24 | ++ |
| I-G-25 | ++ |
| I-G-26 | ++ |
| I-G-27 | ++ |
| I-G-28 | ++ |
| I-G-29 | ++ |
| I-G-30 | ++ |
| I-G-31 | ++ |
| I-G-32 | ++ |
| I-G-33 | ++ |
| I-G-34 | ++ |
| I-G-35 | ++ |
| I-G-36 | ++ |
| I-G-37 | ++ |
| I-G-38 | ++ |
| I-G-40 | ++ |
| I-G-41 | + |
| I-G-42 | ++ |
| I-G-43 | ++ |
| I-G-44 | ++ |
| I-G-45 | ++ |
| I-G-46 | + |
| I-G-47 | ++ |
| I-G-48 | ++ |
| I-G-49 | ++ |
| I-G-50 | ++ |
| I-G-51 | ++ |
| I-G-52 | ++ |
| I-G-53 | ++ |
| I-G-54 | ++ |
| I-G-55 | ++ |
| I-G-56 | ++ |
| I-G-57 | ++ |
| I-G-58 | ++ |
| I-G-59 | ++ |
| I-G-60 | ++ |
| I-G-61 | ++ |
| I-G-62 | ++ |
| I-G-63 | ++ |
| I-G-64 | ++ |
| I-G-65 | ++ |
| I-G-66 | ++ |
| I-G-67 | +++ |
| I-G-68 | +++ |
| I-G-69 | ++ |
| I-G-70 | ++ |
| I-G-71 | ++ |
| I-G-72 | ++ |
| I-G-73 | ++ |
| I-G-74 | ++ |
| I-G-75 | ++ |
| I-G-76 | ++ |
| I-G-77 | ++ |
| I-G-78 | ++ |
| I-G-79 | ++ |
| I-G-80 | ++ |
| I-G-81 | ++ |
| I-G-82 | ++ |
| I-G-83 | ++ |
| I-G-84 | ++ |
| I-G-85 | ++ |
| I-G-86 | ++ |
| I-G-87 | ++ |
| I-G-88 | ++ |
| I-G-89 | ++ |
| I-G-90 | ++ |
| I-G-91 | ++ |
| I-G-92 | ++ |
| I-G-93 | ++ |
| I-G-94 | ++ |
| I-G-95 | ++ |
| I-G-96 | ++ |
| I-G-98 | ++ |
| I-G-99 | ++ |

Example 21: Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al; *Oncogene* 21:3864 (2002); see also, Takemura et al.; *JBC* 281:30814 (2006)) are plated at 470 cells per well in 96-well polystyrene plates (Costar 3596) in 150 μl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 μM as a full matrix of concentrations in a final cell volume of 200 μl, and the cells are then incubated at 37° C. in 5% $CO_2$. After 96 h, 40 μl of MTS reagent (Promega G358a) is added to each well and the cells are incubated for 1 h at 37° C. in 5% $CO_2$.

Finally, absorbance is measured at 490 nm using a Spectra-Max Plus 384 reader (Molecular Devices) and the concentration of compound required to reduce the $IC_{50}$ of Cisplatin alone by at least 3-fold (to 1 decimal place) can be reported.

Table 6, below, shows the Cisplatin sensitization values of compounds of the disclosure. Compounds with a Cisplatin sensitization value of <0.02 μM are marked with "+++." Compounds with a Cisplatin sensitization value >0.02 μM but <0.2 μM are marked with "++." Compounds with a Cisplatin sensitization value >0.2 μM but <5 μM are marked with "+."

TABLE 6

| Cmpd. # | Cisplatin Sensitization Assay |
|---|---|
| I-N-1 | ++ |
| I-N-2 | +++ |
| I-N-3 | +++ |
| I-N-4 | +++ |
| I-N-5 | ++ |
| I-N-6 | ----- |
| I-N-7 | ++ |
| I-N-8 | + |
| I-N-9 | + |
| I-N-10 | ++ |
| I-N-11 | ++ |
| I-N-12 | +++ |
| I-N-13 | +++ |
| I-N-14 | +++ |
| I-N-15 | +++ |
| I-N-16 | +++ |
| I-N-17 | +++ |
| I-N-18 | ++ |
| I-N-19 | +++ |
| I-N-20 | +++ |
| I-N-21 | +++ |
| I-N-22 | ----- |
| I-N-23 | +++ |
| I-N-24 | +++ |
| I-N-25 | ----- |
| I-N-26 | + |
| I-N-27 | ++ |
| I-N-28 | +++ |
| I-N-29 | ++ |
| I-N-30 | ++ |
| I-N-31 | + |
| I-N-32 | ++ |
| I-N-33 | + |
| I-N-34 | ++ |
| I-N-35 | + |
| I-N-36 | ++ |
| I-N-37 | ++ |
| I-N-38 | ++ |
| I-N-39 | ++ |
| I-N-40 | ++ |
| I-N-41 | +++ |
| I-N-42 | ----- |
| I-N-43 | ++ |
| I-N-44 | ++ |
| I-N-45 | ++ |
| I-N-46 | +++ |
| I-N-47 | ++ |
| I-N-48 | ++ |
| I-N-49 | +++ |
| I-N-50 | + |
| I-N-51 | ----- |
| I-N-52 | ++ |
| I-N-53 | ++ |
| I-N-54 | +++ |
| I-N-55 | ++ |
| I-N-56 | ++ |
| I-N-57 | +++ |
| I-N-58 | ++ |
| I-N-59 | ++ |
| I-N-60 | +++ |
| I-N-61 | +++ |
| I-N-62 | ++ |
| I-N-63 | ++ |
| I-N-64 | +++ |
| I-N-65 | + |
| I-N-66 | +++ |
| I-N-67 | +++ |
| I-N-68 | +++ |
| I-N-69 | +++ |
| I-N-70 | ++ |
| I-N-71 | +++ |
| I-N-72 | +++ |
| I-N-73 | +++ |
| I-N-74 | +++ |
| I-N-75 | +++ |
| I-N-76 | +++ |
| I-N-77 | + |
| I-N-78 | ----- |
| I-N-79 | ++ |
| I-N-80 | ++ |
| I-N-81 | +++ |
| I-N-82 | ++ |
| I-N-83 | ++ |
| I-N-84 | +++ |
| I-N-85 | ++ |
| I-N-86 | +++ |
| I-N-87 | ++ |
| I-N-88 | ++ |
| I-N-89 | ++ |
| I-N-90 | + |
| I-N-91 | ++ |
| I-N-92 | + |
| I-N-93 | ----- |
| I-N-94 | +++ |
| I-N-95 | ++ |
| I-N-96 | ----- |
| I-N-97 | +++ |
| I-N-98 | +++ |
| I-N-99 | +++ |
| I-N-100 | ++ |
| I-N-101 | ++ |
| I-N-102 | ++ |
| I-N-103 | +++ |
| I-N-104 | +++ |
| I-N-105 | +++ |
| I-N-106 | +++ |
| I-N-107 | +++ |
| I-N-108 | +++ |
| I-N-109 | +++ |
| I-N-110 | ----- |
| I-N-111 | ++ |
| I-N-112 | + |
| I-N-113 | + |
| I-N-114 | ----- |
| I-N-115 | +++ |
| I-N-116 | ++ |
| I-N-117 | +++ |
| I-N-118 | +++ |
| I-N-119 | ++ |
| I-N-120 | +++ |
| I-N-121 | +++ |
| I-N-122 | ++ |
| I-N-123 | ++ |
| I-N-124 | +++ |
| I-N-125 | +++ |
| I-N-126 | +++ |
| I-N-127 | +++ |
| I-N-128 | +++ |
| I-N-129 | ----- |
| I-N-130 | ++ |
| I-N-131 | +++ |
| I-N-132 | +++ |
| I-N-133 | ++ |
| I-N-134 | + |
| I-N-135 | +++ |
| I-N-136 | ++ |
| I-N-137 | ++ |
| I-N-138 | ++ |
| I-N-139 | +++ |
| I-N-140 | +++ |
| I-N-141 | +++ |

TABLE 6-continued

| Cmpd. # | Cisplatin Sensitization Assay |
|---|---|
| I-N-142 | ++ |
| I-N-143 | ++ |
| I-N-144 | +++ |
| I-N-145 | ----- |
| I-N-146 | +++ |
| I-N-147 | +++ |
| I-N-148 | +++ |
| I-N-149 | +++ |
| I-N-150 | +++ |
| I-N-151 | + |
| I-N-152 | +++ |
| I-N-153 | ++ |
| I-N-154 | +++ |
| I-N-155 | +++ |
| I-N-156 | +++ |
| I-N-157 | ++ |
| I-N-158 | +++ |
| I-N-159 | +++ |
| I-N-160 | +++ |
| I-N-161 | + |
| I-N-162 | ++ |
| I-N-163 | +++ |
| I-N-164 | +++ |
| I-N-165 | +++ |
| I-N-166 | +++ |
| I-N-167 | +++ |
| I-N-168 | + |
| I-N-169 | +++ |
| I-N-170 | +++ |
| I-N-171 | +++ |
| I-N-172 | +++ |
| I-N-173 | +++ |
| I-N-174 | +++ |
| I-N-175 | +++ |
| I-N-176 | +++ |
| I-N-177 | +++ |
| I-N-178 | +++ |
| I-N-179 | +++ |
| I-N-180 | ----- |
| I-N-181 | +++ |
| I-N-182 | ++ |
| I-N-183 | +++ |
| I-N-184 | ++ |
| I-N-185 | ++ |
| I-N-186 | +++ |
| I-N-187 | +++ |
| I-N-188 | +++ |
| I-N-189 | +++ |
| I-N-190 | +++ |
| I-N-191 | + |
| I-N-192 | +++ |
| I-N-193 | +++ |
| I-N-194 | +++ |
| I-N-195 | +++ |
| I-N-196 | +++ |
| I-N-197 | +++ |
| I-N-198 | ++ |
| I-N-199 | +++ |
| I-N-200 | +++ |
| I-N-201 | +++ |
| I-N-202 | +++ |
| I-N-203 | +++ |
| I-N-204 | ----- |
| I-N-205 | ++ |
| I-N-206 | +++ |
| I-N-207 | ----- |
| I-N-208 | +++ |
| I-N-209 | +++ |
| I-N-210 | +++ |
| I-N-211 | ++ |
| I-N-212 | +++ |
| I-N-213 | +++ |
| I-N-214 | ++ |
| I-N-215 | +++ |
| I-N-216 | +++ |
| I-N-217 | ++ |
| I-N-218 | + |
| I-N-219 | +++ |
| I-N-220 | ++ |
| I-N-221 | ++ |
| I-N-222 | ++ |
| I-N-223 | ++ |
| I-N-224 | + |
| I-N-225 | ++ |
| I-N-226 | +++ |
| I-N-227 | +++ |
| I-N-228 | +++ |
| I-N-229 | +++ |
| I-N-230 | +++ |
| I-N-231 | +++ |
| I-N-232 | ++ |
| I-N-233 | ++ |
| I-N-234 | + |
| I-N-235 | ++ |
| I-N-236 | +++ |
| I-N-237 | + |
| I-N-238 | ++ |
| I-N-239 | +++ |
| I-N-240 | ++ |
| I-N-241 | +++ |
| I-N-242 | + |
| I-N-243 | +++ |
| I-N-244 | +++ |
| I-N-245 | ++ |
| I-N-246 | ++ |
| I-N-247 | +++ |
| I-N-248 | ++ |
| I-N-249 | +++ |
| I-N-250 | ++ |
| I-N-251 | +++ |
| I-N-252 | +++ |
| I-N-253 | +++ |
| I-N-254 | +++ |
| I-N-255 | ++ |
| I-N-256 | ++ |
| I-N-257 | +++ |
| I-N-258 | ++ |
| I-N-259 | + |
| I-N-260 | +++ |
| I-N-261 | +++ |
| I-N-262 | +++ |
| I-N-263 | + |
| I-N-264 | + |
| I-N-265 | ++ |
| I-N-266 | +++ |
| I-N-267 | +++ |
| I-N-268 | +++ |
| I-N-269 | ++ |
| I-N-270 | +++ |
| I-N-271 | +++ |
| I-N-272 | +++ |
| I-N-273 | +++ |
| I-N-274 | +++ |
| I-N-275 | +++ |
| I-N-276 | +++ |
| I-N-277 | +++ |
| I-N-278 | +++ |
| I-N-279 | +++ |
| I-N-280 | +++ |
| I-N-281 | +++ |
| I-N-282 | +++ |
| I-N-283 | ++ |
| I-N-284 | +++ |
| I-N-285 | ++ |
| I-N-286 | ++ |
| I-N-287 | +++ |
| I-N-288 | +++ |
| I-N-289 | ++ |
| I-N-290 | ++ |
| I-O-1 | +++ |
| I-O-2 | ++ |
| I-O-3 | ++ |
| I-O-4 | ++ |
| I-O-5 | +++ |
| I-O-6 | +++ |
| I-O-7 | ++ |

TABLE 6-continued

| Cmpd. # | Cisplatin Sensitization Assay |
|---|---|
| I-O-8 | + |
| I-O-9 | ++ |
| I-O-10 | +++ |
| I-O-11 | +++ |
| I-O-12 | +++ |
| I-O-13 | +++ |
| I-O-14 | +++ |
| I-O-15 | +++ |
| I-O-16 | +++ |
| I-O-17 | +++ |
| I-O-18 | ----- |
| I-O-19 | +++ |
| I-O-20 | ++ |
| I-O-21 | ++ |
| I-O-22 | ----- |
| I-O-23 | +++ |
| I-O-24 | ++ |
| I-O-25 | +++ |
| I-O-26 | ++ |
| I-O-27 | ++ |
| I-O-28 | +++ |
| I-O-29 | +++ |
| I-O-30 | +++ |
| I-O-31 | +++ |
| I-O-32 | +++ |
| I-O-33 | ++ |
| I-O-34 | ++ |
| I-O-35 | +++ |
| I-O-36 | +++ |
| I-O-37 | +++ |
| I-O-38 | +++ |
| I-O-39 | +++ |
| I-O-40 | ++ |
| I-O-41 | +++ |
| I-O-42 | +++ |
| I-O-43 | +++ |
| I-O-44 | ++ |
| I-O-45 | +++ |
| I-O-46 | + |
| I-O-47 | + |
| I-O-48 | ++ |
| I-O-49 | + |
| I-O-50 | + |
| I-O-51 | ----- |
| I-O-52 | + |
| I-O-53 | +++ |
| I-O-54 | +++ |
| I-O-55 | ++ |
| I-O-56 | +++ |
| I-O-57 | +++ |
| I-O-58 | +++ |
| I-O-59 | +++ |
| I-O-60 | ++ |
| I-O-61 | +++ |
| I-O-62 | +++ |
| I-O-63 | ++ |
| I-O-64 | +++ |
| I-O-65 | +++ |
| I-O-66 | + |
| I-O-67 | ++ |
| I-O-68 | ++ |
| I-O-69 | ++ |
| I-O-70 | +++ |
| I-O-71 | + |
| I-O-72 | + |
| I-O-73 | + |
| I-O-74 | ++ |
| I-O-75 | ++ |
| I-O-76 | ++ |
| I-O-77 | ++ |
| I-O-78 | + |
| I-O-79 | ++ |
| I-O-80 | +++ |
| I-O-81 | ++ |
| I-O-82 | ++ |
| I-O-83 | +++ |
| I-O-84 | ++ |
| I-O-85 | +++ |
| I-O-86 | ++ |
| I-O-87 | ++ |
| I-O-88 | +++ |
| I-O-89 | ++ |
| I-O-90 | + |
| I-O-91 | ++ |
| I-O-92 | +++ |
| I-C-1 | ++ |
| I-C-2 | ++ |
| I-C-3 | ----- |
| I-C-4 | ++ |
| I-C-5 | +++ |
| I-C-6 | +++ |
| I-C-7 | ++ |
| I-C-8 | + |
| I-C-9 | + |
| I-C-10 | +++ |
| I-C-11 | +++ |
| I-C-12 | +++ |
| I-C-13 | ++ |
| I-C-14 | + |
| I-C-15 | ++ |
| I-C-16 | + |
| I-C-17 | ++ |
| I-C-18 | + |
| I-C-19 | ++ |
| I-C-20 | +++ |
| I-C-21 | +++ |
| I-C-22 | ++ |
| I-C-23 | + |
| I-C-24 | +++ |
| I-C-25 | +++ |
| I-C-26 | ++ |
| I-C-27 | ++ |
| I-C-28 | ----- |
| I-C-29 | +++ |
| I-C-30 | +++ |
| I-C-31 | +++ |
| I-C-32 | ----- |
| I-C-33 | + |
| I-C-34 | +++ |
| I-C-35 | +++ |
| I-C-36 | +++ |
| I-C-37 | +++ |
| I-C-38 | ++ |
| I-C-39 | +++ |
| I-C-40 | +++ |
| I-C-41 | +++ |
| I-C-42 | ++ |
| I-C-43 | +++ |
| I-C-44 | +++ |
| I-C-45 | +++ |
| I-C-46 | + |
| I-C-47 | +++ |
| I-C-48 | +++ |
| I-C-49 | +++ |
| I-C-50 | +++ |
| I-C-51 | ++ |
| I-C-52 | ++ |
| I-C-53 | +++ |
| I-C-54 | +++ |
| I-C-55 | + |
| I-C-56 | +++ |
| I-C-57 | +++ |
| I-C-58 | +++ |
| I-C-59 | ++ |
| I-C-60 | ++ |
| I-C-61 | +++ |
| I-C-62 | ++ |
| I-C-63 | +++ |
| I-C-64 | +++ |
| I-C-65 | ++ |
| I-C-66 | +++ |
| I-C-67 | ++ |
| I-C-68 | + |
| I-C-69 | +++ |
| I-C-70 | +++ |
| I-C-71 | +++ |

TABLE 6-continued

| Cmpd. # | Cisplatin Sensitization Assay |
|---|---|
| I-C-72 | +++ |
| I-C-73 | ++ |
| I-C-74 | + |
| I-C-75 | ++ |
| I-C-76 | + |
| I-C-77 | +++ |
| I-C-78 | ++ |
| I-C-79 | +++ |
| I-C-80 | +++ |
| I-C-81 | +++ |
| I-C-82 | +++ |
| I-C-83 | ++ |
| I-C-84 | ++ |
| I-G-1 | +++ |
| I-G-2 | +++ |
| I-G-3 | +++ |
| I-G-4 | +++ |
| I-G-5 | +++ |
| I-G-6 | +++ |
| I-G-7 | +++ |
| I-G-8 | +++ |
| I-G-9 | +++ |
| I-G-10 | +++ |
| I-G-11 | +++ |
| I-G-12 | +++ |
| I-G-13 | +++ |
| I-G-14 | +++ |
| I-G-15 | +++ |
| I-G-16 | +++ |
| I-G-17 | + |
| I-G-18 | +++ |
| I-G-19 | ++ |
| I-G-20 | + |
| I-G-21 | +++ |
| I-G-22 | +++ |
| I-G-23 | +++ |
| I-G-24 | +++ |
| I-G-25 | +++ |
| I-G-26 | ++ |
| I-G-27 | ++ |
| I-G-28 | +++ |
| I-G-29 | +++ |
| I-G-30 | +++ |
| I-G-31 | +++ |
| I-G-32 | +++ |
| I-G-33 | +++ |
| I-G-34 | +++ |
| I-G-35 | +++ |
| I-G-36 | +++ |
| I-G-37 | ++ |
| I-G-38 | +++ |
| I-G-40 | +++ |
| I-G-41 | +++ |
| I-G-42 | +++ |
| I-G-43 | +++ |
| I-G-44 | +++ |
| I-G-45 | +++ |
| I-G-46 | +++ |
| I-G-47 | +++ |
| I-G-48 | +++ |
| I-G-49 | +++ |
| I-G-50 | +++ |
| I-G-51 | +++ |
| I-G-52 | +++ |
| I-G-53 | +++ |
| I-G-54 | +++ |
| I-G-55 | +++ |
| I-G-56 | +++ |
| I-G-57 | +++ |
| I-G-58 | +++ |
| I-G-59 | +++ |
| I-G-60 | +++ |
| I-G-61 | +++ |
| I-G-62 | +++ |
| I-G-63 | +++ |
| I-G-64 | +++ |
| I-G-65 | +++ |
| I-G-66 | +++ |
| I-G-67 | +++ |
| I-G-68 | +++ |
| I-G-69 | +++ |
| I-G-70 | ----- |
| I-G-71 | ----- |
| I-G-72 | +++ |
| I-G-73 | +++ |
| I-G-74 | +++ |
| I-G-75 | +++ |
| I-G-76 | +++ |
| I-G-77 | +++ |
| I-G-78 | +++ |
| I-G-79 | +++ |
| I-G-80 | +++ |
| I-G-81 | +++ |
| I-G-82 | +++ |
| I-G-83 | +++ |
| I-G-84 | +++ |
| I-G-85 | +++ |
| I-G-86 | +++ |
| I-G-87 | +++ |
| I-G-88 | +++ |
| I-G-89 | + |
| I-G-90 | +++ |
| I-G-91 | +++ |
| I-G-92 | +++ |
| I-G-93 | +++ |
| I-G-94 | +++ |
| I-G-95 | +++ |
| I-G-96 | +++ |
| I-G-98 | +++ |
| I-G-99 | +++ |

Example 22: Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 µl of McCoy's 5A media (Sigma M8403) supplemented with 10% foetal bovine serum ($J^R$ H Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 µM as a full matrix of concentrations in a final cell volume of 200µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and IC50 values can be calculated.

Example 23: ATR-complex Inhibition Assay

Compounds were screened for their ability to inhibit ATR kinase, in the presence of partner proteins ATRIP, CLK2 and TopBP1, using a radioactive-phosphate incorporation assay. Assays were carried out in a mixture of 50 mM Tris/HCl (pH 7.5), 10 mM $MgCl_2$ and 1 mM DTT. Final substrate concentrations were 10 μM [g-33P]ATP (3.5 μCi 33P ATP/nmol ATP, Perkin Elmer, Massachusetts, USA) and 800 μM target peptide (ASELPASQPQPFSAKKK) (SEQ ID NO: 1); Isca Biochemicals, Cambridgeshire, UK).

Assays were carried out at 25° C. in the presence of 4 nM full-length ATR, 40 nM full-length ATRIP, 40 nM full-length CLK2 and 600 nM TopBP1(A891-S1105). An enzyme stock buffer solution was prepared containing all of the reagents listed above, with the exception of target peptide, ATP and the test compound of interest. This enzyme stock was pre-incubated for 30 minutes at 25° C. 8.5 μL of the enzyme stock solution was placed in a 96-well plate followed by addition of 5 μl of target peptide and 2 μL of DMSO stock containing serial dilutions of the test compound (typically starting from a final concentration of 1.5 μM with 2.5-fold serial dilutions) in duplicate (final DMSO concentration 7%). The plate was pre-incubated for 10 minutes at 25° C. and the reaction initiated by addition of 15 μL [g-33P]ATP (final concentration 10 μM).

The reaction was stopped after 20 hours by the addition of 30 μL, 0.3 M phosphoric acid containing 2 mM ATP. A phosphocellulose filter 96-well plate (Multiscreen HTS MAPHNOB50, Merck-Millipore, Massachusetts, USA) was pretreated with 100 μL, 0.1 M phosphoric acid prior to the addition of 45 μL, of the stopped assay mixture. The plate was washed with 5×200 μL, 0.1 M phosphoric acid. After drying, 50 μL, Optiphase 'SuperMix' liquid scintillation cocktail (Perkin Elmer, Massachusetts, USA) was added to the well prior to scintillation counting (Wallac 1450 Microbeta Liquid Scintillation Counter, Perkin Elmer, Massachusetts, USA).

After removing mean background values for all of the data points, Ki(app) data were calculated from non-linear regression analysis of the initial rate data using the Prism software package (GraphPad Prism version 6.0c for Macintosh, GraphPad Software Inc., San Diego, USA).

Table 7, below, shows the Cisplatin sensitization values of compounds of the disclosure. Compounds with a Cisplatin sensitization value of <0.02 μM are marked with "+++." Compounds with a Ki value >0.02 μM but <0.2 μM are marked with "++." Compounds with a Ki value >0.2 μM but <5 μM are marked with "+."

TABLE 7

| Cmpd. # | ATR Ki |
|---|---|
| I-N-1 | +++ |
| I-N-13 | +++ |
| I-N-58 | +++ |
| I-N-118 | +++ |
| I-N-166 | +++ |
| I-N-186 | +++ |
| I-N-275 | +++ |
| I-C-25 | +++ |
| I-C-31 | +++ |
| I-C-43 | +++ |
| I-C-79 | +++ |
| I-G-4 | +++ |
| I-G-7 | +++ |
| I-G-12 | +++ |
| I-G-21 | +++ |
| I-G-32 | +++ |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A process for preparing a compound of formula I-A:

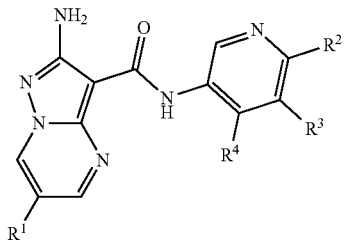

or a pharmaceutically acceptable salt or prodrug thereof, wherein:

$R^1$ is fluoro, chloro, or $C(J^1)_2CN$;

each $J^1$ is independently H or $C_{1-2}$alkyl; or two occurrences of $J^1$, together with the carbon atom to which they are attached, form a 3-4 membered optionally substituted carbocyclic ring;

$R^2$ is H; halo; —CN; $NH_2$; a $C_{1-2}$alkyl optionally substituted with 0-3 occurrences of fluoro; or a $C_{1-3}$ aliphatic chain wherein up to two methylene units of the aliphatic chain are optionally replaced with —O—, —NR—, —C(O)—, or —S(O)$_n$—;

$R^3$ is H; halo; $C_{1-4}$alkyl optionally substituted with 1-3 occurrences of halo; $C_{3-4}$cycloalkyl; —CN; or a $C_{1-3}$ aliphatic chain wherein up to two methylene units of the aliphatic chain are optionally replaced with —O—, —NR—, —C(O)—, or —S(O)$_n$—;

$R^4$ is —CH$_2$R$^7$, wherein $R^7$ is H or a $C_{1-8}$ aliphatic chain wherein up to three methylene units of the aliphatic chain are optionally replaced with —O—, —NR—, —S—, —C(O)—, or —S(O)$_n$; or $R^3$ and $R^4$, taken together with the atoms to which they are bound, form a 5-6 membered non-aromatic ring having 0-2 heteroatoms selected from oxygen, nitrogen and sulfur; the ring formed by $R^3$ and $R^4$ is optionally substituted with 0-3 occurrences of $J^Z$;

each $J^Z$ is independently $C_{1-6}$ aliphatic, =O, halo, or →O;

n is 0, 1 or 2; and each R is independently H or $C_{1-4}$ aliphatic;

comprising reacting a compound of formula 6:

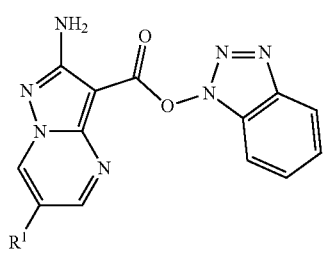

or salt thereof, with a substituted 3-aminopyridine under suitable conditions to form an amide bond.

2. The process of claim 1, further comprising the step of preparing a compound of formula 6:

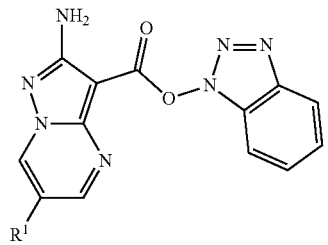

or salt thereof, by reacting a compound of formula 5:

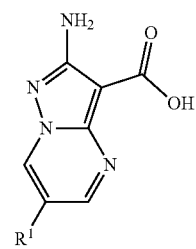

or salt thereof, under suitable conditions to form an activated ester.

3. A process for preparing a compound of formula I-A:

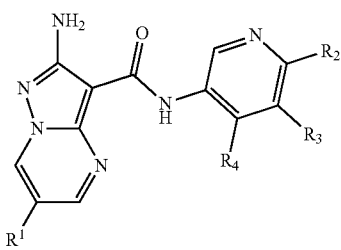

or a pharmaceutically acceptable salt or prodrug thereof, wherein:

$R^1$ is fluoro, chloro, or —$C(J^1)_2CN$;

each $J^1$ is independently H or $C_{1-2}$alkyl; or two occurrences of $J^1$, together with the carbon atom to which they are attached, form a 3-4 membered optionally substituted carbocyclic ring;

$R^2$ is H; halo; —CN; $NH_2$; a $C_{1-2}$alkyl optionally substituted with 0-3 occurrences of fluoro; or a $C_{1-3}$aliphatic chain wherein up to two methylene units of the aliphatic chain are optionally replaced with —O—, —NR—, —C(O)—, or —S(O)$_n$—;

$R^3$ is H; halo; $C_{1-4}$alkyl optionally substituted with 1-3 occurrences of halo; $C_{3-4}$ cycloalkyl; —CN; or a $C_{1-3}$aliphatic chain wherein up to two methylene units of the aliphatic chain are optionally replaced with —O—, —NR—, —C(O)—, —S(O)$_n$—;

$R^4$ is —CH$_2$R$^7$, is H or a $C_{1-8}$ aliphatic chain wherein up to three methylene units of the aliphatic chain are optionally replaced with —O—, —NR—, —S—, —C(O)—, or —S(O)$_n$—; or R³ and R⁴, taken together with the atoms to which they are bound, form a 5-6 membered non-aromatic ring having 0-2 heteroatoms selected from oxygen, nitrogen and sulfur; the ring formed by R³ and R⁴ is optionally substituted with 0-3 occurrences of $J^Z$;

each $J^Z$ is independently $C_{1-6}$aliphatic, =O, halo, or →O;

n is 0, 1 or 2; and each R is independently H or $C_{1-4}$aliphatic;

comprising reacting a compound of formula 5:

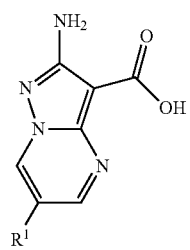

5 or salt thereof, with a substituted 3-aminopyridine under suitable conditions to form an amide bond, and wherein the suitable conditions comprise a coupling agent.

4. The process of claim 2, further comprising the step of preparing a compound of formula 5:

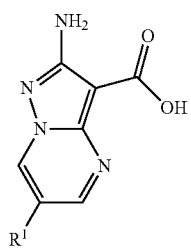

5 or salt thereof, by reacting a compound of formula 4:

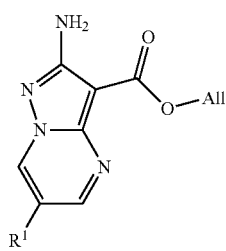

4 or salt thereof, under suitable deprotection conditions.

5. The process of claim 4, further comprising the step of preparing a compound of formula 4:

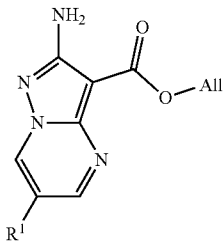

4 or salt thereof, by reacting a compound of formula 3:

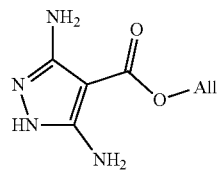

3 or salt thereof, under suitable condensation conditions to form a pyrimidine ring.

6. The process of claim 5, further comprising the step of preparing the compound of formula 3:

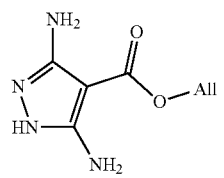

3 or salt thereof, by reacting a compound of formula 2:

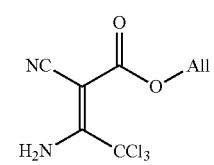

2 or salt thereof, under suitable condensation conditions to form a pyrazole ring.

7. The process of claim 6, further comprising the step of preparing a compound of formula 2:

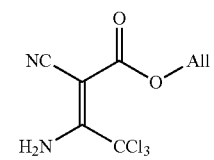

2 or salt thereof, by reacting a compound of formula 1:

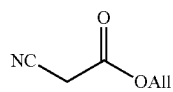

under suitable anion condensation conditions.

8. A process for preparing a compound of formula I-A:

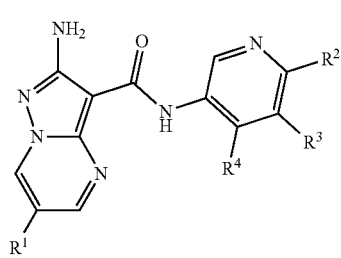

or a pharmaceutically acceptable salt or prodrug thereof, wherein:
$R^1$ is fluoro, chloro, or —C($J^1$)$_2$CN;
each $J^1$ is independently H or $C_{1-2}$alkyl; or
two occurrences of $J^1$, together with the carbon atom to which they are attached, form a 3-4 membered optionally substituted carbocyclic ring;
$R^2$ is H; halo; —CN; NH$_2$; a $C_{1-2}$alkyl optionally substituted with 0-3 occurrences of fluoro; or a $C_{1-3}$aliphatic chain wherein up to two methylene units of the aliphatic chain are optionally replaced with —O—, —NR—, —C(O)—, or —S(O)$_n$—;
$R^3$ is H; halo; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O—, —NR—, —C(O)—, or —S(O)$_n$—;
$R^4$ is —CH$_2$R$^7$, wherein $R^7$ is H or a $C_{1-8}$ aliphatic chain wherein up to three methylene units of the aliphatic chain are optionally replaced with —O—, —NR—, —S—, —C(O)—, or —S(O)$_n$—; or
$R^3$ and $R^4$, taken together with the atoms to which they are bound, form a 5-6 membered non-aromatic ring having 0-2 heteroatoms selected from oxygen, nitrogen and sulfur; the ring formed by $R^3$ and $R^4$ is optionally substituted with 0-3 occurrences of $J^Z$;
each $J^Z$ is independently $C_{1-6}$aliphatic, =O, halo, or →O;
n is 0, 1 or 2; and
each R is independently H or $C_{1-4}$aliphatic;
comprising reacting a compound of formula 9:

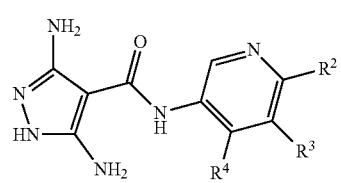

or salt thereof, under suitable condensation conditions to form a pyrimidine ring, wherein suitable condensation conditions comprise reacting the compound of formula 9 with a 1,3-dielectrophilic species in the presence of a solvent.

9. The process of claim 8, further comprising the step of preparing a compound of formula 9:

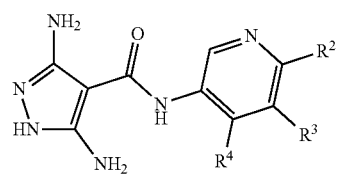

or salt thereof, by reacting a compound of formula 8:

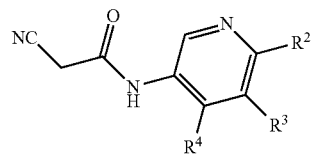

or salt thereof, under suitable condensation conditions to form a pyrazole ring.

10. The process of claim 9, further comprising the step of preparing a compound of formula 8:

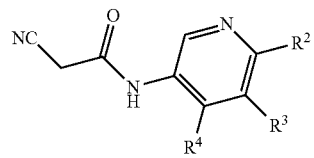

or salt thereof, by reacting a compound of formula 7:

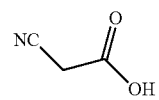

or salt thereof, under suitable conditions to form an amide bond.

11. The process of claim 3, further comprising the step of preparing a compound of formula 5:

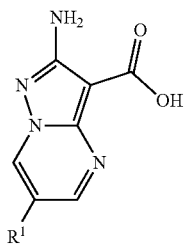
5 or salt thereof, by reacting a compound of formula 4:

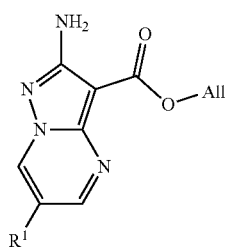
4 or salt thereof, under suitable deprotection conditions.

12. The process of claim 11, further comprising the step of preparing a compound of formula 4:

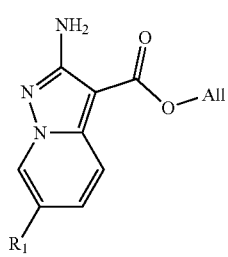
4 or salt thereof, by reacting a compound of formula 3:

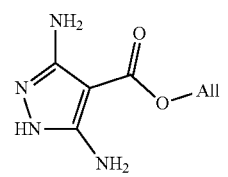
3 or salt thereof, under suitable condensation conditions to form a pyrimidine ring.

13. The process of claim 12, further comprising the step of preparing the compound of formula 3:

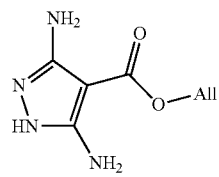
3 or salt thereof, by reacting a compound of formula 2:

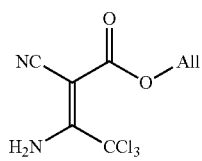
2 or salt thereof, under suitable condensation conditions to form a pyrazole ring.

14. The process of claim 13, further comprising the step of preparing a compound of formula 2:

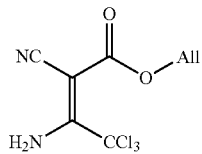
2 or salt thereof, by reacting a compound of formula 1:

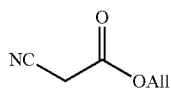
1 under suitable anion condensation conditions.

15. The process of claim 1, wherein $R^1$ is fluoro.
16. The process of claim 1, wherein $R^2$ is H.
17. The process of claim 1, wherein $R^3$ is halo.

* * * * *

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Glu Leu Pro Ala Ser Gln Pro Gln Pro Phe Ser Ala Lys Lys
1               5                   10                  15

Lys
```